United States Patent
Tatlock et al.

(10) Patent No.: US 10,428,104 B2
(45) Date of Patent: Oct. 1, 2019

(54) SUBSTITUTED NUCLEOSIDE DERIVATIVES USEFUL AS ANTICANCER AGENTS

(71) Applicant: Pfizer Inc., New York, NY (US)

(72) Inventors: John Howard Tatlock, San Diego, CA (US); Indrawan James McAlpine, San Diego, CA (US); Michelle Bich Tran-Dube, San Diego, CA (US); Eugene Yuanjin Rui, San Diego, CA (US); Martin James Wythes, Solana Beach, CA (US); Robert Arnold Kumpf, Carlsbad, CA (US); Michele Ann McTigue, Encinitas, CA (US)

(73) Assignee: Pfizer Inc., New York, NY (US)

( * ) Notice: Subject to any disclaimer, the term of this patent is extended or adjusted under 35 U.S.C. 154(b) by 405 days.

(21) Appl. No.: 15/045,679

(22) Filed: Feb. 17, 2016

(65) Prior Publication Data
US 2016/0244475 A1 Aug. 25, 2016

Related U.S. Application Data

(60) Provisional application No. 62/119,932, filed on Feb. 24, 2015, provisional application No. 62/213,801, filed on Sep. 3, 2015, provisional application No. 62/279,209, filed on Jan. 15, 2016.

(51) Int. Cl.
| | | |
|---|---|---|
| C07H 19/14 | (2006.01) | |
| C07H 19/23 | (2006.01) | |
| A61K 31/7064 | (2006.01) | |
| C07H 19/24 | (2006.01) | |
| C07H 19/16 | (2006.01) | |

(52) U.S. Cl.
CPC ......... C07H 19/14 (2013.01); A61K 31/7064 (2013.01); C07H 19/16 (2013.01); C07H 19/23 (2013.01); C07H 19/24 (2013.01)

(58) Field of Classification Search
CPC ......... C07H 19/14; C07H 19/16; C07H 19/24
See application file for complete search history.

(56) References Cited

U.S. PATENT DOCUMENTS

| | | | | |
|---|---|---|---|---|
| 5,646,128 A * | 7/1997 | Firestein | ................ | A61K 31/00 514/45 |
| 5,795,977 A * | 8/1998 | Ugarkar | ................ | A61K 31/00 536/27.1 |
| 5,864,033 A * | 1/1999 | Browne | ................ | A61K 31/00 536/27.1 |
| 6,106,864 A | 8/2000 | Dolan et al. | | |
| 6,492,348 B1 | 12/2002 | Bays et al. | | |
| 6,677,316 B2 * | 1/2004 | Bays | ................ | C07H 19/16 514/263.23 |
| 6,831,069 B2 * | 12/2004 | Tam | ................ | A61K 31/70 514/43 |
| 7,022,681 B2 * | 4/2006 | Zablocki | ................ | C07H 19/16 514/46 |
| 8,575,119 B2 * | 11/2013 | Wang | ................ | C07H 19/12 514/43 |
| 9,416,154 B2 * | 8/2016 | Verma | ................ | C07H 19/14 |
| 9,701,706 B2 * | 7/2017 | Bougher, III | ................ | C07H 19/14 |
| 9,708,359 B2 * | 7/2017 | Bougher, III | ................ | C07H 19/14 |
| 9,840,532 B2 * | 12/2017 | Cortez | ................ | C07H 19/14 |
| 2004/0043960 A1 | 3/2004 | Zablocki et al. | | |
| 2012/0077814 A1 | 3/2012 | Wang et al. | | |

FOREIGN PATENT DOCUMENTS

| | | |
|---|---|---|
| WO | 9111172 | 8/1991 |
| WO | 9402518 | 2/1994 |
| WO | 9855148 | 12/1998 |
| WO | 0035298 | 6/2000 |
| WO | 2015200680 A2 | 6/2015 |

OTHER PUBLICATIONS

Cheng et al., "Small Molecule Regulators of Protein Arginine Methyltransferases*", The Journal of Biological Chemistry, 279, 23, 23892-23899, 2004.
Devkota et al., "Analogues of the Natural Product Sinefungin as Inhibitors of EHMT1 and EHMT2", ACS Medicinal Chemistry Letters, 5, 293-297, 2014.
Haren et al., "Synthesis and evaluation of protein arginine N-methyltransferase inhibitors designed to simultaneously occupy both substrate binding sites", Organic and Biomolecular Chemistry, 13, 549-560, 2015.
Kumar et al., "Activation and inhibition of DNA methyltransferases by S-adenosyl-L-homocysteine analogues", Bioorganic & Medicinal Chemistry, 16, 2276-2285, 2008.
Kung et al., "Design, synthesis, and biological evaluation of novel human d'-deoxy-5'-methylthioadenosine phosphorylase (MTAP) substrates", Bioorganic & Medicinal Chemistry Letters, 15, 2829-2833, 2005.

(Continued)

Primary Examiner — Eric Olson
(74) Attorney, Agent, or Firm — David Rubin

(57) ABSTRACT

Compounds such as:

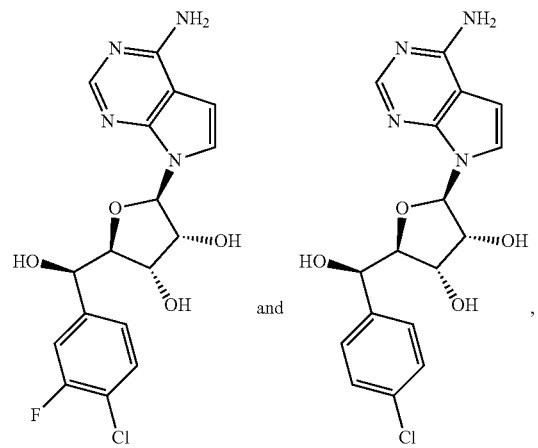

processes for the preparation of these compounds, compositions containing these compounds, and the uses of these compounds to treat neoplasms have been disclosed.

3 Claims, No Drawings

Specification includes a Sequence Listing.

(56) References Cited

OTHER PUBLICATIONS

Muller et al., "Recent developments in adenosine receptor ligands and their potential as novel drugs", Biochimica et Biophysica Acta, 1808, 1290-1308, 2011.
Smil, et al., "Discovery of a Dual PRMT5-PRMT7 Inhibitor", ACS Medicinal Chemistry Letters, 6, 408-412, 2015.
Tilburg et al., "5'-O-Alkyl Ethers of N,2-Substituted Adenosine Derivatives: Partial Agonists for the Adenosine A1 and A3 Receptors", J. Med. Chem. 44, 2966-2975, 2001.
International Search Report and the Written Opinion of the International Searching Authority, PCT/IB2016/050803 dated May 23, 2016.
Aggarwal, "Nuclear Cyclin D1/CDK4 Kinase Regulates CUL4 Expression and Triggers Neoplastic Growth via Activation of the PRMT5 Methyltransferase", Cancer Cell, 18, 329-340, 2010.
Baker, "Dipeptide Isosteres. 1. Synthesis of Dihydroxyethylene Dipeptide Isosteres via Diastereoselective Additions of Alkyllithium Reagents to N,N-Dimethylhydrazones. Preparation of Renin and HIV-1 Protease Inhibitor Transition-State Mimics", J. Org. Chem., 58, 3277-3284, 1993.
Bandyopadhyay, "HOXA9 Methylation by PRMT5 Is Essential for Endothelial Cell Expression of Leukocyte Adhesion Molecules", Molecular and Cellular Biology, 32, 7, 1202-1213, 2012.
Bao, "Overexpression of PRMT5 Promotes Tumor Cell Growth and Is Associates with Poor Disease Prognosis in Epithelial Ovarian Cancer", Journal of Histochemisty & Cytochemistry, 61(3), 206-217, 2013.
Bligh, "Preparation of Both C5' Epimers of 5'-C-Methyladenosine: Reagent Control Trumps Substrate Control", The Journal of Organic Chemistry, 79, 3238-3243, 2014.
Chan, "A Versatile and Stereospecific Synthesis of a Dihydroxyethylene Dipeptide Isostere of Renin Inhibitors From D-Ribose", Tetrahedron Letters, 33, 25, 3567-3570, 1992.
Cho, "Arginine Methylation Controls Growth Regulation by E2F-1", The EMBO Journal, 31, 1785-1797, 2012.
Cohen, "Enantiospecific Synthesis of Leukotrienes C4, D4, and E4 and [14,15-3H2]Leukotrine E4 Dimethyl Ester", J. Chem. Soc., 105, 3661-3672, 1983.
Coward, "Analogs of S-Adenosylhomocysteine as Potential Inhibitors of Biological Transmethylation. Inhibitions of Serveral Methylases by S-Tubercidinylhomocysteine", Journal of Medicinal Chemistry, 17, 12, 1286-1289, 1974.
Finnin, "Transdermal Penetration Enhancers: Applications, Limitations, and Potential", Journal of Pharmaceutical Sciences, 88, 10, 955-958, 1999.
Gu, "Protein arginine methyltransferase 5 is essential for growth of lung cancer cells", Biochem J., 446, 235-241, 2012.
Gu, "Protein Arginine Methyltransferase 5 Functions in Opposite Ways in the Cytoplasm and Nucleus of Prostate Cancer Cells", PLOS One, 7, 8, e44033, 1-13, 2012.
Haleblian, "Characterization of Habits and Crystalline Modification of Solids and Their Pharmaceutical Applications", Journal of Pharmaceutical Sciences, 64, 8, 1269-1288, 1975.
Jansson, "Arginine methylation regulates the p53 response", Nature Cell Biology, 10, 12, 1431-1449, 2008.
Karkhanis, "Versatility of PRMT5-induced methylation in growth control and development", Trends in Biochemical Sciences 36, 12, 633-641, 2011.
Kim, "Identification of Gastric Cancer-related Genes Using a cDNA Microarray Containing Novel Expressed Sequence Tags Expressed in Gastric Cancer Cells", Clinical Cancer Research, 11, 473-482, 2005.
Leadbeater, "A Weinreb amide approach to the synthesis of trifluoromethylketones", Chem Comm, 48, 9610-9612, 2012.
Meyer, "Tethering Small Molecules to a Phage Display Library: Discovery of a Selective Bivalent Inhibitor of Protein Kinase A", J. Am. Chem. Soc., 129, 13812-13813, 2007.
More, "A Simple and Advantageous Protocol for the Oxidation of Alcohols with o-Iodoxybenzoic Acid (IBX)", Organic Letters 4, 17, 3001-3003 2002.
Naus, "Synthesis, Cytostatic, Antimicrobial, and Anti-HCV Activity of 6-Substituted 7-(Het)aryl-7-deazapurine Ribonucleosides", Journal of Medicinal Chemistry, 57, 1097-1110, 2014.
Nicholas, "PRMT5 Is Upregulated in Malignant and Metastatic Melanoma and Regulates Expression of MITF and p27Kip1", PLOS One, 8, 9, e74710, 1-9, 2013.
Powers, "Protein Arginine Methyltransferase 5 Accelerates Tumor Growth by Arginine Methylation of the Tumor Suppressor Programmed Cell Death 4", Cancer Research, 71(16), 5579-87, 2011.
Rajanbabu, "Stereoselective Cyclization of Enynes Mediated by Metallocene Reagents", J. Am. Chem. Soc., 110, 7128-7135, 1988.
Rodenko, "Solid phase synthesis and antiprotozoal evaluation of di- and trisubstituted 5'-carboxamidoadenosine analogues", Bioorganic & Medicinal Chemistry, 14, 1618-1629, 2006.
Rosen, "Synthetic and Biological Studies of Compactin and Related Compounds. 2. Synthesis of the Lactone Moiety of Compactin1", J. Org. Chem., 49, 3994-4003, 1984.
Shin, "Emissive RNA Alphabet", J. Am. Chem. Soc., 133, 14912-14915, 2011.
Singleton, "Synthesis of 2,3-Dihydroxyhex-4-enoates by Palladium-Catalyzed Allylic Alkylations of Carbohydrate Derived Vinyl Lactones", Synthesis, 22, 3682-3686, 2008.
Thiyagarajan, "Structure based medicinal chemistry approach to develop 4-methyl-7-deazaadenine carbocyclic nucleosides as anti-HCV agent", Bioorganic & Medicinal Chemistry Letters, 22, 7742-7747, 2012.
Ting, "Synthesis of diastereomeric, deoxy and ring-expanded sulfone analogues of aigialomycin D", Tetrahedron, 69, 2013, 10581-10592, 2013.
Verma, "Drug Delivery Technologies and Future Directions", Pharmaceutical Technology On-Line, 25(2), 1-14, 2001.
Wang, "Protein Arginine Methyltransferase 5 Suppresses the Transcription of the RB Family of Tumor Suppressors in Leukemia and Lymphoma Cells", Molecular & Cellular Biology, 28, 20, 6262-6277, 2008.
Wei, "PRMT5 dimethylates R30 of the p65 subunit to activate NF-kB", PNAS, 110, 33, 13516-13521, 2013.
Zheng, "Arginine Methylation-Dependent Reader-Writer Interplay Governs Growth Control by E2F-1", Molecular Cell, 52, 37-51, 2013.
Stopa et al., "The PRMT5 arginine methyltransferase: many roles in development, cancer and beyond", Cell. Mol. Life Sci., (2015), 72:2041-2059.
Mundade et al., "PRMT5, A Pivotal Player in Cancer", Austin J. Pharmacol. Ther., (2014), 2(2), 4.
Wang et al., "Protein Arginine Methyltransferase 5 Catalyzes Substrate Dimethylation in a Distributive Fashion", Biochemistry, (2014), 53, 7884-7892.
Zhang et al., "Transcriptional activation of PRMT5 by NF-Y is required for cell growth and negatively regulated by the PKC/c-FOS signaling in prostate", Biochimica et Biophysica Acta, (2014), 1839, 1330-1340.

* cited by examiner

SUBSTITUTED NUCLEOSIDE DERIVATIVES USEFUL AS ANTICANCER AGENTS

REFERENCE TO SEQUENCE LISTING

This application is being filed electronically via EFS-Web and includes an electrically submitted sequence listing in .txt format. The .txt file contains a sequence listing entitled "PC72171A_SequenceListing_ST25.txt" created on Mar. 11, 2016, and having a size of 9 KB. The sequence listing contained in this .txt file is part of the specification and is herein incorporated by reference in its entireity.

FIELD OF THE INVENTION

This invention relates to novel nucleoside derivatives useful in the treatment of abnormal cell growth, such cancer, in mammals. This invention also relates to a method of using such compounds in the treatment of abnormal cell growth in mammals, especially humans, and to pharmaceutical compositions as anticancer agents.

BACKGROUND OF THE INVENTION

Post-translational modification of arginine residues by methylation is important for many critical cellular processes including chromatin remodeling, gene transcription, protein translation, signal transduction, RNA splicing and cell proliferation. Arginine methylation is catalyzed by protein arginine methyltransferase (PRMT) enzymes. There are nine PRMT members in all, and eight have reported enzymatic activity on target substrates.

The protein arginine methyltransferase (PRMT) family of enzymes utilize S-adenosyl methionine (SAM) to transfer methyl groups to arginine residues on target proteins. Type I PRMTs catalyze formation of mono-methyl arginine and asymmetric di-methyl arginines while Type II PRMTs catalyze mono-methyl arginine and symmetric di-methyl arginines. PRMT5 is a Type II enzyme, twice transferring a methyl group from SAM to the two ω-guanidino nitrogen atoms of arginine, leading to ω-NG, N'G di-symmetric methylation of protein substrates.

PRMT5 protein is found in both the nucleus and cytoplasm, and has multiple protein substrates such as histones, transcription factors and spliceosome proteins. PRMT5 has a binding partner, Mep50 (methylosome protein 50) and functions in multiple protein complexes. PRMT5 is associated with chromatin remodeling complexes (SWI/SNF, NuRD) and epigenetically controls genes involved in development, cell proliferation, and differentiation, including tumor suppressors, through methylation of histones (Karkhanis, V. et al., Versatility of PRMT5 Induced Methylation in Growth Control and Development, *Trends Biochem Sci* 36(12) 633-641 (2011)). PRMT5 also controls gene expression through association with protein complexes that recruit PRMT5 to methylate several transcription factors p53 (Jansson, M. et al., Arginine Methylation Regulates the p53 Response, *Nat. Cell Biol.* 10, 1431-1439 (2008)); E2F1 (Zheng, S. et al., Arginine Methylation-Dependent Reader-Writer Interplay Governs Growth Control by E2F-1, *Mol Cell* 52(1), 37-51 (2013)); HOXA9 (Bandyopadhyay, S. et al., HOXA9 Methylation by PRMT5 is Essential for Endothelial Cell Expression of Leukocyte Adhesion Molecules, *Mol. Cell. Biol.* 32(7):1202-1213 (2012)); and NFκB (Wei, H. et al., PRMT5 dimethylates $R^{30}$ of the p65 Subunit to Activate NFκB, *PNAS* 110(33), 13516-13521 (2013)). In the cytoplasm, PRMT5 has a diverse set of substrates involved in other cellular functions including RNA splicing (Sm proteins), golgi assembly (gm130), ribosome biogenesis (RPS10), piRNA mediated gene silencing (Piwi proteins) and EGFR signaling (Karkhanis, 2011).

Additional papers relating to PRMT5 include: Aggarwal, P. et al., (2010) Nuclear Cyclin D1/CDK4 Kinase Regulates CUL4B Expression and Triggers Neoplastic Growth via Activation of the PRMT5 Methyltransferase, *Cancer Cell* 18: 329-340; Bao, X. et al., Overexpression of PRMT5 Promotes Tumor Cell Growth and is Associated with Poor Disease Prognosis in Epithelial Ovarian Cancer, *J Histochem Cytochem* 61: 206-217 (2013); Cho E. et al., Arginine Methylation Controls Growth Regulation by E2F1, *EMBO J.* 31(7) 1785-1797 (2012); Gu, Z. et al., Protein Arginine Methyltransferase 5 Functions in Opposite Ways in the Cytoplasm and Nucleus of Prostate Cancer Cells, *PLoS One* 7(8) e44033 (2012); Gu, Z. et al., Protein Arginine Methyltransferase 5 is Essential for Growth of Lung Cancer Cells, *Biochem J.* 446: 235-241 (2012); Kim, J. et al., Identification of Gastric Cancer Related Genes Using a cDNA Microarray Containing Novel Expressed Sequence Tags Expressed in Gastric Cancer Cells, *Clin Cancer Res.* 11(2) 473-482 (2005); Nicholas, C. et al., PRMT5 is Upregulated in Malignant and Metastatic Melanoma and Regulates Expression of MITF and p27(Kip1), *PLoS One* 8(9) e74710 (2012); Powers, M. et al., Protein Arginine Methyltransferase 5 Accelerates Tumor Growth by Arginine Methylation of the Tumor Suppressor Programmed Cell Death 4, *Cancer Res.* 71(16) 5579-5587 (2011); Wang, L. et al., Protein Arginine Methyltransferase 5 Suppresses the Transcription of the RB Family of Tumor Suppressors in Leukemia and Lymphoma Cells, *Mol. Cell Biol.* 28(20), 6262-6277 (2008).

PRMT5 is overexpressed in many cancers and has been observed in patient samples and cell lines including B-cell lymphoma and leukemia (Wang, 2008) and the following solid tumors: gastric (Kim 2005) esophageal (Aggarwal, 2010), breast (Powers, 2011), lung (Gu, 2012), prostate (Gu, 2012), melanoma (Nicholas 2012), colon (Cho, 2012) and ovarian (Bao, 2013). In many of these cancers, overexpression of PRMT5 correlated with poor prognosis. Aberrant arginine methylation of PRMT5 substrates has been linked to other indications in addition to cancer, such as metabolic disorders, inflammatory and autoimmune disease and hemaglobinopathies.

SUMMARY OF THE INVENTION

Given its role in regulating various biological processes, PRMT5 is an attractive target for modulation with small molecule inhibitors. To date, few effective PRMT5 inhibitors have been developed, and no PRMT5 inhibitors have entered the clinic.

Each of the embodiments of the compounds of the present invention described below can be combined with any other embodiment of the compounds of the present invention described herein not inconsistent with the embodiment with which it is combined. Furthermore, each of the embodiments below describing the invention envisions within its scope pharmaceutically acceptable salts of the compounds of the invention. Accordingly, the phrase "or a pharmaceutically acceptable salt thereof" is implicit in the description of all compounds described herein.

The invention includes embodiments wherein there is provided a compound of formula (I):

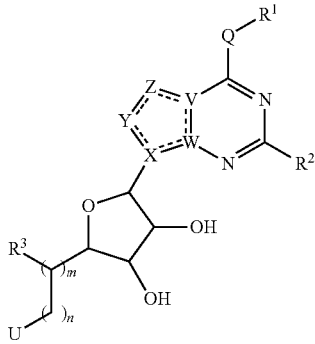

or a pharmaceutically acceptable salt thereof, wherein:

$R^1$ is selected from the group consisting of $(C_1-C_8)$alkyl, $(C_1-C_8)$haloalkyl, hydroxy, $(C_1-C_8)$alkoxy, $(C_5-C_{12})$aryl, 5-12 membered heteroaryl, $(C_3-C_{10})$cycloalkyl, 3-12 membered heterocyclyl, $OR^4$, $SR^4$ and $N(R^4)_2$, where each $R^4$ is independently $A-R^{14}$, where A is absent, $(C_1-C_3)$alkyl, —C(O)— or —SO$_2$—, and $R^{14}$ is hydrogen, $(C_1-C_8)$alkyl, $(C_5-C_{12})$aryl, 5-12 membered heteroaryl, $(C_3-C_{10})$cycloalkyl or 3-12 membered heterocyclyl, or two $R^4$ join to form a 4-6 membered heterocyclic ring containing 1-3 heteroatoms selected from N, O and S;

$R^2$ is hydrogen, halogen, $(C_1-C_8)$alkyl, hydroxy, $(C_1-C_8)$alkoxy or $N(R^5)_2$, where each $R^5$ is independently hydrogen or $(C_1-C_8)$alkyl, or two $R^5$ join to form a 4-6 membered heterocyclic ring containing 1-3 heteroatoms selected from N, O and S;

$R^3$ is hydrogen, hydroxy or $NH_2$, or $R^3$ is absent if m is 0;

Q is absent or is a divalent moiety selected from O, S, NH and $(C_1-C_8)$alkylene;

U is selected from the group consisting of $OR^6$, $SR^6$, $N(R^6)_2$, $(C_1-C_8)$alkyl-$N(R^6)_2$, $(C_5-C_{12})$aryl, 5-12 membered heteroaryl, $(C_3-C_{10})$cycloalkyl, 3-12 membered heterocyclyl, $(C_1-C_8)$alkyl, $(C_1-C_8)$heteroalkyl and $(C_1-C_8)$haloalkyl, where U is not CH$_2$-hydroxy if m+n=0, and where U is not hydroxy if m+n=1 and $R^3$ is hydrogen, where U is optionally substituted with one or more substituents each independently selected from $(C_1-C_8)$alkyl, $(C_1-C_8)$alkyl-N$(R^6)_2$, $O(C_2-C_8)$alkyl-$N(R^6)_2$, $(C_1-C_8)$haloalkyl, hydroxy, $(C_1-C_8)$alkoxy, halogen, $(C_5-C_{12})$aryl, 5-12 membered heteroaryl, $(C_3-C_{10})$cycloalkyl, 3-12 membered heterocyclyl, $OR^6$, $N(R^6)_2$ and $SO_2R^6$, and where each $R^6$ is independently hydrogen, $(C_1-C_8)$alkyl, $(C_1-C_8)$alkyl-$N(R^7)_2$ where each $R^7$ is hydrogen or $(C_1-C_8)$alkyl, $(C_5-C_{12})$aryl, 5-12 membered heteroaryl, $(C_3-C_{10})$cycloalkyl or 3-12 membered heterocyclyl, or two $R^6$ join to form a 4-6 membered heterocyclic ring containing 1-3 heteroatoms selected from N, O and S;

V is N or C, where if V forms a double bond V is carbon;
W is N or C, where if W forms a double bond W is carbon;
X is N or C where if X forms a double bond X is carbon;
Y is $CR^{10}$, N, $NR^{10}$, O or S, where each $R^{10}$ is independently selected from hydrogen, $(C_1-C_8)$alkyl, hydroxy, $(C_1-C_8)$alkoxy, halogen, SH, S—$(C_1-C_8)$alkyl and $N(R^{11})_2$ if Y is $CR^{10}$, where Y forms a double with an adjacent ring member when Y is $CR^{10}$ or N, and where each $R^{11}$ is independently hydrogen, $(C_1-C_8)$alkyl, $(C_5-C_{12})$aryl or 5-12 membered heteroaryl or two $R^{11}$ join to form a 4-6 membered heterocyclic ring containing 1-3 heteroatoms selected from N, O and S, or Y is $C(R^{10})_2$ and the two $R^{10}$ and the carbon to which they are associated form a carbonyl or a thiocarbonyl;

Z is $CR^{12}$, N, $NR^{12}$, O or S, where each $R^{12}$ is independently selected from hydrogen, $(C_1-C_8)$alkyl, hydroxy, $(C_1-C_8)$alkoxy, fluoro, chloro, bromo, SH, S—$(C_1-C_8)$alkyl and $N(R^{13})_2$, where Z forms a double bond with an adjacent ring member if it is $CR^{12}$ or N, where each $R^{13}$ is independently hydrogen, $(C_1-C_8)$alkyl, $(C_5-C_{12})$aryl or 5-12 membered heteroaryl, or two $R^{13}$ join to form a 4-6 membered heterocyclic ring containing 1-3 heteroatoms selected from N, O and S, and where Z is not $NR^{12}$ if X is N, V is C, W is C and Y is $CR^{10}$, or Z is $C(R^{12})_2$ and the two $R^{12}$ and the carbon to which they are associated form a carbonyl or a thiocarbonyl;

each ----- is an optional bond, where no more than two non-adjacent ----- may be present;
m is 0-1; and
n is 0-1.

The invention also provides a compound of formula (I):

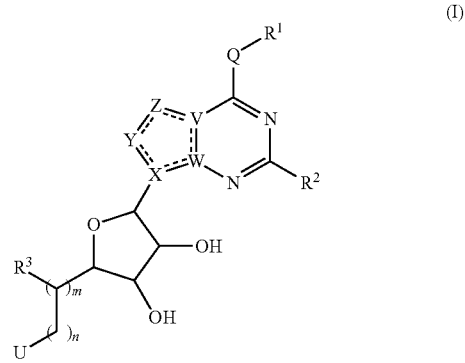

or a pharmaceutically acceptable salt thereof, wherein:

$R^1$ is selected from the group consisting of $(C_1-C_8)$alkyl, $(C_1-C_8)$haloalkyl, hydroxy, $(C_1-C_8)$alkoxy, $(C_5-C_{12})$aryl, 5-12 membered heteroaryl, $(C_3-C_{10})$cycloalkyl, 3-12 membered heterocyclyl, $OR^4$, $SR^4$ and $N(R^4)_2$, where each $R^4$ is independently $A-R^{14}$, where A is absent, $(C_1-C_3)$alkyl, —C(O)— or —SO$_2$—, and $R^{14}$ is hydrogen, $(C_1-C_8)$alkyl, $(C_5-C_{12})$aryl, 5-12 membered heteroaryl, $(C_3-C_{10})$cycloalkyl or 3-12 membered heterocyclyl, or two $R^4$ join to form a 4-6 membered heterocyclic ring containing 1-3 heteroatoms selected from N, O and S;

$R^2$ is hydrogen, halogen, $(C_1-C_8)$alkyl, hydroxy, $(C_1-C_8)$alkoxy or $N(R^5)_2$, where each $R^5$ is independently hydrogen or $(C_1-C_8)$alkyl, or two $R^5$ join to form a 4-6 membered heterocyclic ring containing 1-3 heteroatoms selected from N, O and S;

$R^3$ is hydrogen, hydroxy or $NH_2$, or $R^3$ is absent if m is 0;

Q is absent or is a divalent moiety selected from O, S, NH and $(C_1-C_8)$alkylene;

U is selected from the group consisting of $OR^6$, $SR^6$, $N(R^6)_2$, $(C_1-C_8)$alkyl-$N(R^6)_2$, $(C_5-C_{12})$aryl, 5-12 membered heteroaryl, $(C_3-C_{10})$cycloalkyl, 3-12 membered heterocyclyl, $(C_1-C_8)$alkyl, $(C_1-C_8)$heteroalkyl and $(C_1-C_8)$haloalkyl, where U is not CH$_2$-hydroxy if m+n=0, and where U is not hydroxy if m+n=1 and $R^3$ is hydrogen, where U is optionally substituted with one or more substituents each independently selected from $(C_1-C_8)$alkyl, $(C_1-C_8)$alkyl-N$(R^6)_2$, $O(C_2-C_8)$alkyl-$N(R^6)_2$, $(C_1-C_8)$haloalkyl, hydroxy, $(C_1-C_8)$alkoxy, halogen, $(C_5-C_{12})$aryl, 5-12 membered heteroaryl, $(C_3-C_{10})$cycloalkyl, 3-12 membered heterocyclyl, OR⁶, N(R⁶)₂ and SO₂R⁶, and where each R⁶ is independently hydrogen, $(C_1-C_8)$alkyl, $(C_1-C_8)$alkyl-N(R⁷)₂ where each R⁷ is hydrogen or $(C_1-C_8)$alkyl, $(C_5-C_{12})$aryl, 5-12 membered heteroaryl, $(C_3-C_{10})$cycloalkyl or 3-12 membered heterocyclyl, or two R⁶ join to form a 4-6 membered heterocyclic ring containing 1-3 heteroatoms selected from N, O and S, where if -Q-R¹ is NH₂ or H,

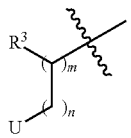

is not —CH₂—SH, —CH₂—S—$(C_1-C_8$ alkyl), —CH₂—NH₂, —CH₂(H)$(C_1-C_8$alkyl or —CH₂—$(C_1-C_8$ alkyl)₂;

V is N or C, where if V forms a double bond V is carbon;
W is N or C, where if W forms a double bond W is carbon;
X is N or C where if X forms a double bond X is carbon;
Y is CR¹⁰, N, NR¹⁰, O or S, where each R¹⁰ is independently selected from hydrogen, $(C_1-C_8)$alkyl, hydroxy, $(C_1-C_8)$alkoxy, halogen, SH, S—$(C_1-C_8)$alkyl and N(R¹¹)₂ if Y is CR¹⁰, where Y forms a double with an adjacent ring member when Y is CR¹⁰ or N, and where each R¹¹ is independently hydrogen, $(C_1-C_8)$alkyl, $(C_5-C_{12})$aryl or 5-12 membered heteroaryl or two R¹¹ join to form a 4-6 membered heterocyclic ring containing 1-3 heteroatoms selected from N, O and S, or Y is C(R¹⁰)₂ and the two R¹⁰ and the carbon to which they are associated form a carbonyl or a thiocarbonyl;
Z is CR¹², N, NR¹², O or S, where each R¹² is independently selected from hydrogen, $(C_1-C_8)$alkyl, hydroxy, $(C_1-C_8)$alkoxy, fluoro, chloro, bromo, SH, S—$(C_1-C_8)$alkyl and N(R¹³)₂, where Z forms a double bond with an adjacent ring member if it is CR¹² or N, where each R¹³ is independently hydrogen, $(C_1-C_8)$alkyl, $(C_5-C_{12})$aryl or 5-12 membered heteroaryl, or two R¹³ join to form a 4-6 membered heterocyclic ring containing 1-3 heteroatoms selected from N, O and S, and where Z is not NR¹² if X is N, V is C, W is C and Y is CR¹⁰, or Z is C(R¹²)₂ and the two R¹² and the carbon to which they are associated form a carbonyl or a thiocarbonyl;
each ----- is an optional bond, where no more than two non-adjacent ----- may be present;
m is 0-1; and
n is 0-1.

The invention further provides a compound of formula (I):

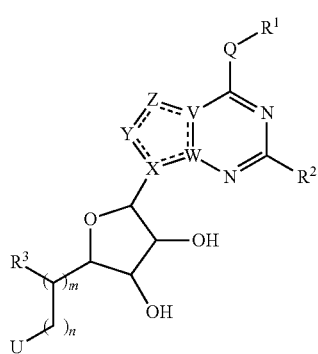

or a pharmaceutically acceptable salt thereof, wherein:

R¹ is selected from the group consisting of $(C_1-C_8)$alkyl, $(C_1-C_8)$haloalkyl, hydroxy, $(C_1-C_8)$alkoxy, $(C_5-C_{12})$aryl, 5-12 membered heteroaryl, $(C_3-C_{10})$cycloalkyl, 3-12 membered heterocyclyl, OR⁴, SR⁴ and N(R⁴)₂, where each R⁴ is independently A-R¹⁴, where A is absent, $(C_1-C_3)$alkyl, —C(O)— or —SO₂—, and R¹⁴ is hydrogen, $(C_1-C_5)$alkyl, $(C_5-C_{12})$aryl, 5-12 membered heteroaryl, $(C_3-C_{10})$cycloalkyl or 3-12 membered heterocyclyl, or two R⁴ join to form a 4-6 membered heterocyclic ring containing 1-3 heteroatoms selected from N, O and S;

R² is hydrogen, halogen, $(C_1-C_5)$alkyl, hydroxy, $(C_1-C_5)$alkoxy or N(R⁵)₂, where each R⁵ is independently hydrogen or $(C_1-C_5)$alkyl, or two R⁵ join to form a 4-6 membered heterocyclic ring containing 1-3 heteroatoms selected from N, O and S;

R³ is hydrogen, hydroxy or NH₂, or R³ is absent if m is 0;

Q is absent or is a divalent moiety selected from O, S, NH and $(C_1-C_5)$alkylene;

U is selected from the group consisting of OR⁶, $(C_1-C_8)$alkyl-N(R⁶)₂, $(C_5-C_{12})$aryl, 5-12 membered heteroaryl, $(C_3-C_{10})$cycloalkyl, 3-12 membered heterocyclyl, $(C_1-C_8)$alkyl, $(C_1-C_8)$heteroalkyl and $(C_1-C_8)$haloalkyl, where U is not CH₂-hydroxy if m+n=0, and where U is not hydroxy if m+n=1 and R³ is hydrogen, where U is optionally substituted with one or more substituents each independently selected from $(C_1-C_8)$alkyl, $(C_1-C_8)$alkyl-N(R⁶)₂, O$(C_2-C_8)$alkyl-N(R⁶)₂, $(C_1-C_8)$haloalkyl, hydroxy, $(C_1-C_8)$alkoxy, halogen, $(C_5-C_{12})$aryl, 5-12 membered heteroaryl, $(C_3-C_{10})$cycloalkyl, 3-12 membered heterocyclyl, OR⁶, N(R⁶)₂ and SO₂R⁶, and where each R⁶ is independently hydrogen, $(C_1-C_8)$alkyl, $(C_1-C_8)$alkyl-N(R⁷)₂ where each R⁷ is hydrogen or $(C_1-C_8)$alkyl, $(C_5-C_{12})$aryl, 5-12 membered heteroaryl, $(C_3-C_{10})$cycloalkyl or 3-12 membered heterocyclyl, or two R⁶ join to form a 4-6 membered heterocyclic ring containing 1-3 heteroatoms selected from N, O and S;

V is N or C, where if V forms a double bond V is carbon;
W is N or C, where if W forms a double bond W is carbon;
X is N or C where if X forms a double bond X is carbon;
Y is CR¹⁰, N, NR¹⁰, O or S, where each R¹⁰ is independently selected from hydrogen, $(C_1-C_8)$alkyl, hydroxy, $(C_1-C_8)$alkoxy, halogen, SH, S—$(C_1-C_8)$alkyl and N(R¹¹)₂ if Y is CR¹⁰, where Y forms a double with an adjacent ring member when Y is CR¹⁰ or N, and where each R¹¹ is independently hydrogen, $(C_1-C_8)$alkyl, $(C_5-C_{12})$aryl or 5-12 membered heteroaryl or two R¹¹ join to form a 4-6 membered heterocyclic ring containing 1-3 heteroatoms selected from N, O and S, or Y is C(R¹⁰)₂ and the two R¹⁰ and the carbon to which they are associated form a carbonyl or a thiocarbonyl;
Z is CR¹², N, NR¹², O or S, where each R¹² is independently selected from hydrogen, $(C_1-C_8)$alkyl, hydroxy, $(C_1-C_8)$alkoxy, fluoro, chloro, bromo, SH, S—$(C_1-C_8)$alkyl and N(R¹³)₂, where Z forms a double bond with an adjacent ring member if it is CR¹² or N, where each R¹³ is independently hydrogen, $(C_1-C_8)$alkyl, $(C_5-C_{12})$aryl or 5-12 membered heteroaryl, or two R¹³ join to form a 4-6 membered heterocyclic ring containing 1-3 heteroatoms selected from N, O and S, and where Z is not NR¹² if X is N, V is C, W is C and Y is CR¹⁰, or Z is C(R¹²)₂ and the two R¹² and the carbon to which they are associated form a carbonyl or a thiocarbonyl;
each ----- is an optional bond, where no more than two non-adjacent ----- may be present;
m is 0-1; and
n is 0-1.

Additionally, the instant invention provides a compound of formula (I):

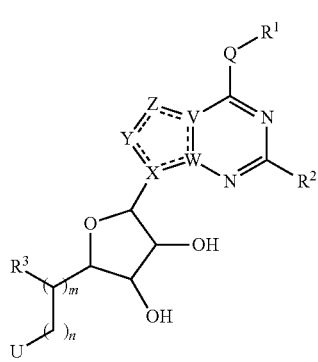
(I)

or a pharmaceutically acceptable salt thereof, wherein:

$R^1$ is selected from the group consisting of $(C_1-C_8)$alkyl, $(C_1-C_8)$haloalkyl, hydroxy, $(C_1-C_8)$alkoxy, $(C_5-C_{12})$aryl, 5-12 membered heteroaryl, $(C_3-C_{10})$cycloalkyl, 3-12 membered heterocyclyl, $OR^4$, $SR^4$ and $N(R^4)_2$, where each $R^4$ is independently $A-R^{14}$, where A is absent, $(C_1-C_3)$alkyl, —C(O)— or —SO$_2$—, and $R^{14}$ is hydrogen, $(C_1-C_8)$alkyl, $(C_5-C_{12})$aryl, 5-12 membered heteroaryl, $(C_3-C_{10})$cycloalkyl or 3-12 membered heterocyclyl, or two $R^4$ join to form a 4-6 membered heterocyclic ring containing 1-3 heteroatoms selected from N, O and S;

$R^2$ is hydrogen, $(C_1-C_8)$alkyl or $N(R^5)_2$, where each $R^5$ is independently hydrogen or $(C_1-C_8)$alkyl, or two $R^5$ join to form a 4-6 membered heterocyclic ring containing 1-3 heteroatoms selected from N, O and S;

$R^3$ is hydrogen, hydroxy or $NH_2$, or $R^3$ is absent if m is 0;

Q is absent or is a divalent moiety selected from O, S, NH and $(C_1-C_8)$alkylene;

U is $(C_5-C_{12})$aryl or 5-12 membered heteroaryl, where U is optionally substituted with one or more substituents each independently selected from $(C_1-C_8)$alkyl, $(C_1-C_8)$alkyl-N$(R^6)_2$, $O(C_2-C_8)$alkyl-N$(R^6)_2$, $(C_1-C_8)$haloalkyl, hydroxy, $(C_1-C_8)$alkoxy, halogen, $(C_5-C_{12})$aryl, 5-12 membered heteroaryl, $(C_3-C_{10})$cycloalkyl, 3-12 membered heterocyclyl, $OR^6$, $N(R^6)_2$ and $SO_2R^6$, where each $R^6$ is independently hydrogen, $(C_1-C_8)$alkyl, $(C_1-C_8)$alkyl-N$(R^7)_2$ where each $R^7$ is hydrogen or $(C_1-C_8)$alkyl, $(C_5-C_{12})$aryl, 5-12 membered heteroaryl, $(C_3-C_{10})$cycloalkyl or 3-12 membered heterocyclyl, or two $R^6$ join to form a 4-6 membered heterocyclic ring containing 1-3 heteroatoms selected from N, O and S;

V is N or C, where if V forms a double bond V is carbon;

W is N or C, where if W forms a double bond W is carbon;

X is N or C where if X forms a double bond X is carbon;

Y is CH, C(O), C(S), N or $NR^{10}$, where $R^{10}$ is hydrogen, $(C_1-C_8)$alkyl, hydroxy, $(C_1-C_8)$alkoxy, halogen, SH, S—$(C_1-C_8)$alkyl, and where Y forms a double with an adjacent ring member when Y is CH or N;

Z is $CR^{12}$, N, $NR^{12}$ or O, where each $R^{12}$ is hydrogen, $(C_1-C_8)$alkyl or halogen, and where Z forms a double bond with an adjacent ring member if it is $CR^{12}$ or N;

each ----- is an optional bond, where no more than two non-adjacent ----- may be present;

m is 0-1; and n is 0-1.

The invention also provides for a compound of formula (II):

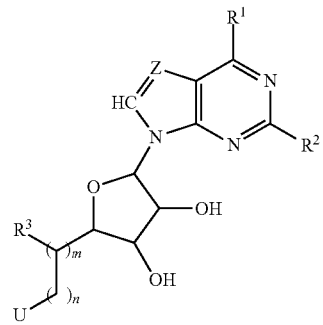
(II)

or a pharmaceutically acceptable salt thereof, wherein:

$R^1$ is selected from the group consisting of $(C_1-C_8)$alkyl, $N(R^4)_2$ or $(C_3-C_{10})$cycloalkyl, where each $R^4$ is independently hydrogen, $(C_1-C_8)$alkyl, $(C_5-C_{12})$aryl or 5-12 membered heteroaryl;

$R^2$ is hydrogen methyl or $NH_2$;

$R^3$ is hydroxy or $NH_2$;

U is $(C_5-C_{12})$aryl or 5-12 membered heteroaryl, where U is optionally substituted with one or more substituents each independently selected from $(C_1-C_8)$alkyl, $(C_1-C_8)$alkyl-N$(R^6)_2$, $O(C_2-C_8)$alkyl-N$(R^6)_2$, $(C_1-C_8)$haloalkyl, hydroxy, $(C_1-C_8)$alkoxy, halogen, $(C_5-C_{12})$aryl, 5-12 membered heteroaryl, $(C_3-C_{10})$cycloalkyl, 3-12 membered heterocyclyl, $OR^6$, $N(R^6)_2$ and $SO_2R^6$, where each $R^6$ is independently hydrogen, $(C_1-C_8)$alkyl, $(C_1-C_8)$alkyl-N$(R^7)_2$ where each $R^7$ is hydrogen or $(C_1-C_8)$alkyl, $(C_5-C_{12})$aryl, 5-12 membered heteroaryl, $(C_3-C_{10})$cycloalkyl or 3-12 membered heterocyclyl, or two $R^6$ join to form a 4-6 membered heterocyclic ring containing 1-3 heteroatoms selected from N, O and S;

Z is $CR^{12}$, where each $R^{12}$ is hydrogen, $(C_1-C_8)$alkyl or halogen;

m is 0-1; and n is 0-1.

In certain embodiments, formula (II) is:

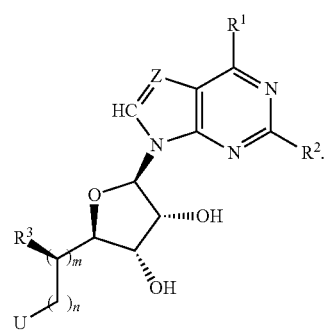

In certain embodiments, formula (II) is:

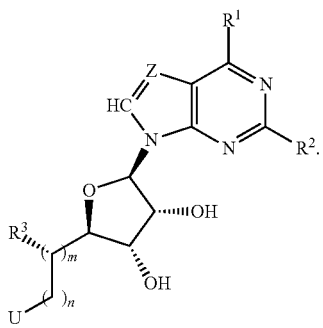

In certain embodiments, formula (II) is:

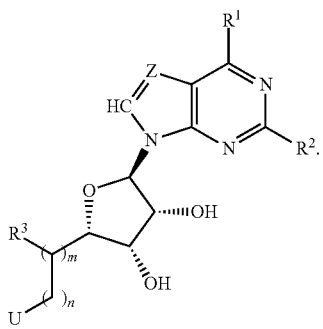

In certain embodiments of the invention there is provided a compound or pharmaceutically acceptable salt of formula I wherein $R^1$ is $NH_2$, Z is CF, $R^2$ is hydrogen, $R^3$ is hydroxy, m is 1 and n is 0.

In certain embodiments of the invention there is provided a compound or pharmaceutically acceptable salt of formula I wherein $R^1$ is $NH_2$, Z is CH, $R^2$ is hydrogen, $R^3$ is hydroxy, m is 1 and n is 0.

In certain embodiments of the invention there is provided a compound or pharmaceutically acceptable salt of formula I wherein $R^1$ is $CH_3$, Z is CH, $R^2$ is hydrogen, $R^3$ is hydroxy, m is 1 and n is 0.

In certain embodiments of the invention there is provided a compound or pharmaceutically acceptable salt of formula I wherein $R^1$ is $CH_3$, Z is CF, $R^2$ is hydrogen, $R^3$ is hydroxy, m is 1 and n is 0.

In certain embodiments of the invention there is provided a compound or pharmaceutically acceptable salt of formula I wherein $R^1$ is $CH_3$, Z is CH, $R^2$ is $NH_2$, $R^3$ is hydroxy, m is 1 and n is 0.

In certain embodiments of the invention there is provided a compound or pharmaceutically acceptable salt of formula I wherein $R^1$ is $CH_3$, Z is CH, $R^2$ is $CH_3$, $R^3$ is hydroxy, m is 1 and n is 0.

In certain embodiments of the invention there is provided a compound or pharmaceutically acceptable salt of formula II wherein $R^1$ is $NH_2$, Z is CF, $R^2$ is hydrogen, $R^3$ is hydroxy, m is 1 and n is 0.

In certain embodiments of the invention there is provided a compound or pharmaceutically acceptable salt of formula II wherein $R^1$ is $NH_2$, Z is CH, $R^2$ is hydrogen, $R^3$ is hydroxy, m is 1 and n is 0.

In certain embodiments of the invention there is provided a compound or pharmaceutically acceptable salt of formula II wherein $R^1$ is $CH_3$, Z is CH, $R^2$ is hydrogen, $R^3$ is hydroxy, m is 1 and n is 0.

In certain embodiments of the invention there is provided a compound or pharmaceutically acceptable salt of formula II wherein $R^1$ is $CH_3$, Z is CF, $R^2$ is hydrogen, $R^3$ is hydroxy, m is 1 and n is 0.

In certain embodiments of the invention there is provided a compound or pharmaceutically acceptable salt of formula II wherein $R^1$ is $CH_3$, Z is CH, $R^2$ is $NH_2$, $R^3$ is hydroxy, m is 1 and n is 0.

In certain embodiments of the invention there is provided a compound or pharmaceutically acceptable salt of formula II wherein $R^1$ is $CH_3$, Z is CH, $R^2$ is $CH_3$, $R^3$ is hydroxy, m is 1 and n is 0.

In certain embodiments of the invention there is provided a compound or pharmaceutically acceptable salt of formula III wherein $R^1$ is $NH_2$, Z is CF, $R^2$ is hydrogen, $R^3$ is hydroxy, m is 1 and n is 0.

In certain embodiments of the invention there is provided a compound or pharmaceutically acceptable salt of formula III wherein $R^1$ is $NH_2$, Z is CH, $R^2$ is hydrogen, $R^3$ is hydroxy, m is 1 and n is 0.

In certain embodiments of the invention there is provided a compound or pharmaceutically acceptable salt of formula III wherein $R^1$ is $CH_3$, Z is CH, $R^2$ is hydrogen, $R^3$ is hydroxy, m is 1 and n is 0.

In certain embodiments of the invention there is provided a compound or pharmaceutically acceptable salt of formula III wherein $R^1$ is $CH_3$, Z is CF, $R^2$ is hydrogen, $R^3$ is hydroxy, m is 1 and n is 0.

In certain embodiments of the invention there is provided a compound or pharmaceutically acceptable salt of formula III wherein $R^1$ is $CH_3$, Z is CH, $R^2$ is $NH_2$, $R^3$ is hydroxy, m is 1 and n is 0.

In certain embodiments of the invention there is provided a compound or pharmaceutically acceptable salt of formula III wherein $R^1$ is $CH_3$, Z is CH, $R^2$ is $CH_3$, $R^3$ is hydroxy, m is 1 and n is 0.

In certain embodiments of the invention there is provided a compound or pharmaceutically acceptable salt of formula I wherein U is optionally substituted $(C_5-C_{12})$aryl or 5-12 membered heteroaryl.

In certain embodiments of the invention there is provided a compound or pharmaceutically acceptable salt of formula II wherein U is optionally substituted $(C_5-C_{12})$aryl or 5-12 membered heteroaryl.

The invention further provides for embodiments wherein:

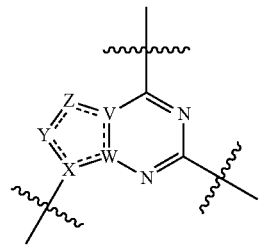

As found in formula I or formula II is selected from:
Additional embodiments of the invention include one of more of the compounds:
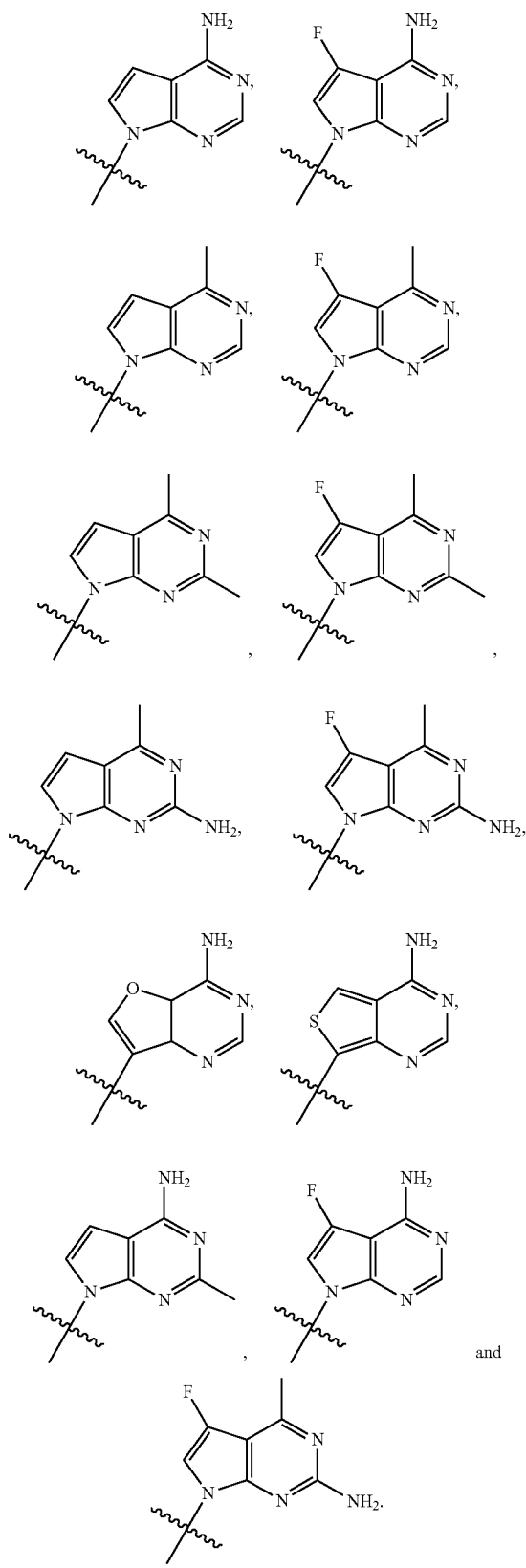
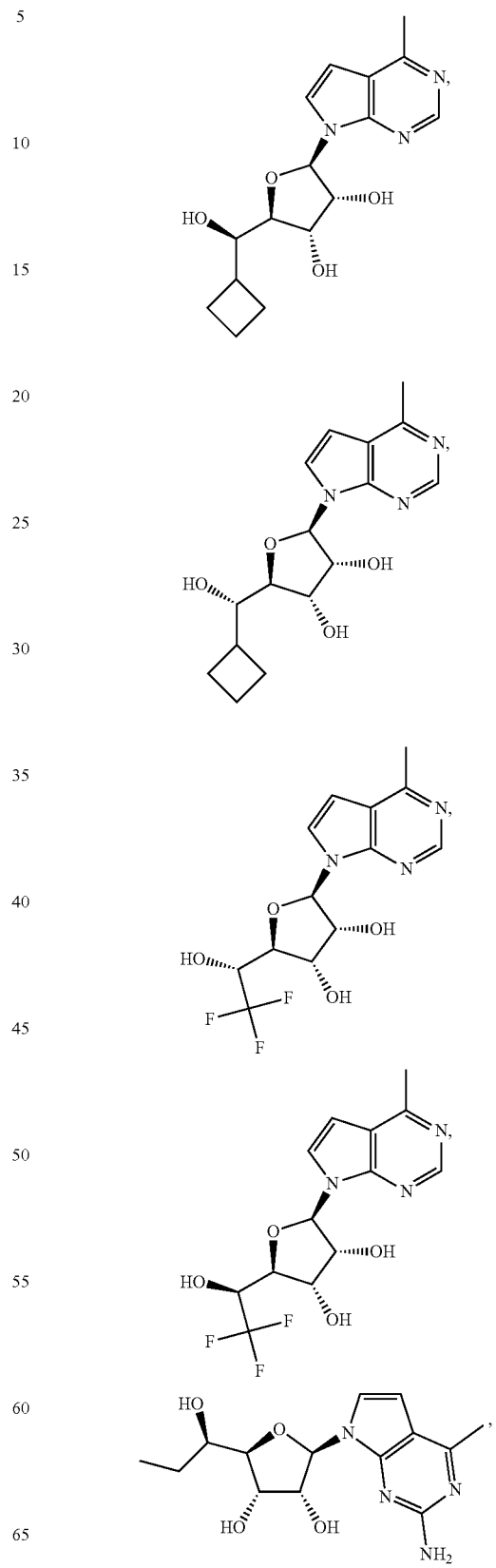

-continued
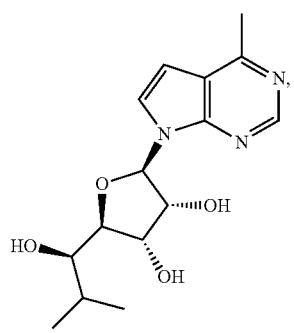
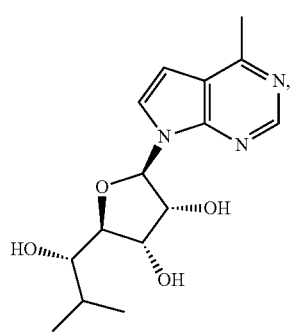
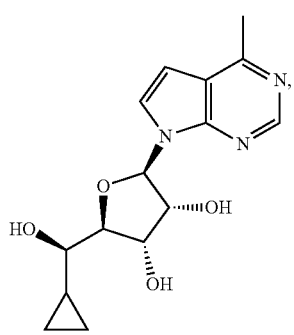
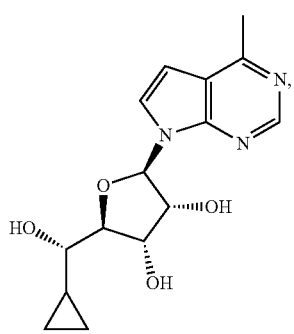
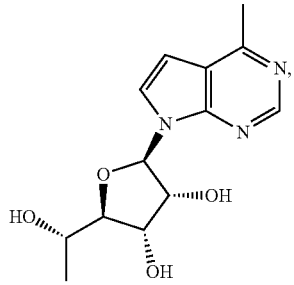
-continued
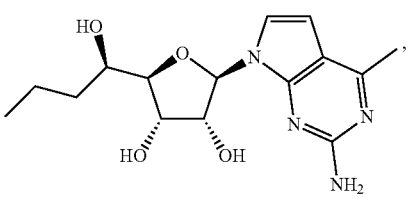
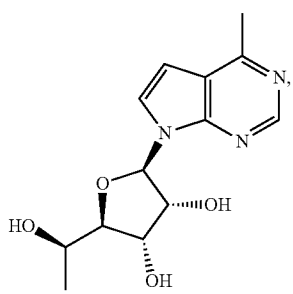
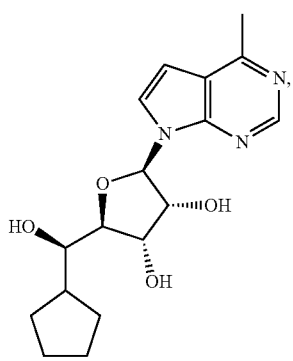
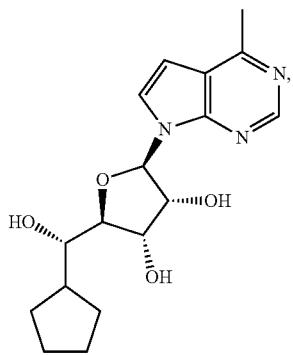
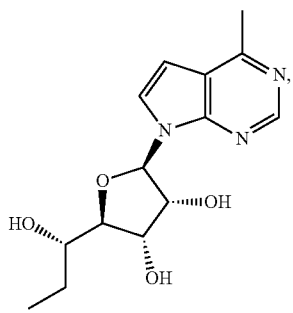

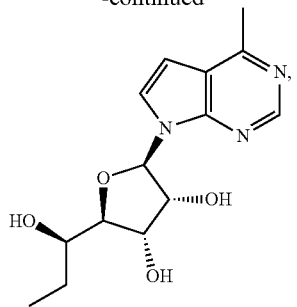
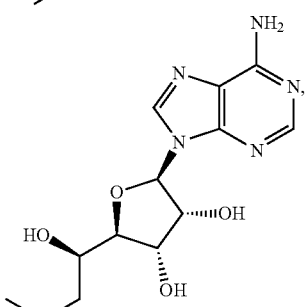
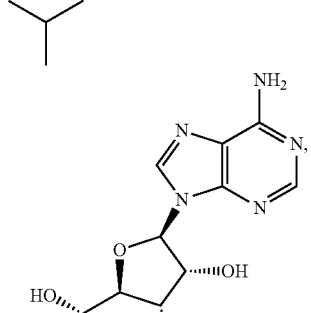
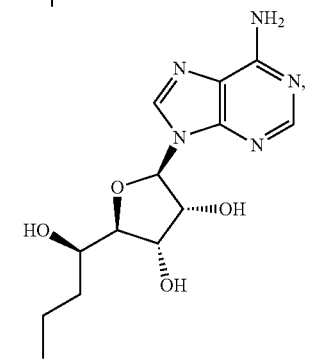
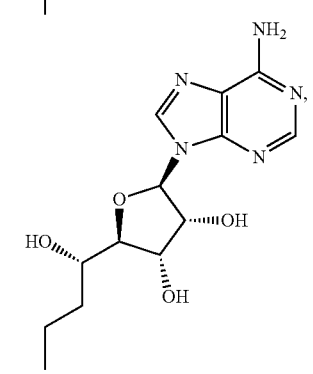
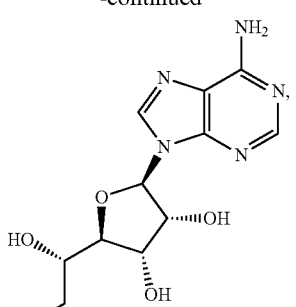
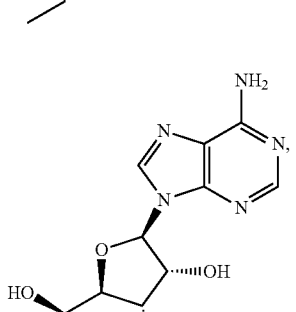
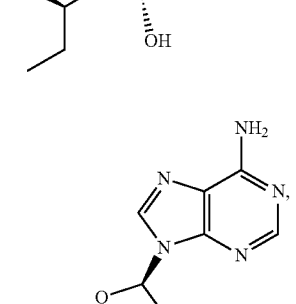
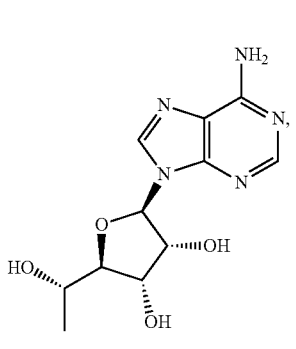
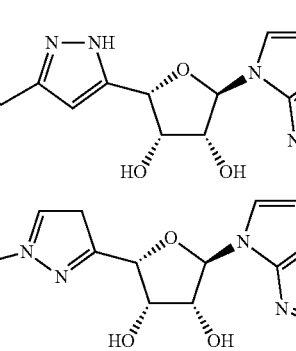

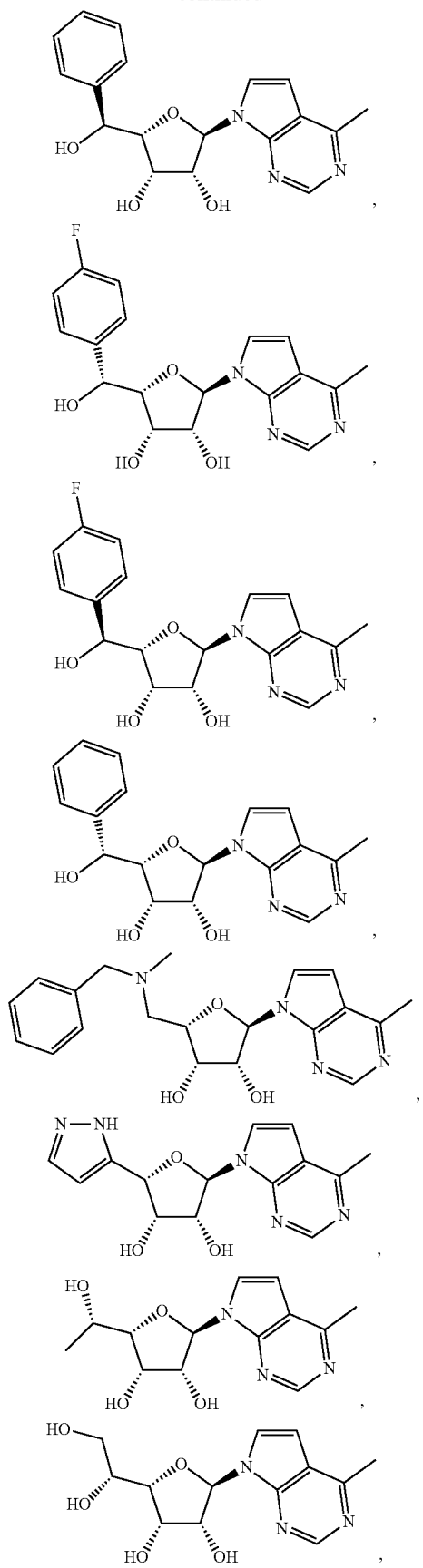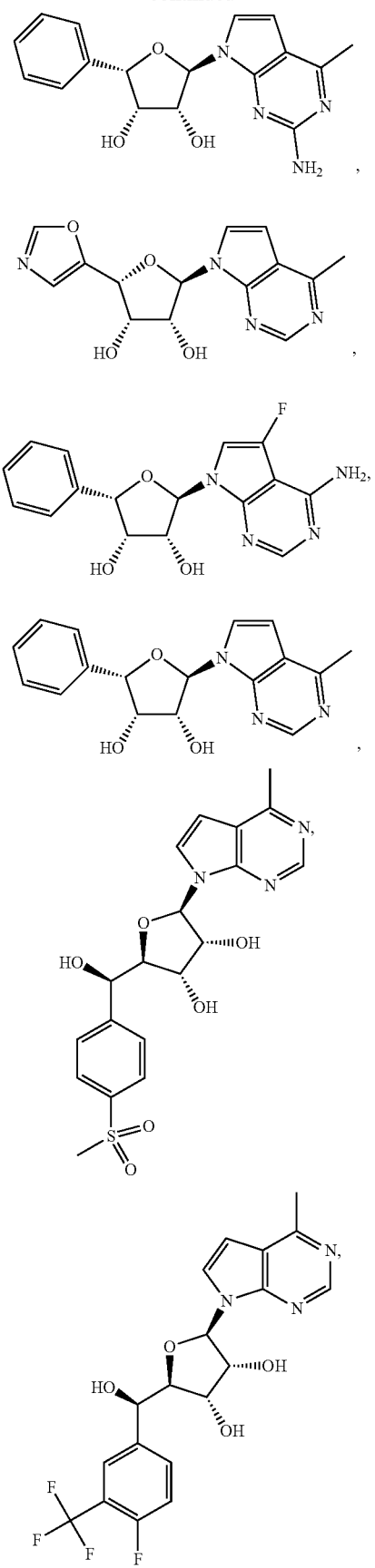

-continued
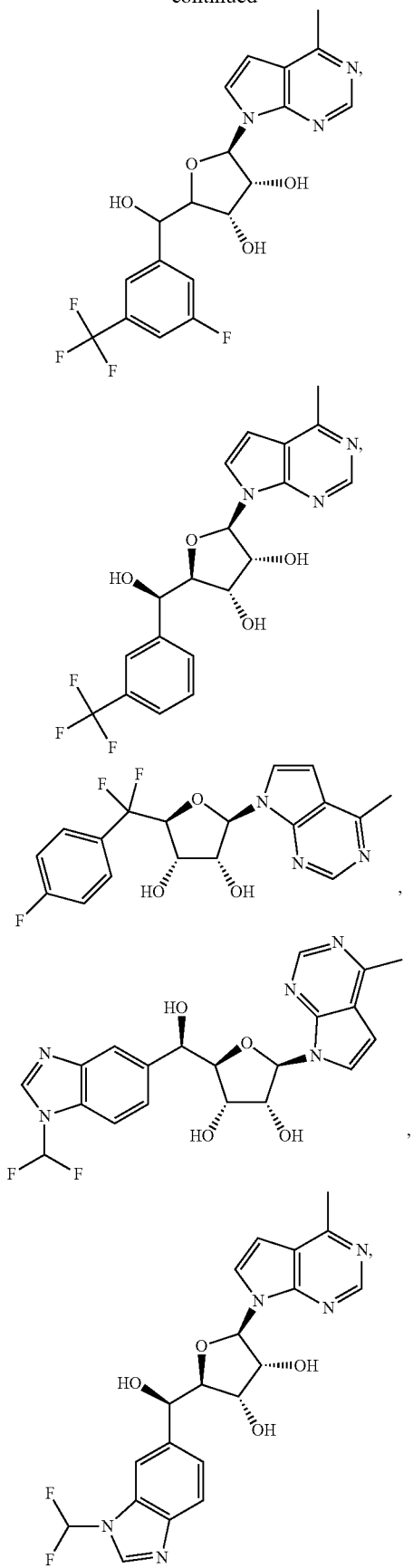
-continued
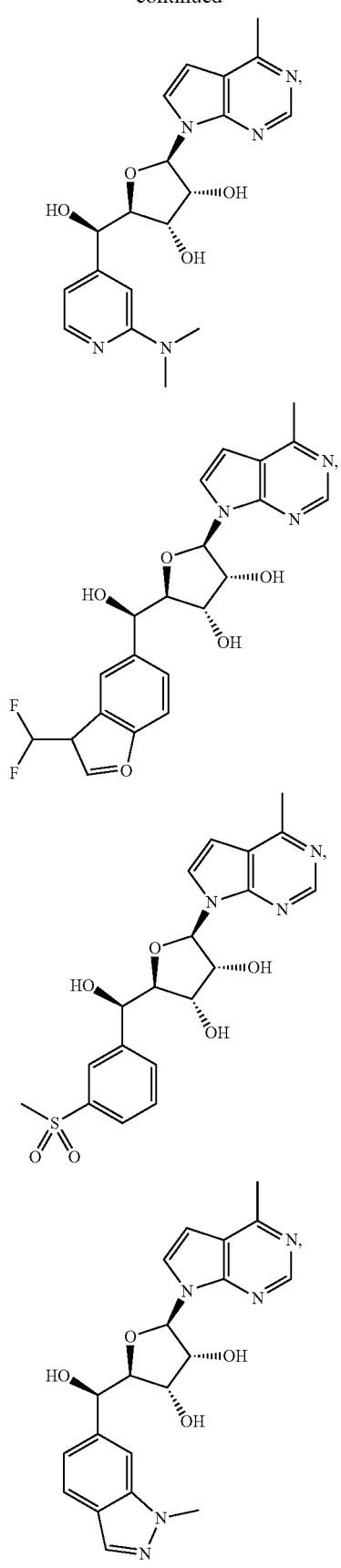

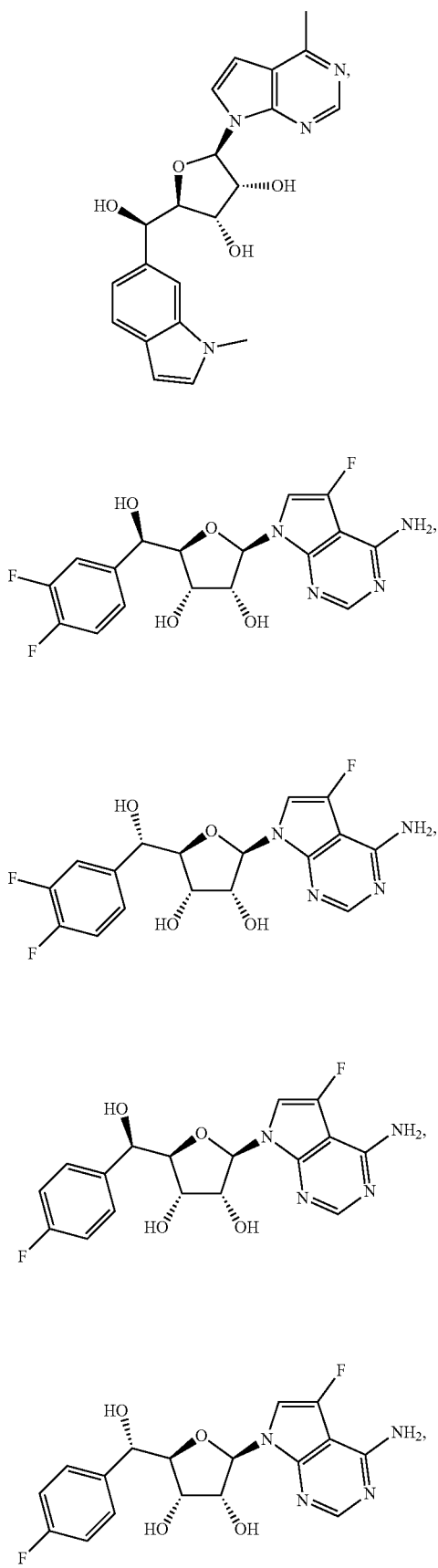
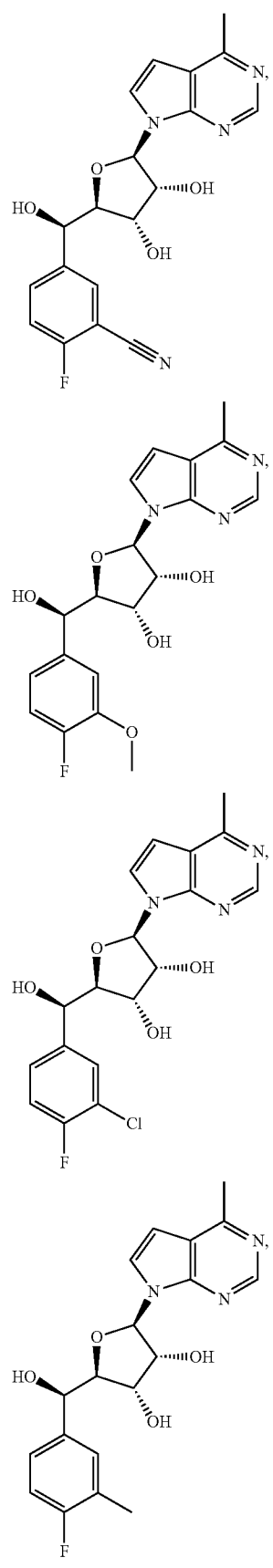

23
-continued
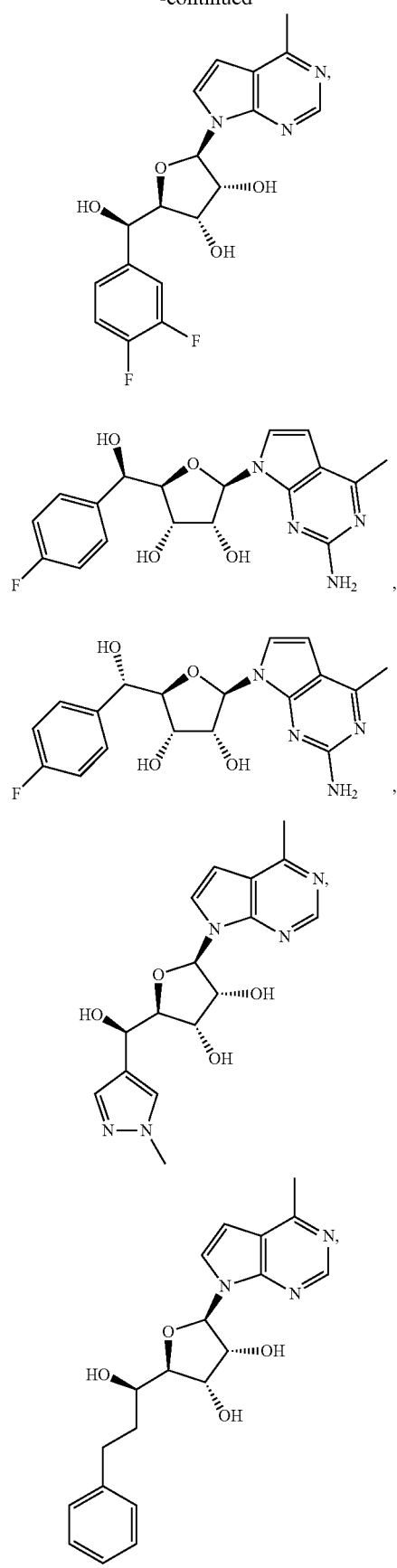
24
-continued
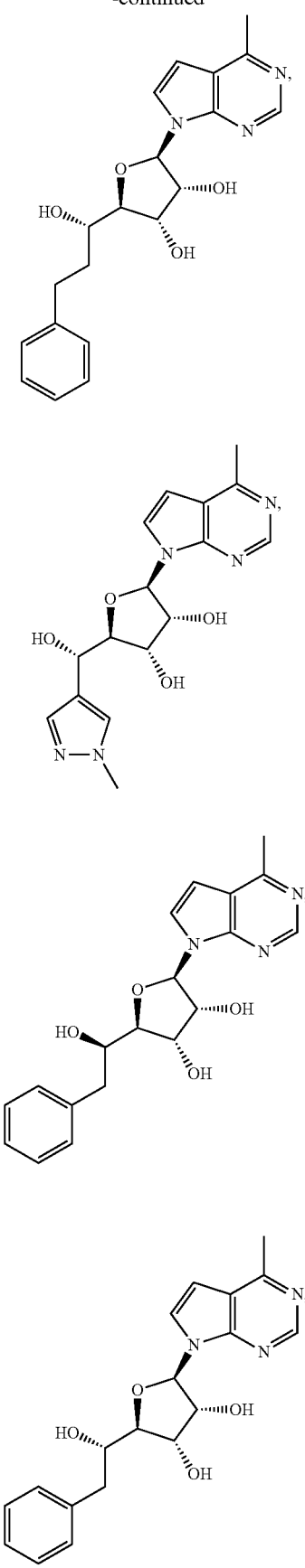

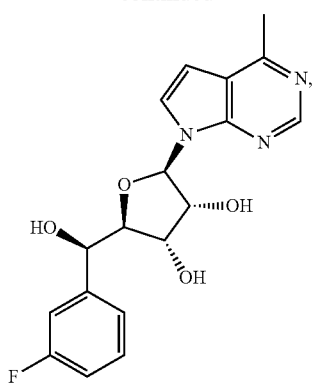
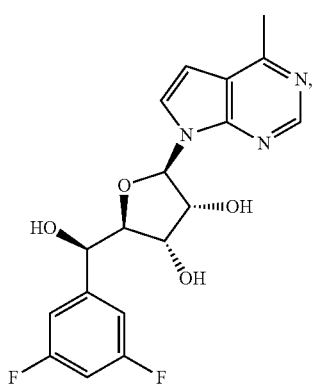
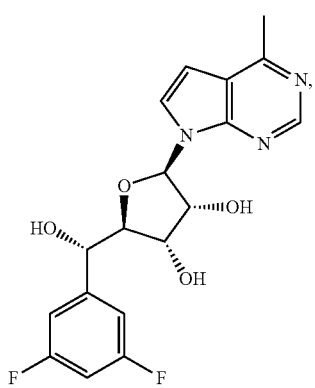
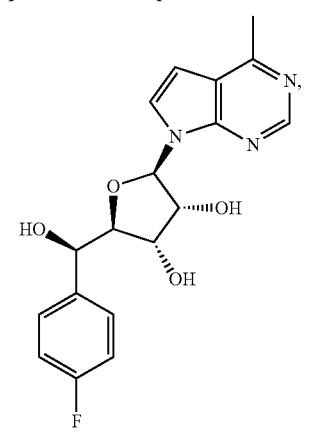
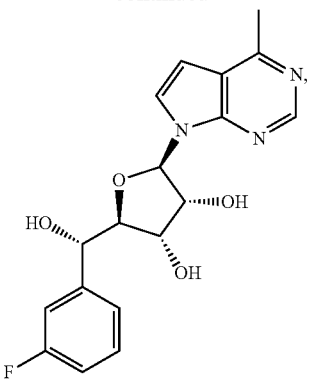
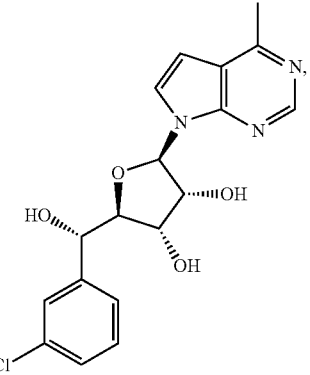
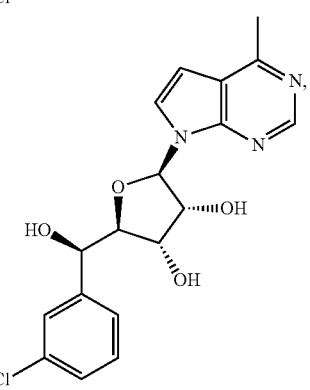
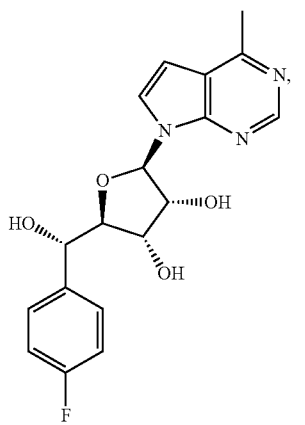
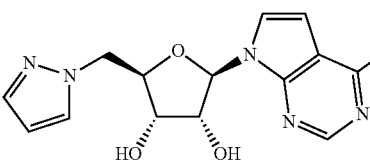

27
-continued
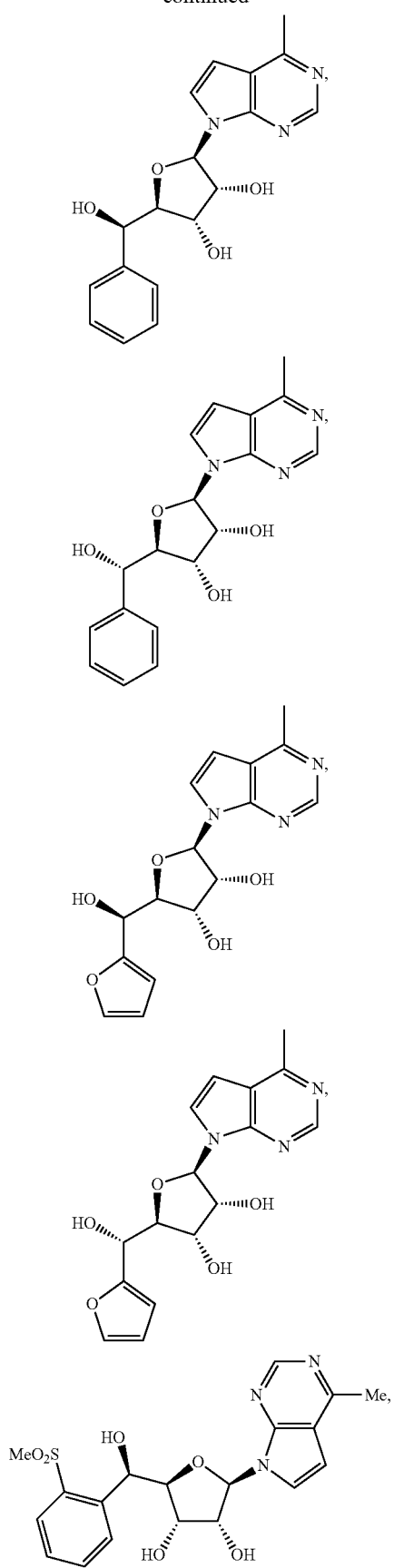
28
-continued
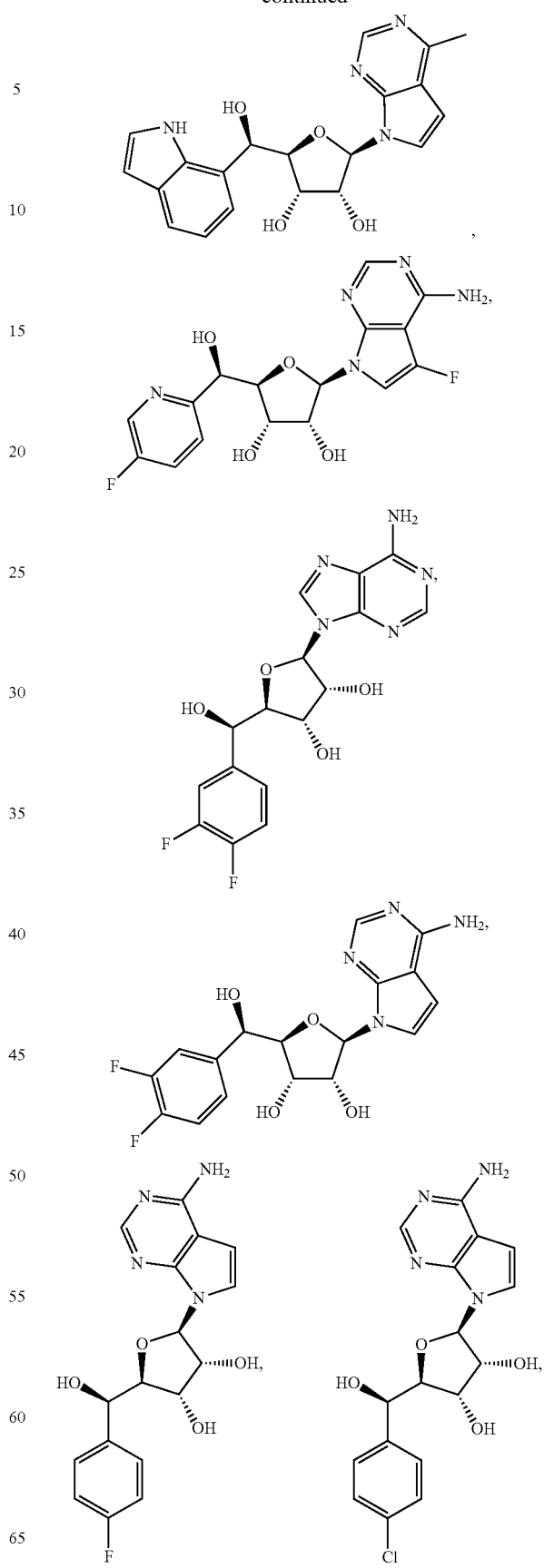

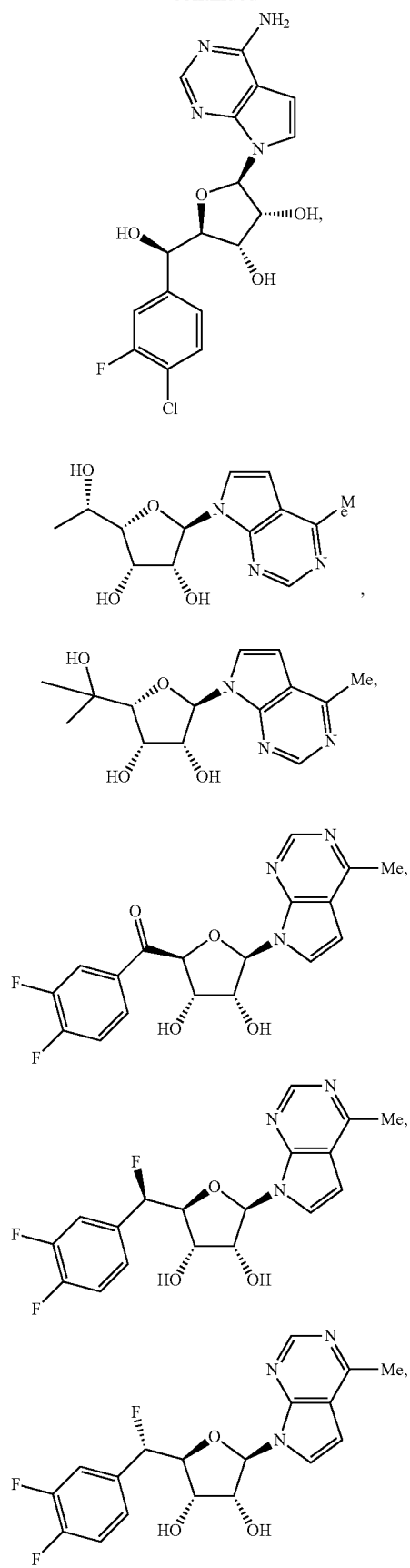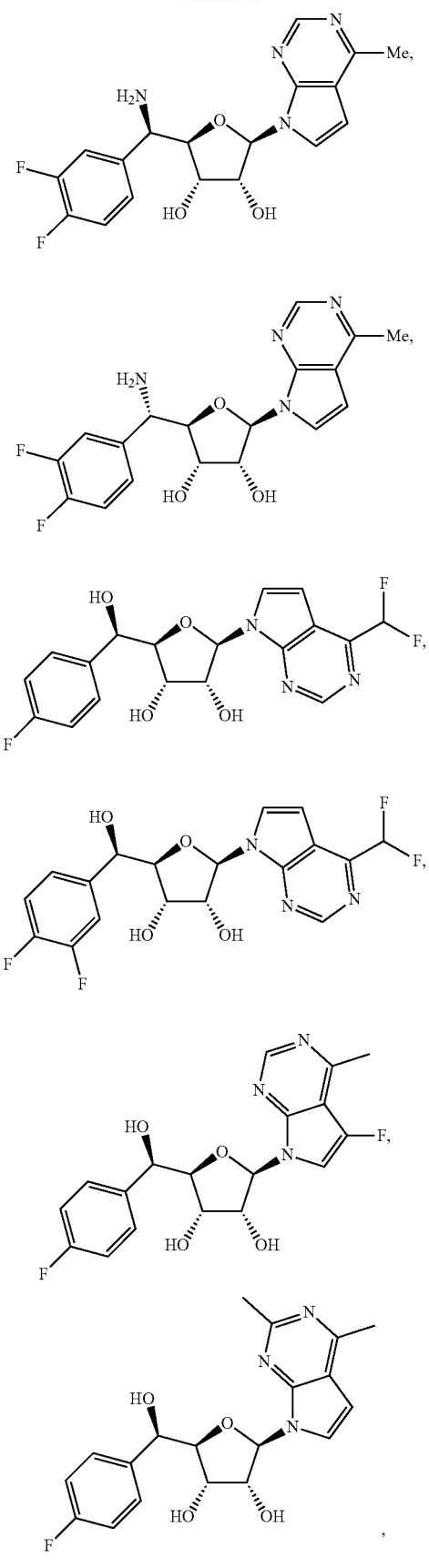

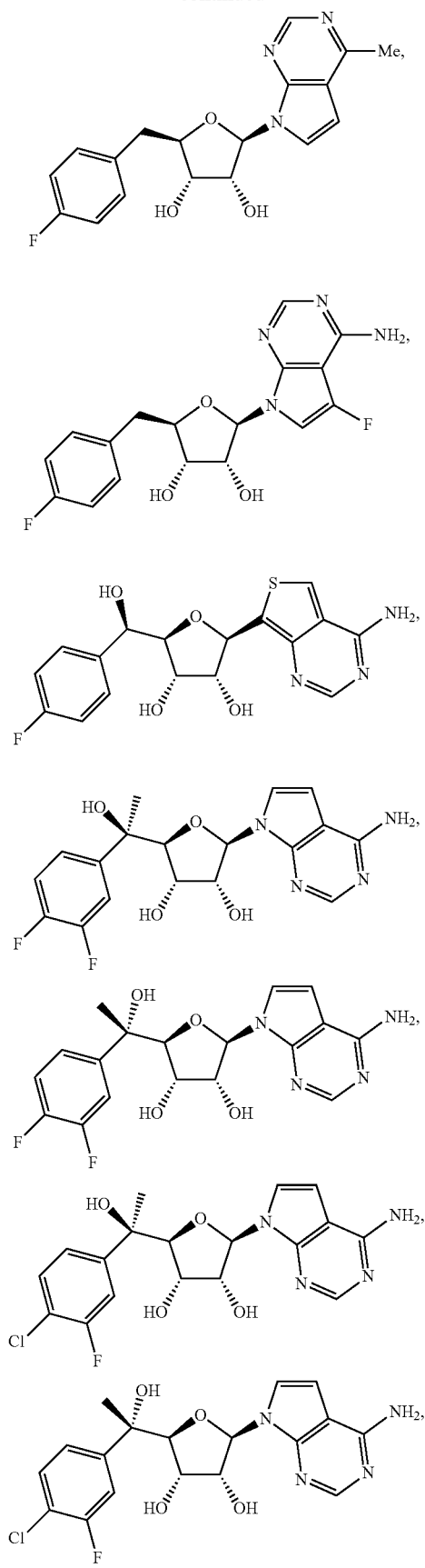
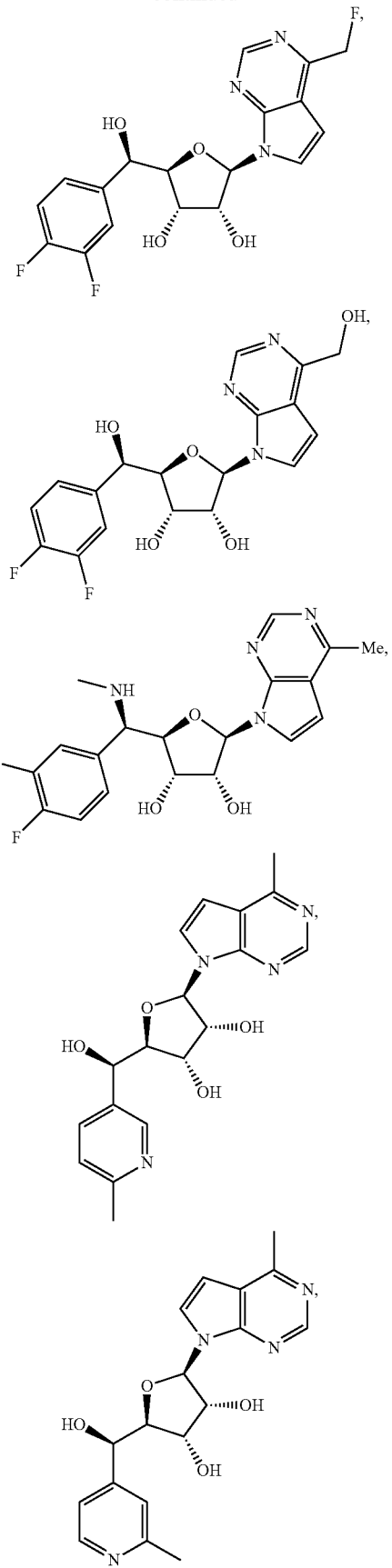

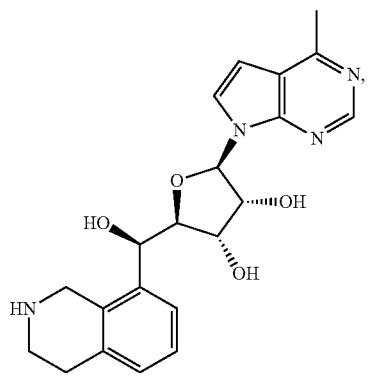
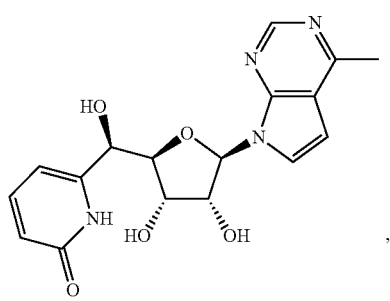
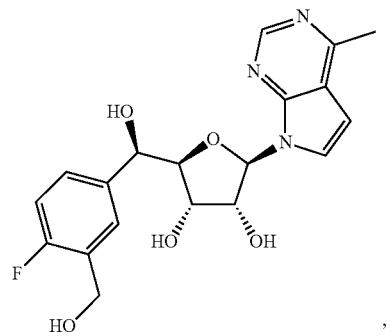
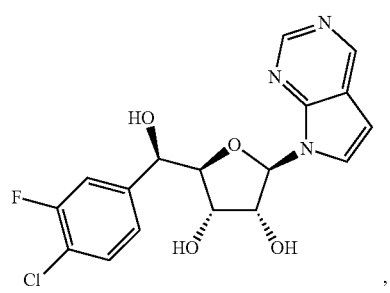
,
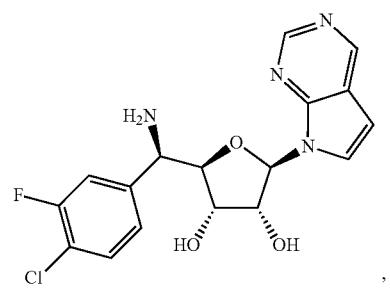
,
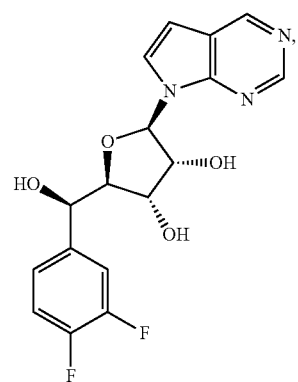
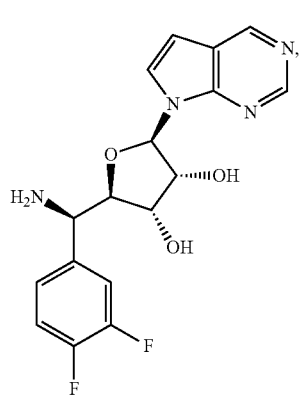
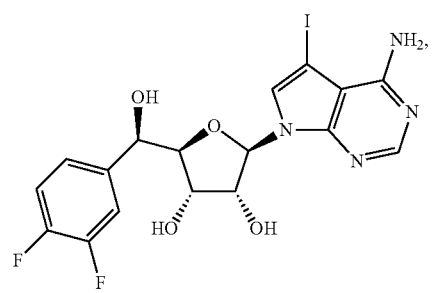
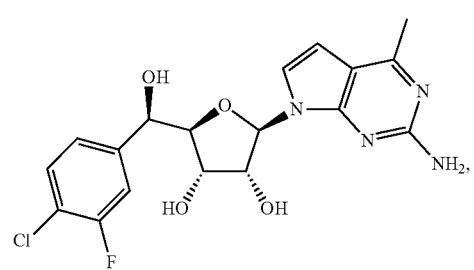
,
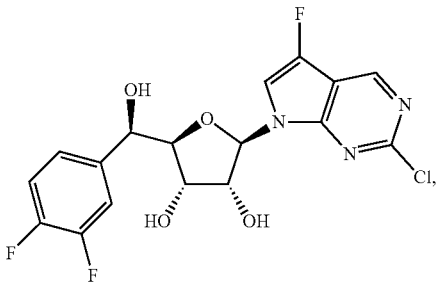

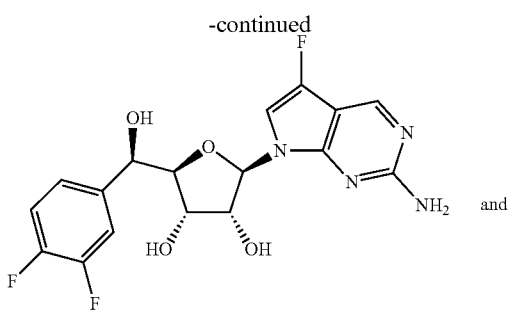
and
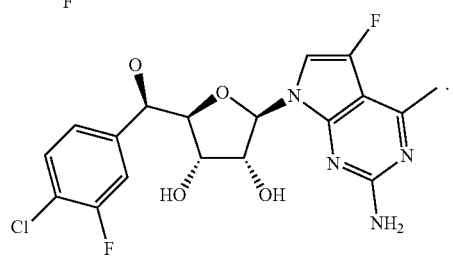
or a pharmaceutically acceptable salt or salts thereof.
Additional embodiments of the invention include one or more of the compounds:
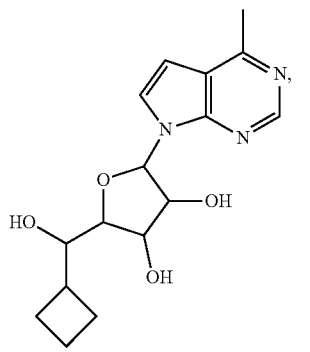
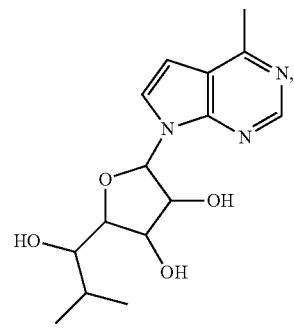
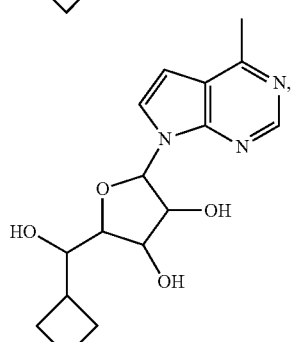
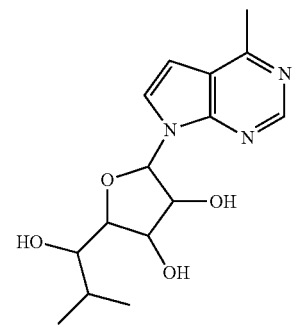
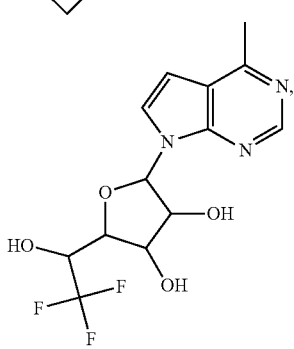
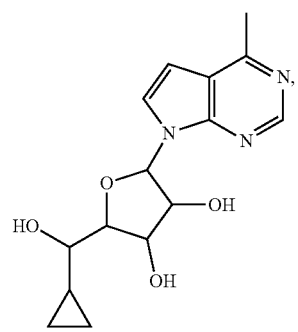

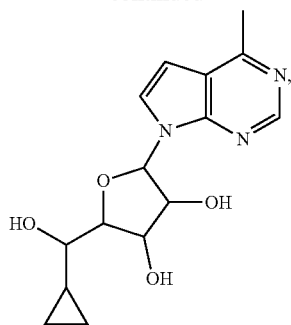
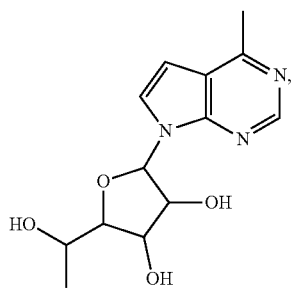
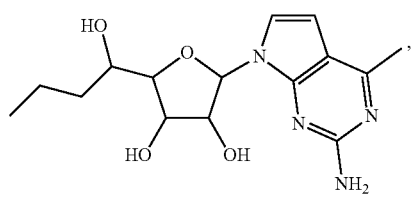
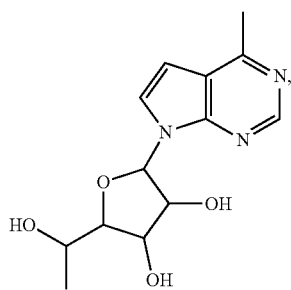
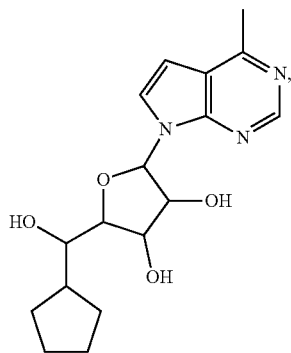
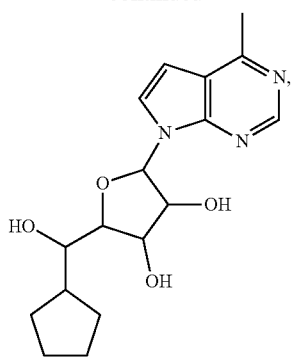
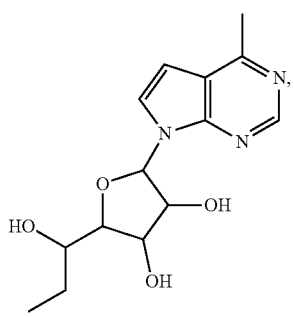
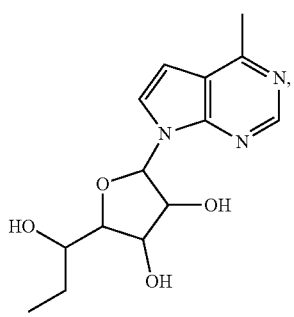
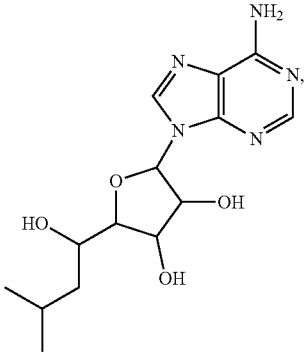
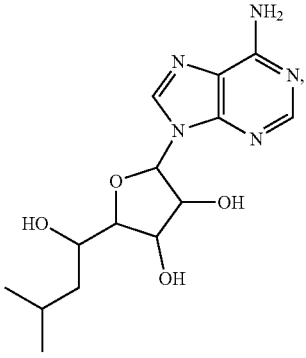

-continued
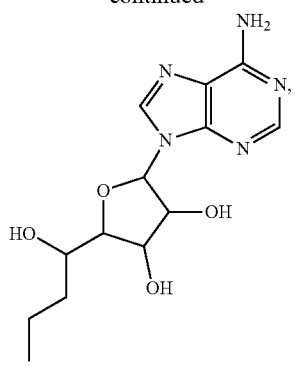
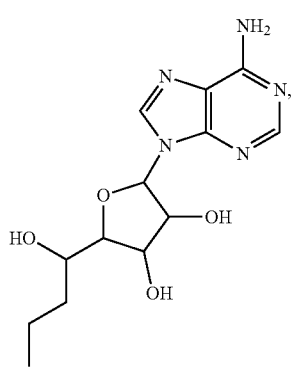
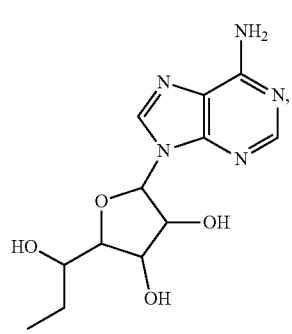
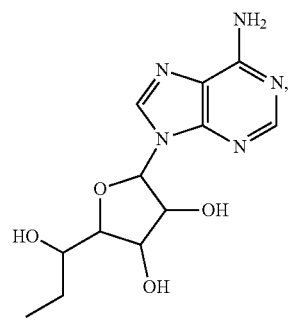
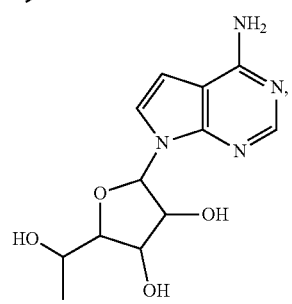
-continued
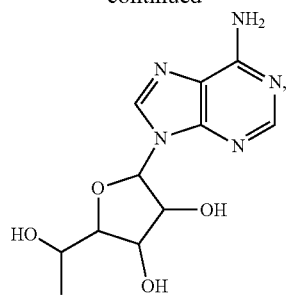
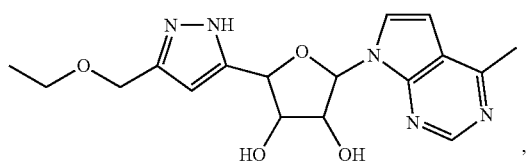
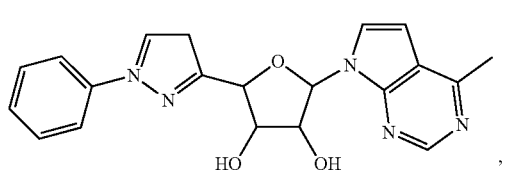
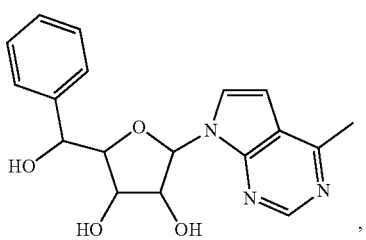
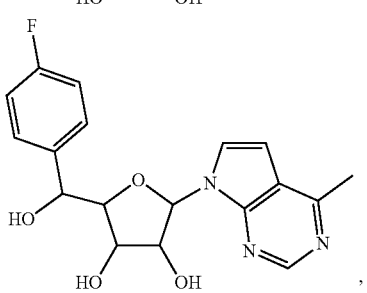
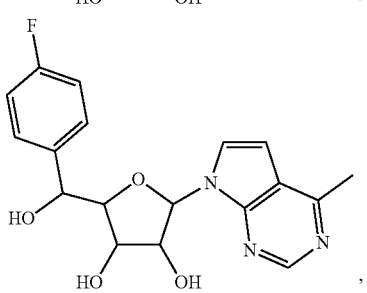
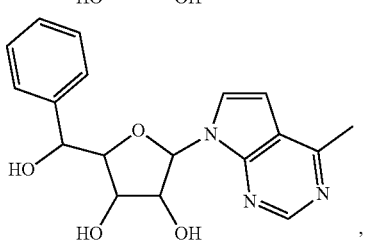

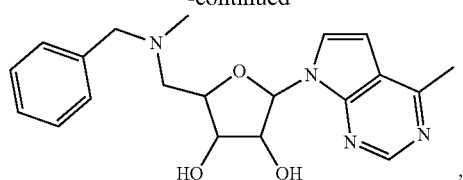
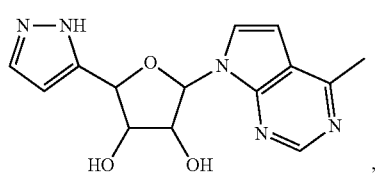
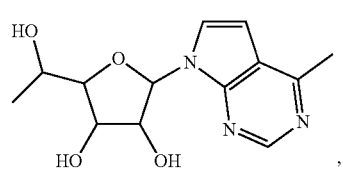
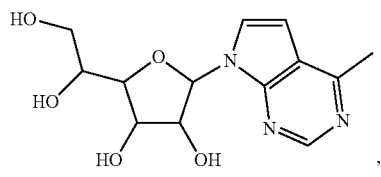
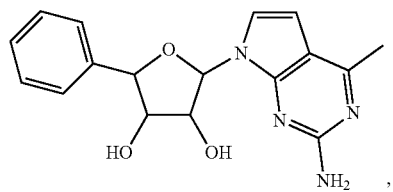
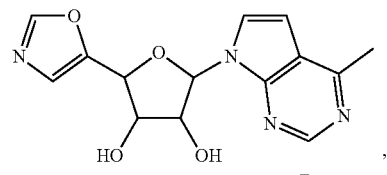
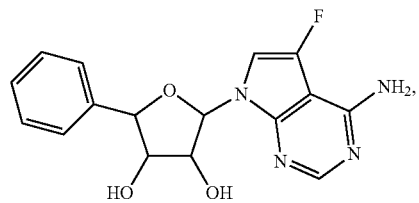
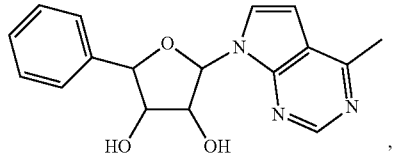
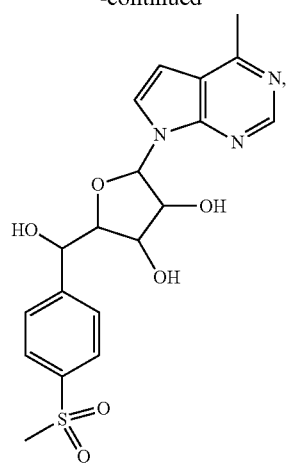
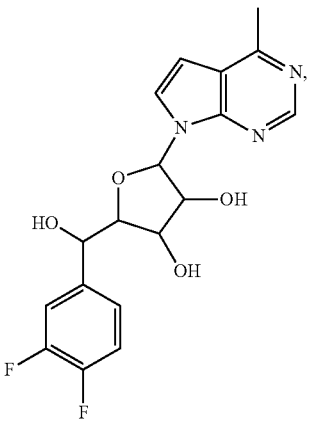
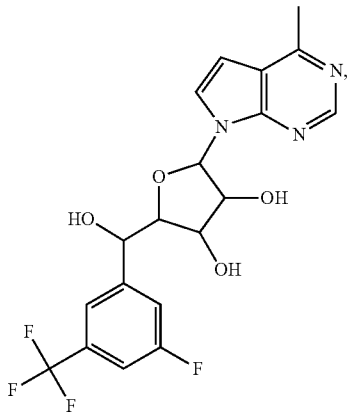
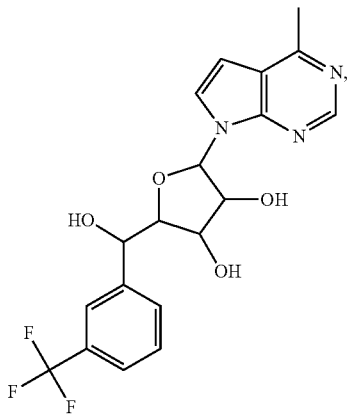

43
-continued
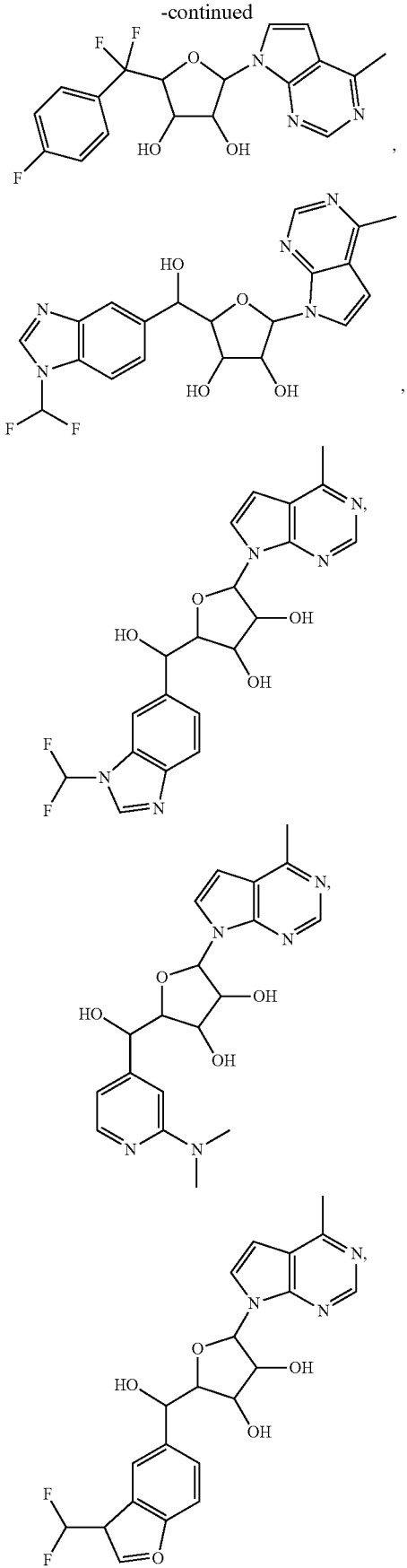
44
-continued
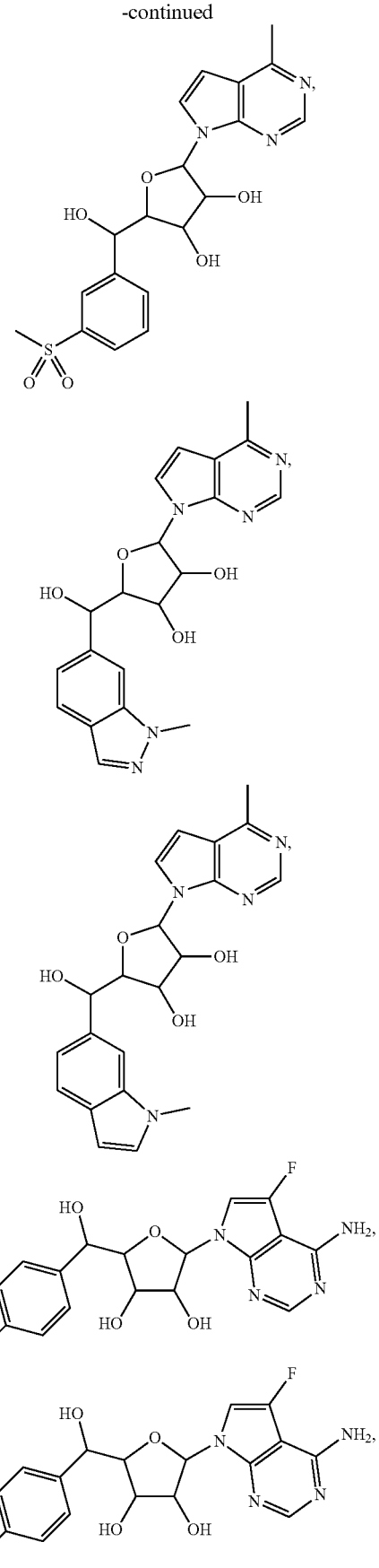

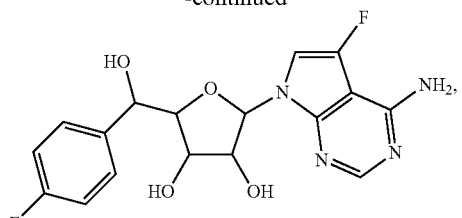
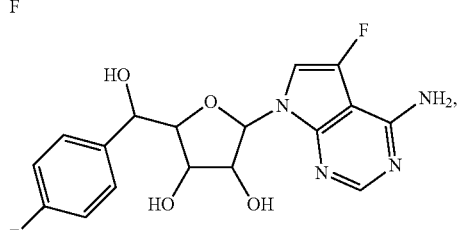
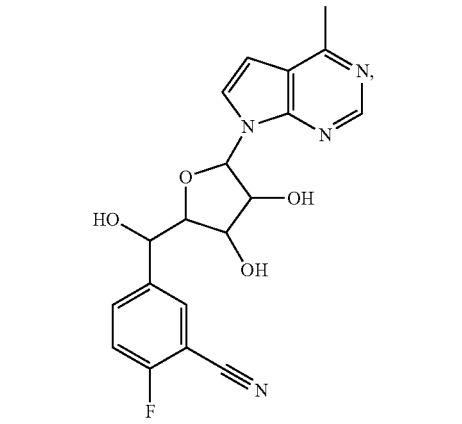
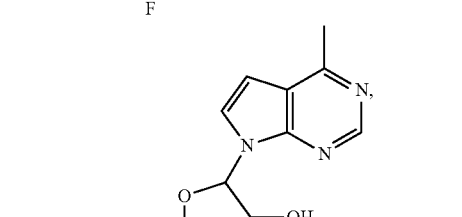
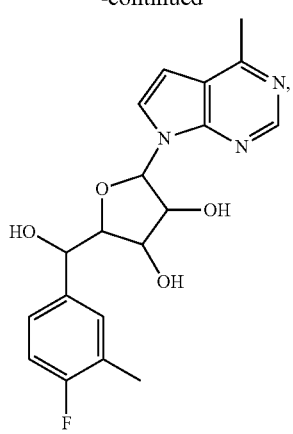
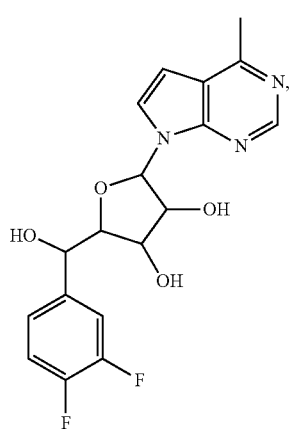
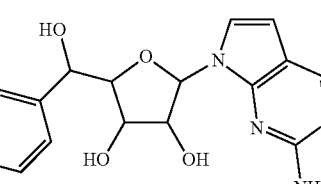
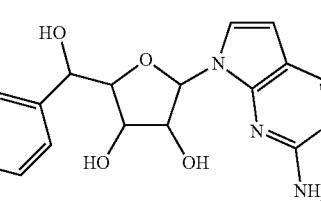
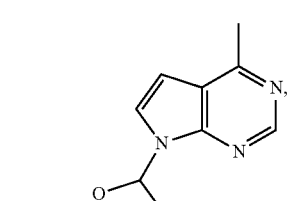
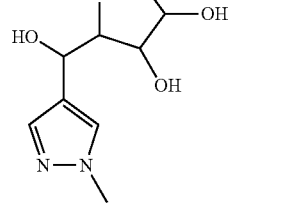

-continued
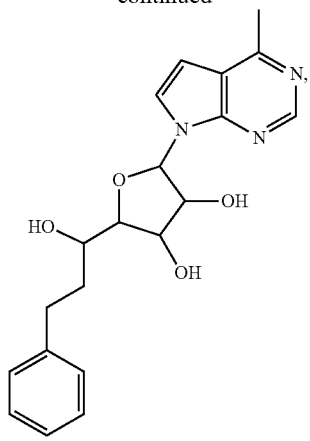
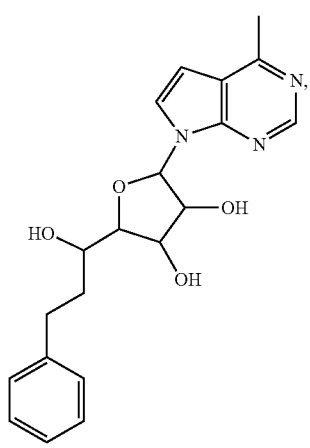
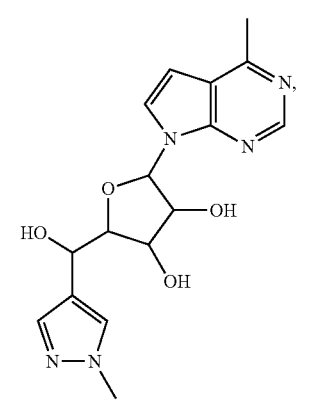
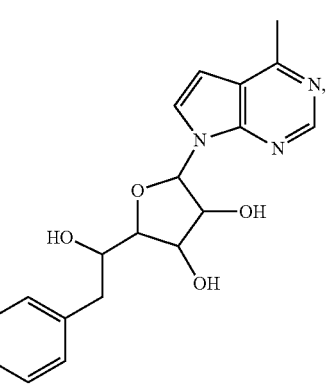
-continued
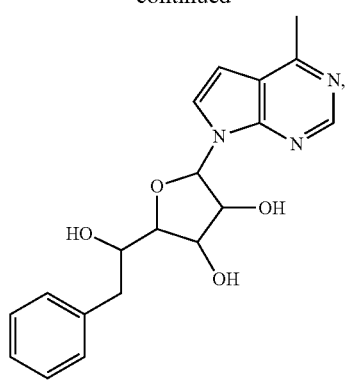
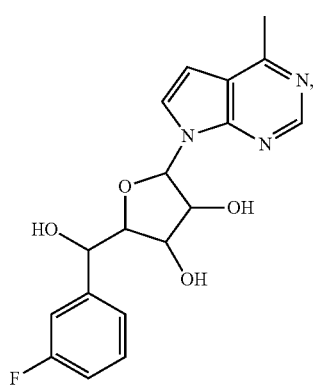
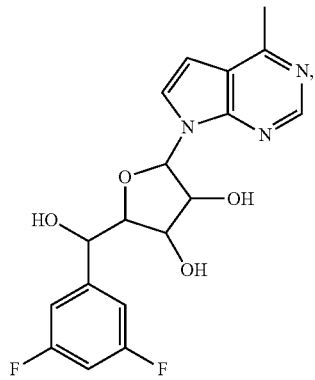
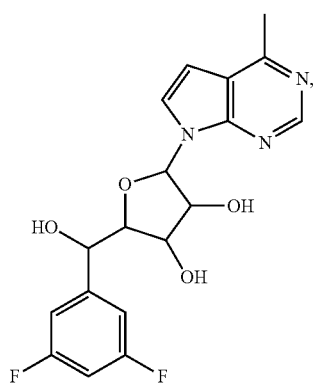

49
-continued
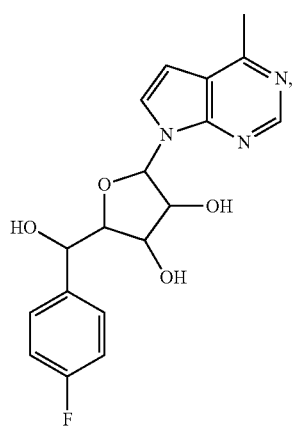
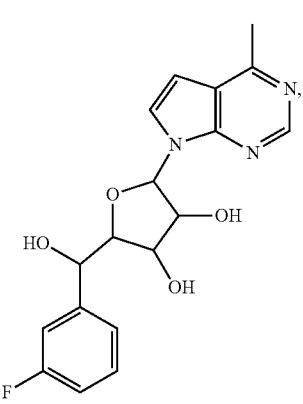
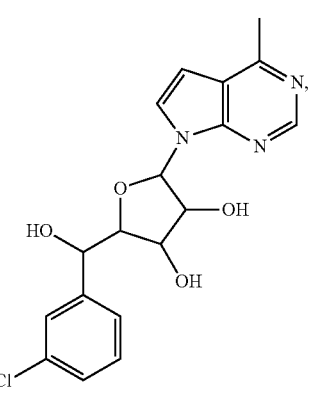
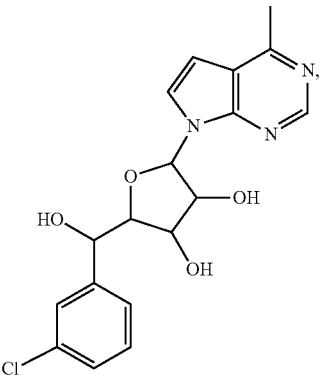
50
-continued
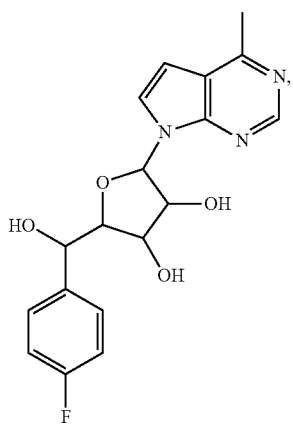
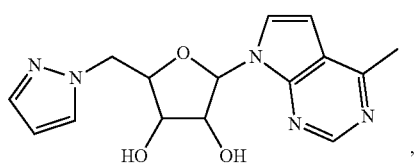
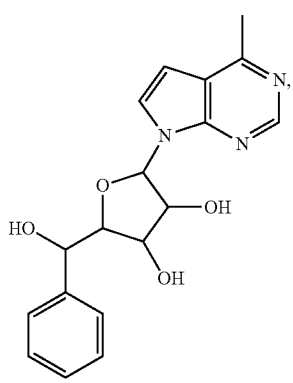
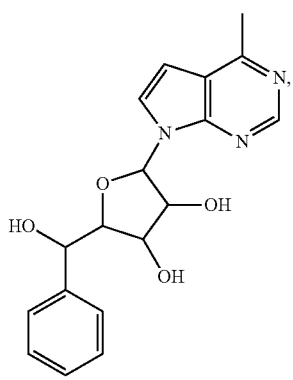
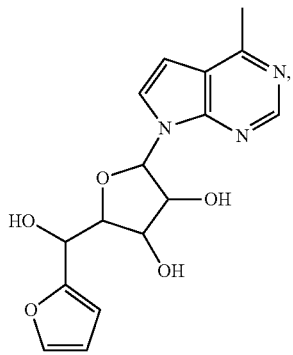

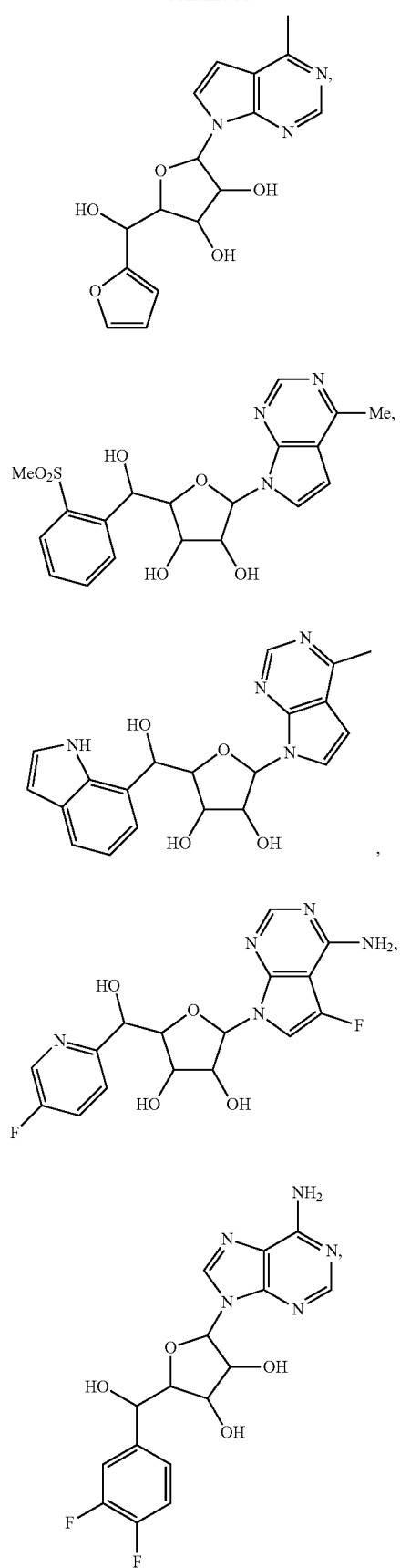

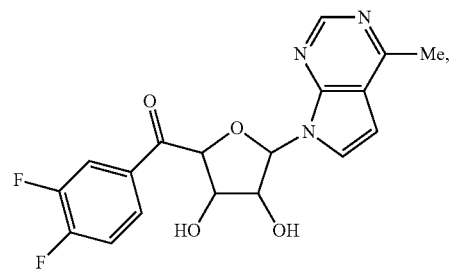
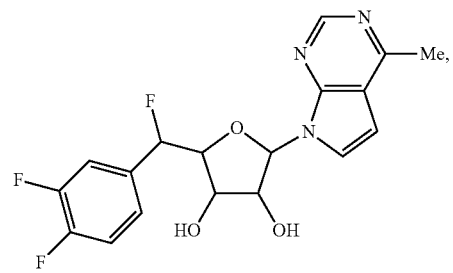
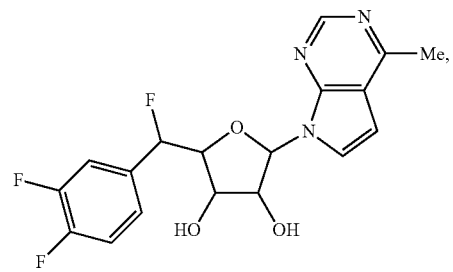
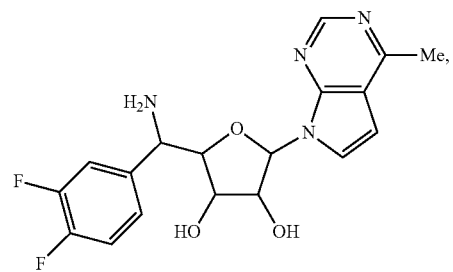
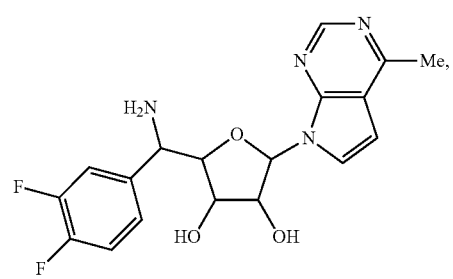
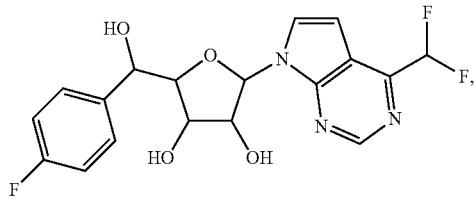
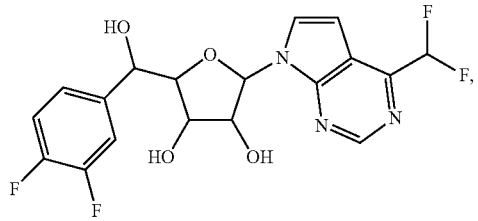
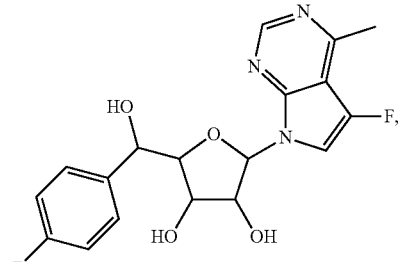
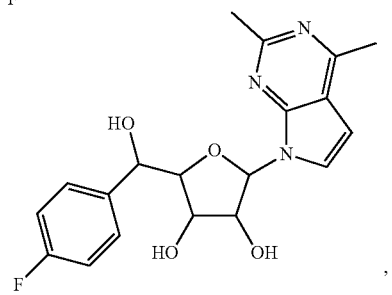
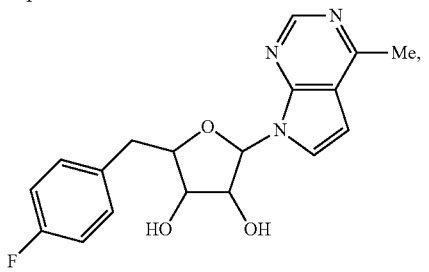
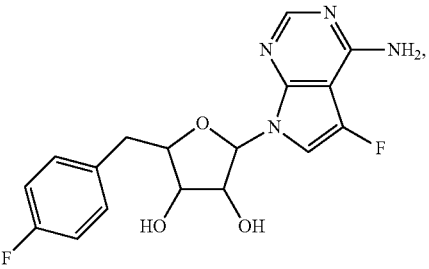
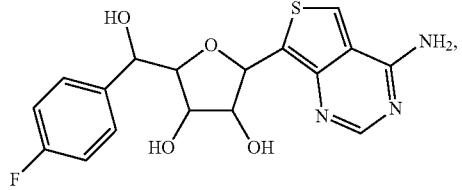
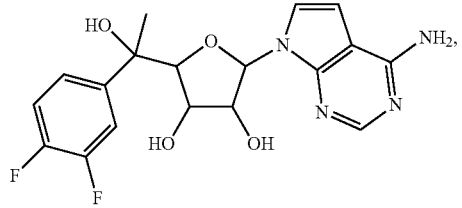

-continued
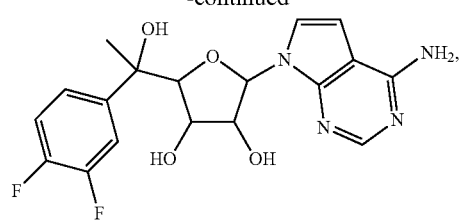
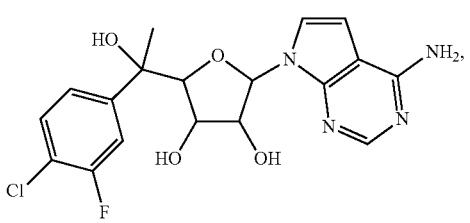
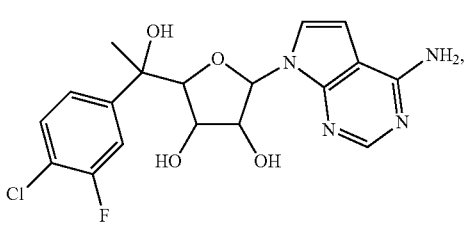
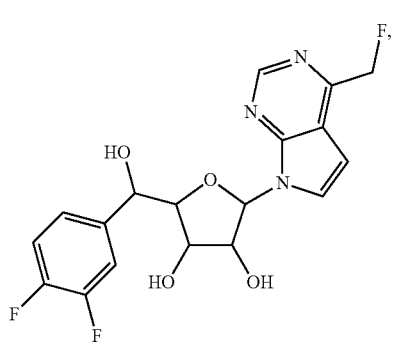
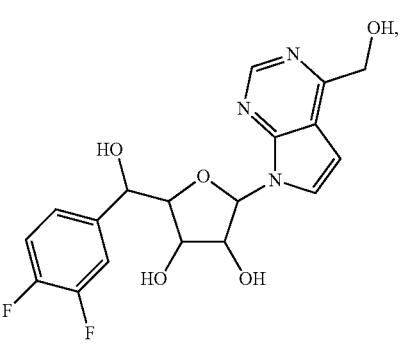
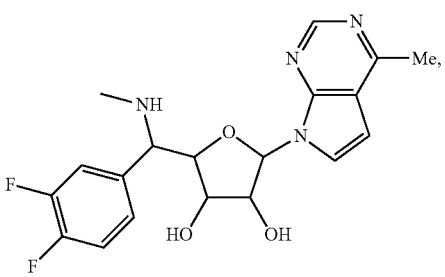
-continued
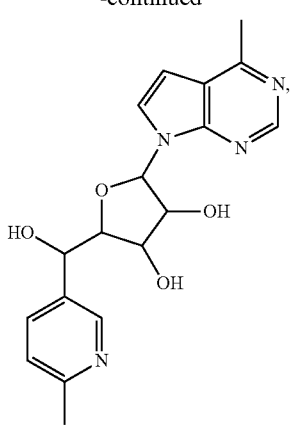
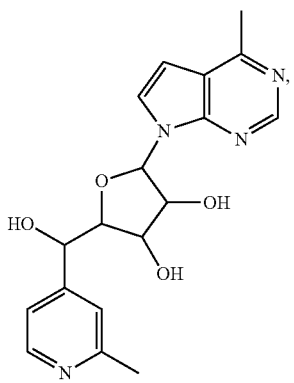
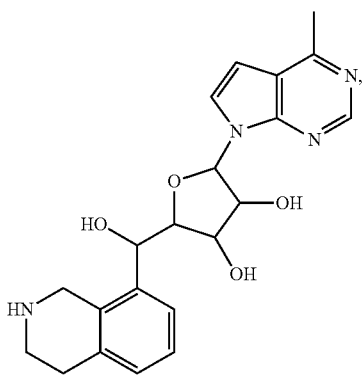
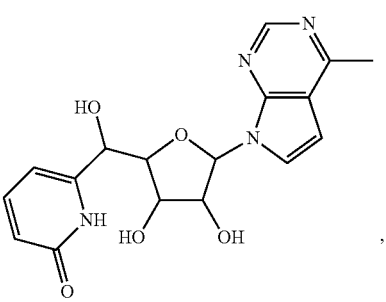

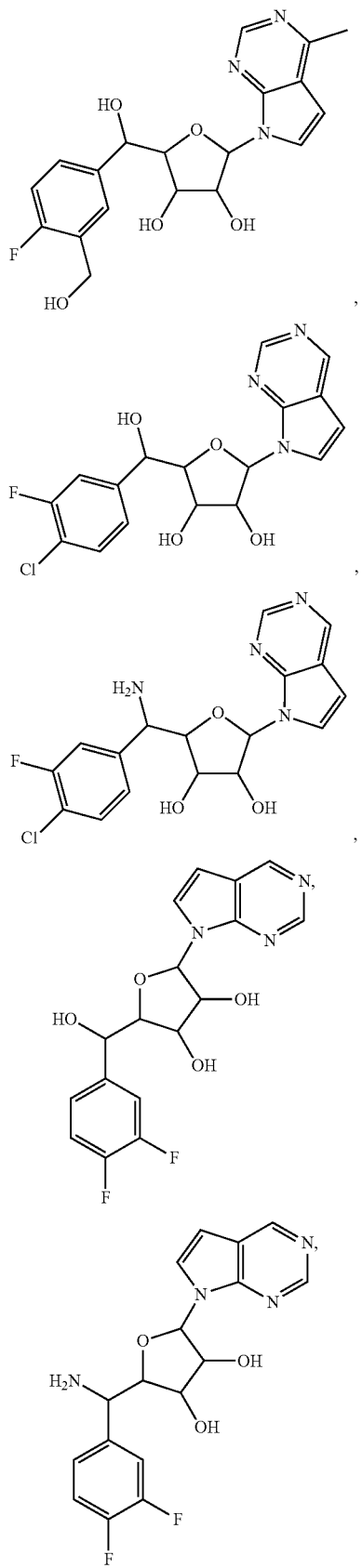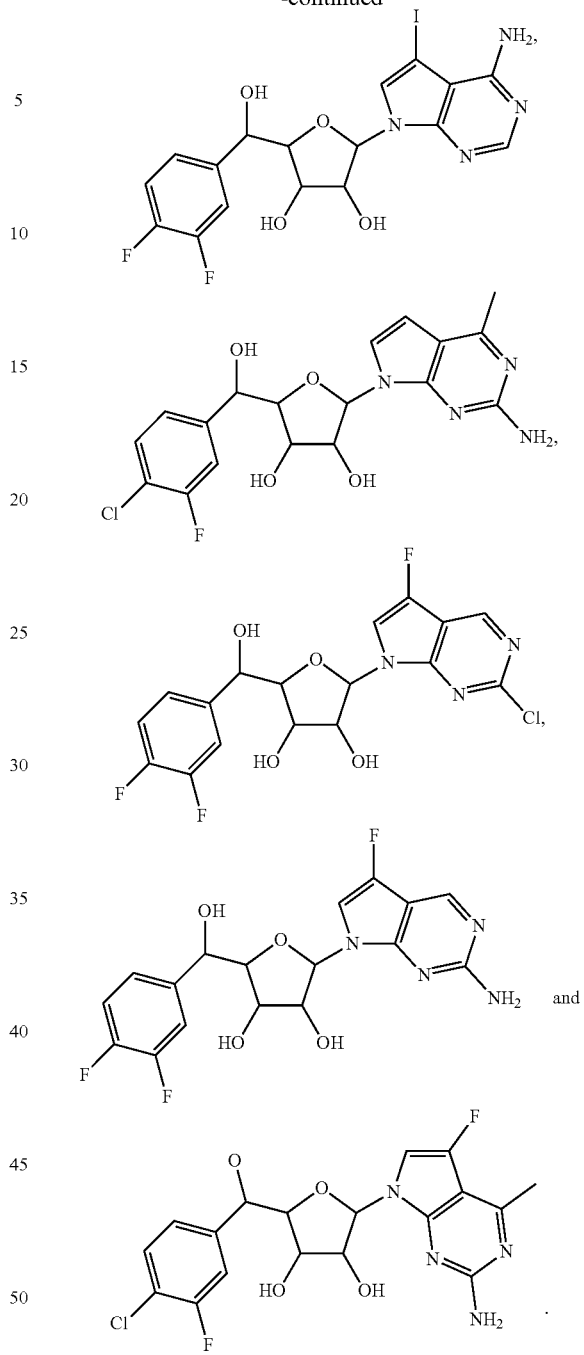

or a pharmaceutically acceptable salt or salts thereof.

Additional embodiments of the invention include pharmaceutical composition comprising of a compound described herein or a pharmaceutically acceptable salt thereof, and a pharmaceutically acceptable carrier.

Additional embodiments of the invention include methods of treating abnormal cell growth in a mammal, the method comprising administering to the mammal a therapeutically effective amount of a compound described herein or a pharmaceutically acceptable salt thereof, and a pharmaceutically acceptable carrier.

Additional embodiments of the invention include such methods of treatment as are described herein, wherein the abnormal cell growth is cancer. In particular, such methods wherein the cancer is lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma.

There is also provided an embodiment of the invention which is the use of a compound described herein, or a pharmaceutically acceptable salt thereof for the preparation of a medicament useful in the treatment of abnormal cell growth in a mammal, particularly wherein the abnormal cell growth is cancer, and more particularly wherein the cancer is lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma.

In another embodiment, the invention provides a pharmaceutical composition comprising a compound of the invention or a pharmaceutically acceptable salt thereof, and a pharmaceutically acceptable carrier.

In another embodiment, the invention provides a method of treating abnormal cell growth in a mammal, including a human, the method comprising administering to the mammal a therapeutically effective amount of a compound of the invention or a pharmaceutically acceptable salt thereof. In another embodiment, the abnormal cell growth is cancer. In another embodiment, the cancer is lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, or pituitary adenoma.

DEFINITIONS

Unless otherwise stated, the following terms used in the specification and claims have the meanings discussed below. Variables defined in this section, such as R, X, n and the like, are for reference within this section only, and are not meant to have the same meaning as may be used outside of this definitions section. Further, many of the groups defined herein can be optionally substituted. The listing in this definitions section of typical substituents is exemplary and is not intended to limit the substituents defined elsewhere within this specification and claims.

"Alkenyl" refers to an alkyl group, as defined herein, consisting of at least two carbon atoms and at least one carbon-carbon double bond. Representative examples include, but are not limited to, ethenyl, 1-propenyl, 2-propenyl, 1-, 2-, or 3-butenyl, and the like. "Alkenylene" refers to a di-valent form of alkenyl.

"Alkoxy" refers to —O-alkyl where alkyl is preferably $C_1$-$C_8$, $C_1$-$C_7$, $C_1$-$C_6$, $C_1$-$C_5$, $C_1$-$C_4$, $C_1$-$C_3$, $C_1$-$C_2$ or $C_1$ alkyl.

"Alkyl" refers to a saturated aliphatic hydrocarbon radical including straight chain and branched chain groups of 1 to 20 carbon atoms ("($C_1$-$C_{20}$)alkyl"), preferably 1 to 12 carbon atoms ("($C_1$-$C_{12}$)alkyl"), more preferably 1 to 8 carbon atoms ("($C_1$-$C_8$)alkyl"), or 1 to 6 carbon atoms ("($C_1$-$C_6$) alkyl"), or 1 to 4 carbon atoms ("($C_1$-$C_4$)alkyl"). Examples of alkyl groups include methyl, ethyl, propyl, 2-propyl, n-butyl, iso-butyl, tert-butyl, pentyl, neopentyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halogen, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —$NR^xR^y$, where $R^x$ and $R^y$ are for example hydrogen, alkyl, cycloalkyl, aryl, carbonyl, acetyl, sulfonyl, trifluoromethanesulfonyl and, combined, a five- or six-member heteroalicyclic ring. "Haloalkyl" for instance ($C_1$-$C_8$)haloalkyl, refers to an alkyl having one or more, halogen substituents. "Alkylene" refers to a di-valent form of alkyl.

"Alkynyl" refers to an alkyl group, as defined herein, consisting of at least two carbon atoms and at least one carbon-carbon triple bond. Representative examples include, but are not limited to, ethynyl, 1-propynyl, 2-propynyl, 1-, 2-, or 3-butynyl, and the like. "Alkynylene" refers to a di-valent form of alkynyl.

"Amino" refers to an —$NR^xR^y$ group, wherein $R^x$ and $R^y$ are both hydrogen.

"($C_6$-$C_{12}$)aryl" refers to an all-carbon monocyclic or fused-ring polycyclic groups of 6 to 12 carbon atoms having a completely conjugated pi-electron system. Examples, without limitation, of aryl groups are phenyl, naphthalenyl and anthracenyl. The aryl group may be substituted or unsubstituted. Typical substituents include halo, trihalomethyl, alkyl, hydroxy, alkoxy, aryloxy, mercapto, alkylthio, arylthio, cyano, nitro, carbonyl, thiocarbonyl, C-carboxy, O-carboxy, O-carbamyl, N-carbamyl, O-thiocarbamyl, N-thiocarbamyl, C-amido, N-amido, sulfinyl, sulfonyl, amino and —$NR^xR^y$, with $R^x$ and $R^y$ as defined above.

"Cyano" refers to a —C≡N group. Cyano may be expressed as CN.

"($C_3$-$C_{10}$)cycloalkyl" refers to a 3 to 10 member all-carbon monocyclic ring, a 3 to 10 member all-carbon bicyclic ring, an all-carbon 5-member/6-member or 6-member/6-member fused bicyclic ring, a multicyclic fused ring (a "fused" ring system means that each ring in the system shares an adjacent pair of carbon atoms with each other ring in the system) group wherein one or more of the rings may contain one or more double bonds but none of the rings has a completely conjugated pi-electron system, and a bridged all-carbon ring system. Examples, without limitation, of cycloalkyl groups are cyclopropane, cyclobutane, cyclopentane, cyclopentene, cyclohexane, cyclohexadiene, adamantane, cycloheptane, cycloheptatriene, and the like. A cycloalkyl group may be substituted or unsubstituted. Typical substituent groups include alkyl, aryl, heteroaryl, heteroalicyclic, hydroxy, alkoxy, aryloxy, mercapto, alkylthio, arylthio, cyano, halo, carbonyl, thiocarbonyl, C-carboxy, O-carboxy, O-carbamyl, N-carbamyl, C-amido, N-amido, nitro, amino and —NR$^x$R$^y$, with R$^x$ and R$^y$ as defined above. Illustrative examples of cycloalkyl are derived from, but not limited to, the following:

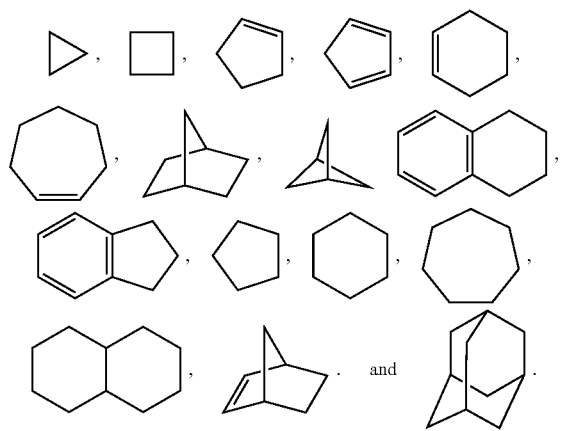

"Halogen" or the prefix "halo" refers to fluoro, chloro, bromo and iodo. Preferably halogen refers to fluoro or chloro.

"Heteroalkyl" refers to a straight chain or branched chain alkyl group of 1 to 20 carbon atoms, preferably 1 to 12 carbon atoms, more preferably 1 to 8 carbon atoms, or 1 to 6 carbon atoms, or 1 to 4 carbon atoms, wherein one, two or three of which carbon atoms are replaced by a heteroatom selected from NR$^x$, O, and S(O)$_n$ (where n is 0, 1 or 2). Exemplary heteroalkyl include alkyl ethers, secondary and tertiary alkyl amines, amides, alkyl sulfides, and the like. The group may be a terminal group or a bridging group. As used herein, reference to the normal chain when used in the context of a bridging group refers to the direct chain of atoms linking the two terminal positions of the bridging group. As with "alkyl", typical substituent groups on "heteroalkyl" include cycloalkyl, aryl, heteroaryl, heteroalicyclic, hydroxy, alkoxy, aryloxy, mercapto, alkylthio, arylthio, cyano, halogen, carbonyl, thiocarbonyl, O-carbamyl, N-carbamyl, O-thiocarbamyl, N-thiocarbamyl, C-amido, N-amido, C-carboxy, O-carboxy, nitro, silyl, amino and —NR$^x$R$^y$, where R$^x$ and R$^y$ are for example hydrogen, alkyl, cycloalkyl, aryl, carbonyl, acetyl, sulfonyl, trifluoromethanesulfonyl and, combined, a five- or six-member heteroalicyclic ring. "Heteroalkenyl" refers to a heteroalkyl possessing one or more carbon-carbon double bonds. "Heteroalkylene" refers to a di-valent form of heteroalkyl. "Heteroalkenylene" refers to a di-valent form of heteroalkenyl.

"Heteroaryl" refers to a monocyclic or fused ring group of 5 to 12 carbon ring atoms containing one, two, three or four ring heteroatoms selected from NR$^x$, O, and S(O)$_n$ (where n is 0, 1 or 2) and, in addition, having a completely conjugated pi-electron system. Preferred heteroaryl groups include (C$_2$-C$_7$)heteroaryl in accordance with the definition above. Examples, without limitation, of unsubstituted heteroaryl groups are pyrrole, furan, thiophene, imidazole, oxazole, thiazole, pyrazole, pyridine, pyrimidine, quinoline, isoquinoline, purine, tetrazole, triazine, and carbazole. The heteroaryl group may be substituted or unsubstituted. Typical substituents include alkyl, cycloalkyl, halo, trihalomethyl, hydroxy, alkoxy, aryloxy, mercapto, alkylthio, arylthio, cyano, nitro, carbonyl, thiocarbonyl, sulfonamido, C-carboxy, O-carboxy, sulfinyl, sulfonyl, O-carbamyl, N-carbamyl, O-thiocarbamyl, N-thiocarbamyl, C-amido, N-amido, amino and —NR$^x$R$^y$ with R$^x$ and R$^y$ as defined above. A pharmaceutically acceptable heteroaryl is one that is sufficiently stable to be attached to a compound of the invention, formulated into a pharmaceutical composition and subsequently administered to a patient in need thereof. Examples of typical monocyclic heteroaryl groups include, but are not limited to:

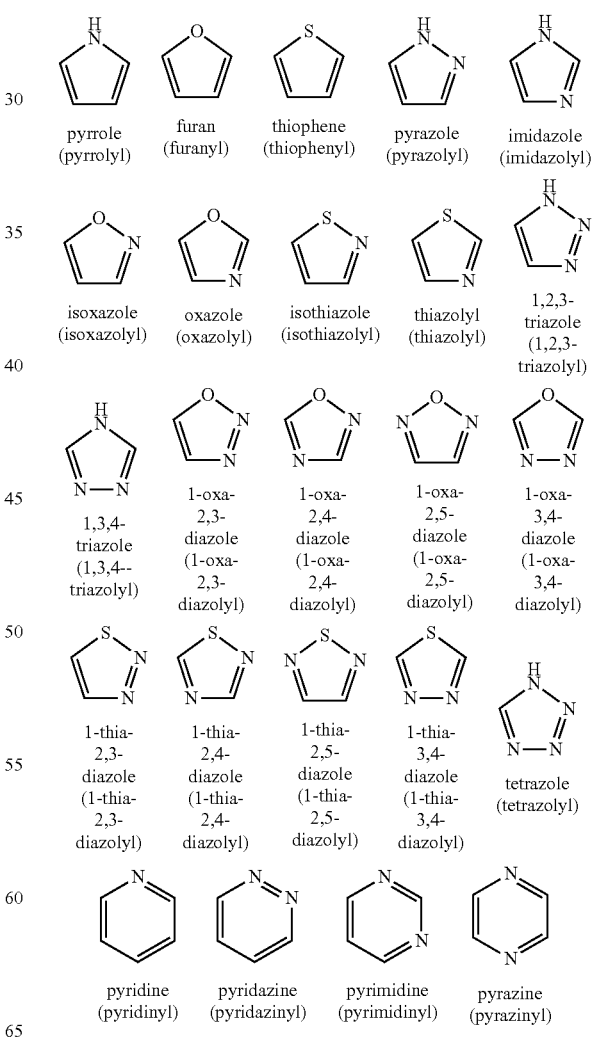

Examples of suitable fused ring heteroaryl groups include, but are not limited to:
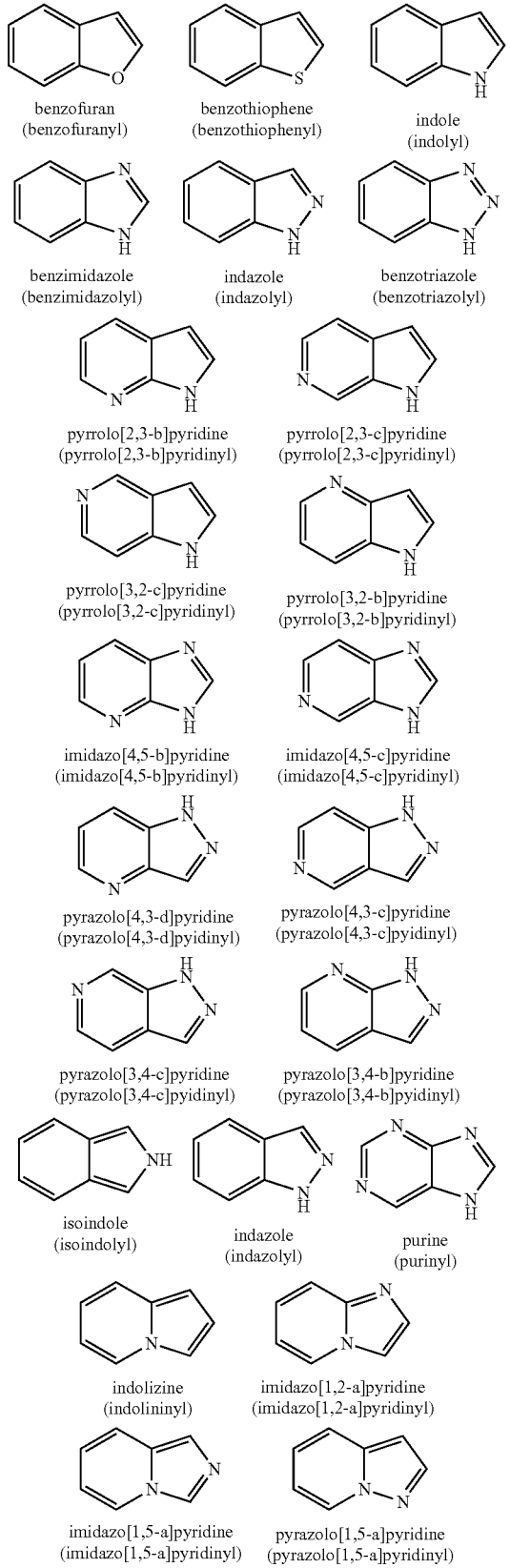
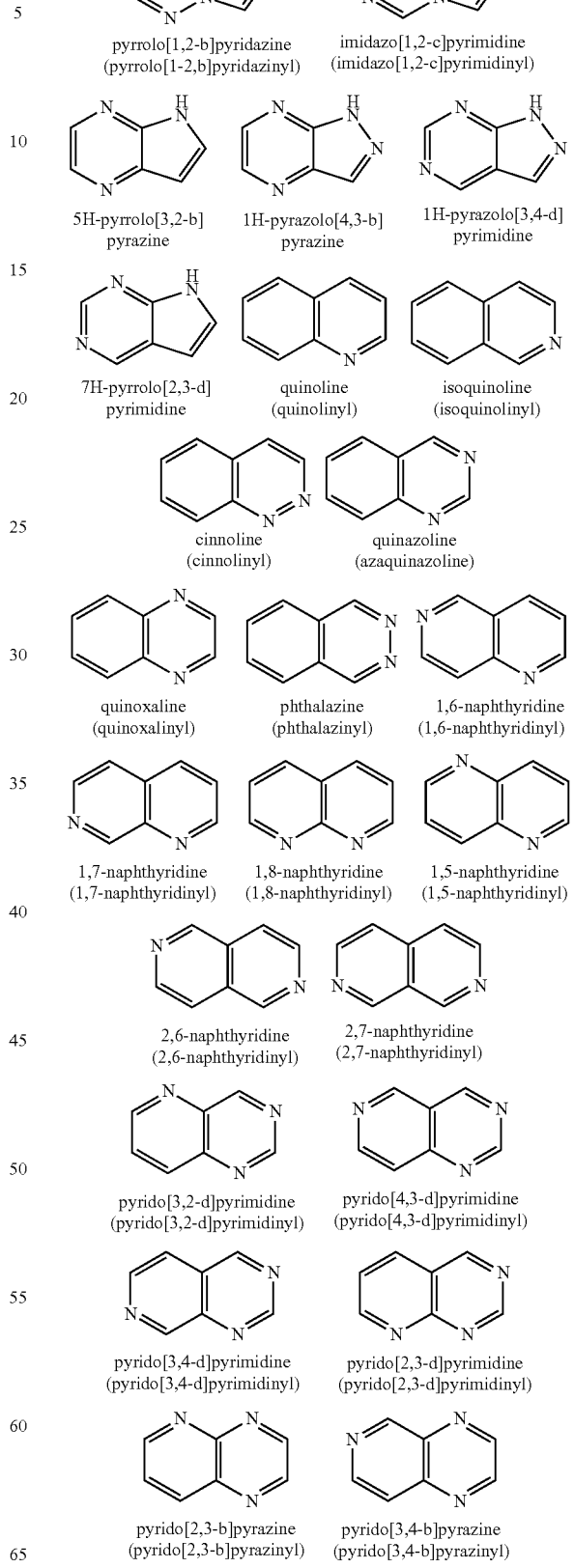

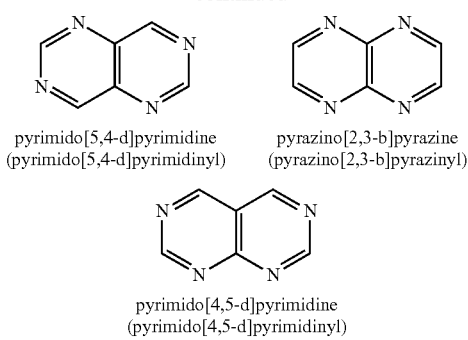

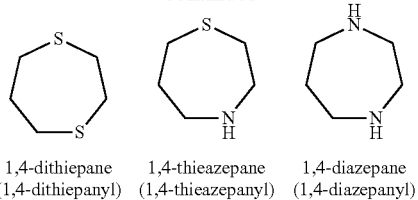

Examples of suitable partially unsaturated heteroalicyclic groups include, but are not limited to:

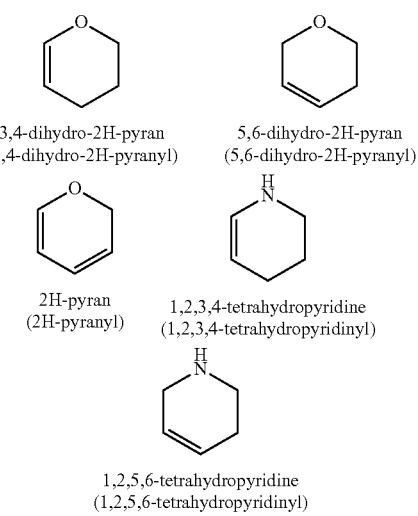

"Heterocyclyl" refers to a monocyclic or fused ring system having 3 to 12 ring atoms containing one, two, three or four ring heteroatoms selected from N, O, and $S(O)_n$ (where n is 0, 1 or 2), and 1-9 carbon atoms The rings may also have one or more double bonds. However, the rings do not have a completely conjugated pi-electron system. Preferred heterocycles include ($C_2$-$C_6$)heterocycles in accordance with the definition above. Examples of suitable saturated heteroalicyclic groups include, but are not limited to:

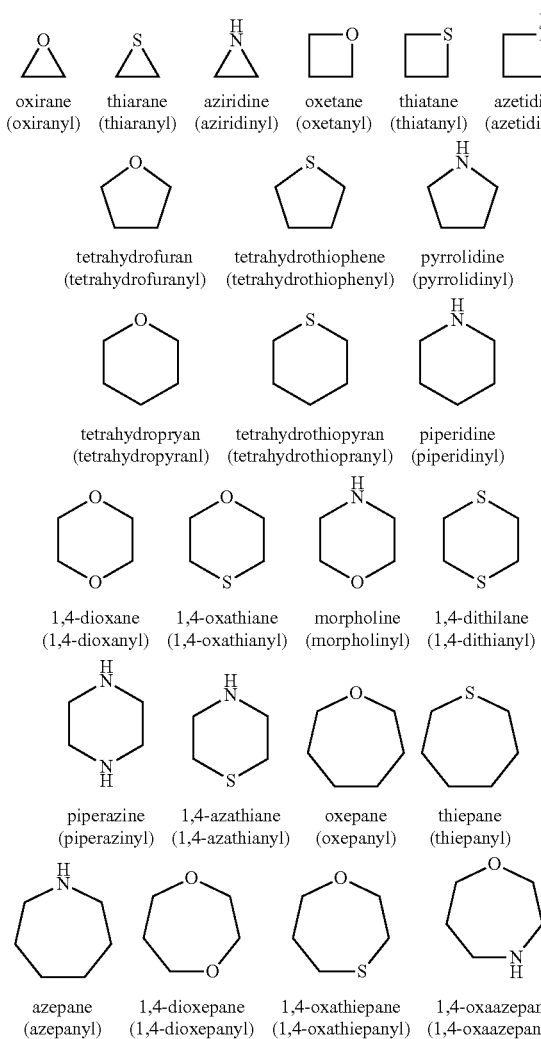

The heterocyclyl group is optionally substituted with one or two substituents independently selected from halo, lower alkyl, lower alkyl substituted with carboxy, ester hydroxy, or mono or dialkylamino. Moreover, the heterocycle may contain bridging, including bridging between non-adjacent carbons on the heterocycle, with the bridge containing 1-2 carbons and 0-1 heteroatoms selected from selected from NRx, 0, and $S(O)_n$ (where n is 0, 1 or 2).

"Hydroxy" or "hydroxyl" refers to an —OH group.

"In vitro" refers to procedures performed in an artificial environment such as, e.g., without limitation, in a test tube or culture medium.

"In vivo" refers to procedures performed within a living organism such as, without limitation, a mouse, rat or rabbit.

"Optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocycle group is not substituted with the alkyl group.

"Organism" refers to any living entity comprised of at least one cell. A living organism can be as simple as, for example, a single eukariotic cell or as complex as a mammal, including a human being.

A "pharmaceutically acceptable excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, the term "pharmaceutically acceptable salt" refers to those salts which retain the biological effectiveness and properties of the parent compound. Such salts include:

(i) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, citric acid, succinic acid or malonic acid and the like; or (ii) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "pharmaceutical composition" refers to a mixture of one or more of the compounds described herein, or physiologically/pharmaceutically acceptable salts, solvates, hydrates or prodrugs thereof, with other chemical components, such as physiologically/pharmaceutically acceptable carriers and excipients. The purpose of a pharmaceutical composition is to facilitate administration of a compound to an organism.

As used herein, a "physiologically/pharmaceutically acceptable carrier" refers to a carrier or diluent that does not cause significant irritation to an organism and does not abrogate the biological activity and properties of the administered compound.

"Therapeutically effective amount" refers to that amount of the compound being administered which will relieve to some extent one or more of the symptoms of the disorder being treated. In reference to the treatment of cancer, a therapeutically effective amount refers to that amount which has at least one of the following effects:

(1) reducing the size of the tumor;
(2) inhibiting (that is, slowing to some extent, preferably stopping) tumor metastasis;
(3) inhibiting to some extent (that is, slowing to some extent, preferably stopping) tumor growth, and
(4) relieving to some extent (or, preferably, eliminating) one or more symptoms associated with the cancer.

"Treat", "treating" and "treatment" refer to a method of alleviating or abrogating a methyltransferase mediated cellular disorder and/or its attendant symptoms. With regard particularly to cancer, these terms simply mean that the life expectancy of an individual affected with a cancer will be increased or that one or more of the symptoms of the disease will be reduced.

DETAILED DESCRIPTION

General schemes for synthesizing the compounds of the invention can be found in the Examples section herein.

Unless indicated otherwise, all references herein to the inventive compounds include references to salts, solvates, hydrates and complexes thereof, and to solvates, hydrates and complexes of salts thereof, including polymorphs, stereoisomers, and isotopically labeled versions thereof.

Pharmaceutically acceptable salts include acid addition and base salts (including disalts).

Suitable acid addition salts are formed from acids which form non-toxic salts. Examples include the acetate, aspartate, benzoate, besylate, bicarbonate/carbonate, bisulphate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminum, arginine, benzathine, calcium, choline, diethylamine, diolamine, glycine, lysine, magnesium, meglumine, olamine, potassium, sodium, tromethamine and zinc salts. For a review on suitable salts, see "Handbook of Pharmaceutical Salts: Properties, Selection, and Use" by Stahl and Wermuth (Wiley-VCH, Weinheim, Germany, 2002), the disclosure of which is incorporated herein by reference in its entirety.

A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g. $D_2O$, $d_6$-acetone, $d_6$-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized. For a review of such complexes, see J Pharm Sci, 64 (8), 1269-1288 by Haleblian (August 1975), the disclosure of which is incorporated herein by reference in its entirety.

Also within the scope of the invention are polymorphs, prodrugs, and isomers (including optical, geometric and tautomeric isomers) of the inventive compounds Derivatives of compounds of the invention which may have little or no pharmacological activity themselves but can, when administered to a patient, be converted into the inventive compounds, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association), the disclosures of which are incorporated herein by reference in their entireties.

Prodrugs in accordance with the invention can, for example, be produced by replacing appropriate functionalities present in the inventive compounds with certain moieties known to those skilled in the art as 'pro-moieties' as described, for example, in "Design of Prodrugs" by H Bundgaard (Elsevier, 1985), the disclosure of which is incorporated herein by reference in its entirety.

Some examples of prodrugs in accordance with the invention include:

(i) where the compound contains a carboxylic acid functionality —(COOH), an ester thereof, for example, replacement of the hydrogen with $(C_1-C_8)$alkyl;

(ii) where the compound contains an alcohol functionality (—OH), an ether thereof, for example, replacement of the hydrogen with $(C_1-C_6)$alkanoyloxymethyl; and (iii) where the compound contains a primary or secondary amino functionality (—NH$_2$ or —NHR where R≠H), an amide thereof, for example, replacement of one or both hydrogens with $(C_1-C_{10})$alkanoyl.

Further examples of replacement groups in accordance with the foregoing examples and examples of other prodrug types may be found in the aforementioned references.

Finally, certain inventive compounds may themselves act as prodrugs of other of the inventive compounds.

Compounds of the invention containing one or more asymmetric carbon atoms can exist as two or more stereoisomers. Where the compounds according to this invention have at least one chiral center, they may accordingly exist as enantiomers. Where the compounds possess two or more chiral centers, they may additionally exist as diastereomers. Similarly, where a compound of the invention contains a cyclopropyl group or other cyclic group where chirality exists, and alkenyl or alkenylene group, geometric cis/trans (or Z/E) isomers are possible. Where the compound contains, for example, a keto or oxime group or an aromatic moiety, tautomeric isomerism ('tautomerism') can occur. A single compound may exhibit more than one type of isomerism.

Included within the scope of the invention are all stereoisomers, geometric isomers and tautomeric forms of the inventive compounds, including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC) or supercritical fluid chromatography (SFC).

Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art.

Stereoisomeric conglomerates may be separated by conventional techniques known to those skilled in the art; see, for example, "Stereochemistry of Organic Compounds" by E L Eliel (Wiley, New York, 1994), the disclosure of which is incorporated herein by reference in its entirety.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Pharmaceutically acceptable solvates in accordance with the invention include those wherein the solvent of crystallization may be isotopically substituted, e.g. D$_2$O, de-acetone, de-DMSO.

Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

The compounds can be administered alone or in combination with one or more other compounds of the invention. Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the invention and methods for their preparation will be readily apparent to those skilled in the art. Such compositions and methods for their preparation can be found, for example, in 'Remington's Pharmaceutical Sciences', 19th Edition (Mack Publishing Company, 1995), the disclosure of which is incorporated herein by reference in its entirety.

Oral Administration: The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be used as fillers in soft or hard capsules and typically include a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986 by Liang and Chen (2001), the disclosure of which is incorporated herein by reference in its entirety.

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally include surface active agents, such as sodium lauryl sulfate and polysorbate 80, and glidants such as silicon dioxide and talc. When present, surface active agents are typically in amounts of from 0.2 wt % to 5 wt % of the tablet, and glidants typically from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally are present in amounts from 0.25 wt % to 10 wt %, preferably from 0.5 wt % to 3 wt % of the tablet.

Other conventional ingredients include anti-oxidants, colorants, flavoring agents, preservatives and taste-masking agents.

Exemplary tablets contain up to about 80 wt % drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tableting. The final formulation may include one or more layers and may be coated or uncoated; or encapsulated.

The formulation of tablets is discussed in detail in "Pharmaceutical Dosage Forms: Tablets, Vol. 1", by H. Lieberman and L. Lachman, Marcel Dekker, N.Y., N.Y., 1980 (ISBN 0-8247-6918-X), the disclosure of which is incorporated herein by reference in its entirety. Solid formulations for oral administration may be formulated to be immediate and/or modified release. Modified release formulations include delayed-, sustained-, pulsed-, controlled-, targeted and programmed release.

Suitable modified release formulations are described in U.S. Pat. No. 6,106,864. Details of other suitable release technologies such as high energy dispersions and osmotic and coated particles can be found in Verma et al, Pharmaceutical Technology On-line, 25(2), 1-14 (2001). The use of chewing gum to achieve controlled release is described in WO 00/35298. The disclosures of these references are incorporated herein by reference in their entireties.

Parenteral Administration

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including micro needle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of the invention used in the preparation of parenteral solutions may be increased by the use of appropriate formulation techniques, such as the incorporation of solubility-enhancing agents. Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

Topical Administration

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J Pharm Sci, 88 (10), 955-958 by Finnin and Morgan (October 1999). Other means of topical administration include delivery by electroporation, iontophoresis, phonophoresis, sonophoresis and micro needle or needle-free (e.g. Powderject™, Bioject™, etc.) injection. The disclosures of these references are incorporated herein by reference in their entireties.

Formulations for topical administration may be formulated to be immediate and/or modified release. Modified release formulations include delayed-, sustained-, pulsed-, controlled-, targeted and programmed release.

Inhaled/Intranasal Administration

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3, 3-heptafluoropropane. For intranasal use, the powder may include a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 μg to 20 mg of the compound of the invention per actuation and the actuation volume may vary from 1 μL to 100 μL. A typical formulation includes a compound of the invention, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing a desired mount of the compound of the invention. The overall daily dose may be administered in a single dose or, more usually, as divided doses throughout the day.

Rectal/Intravaginal Administration: Compounds of the invention may be administered rectally or vaginally, for example, in the form of a suppository, pessary, or enema. Cocoa butter is a traditional suppository base, but various alternatives may be used as appropriate. Formulations for rectal/vaginal administration may be formulated to be immediate and/or modified release. Modified release formulations include delayed-, sustained-, pulsed-, controlled-, targeted and programmed release.

Ocular Administration: Compounds of the invention may also be administered directly to the eye or ear, typically in the form of drops of a micronized suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

Other Technologies

Compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubilizer. Most commonly used for these purposes are alpha-, beta- and gamma-cyclodextrins, examples of which may be found in PCT Publication Nos. WO 91/11172, WO 94/02518 and WO 98/55148, the disclosures of which are incorporated herein by reference in their entireties.

Dosage: The amount of the active compound administered will be dependent on the subject being treated, the severity of the disorder or condition, the rate of administration, the disposition of the compound and the discretion of the prescribing physician. However, an effective dosage is typically in the range of about 0.001 to about 100 mg per kg body weight per day, preferably about 0.01 to about 35 mg/kg/day, in single or divided doses. For a 70 kg human, this would amount to about 0.07 to about 7000 mg/day, preferably about 0.7 to about 2500 mg/day. In some instances, dosage levels below the lower limit of the aforesaid range may be more than adequate, while in other cases still larger doses may be used without causing any harmful side effect, with such larger doses typically divided into several smaller doses for administration throughout the day.

Kit-of-Parts: Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions. Thus the kit of the invention includes two or more separate pharmaceutical compositions, at least one of which contains a compound of the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically includes directions for administration and may be provided with a memory aid.

EXAMPLES

General Synthetic Schemes for Ribose Compounds

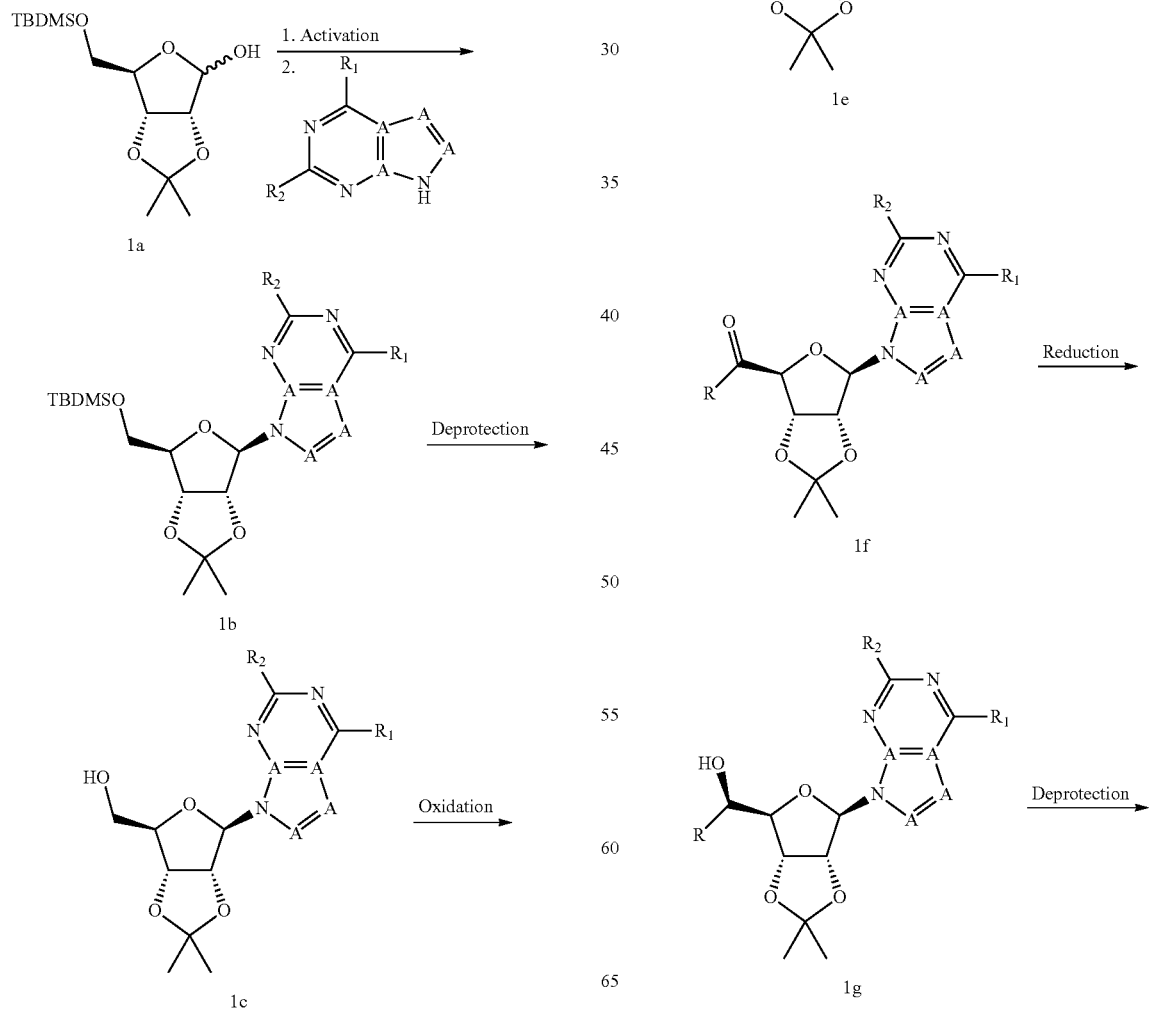

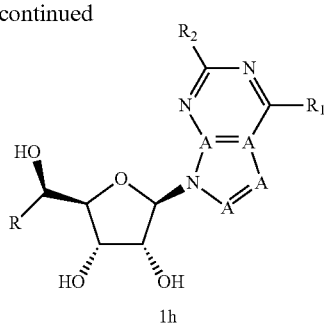

1h

As exemplified in Scheme 1, an appropriately protected ribose such as 1a can be purchased or synthesized (*J. Am. Chem. Soc.* 1988, 110, 7128-7135). Typically, (3aR,6R, 6aR)-6-(((tert-butyldimethylsilyl)oxy)methyl)-2,2-dimethyltetrahydrofuro[3,4-d][1,3]dioxol-4-ol (1a) is activated at the C1 position to a leaving group such as; fluoride using N,N-diethyl-α,α-difluoro-(m-methylbenzyl)amine, diethylamino sulphur trifluoride (DAST) or pyridine hydrogenfluoride; chloride using $CCl_4$ and HMPT, dimethyltrichloromethylamine, or methane sulfonyl chloride; bromide using trimethylsilyl bromide, hydrogen bromide or carbon tetrabromide; or acetate using acetic anhydride and pyridine. Typically these reactions are run at low temperatures ranging from −78° C. to −20° C. in solvents such as toluene. Displacement of the C1 activated sugar with a nucleoside or nitrogen containing heterocycle is done with a base such as sodium hydride, potassium hydroxide or TDA-1 to give compounds such as 1b. These reactions are typically run at room temperature in the same solvent as the activation. Alternatively, displacement of the C1 activated sugar can be done with a nucleoside or nitrogen containing heterocycle and trimethylsilyl trifluoromethanesulfonate or a Lewis acid such as diethylaluminum dichloride to give compounds such as 1b. These reactions are typically run in solvents such as toluene, acetonitrile, THF or similar solvent at temperatures ranging from −78° C. to 60° C. Deprotection of the primary alcohol of 1b is typically done with a fluoride source such as TBAF to give compounds such as 1c. Typically, these reactions are run in THF solvent at temperatures ranging from 0° C. to room temperature. Oxidation of the primary alcohol 1c to compounds such as the carboxylic acid 1d are typically done with TEMPO and $NaClO_2$ or $PhI(OAc)_2$. Typically, these reactions are run in acetonitrile and water mixtures at temperatures ranging from −20° C. to 60° C. Compounds similar to the carboxylic acid 1d are converted to compounds such as the Weinreb amide 1e via treatment with N,O-dimethylhydroxylamine HCl and standard amide coupling reagents such as HOBT and EDCl, T3P or HATU with a base such as DIPEA or TEA. Typically, these reactions are done in solvents such as DMF or THF and run at temperatures ranging from 0° C. to 60° C. Weinreb amides such as 1e are converted into alkyl and aryl ketones such as 1f using alkyl and aryl metal reagents such as alkyl and aryl Grignards (M=Mg), alkyl and aryl lithium reagents, alkyl and aryl cuprates, alkyl and aryl zincates as well as other organometal reagents. Typically these reactions are run in ethereal solvents such as THF, MeTHF, dioxane or similar solvent at temperatures ranging from −78° C. to 60° C. Alkyl and aryl ketones such as 1f can be converted to secondary alcohols such as 1g using reducing reagents such as $NaBH_4$, $LiBH_4$, $LiAlH_4$, DIBAL and others. Typically these reactions can be run in a variety of solvents such as DCM, THF, MeOH, EtOH or others at varying temperatures. Alkyl and aryl ketones such as 1f can be preferentially converted to diastereomerically enriched secondary alcohols such as 1g using chiral reducing conditions such as RuCl(p-cymene) [(R,R)-Ts-DPEN] and sodium formate (*J. Org. Chem*, 2014, 79, 3238-3243). Typically, these reactions are done in EtOAc solvent and run at room temperature. Finally, compounds such as 1g can be deprotected to reveal the triol compounds such as 1h by treatment with acid such as TFA or dilute HCl. Typically these reactions are done in the presence of water at 0° C. or rt. Compounds at every step may be purified by standard techniques such as column chromatography, crystallization, reverse phase HPLC or SFC. If necessary, separation of the diastereomers of 1g or 1h may be carried out under standard methods known in the art such as chiral SFC or HPLC to afford single diastereomers.

Scheme 2:

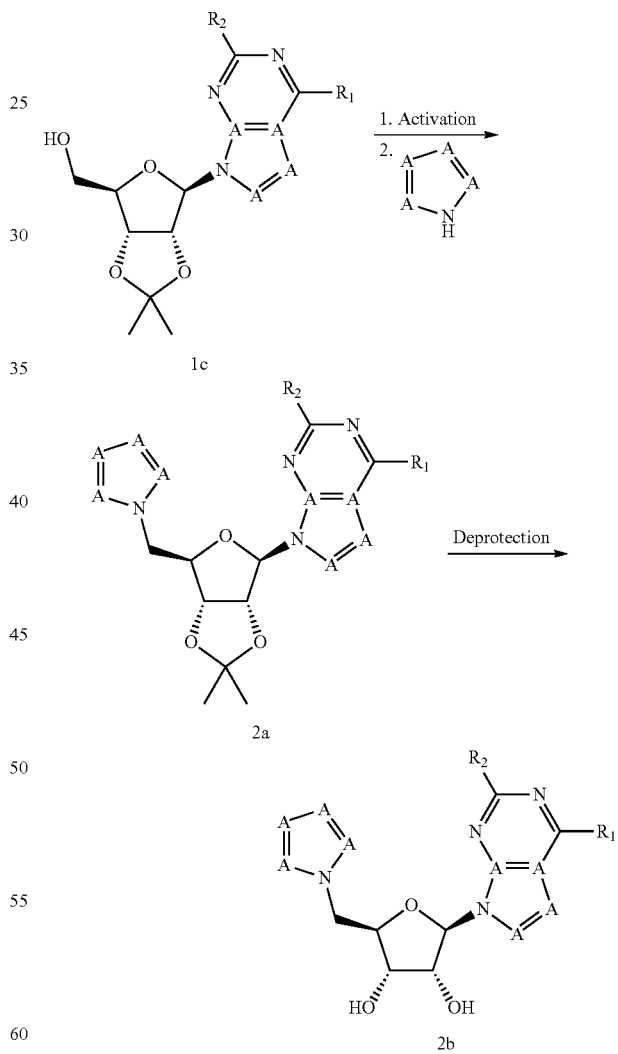

As exemplified in Scheme 2, compounds such as 1c can be activated at the primary alcohol with reagents such as cyanomethylenetributylphosphorane. A nitrogen containing aromatic heterocycle such as pyrrole, pyrazole, imidazole or similar heterocycle can be used in the reaction to generate compounds such as 2a. Typically, these reactions are done in toluene, THF, acetonitrile or similar solvent at temperatures ranging from room temperature to 100° C. Compounds such as 2a can be deprotected to reveal the diol compounds such as 2b by treatment with acid such as TFA or dilute HCl. Typically these reactions are done in the presence of water at 0° C. or rt. Compounds at each step may be purified by standard techniques such as column chromatography, crystallization, reverse phase HPLC or chiral SFC.

Scheme 3:

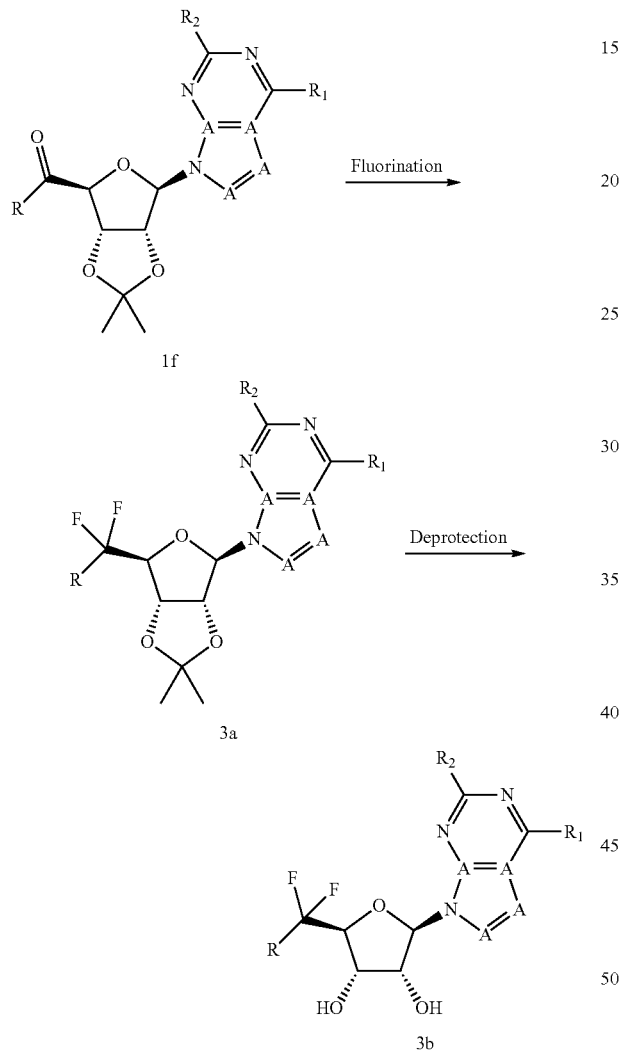

As exemplified in Scheme 3, alkyl and aryl ketones such as compound 1f can be converted to the corresponding germinal difluoro compound such as 3a using fluorinating reagents such as diethylaminosulfurtrifluoride, DAST, BAST, NFSI or similar reagent. These reactions are typically run in halogenated solvents such as DCM or DCE. Compounds such as 3a can be deprotected to reveal the diol compounds such as 3b by treatment with acid such as TFA or dilute HCl. Typically these reactions are done in the presence of water at 0° C. or rt. Compounds at each step may be purified by standard techniques such as column chromatography, crystallization, reverse phase HPLC or chiral SFC.

General Synthetic Schemes for Lyxose Compounds

Scheme 4:

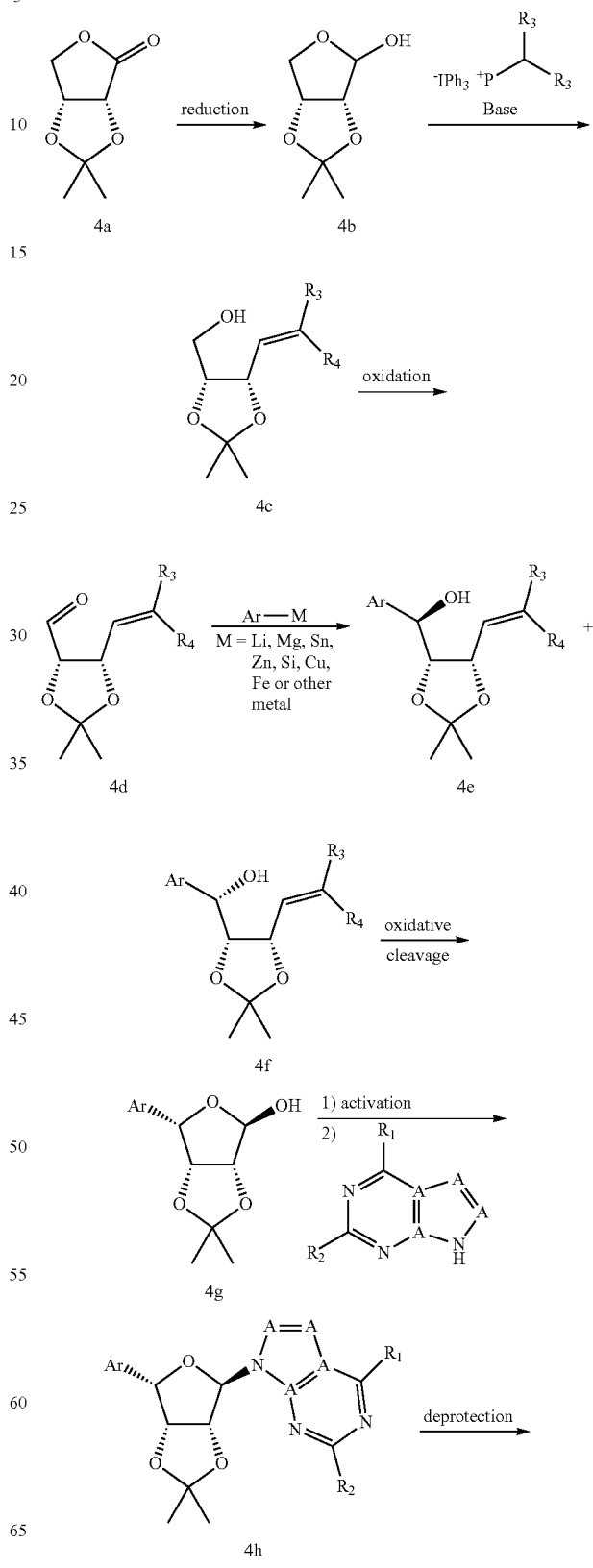

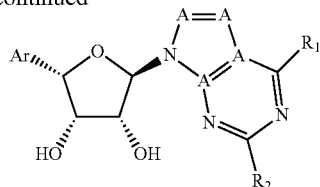

4i

As exemplified in Scheme 4, lactone compounds such as 4a can be converted to lactol compounds such as 4b using reducing regents such as LiAlH$_4$, NaBH$_4$, LiBH$_4$, DIBAL or similar reagent. Typically these reactions can be run in a variety of solvents such as DCM, THF, MeOH, EtOH or others at varying temperatures (*J. Am. Chem. Soc.* 1983, 105, 3661-3672). Lactol compounds such as 4b can be converted alkene compounds such as 4c by reaction with an alkylphosphonium salt such as isopropyltriphenylphosphonium iodide and a base such as butyllithium, sodium hydride, lithium hexamethyldisilylamide or similar base. Typically these reactions are run in solvent such as toluene, THF or similar solvent at temperatures ranging from –78° C. to room temperature (*J. Org. Chem.* 1993, 58, 3277-3284). Primary alcohol compounds such as 4c are oxidized to aldehydes such as compound 4d using hypervalent iodide reagents such as Dess-Martin Periodinane, activation of DMSO with oxalyl chloride or thionyl chloride, or through other oxidative reagents. These reactions are typically run in a variety of solvents such as DCM, THF, acetonitrile or DCE at temperatures ranging from 0° C. to 80° C. Aldehydes such as 4d are converted into aryl alcohols such as 4e and 4f using aryl metal reagents such as aryl Grignards (M=Mg), aryl lithium reagents, aryl cuprates, aryl zincates as well as other organometal reagents. Typically these reactions are run in ethereal solvents such as THF, MeTHF, dioxane or similar solvent at temperatures ranging from –78° C. to 60° C. Aryl alcohols such as 4f can be converted into lactols such as 4g by treatment with ozone and a reducing reagent such as dimethylsulfide or triphenylphosphine. Typically, these reactions are run in solvents such as DCM, THF, MeOH or similar solvent at temperatures ranging from –78° C. to 0° C. Typically, lactols such as compound 4g are activated at the C1 position to a leaving group such as; fluoride using N,N-diethyl-α,α-difluoro-(m-methylbenzyl)amine, diethylamino sulphur trifluoride (DAST) or pyridine hydrogenfluoride; chloride using CCl$_4$ and HMPT, dimethyltrichloromethylamine, or methane sulfonyl chloride; bromide using trimethylsilyl bromide, hydrogen bromide or carbon tetrabromide; or acetate using acetic anhydride and pyridine. Typically these reactions are run at low temperatures ranging from –78° C. to –20° C. in solvents such as toluene. Displacement of the C1 activated lactol with a nucleoside or nitrogen containing heterocycle is done with a base such as sodium hydride, potassium hydroxide or TDA-1 to give compounds such as 4h. These reactions are typically run at room temperature in the same solvent as the activation. Alternatively, displacement of the C1 activated lactol can be done with a nucleoside or nitrogen containing heterocycle and trimethylsilyl trifluoromethanesulfonate or a Lewis acid such as diethylaluminum dichloride to give compounds such as 4h. These reactions are typically run in solvents such as toluene, acetonitrile, THF or similar solvent at temperatures ranging from –78° C. to 60° C. Compounds such as 4h can be deprotected to reveal the diol compounds such as 4i by treatment with acid such as TFA or dilute HCl. Typically these reactions are done in the presence of water at 0° C. or rt. Compounds at every step may be purified by standard techniques such as column chromatography, crystallization, reverse phase HPLC or SFC. If necessary, separation of the diastereomers of 4e and 4f may be carried out under standard methods known in the art such as chiral SFC or HPLC to afford single diastereomers.

Scheme 5:

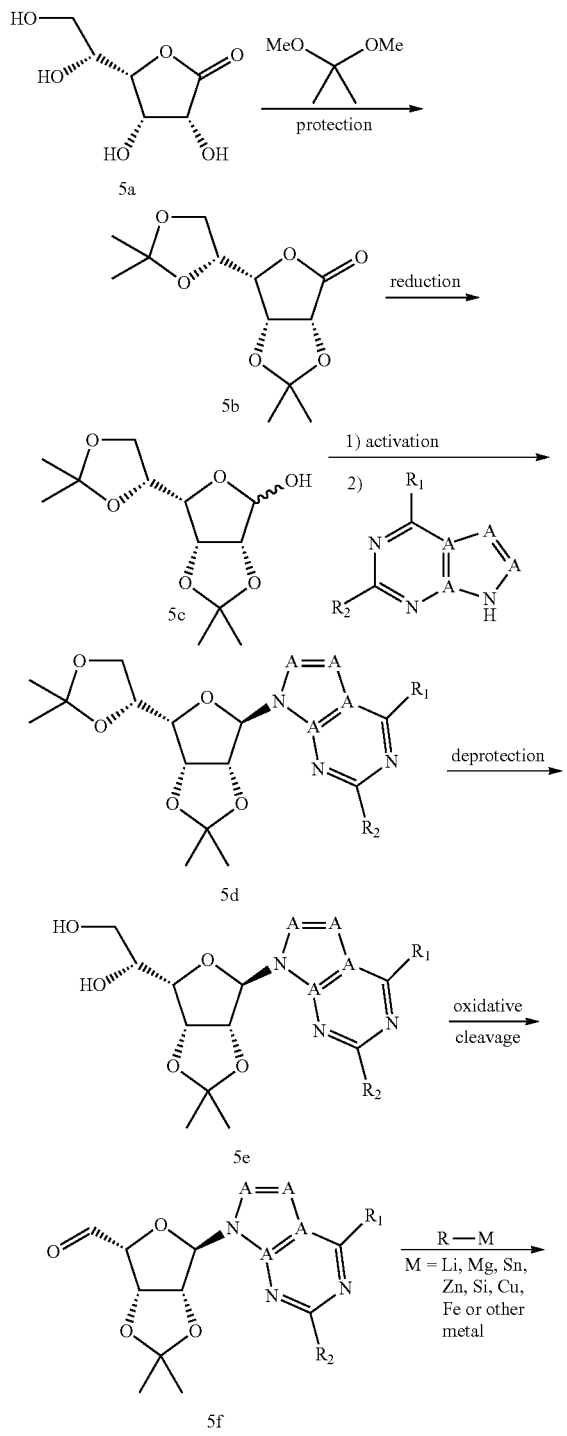

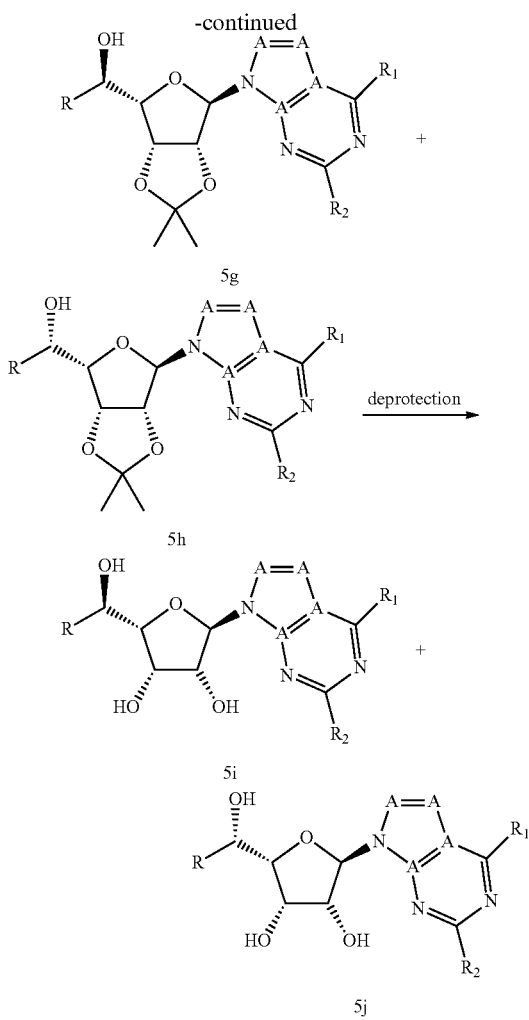

As exemplified in Scheme 5, lactols such as compound 5c can be purchased or synthesized by protecting D-gulonic lactone (5a) or (3R,4S,5S)-5-((R)-1,2-dihydroxyethyl)-3,4-dihydroxydihydrofuran-2(3H)-one and protecting it to form compounds such as 5b by treatment with acetone or 2,2-dimethoxypropane and acid such as p-toluenesulfonic acid or dilute HCl. Typically, these reactions are run in solvents such as toluene or acetone at room temperature (*Synthesis* 2008, 22, 3682-3686). Protected lactone compounds such as 5b can be converted to lactol compounds such as 5c using reducing regents such as LiAlH$_4$, NaBH$_4$, LiBH$_4$, DIBAL or similar reagent. Typically these reactions can be run in a variety of solvents such as DCM, THF, MeOH, EtOH or others at varying temperatures (*J. Org. Chem.* 1984, 49, 3994-4003). Activation of lactols such as 5c can be achieved at the C1 position to a leaving group such as; fluoride using N,N-diethyl-α,α-difluoro-(m-methylbenzyl)amine, diethylamino sulphur trifluoride (DAST) or pyridine hydrogenfluoride; chloride using CCl$_4$ and HMPT, dimethyltrichloromethylamine, or methane sulfonyl chloride; bromide using trimethylsilyl bromide, hydrogen bromide or carbon tetrabromide; or acetate using acetic anhydride and pyridine. Typically these reactions are run at low temperatures ranging from −78° C. to −20° C. in solvents such as toluene. Displacement of the C1 activated sugar with a nucleoside or nitrogen containing heterocycle is done with a base such as sodium hydride, potassium hydroxide or TDA-1 to give compounds such as 5d. These reactions are typically run at room temperature in the same solvent as the activation. Alternatively, displacement of the C1 activated sugar can be done with a nucleoside or nitrogen containing heterocycle and trimethylsilyl trifluoromethanesulfonate or a Lewis acid such as diethylaluminum dichloride to give compounds such as 5d. These reactions are typically run in solvents such as toluene, acetonitrile, THF or similar solvent at temperatures ranging from −78° C. to 60° C. Compounds such as 5d can be selectively deprotected to give diols such as 5e by treatment with mild acetic acid. Typically, these reactions are run in aqueous acetic acid at room temperature. Diol compounds such as 5e can be converted to aldehyde compounds such as 5f by treatment with mild oxidants such as sodium periodate or similar reagents. Typically, these reactions are run in solvents such as THF, acetonitrile or water at room temperature. Aldehyde compounds such as 5f are converted into alkyl and aryl alcohols such as 5g and 5h using alkyl and aryl metal reagents such as alkyl and aryl Grignards (M=Mg), aryl lithium reagents, alkyl and aryl cuprates, alkyl and aryl zincates as well as other organometal reagents. Typically these reactions are run in ethereal solvents such as THF, MeTHF, dioxane or similar solvent at temperatures ranging from −78° C. to 60° C. Compounds such as 5g and 5h can be deprotected to reveal the triol compounds such as 5i and 5j by treatment with acid such as TFA or dilute HCl. Typically these reactions are done in the presence of water at 0° C. or rt. Compounds at every step may be purified by standard techniques such as column chromatography, crystallization, reverse phase HPLC or SFC. If necessary, separation of the diastereomers of 5g and 5h or 5i and 5j may be carried out under standard methods known in the art such as chiral SFC or HPLC to afford single diastereomers.

Scheme 6:

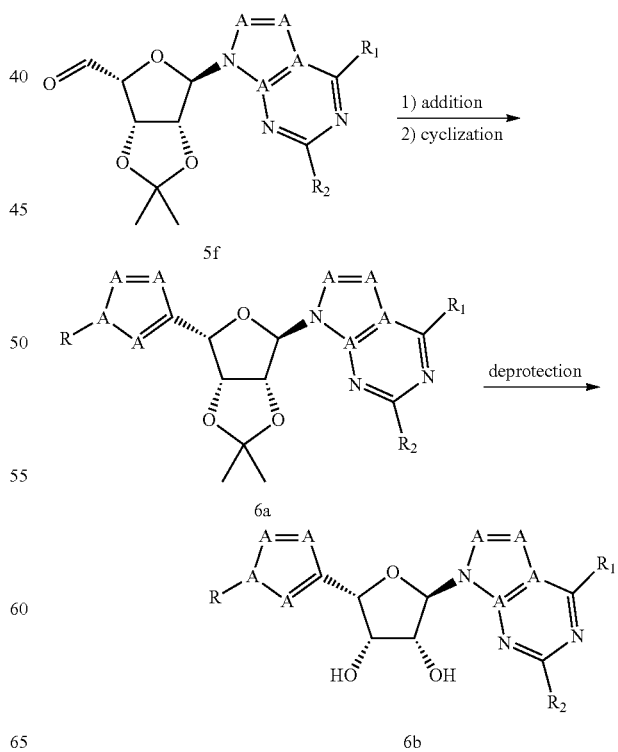

As exemplified in Scheme 6, aldehyde compounds such as 5f can be treated with reagents such as TOSMIC and then cyclization can be promoted with reagents such as potassium carbonate or ammonia to form 5-membered ring heterocyclic compounds such as 6a. Typically, these reactions are run in solvents such as MeOH, EtOH, THF or similar solvent at temperatures ranging from 25° C.-80° C. In another alternative, aldehyde compounds such as 5f can be treated with acetylinicmetal compounds such as ethynylmagnesium bromide or similar reagent to form propargyl alcohols. These reactions are typically done in ethereal solvents such as THF, MeTHF, dioxane or similar solvent at temperatures ranging from −78° C.-0° C. The propargyl alcohols are then oxidized to propargyl ketones using oxidants such as Dess Martin Periodinane or similar reagent and then cyclized with hydrazines to give 5-membered ring heterocyclic compounds such as 6a. Typically, the oxidation reaction is run in solvents such as DCM, DCE or similar solvent at room temperature. The crude material is then extracted and redissolved in solvent such as MeOH, EtOH or similar solvent with the desired hydrazine at temperatures ranging from 25° C.-80° C. Compounds such as 6a can be deprotected to reveal the diol compounds such as 6b by treatment with acid such as TFA or dilute HCl. Typically these reactions are done in the presence of water at 0° C. or rt. Compounds at every step may be purified by standard techniques such as column chromatography, crystallization, reverse phase HPLC or SFC. If necessary, separation of 6b may be carried out under standard methods known in the art such as chiral SFC or HPLC to afford a single enantiomer.

General Synthetic Schemes for C-Glycoside Compounds

Scheme 7:

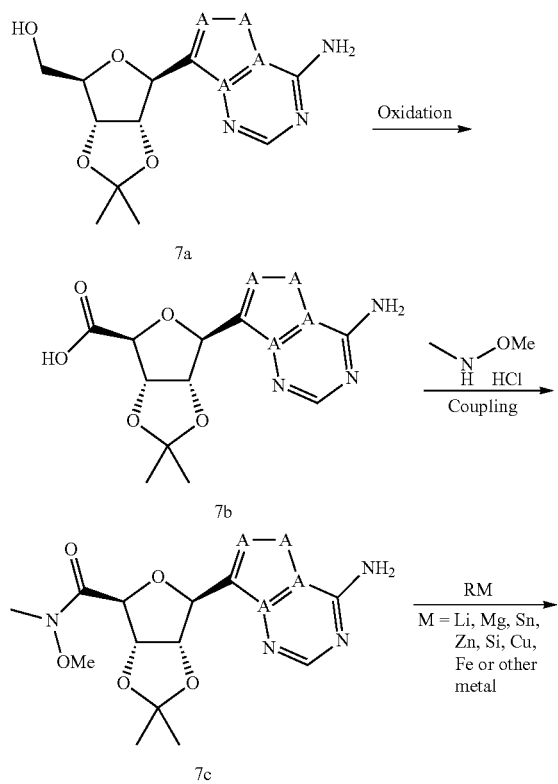

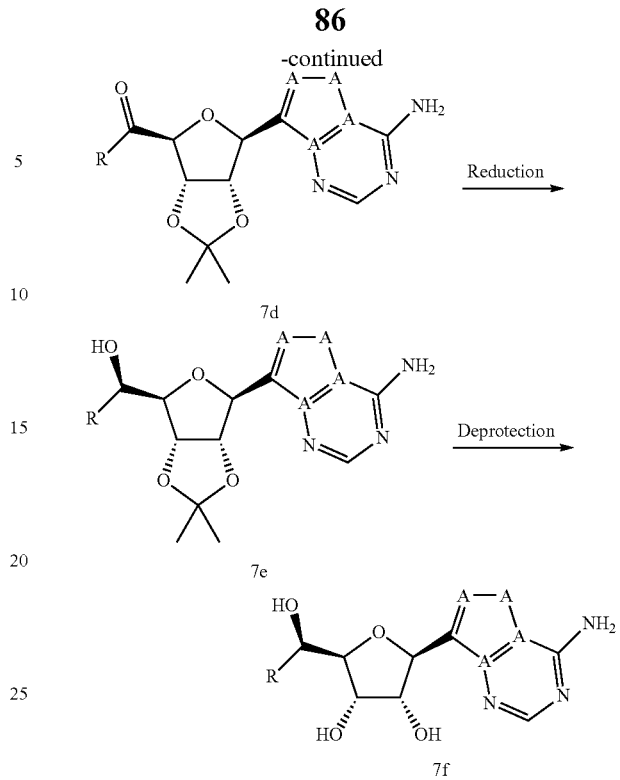

As exemplified in Scheme 7, compounds such as 7a which can be synthesized by a variety of methods (*J. Med. Chem.* 1974, 17, 1286-1289; US2012/77814 A1, 2012) can be oxidized to carboxylic acids such as 7b by treatment with TEMPO and $NaClO_2$ or $PhI(OAc)_2$ or similar oxidizing reagent. Typically, these reactions are run in acetonitrile and water mixtures at temperatures ranging from −20° C. to 60° C. Compounds similar to the carboxylic acid 7b are converted to compounds such as the Weinreb amide 7c via treatment with N,O-dimethylhydroxylamine HCl and standard amide coupling reagents such as HOBT and EDCl, T3P or HATU with a base such as DIPEA or TEA. Typically, these reactions are done in solvents such as DMF or THF and run at temperatures ranging from 0° C. to 60° C. Weinreb amides such as 7c are converted into alkyl and aryl ketones such as 7d using alkyl and aryl metal reagents such as alkyl and aryl Grignards (M=Mg), alkyl and aryl lithium reagents, alkyl and aryl cuprates, alkyl and aryl zincates as well as other organometal reagents. Typically these reactions are run in ethereal solvents such as THF, MeTHF, dioxane or similar solvent at temperatures ranging from −78° C. to 60° C. Alkyl and aryl ketones such as 7d can be converted to secondary alcohols such as 7e using reducing reagents such as $NaBH_4$, $LiBH_4$, $LiAlH_4$, DIBAL and others. Typically these reactions can be run in a variety of solvents such as DCM, THF, MeOH, EtOH or others at varying temperatures. Alkyl and aryl ketones such as 7d can be preferentially converted to diastereotopically enriched secondary alcohols such as 7e using chiral reducing conditions such as RuCl (p-cymene)[(R,R)-Ts-DPEN] and sodium formate (*J. Org. Chem*, 2014, 79, 3238-3243). Typically, these reactions are done in EtOAc solvent and run at room temperature. Finally, compounds such as 7e can be deprotected to reveal the triol compounds such as 7f by treatment with acid such as TFA or dilute HCl. Typically these reactions are done in the presence of water at 0° C. or rt. Compounds at every step may be purified by standard techniques such as column chromatography, crystallization, reverse phase HPLC or SFC. If necessary, separation of the diastereomers of 7e or 7f may be carried out under standard methods known in the art such as chiral SFC or HPLC to afford single diastereomers.

Examples

For some of the steps of the here above described process of preparation of the compounds of the invention, it may be necessary to protect potential reactive functions that are not wished to react, and to cleave said protecting groups in consequence. In such a case, any compatible protecting radical may be used. In particular methods of protection and deprotection such as those described by T. W. Greene (*Protective Groups in Organic Synthesis*, A. Wiley-Interscience Publication, 1981) or by P. J. Kocienski (*Protecting groups*, Georg Thieme Verlag, 1994), may be used.

All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

The following abbreviations may be used herein:

Ac (acetyl); AcCl (acetyl chloride); AcOH or HOAc (acetic acid); Ac₂O (acetic anhydride); aq. (aqueous); Boc or boc (tert-butoxycarbonyl); ca. (about or approximately); CDCl₃ (deuterated chloroform); CH₂Cl₂ and/or DCM (dichloromethane); DAST (Diethylaminosulfur trifluoride); DCE (dichloroethane); DEA (diethylamine); DIBAL or DIBAL-H (diisobutylaluminum hydride); DIC (diisopropylcarbodiimide); DIPEA or Hunig's base (N,N-diisopropylethylamine); DMA (dimethylacetamide); DMF (dimethylformamide); DME (ethylene glycol); DMP (Dess-Martin Periodinane); DMAP (4-dimethylaminopyridine); DMSO (dimethylsulfoxide); DMSO-d₆ (deuterated dimethylsulfoxide); EDC or EDCI (1-ethyl-3-(3-dimethylaminopropyl)-carbodiimide); Et (ethyl); Et₃N or TEA (triethylamine); EtOH (ethanol); EtOAc (ethyl acetate); Et₂O (diethyl ether); g or gm (gram or grams); HATU (2-(7-aza-1H-benzotriazole-1-yl)-1,1,3,3-tetramethyluronium hexafluorophosphate); HBTU (o-(benzotriazole-1-yl)-1,1,3,3-tetramethyluronium hexafluorophosphate); HMPT (Tris(dimethylamino)phosphine); HPLC (high-performance liquid chromatography); HOBT (1-hydroxy benzotriazole); h or hr (hour or hours, as appropriate); iBu (isobutyl); IPA (iso-propyl alcohol); iPr (isopropyl); iPrOAc (isopropyl acetate); KHMDS (potassium bis(trimethylsilyl)amide); KOAc (potassium acetate); LCMS (liquid chromatography-mass spectrometry); LiHMDS (lithium bis(trimethylsilyl)amide); Me (methyl); MeOH (methanol); MeOD (deuterated methanol); MeCN (acetonitrile); m or min (minute or minutes, as appropriate); mg (milligram or milligrams); Ms (methylsulfonyl); MsCl (methanesulfonyl chloride); N (normal); NBS (N-Bromosuccinimide); NFSI (N-Fluorodibenzenesulfonimide); NMR (nuclear magnetic resonance); nBu (n-butyl); nBuLi (n-butyl lithium); nPr (n-propyl); Pd/C (palladium on carbon); Pd₂(dba)₃ (tris(dibenzylideneacetone)dipalladium(0)); Pd(dppf)Cl₂ ([1,1'-bis(diphenylphosphino)ferrocene]dichloropalladium(II)); Ph (phenyl); PTSA or pTSA (p-Toluene sulfonic acid); Rt (retention time); rt (room temperature); RuCl(p-cymene)[(R,R)-Ts-DPEN]([N-[(1R,2R)-2-(Amino-κN)-1,2-diphenylethyl]-4-methylbenzenesulfonamidato-κN]chloro[(1,2,3,4,5,6-η)-1-methyl-4-(1-methylethyl)benzene]-ruthenium); s or sec (second or seconds, as appropriate); Selectfluor (N-Chloromethyl-N'-fluorotriethylenediammonium bis(tetrafluoroborate)); SEM (2-Trimethylsilylethoxymethoxy); SFC (supercritical fluid chromatography); Si-Thiol (silica 1-propanethiol); T3P (propylphosphonic anhydride); TBAF (tetrabutyl ammonium fluoride); TBDMSCl (t-butyl-dimethylsilyl chloride); TBME or MTBE (tert-butyl methyl ether); t-BuOH (2-methyl-2-propanol, tert-butanol or tert-butyl alcohol); TDA-1 (Tris[2-(2-methoxyethoxy)ethyl]amine or Tris(3,6-dioxaheptyl)amine); TEA, NEt₃ or Et₃N (triethylamine); TFA (trifluoroacetic acid); THF (tetrahydrofuran); THP (tetrahydropyran); TLC (thin layer chromatography); TMS (trimethylsilyl); TMSCl (trimethylsilyl chloride); TMSCF₃ (Trimethyl(trifluoromethyl)silane); Tos or tosyl (4-toluenesulfonyl); TOSMIC (p-Toluenesulfonylmethyl isocyanide); UV (ultraviolet).

Example 1

(Scheme A) (2R,3R,4S,5R)-2-(6-amino-9H-purin-9-yl)-5-((R)-1-hydroxyethyl)tetrahydrofuran-3,4-diol (A-8)

Example 2

(Scheme A) (2R,3R,4S,5R)-2-(6-amino-9H-purin-9-yl)-5-((S)-1-hydroxyethyl)tetrahydrofuran-3,4-diol (A-9)

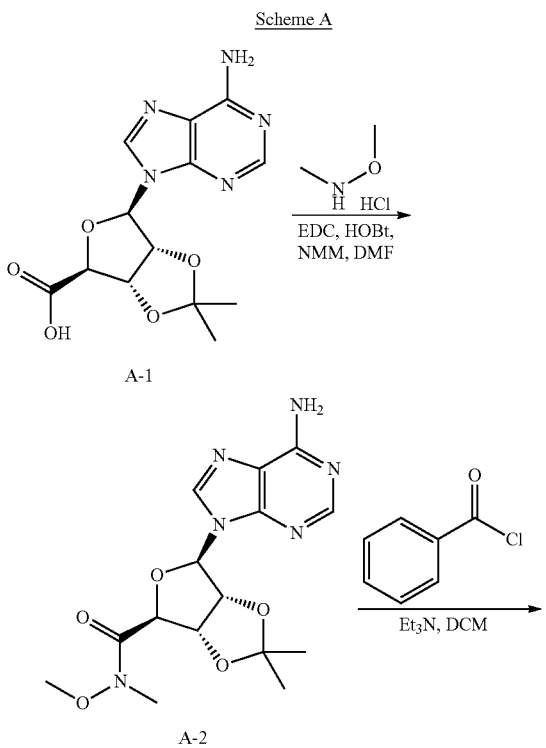

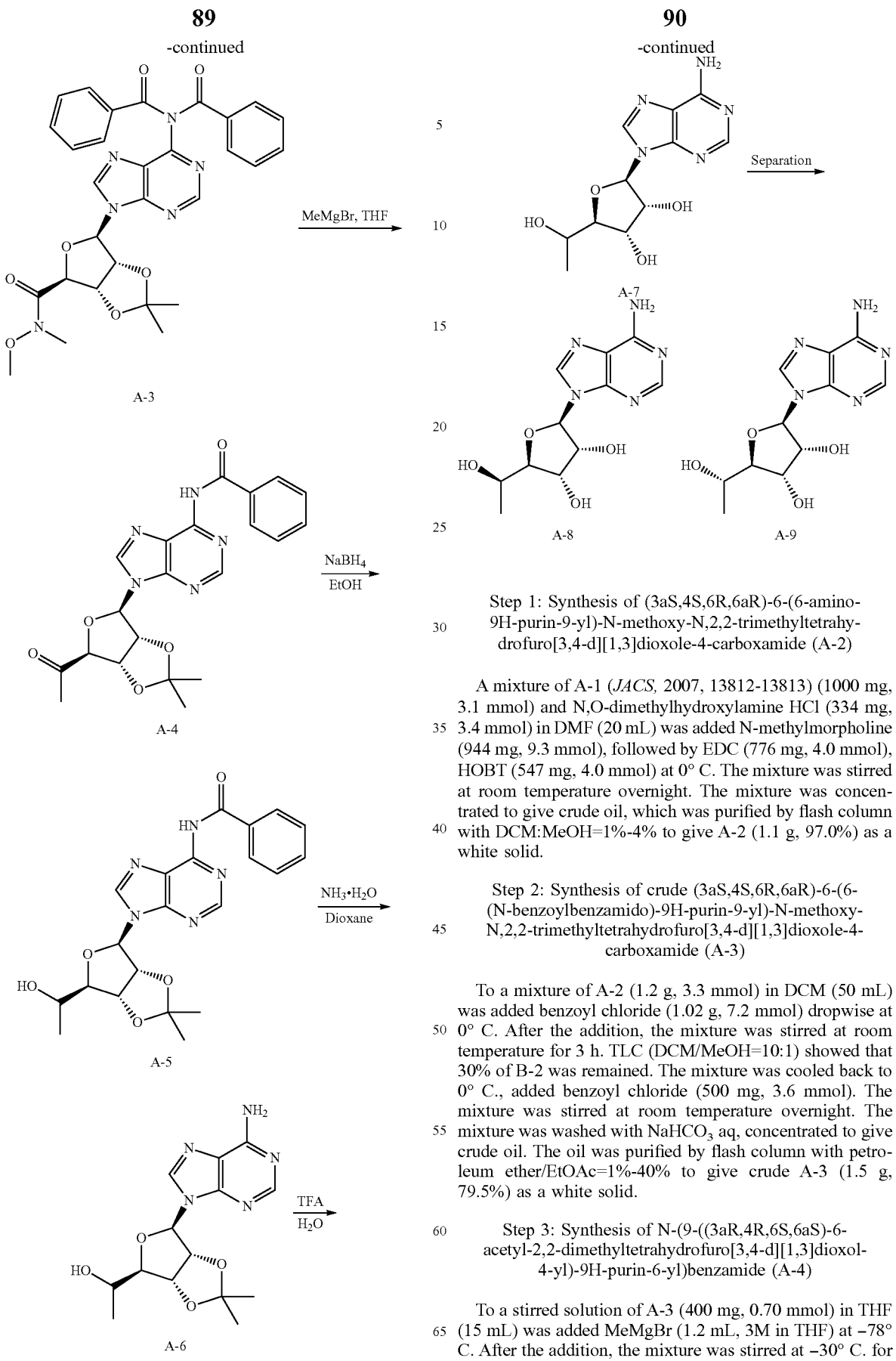

Step 1: Synthesis of (3aS,4S,6R,6aR)-6-(6-amino-9H-purin-9-yl)-N-methoxy-N,2,2-trimethyltetrahydrofuro[3,4-d][1,3]dioxole-4-carboxamide (A-2)

A mixture of A-1 (*JACS*, 2007, 13812-13813) (1000 mg, 3.1 mmol) and N,O-dimethylhydroxylamine HCl (334 mg, 3.4 mmol) in DMF (20 mL) was added N-methylmorpholine (944 mg, 9.3 mmol), followed by EDC (776 mg, 4.0 mmol), HOBT (547 mg, 4.0 mmol) at 0° C. The mixture was stirred at room temperature overnight. The mixture was concentrated to give crude oil, which was purified by flash column with DCM:MeOH=1%-4% to give A-2 (1.1 g, 97.0%) as a white solid.

Step 2: Synthesis of crude (3aS,4S,6R,6aR)-6-(6-(N-benzoylbenzamido)-9H-purin-9-yl)-N-methoxy-N,2,2-trimethyltetrahydrofuro[3,4-d][1,3]dioxole-4-carboxamide (A-3)

To a mixture of A-2 (1.2 g, 3.3 mmol) in DCM (50 mL) was added benzoyl chloride (1.02 g, 7.2 mmol) dropwise at 0° C. After the addition, the mixture was stirred at room temperature for 3 h. TLC (DCM/MeOH=10:1) showed that 30% of B-2 was remained. The mixture was cooled back to 0° C., added benzoyl chloride (500 mg, 3.6 mmol). The mixture was stirred at room temperature overnight. The mixture was washed with NaHCO₃ aq, concentrated to give crude oil. The oil was purified by flash column with petroleum ether/EtOAc=1%-40% to give crude A-3 (1.5 g, 79.5%) as a white solid.

Step 3: Synthesis of N-(9-((3aR,4R,6S,6aS)-6-acetyl-2,2-dimethyltetrahydrofuro[3,4-d][1,3]dioxol-4-yl)-9H-purin-6-yl)benzamide (A-4)

To a stirred solution of A-3 (400 mg, 0.70 mmol) in THF (15 mL) was added MeMgBr (1.2 mL, 3M in THF) at -78° C. After the addition, the mixture was stirred at -30° C. for 30 min, TLC (DCM/MeOH=20:1) showed that the reaction was complete. The mixture was quenched by H₂O (5 mL), extracted with EtOAc (15 mL×2). The organic layer was concentrated to give crude oil. The oil was purified by DCM:EtOAc=1%-60% to give A-4 (180 mg, 60.9%) as a white solid. LCMS: 424.0 (M+H)+

Step 4: Synthesis of N-(9-((3aR,4R,6R,6aR)-6-((S)-1-hydroxyethyl)-2,2-dimethyltetrahydrofuro[3,4-d][1,3]dioxol-4-yl)-9H-purin-6-yl)benzamide (A-5)

To a solution of A-4 (180 mg, 0.42 mmol) in EtOH was added NaBH₄ (32.2 mg, 0.85 mmol) at 0° C. The mixture was stirred at 0° C. for 1 h. TLC (DCM/MeOH=20:1) showed that the reaction was completed. The mixture was concentrated to give crude oil, which was purified by flash column with DCM/MeOH=0%-4% to give A-5 (140 mg, 77.4%) as a white solid.

Step 5: Synthesis of (S)-1-((3aR,4R,6R,6aR)-6-(6-amino-9H-purin-9-yl)-2,2-dimethyltetrahydrofuro[3,4-d][1,3]dioxol-4-yl)ethan-1-ol (A-6)

A mixture of A-5 (140 mg, 0.33 mmol) in Dioxane/NH₃.H₂O (1 mL/1 mL) was stirred at 90° C. in autoclave for 4 h. TLC (DCM/MeOH=10:1) showed that the reaction was complete. The mixture was concentrated to give product, which was purified by flash column with DCM/MeOH=0-5% to give A-6 (94 mg, 89%) as a white solid. LCMS: 343.8 (M+Na)+

Step 6: Synthesis of (2R,3R,4S,5R)-2-(6-amino-9H-purin-9-yl)-5-(1-hydroxyethyl)tetrahydrofuran-3,4-diol (A-7)

A solution of A-6 (90 mg, 0.28 mmol) in TFA/H₂O (1 mL/1 mL) was stirred at rt for 2 h. TLC (DCM/MeOH=10:1) showed that the reaction was completed. The mixture was concentrated to give crude oil, which was dissolved in H₂O, washed with EtOAc (1 mL×2). The water layer was lyophilization directly to give A-7 (45 mg, 57%) as a white solid. LCMS: 282.12 (M+H)+

¹H NMR (400 MHz, MeOD) δ ppm 8.64-8.53 (m, 1H), 8.38-8.36 (m, 1H), 6.10-6.02 (m, 1H), 4.66-4.63 (m, 1H), 4.33-4.31 (m, 1H), 4.01-4.00 (m, 2H), 1.30-1.26 (m, 3H).

Step 7: Separation of Diastereomers using SFC Chiralpak AD-3 4.6×100 mm 3 u column, 40% MeOH @ 120 bar, 4 mL/min A-8: (2R,3R,4S,5R)-2-(6-amino-9H-purin-9-yl)-5-((R)-1-hydroxyethyl)tetrahydrofuran-3,4-diol ¹H NMR (400 MHz, MeOD) δ ppm 8.26 (s, 1H), 8.17 (s, 1H), 5.90 (d, J=7.34 Hz, 1H), 4.77 (dd, J=5.38, 7.34 Hz, 1H), 4.33 (d, J=5.26 Hz, 1H), 4.03-4.11 (m, 1H), 4.02 (d, J=1.47 Hz, 1H), 1.25 (d, J=6.72 Hz, 3H)

LCMS: 282.12 (M+H)+

A-9: (2R,3R,4S,5R)-2-(6-amino-9H-purin-9-yl)-5-((S)-1-hydroxyethyl)tetrahydrofuran-3,4-diol ¹H NMR (400 MHz, MeOD) δ ppm 8.31 (s, 1H), 8.18 (s, 1H), 5.96 (d, J=6.60 Hz, 1H), 4.70-4.77 (m, 1H), 4.28 (dd, J=2.32, 5.14 Hz, 1H), 4.01 (t, J=2.26 Hz, 1H), 3.94 (dd, J=2.32, 6.60 Hz, 1H), 1.26 (d, J=6.60 Hz, 3H)

LCMS: 282.12 (M+H)+.

Examples 3-8

Scheme B

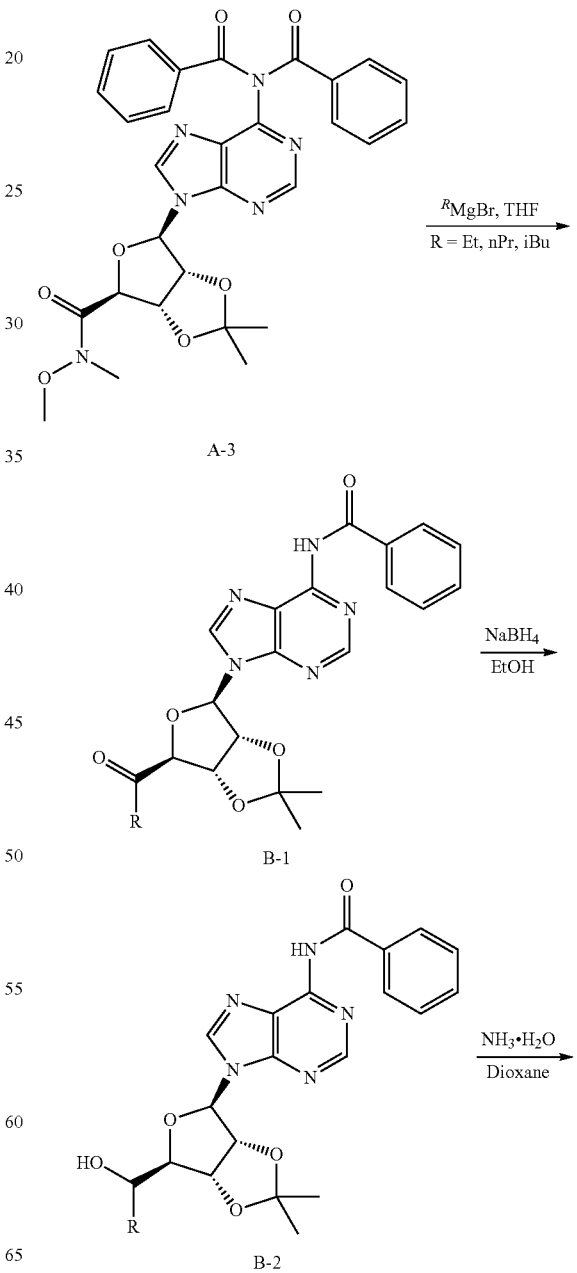

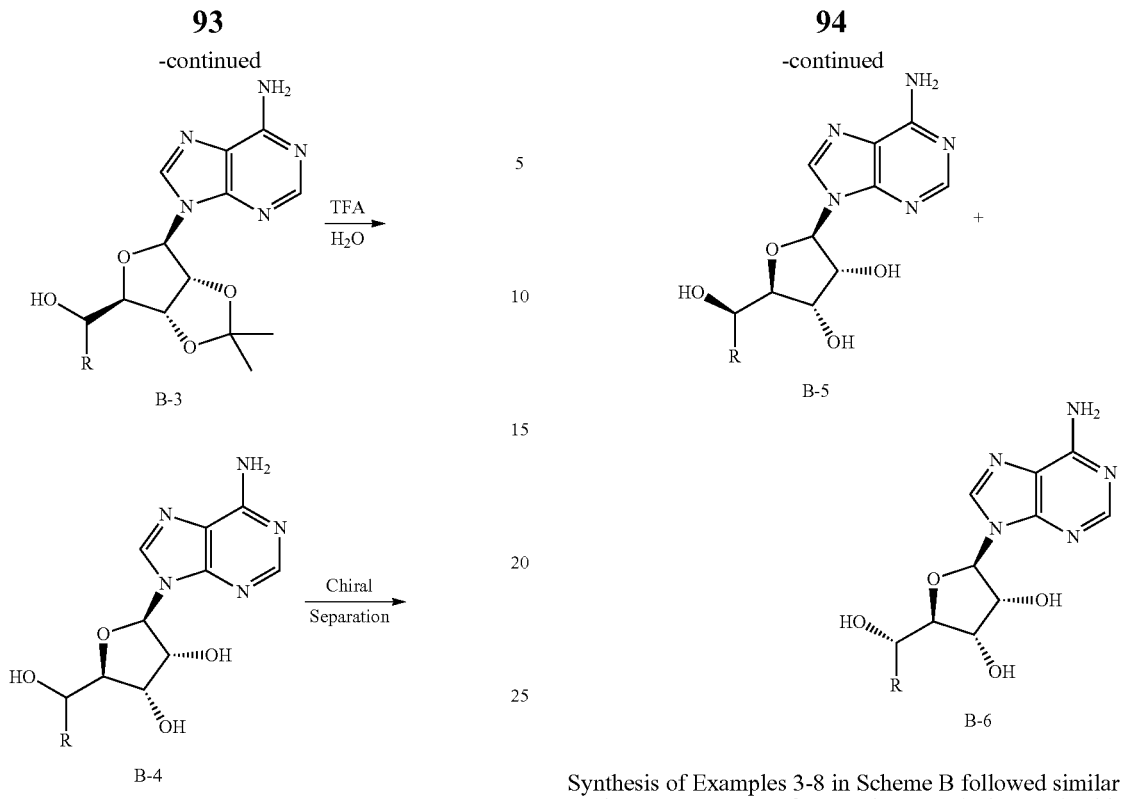

Synthesis of Examples 3-8 in Scheme B followed similar procedures to Steps 3-7 of Example 1 & 2 (Scheme A) with the appropriate alkyl Grignard reagent.

| Example | Structure | MW [M + 1] | IUPAC |
|---|---|---|---|
| 3<br>R = Et<br>(B-5) | 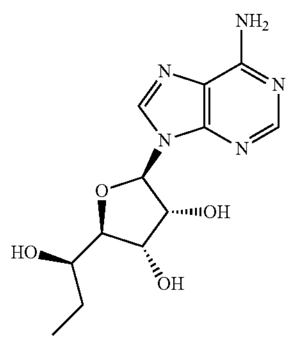 [SMILES: CC[C@@H](O)[C@H]1O[C@@H](n2cnc3c(N)ncnc32)[C@H](O)[C@@H]1O] | 296 | (2R,3R,4S,5R)-2-(6-amino-9H-purin-9-yl)-5-((R)-1-hydroxypropyl)tetrahydrofuran-3,4-diol<br>$^1$H NMR (400 MHz, METHANOL-d4) δ ppm 8.28 (s, 1H), 8.13-8.22 (m, 1H), 5.91 (d, J = 7.21 Hz, 1H), 4.73-4.78 (m, 1H), 4.31 (d, J = 4.52 Hz, 1H), 4.07 (br. s., 1H), 3.73-3.81 (m, 1H), 1.50-1.64 (m, 2H), 1.06 (t, J = 7.27 Hz, 3H) |
| 4<br>R = Et<br>(B-6) | 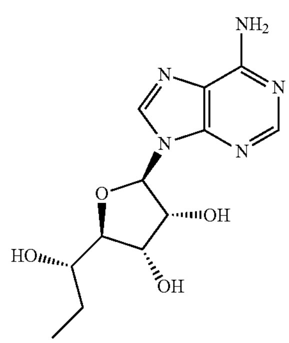 [SMILES: CC[C@H](O)[C@H]1O[C@@H](n2cnc3c(N)ncnc32)[C@H](O)[C@@H]1O] | 296 | (2R,3R,4S,5R)-2-(6-amino-9H-purin-9-yl)-5-((S)-1-hydroxypropyl)tetrahydrofuran-3,4-diol<br>$^1$H NMR (400 MHz, METHANOL-d4) δ ppm 8.32 (s, 1H), 8.19 (s, 1H), 5.95 (d, J = 6.72 Hz, 1H), 4.72-4.76 (m, 1H), 4.30 (dd, J = 2.14, 5.07 Hz, 1H), 4.13 (s, 1H), 3.62 (t, J = 6.05 Hz, 1H), 1.61 (dt, J = 4.58, 7.18 Hz, 2H), 1.00 (t, J = 7.46 Hz, 3H) |

-continued

| Example | Structure | MW [M + 1] | IUPAC |
|---|---|---|---|
| 5<br>R = nPr<br>(B-5) | 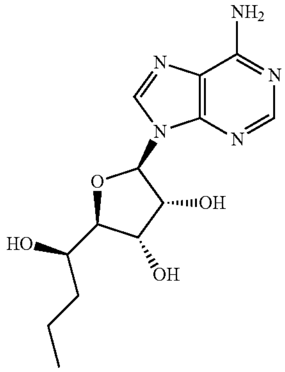 [SMILES: CCC[C@@H](O)[C@H]1O[C@@H](n2cnc3c(N)ncnc32)[C@H](O)[C@@H]1O] | 310 | (2R,3R,4S,5R)-2-(6-amino-9H-purin-9-yl)-5-((R)-1-hydroxybutyl)tetrahydrofuran-3,4-diol<br>$^1$H NMR (400 MHz, METHANOL-d4) δ ppm 8.15 (s, 1H), 8.08 (s, 1H), 5.79 (d, J = 7.46 Hz, 1H), 4.67 (dd, J = 5.38, 7.34 Hz, 1H), 4.21 (d, J = 5.38 Hz, 1H), 3.95 (s, 1H), 3.71-3.81 (m, 1H), 1.32-1.55 (m, 4H), 0.88 (t, J = 7.15 Hz, 3H) |
| 6<br>R = nPr<br>(B-6) | 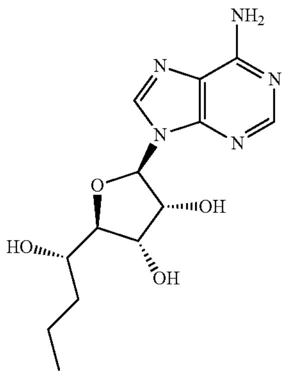 [SMILES: CCC[C@H](O)[C@H]1O[C@@H](n2cnc3c(N)ncnc32)[C@H](O)[C@@H]1O] | 310 | (2R,3R,4S,5R)-2-(6-amino-9H-purin-9-yl)-5-((S)-1-hydroxybutyl)tetrahydrofuran-3,4-diol<br>$^1$H NMR (400 MHz, METHANOL-d4) δ ppm 8.31 (s, 1H), 8.19 (s, 1H), 5.95 (d, J = 6.72 Hz, 1H), 4.75 (dd, J = 5.26, 6.60 Hz, 1H), 4.30 (dd, J = 2.08, 5.14 Hz, 1H), 4.11 (t, J = 1.96 Hz, 1H), 3.68-3.76 (m, 1H), 1.36-1.65 (m, 4H), 0.95 (t, J = 7.09 Hz, 3H) |
| 7<br>R = iBu<br>(B-5) | 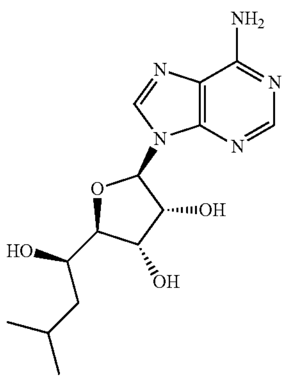 [SMILES: CC(C)C[C@@H](O)[C@H]1O[C@@H](n2cnc3c(N)ncnc32)[C@H](O)[C@@H]1O] | 324 | (2R,3R,4S,5R)-2-(6-amino-9H-purin-9-yl)-5-((R)-1-hydroxy-3-methylbutyl)tetrahydrofuran-3,4-diol<br>$^1$H NMR (400 MHz, METHANOL-d4) δ ppm 8.30 (s, 1H), 8.24 (s, 1H), 5.94 (d, J = 7.21 Hz, 1H), 4.90-4.94 (m, 1H), 4.35 (d, J = 6.36 Hz, 1H), 4.07 (s, 1H), 3.93-4.05 (m, 1H), 1.84-2.00 (m, J = 7.20 Hz, 1H), 1.53 (dd, J = 5.32, 9.48 Hz, 1H), 1.33-1.42 (m, 1H), 1.02 (dd, J = 6.60, 11.86 Hz, 6H) |
| 8<br>R = iBu<br>(B-6) | 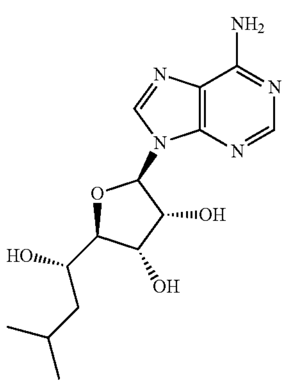 [SMILES: CC(C)C[C@H](O)[C@H]1O[C@@H](n2cnc3c(N)ncnc32)[C@H](O)[C@@H]1O] | 324 | (2R,3R,4S,5R)-2-(6-amino-9H-purin-9-yl)-5-((S)-1-hydroxy-3-methylbutyl)tetrahydrofuran-3,4-diol<br>$^1$H NMR (400 MHz, METHANOL-d4) δ ppm 8.35 (s, 1H), 8.22 (s, 1H), 5.99 (d, J = 6.85 Hz, 1H), 4.75-4.81 (m, J = 6.60 Hz, 1H), 4.35 (dd, J = 2.14, 5.07 Hz, 1H), 4.12 (t, J = 2.02 Hz, 1H), 3.83-3.92 (m, 1H), 1.82-1.93 (m, 1H), 1.55-1.69 (m, 1H), 1.28-1.39 (m, 1H), 0.99 (dd, J = 2.08, 6.60 Hz, 6H) |

Example 9
(Scheme C) (2R,3S,4R,5R)-2-((R)-(3,4-difluorophenyl)(hydroxy)methyl)-5-(4-methyl-7H-pyrrolo[2,3-d]pyrimidin-7-yl)tetrahydrofuran-3,4-diol (C-12)
Scheme C
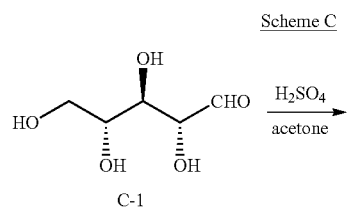
C-1
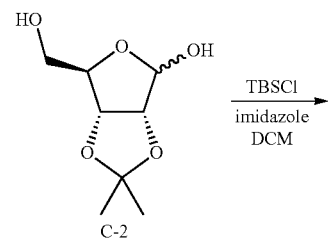
C-2
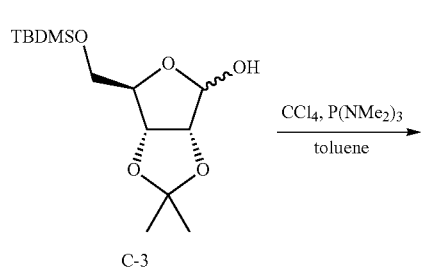
C-3
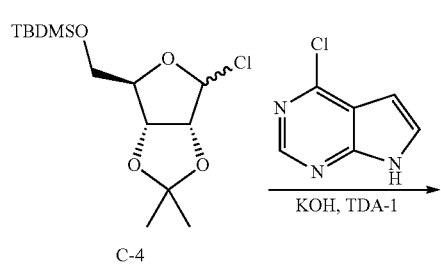
C-4
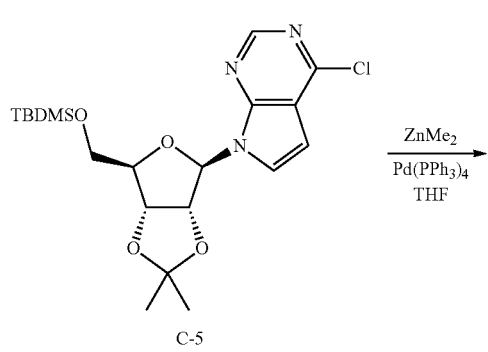
C-5
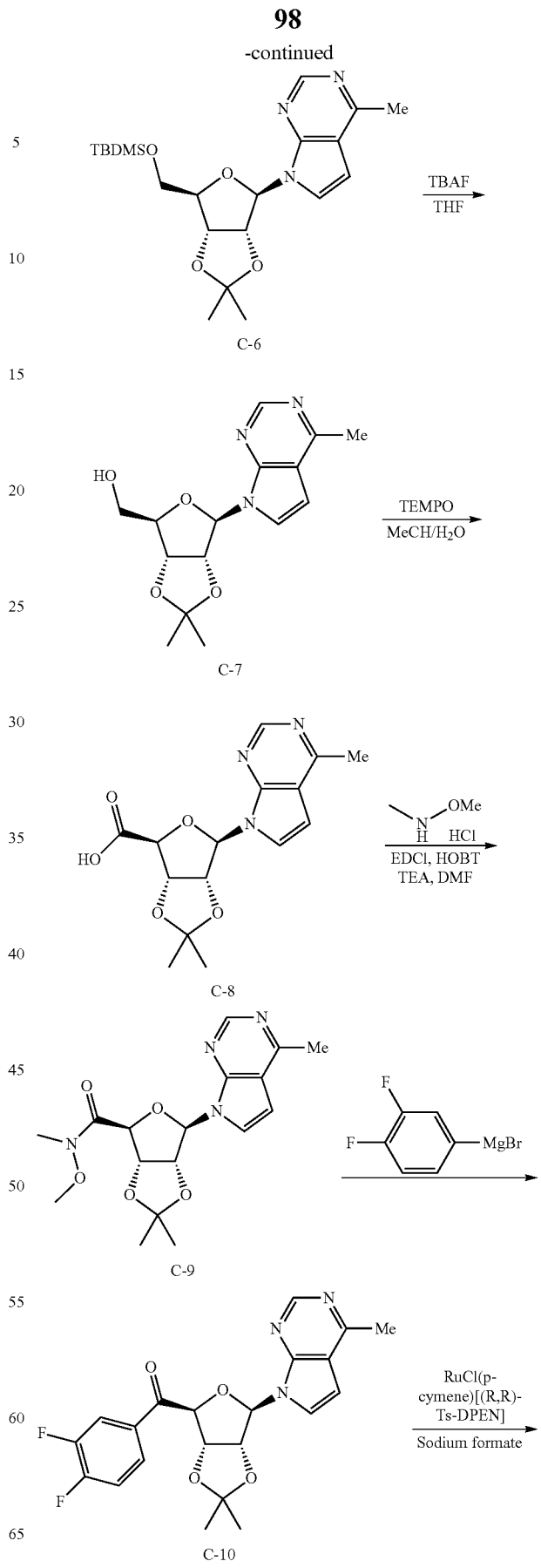

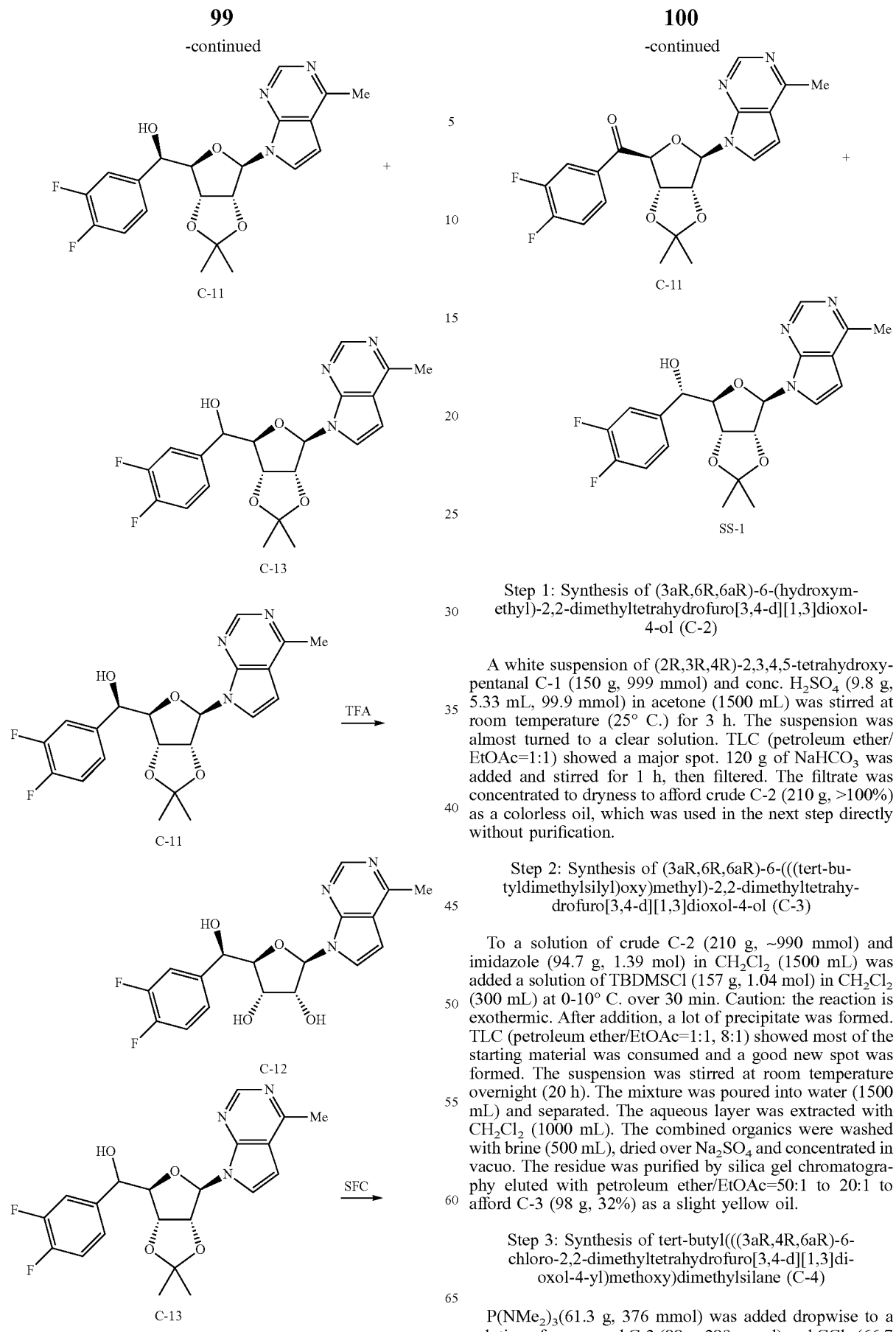

Step 1: Synthesis of (3aR,6R,6aR)-6-(hydroxymethyl)-2,2-dimethyltetrahydrofuro[3,4-d][1,3]dioxol-4-ol (C-2)

A white suspension of (2R,3R,4R)-2,3,4,5-tetrahydroxypentanal C-1 (150 g, 999 mmol) and conc. $H_2SO_4$ (9.8 g, 5.33 mL, 99.9 mmol) in acetone (1500 mL) was stirred at room temperature (25° C.) for 3 h. The suspension was almost turned to a clear solution. TLC (petroleum ether/EtOAc=1:1) showed a major spot. 120 g of $NaHCO_3$ was added and stirred for 1 h, then filtered. The filtrate was concentrated to dryness to afford crude C-2 (210 g, >100%) as a colorless oil, which was used in the next step directly without purification.

Step 2: Synthesis of (3aR,6R,6aR)-6-(((tert-butyldimethylsilyl)oxy)methyl)-2,2-dimethyltetrahydrofuro[3,4-d][1,3]dioxol-4-ol (C-3)

To a solution of crude C-2 (210 g, ~990 mmol) and imidazole (94.7 g, 1.39 mol) in $CH_2Cl_2$ (1500 mL) was added a solution of TBDMSCl (157 g, 1.04 mol) in $CH_2Cl_2$ (300 mL) at 0-10° C. over 30 min. Caution: the reaction is exothermic. After addition, a lot of precipitate was formed. TLC (petroleum ether/EtOAc=1:1, 8:1) showed most of the starting material was consumed and a good new spot was formed. The suspension was stirred at room temperature overnight (20 h). The mixture was poured into water (1500 mL) and separated. The aqueous layer was extracted with $CH_2Cl_2$ (1000 mL). The combined organics were washed with brine (500 mL), dried over $Na_2SO_4$ and concentrated in vacuo. The residue was purified by silica gel chromatography eluted with petroleum ether/EtOAc=50:1 to 20:1 to afford C-3 (98 g, 32%) as a slight yellow oil.

Step 3: Synthesis of tert-butyl(((3aR,4R,6aR)-6-chloro-2,2-dimethyltetrahydrofuro[3,4-d][1,3]dioxol-4-yl)methoxy)dimethylsilane (C-4)

$P(NMe_2)_3$ (61.3 g, 376 mmol) was added dropwise to a solution of compound C-3 (88 g, 289 mmol) and $CCl_4$ (66.7 g, 434 mmol) in dry toluene (500 mL) at −30° C. The inner temperature rose to −20° C. and the color of reaction solution was changed from colorless to red. After addition, the mixture was stirred at 0° C. for another 2 h. TLC (petroleum ether/EtOAc=8:1) showed about 50% of the starting material was remaining and a good spot was formed. The reaction was quenched with cooled brine (300 mL) and separated. The yellow organic layer (~500 mL) was washed with brine (200 mL), dried over $Na_2SO_4$ to afford C-4 and used in the next step directly.

Step 4: Synthesis of 7-((3aR,4R,6R,6aR)-6-(((tert-butyldimethylsilyl)oxy)methyl)-2,2-dimethyltetrahydrofuro[3,4-d][1,3]dioxol-4-yl)-4-chloro-7H-pyrrolo[2,3-d]pyrimidine (C-5)

To a suspension 4-chloro-7H-pyrrolo[2,3-d]pyrimidine (44.4 g, 289 mmol) and powered KOH (19.5 g, 347 mmol) in dry toluene (400 mL) was added tris[2-(2-methoxyethoxy)ethyl]amine(TDA-1) (46.7 g, 144 mmol) (the suspension turned almost clear) and the inner temperature rose to 35° C. A solution of crude A-4 (93.3 g, 288.9 mmol) in toluene (500 mL) was added dropwise without cooling (inner temperature 35° C.). The resulting solution was stirred at room temperature (25° C.) for 20 h. TLC (petroleum ether/EtOAc=8:1) showed an UV absorption new spot was formed. The red clear solution was quenched by $NH_4Cl$ aq (300 mL). The excess 4-chloro-7H-pyrrolo[2,3-d]pyrimidine precipitated. The mixture was filtered. The organic layer was separated, washed with brine (200 mL) and dried over $Na_2SO_4$ and concentrated to dryness to afford crude C-5 (156 g). The residue was purified by silica gel chromatography eluted with petroleum ether/EtOAc=40:1 to 20:1 to afford A-5 (49 g, 38.5%) as a colorless oil. $^1$H NMR (400 MHz, $CDCl_3$) δ ppm 8.66 (s, 1H), 7.57 (d, 1H), 6.63 (d, 1H), 6.41 (br, 1H), 5.07-5.05 (m, 1H), 4.96-4.94 (m, 1H), 4.36-4.35 (m, 1H), 3.90-3.79 (m, 2H), 1.65 (s, 3H), 1.39 (s, 3H), 0.90 (s, 9H), 0.06 (s, 6H)

Step 5: Synthesis of 7-((3aR,4R,6R,6aR)-6-(((tert-butyldimethylsilyl)oxy)methyl)-2,2-dimethyltetrahydrofuro[3,4-d][1,3]dioxol-4-yl)-4-methyl-7H-pyrrolo[2,3-d]pyrimidine (C-6)

$Pd(PPh_3)_4$ (5.15 g, 4.45 mmol) was added to a solution of C-5 (49 g, 111.36 mmol) in dry THF (500 mL). The suspension was degassed with Ar four times. A 1M solution of dimethylzinic in toluene (557 mL, 557 mmol) was added to the mixture. The mixture was degassed with Ar again four times. The yellow solution was heated at 70° C. for 4 h then stand at room temperature overnight. TLC (petroleum ether/EtOAc=8:1, 3:1) showed most of the starting material was consumed and the product was clean. The mixture was poured into cooled $NH_4Cl$ aq (1000 mL) carefully. The mixture was extracted with EtOAc (800 mL×3). The extract was washed with brine (500 mL), dried over $Na_2SO_4$ and concentrated in vacuo to afford crude (60 g). The crude was purified by silica gel chromatography eluted with petroleum ether/EtOAc=10:1 to 4:1 to afford C-6 (37 g, 79.2%) as a yellow oil. LCMS [M+1] 420; $^1$H NMR (400 MHz, $CDCl_3$) δ ppm 8.77 (s, 1H), 7.43 (d, 1H), 6.57 (d, 1H), 6.40 (d, 1H), 5.14-5.11 (m, 1H), 4.99-4.96 (m, 1H), 4.32-4.31 (m, 1H), 3.88-3.77 (m, 2H), 2.72 (s, 3H), 1.64 (s, 3H), 1.38 (s, 3H), 0.89 (s, 9H), 0.05 (d, 6H)

Step 6: Synthesis of ((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)methanol (C-7)

To a solution of C-6 (37 g, 88.2 mmol) in THF (370 mL) was added 1M solution of TBAF in THF (8.82 mL, 8.82 mmol) at room temperature. The mixture was stirred at room temperature (25° C.) for a weekend. TLC (petroleum ether/EtOAc=1:1) showed most of the starting material was consumed. The mixture was concentrated in vacuo to afford crude (40 g). The residue was purified by silica gel chromatography eluted with petroleum ether/EtOAc=3:1 to 1:3 to afford C-7 (24.1 g, 89.2%) as a yellow gum. LCMS [M+1] 306; $^1$H NMR (400 MHz, $CDCl_3$) δ ppm 8.72 (s, 1H), 7.22 (d, 1H), 6.56 (d, 1H), 6.11 (br, 1H), 5.84 (d, 1H), 5.29-5.26 (m, 1H), 5.14 (d, 1H), 4.50 (s, 1H), 4.00-3.79 (m, 2H), 2.74 (s, 3H), 1.64 (s, 3H), 1.37 (s, 3H).

Step 7: Synthesis of (3aS,4S,6R,6aR)-2,2-dimethyl-6-(4-methyl-7H-pyrrolo[2,3-d]pyrimidin-7-yl)tetrahydrofuro[3,4-d][1,3]dioxole-4-carboxylic acid (C-8)

To a solution of C-7 (24.1 g, 78.931 mmol) in MeCN (66 mL) was added $H_2O$ (66 mL), TEMPO (9.64 g, 61.7 mmol) and $PhI(OAc)_2$ (56.8 g, 150 mmol) in portions at room temperature (25° C.) without cooling. The reaction was exothermic. After stirred at room temperature (25° C.) for 5 min, the reaction mixture temperature rose to 65° C. The mixture was stirred for another 10 min without cooling. TLC (petroleum ether/EtOAc=1:2, $CH_2Cl_2$/MeOH/HOAc=100:10:1) showed most of the starting material was consumed and a new spot was formed. The mixture was stand at room temperature (25° C.) overnight. The liquid was poured out. The residue was triturated with TBME (400 mL). The solid was filtered and dried in vacuo to afford compound C-8 (12 g, 47.6%) as a white solid. The liquid was concentrated in vacuo to remove MeCN. The residue was diluted with water (100 mL) and washed with TBME (50 mL×3). The aqueous layer was extracted with EtOAc/THF (1:1, 100 mL×4). The extract was dried over $Na_2SO_4$ and concentrated in vacuo to afford compound C-8 (~80% purity determined by TLC, 3.6 g, 14.3%) as a yellow solid. LCMS [M+1] 320; $^1$H NMR (400 MHz, DMSO-$d_6$) δ ppm 12.79 (br, 1H), 8.61 (s, 1H), 7.67 (d, 1H), 6.74 (d, 1H), 6.41 (s, 1H), 5.53 (d, 1H), 5.42 (d, 1H), 4.66 (s, 1H), 2.65 (s, 3H), 1.54 (s, 3H), 1.36 (s, 3H)

Step 8: Synthesis of (3aS,4S,6R,6aR)-N-methoxy-N,2,2-trimethyl-6-(4-methyl-7H-pyrrolo[2,3-d]pyrimidin-7-yl)tetrahydrofuro[3,4-d][1,3]dioxole-4-carboxamide (C-9)

To a suspension of C-8 (11.4 g, 35.702 mmol) and N,O-dimethylhydroxylamine HCl (5.22 g, 53.6 mmol) in $CH_2Cl_2$ (300 mL) was added DIPEA (13.8 g, 107 mmol), HOBt (5.31 g, 39.3 mmol) and EDC (7.53 g, 39.3 mmol) at 10° C. After addition of DIPEA, the solids were dissolved. The resulting colorless solution was stirred at room temperature (25° C.) for 24 h. LCMS showed the reaction was complete and clean. The mixture was poured into water (300 mL) and separated. The aqueous layer was extracted with $CH_2Cl_2$ (100 mL×3). The extract was washed with brine (300 mL), dried over $Na_2SO_4$ and concentrated in vacuo to afford crude (13 g) as a colorless gum. The crude was purified by silica gel chromatography eluted with petroleum ether/EtOAc=1:1 to 1:3 to afford C-9 (11 g, 85%) as a yellow gum. LCMS [M+1] 363; $^1$H NMR (400 MHz, $CDCl_3$) δ ppm 8.74 (s, 1H), 7.55 (br, 1H), 6.67 (s, 1H), 6.59

(d, 1H), 5.29 (br, 1H), 5.22-5.17 (m, 2 H), 3.68 (s, 3H), 3.16 (s, 3H), 2.71 (s, 3H), 1.66 (s, 3H), 1.40 (s, 3H)

Step 9: Synthesis of (3,4-difluorophenyl)((3aS,4S, 6R,6aR)-2,2-dimethyl-6-(4-methyl-7H-pyrrolo[2,3-d]pyrimidin-7-yl)tetrahydrofuro[3,4-d][1,3]dioxol-4-yl)methanone (C-10)

To a solution of C-9 (20.0 g, 55.2 mmol) in dry THF (800 mL) was added 3,4-difluorophenylmagnesium bromide (0.5 M in 2-Me-THF, 375 mL, 188 mmol) at 5° C. The resulting yellow solution was stirred at 5° C. for 0.5 h. TLC (petroleum ether/EtOAc=1:1) showed most of the starting material was consumed and a new spot was formed. The mixture was poured into $NH_4Cl$ aq (500 mL) and extracted with EtOAc (1000 mL). The extract was washed with brine (500 mL×2), dried over $Na_2SO_4$ and concentrated in vacuo to afford crude compound C-10 (27 g, >100%) as a yellow gum, which solidified upon standing and used in the next step directly. LCMS [M+1] 416; $^1$H NMR (400 MHz, DMSO-$d_6$) δ ppm 8.49 (s, 1H), 7.54-7.35 (m, 4H), 6.60 (d, 1H), 6.47 (s, 1H), 5.66-5.64 (m, 1 H), 5.54 (d, 1 H), 5.48 (d, 1H), 2.54 (s, 3H), 1.60 (s, 3H), 1.35 (s, 3H)

Step 10: Synthesis of (R)-(3,4-difluorophenyl)((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)methanol (C-11) and (3,4-difluorophenyl)((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)methanol (C-12)

To a slight yellow solution of crude C-10 (172 g, ~377.5 mmol) in EtOAc (1800 mL) was added 2.5 M aq sodium formate (6040 mL, 1.51 mol) at 20° C. The mixture was bubbled with $N_2$ for 1 h. Ru(p-cymene)[(R,R)TsDPEN](2.5 g, 3.93 mmol) was added and bubbled with $N_2$ for 5 min. The resulting yellow mixture was stirred at 20° C. for a weekend. TLC (petroleum ether/EtOAc=1:1) showed most of SM was consumed and a good spot formed. The mixture was separated and the organic layer was dried over $Na_2SO_4$ and concentrated in vacuo to afford crude (180 g). The crude was purified by silica gel chromatography eluted with petroleum ether/EtOAc=10:1 to 2:1. The eluent was concentrated in vacuo to about 200 mL then filtered. The solid was dried in vacuo to afford C-11 (95 g, 60%) as a light yellow solid and C-13 (27 g, 17%) a light yellow solid.

C-11: LCMS [M+H]418; $^1$H NMR (400 MHz, CDCl$_3$) δ ppm 8.79 (s, 1H), 7.45 (s, 1H), 7.43-7.36 (m, 1H), 7.27-7.13 (m, 3H), 6.59 (d, J=3.8 Hz, 1H), 5.82 (d, J=5.0 Hz, 1H), 5.27 (t, J=5.5 Hz, 1H), 5.09 (s, 1H), 4.92 (dd, J=1.3, 6.0 Hz, 1H), 4.55 (s, 1H), 2.81-2.72 (m, 3H), 1.60-1.52 (m, 3H), 1.33-1.24 (m, 3H)

C-13: LCMS [M+H]418

Step 11: Synthesis of (2R,3S,4R,5R)-2-((R)-(3,4-difluorophenyl)(hydroxy)methyl)-5-(4-methyl-7H-pyrrolo[2,3-d]pyrimidin-7-yl)tetrahydrofuran-3,4-diol (C-12)

To a suspension of C-11 (14 g, 33.5 mmol) in H$_2$O (100 mL) was added TFA (100 mL) at 0° C. The resulted red solution was stirred at rt (25° C.) for 1 hr. LCMS showed 5% of the starting material was consumed and 93% of product was detected. The mixture as stirred at rt (25° C.) for another 20 min. The mixture was added to 20% $K_2CO_3$ aq (800 mL) at 0° C. The mixture was extracted with EtOAc (250 mL×2). The extract was washed with brine (200 mL×2), dried over $Na_2SO_4$ and concentrated in vacuo to afford C-12 (12.2 g, 96.4%) as a white solid. LCMS [M+H]378; $^1$H NMR (400 MHz, MeOD) δ ppm 8.65 (s, 1H), 7.64 (d, J=3.8 Hz, 1H), 7.46-7.31 (m, 1H), 7.28-7.13 (m, 2H), 6.77 (d, J=3.7 Hz, 1H), 6.15 (d, J=7.1 Hz, 1H), 4.98 (d, J=2.7 Hz, 1H), 4.80-4.75 (m, 1H), 4.30-4.22 (m, 2H), 2.76 (s, 3H)

Isolation of (S)-(3,4-difluorophenyl)((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)methanol (SS-1)

C-12 (1 g, 2.4 mmol) was separated by SFC chiral chromatography to give C-11 (386 mg, 39%) and SS-1 (494 mg, 49%).

SS-1: LCMS [M+1] 418; $^1$H NMR (400 MHz, CDCl$_3$) δ ppm 8.84 (s, 1H), 7.21-7.11 (m, 3H), 7.07-7.00 (m, 2H), 6.56 (d, J=3.7 Hz, 1H), 5.79 (d, J=3.8 Hz, 1H), 5.30-5.20 (m, 2H), 4.99 (d, J=10.6 Hz, 1H), 4.64 (s, 1H), 1.65 (s, 3H), 1.40 (s, 3H)

Examples 10-24

Scheme D

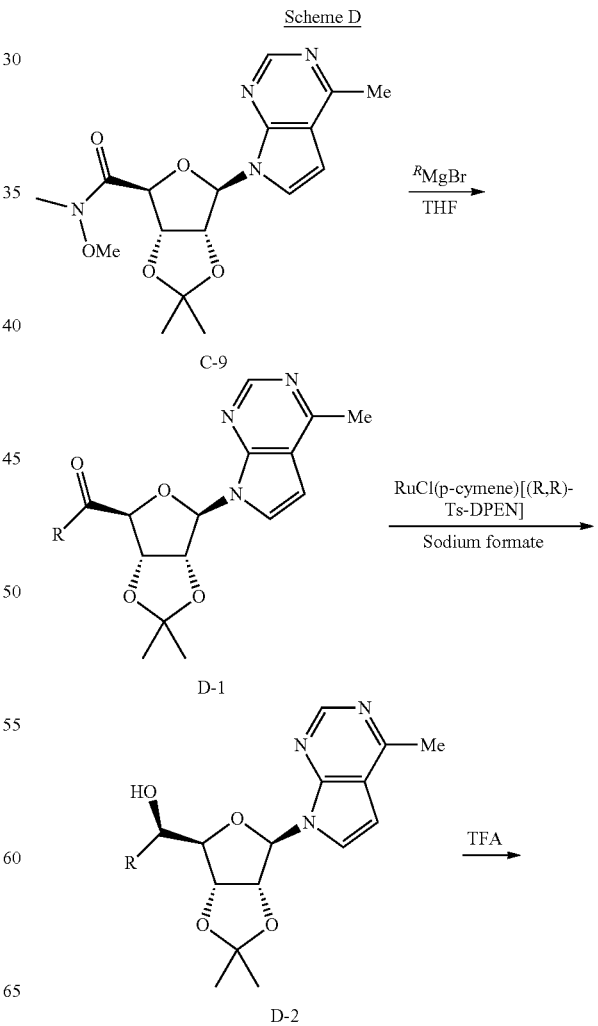

-continued

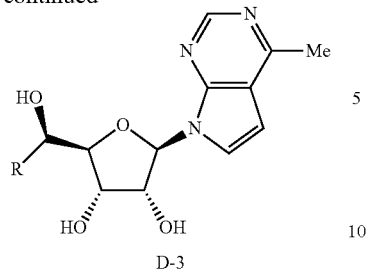

D-3

Synthesis of Examples 10-24 in Scheme D followed similar procedures to Steps 9-11 of Example 9 (Scheme C) with the appropriate Grignard reagent.

Examples 10-11 used commercially available Grignard reagents.

| Example | Structure | MW | IUPAC |
|---|---|---|---|
| 10 | 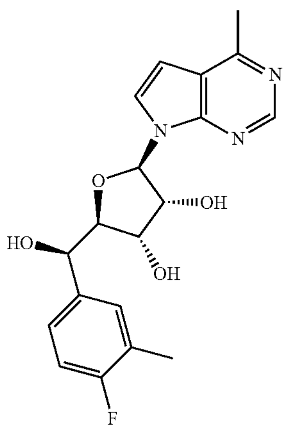 [SMILES: Cc1cc([C@@H](O)[C@H]2O[C@@H](n3ccc4c(C)ncnc43)[C@H](O)[C@@H]2O)ccc1F] | 374 [M + 1] | (2R,3S,4R,5R)-2-((R)-(4-fluoro-3-methylphenyl)(hydroxy)methyl)-5-(4-methyl-7H-pyrrolo[2,3-d]pyrimidin-7-yl)tetrahydrofuran-3,4-diol<br>$^1$H NMR (400 MHz, MeOD) δ ppm 8.64 (s, 1H), 7.62 (d, 1H), 7.34-7.27 (m, 2H), 7.03-6.97 (m, 1H), 6.77 (d, 1H), 6.16 (d, 1 H), 4.96 (d, 1H), 4.79-4.77 (m, 1H), 4.28-4.27 (m, 2H), 2.76 (s, 3H), 2.26 (s, 3H) |
| 11 | 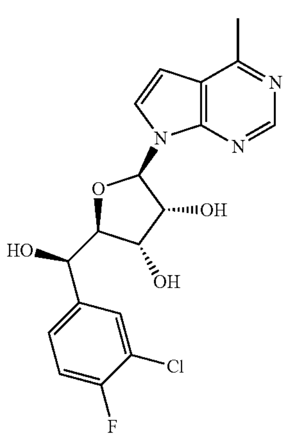 [SMILES: Cc1ncnc2c1ccn2[C@@H]1O[C@H]([C@H](O)c2ccc(F)c(Cl)c2)[C@@H](O)[C@H]1O] | 394 [M + 1] | (2R,3S,4R,5R)-2-((R)-(3-chloro-4-fluorophenyl)(hydroxy)methyl)-5-(4-methyl-7H-pyrrolo[2,3-d]pyrimidin-7-yl)tetrahydrofuran-3,4-diol<br>$^1$H NMR (400 MHz, MeOD) δ ppm 8.64 (s, 1H), 7.63 (d, 1H), 7.59 (d, 1H), 7.40-7.30 (m, 1H), 7.23-7.18 (m, 1H), 6.77 (d, 1H), 6.16 (d, 1 H), 4.98 (d, 1H), 4.81-4.78 (m, 1H), 4.28-4.25 (m, 2H), 2.75 (s, 3H) |

-continued

| Example | Structure | MW | IUPAC |
|---------|-----------|-----|-------|
| 12 | 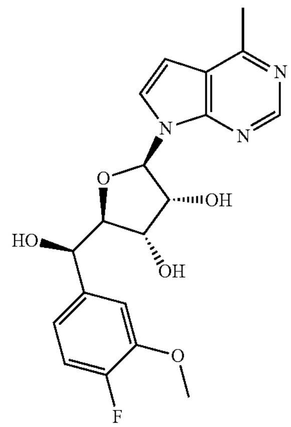 [SMILES: COc1cc([C@@H](O)[C@H]2O[C@@H](n3ccc4c(C)ncnc43)[C@H](O)[C@@H]2O)ccc1F] | 390 [M + 1] | (2R,3S,4R,5R)-2-((R)-(4-fluoro-3-methoxyphenyl)(hydroxy)methyl)-5-(4-methyl-7H-pyrrolo[2,3-d]pyrimidin-7-yl)tetrahydrofuran-3,4-diol<br>$^1$H NMR (400 MHz, MeOD) δ ppm 8.64 (s, 1H), 7.61 (d, 1H), 7.20 (d, 1H), 7.09-7.01 (m, 2H), 6.76 (d, 1H), 6.16 (d, 1H), 4.98 (d, 1 H), 4.81-4.78 (m, 1H), 4.31-4.28 (m, 2H), 3.82 (s, 3H), 2.75 (s, 3H) |
| 13 | 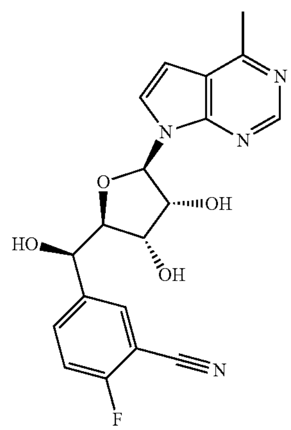 [SMILES: Cc1ncnc2c1ccn2[C@@H]1O[C@H]([C@H](O)c2ccc(F)c(C#N)c2)[C@@H](O)[C@H]1O] | 385 [M + 1] | 5-((R)-((2R,3S,4R,5R)-3,4-dihydroxy-5-(4-methyl-7H-pyrrolo[2,3-d]pyrimidin-7-yl)tetrahydrofuran-2-yl)(hydroxy)methyl)-2-fluorobenzonitrile<br>$^1$H NMR (400 MHz, DMSO-d$_6$) δ ppm 8.65 (s, 1H), 7.87 (d, 1H), 7.80-7.77 (m, 2H), 7.48-7.43 (m, 1H), 6.99 (d, 1H), 6.24 (d, 1H), 6.16 (d, 1 H), 5.33 (d, 1H), 5.18 (d, 1H), 4.87-4.85 (m, 1H), 4.61-4.56 (m, 1H), 4.13-4.13 (m, 1H), 4.02 (d, 1H), 2.67 (s, 3H) |
| 14 | 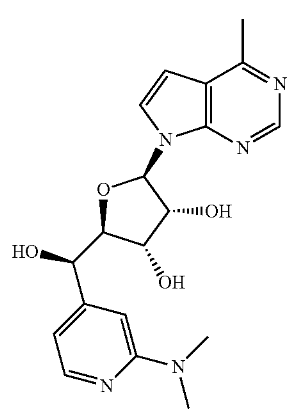 [SMILES: Cc1ncnc2c1ccn2[C@@H]1O[C@H]([C@H](O)c2ccnc(N(C)C)c2)[C@@H](O)[C@H]1O] | 386 [M + 1] | (2R,3S,4R,5R)-2-((R)-(2-(dimethylamino)pyridin-4-yl)(hydroxy)methyl)-5-(4-methyl-7H-pyrrolo[2,3-d]pyrimidin-7-yl)tetrahydrofuran-3,4-diol<br>$^1$H NMR (400 MHz, DMSO-d$_6$) δ ppm 8.66 (s, 1H), 8.00 (d, 1H), 7.82 (d, 1H), 6.78 (d, 1H), 6.20-6.60 (m, 2H), 6.15 (d, 1H), 6.11 (d, 1 H), 5.27 (d, 1H), 5.11 (d, 1H), 4.72-4.62 (m, 2H), 4.11-4.09 (m, 1H), 4.03 (d, 1H), 2.96 (s, 6H), 2.67 (s, 3H) |

-continued

| Example | Structure | MW | IUPAC |
|---|---|---|---|
| 15 | 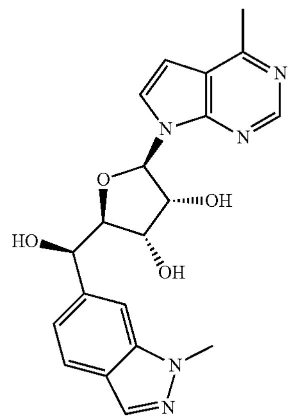 [SMILES: Cc1ncnc2c1ccn2[C@@H]1O[C@H]([C@H](O)c2ccc3cnn(C)c3c2)[C@@H](O)[C@H]1O] | 396 [M + 1] | (2R,3S,4R,5R)-2-((R)-hydroxy(1-methyl-1H-indazol-6-yl)methyl)-5-(4-methyl-7H-pyrrolo[2,3-d]pyrimidin-7-yl)tetrahydrofuran-3,4-diol<br>$^1$H NMR (400 MHz, DMSO-d$_6$) δ ppm 8.67 (s, 1H), 7.99 (s, 1H), 7.82 (d, 1H), 7.69-7.65 (m, 2H), 7.20 (d, 1H), 6.79 (d, 1H), 6.23 (d, 1 H), 6.18 (d, 1H), 5.27 (d, 1H), 5.07 (d, 1H), 4.98-4.96 (m, 1H), 4.68-4.67 (m 1H), 4.19-4.15 (m, 2H), 4.01 (s, 3H), 2.67 (s, 3H) |
| 16 | 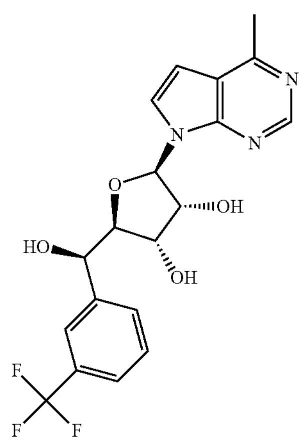 [SMILES: Cc1ncnc2c1ccn2[C@@H]1O[C@H]([C@H](O)c2cccc(C(F)(F)F)c2)[C@@H](O)[C@H]1O] | 410 [M + 1] | (2R,3S,4R,5R)-2-((R)-hydroxy(3-(trifluoromethyl)phenyl)methyl)-5-(4-methyl-7H-pyrrolo[2,3-d]pyrimidin-7-yl)tetrahydrofuran-3,4-diol<br>$^1$H NMR (400 MHz, DMSO-d$_6$) δ ppm 8.65 (s, 1H), 7.80 (s, 1H), 7.73-7.68 (m, 2H), 7.59-7.54 (m, 2H), 6.78 (d, 1H), 6.22 (d, 1H), 6.16 (d, 1 H), 5.31 (d, 1H), 5.16 (d, 1H), 4.93-4.90 (m, 1H), 4.13 (br, 1H), 4.04 (d, 1H), 2.66 (s, 3H) |
| 17 | 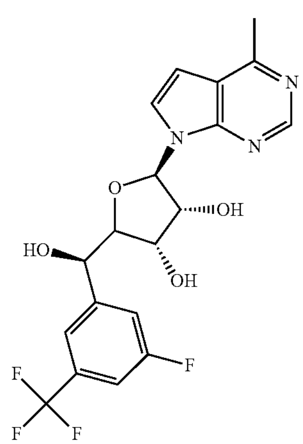 [SMILES: Cc1ncnc2c1ccn2[C@@H]1OC([C@H](O)c2cc(F)cc(C(F)(F)F)c2)[C@@H](O)[C@H]1O] | 428 [M + 1] | (3S,4R,5R)-2-((3-fluoro-5-(trifluoromethyl)phenyl)(hydroxy)methyl)-5-(4-methyl-7H-pyrrolo[2,3-d]pyrimidin-7-yl)tetrahydrofuran-3,4-diol<br>$^1$H NMR (400 MHz, DMSO-d6) δ ppm 8.67 (s, 1H), 7.84 (s, 1H), 7.68 (d, 1H), 7.61 (d, 2H), 6.79 (d, 1H), 6.33 (d, 1H), 5.69 (d, 1 H), 5.52 (d, 1H), 5.14 (d, 1H), 4.98-4.95 (m, 1H), 4.42-4.40 (m 1H), 3.68 (br, 1H), 2.66 (s, 3H) |

-continued

| Example | Structure | MW | IUPAC |
|---------|-----------|-----|-------|
| 18 | 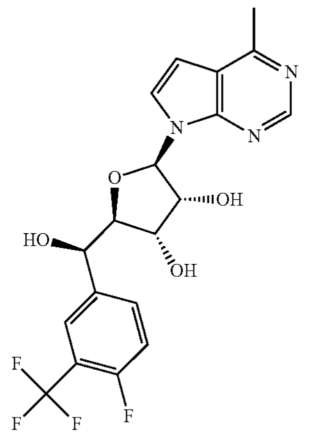 [SMILES: Cc1ncnc2c1ccn2[C@@H]1O[C@H]([C@H](O)c2ccc(F)c(C(F)(F)F)c2)[C@@H](O)[C@H]1O] | 428 [M + 1] | (2R,3S,4R,5R)-2-((R)-(4-fluoro-3-(trifluoromethyl)phenyl)(hydroxy)methyl)-5-(4-methyl-7H-pyrrolo[2,3-d]pyrimidin-7-yl)tetrahydrofuran-3,4-diol<br>$^1$H NMR (400 MHz, DMSO-d$_6$) δ ppm 8.65 (s, 1H), 7.80 (d, 1H), 7.74 (d, 2H), 7.46-7.41 (m, 1H), 6.78 (d, 1H), 6.22 (d, 1H), 6.15 (d, 1 H), 5.32 (d, 1H), 5.19 (d, 1H), 4.92-4.89 (m, 1H), 4.65-4.62 (m, 1H), 4.15-4.13 (m 1H), 4.00 (d, 1H), 2.66 (s, 3H) |
| 19 | 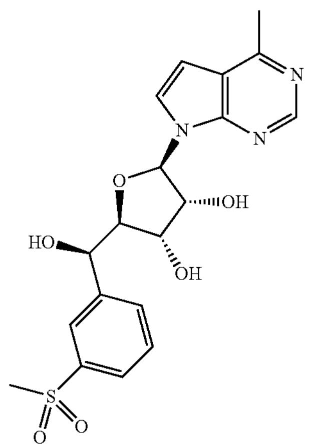 [SMILES: Cc1ncnc2c1ccn2[C@@H]1O[C@H]([C@H](O)c2cccc(S(C)(=O)=O)c2)[C@@H](O)[C@H]1O] | 442 [M + 23] | (2R,3S,4R,5R)-2-((R)-hydroxy(3-(methylsulfonyl)phenyl)methyl)-5-(4-methyl-7H-pyrrolo[2,3-d]pyrimidin-7-yl)tetrahydrofuran-3,4-diol<br>$^1$H NMR (400 MHz, DMSO-d$_6$) δ ppm 8.67 (s, 1H), 7.99 (s, 1H), 7.83-7.80 (m, 2H), 7.75-7.73 (m, 1H), 7.60 (t, 1H), 6.79 (d, 1H), 6.29 (d, 1H), 6.18 (d, 1H), 5.32 (d, 1H), 5.18 (d, 1H), 4.95 (t, 1H), 4.68-4.63 (m, 1H), 4.16 (t, 1H), 4.05 (d, 1H), 3.15 (s, 3H), 2.68 (3H) |
| 20 | 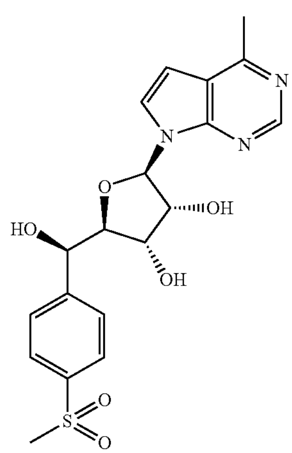 [SMILES: Cc1ncnc2c1ccn2[C@@H]1O[C@H]([C@H](O)c2ccc(S(C)(=O)=O)cc2)[C@@H](O)[C@H]1O] | 420 [M + 1] | (2R,3S,4R,5R)-2-((R)-hydroxy(4-(methylsulfonyl)phenyl)methyl)-5-(4-methyl-7H-pyrrolo[2,3-d]pyrimidin-7-yl)tetrahydrofuran-3,4-diol<br>$^1$H NMR (400 MHz, MeOD): δ ppm 8.75 (s, 1H), 7.95 (d, 2H), 7.80 (d, 1H), 7.75 (d, 2H), 6.90 (d, 1H), 6.24 (d, 1H), 5.11 (d, 1H), 4.79 (t, 1H), 4.33-4.28 (m, 2H), 3.13 (s, 3H), 2.83 (s, 3H) |

-continued

| Example | Structure | MW | IUPAC |
|---|---|---|---|
| 21 | 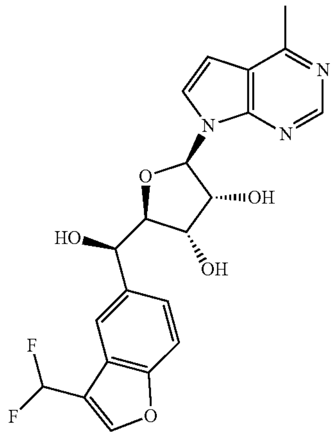 [SMILES: Cc1ncnc2c1ccn2[C@@H]1O[C@H]([C@H](O)c2ccc3occ(C(F)F)c3c2)[C@@H](O)[C@H]1O] | 432 [M + 1] | (2R,3S,4R,5R)-2-((R)-(3-(difluoromethyl)benzofuran-5-yl)(hydroxy)methyl)-5-(4-methyl-7H-pyrrolo[2,3-d]pyrimidin-7-yl)tetrahydrofuran-3,4-diol<br>$^1$H NMR (400 MHz, DMSO-d$_6$) δ ppm 8.66 (s, 1H), 8.39 (s, 1H), 7.82-7.93 (m, 2H), 7.63 (d, 1H), 7.46 (d, 1H), 7.44-7.16 (m, 1H), 6.78 (d, 1H), 6.17-6.15 (m, 2H), 5.29 (d, 1H), 5.11 (br, 1H), 4.95-4.94 (m, 1H), 4.69-4.64 (m, 1H), 4.16 (br, 1H), 4.09 (d, 1H), 2.67 (s, 3H) |
| 22 | 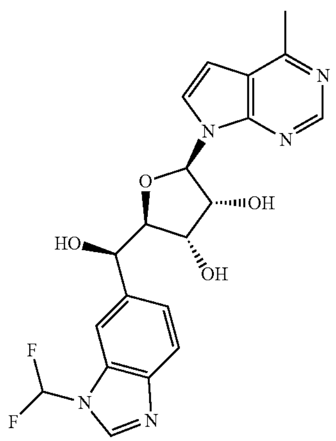 [SMILES: Cc1ncnc2c1ccn2[C@@H]1O[C@H]([C@H](O)c2ccc3ncn(C(F)F)c3c2)[C@@H](O)[C@H]1O] | 432 [M + 1] | (2R,3S,4R,5R)-2-((R)-(1-(difluoromethyl)-1H-benzo[d]imidazol-6-yl)(hydroxy)methyl)-5-(4-methyl-7H-pyrrolo[2,3-d]pyrimidin-7-yl)tetrahydrofuran-3,4-diol<br>$^1$H NMR (400 MHz, DMSO-d6) δ ppm 8.65 (s, 1H), 8.53 (s, 1H), 8.21-7.91 (m, 1H), 7.80-7.79 (m, 2H), 7.70 (d, 1H), 7.40 (d, 1H), 6.76 (d, 1H), 6.21 (d, 1H), 6.16 (d, 1H), 5.27 (d, 1H), 5.09 (d, 1H), 4.98-4.96 (m, 1H), 4.69-4.64 (m, 1H), 4.17-4.15 (m, 1H), 4.10 (d, 1H), 2.66 (s, 3H) |
| 23 | 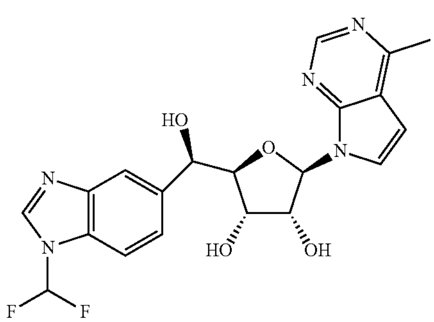 [SMILES: Cc1ncnc2c1ccn2[C@@H]1O[C@H]([C@H](O)c2ccc3c(c2)ncn3C(F)F)[C@@H](O)[C@H]1O] | 432 [M + 1] | (2R,3S,4R,5R)-2-((R)-(1-(difluoromethyl)-1H-benzo[d]imidazol-5-yl)(hydroxy)methyl)-5-(4-methyl-7H-pyrrolo[2,3-d]pyrimidin-7-yl)tetrahydrofuran-3,4-diol<br>$^1$H NMR (400 MHz, DMSO-d$_6$) δ ppm 8.65 (s, 1H), 8.55 (s, 1H), 8.20-7.91 (m, 1H), 7.82 (d, 1H), 7.78 (s, 1H), 7.66 (d, 1H), 7.47 (d, 1 H), 6.78 (d, 1H), 6.17 (d, 1H), 6.11 (d, 1H), 5.26 (d, 1H), 5.08 (d, 1H), 4.95-4.94 (m, 1H), 4.64-4.63 (m, 1H), 4.17 (br, 1H), 4.09 (d, 1H), 2.66 (s, 3H) |
| 24 | 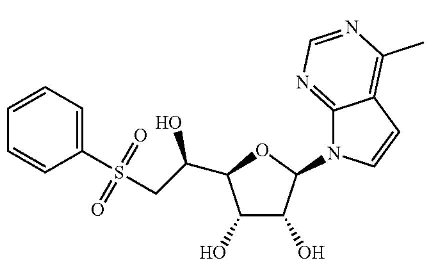 [SMILES: Cc1ncnc2c1ccn2[C@@H]1O[C@H]([C@H](O)CS(=O)(=O)c2ccccc2)[C@@H](O)[C@H]1O] | 442 [M + 23] | (2S,3S,4R,5R)-2-((R)-1-hydroxy-2-(phenylsulfonyl)ethyl)-5-(4-methyl-7H-pyrrolo[2,3-d]pyrimidin-7-yl)tetrahydrofuran-3,4-diol<br>$^1$H NMR (400 MHz, MeOD) δ ppm 8.64 (s, 1H), 7.96-7.94 (m, 2H), 7.70-7.68 (m, 1H), 7.62-7.60 (m, 3H), 6.77 (d, 1H), 6.18 (d, 1H), 4.98-4.96 (m, 1H), 4.53-4.52 (m, 1H), 4.38-4.32 (m, 2H), 3.53 (d, 1H), 3.41-3.38 (m, 1H), 2.74 (s, 3H) |

For Example 12, the Grignard reagent was prepared from the arylbromide and used directly in the next reaction with C-9 as shown in Scheme E.

Scheme E

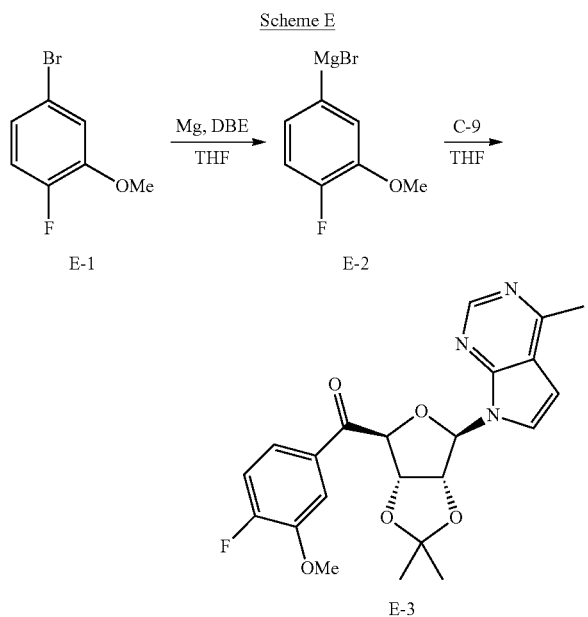

Synthesis of ((3aS,4S,6R,6aR)-2,2-dimethyl-6-(4-methyl-7H-pyrrolo[2,3-d]pyrimidin-7-yl)tetrahydrofuro[3,4-d][1,3]dioxol-4-yl)(4-fluoro-3-methoxyphenyl)methanone (E-3)

Step 1: Synthesis of (4-fluoro-3-methoxyphenyl)magnesium bromide (E-2)

Refined Mg turnings (593 mg, 24.4 mmol) were suspended in dry THF (10 mL). 5-bromo-2-fluoroanisole (1 g, 4.877 mmol) and 1, 2-dibromoethane (500 mg, 2.66 mmol) were dissolved in dry THF (10 mL). The above solution was added to the Mg suspension at room temperature (25° C.) without cooling. After the addition, the reaction was heated to a slight reflux with a heat gun. The reaction was initiated and maintained at reflux for another 0.5 h. An aliquot was quenched with acetone and TLC (petroleum ether) showed most of the starting material was consumed. The mixture of compound E-2 (~0.244 M in THF) was used in the next step directly.

Step 2: Synthesis of ((3aS,4S,6R,6aR)-2,2-dimethyl-6-(4-methyl-7H-pyrrolo[2,3-d]pyrimidin-7-yl)tetrahydrofuro[3,4-d][1,3]dioxol-4-yl)(4-fluoro-3-methoxyphenyl)methanone (E-3)

To a solution of compound C-9 (200 mg, 0.552 mmol) in dry THF (5 mL) was added to Grignard reagent compound E-2 (~0.244 M in THF, 20 mL, 4.88 mmol) at room temperature (25° C.). The resulting yellow solution was stirred at room temperature (25° C.) for 0.5 h. TLC (petroleum ether/EtOAc=1:1) showed most of the starting material was consumed and a new spot was formed. The mixture was poured into NH$_4$Cl aq (40 mL) and extracted with EtOAc (20 mL×2). The extract was washed with brine (20 mL), dried over Na$_2$SO$_4$ and concentrated in vacuo to afford (600 mg) as a yellow oil. The crude was purified by silica gel chromatography eluted with petroleum ether/EtOAc=3:1 to 1:1 to afford compound E-3 (113 mg, 47.9%) as a colorless gum.

For Example 13, the Grignard reagent was prepared from the arylbromide and used directly in the next reaction with C-9 as shown in Scheme F.

Scheme F

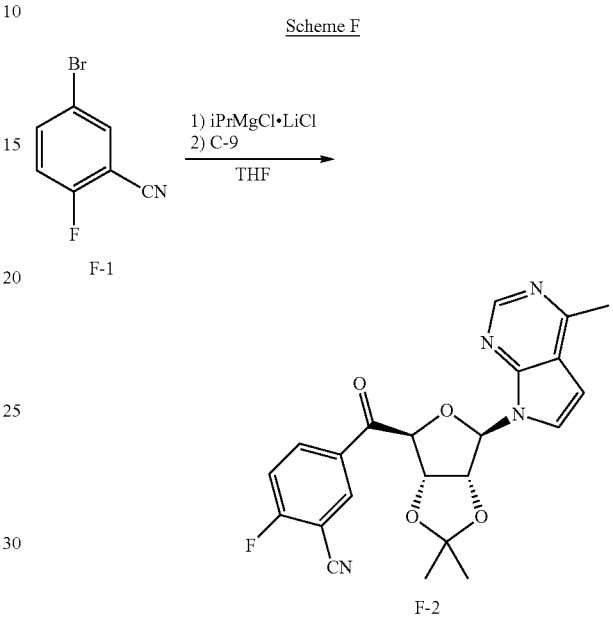

Synthesis of 5-((3aS,4S,6R,6aR)-2,2-dimethyl-6-(4-methyl-7H-pyrrolo[2,3-d]pyrimidin-7-yl)tetrahydrofuro[3,4-d][1,3]dioxole-4-carbonyl)-2-fluorobenzonitrile (F-2)

To a solution of 5-bromo-2-fluorobenzonitrile (400 mg, 2.00 mmol) in dry THF (4 mL) was added 1.3 M i-PrMgCl.LiCl (1.69 mL, 2.2 mmol) at −60° C. The resulting red solution was stirred at −60° C. for 5 min then at 0° C. for 15 min. A solution of C-9 (150 mg, 0.414 mmol) in dry THF (1.5 mL) was added at 0° C. The mixture was stirred at 0° C. for 1 h. TLC (petroleum ether/EtOAc=1:1) showed most of C-9 was consumed and a good spot was formed. The mixture was quenched with NH$_4$Cl aq (10 mL) and extracted with EtOAc (10 mL×2). The extract was dried over Na$_2$SO$_4$ and concentrated in vacuo to afford crude (500 mg) as yellow solid. The crude was purified by silica gel chromatography eluted with petroleum ether/EtOAc=5:1 to 1:1 to afford compound F-2 (150 mg, 85.8%) as a slight yellow solid. LCMS [M+1] 423

For Example 21, the aryliodide was prepared, used to make the corresponding Grignard reagent and reacted with C-9 as shown in Scheme G.

Scheme G

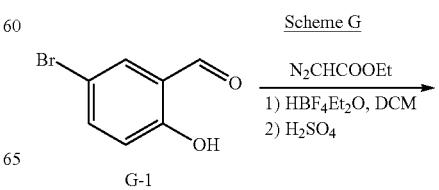

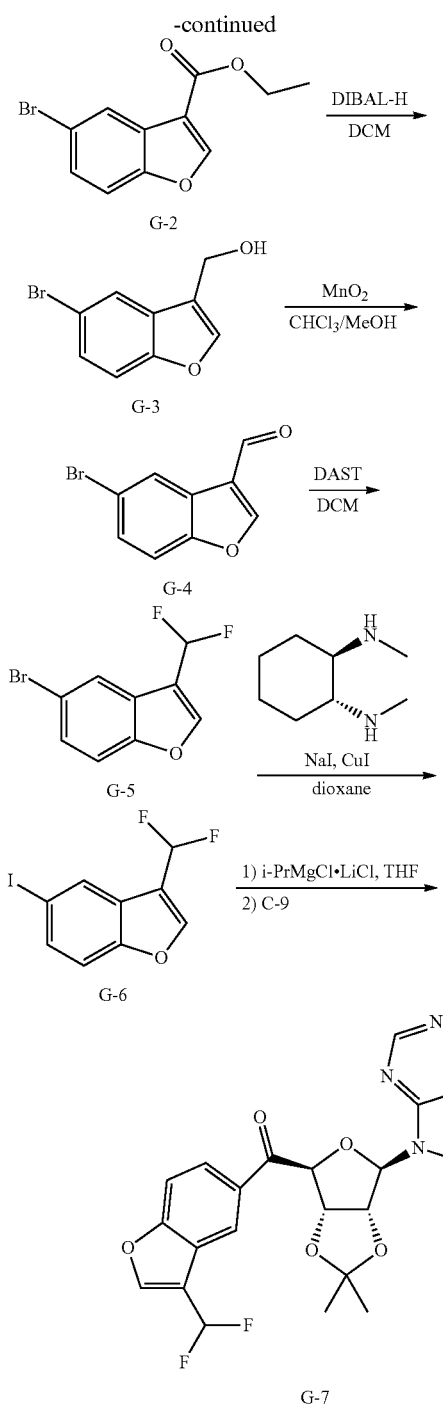

Synthesis of (3-(difluoromethyl)benzofuran-5-yl)
((3aS,4S,6R,6aR)-2,2-dimethyl-6-(4-methyl-7H-
pyrrolo[2,3-d]pyrimidin-7-yl)tetrahydrofuro[3,4-d]
[1,3]dioxol-4-yl)methanone (G-7)

Step 1: Synthesis of ethyl
5-bromobenzofuran-3-carboxylate (G-2)

To a solution of 5-bromosalicylaldehyde (10 g, 49.747 mmol) in CH$_2$Cl$_2$ (20 mL) was added HBF$_4$·Et$_2$O (806 mg, 4.97 mmol), followed by a solution of N$_2$CH$_2$COOEt (9.08 g, 79.6 mmol) in CH$_2$Cl$_2$ (10 mL) below 38° C. dropwise carefully. Caution: gas evolved. After addition, the mixture was stirred at room temperature (25° C.) for 10 min. TLC (petroleum ether/EtOAc=8/1, 3/1) showed most of the starting material was consumed and a good spot was formed. The mixture was concentrated in vacuo to dryness to afford yellow thick oil. To the resulting oil was added conc. H$_2$SO$_4$ (5 mL) slowly. The mixture was stirred at rt (25° C.) for 10 min. The color was changed into brown. The mixture was diluted with DCM (100 mL). NaHCO$_3$ (20 g) was added in portions. The mixture was stirred at room temperature (25° C.) for 20 hrs. TLC (petroleum ether/EtOAc=3/1, 8/1) showed most of intermediate was consumed and a good spot was formed. The mixture was filtered through silica gel and concentrated in vacuo to afford G-2 (14 g, >99%) as a yellow oil, which solidified upon standing. $^1$H NMR (400 MHz, CDCl$_3$) δ ppm 8.24 (s, 1H), 8.19 (s, 1H), 7.47 (d, 1H), 7.40 (d, 1H), 4.43-4.38 (m, 2H), 1.44-1.40 (m, 3H)

Step 2: Synthesis of
(5-bromobenzofuran-3-yl)methanol (G-3)

To a yellow solution of G-2 (13 g, 48.311 mmol) in dry CH$_2$Cl$_2$ (220 mL) was added 1 M DIBAL-H in toluene (116 mL, 116 mmol) at 5-10° C. The resulting yellow solution was stirred at room temperature (25° C.) for 30 min. TLC (petroleum ether/EtOAc=8/1, 3/1) showed most of the starting material was consumed and a good spot was formed. The mixture was quenched with NH$_4$Cl aq (10 mL) at rt 10° C. carefully. To the mixture was added Na$_2$SO$_4$ and celite. After stirred for 30 min, the mixture was filtered through celite. The filtrate was concentrated in vacuo to afford G-3 (6 g, 54.7%) as a yellow solid.

Step 3: Synthesis of
5-bromobenzofuran-3-carbaldehyde (G-4)

To a yellow solution of G-3 (5.8 g, 25.54 mmol) in CHCl$_3$/MeOH (120 mL/12 mL) was added MnO$_2$ (22.2 g, 255 mmol) at room temperature (25° C.). The black suspension was stirred at reflux for 3 h. TLC (petroleum ether/EtOAc=3/1) showed about 20% of the starting material was remaining. The mixture was refluxed for another 3 h then stand at room temperature overnight. TLC (petroleum ether/EtOAc=3/1) showed most of the starting material was consumed and a good spot was formed. The mixture was filtered through celite. The filtrate was concentrated in vacuo to afford G-4 (5.1 g, 88.7%) as a yellow solid and used in the next step directly.

Step 4: Synthesis of
5-bromo-3-(difluoromethyl)benzofuran (G-5)

To a yellow solution of G-4 (5.1 g, 22.66 mmol) in dry CH$_2$Cl$_2$ (110 mL) was added DAST (14.6 g, 90.7 mmol) at 0° C. The mixture was stirred at room temperature (25° C.) over weekend. TLC (petroleum ether/EtOAc=3/1, 8/1) showed the starting material was remaining and a good spot was formed. The mixture was poured into NaHCO$_3$ aq (200 mL) and filtered through celite. The organic layer was concentrated in vacuo to afford crude (6 g). The crude was purified by silica gel chromatography eluted with EtOAc in petroleum ether from 0 to 10% to afford G-5 (4 g, 71.4%) as a colorless oil. $^1$H NMR (400 MHz, CDCl$_3$) δ ppm 7.87 (d, 1H), 7.83 (s, 1H), 7.50 (d, 1H), 7.47 (d, 1H), 7.01-6.73 (m, 1H)

Step 5: Synthesis of 3-(difluoromethyl)-5-iodobenzofuran (G-6)

A mixture of G-5 (1000 mg, 4.048 mmol), NaI (1.82 g, 12.1 mmol), CuI (77.1 mg, 0.405 mmol) and trans-N,N-dimethylcyclohexane (115 mg, 0.810 mmol) in dry dioxane (12 mL) was purged with Ar. The resulting yellow suspension was stirred at 110° C. in a sealed tube for 24 hrs. The mixture was poured into water/NH$_3$.H$_2$O (50 mL/10 mL) and extracted with EtOAc (20 mL×3). The extract was washed with brine/NH$_3$.H$_2$O (20 mL/5 mL) twice, dried over Na$_2$SO$_4$ and concentrated in vacuo to afford crude (1.4 g). The crude was purified by silica gel chromatography eluted with EtOAc in petroleum ether from 0 to 50% to afford G-6 (1200 mg, 101%) as a colorless oil, which solidified upon standing. $^1$H NMR (400 MHz, CDCl$_3$) δ ppm 8.06 (s, 1H), 7.92 (t, 1H), 7.66 (dd, 1H), 7.31 (s, 1H), 6.86 (t, 1H)

Step 6: Synthesis of (3-(difluoromethyl)benzofuran-5-yl)((3aS,4S,6R,6aR)-2,2-dimethyl-6-(4-methyl-7H-pyrrolo[2,3-d]pyrimidin-7-yl)tetrahydrofuro[3,4-d][1,3]dioxol-4-yl)methanone (G-7)

To a solution of G-6 (230 mg, 0.782 mmol) in dry THF (2 mL) was added 1.3 M i-PrMgCl.LiCl (0.722 mL, 0.939 mmol) at −60° C. The mixture was stirred at −30° C. for 1 h. The mixture was changed into slight yellow. A solution of compound C-9 (90 mg, 0.25 mmol) in THF (1 mL) was added to the reaction mixture. The mixture was stirred at −30° C. for 30 min then at 0° C. for 30 min. TLC (petroleum ether/EtOAc=1/1) showed most of compound C-9 was consumed and a good spot was formed. The mixture was quenched with sat. aq. NH$_4$Cl aq (5 mL). The mixture was extracted with EtOAc (5 mL×3). The extract was concentrated in vacuo to afford crude (300 mg). The crude was purified by silica gel chromatography eluted with EtOAc in petroleum ether from 0 to 100% to afford compound G-7 (100 mg, 86%) as a colorless gum, which solidified upon standing.

For Examples 14-20, the appropriate arylbromide was converted to the aryl Grignard via the aryliodide and reacted with compound C-9 to form the corresponding aryl ketone in a similar fashion to Steps 5 & 6 of Scheme G. The resulting aryl ketones were subject to reduction and deprotection in a similar fashion to Steps 10 & 11 of Scheme C.

For Examples 22 and 23, the aryliodide was prepared, used to make the corresponding Grignard reagent and reacted with C-9 as shown in Scheme H.

Scheme H

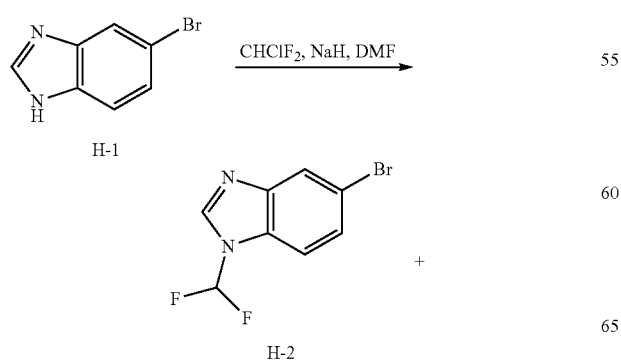

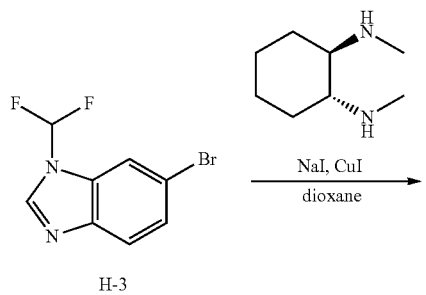

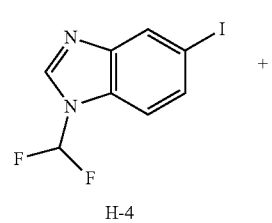

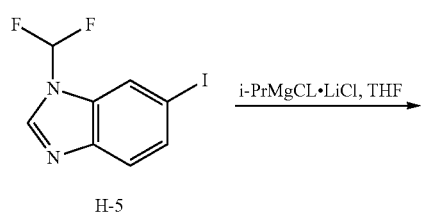

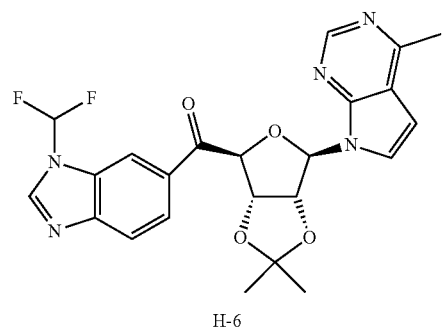

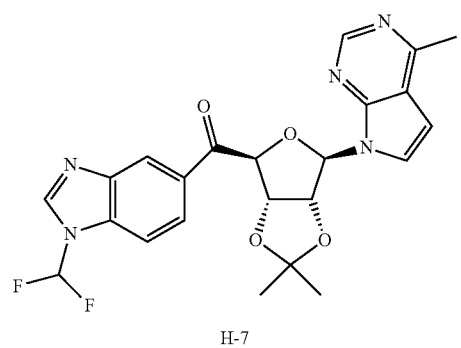

Step 1: Synthesis of 5-bromo-1-(difluoromethyl)-1H-benzo[d]imidazole (H-2) and 6-bromo-1-(difluoromethyl)-1H-benzo[d]imidazole (H-3)

To a red suspension of 5-bromo-1H-benzo[d]imidazole (5000 mg, 25.38 mmol) and $K_2CO_3$ (14 g, 102 mmol) in dry DMF (80 mL) was bubbled with $CHClF_2$ at 90° C. for 20 min. TLC (petroleum ether/EtOAc=8:1) showed a lot of the starting material was remaining and a good spot was formed. To the mixture was bubbled with $CHClF_2$ at 90° C. for another 1 hr. TLC (petroleum ether/EtOAc=1:1) showed most of SM was consumed and a good spot was formed. The mixture was poured into water (150 mL) and extracted with TBME (50 mL×3). The extract was dried over $Na_2SO_4$ and concentrated in vacuo to afford crude (5.8 g). The crude was purified by silica gel chromatography (Biotage, 120 g column) eluted with EtOAc in petroleum ether from 0 to 50% to afford a mixture of compound H-2 and H-3 (5 g, 79.8%) as a yellow gum, which solidified on standing.

Step 2: Synthesis of 1-(difluoromethyl)-5-iodo-1H-benzo[d]imidazole (H-4) and 1-(difluoromethyl)-6-iodo-1H-benzo[d]imidazole (H-5)

A mixture of compound H-2 and H-3 (1000 mg, 4.048 mmol), NaI (1.82 g, 12.1 mmol), CuI (77.1 mg, 0.405 mmol) and trans-N,N'-demethylcyclohexane (115 mg, 0.81 mmol) in dry dioxane (10 mL) was purged with Ar. The resulting yellow suspension was stirred at 110° C. in a sealed tube for 20 hr. LCMS showed the reaction was complete and clean. The mixture was poured into water/$NH_3.H_2O$ (50 mL/10 mL) and extracted with EtOAc (20 mL×3). The extract was washed with brine/$NH_3.H_2O$ (20 mL/5 mL) for 2 times, dried over $Na_2SO_4$ and concentrated in vacuo to afford crude (1.4 g). The crude was purified by silica gel chromatography eluted with EtOAc in petroleum ether from 0 to 50% to afford compounds H-4 and H-5 (1000 mg, 84%) as a inseparable mixture, which solidified upon standing.

Step 3: Synthesis of (1-(difluoromethyl)-1H-benzo[d]imidazol-6-yl)((3aS,4S,6R,6aR)-2,2-dimethyl-6-(4-methyl-7H-pyrrolo[2,3-d]pyrimidin-7-yl)tetrahydrofuro[3,4-d][1,3]dioxol-4-yl)methanone (H-6) and (1-(difluoromethyl)-1H-benzo[d]imidazol-5-yl)((3aS,4S,6R,6aR)-2,2-dimethyl-6-(4-methyl-7H-pyrrolo[2,3-d]pyrimidin-7-yl)tetrahydrofuro[3,4-d][1,3]dioxol-4-yl)methanone (H-7)

To a red solution of compounds H-4 and H-5 (230 mg, 0.782 mmol) in dry THF (2 mL) was added 1.3 M i-PrMgCl.LiCl (0.722 mL, 0.939 mmol) at −60° C. The red mixture was stirred at −30° C. for 1 h. A solution containing C-9 (100 mg, 0.276 mmol) in THF (1 mL) was added. The mixture was stirred at −30° C. for 30 min then at 0° C. for 30 min. The mixture was quenched with $NH_4Cl$ aq (5 mL). The mixture was extracted with EtOAc (5 mL×3). The extract was concentrated in vacuo to afford crude (300 mg). The crude was purified by silica gel chromatography eluted with EA in PE from 0 to 100% to afford compound H-6 and H-7 (100 mg, 77.2%) as colorless gum. This mixture was purified by SFC to afford compound G-6 (13 mg) and compound G-7 (53 mg). LCMS [M+1] 470

Compound H-6: $^1$H NMR (400 MHz, $CDCl_3$) δ ppm 8.54 (s, 1H), 8.23 (s, 1H), 8.05 (s, 1H), 7.84 (d, 1H), 7.76 (d, 1H), 7.47-7.18 (m, 1H), 7.18 (d, 1H), 6.42-6.39 (m, 2H), 5.79 (d, 1H), 5.52-5.49 (m, 2H), 2.56 (s, 3H), 1.71 (s, 3H), 1.46 (s, 3H).

Compound H-7: $^1$H NMR (400 MHz, $CDCl_3$) δ ppm 8.53 (s, 1H), 8.38 (s, 1H), 8.17 (s, 1H), 7.84 (d, 1H), 7.54 (d, 1H), 7.31-7.16 (m, 1H), 7.20 (d, 1H), 6.44 (s, 2H), 5.77-5.76 (m, 1H), 5.52 (s, 1H), 5.47 (d, 1H), 2.59 (s, 3H), 1.71 (s, 3H), 1.45 (s, 3H).

For Examples 24, the aryliodide was used and reacted with C-9 as shown in Scheme I.

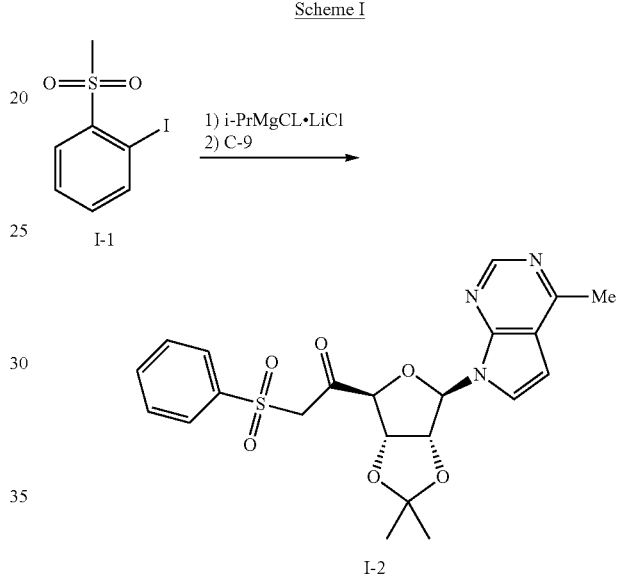

Scheme I

Synthesis of 1-((3aS,4S,6R,6aR)-2,2-dimethyl-6-(4-methyl-7H-pyrrolo[2,3-d]pyrimidin-7-yl)tetrahydrofuro[3,4-d][1,3]dioxol-4-yl)-2-(phenylsulfonyl)ethan-1-one (I-2)

To a solution of 1-iodo-2-(methylsulfonyl)benzene (400 mg, 1.42 mmol) in dry THF (4 mL) was added 1.3 M i-PrMgCl.LiCl (1.48 mL, 1.9 mmol) at −60° C. The mixture was stirred at −30° C. for 1 h. The mixture was changed into yellow. A solution of compound C-9 (200 mg, 0.552 mmol) in THF (2 mL) was added. The mixture was stirred at −30° C. for 30 min then at 0° C. for 30 min. LCMS showed the reaction was complete and the main peak was desired compound. The mixture was quenched with $NH_4Cl$ aq (5 mL). The mixture was extracted with EtOAc (5 mL×3). The extract was concentrated in vacuo to afford crude (370 mg). The crude material was purified by silica gel chromatography eluted with EtOAc in petroleum ether from 0-100% to afford compound I-2 (100 mg, 39.6%) as yellow solid. LCMS [M+1] 458

Compound I-2 was subjected to reduction and deprotection in a similar fashion to Steps 10 & 11 of Scheme C to give (2S,3S,4R,5R)-2-((R)-1-hydroxy-2-(phenylsulfonyl)ethyl)-5-(4-methyl-7H-pyrrolo[2,3-d]pyrimidin-7-yl)tetrahydrofuran-3,4-diol (Example 24).

Example 25

(Scheme J) (2R,3S,4R,5R)-2-((R)-hydroxy(1-methyl-1H-indol-6-yl)methyl)-5-(4-methyl-7H-pyrrolo[2,3-d]pyrimidin-7-yl)tetrahydrofuran-3,4-diol
(J-5)

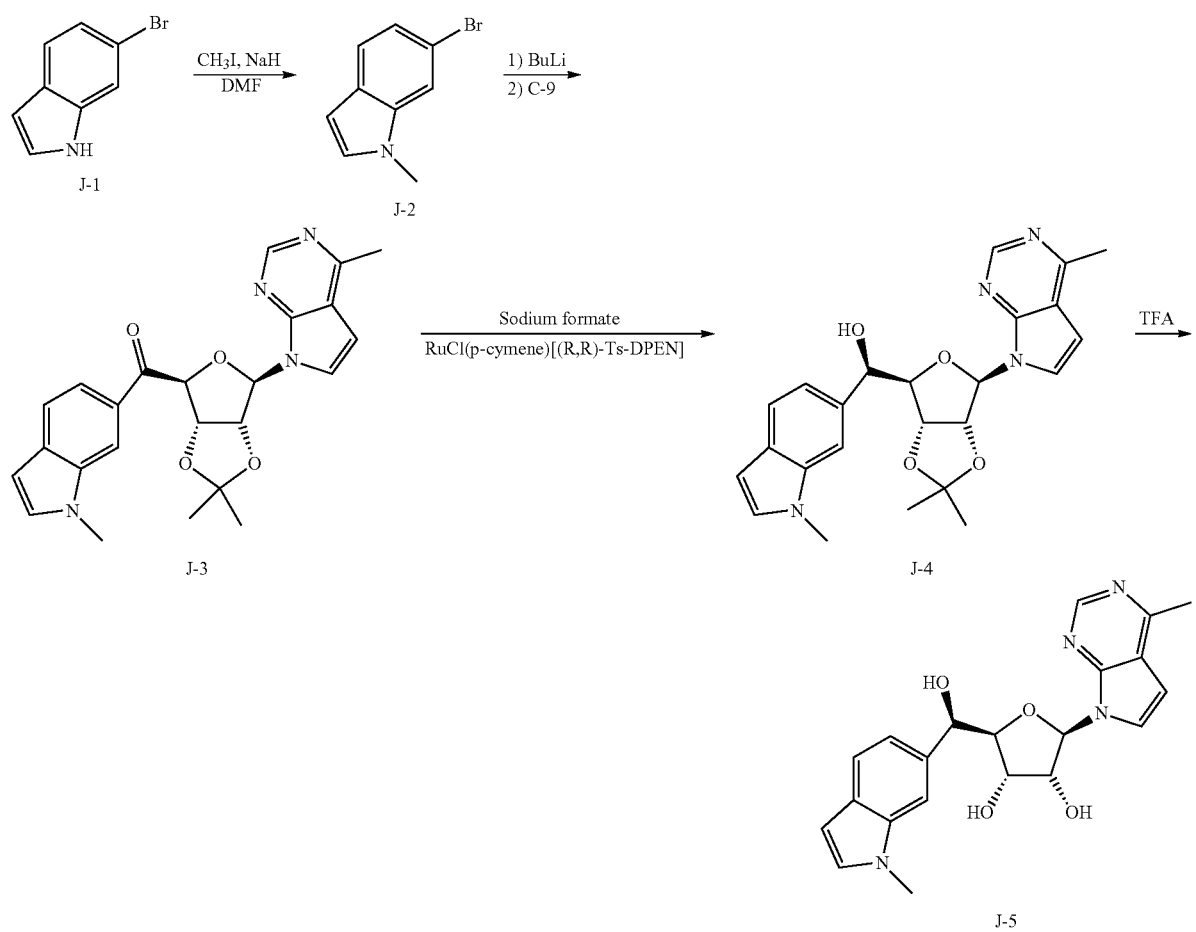

Scheme J

Step 1: Synthesis of 6-bromo-1-methyl-1H-indole (J-2)

To a suspension of 60% NaH (3.61 g, 90.3 mmol) in dry DMF (150 mL) was added 6-bromoindole (11.8 g, 60.191 mmol) at 0° C. in portions. Caution: gas evolved. The inner temperature rose to 7° C. The mixture was re-cooled to 0° C. To the resulting red suspension was stirred at 0° C. for 3 h. CH$_3$I (3.26 g, 23 mmol) was added dropwise at 0° C.-5° C. The reaction suspension was stirred at room temperature (25° C.) for 2 h. TLC (petroleum ether/EtOAc=8/1) showed most of the starting material was consumed and a good spot was formed. The mixture was poured into ice water (200 mL) and extracted with petroleum ether (100 mL×3). The extract was washed with brine (100 mL), dried over Na$_2$SO$_4$ and concentrated in vacuo to dryness to afford crude (15 g). The crude was purified by silica gel chromatography eluted with EtOAc in petroleum ether from 0 to 10% to afford J-2 (10 g, 79.1%) as a slight yellow oil. $^1$H NMR (400 MHz, CDCl$_3$) δ ppm 7.49-7.47 (m, 2H), 7.22 (d, 1H), 7.03 (d, 1H), 6.46 (d, 1H), 3.76 (s, 3H).

Step 2: Synthesis of ((3aS,4S,6R,6aR)-2,2-dimethyl-6-(4-methyl-7H-pyrrolo[2,3-d]pyrimidin-7-yl)tetrahydrofuro[3,4-d][1,3]dioxol-4-yl)(1-methyl-1H-indol-6-yl)methanone To a colorless solution of J-2 (700 mg, 3.33 mmol) in dry THF (10 mL) was added 2.5 M n-BuLi (1.5 mL, 3.8 mmol) at −60~−55° C. over 5 min. At the end of the addition, a lot of solid was formed and the color changed into yellow. The resulting yellow suspension was stirred at −65° C. for 1 h. A solution of compound C-9 (220 mg, 0.607 mmol) in dry THF (2 mL) was added at −65° C. over 5 min. The resulting suspension was changed into yellow solution and stirred at −65° C. for 1 h. TLC (petroleum ether/EtOAc=1/1) showed most the starting material was consumed and a good spot was formed. The reaction was poured into NH$_4$Cl aq (10 mL) and extracted with EtOAc (10 mL×3). The extract was washed with brine (10 mL), dried over Na$_2$SO$_4$ and concentrated in vacuo to afford crude (1 g). The crude was purified by silica gel chromatography eluted with EtOAc in petroleum ether from 0 to 100% (10 g column) to afford J-3 (200 mg, 76.2%) as a yellow gum. LCMS [M+H]433

Compound J-3 was subjected to reduction and deprotection in a similar fashion to Steps 10 & 11 of Scheme C to give (2R,3S,4R,5R)-2-((R)-hydroxy(1-methyl-1H-indazol-6-yl)methyl)-5-(4-methyl-7H-pyrrolo[2,3-d]pyrimidin-7-yl)tetrahydrofuran-3,4-diol (Example 25).

¹H NMR (400 MHz, DMSO-d₆) δ ppm 8.67 (s, 1H), 7.99 (s, 1H), 7.82 (d, 1H), 7.69-7.65 (m, 2H), 7.20 (d, 1H), 6.79 (d, 1H), 6.23 (d, 1 H), 6.18 (d, 1H), 5.27 (d, 1H), 5.07 (d, 1H), 4.98-4.96 (m, 1H), 4.68-4.67 (m 1H), 4.19-4.15 (m, 2H), 4.01 (s, 3H), 2.67 (s, 3H)

Example 26

(Scheme K)—(2R,3S,4R,5R)-2-((R)-hydroxy(phenyl)methyl)-5-(4-methyl-7H-pyrrolo[2,3-d]pyrimidin-7-yl)tetrahydrofuran-3,4-diol (K-4)

Example 27

(Scheme K)—(2R,3S,4R,5R)-2-((S)-hydroxy(phenyl)methyl)-5-(4-methyl-7H-pyrrolo[2,3-d]pyrimidin-7-yl)tetrahydrofuran-3,4-diol (K-5)

Scheme K

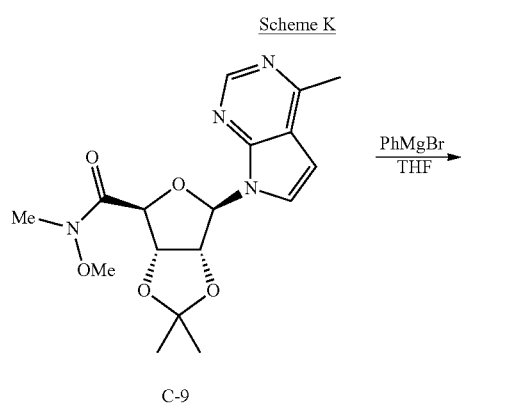

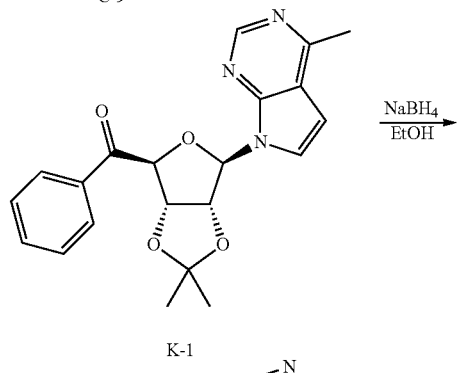

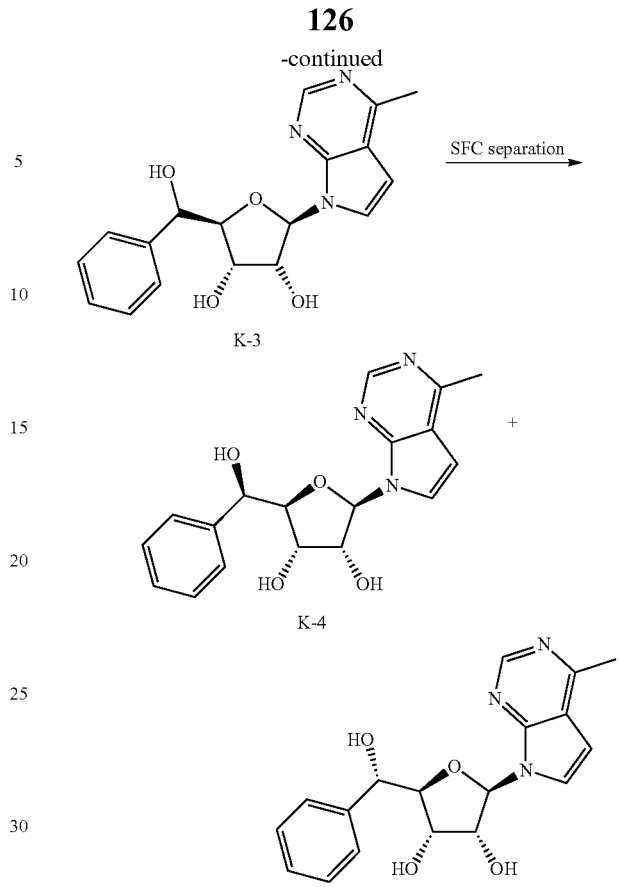

Step 1: Synthesis of ((3aS,4S,6R,6aR)-2,2-dimethyl-6-(4-methyl-7H-pyrrolo[2,3-d]pyrimidin-7-yl)tetrahydrofuro[3,4-d][1,3]dioxol-4-yl)(phenyl)methanone (K-1)

To a solution of C-9 (740 mg, 2.04 mmol) in dry THF (30 mL) was added PhMgBr (3M in Et₂O, 6.81 mL, 20.4 mmol) at −5-0° C. The resulting yellow suspension was stirred at −5° C. for 0.5 h. TLC (petroleum ether/EtOAc=1:1) showed most of the starting material was consumed and a new spot was formed. The mixture was poured into NH₄Cl aq (60 mL) and extracted with EtOAc (50 mL×2). The extract was washed with brine (50 mL), dried over NaSO₄ and concentrated in vacuo to afford crude product (1.5 g) as a yellow oil. The crude product was purified by silica gel chromatography (40 g column) eluted with EtOAc in petroleum ether from 0 to 100% to afford K-1 (750 mg, 96.8%) as a yellow gum.

Step 2: Synthesis of (S)-((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)(phenyl)methanol (K-2)

To a solution of K-1 (90 mg, 0.25 mmol) in EtOH (5 mL) was added NaBH₄ (40 mg) at room temperature. The mixture was stirred at room temperature for 30 min. TLC (petroleum ether/EtOAc=1:2) showed the reaction was complete and clean. The mixture was concentrated in vacuo to dryness to afford K-2 (100 mg, >100%) which was used in the next step directly.

Step 3 & 4: Synthesis of (2R,3S,4R,5R)-2-((R)-hydroxy(phenyl)methyl)-5-(4-methyl-7H-pyrrolo[2,3-d]pyrimidin-7-yl)tetrahydrofuran-3,4-diol (K-4) and (2R,3S,4R,5R)-2-((S)-hydroxy(phenyl)methyl)-5-(4-methyl-7H-pyrrolo[2,3-d]pyrimidin-7-yl)tetrahydrofuran-3,4-diol (K-5)

To a suspension of K-2 (100 mg, 0.262 mmol) in H$_2$O (2 mL) was added TFA (2 mL) at room temperature. The resulting slight yellow solution was stirred at room temperature for 4.5 h. LCMS showed most of the starting material was consumed and 95% of product was detected. The mixture was added to 10% K$_2$CO$_3$ aq (40 mL) at 0° C. The mixture was extracted with EtOAc (20 mL×4). The extract was dried over Na$_2$SO$_4$ and concentrated in vacuo to afford crude K-3 (100 mg). The crude K-3 was purified by SFC to afford K-4 (10 mg, 12%) and K-5 (58 mg, 66%).

Example 26 (K-4): LCMS [M+23]364; 1H NMR (400 MHz, MeOD) δ ppm 8.64 (s, 1H), 7.61 (d, J=3.7 Hz, 1H), 7.47 (d, J=7.6 Hz, 2H), 7.36 (t, J=7.5 Hz, 2H), 7.29-7.22 (m, J=7.3 Hz, 1H), 6.75 (d, J=3.7 Hz, 1H), 6.14 (d, J=7.5 Hz, 1H), 5.00 (d, J=2.8 Hz, 1H), 4.78-4.73 (m, 1H), 4.32-4.24 (m, 2H), 2.74 (s, 3H)

Example 27 (K-5): LCMS [M+23]364; 1H NMR (400 MHz, MeOD) δ ppm 8.68 (s, 1H), 7.78 (d, 1H), 7.43 (d, 2H), 7.30-7.26 (m, 2H), 7.24-7.22 (m, 1H), 6.80 (d, 1H), 6.20 (d, 1H), 4.93 (s, 1H), 4.65-4.62 (m, 1H), 4.40-4.39 (m, 1H), 4.30 (br, 1H), 2.76 (s, 3H)

Examples 28-43

Scheme L

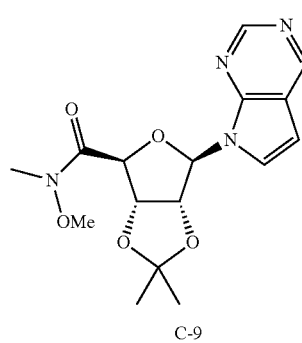

C-9

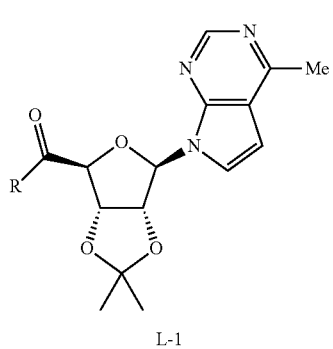

L-1

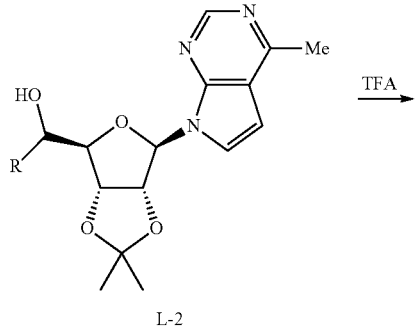

L-2

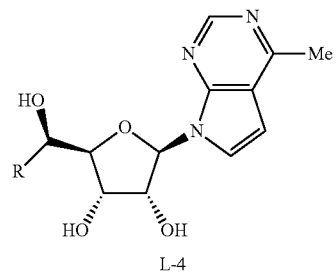

L-3

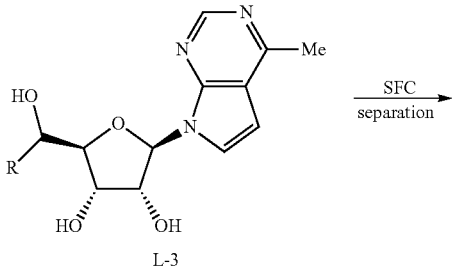

L-4

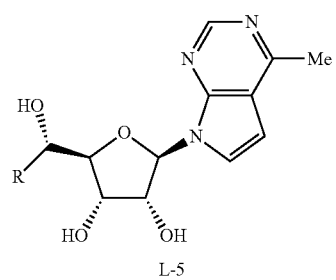

L-5

Synthesis of Examples 28-55 in Scheme L followed similar procedures to Steps 1-4 of Example 26 & 27 (Scheme K) with the appropriate Grignard reagent.

Examples 28-49 used commercially available Grignard reagents.

| | | | |
|---|---|---|---|
| 28<br>R = Bn<br>(L-4) | 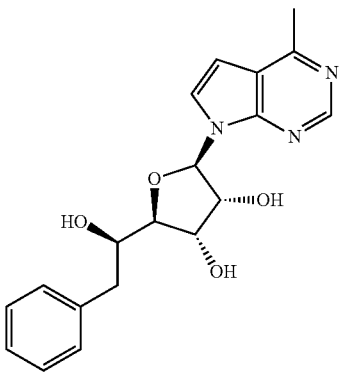 [SMILES: Cc1ncnc2c1ccn2[C@@H]1O[C@H]([C@H](O)Cc2ccccc2)[C@@H](O)[C@H]1O] | 356<br>[M + 1] | (2R,3S,4R,5R)-2-((R)-1-hydroxy-2-phenylethyl)-5-(4-methyl-7H-pyrrolo[2,3-d]pyrimidin-7-yl)tetrahydrofuran-3,4-diol<br>$^1$H NMR (400 MHz, MeOD) δ ppm 8.66 (s, 1H), 7.72 (d, 1H), 7.31-7.30 (m, 4H), 7.23-7.20 (m, 1H), 6.81 (d, 1H), 6.14 (d, 1H), 4.77-4.74 (m, 1H), 4.47-4.46 (m, 1 H), 4.09-4.04 (m, 2H), 2.95-2.90 (m, 1H), 2.85-2.80 (m, 1H), 2.75 (s, 3H) |
| 29<br>R = Bn<br>(L-5) | 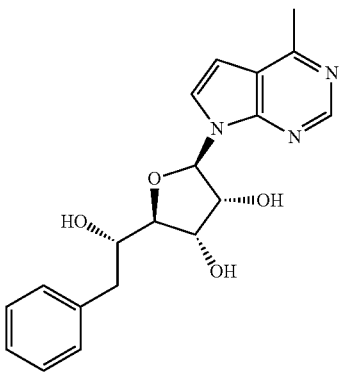 [SMILES: Cc1ncnc2c1ccn2[C@@H]1O[C@H]([C@@H](O)Cc2ccccc2)[C@@H](O)[C@H]1O] | 356<br>[M + 1] | (2R,3S,4R,5R)-2-((S)-1-hydroxy-2-phenylethyl)-5-(4-methyl-7H-pyrrolo[2,3-d]pyrimidin-7-yl)tetrahydrofuran-3,4-diol<br>$^1$H NMR (400 MHz, MeOD) δ ppm 8.66 (s, 1H), 7.80 (d, 1H), 7.31-7.20 (m, 5H), 6.80 (d, 1H), 6.17 (d, 1H), 4.74-4.71 (m, 1H), 4.30-4.28 (m, 1 H), 4.00-3.98 (m, 2H), 2.90 (d, 2H), 2.77 (s, 3H) |
| 30<br>R = PhCH$_2$CH$_2$<br>(L-4) | 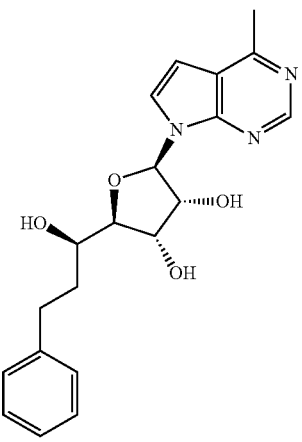 [SMILES: Cc1ncnc2c1ccn2[C@@H]1O[C@H]([C@H](O)CCc2ccccc2)[C@@H](O)[C@H]1O] | 392<br>[M + 23] | (2R,3S,4R,5R)-2-((R)-1-hydroxy-3-phenylpropyl)-5-(4-methyl-7H-pyrrolo[2,3-d]pyrimidin-7-yl)tetrahydrofuran-3,4-diol<br>$^1$H NMR (400 MHz, MeOD) δ ppm 8.65 (s, 1H), 7.62 (d, 1H), 7.29-7.23 (m, 4H), 7.19-7.15 (m, 1H), 6.78 (d, 1H), 6.13 (d, 1H), 4.70-4.67 (m, 1H), 4.38-4.36 (m, 1 H), 4.02-4.00 (m, 1H), 3.84-3.81 (m, 1H), 2.95-2.85 (m, 1H), 2.76 (s, 3H), 2.76-2.72 (m, 1H), 1.91-1.80 (m, 2H) |
| 31<br>R = PhCH$_2$CH$_2$<br>(L-4) | 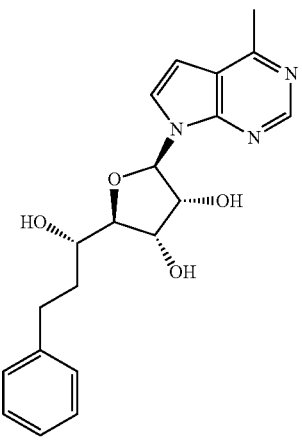 [SMILES: Cc1ncnc2c1ccn2[C@@H]1O[C@H]([C@@H](O)CCc2ccccc2)[C@@H](O)[C@H]1O] | 392<br>[M + 23] | (2R,3S,4R,5R)-2-((S)-1-hydroxy-3-phenylpropyl)-5-(4-methyl-7H-pyrrolo[2,3-d]pyrimidin-7-yl)tetrahydrofuran-3,4-diol<br>$^1$H NMR (400 MHz, MeOD) δ ppm 8.63 (s, 1H), 7.75 (d, 1H), 7.27-20 (m, 4H), 7.16-7.13 (m, 1H), 6.78 (d, 1H), 6.18 (d, 1H), 4.68-4.65 (m, 1H), 4.31-4.29 (m, 1 H), 4.08-4.07 (m, 1H), 3.76-3.75 (m, 1H), 2.83-2.81 (m, 1H), 2.75 (s, 3H), 2.75-2.72 (m, 1H), 1.93-1.85 (m, 2H) |

| | | | |
|---|---|---|---|
| 32<br>R = 3-Cl—Ph<br>(L-4) | 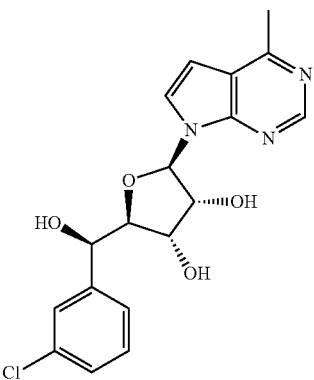 [SMILES: Cc1ncnc2c1ccn2[C@@H]1O[C@H]([C@H](O)c2cccc(Cl)c2)[C@@H](O)[C@H]1O] | 376<br>[M + 1] | (2R,3S,4R,5R)-2-((R)-(3-chlorophenyl)(hydroxy)methyl)-5-(4-methyl-7H-pyrrolo[2,3-d]pyrimidin-7-yl)tetrahydrofuran-3,4-diol<br>$^1$H NMR (400 MHz, DMSO-d$_6$) δ ppm 8.65 (s, 1H), 7.95 (d, 1H), 7.44 (s, 1H), 7.35-7.32 (m, 2H), 7.29-7.28 (m, 1H), 6.79 (d, 1H), 6.17 (d, 2H), 5.32 (br, 1 H), 5.18 (br, 1H), 4.81 (br, 1H), 4.59 (br, 1H), 4.11 (br, 1H), 4.02 (d, 1H), 2.66 (s, 3H) |
| 33<br>R = 3-Cl—Ph<br>(L-5) | 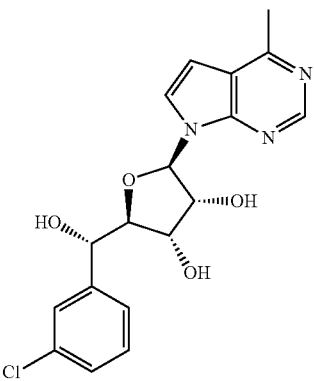 [SMILES: Cc1ncnc2c1ccn2[C@@H]1O[C@H]([C@@H](O)c2cccc(Cl)c2)[C@@H](O)[C@H]1O] | 376<br>[M + 1] | (2R,3S,4R,5R)-2-((S)-(3-chlorophenyl)(hydroxy)methyl)-5-(4-methyl-7H-pyrrolo[2,3-d]pyrimidin-7-yl)tetrahydrofuran-3,4-diol<br>$^1$H NMR (400 MHz, MeOD) δ ppm 8.65 (s, 1H), 7.77 (d, 1H), 7.41 (s, 1H), 7.33 (d, 1H), 7.28-7.24 (m, 1H), 7.23 (d, 1H), 6.77 (d, 1H), 6.18 (br, 1 H), 4.93 (d, 1H), 4.61-4.59 (m, 1H), 4.40-4.38 (m, 1H), 4.27-4.26 (m, 1H), 2.74 (s, 3H) |
| 34<br>R = 3-F—Ph<br>(L-4) | 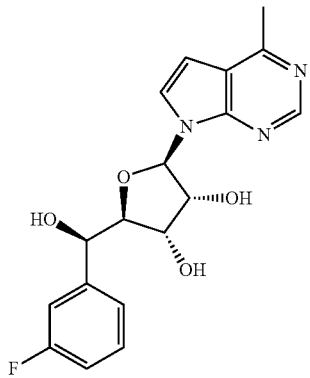 [SMILES: Cc1ncnc2c1ccn2[C@@H]1O[C@H]([C@H](O)c2cccc(F)c2)[C@@H](O)[C@H]1O] | 360<br>[M + 1] | (2R,3S,4R,5R)-2-((R)-(3-fluorophenyl)(hydroxy)methyl)-5-(4-methyl-7H-pyrrolo[2,3-d]pyrimidin-7-yl)tetrahydrofuran-3,4-diol<br>$^1$H NMR (400 MHz, DMSO-d$_6$) δ ppm 8.65 (s, 1H), 7.80 (d, 1H), 7.36-7.32 (m, 1H), 7.25-7.19 (m, 2H), 7.07-7.03 (m, 1H), 6.79 (d, 1H), 6.17-6.15 (m, 2H), 5.30 (d, 1 H), 5.13 (d, 1H), 4.82 (br, 1H), 4.60-4.59 (m, 1H), 4.11 (br, 1H), 4.05-4.02 (m, 1H), 2.67 (s, 3H) |
| 35<br>R = 3-F—Ph<br>(L-5) | 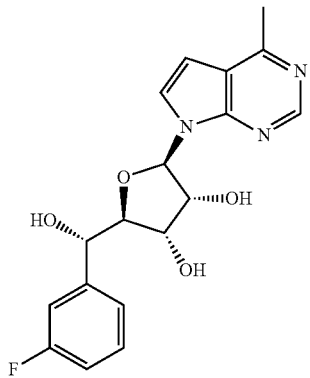 | 360<br>[M + 1] | (2R,3S,4R,5R)-2-((S)-(3-fluorophenyl)(hydroxy)methyl)-5-(4-methyl-7H-pyrrolo[2,3-d]pyrimidin-7-yl)tetrahydrofuran-3,4-diol<br>$^1$H NMR (400 MHz, MeOD) δ ppm 8.67 (s, 1H), 7.80 (d, 1H), 7.34-7.30 (m, 1H), 7.22 (d, 1H), 7.17 (d, 1H), 6.96-6.90 (m, 1H), 6.79 (d, 1H), 6.20 (d, 1 H), 4.76 (d, 1H), 4.65-4.64 (m, 1H), 4.42-4.40 (m, 1H), 4.29-4.28 (m, 1H), 2.76 (s, 3H) |

-continued

| | | | |
|---|---|---|---|
| 36<br>R = 3,5-diF-Ph<br>(L-4) | 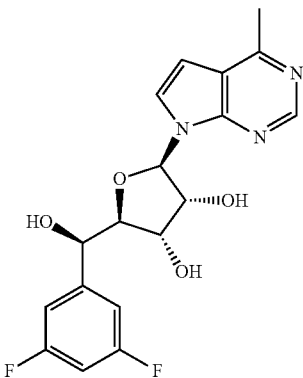 [SMILES: Cc1ncnc2c1ccn2[C@@H]1O[C@H]([C@H](O)c2cc(F)cc(F)c2)[C@@H](O)[C@H]1O] | 378<br>[M + 1] | (2R,3S,4R,5R)-2-((R)-(3,5-difluorophenyl)(hydroxy)methyl)-5-(4-methyl-7H-pyrrolo[2,3-d]pyrimidin-7-yl)tetrahydrofuran-3,4-diol<br>$^1$H NMR (400Hz, DMSO-d$_6$) δ ppm 8.66 (s, 1H), 7.82 (d, 1H), 7.11-7.05 (m, 3H), 6.80 (d, 1H), 6.27 (br, 1H), 6.17 (d, 1H), 5.34 (br, 1H), 5.20 (br, 1 H), 4.83 (br, 1H), 4.58 (br, 1H), 4.11 (br, 1H), 4.02 (d, 1H), 2.67 (s, 3H) |
| 37<br>R = 3,5-diF-Ph<br>(L-5) | 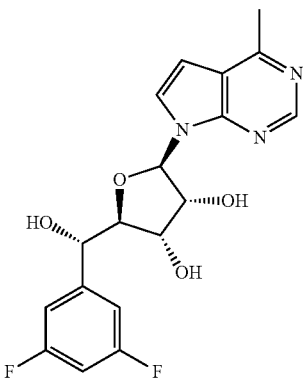 [SMILES: Cc1ncnc2c1ccn2[C@@H]1O[C@H]([C@@H](O)c2cc(F)cc(F)c2)[C@@H](O)[C@H]1O] | 378<br>[M + 1] | (2R,3S,4R,5R)-2-((S)-(3,5-difluorophenyl)(hydroxy)methyl)-5-(4-methyl-7H-pyrrolo[2,3-d]pyrimidin-7-yl)tetrahydrofuran-3,4-diol<br>$^1$H NMR (400Hz, MeOD) δ ppm 8.67 (s, 1H), 7.83 (d, 1H), 7.02 (d, 2H), 6.80-6.76 (m, 2H), 6.21 (d, 1H), 4.96 (br, 1H), 4.68-4.65 (m, 1H), 4.44-4.42 (m, 1 H), 4.29 (br, 1H), 2.75 (s, 3H) |
| 38<br>R = 4-F—Ph<br>(L-4) | 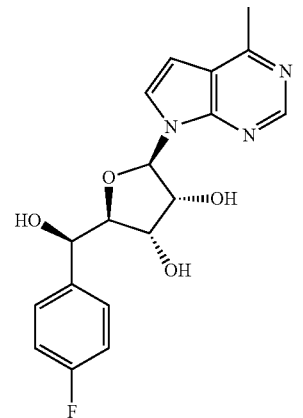 [SMILES: Cc1ncnc2c1ccn2[C@@H]1O[C@H]([C@H](O)c2ccc(F)cc2)[C@@H](O)[C@H]1O] | 360<br>[M + 1] | (2R,3S,4R,5R)-2-((R)-(4-fluorophenyl)(hydroxy)methyl)-5-(4-methyl-7H-pyrrolo[2,3-d]pyrimidin-7-yl)tetrahydrofuran-3,4-diol<br>$^1$H NMR (400 MHz, DMSO-d$_6$) δ ppm 8.65 (s, 1H), 7.77 (d, J = 3.8 Hz, 1H), 7.43 (dd, J = 5.7, 8.6 Hz, 2H), 7.12 (t, J = 8.9 Hz, 2H), 6.77 (d, J = 3.7 Hz, 1H), 6.15 (d, J = 7.7 Hz, 1H), 6.03 (d, J = 4.2 Hz, 1H), 5.25 (d, J = 7.0 Hz, 1H), 5.08 (d, J = 4.0 Hz, 1H), 4.80 (t, J = 4.6 Hz, 1H), 4.64-4.56 (m, 1H), 4.13 (t, J = 4.7 Hz, 1H), 4.04-3.97 (m, J = 5.0 Hz, 1H), 2.67 (s, 3H) |
| 39<br>R = 4-F—Ph<br>(L-5) | 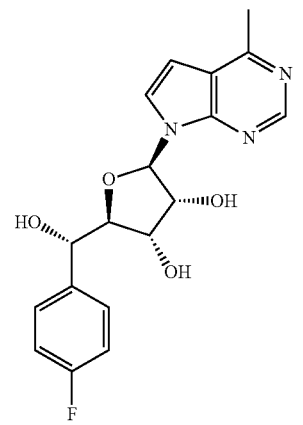 [SMILES: Cc1ncnc2c1ccn2[C@@H]1O[C@H]([C@@H](O)c2ccc(F)cc2)[C@@H](O)[C@H]1O] | 360<br>[M + 1] | (2R,3S,4R,5R)-2-((S)-(4-fluorophenyl)(hydroxy)methyl)-5-(4-methyl-7H-pyrrolo[2,3-d]pyrimidin-7-yl)tetrahydrofuran-3,4-diol<br>$^1$H NMR (400 MHz, DMSO-d$_6$) δ ppm 8.66 (s, 1H), 7.79 (d, 1H), 7.44-7.41 (m, 2H), 7.04-7.00 (m, 2H), 6.79 (d, 1H), 6.20 (d, 1H), 4.94 (s, 1 H), 4.65-4.64 (m, 1H), 4.40-4.38 (m, 1H), 4.27-4.26 (m, 1H), 2.75 (s, 3H) |

| | | | |
|---|---|---|---|
| 40<br>R = Et<br>(L-4) | 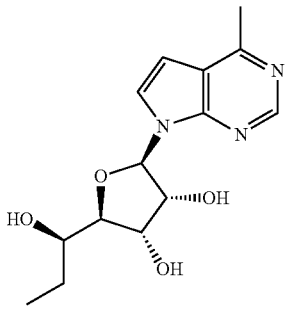 [SMILES: CC[C@@H](O)[C@H]1O[C@@H](n2ccc3c(C)ncnc32)[C@H](O)[C@@H]1O] | 294<br>[M + 1] | (2R,3S,4R,5R)-2-((R)-1-hydroxypropyl)-5-(4-methyl-7H-pyrrolo[2,3-d]pyrimidin-7-yl)tetrahydrofuran-3,4-diol<br>$^1$H NMR (400 MHz, MeOD) δ ppm 8.64 (s, 1H), 7.67 (d, 1H), 6.77 (d, 1H), 6.11 (d, 1H), 4.70-4.73 (m, 1H), 4.34-4.32 (m, 1H), 4.03 (d, 1H), 3.77-3.73 (m, 1H), 2.75 (s, 3H), 1.67-1.53 (m, 2H), 1.08-1.05 (m, 3H) |
| 41<br>R = Et<br>(L-5) | 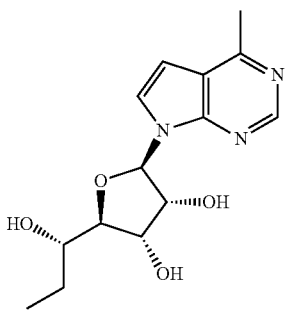 [SMILES: CC[C@H](O)[C@H]1O[C@@H](n2ccc3c(C)ncnc32)[C@H](O)[C@@H]1O] | 294<br>[M + 1] | (2R,3S,4R,5R)-2-((S)-1-hydroxypropyl)-5-(4-methyl-7H-pyrrolo[2,3-d]pyrimidin-7-yl)tetrahydrofuran-3,4-diol<br>$^1$H NMR (400 MHz, MeOD) δ ppm 8.65 (s, 1H), 7.78 (d, 1H), 6.79 (d, 1H), 6.18 (d, 1H), 4.68-4.65 (m, 1H), 4.31 (m, 1H), 4.08 (s, 1H), 3.67-3.64 (m, 1H), 2.76 (s, 3H), 1.65-1.58 (m, 2H), 1.03-0.99 (m, 3H). |
| 42<br>R = cyclopentyl<br>(L-4) | 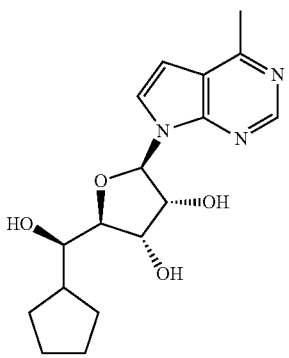 [SMILES: Cc1ncnc2c1ccn2[C@@H]1O[C@H]([C@H](O)C2CCCC2)[C@@H](O)[C@H]1O] | 334<br>[M + 1] | (2R,3S,4R,5R)-2-((R)-cyclopentyl(hydroxy)methyl)-5-(4-methyl-7H-pyrrolo[2,3-d]pyrimidin-7-yl)tetrahydrofuran-3,4-diol<br>$^1$H NMR (400 MHz, MeOD) δ ppm 8.73 (s, 1H), 7.81 (d, 1H), 6.87 (d, 1H), 6.16 (d, 1H), 4.68-4.65 (m, 1H), 4.39 (d, 1H), 4.15 (d, 1H), 3.62 (d, 1H), 2.81 (s, 3 H), 2.05-1.96 (m, 2H), 1.90-1.80 (m, 1H), 1.75-1.63 (m, 4H), 1.61-1.45 (m, 1H), 1.35-1.25 (m, 1H) |
| 43<br>R = cyclopentyl<br>(L-5) | 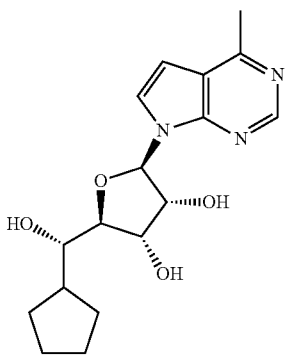 [SMILES: Cc1ncnc2c1ccn2[C@@H]1O[C@H]([C@@H](O)C2CCCC2)[C@@H](O)[C@H]1O] | 334<br>[M + 1] | (2R,3S,4R,5R)-2-((S)-cyclopentyl(hydroxy)methyl)-5-(4-methyl-7H-pyrrolo[2,3-d]pyrimidin-7-yl)tetrahydrofuran-3,4-diol<br>$^1$H NMR (400 MHz, MeOD) δ ppm 8.63 (s, 1H), 7.75 (d, 1H), 6.76 (d, 1H), 6.13 (d, 1H), 4.71-4.68 (m, 1H), 4.31-4.30 (m, 1H), 4.17 (s, 1H), 3.48 (d, 1 H), 2.75 (s, 3H), 2.11-2.09 (m, 1H), 1.92-1.91 (m, 1H), 1.74-1.44 (m, 6H), 1.30-1.26 (m, 1H) |
| 44<br>R = Me<br>(L-4) | 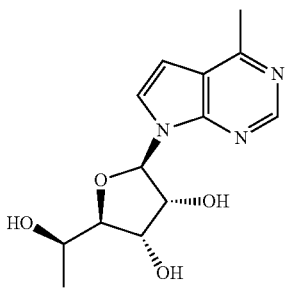 [SMILES: Cc1ncnc2c1ccn2[C@@H]1O[C@H]([C@@H](C)O)[C@@H](O)[C@H]1O] | 280<br>[M + 1] | (2R,3S,4R,5R)-2-((R)-1-hydroxyethyl)-5-(4-methyl-7H-pyrrolo[2,3-d]pyrimidin-7-yl)tetrahydrofuran-3,4-diol<br>$^1$H NMR (400 MHz, DMSO-d$_6$) δ ppm 8.65 (s, 1H), 7.77-7.76 (d, 1H), 6.77-6.76 (d, 1H), 6.14-6.12 (d, 1H), 5.28-5.18 (m, 3H), 4.49-4.46 (m, 1H), 4.17-4.16 (m, 1H), 3.80-3.71 (m, 2H), 2.66 (s, 3H), 1.10-1.08 (d, 3H) |

| # | | | |
|---|---|---|---|
| 45<br>R = Me<br>(L-5) | 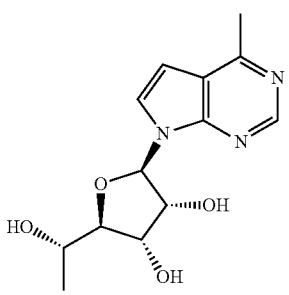 [SMILES: Cc1ncnc2c1ccn2[C@@H]1O[C@H]([C@H](C)O)[C@@H](O)[C@H]1O] | 280<br>[M + 1] | (2R,3S,4R,5R)-2-((S)-1-hydroxyethyl)-5-(4-methyl-7H-pyrrolo[2,3-d]pyrimidin-7-yl)tetrahydrofuran-3,4-diol<br>$^1$H NMR (400 MHz, DMSO-d$_6$) δ ppm 8.55 (s, 1H), 7.85-7.84 (d, 1H), 6.77-6.76 (d, 1H), 6.19-6.17 (d, 1H), 5.32-5.30 (m, 1H), 5.11-5.06 (m, 2H), 4.41-4.38 (m, 1H), 4.11-4.09 (m, 1H), 3.81-3.76 (m, 2H), 2.67 (s, 3H), 1.12-1.11 (d, 3H) |
| 46<br>R = cyclopropyl<br>(L-4) | 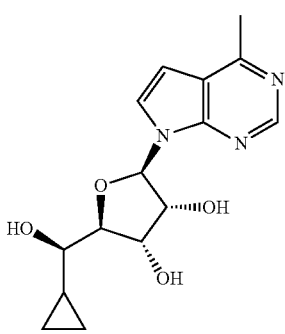 [SMILES: Cc1ncnc2c1ccn2[C@@H]1O[C@H]([C@H](O)C2CC2)[C@@H](O)[C@H]1O] | 306<br>[M + 1] | (2R,3S,4R,5R)-2-((R)-cyclopropyl(hydroxy)methyl)-5-(4-methyl-7H-pyrrolo[2,3-d]pyrimidin-7-yl)tetrahydrofuran-3,4-diol<br>$^1$H NMR (400 MHz, MeOD) δ ppm 8.65 (s, 1H), 7.71 (d, 1H), 6.77 (d, 1H), 6.14 (d, 1H), 4.75-4.72 (m, 1H), 4.47-4.46 (m, 1H), 4.21-4.20 (m, 1H), 3.16-3.14 (m, 1H), 2.75 (s, 3H), 1.03-1.00 (m, 1H), 0.63-0.58 (m, 2H), 0.45-0.44 (m, 1), 0.35-0.34 (m, 1H) |
| 47<br>R = cyclopropyl<br>(L-5) | 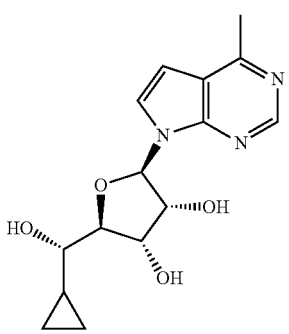 [SMILES: Cc1ncnc2c1ccn2[C@@H]1O[C@H]([C@@H](O)C2CC2)[C@@H](O)[C@H]1O] | 306<br>[M + 1] | (2R,3S,4R,5R)-2-((S)-cyclopropyl(hydroxy)methyl)-5-(4-methyl-7H-pyrrolo[2,3-d]pyrimidin-7-yl)tetrahydrofuran-3,4-diol<br>$^1$H NMR (400 MHz, MeOD) δ ppm 8.68 (s, 1H), 7.86 (d, 1H), 6.81 (d, 1H), 6.26 (d, 1H), 4.67-4.64 (m, 1H), 4.31-4.30 (m, 1H), 4.18-4.17 (m, 1H), 3.02 (d, 1H), 2.77 (s, 3 H), 1.20-1.10 (m, 1H), 0.57-0.52 (m, 2H), 0.41-0.40 (m, 1H), 0.30-0.28 (m, 1H). |
| 48<br>R = isopropyl<br>(L-4) | 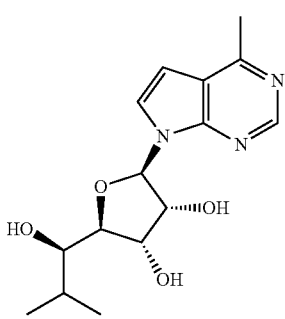 [SMILES: Cc1ncnc2c1ccn2[C@@H]1O[C@H]([C@H](O)C(C)C)[C@@H](O)[C@H]1O] | 308<br>[M + 1] | (2R,3S,4R,5R)-2-((R)-1-hydroxy-2-methylpropyl)-5-(4-methyl-7H-pyrrolo[2,3-d]pyrimidin-7-yl)tetrahydrofuran-3,4-diol<br>$^1$H NMR (400 MHz, MeOD) δ ppm 8.66 (s, 1H), 7.68 (d, 1H), 6.79 (d, 1H), 6.11 (d, 1H), 4.74-4.70 (m, 1H), 4.36 (d, 1H), 4.22-4.21 (m, 1H), 3.52-3.50 (m, 1 H), 2.76 (s, 3H), 1.87-1.82 (m, 1H), 1.07 (d, 3H), 1.03 (d, 3H) |
| 49<br>R = isopropyl<br>(L-5) | 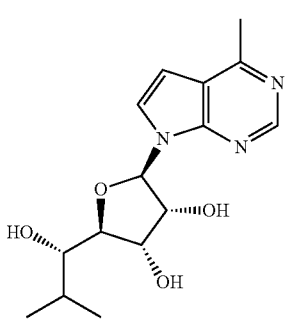 [SMILES: Cc1ncnc2c1ccn2[C@@H]1O[C@H]([C@@H](O)C(C)C)[C@@H](O)[C@H]1O] | 308<br>[M + 1] | (2R,3S,4R,5R)-2-((S)-1-hydroxy-2-methylpropyl)-5-(4-methyl-7H-pyrrolo[2,3-d]pyrimidin-7-yl)tetrahydrofuran-3,4-diol<br>$^1$H NMR (400 MHz, MeOD) δ ppm 8.64 (s, 1H), 7.76 (d, 1H), 6.78 (d, 1H), 6.13 (d, 1H), 4.72-4.69 (m, 1H), 4.32-4.28 (m, 2H), 3.34-3.33 (m, 1 H), 2.76 (s, 3H), 1.86-1.79 (m, 1H), 1.07 (d, 3H), 0.96 (d, 3H) |

| | | |
|---|---|---|
| 50<br>R = N—Me-4-pyrazole<br>(L-4) | 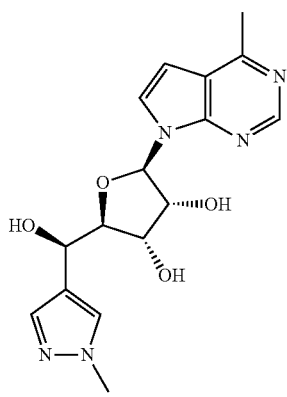 [SMILES: Cc1ncnc2c1ccn2[C@@H]1O[C@H]([C@H](O)c2cnn(C)c2)[C@@H](O)[C@H]1O] | 345<br>[M + 1] | (2R,3S,4R,5R)-2-((R)-hydroxy(1-methyl-1H-pyrazol-4-yl)methyl)-5-(4-methyl-7H-pyrrolo[2,3-d]pyrimidin-7-yl)tetrahydrofuran-3,4-diol<br>$^1$H NMR (400 MHz, MeOD) δ ppm 8.66 (s, 1H), 7.65 (d, 1H), 7.59 (s, 1H), 7.51 (s, 1H), 6.80 (d, 1H), 6.17 (d, 1H), 4.98 (d, 1H), 4.78-4.75 (m, 1 H), 4.32 (d, 1H), 4.26 (d, 1H), 3.87 (s, 3H), 2.77 (s, 3H) |
| 51<br>R = N—Me-4-pyrazole<br>(L-5) | 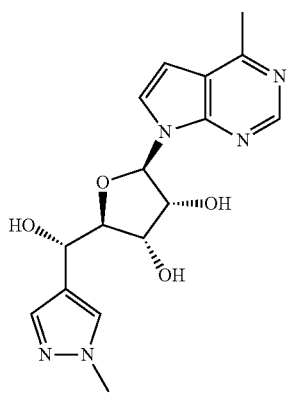 [SMILES: Cc1ncnc2c1ccn2[C@@H]1O[C@H]([C@@H](O)c2cnn(C)c2)[C@@H](O)[C@H]1O] | 345<br>[M + 1] | (2R,3S,4R,5R)-2-((S)-hydroxy(1-methyl-1H-pyrazol-4-yl)methyl)-5-(4-methyl-7H-pyrrolo[2,3-d]pyrimidin-7-yl)tetrahydrofuran-3,4-diol<br>$^1$H NMR (400 MHz, DMSO-d$_6$) δ ppm 8.66 (s, 1H), 7.80 (d, 1H), 7.52 (s, 1H), 7.31 (s, 1H), 6.78 (d, 1H), 6.20 (d, 1H), 5.64 (d, 1H), 5.37 (br, 1 H), 5.24 (br, 1H), 4.74 (br, 1H), 4.39-4.83 (br, 1H), 4.13 (br, 1H), 4.04-4.03 (m, 1H), 3.76 (s, 3H), 2.67 (s, 3H) |
| 52<br>R = cyclobutyl<br>(L-4) | 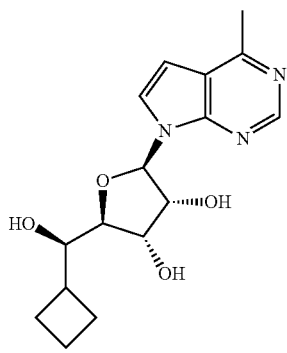 [SMILES: Cc1ncnc2c1ccn2[C@@H]1O[C@H]([C@H](O)C2CCC2)[C@@H](O)[C@H]1O] | 320<br>[M + 1] | (2R,3S,4R,5R)-2-((R)-cyclobutyl(hydroxy)methyl)-5-(4-methyl-7H-pyrrolo[2,3-d]pyrimidin-7-yl)tetrahydrofuran-3,4-diol<br>$^1$H NMR (400 MHz, MeOD) δ ppm 8.63 (s, 1H), 7.74 (d, 1H), 6.76 (d, 1H), 6.13 (d, 1H), 4.67-4.64 (m, 1H), 4.30-4.28 (m, 1H), 4.06-4.05 (m, 1H), 3.66-3.63 (m, 1 H), 2.75 (s, 3H), 2.60-2.55 (m, 1H), 1.99-1.83 (m, 6H) |
| 53<br>R = cyclobutyl<br>(L-5) | 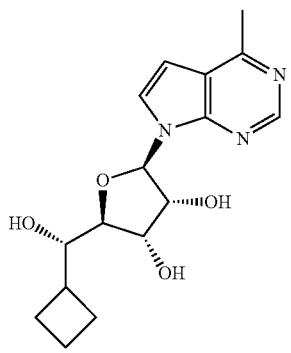 [SMILES: Cc1ncnc2c1ccn2[C@@H]1O[C@H]([C@@H](O)C2CCC2)[C@@H](O)[C@H]1O] | 320<br>[M + 1] | (2R,3S,4R,5R)-2-((S)-cyclobutyl(hydroxy)methyl)-5-(4-methyl-7H-pyrrolo[2,3-d]pyrimidin-7-yl)tetrahydrofuran-3,4-diol<br>$^1$H NMR (400 MHz, MeOD) δ ppm 8.64 (s, 1H), 7.69 (d, 1H), 6.77 (d, 1H), 6.09 (d, 1H), 4.70-4.67 (m, 1H), 4.29-4.28 (m, 1H), 3.99-3.98(m, 1H), 3.79 (d, 1 H), 2.75 (s, 3H), 2.54-2.52 (m, 1H), 2.05-1.86 (m, 6H) |

| | | | |
|---|---|---|---|
| 54<br>R = 2-furan<br>(L-4) | 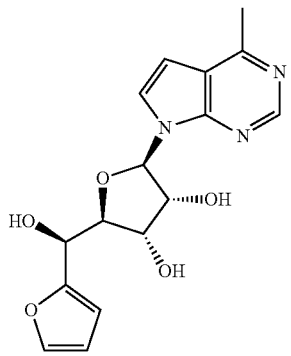 [SMILES: Cc1ncnc2c1ccn2[C@@H]1O[C@H]([C@H](O)c2ccco2)[C@@H](O)[C@H]1O] | 354<br>[M + 23] | (2S,3S,4R,5R)-2-((S)-furan-2-yl(hydroxy)methyl)-5-(4-methyl-7H-pyrrolo[2,3-d]pyrimidin-7-yl)tetrahydrofuran-3,4-diol<br>$^1$H NMR (400 MHz, MeOD) δ ppm 8.66 (s, 1H), 7.69 (d, 1H), 7.51 (s, 1H), 6.79 (d, 1H), 6.42 (s, 2H), 6.22 (d, 1 H), 4.97 (d, 1H), 4.78-4.75 (m, 1H), 4.47 (d, 1H), 4.38 (d, 1H), 2.76 (s, 3H) |
| 55<br>R = 2-furan<br>(L-5) | 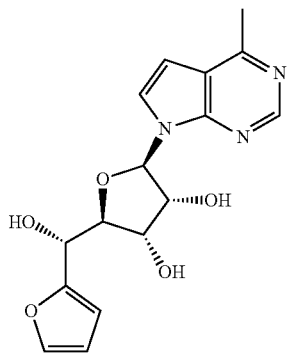 [SMILES: Cc1ncnc2c1ccn2[C@@H]1O[C@H]([C@@H](O)c2ccco2)[C@@H](O)[C@H]1O] | 354<br>[M + 23] | (2S,3S,4R,5R)-2-((R)-furan-2-yl(hydroxy)methyl)-5-(4-methyl-7H-pyrrolo[2,3-d]pyrimidin-7-yl)tetrahydrofuran-3,4-diol<br>$^1$H NMR (400 MHz, MeOD) δ ppm 8.65 (s, 1H), 7.68 (d, 1H), 7.45 (s, 1H), 6.76 (d, 1H), 6.38 (s, 2H), 6.23 (d, 1 H), 4.93 (d, 1H), 4.67-4.61 (m, 1H), 4.42-4.41 (m, 1H), 4.39-4.38 (m, 1H), 2.74 (s, 3H) |

For Examples 50-53, the Grignard reagent was prepared from the appropriate aryl or alkyl bromide in a similar fashion to Step 1 in Scheme E (Example 12). This material was used directly with compound C-9 to generate the ketone in a similar fashion to Step 1 of Scheme K. Subsequent reduction with NaBH$_4$, deprotection with TFA and final chiral separation by SFC were done in a similar manner to Steps 2-4 in Scheme K to give the final compounds Example 50, 51, 52 & 53.

Examples 54 & 55

Preparation of the Grignard Reagent is Described in Scheme M

Scheme M

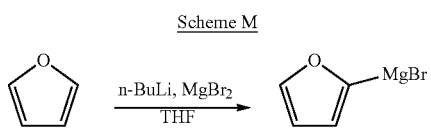

Step 1: Synthesis of furan-2-ylmagnesium bromide

To a solution of furan (0.4 mL, 5.52 mmol) in dry THF (5 mL) was added 2.5 M n-BuLi (2.21 mL, 5.52 mmol) at 0° C. The mixture was stirred at 0° C. for 30 min. MgBr$_2$ (1.3 g, 7.06 mmol) was added in one portion. The temperature rose to 15° C. The mixture was stirred at 0° C. for 20 min and a lot of solid formed. The mixture was used in the next step directly.

The Grignard reagent was used directly with compound C-9 to generate the aryl ketone in a similar fashion to Step 1 of Scheme K. Subsequent reduction with NaBH$_4$, deprotection with TFA and final chiral separation by SFC were done in a similar manner to Steps 2-4 in Scheme K to give the final compounds Example 54 & 55.

Example 56

(Scheme N) (2R,3R,4S,5S)-2-(4-methyl-7H-pyrrolo[2,3-d]pyrimidin-7-yl)-5-((S)-2,2,2-trifluoro-1-hydroxyethyl)tetrahydrofuran-3,4-diol (N-4)

Example 57

(Scheme N) (2R,3R,4S,5S)-2-(4-methyl-7H-pyrrolo[2,3-d]pyrimidin-7-yl)-5-((R)-2,2,2-trifluoro-1-hydroxyethyl)tetrahydrofuran-3,4-diol (N-5)

Scheme N

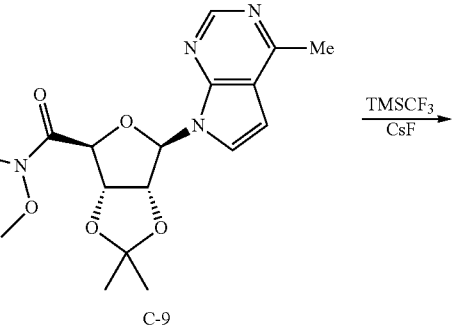

C-9

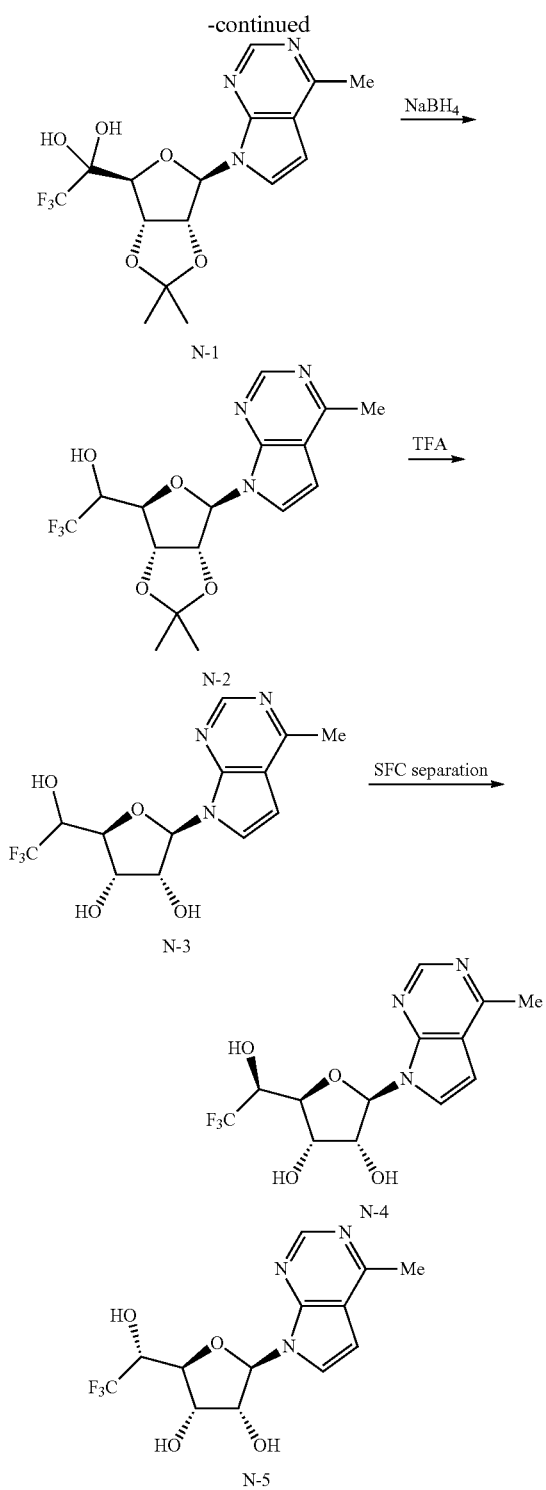

Step 1: Synthesis of 1-((3aS,4S,6R,6aR)-2,2-dimethyl-6-(4-methyl-7H-pyrrolo[2,3-d]pyrimidin-7-yl)tetrahydrofuro[3,4-d][1,3]dioxol-4-yl)-2,2,2-trifluoroethane-1,1-diol (N-1)

CsF (21.8 mg, 0.143 mmol) was added to a dry reaction vessel purged with N$_2$. A solution of C-9 (260 mg, 0.717 mmol) in toluene (1.43 mL) was added into the vessel. The mixture was cooled to 0° C. in an ice bath. TMSCF$_3$ (408 mg, 2.87 mmol) was added dropwise into the reaction mixture over 5 min. The reaction mixture was warmed to 25° C. and stirred at this temperature for 20 h. TLC (CH$_2$Cl$_2$/MeOH=20:1, UV active) showed the completion of the reaction and a new spot was formed. MeOH (2 mL) was added to the reaction mixture and the mixture became clear. And the mixture was stirred at room temperature for 2 h. The mixture was added to a solution of KHSO$_4$ aq. (100 mg/10 mL). The mixture was extracted with EtOAc (15 mL×2). The organic layer was separated, dried and evaporated to give the crude N-1 (150 mg, 53.7%) as a yellow oil. (Ref. Leadbeater, N. et al, *Chem. Commun.*, 2012, 48, 9610-9612.)

Step 2: Synthesis of 1-((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)-2,2,2-trifluoroethan-1-ol (N-2)

N-1 (150 mg, 0.385 mmol) was dissolved in ethanol (5 mL). NaBH$_4$ (79.2 mg, 1.93 mmol) was added to the above mixture in two portions on an ice bath in which evolution of gas occurred. The clear yellow solution was stirred at 25° C. for 2 h. TLC (CH$_2$Cl$_2$/MeOH=20:1, UV active) showed the completion of the reaction, TLC (petroleum ether/EtOAc=2:1, UV active) showed two main spots were formed. The mixture was filtered to remove the solvent. The residue was extracted with EtOAc (10 mL×2) and water (10 mL). The organic layer was separated, dried and evaporated to give the crude product N-2 (120 mg, 83.4%).

Step 3: Synthesis of (2R,3R,4S,5S)-2-(4-methyl-7H-pyrrolo[2,3-d]pyrimidin-7-yl)-5-(2,2,2-trifluoro-1-hydroxyethyl)tetrahydrofuran-3,4-diol (N-3)

To a suspension of N-2 (120 mg, 0.321 mmol) in H$_2$O (10 mL) was added TFA (5 mL) at 0° C. The resulting light yellow solution was stirred at 25° C. for 1 h. LCMS showed most of the starting material was consumed and a main peak was formed. The mixture was added to 10% K$_2$CO$_3$ aq. (5 mL) at 0° C. (pH of the reaction became 7-9). The mixture was extracted with EtOAc (20 mL×3). The extract was washed with brine (20 mL) dried over Na$_2$SO$_4$ and concentrated in vacuum to afford crude product (120 mg), which was purified by Biotage, eluted with DCM/MeOH from 0% to 10% to give N-3 (60 mg, 56%).

Step 4: Separation of diastereomers using SFC

N-3 was separated by SFC. Two of the desired part was evaporated and lyophilized separately to give N-4 (6.9 mg, 12.8%) as white solid and N-5 (8.9 mg, 16.6%) as white solid. SFC conditions: Column, AD (250*30 mm 5 um); Mobile phase: 20% EtOH+NH$_3$H$_2$O 60 mL/min 220 nm water.

(2R,3R,4S,5S)-2-(4-methyl-7H-pyrrolo[2,3-d]pyrimidin-7-yl)-5-((S)-2,2,2-trifluoro-1-hydroxyethyl)tetrahydrofuran-3,4-diol (N-4)

LCMS [M+1] 334; $^1$H NMR (400 MHz, DMSO-d$_6$) δ ppm 8.66 (s, 1H), 7.76-7.75 (d, 1H), 6.91 (br, 1H), 6.80-6.79 (d, 1H), 6.24-6.22 (d, 1H), 5.43-5.37 (m, 2H), 4.59-4.57 (m, 1H), 4.26-4.24 (m, 2H), 4.03-4.03 (d, 1H), 2.66 (s, 3H)

(2R,3R,4S,5S)-2-(4-methyl-7H-pyrrolo[2,3-d]pyrimidin-7-yl)-5-((R)-2,2,2-trifluoro-1-hydroxyethyl)tetrahydrofuran-3,4-diol (N-5)

LCMS [M+1] 334; ¹H NMR (400 MHz, DMSO-de) δ ppm 8.65 (s, 1H), 7.80-7.79 (d, 1H), 7.02-7.00 (d, 1H), 6.77-6.76 (d, 1H), 6.21-6.20 (d, 1H), 5.50-5.36 (m, 2H), 4.41-4.17 (m, 4H), 2.66 (s, 3H)

Example 58

(Scheme O) (2R,3S,4R,5R)-2-((1H-pyrazol-1-yl)methyl)-5-(4-methyl-7H-pyrrolo[2,3-d]pyrimidin-7-yl)tetrahydrofuran-3,4-diol (O-2)

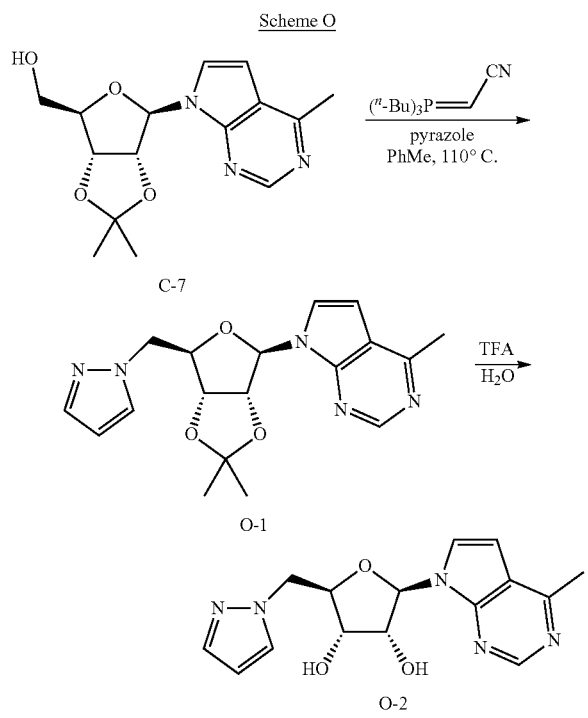

Step 1: Synthesis of 7-((3aR,4R,6R,6aR)-6-((1H-pyrazol-1-yl)methyl)-2,2-dimethyltetrahydrofuro[3,4-d][1,3]dioxol-4-yl)-4-methyl-7H-pyrrolo[2,3-d]pyrimidine (O-1)

To an oven dried microwave vial, cooled under a stream of argon and equipped with a magnetic stirbar, was added pyrazole (49.1 mg, 0.721 mmol). The vial was sealed with a teflon cap and C-7 (200 mg, 0.655 mmol) was added as a solution in toluene (7 mL, 0.09M) followed by the addition of cyanomethylenetributylphosphorane (174 mg, 0.721 mmol). The vial was placed in a heating block and stirred at 90° C. for 16 h. The vial was removed from the heating block and allowed to cool to rt. The solution was transferred to a round bottom flask and concentrated under vacuum. The dark brown residue was purified via flash column chromatography (10 g SiO₂, Biotage, 100% Hept. to 100% EtOAc) to afford compound O-1 (116 mg, 50%) as a dark brown gum. TLC (100% EtOAc): Rf=0.35; LCMS [M+H]356; ¹H NMR (400 MHz, CHLOROFORM-d) δ ppm 8.84 (s, 1H), 7.58 (d, J=1.59 Hz, 1H), 7.21-7.26 (m, 1H), 7.02 (d, J=3.67 Hz, 1H), 6.67 (br. s., 1H), 6.31 (br. s., 1H), 6.25 (br. s, 1H), 5.21 (dd, J=3.67, 6.36 Hz, 1H), 5.06 (br. s., 1H), 4.59 (dd, J=4.50, 8.70 Hz, 1H), 4.48 (d, J=4.65 Hz, 2H), 2.89 (br. s., 3H), 1.63 (s, 3H), 1.38 (s, 3H).

Step 2: Synthesis of (2R,3S,4R,5R)-2-((1H-pyrazol-1-yl)methyl)-5-(4-methyl-7H-pyrrolo[2,3-d]pyrimidin-7-yl)tetrahydrofuran-3,4-diol (O-2)

To a round bottom flask, equipped with a magnetic stir bar and containing O-1 (116 mg, 0.326 mmol), was added water (1 mL) and trifluoroacetic acid (5 mL). The reaction was stirred at rt for 30 minutes. The reaction was concentrated under vacuum. The brown residue was taken up in methanol (5 mL) and re-concentrated under vacuum. This process was repeated an additional 3 times. The residue was purified via supercritical fluid chromatography (ZymorSpher 4-pyridine 150×21.2 mm column with 15-23% MeOH @3%/min, 100 bar, 58 mL/min.) to afford compound O-2 (62.2 mg, 60%) as a white solid. LCMS [M+H]316; ¹H NMR (400 MHz, CD₃OD) δ ppm 8.63 (s, 1H), 7.54 (d, J=2.20 Hz, 1H), 7.52 (d, J=1.71 Hz, 1H), 7.27 (d, J=3.79 Hz, 1H), 6.72 (d, J=3.79 Hz, 1H), 6.26 (t, J=2.08 Hz, 1H), 6.23 (d, J=4.65 Hz, 1H), 4.82 (br. s, 2H), 4.47-4.59 (m, 2H), 4.27-4.38 (m, 3H), 2.71 (s, 3H).

Example 59

(Scheme P) (3S,4R,5R)-2-(difluoro(4-fluorophenyl)methyl)-5-(4-methyl-7H-pyrrolo[2,3-d]pyrimidin-7-yl)tetrahydrofuran-3,4-diol (P-3)

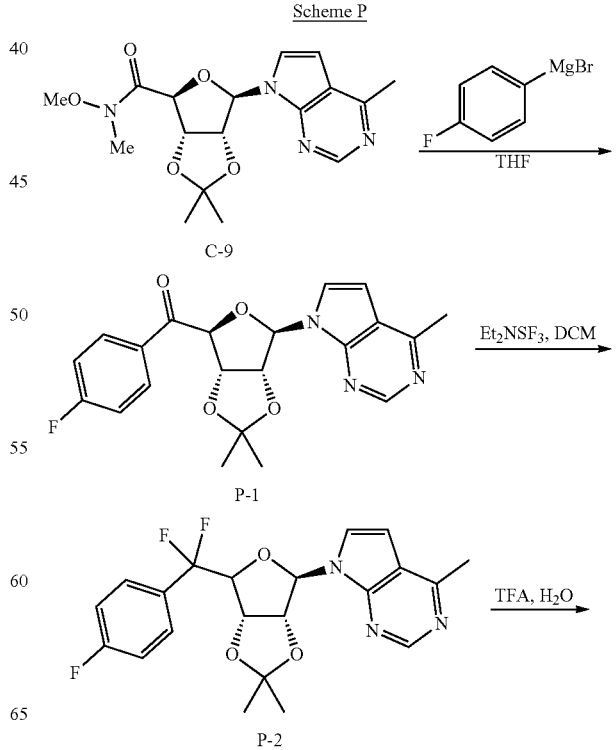

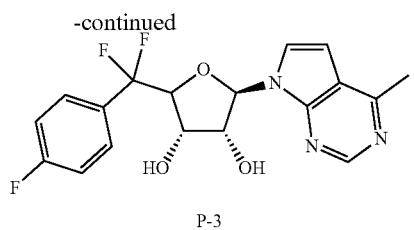

P-3

Step 1: Synthesis of ((3aS,4S,6R,6aR)-2,2-dimethyl-6-(4-methyl-7H-pyrrolo[2,3-d]pyrimidin-7-yl)tetrahydrofuro[3,4-d][1,3]dioxol-4-yl)(4-fluorophenyl)methanone (P-1)

To a solution of compound C-9 (800 mg, 2.21 mmol) in dry THF (30 mL) was added (4-fluorophenyl) magnesium bromide (24.3 mL, 24.3 mmol) at 0° C. The resulting yellow suspension was stirred at 0° C. for 0.5 h. TLC (petroleum ether/EtOAc=1:2) showed the reaction was complete and a good spot was formed. The mixture was added to $NH_4Cl$ aq (100 mL) dropwise. The mixture was extracted with EtOAc (50 mL×2). The extract was washed with brine (50 mL), dried over $Na_2SO_4$ and concentrated in vacuo to afford crude product (1.2 g). The crude product was purified by silica gel chromatography (40 g column) eluted with EtOAc in petroleum ether from 0-100% to afford compound P-1 (820 mg, 93.5%) as a slight yellow oil, which solidified upon standing. LCMS [M+1] 398

Step 2: Synthesis of 7-((3aR,4R,6aS)-6-(difluoro(4-fluorophenyl)methyl)-2,2-dimethyltetrahydrofuro[3,4-d][1,3]dioxol-4-yl)-4-methyl-7H-pyrrolo[2,3-d]pyrimidine (P-2)

To a Teflon vial, equipped with a magnetic stirbar, was added P-1 (143 mg, 0.360 mmol) and DCM followed by the dropwise addition of diethylaminosulfurtrifluoride (150 µL, 1.14 mmol). The reaction was stirred at rt for 48 h. The reaction was quenched with water, transferred to a separatory funnel with DCM, and diluted with more water. The phases were separated and the aqueous phase was extracted with 3 portions of DCM. The combined organic extracts were concentrated under vacuum and the residue purified via flash column chromatography (12 g $SiO_2$, Isco, 100% Hept. to 100% EtOAc, 9 mL fractions) to afford compound P-2 (24.9 mg, 16%) as a dark brown gum. LCMS [M+H]420; $^1$H NMR (400 MHz, CHLOROFORM-d) δ ppm 8.75 (br. s., 1H), 7.41 (dd, J=5.26, 8.44 Hz, 2H), 7.25 (d, J=3.67 Hz, 1H), 6.96-7.06 (m, 2H), 6.65 (d, J=3.67 Hz, 1H), 6.53 (d, J=2.81 Hz, 1H), 5.21 (ddd, J=3.30, 6.36, 18.10 Hz, 2H), 4.57 (ddd, J=3.18, 5.62, 17.61 Hz, 1H), 2.76 (s, 3H), 1.66 (s, 3H), 1.40 (s, 3H).

Step 3: Synthesis of (3S,4R,5R)-2-(difluoro(4-fluorophenyl)methyl)-5-(4-methyl-7H-pyrrolo[2,3-d]pyrimidin-7-yl)tetrahydrofuran-3,4-diol (P-3)

To a scintillation vial, equipped with a magnetic stirbar and containing P-2 (47.2 mg, 0.113 mmol), was added was added water (2 mL) and trifluoroacetic acid (2 mL). The reaction was stirred at rt for 1 h. The reaction was concentrated under vacuum. The residue was taken up in methanol (5 mL) and re-concentrated under vacuum. This process was repeated an additional 3 times. The residue was purified via supercritical fluid chromatography (Nacalai Cosmosil 3-Hydroxyphenyl bonded 20×150 mm column with 10-18% MeOH @3%/min, 100 bar, 58 mL/min.) to afford the compound P-3 (21.2 mg, 50%) as a white solid. LCMS [M+H]380; $^1$H NMR (400 MHz, DMSO-d6) δ ppm 2.65 (s, 3 H) 4.36 (br. s., 1 H) 4.39-4.53 (m, 2 H) 5.59 (d, J=6.48 Hz, 1 H) 5.64 (d, J=5.01 Hz, 1H) 6.28 (d, J=6.72 Hz, 1H) 6.80 (d, J=3.55 Hz, 1 H) 7.27 (t, J=8.62 Hz, 2 H) 7.49 (d, J=3.55 Hz, 1 H) 7.57 (dd, J=7.95, 5.62 Hz, 2 H) 8.64 (s, 1 H). $^{19}$F NMR (376 MHz, DMSO-d6) δ ppm −110.54 (br. s., 1 F) −106.97 (d, J=258.64 Hz, 1 F) −100.57 (d, J=254.06 Hz, 1 F).

Example 60

(Scheme R) (2R,3R,4S,5R)-2-(4-amino-5-fluoro-7H-pyrrolo[2,3-d]pyrimidin-7-yl)-5-((R)-(3,4-difluorophenyl)(hydroxy)methyl)tetrahydrofuran-3,4-diol (R-8)

Scheme Q

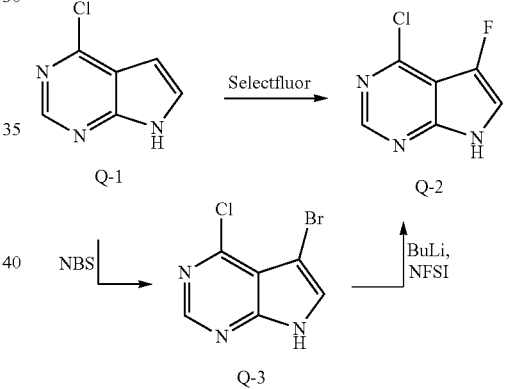

Synthesis of 4-chloro-5-fluoro-7H-pyrrolo[2,3-d]pyrimidine (Q-2)

The solution of 4-chloro-7H-pyrrolo[2,3-d]pyrimidine Q-1 (10 g, 65.1 mmol) and Selectfluor (27.7 g, 78.1 mmol) in $CH_3CN$ (500 mL) and AcOH (100 mL) was stirred at 70° C. for 16 h. (The reaction was done four times, 10 g of Q-1 in each vessel). The reaction solution turned from colorless to black. TLC ($CH_2Cl_2/CH_3OH$=20:1) showed 20% of the starting material remained, and then the reaction solution was concentrated to give crude solid. The solid was dissolved in EtOAc (1 L), washed with $H_2O$ (300 mL×2). The organic layer was concentrated to give Q-2 (7 g) as brown solid. The combined batch four batches were purified by prep-HPLC (0.225% formic acid/acetonitrile) to give Q-2 (11.6 g, 26%) as a white solid. LCMS [M+1] 172; $^1$H NMR (400 MHz, DMSO-d$_6$) δ ppm 12.47 (s, 1H), 8.62 (s, 1H), 7.72 (d, 1H)

Alternative Procedure to Q-2

Step 1: To a solution of 4-chloro-7H-pyrrolo[2,3-d]pyrimidine Q-1 (870 mg, 5.67 mmol) in DMF (14.2 mL, 0.4M) was added NBS (1.1 g, 6.23 mmol) at room temperature. The reaction was stirred overnight for 16 h. LCMS showed the starting material was consumed and product formed. The reaction mixture was quenched with sat. aq. NaHCO$_3$, then extracted with EtOAc. The EtOAc was washed with brine, dried with Na$_2$SO$_4$, filtered and concentrated to give a dark brown solid. The solid was suspended in CH$_2$Cl$_2$, then loaded onto a 12 g ISCO solid load cartridge and purified 0-50% EtOAc/Heptane to give 204 mg as a light tan solid. The insoluble light brown solid was also the product and dried to give 839 mg as a light brown solid. The combined material gave 5-bromo-4-chloro-7H-pyrrolo[2,3-d]pyrimidine (Q-3) (1.043 g, 79%). LCMS [M+1] 232/234; $^1$H NMR (400 MHz, DMSO-d$_6$) δ ppm 12.96 (br. s., 1H), 8.62 (s, 1H), 7.94 (s, 1H)

Step 2: To a solution of 5-bromo-4-chloro-7H-pyrrolo[2,3-d]pyrimidine (Q-3) (465 mg, 2 mmol) in THF (10 mL, 0.2M) cooled in a dry-ice acetone bath was added BuLi (2.62 mL, 4.20 mmol, 1.6M) dropwise. The mixture was added to stir at −78° C. for 20 minutes. The reaction mixture became a viscous suspension. A solution of Accufluor (NFSI) (757 mg, 2.4 mmol) in THF (2 mL, 0.2M) was added dropwise. Upon complete addition, the reaction mixture became homogenous. The reaction mixture was allowed to slowly warm up to room temperature overnight 16 h. LCMS shows ~1:1 mixture of product to starting material. The reaction mixture was quenched with sat. aq. NH$_4$Cl then diluted with water and EtOAc. The EtOAc was washed with brine, dried with Na$_2$SO$_4$, filtered and concentrated to an oil. The material was purified by column chromatography on an ISCO column eluting with 0-100% EtOAc/Heptane to give 75% pure of Q-2. LCMS [M+1] 172/174; $^1$H NMR (400 MHz, DMSO-d$_6$) δ ppm 8.62 (s, 1H), 7.71 (d, J=2.2 Hz, 1H)

Scheme R

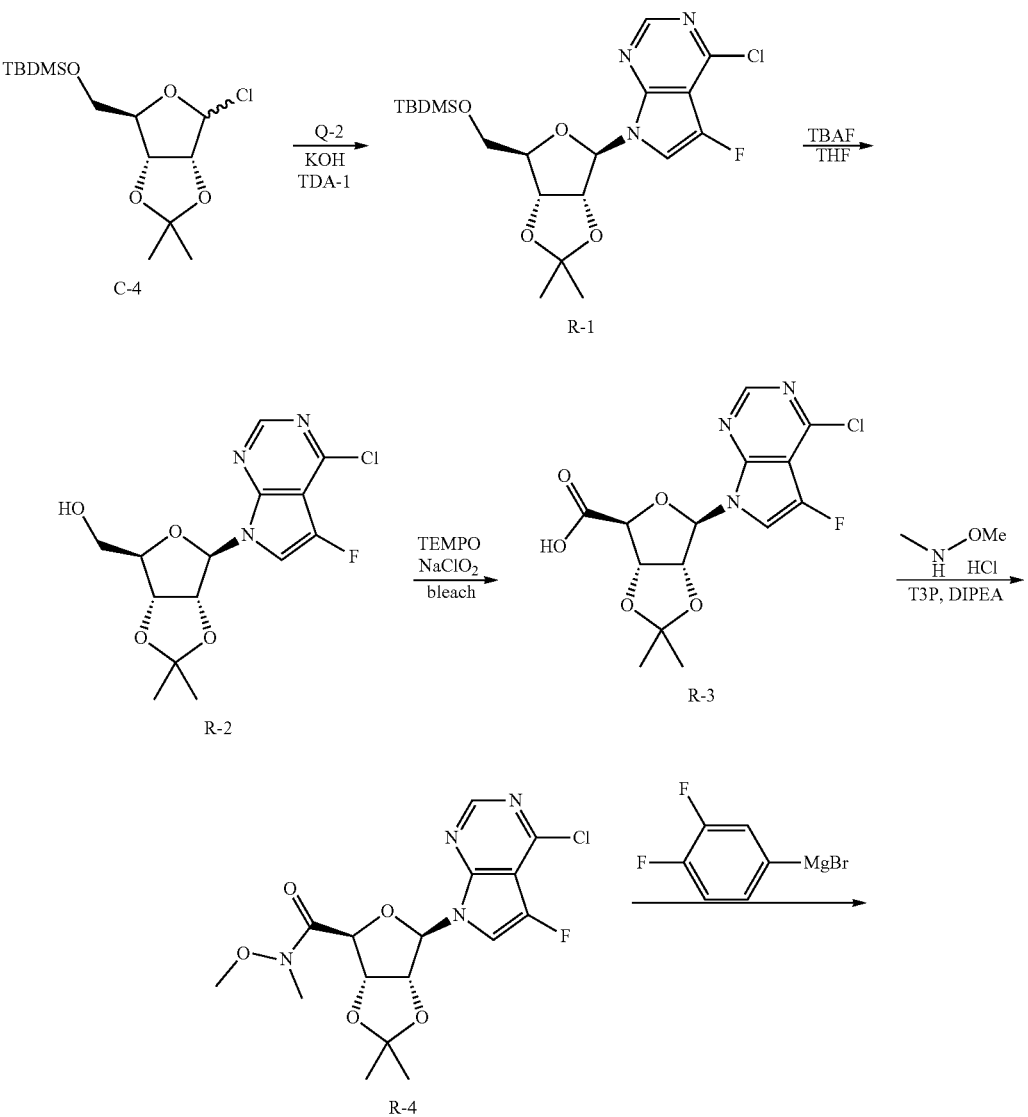

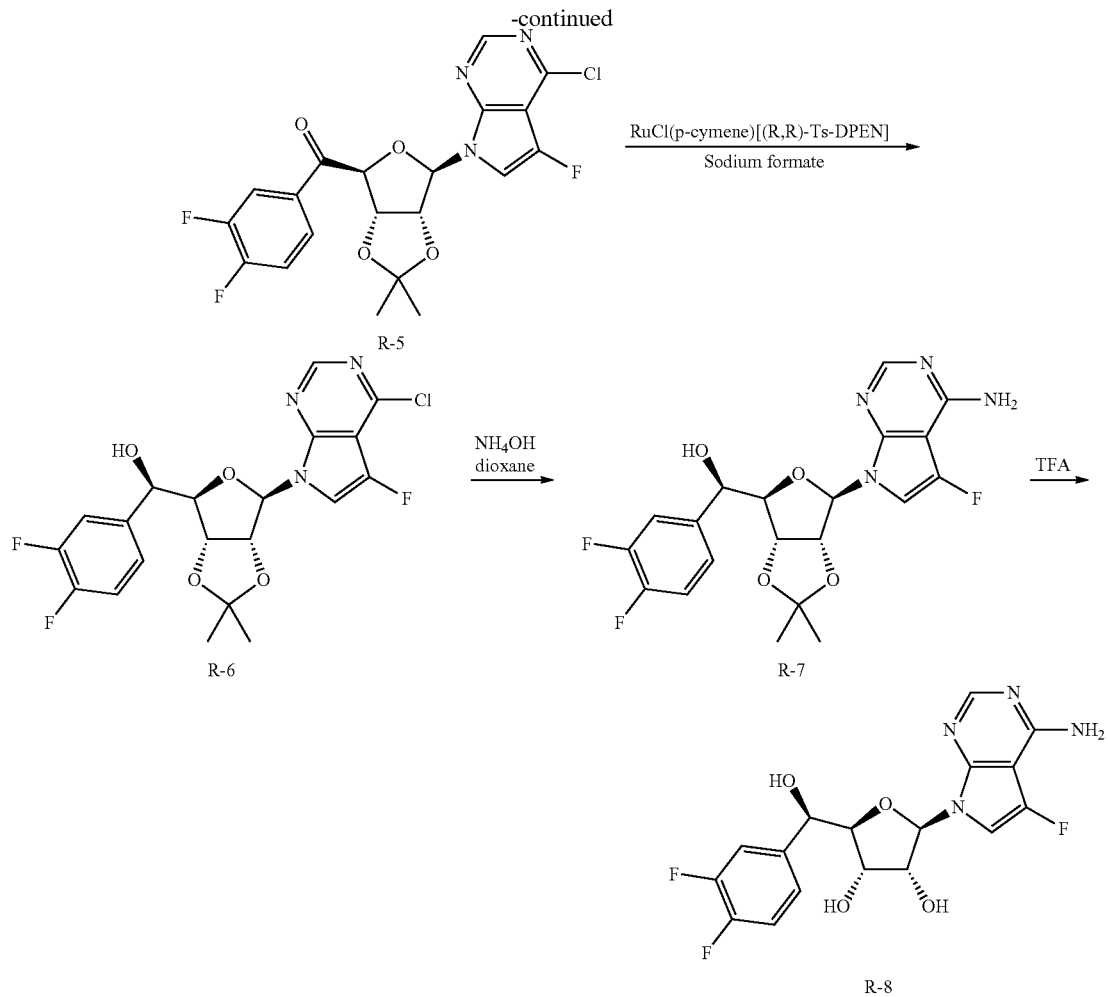

Step 1: Synthesis of 7-((3aR,4R,6R,6aR)-6-(((tert-butyldimethylsilyl)oxy)methyl)-2,2-dimethyltetrahydrofuro[3,4-d][1,3]dioxol-4-yl)-4-chloro-5-fluoro-7H-pyrrolo[2,3-d]pyrimidine (R-1)

To a stirred suspension of Q-2 (7.6 g, 44.3 mmol), powdered KOH (5.59 g, 99.7 mmol) and tris[2-(2-methoxyethoxy)ethyl]amine (TDA-1) (7.16 g, 22.1 mmol) in toluene (125 mL) was added C-4 (~31 g, 96 mmol, in toluene (120 mL)) dropwise. After the addition, the reaction mixture was stirred at room temperature for 16 h. TLC (petroleum ether/EtOAc=10:1, Rf~0.25) detected a new spot. The mixture was quenched with saturated NH₄Cl solution (100 mL) and extracted with CH₂Cl₂ (200 mL×2). The combined organic layers were washed with brine (100 mL×2), dried over Na₂SO₄ and concentrated to give the residue, which was purified by SiO₂ column chromatography (petroleum ether/EtOAc=100:1 to 20:1) to give R-1 (10 g, 49.3%) as a colorless oil as ~80% pure (20% hydrolyzed A-3).

Step 2: Synthesis of ((3aR,4R,6R,6aR)-6-(4-chloro-5-fluoro-7H-pyrrolo[2,3-d]pyrimidin-7-yl)-2,2-dimethyltetrahydrofuro[3,4-d][1,3]dioxol-4-yl)methanol (R-2)

To a stirred solution of R-1 (20 g, 43.668 mmol, ~80% of purity) in THF (100 mL) was added TBAF (20 mL, 20 mmol, 1M in THF) at 0° C. After the addition, the reaction mixture was stirred at the same temperature for 1 h. TLC (petroleum ether/EtOAc=5:1, Rf~0.1) showed the reaction was complete. The mixture was quenched with H₂O (20 mL) and extracted with EtOAc (50 mL×2). The combined organic layers were washed with brine (30 mL×2), dried over Na₂SO₄ and concentrated to give the residue, which was purified by SiO₂ column chromatography (petroleum ether/EtOAc=10:1 to 5:1) to give R-2 (9 g, 60%) as a white solid. LCMS [M+1] 344; $^1$H NMR (400 MHz, CDCl₃) δ ppm 8.63 (s, 1H), 7.17 (d, J=2.9 Hz, 1H), 5.86 (d, J=4.5 Hz, 1H), 5.16 (t, J=5.2 Hz, 1H), 5.08-5.06 (m, 1H), 4.56 (d, J=9.2 Hz, 1H), 4.45 (d, J=1.6 Hz, 1H), 3.94 (d, J=12 Hz, 1H), 3.81 (t, J=10.4 Hz, 1H), 1.63 (s, 3H), 1.37 (s, 3H)

Step 3: Synthesis of (3aS,4S,6R,6aR)-6-(4-chloro-5-fluoro-7H-pyrrolo[2,3-d]pyrimidin-7-yl)-2,2-dimethyltetrahydrofuro[3,4-d][1,3]dioxole-4-carboxylic acid (R-3)

To a solution of R-2 (5 g, 14.5 mmol) in MeCN (15 mL) was added H₂O (15 mL), TEMPO (1.78 g, 11.4 mmol) and PhI(OAc)2 (10.5 g, 27.6 mmol) in portions at room temperature (25° C.) without cooling. The reaction was exothermic. The mixture was stirred at room temperature (25° C.) for 20 h. TLC (petroleum ether/EtOAc=1:1) showed most of the starting material was consumed. The mixture was diluted with water (200 mL) and the liquid was poured out. The residue was washed with water (20 mL×3). The residue was triturated with TBME (20 mL) for 10 min then petroleum ether (200 mL) was added. The solid was collected by filtration and dried in vacuo to afford R-3 (2.6 g, 50%) as a slight yellow solid. LCMS [M+1] 358; $^1$H NMR (400 MHz, DMSO-$d_6$) δ ppm 8.67 (s, 1H), 7.94 (d, 1H), 6.40 (s, 1H), 5.51-5.48 (m, 2H), 4.71 (d, 1H), 1.52 (s, 3H), 1.36 (s, 3H)

Step 4: Synthesis of (3aS,4S,6R,6aR)-6-(4-chloro-5-fluoro-7H-pyrrolo[2,3-d]pyrimidin-7-yl)-N-methoxy-N,2,2-trimethyltetrahydrofuro[3,4-d][1,3]dioxole-4-carboxamide (R-4)

To a suspension of R-3 (2.6 g, 7.268 mmol) and N,O-dimethoxyhydroxylamine HCl (1.06 g, 10.9 mmol) in THF (50 mL) was added DIPEA (2.82 g, 21.8 mmol) and 50% T3P (6.94, 6.36 mL, 10.9 mmol) at room temperature (15° C.). The resulting colorless solution was stirred at room temperature (15° C.) for 20 h. TLC (petroleum ether/EtOAc=1:1) showed most of the starting material was consumed and a good spot was formed. The mixture was diluted with EtOAc (100 mL) and washed with NH$_4$Cl aq (100 mL), NaHCO$_3$ aq (50 mL), brine (50 mL×2), dried over Na$_2$SO$_4$ and concentrated in vacuo to afford R-4 (2.6 g, 89.3%) as a yellow gum. LCMS [M+1]401; $^1$H NMR (400 MHz, CDCl$_3$) δ ppm 8.62 (s, 1H), 7.59 (br, 1H), 6.70 (s, 1H), 5.30-5.12 (m, 3H), 3.72 (s, 3H), 3.21 (s, 3H), 1.67 (s, 3H), 1.39 (s, 3H)

Step 5: Synthesis of ((3aS,4S,6R,6aR)-6-(4-chloro-5-fluoro-7H-pyrrolo[2,3-d]pyrimidin-7-yl)-2,2-dimethyltetrahydrofuro[3,4-d][1,3]dioxol-4-yl)(3,4-difluorophenyl)methanone (R-5)

To a cooled (ice bath) solution of R-4 (214 mg, 0.534 mmol) in THF (3.0 mL, 0.178M) was added 3,4-difluorophenylmagnesium bromide (2.14 mL, 1.07 mmol, 0.50 M). The reaction was stirred in the ice bath for 30 min. LCMS indicated the reaction was complete. NH$_4$Cl (sat) was added, the reaction was warmed to room temperature then extracted with EtOAc (2 x). The combined extracts were washed with brine then dried (MgSO$_4$), filtered and concentrated. The crude residue was purified by column chromatography using the ISCO and a 12 g Si column with 0-50% EtOAc/Heptanes to give R-5 (206 mg, 85%). LCMS [M+1] 454; $^1$H NMR (400 MHz, CDCl$_3$) δ ppm 8.49 (s, 1H), 7.69 (ddd, J=2.08, 7.83, 10.39 Hz, 1H), 7.60-7.66 (m, 1H), 7.15-7.24 (m, 1H), 7.12 (d, J=2.57 Hz, 1H), 6.38 (s, 1H), 5.61 (dd, J=2.26, 6.05 Hz, 1H), 5.38-5.43 (m, 2H), 1.70 (s, 3H), 1.45 (s, 3H)

Step 6: Synthesis of (R)-((3aR,4R,6R,6aR)-6-(4-chloro-5-fluoro-7H-pyrrolo[2,3-d]pyrimidin-7-yl)-2,2-dimethyltetrahydrofuro[3,4-d][1,3]dioxol-4-yl)(3,4-difluorophenyl)methanol (R-6)

To suspension of crude R-5 (3.7 g, ~6.8 mmol) in EtOAc/H$_2$O (30 mL/120 mL) was added RuCl(p-cymene)[(R,R)-Ts-DPEN](65 mg, 0.102 mmol) and sodium formate (18.4 g, 271 mmol) at room temperature (15° C.). The resulting yellow mixture was stirred at room temperature (15° C.) over the weekend. LCMS showed about 24% of the starting material was remaining and 47% of desired compound was detected. Additional RuCl(p-cymene)[(R,R)-Ts-DPEN](130 mg, 0.204 mmol) was added. The mixture was stirred at room temperature (15° C.) for 4 h. LCMS showed most of the starting material was consumed and the main peak was desired compound and no isomer was observed. TLC (petroleum ether/EtOAc=3:1) showed two main spots were formed. The mixture was extracted with EtOAc (30 mL×2). The extract was washed with brine (50 mL), dried over Na$_2$SO$_4$ and concentrated in vacuo to afford crude R-6 (5 g). The crude material was purified by silica gel chromatography eluted with EtOAc in petroleum ether from 0 to 50% to afford R-6 (1.9 g, 62%) as a white solid and the unwanted diastereomer (640 mg, 21%) as a white solid. LCMS [M+1] 456

Step 7: Synthesis of (R)-((3aR,4R,6R,6aR)-6-(4-amino-5-fluoro-7H-pyrrolo[2,3-d]pyrimidin-7-yl)-2,2-dimethyltetrahydrofuro[3,4-d][1,3]dioxol-4-yl)(3,4-difluorophenyl)methanol (R-7)

A solution of R-6 (950 mg, 2.08 mmol) in dioxane/NH$_3$.H$_2$O (5 mL/5 mL) was heated under microwave at 120° C. or 20 min. LCMS showed most of the starting material was consumed and the product was clean. The mixture was concentrated in vacuo to afford crude R-7 (1200 mg, >100%) as a slight yellow solid, used in the next step directly.

Step 8: Synthesis of (2R,3R,4S,5R)-2-(4-amino-5-fluoro-7H-pyrrolo[2,3-d]pyrimidin-7-yl)-5-((R)-(3,4-difluorophenyl)(hydroxy)methyl)tetrahydrofuran-3,4-diol (R-8)

To a suspension of crude R-7 (2.4 g, ~4.1 mmol) in H$_2$O (20 mL) was added TFA (20 mL) at 0° C. The mixture was stirred at room temperature (15° C.) for 1 h. LCMS most of the starting material was consumed and the desired product was clean. The mixture was poured into 20% K$_2$CO$_3$ aq (100 mL) and extracted with EtOAc (50 mL×2). The extract was washed with brine (50 mL×2), dried over Na$_2$SO$_4$ and concentrated in vacuo then dried in vacuo overnight to afford R-8 (1500 mg, 93%) as a white solid. LCMS [M+H]397; $^1$H NMR (400 MHz, DMSO-$d_6$) δ ppm 8.06 (s, 1H), 7.47-7.30 (m, 3H), 7.26-7.20 (m, 1H), 7.02 (br. s., 2H), 6.25 (d, J=4.3 Hz, 1H), 6.02 (d, J=7.5 Hz, 1H), 5.23 (d, J=6.8 Hz, 1H), 5.04 (d, J=4.2 Hz, 1H), 4.80-4.72 (m, 1H), 4.49-4.41 (m, J=5.1 Hz, 1H), 4.07-4.01 (m, 1H), 3.96 (d, J=4.9 Hz, 1H)

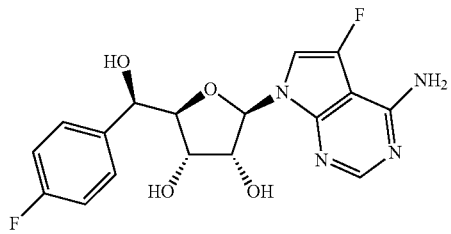 [SMILES: Nc1ncnc2c1c(F)cn2[C@@H]1O[C@H]([C@H](O)c2ccc(F)cc2)[C@@H](O)[C@H]1O]

Example 61

(2R,3R,4S,5R)-2-(4-amino-5-fluoro-7H-pyrrolo[2,3-d]pyrimidin-7-yl)-5-((R)-(4-fluorophenyl)(hydroxy)methyl)tetrahydrofuran-3,4-diol The title compound (Example 61) was prepared analogously to Example 60 (Scheme R) where 4-fluorophenyl magnesium chloride was substituted in place of 3,4-difluorophenylmagnesium bromide. LCMS [M+H]378.8; $^1$H NMR (700 MHz, DMSO-d6) δ ppm 8.05 (s, 1H), 7.41 (dd, J=5.7, 8.3 Hz, 2H), 7.29 (d, J=1.2 Hz, 1H), 7.12 (t, J=8.9 Hz, 2H), 7.00 (br. s., 2H), 5.99 (d, J=7.7 Hz, 1H), 4.75 (br. s., 1H), 4.45 (br. s., 1H), 4.04 (d, J=3.9 Hz, 1H), 3.99-3.91 (m, 1H).

Example 62

(Scheme S) (2R,3R,4S,5R)-2-(2-amino-4-methyl-7H-pyrrolo[2,3-d]pyrimidin-7-yl)-5-((R)-1-hydroxypropyl)tetrahydrofuran-3,4-diol (S-10)

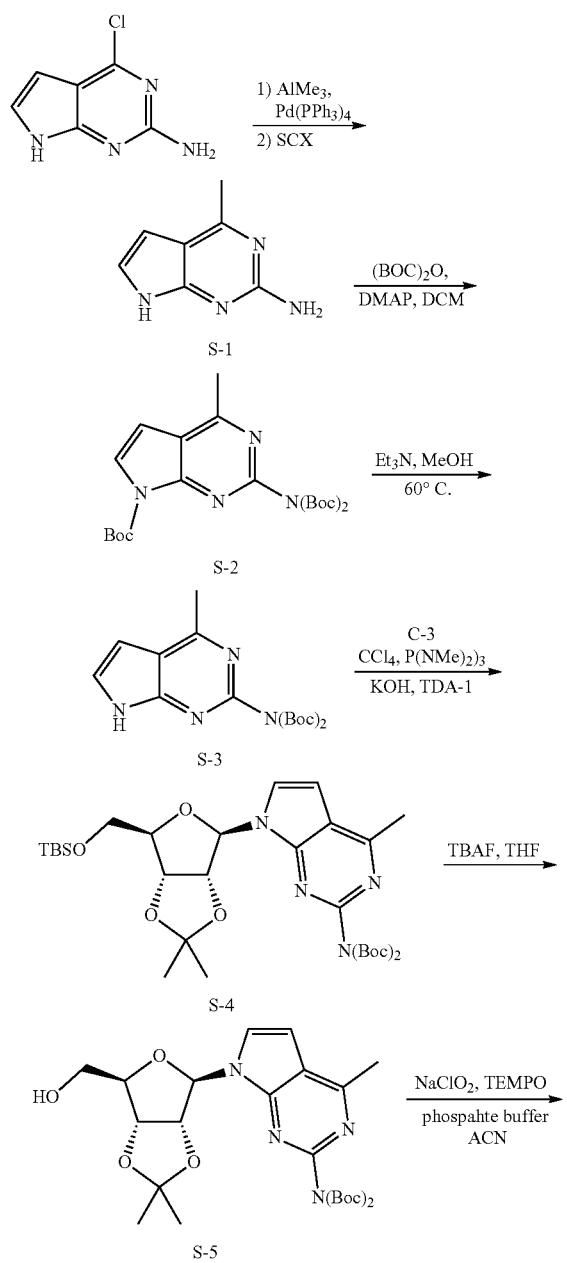

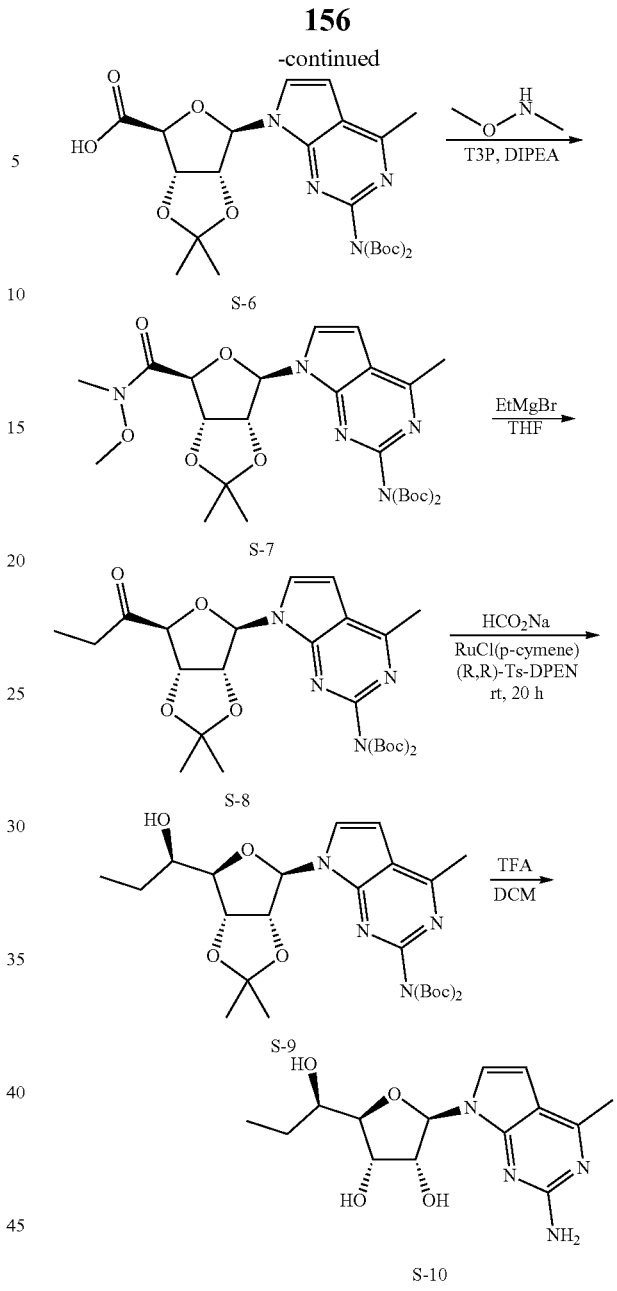

Step 1: Synthesis of 4-methyl-7H-pyrrolo[2,3-d]pyrimidin-2-amine (S-1)

To a solution of 4-chloro-7H-pyrrolo[2,3-d]pyrimidin-2-amine (2200 mg, 11.74 mmol) in THF (45 mL) was added Pd(PPh$_3$)$_4$ (679 mg, 0.59 mmol) followed by drop-wise addition of AlMe$_3$ (1750 mg, 23.5 mmol, 11.7 mL, 2M in Hexane). The reaction was heated in a sealed tube to 75° C. for 16 h. LCMS analysis indicated approximately 40% starting material remained. Additional Pd(PPh$_3$)$_4$ (679 mg,) was added and heating was continued at 75° C. for 18 h. The crude reaction was cooled in an ice bath then quenched carefully with Rochelle salt (KNa tartarate, sat, 10 mL). Water (75 mL) was added and the mixture was extracted with EtOAc (3×50 mL). The combined extracts were washed with brine (75 mL) then dried (MgSO4), filtered and concentrated. The crude residue was taken up in MeOH and poured onto 2×10 g SCX columns. Non-basic impurities were elute with MeOH (100 mL/each) followed by release of the desired product with 7N NH$_3$/MeOH (50 mL/each). The basic rinse was concentrated and dried on high vacuum to give 1740 mg (100%) of compound S-1 as a solid. LCMS [M+H]149.1; $^1$H NMR (400 MHz, DMSO-d6) δ ppm 10.99 (br. s., 1H), 6.92 (dd, J=2.38, 3.24 Hz, 1H), 6.30 (dd, J=1.71, 3.42 Hz, 1H), 5.90 (s, 2H), 2.41 (s, 3H).

Step 2: Synthesis of tert-butyl 2-[bis(tert-butoxycarbonyl)amino]-4-methyl-7H-pyrrolo[2,3-d]pyrimidine-7-carboxylate (S-2)

To a solution of 4-methyl-7H-pyrrolo[2,3-d]pyrimidin-2-amine (S-1) (1320 mg, 8.91 mmol) in ACN/DCM (25 mL:25 mL) was added di-tert-butyl dicarbonate (6.81 g, 31.2 mmol) and 4-dimethylaminopyridine (218 mg, 1.78 mmol). The reaction was stirred at rt for 18 h then concentrated then purified by column chromatography using the ISCO and a 40 g Si column with 0-60% EtOAc/Heptane to give 1791 mg (44.8%) of S-2 as a white solid. LCMS [M+H]448.9; $^1$H NMR (400 MHz, METHANOL-d4) δ ppm 7.83 (d, J=4.16 Hz, 1H), 6.85 (d, J=4.03 Hz, 1H), 2.74 (s, 3H), 1.68 (s, 9H), 1.41 (s, 18H).

Step 3: Synthesis of di-tert-butyl (4-methyl-7H-pyrrolo[2,3-d]pyrimidin-2-yl)-imidodicarbonate (S-3)

To a solution of tert-butyl 2-[bis(tert-butoxycarbonyl)amino]-4-methyl-7H-pyrrolo[2,3-d]pyrimidine-7-carboxylate (S-2) (1791 mg, 3.993 mmol) in MeOH (7.0 mL) was added triethylamine (4360 mg, 43.0 mmol, 6.00 mL) at rt. The reaction was heated to 60° C. for 18 h then concentrated and purified by column chromatography using the ISCO and a 40 g Si column with 0-90% EtOAc/Heptane to afford 1761 mg (78%) of S-3 as a white solid. LCMS [M+H]348.9; $^1$H NMR (400 MHz, DMSO-d6) δ ppm 12.10 (br. s., 1H), 7.52 (d, J=3.42 Hz, 1H), 6.67 (d, J=3.55 Hz, 1H), 2.64 (s, 3H), 1.39 (s, 18H).

Step 4: Synthesis of di-tert-butyl (7-((3aR,4R,6R,6aR)-6-(((tert-butyldimethylsilyl)oxy)methyl)-2,2-dimethyltetrahydrofuro[3,4-d][1,3]dioxol-4-yl)-4-methyl-7H-pyrrolo[2,3-d]pyrimidin-2-yl)-imidodicarbonate (S-4)

To a solution of (3aR,6R,6aR)-6-(((tert-butyldimethylsilyl)oxy)methyl)-2,2-dimethyltetrahydrofuro[3,4-d][1,3]dioxol-4-ol (C-3) (1170 mg, 3.83 mmol) in toluene (15 mL) was added carbon tetrachloride (883 mg, 5.74 mmol, 0.555 mL). The reaction was cooled in a dry ice/MeCN bath (~−50° C.) then tris-(dimethylamino) phosphine (955 mg, 4.98 mmol, 1.06 mL) was added drop-wise. The internal temperature rose to −35° C. during addition and the clear solution changed to a pale yellow color. The reaction was taken out of the cold bath and the temperature was maintained between −15° C. and 0° C. for 1 h. The reaction was quenched with ice cold brine (3 mL) and the layers were separated. The organic phase was dried (MgSO$_4$) and filtered then added to a pre-stirred mixture of compound S-3 (1000 mg, 2.870 mmol) in toluene (10 mL), KOH (322 mg, 5.74 mmol) and tris-(3,6-dioxaheptyl)-amine (521 mg, 1.53 mmol, 0.516 mL). The reaction mixture was stirred at rt for 40 h then quenched with NH$_4$Cl (sat, 25 mL) and extracted with DCM (2×30 mL). The combined organic extracts were dried (MgSO$_4$), filtered and concentrated. The crude residue was purified by column chromatography using the ISCO and a 24 g Si column with 0-100% EtOAc/Hep to provide 751 mg (41.2%) of S-4 as a pale yellow solid. LCMS [M+H] 634.8; $^1$H NMR (400 MHz, DMSO-d6) δ ppm 7.75 (d, J=3.67 Hz, 1H), 6.81 (d, J=3.67 Hz, 1H), 6.24 (d, J=2.81 Hz, 1H), 5.21 (dd, J=2.75, 6.30 Hz, 1H), 4.91 (dd, J=3.18, 6.24 Hz, 1H), 4.09-4.26 (m, 1H), 3.61-3.81 (m, 2H), 2.65 (s, 3H), 1.53 (s, 3H), 1.40 (s, 18H), 1.31 (s, 3H), 0.83 (s, 9H), −0.02 (d, J=1.47 Hz, 6H).

Step 5: Synthesis of di-tert-butyl (7-((3aR,4R,6R,6aR)-6-(hydroxymethyl)-2,2-dimethyltetrahydrofuro[3,4-d][1,3]dioxol-4-yl)-4-methyl-7H-pyrrolo[2,3-d]pyrimidin-2-yl)-imidodicarbonate (S-5)

To a solution of S-4 (751 mg, 1.18 mmol) in THF (6 mL) was added tetra-n-butylammonium fluoride (464 mg, 1.77 mmol, 1.8 mL, 1.0 M in THF). The reaction stirred at rt for 1.5 h then concentrated and purified by column chromatography using the ISCO and a 24 g Si column with 0-90% EtOAc/Heptane to afford 596 mg (96.8%) of compound S-5 as a gummy solid. LCMS [M+H]520.8; $^1$H NMR (400 MHz, DMSO-d6) δ ppm 7.83 (d, J=3.8 Hz, 1H), 6.82 (d, J=3.7 Hz, 1H), 6.24 (d, J=3.4 Hz, 1H), 5.17 (dd, J=3.4, 6.4 Hz, 1H), 5.05 (t, J=5.4 Hz, 1H), 4.92 (dd, J=2.9, 6.3 Hz, 1H), 4.21-4.11 (m, 1H), 3.54 (t, J=5.1 Hz, 2H), 2.66 (s, 3H), 1.53 (s, 3H), 1.39 (s, 18H), 1.31 (s, 3H).

Step 6: Synthesis of (3aS,4S,6R,6aR)-6-(2-[bis(tert-butoxycarbonyl)amino]-4-methyl-7H-pyrrolo[2,3-d]pyrimidin-7-yl)-2,2-dimethyltetrahydrofuro[3,4-d][1,3]dioxole-4-carboxylic acid (S-6)

A mixture of di-tert-butyl (7-((3aR,4R,6R,6aR)-6-(hydroxymethyl)-2,2-dimethyltetrahydrofuro[3,4-d][1,3]dioxol-4-yl)-4-methyl-7H-pyrrolo[2,3-d]pyrimidin-2-yl)-imidodicarbonate (S-5) (363 mg, 0.863 mmol), TEMPO (11.0 mg, 0.0697 mmol), ACN (3.5 mL) and 0.67 M Phosphate Buffer (3000 mg, 16.2 mmol, 3 mL) was heated to 35° C. Aqueous sodium chlorite (158 mg, 1.39 mmol, 1.39 M) and dilute bleach (0.6 mL, solution made from 1 mL commercial bleach diluted with 19 mL water) were added simultaneously. The reaction was stirred for 18 h at 35° C. then cooled to rt. The pH was adjusted to 8-9 with 1M NaOH and extracted with MTBE (10 mL). The organic phase was set aside and the aqueous phase was adjusted to pH 4 with 1N HCl then extracted with MTBE (2×10 mL) The combined organic extracts were washed with brine (10 mL) then dried (MgSO$_4$), filtered and concentrated to provide 237 mg (64%) of compound S-6 as a white solid. LCMS [M+H] 535.2; $^1$H NMR (400 MHz, DMSO-d$_6$) δ ppm 7.69 (d, J=3.8 Hz, 1H), 6.81 (d, J=3.8 Hz, 1H), 6.37 (d, J=2.0 Hz, 1H), 5.34 (dd, J=2.6, 6.1 Hz, 1H), 5.27 (dd, J=1.7, 6.1 Hz, 1H), 4.65 (d, J=2.4 Hz, 1H), 2.65 (s, 3H), 1.54 (s, 3H), 1.41 (s, 18H), 1.34 (s, 3H).

Step 7: Synthesis of di-tert-butyl (7-((3aR,4R,6S,6aS)-6-(methoxy(methyl)carbamoyl)-2,2-dimethyltetrahydrofuro[3,4-d][1,3]dioxol-4-yl)-4-methyl-7H-pyrrolo[2,3-d]pyrimidin-2-yl)-imidodicarbonate (S-7)

To a solution of compound S-6 (237.0 mg, 0.443 mmol) in THF (2 mL) was added N,O-dimethylhydroxylamine hydrochloride (64.9 mg, 0.665 mmol) followed by diisopropyl ethylamine (172 mg, 1.33 mmol, 0.232 mL) and 50% propylphosphonic anhydride in DMF (339 mg, 0.532 mmol, 0.311 mL). The reaction was stirred at rt for 18 h then diluted with water (5 mL) and extracted with EtOAc (2×10 mL). The combined organic extracts were dried (MgSO$_4$), filtered and concentrated, then purified by column chromatography using the ISCO and a 12 g Si column with 20-100% EtOAc/Hep to give 112.0 mg (43.7%) of compound S-7 as a tan gummy solid. LCMS [M+H]578.2; $^1$H NMR (400 MHz, CHLOROFORM-d) δ ppm 7.57 (br. s., 1H), 6.63 (s, 1H), 6.59 (d, J=3.79 Hz, 1H), 5.29 (br. s., 1H), 5.16 (d, J=3.67 Hz, 2H), 3.67 (s, 3H), 3.18 (s, 3H), 2.71 (s, 3H), 1.64 (s, 3H), 1.45 (s, 18H), 1.39 (s, 3H).

Step 8: Synthesis of di-tert-butyl (7-((3aR,4R,6S,6aS)-2,2-dimethyl-6-propionyltetrahydrofuro[3,4-d][1,3]dioxol-4-yl)-4-methyl-7H-pyrrolo[2,3-d]pyrimidin-2-yl)-imidodicarbonate (S-8)

A solution of di-tert-butyl (7-((3aR,4R,6S,6aS)-6-(methoxy(methyl)carbamoyl)-2,2-dimethyltetrahydrofuro[3,4-d][1,3]dioxol-4-yl)-4-methyl-7H-pyrrolo[2,3-d]pyrimidin-2-yl)-imidodicarbonate (S-7) (113.0 mg, 0.196 mmol) in THF (1.0 mL) was cooled in an ice bath then ethylmagnesiumbromide (52.1 mg, 0.391 mmol, 0.196 mL, 2.00 M) was added. The reaction was stirred in the ice bath for 10 min then quenched with sat NH$_4$Cl (5 mL). The reaction was warmed to rt and extracted with EtOAc (2×10 mL). The combined organic extracts were dried (MgSO$_4$), filtered and concentrated to afford 52 mg (49%) of compound S-8 as a tan solid. LCMS [M+H– Boc]447.3.

Step 9: Synthesis of di-tert-butyl (7-((3aR,4R,6R,6aR)-6-((R)-1-hydroxypropyl)-2,2-dimethyltetrahydrofuro[3,4-d][1,3]dioxol-4-yl)-4-methyl-7H-pyrrolo[2,3-d]pyrimidin-2-yl)-imidodicarbonate (S-9)

Di-tert-butyl (7-((3aR,4R,6S,6aS)-2,2-dimethyl-6-propionyltetrahydrofuro[3,4-d][1,3]dioxol-4-yl)-4-methyl-7H-pyrrolo[2,3-d]pyrimidin-2-yl)-imidodicarbonate (S-8) (52 mg, 0.095 mmol) and (R,R)—N-(p-tolenensulfonyl)-1,2-diphenylethanediamine(chloro)(p-cymene)ruthenium(I) (5.0 mg, 0.0075 mmol) were combined in a round bottom flask and purged with nitrogen. Aqueous sodium formate (262 mg, 3.81 mmol, 1.52 mL, 2.5 M in water) was added followed by EtOAc (0.5 mL). The bi-phasic mixture was stirred at rt under nitrogen for 20 hours. The reaction was diluted with EtOAc (5 mL) and water (5 mL). The layers were separated and the organic phase was washed with brine (5 mL) then dried (MgSO$_4$), filtered and concentrated to give 52 mg (100%) of S-9. LCMS [M+H– Boc]448.9.

Step 10: Synthesis of (2R,3R,4S,5R)-2-(2-amino-4-methyl-7H-pyrrolo[2,3-d]pyrimidin-7-yl)-5-((R)-1-hydroxypropyl)tetrahydrofuran-3,4-diol (S-10)

To a solution of di-tert-butyl (7-((3aR,4R,6R,6aR)-6-((R)-1-hydroxypropyl)-2,2-dimethyltetrahydrofuro[3,4-d][1,3]dioxol-4-yl)-4-methyl-7H-pyrrolo[2,3-d]pyrimidin-2-yl)-imidodicarbonate (S-9) (52 mg, 0.095 mmol) in dichloromethane (0.2 mL) was added trifluoroacetic acid (740 mg, 6.5 mmol, 0.5 mL) The reaction was stirred at rt for 6 h. The crude reaction was concentrated then purified by SFC with Chiralpak AS-3 4.6×100 mm 3 u column with 10% MeOH at 120 bar and 4 mL/min to provide S-10 (12.29 mg, 42%, 99% de) as a white solid. LCMS [M+H]308.9; $^1$H NMR (400 MHz, DMSO-d6) δ ppm 7.20 (d, J=3.79 Hz, 1H), 6.42 (d, J=3.67 Hz, 1H), 6.06 (s, 2H), 5.94 (d, J=7.46 Hz, 1H), 5.11 (d, J=6.36 Hz, 1H), 5.02 (d, J=5.01 Hz, 1H), 4.97 (d, J=2.81 Hz, 1H), 4.30-4.40 (m, 1H), 4.12 (br. s., 1H), 3.68 (d, J=3.67 Hz, 1H), 3.47 (dd, J=4.34, 8.25 Hz, 1H), 2.42 (s, 3H), 1.42-1.56 (m, 1H), 1.39 (s, 1H), 1.32 (td, J=7.35, 14.27 Hz, 1H), 0.90 (t, J=7.34 Hz, 2H).

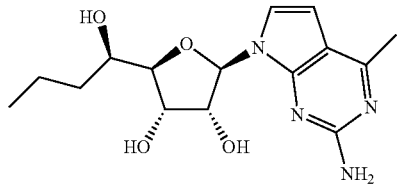 [SMILES: CCC[C@@H](O)[C@H]1O[C@@H](n2ccc3c(C)nc(N)nc32)[C@H](O)[C@@H]1O]

Example 63

(2R,3R,4S,5R)-2-(2-amino-4-methyl-7H-pyrrolo[2,3-d]pyrimidin-7-yl)-5-((R)-1-hydroxybutyl)tetrahydrofuran-3,4-diol The title compound (Example 63) was prepared analogously to Example 62 (Scheme S) where propyl magnesium chloride was substituted in place of ethylmagnesium bromide. Chiralpak AD-3 4.6×100 mm 3 u column/30% MeOH/DEA@120 bar, 4 mL/min. 18.51 mg (44%) 99% de; LCMS [M+H]322.9; $^1$H NMR (400 MHz, DMSO-d6) δ ppm 7.20 (d, J=3.67 Hz, 1H), 6.42 (d, J=3.67 Hz, 1H), 6.07 (s, 2H), 5.94 (d, J=7.46 Hz, 1H), 5.12 (d, J=6.72 Hz, 1H), 5.02 (d, J=5.26 Hz, 1H), 4.97 (d, J=3.79 Hz, 1H), 4.30-4.40 (m, 1H), 4.11 (br. s., 1H), 3.66 (d, J=3.42 Hz, 1H), 3.55 (d, J=3.67 Hz, 1H), 2.42 (s, 3H), 1.20-1.54 (m, 4H), 0.86 (t, J=6.54 Hz, 3H).

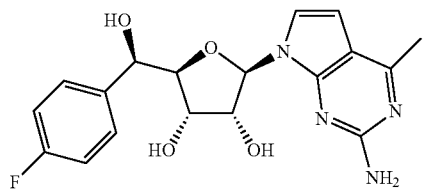 [SMILES: Cc1nc(N)nc2c1ccn2[C@@H]1O[C@H]([C@H](O)c2ccc(F)cc2)[C@@H](O)[C@H]1O]

Example 64

(Scheme T) (2R,3R,4S,5R)-2-(2-amino-4-methyl-7H-pyrrolo[2,3-d]pyrimidin-7-yl)-5-((R)-(4-fluorophenyl)(hydroxy)methyl)tetrahydrofuran-3,4-diol (T-4)

LCMS [M+H]374.9; $^1$H NMR (400 MHz, DMSO-d6) δ ppm 7.41 (d, J=3.79 Hz, 1H), 7.37 (dd, J=5.75, 8.56 Hz, 2H), 7.11 (t, J=8.86 Hz, 2H), 6.58 (d, J=3.79 Hz, 1H), 6.52 (br. s., 1H), 5.96 (d, J=6.72 Hz, 1H), 5.93 (d, J=5.99 Hz, 1H), 5.24 (d, J=4.77 Hz, 1H), 5.09 (br. s., 1H), 4.80 (br. s., 1H), 4.23-4.33 (m, J=5.26 Hz, 1H), 4.13 (br. s., 1H), 4.00 (t, J=2.57 Hz, 1H).

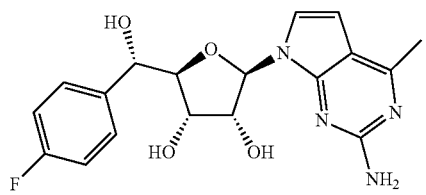 [SMILES: Cc1nc(N)nc2c1ccn2[C@@H]1O[C@H]([C@@H](O)c2ccc(F)cc2)[C@@H](O)[C@H]1O]

Example 65

(Scheme T) (2R,3R,4S,5R)-2-(2-amino-4-methyl-7H-pyrrolo[2,3-d]pyrimidin-7-yl)-5-((S)-(4-fluorophenyl)(hydroxy)methyl)tetrahydrofuran-3,4-diol (T-5)

LCMS [M+H]374.8; $^1$H NMR (400 MHz, DMSO-d6) δ ppm 7.42 (dd, J=5.75, 8.44 Hz, 2H), 7.25 (d, J=3.67 Hz, 1H), 7.13 (t, J=8.86 Hz, 2H), 6.46 (d, J=3.67 Hz, 1H), 6.16 (br. s., 2H), 5.98 (d, J=7.95 Hz, 1H), 5.95 (d, J=4.28 Hz, 1H), 5.17 (d, J=6.72 Hz, 1H), 4.97 (d, J=3.55 Hz, 1H), 4.75 (t, J=4.59 Hz, 1H), 4.43-4.54 (m, 1H), 4.09 (br. s., 1H), 3.93 (d, J=5.14 Hz, 1H), 2.44 (s, 3H).

The compounds Example 64 and 65 were prepared analogously to Example 62 (Scheme S) where 4-fluorophenylmagnesium bromide was substituted in place of ethylmagnesium bromide and where NaBH$_4$ was used in place of (R,R)—N-(p-tolenensulfonyl)-1,2-diphenylethanediamine (chloro)(p-cymene)ruthenium(II) and sodium formate.

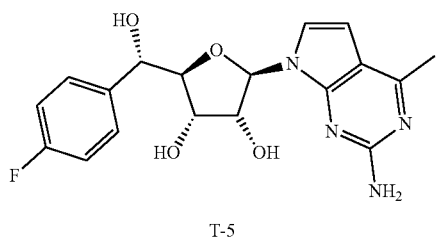

To a solution of di-tert-butyl (7-((3aR,4R,6S,6aS)-6-(4-fluorobenzoyl)-2,2-dimethyltetrahydrofuro[3,4-d][1,3]dioxol-4-yl)-4-methyl-7H-pyrrolo[2,3-d]pyrimidin-2-yl)-imidodicarbonate (T-1) (249 mg, 0.406 mmol) in EtOH (10 mL) was added NaBH$_4$ (76.9 mg, 2.03 mmol). LCMS indicated the reaction was done in 5 min. The reaction was concentrated to give 250 mg as a crude mixture of diastereomers (T-2) that were carried directly on to the next step. Deprotection and chiral separation were done following similar procedures to Step 10 in Scheme S to give compounds T-4 and T-5.

Example 66

(Scheme U) (2R,3R,4S,5S)-2-(4-methyl-7H-pyrrolo[2,3-d]pyrimidin-7-yl)-5-phenyltetrahydrofuran-3,4-diol (U-7)

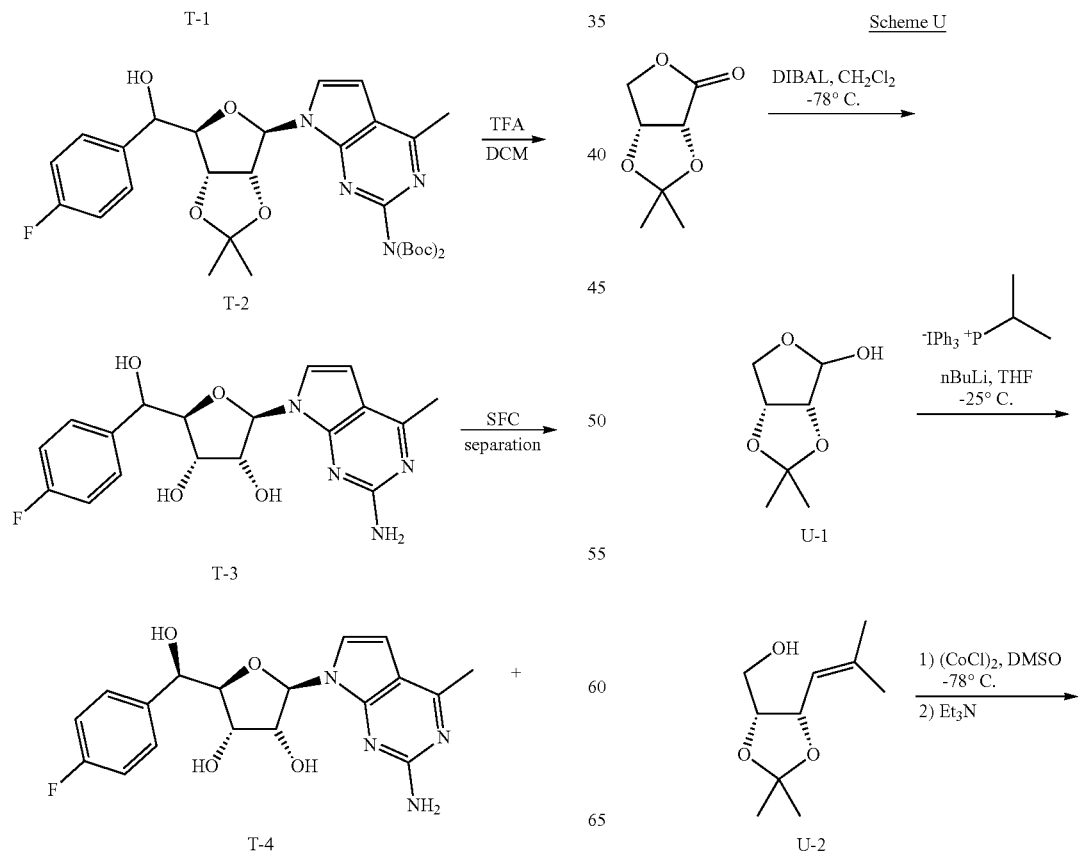

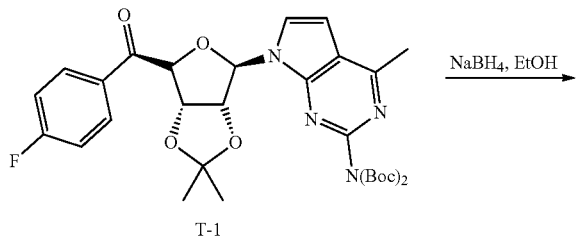

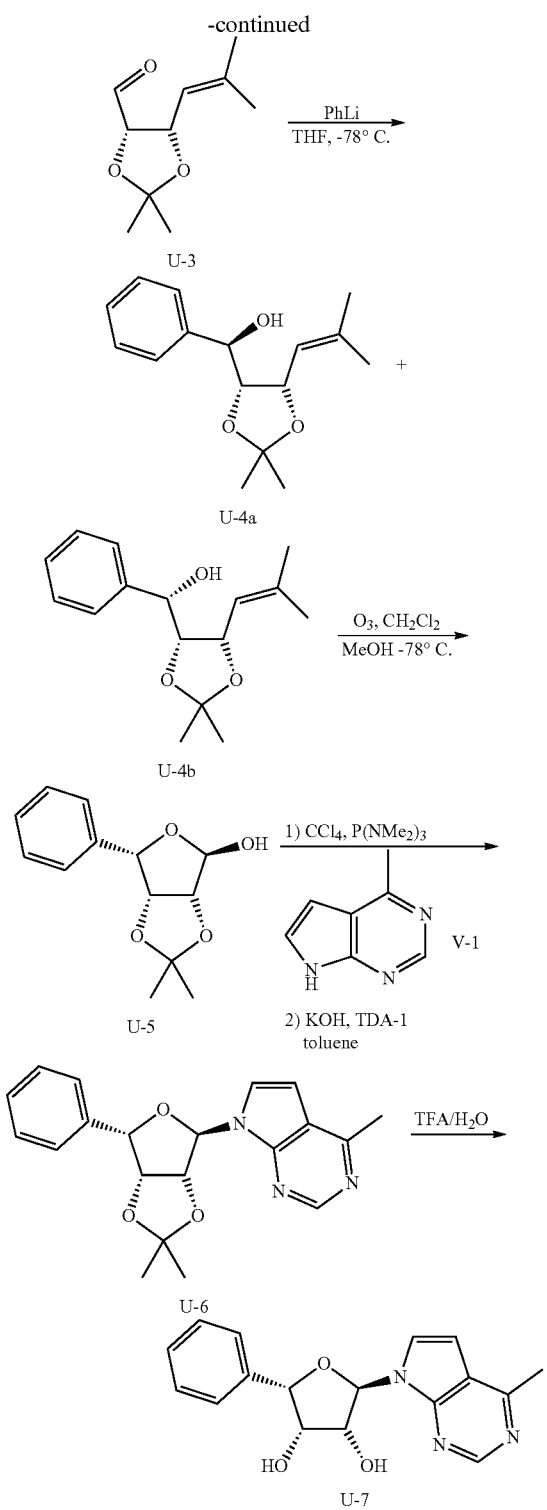

around −70° C., the reaction was stirred at −78° C. for 1.5 hrs. The reaction was quenched by slow addition of 14 mL MeOH at −78° C., allowed to warm to rt, added more MeOH, filtered through celite, rinsed with 10% MeOH/ $CH_2Cl_2$, concentrated to give 8 g yellow oil U-1. The celite cake was placed in an Erlenmeyer, added 10% MeOH/ $CH_2Cl_2$, stirred overnight, filtered and concentrated, the combined crude was purified by ISCO 80 g Si column with 0-10% MeOH/$CH_2Cl_2$ to give 8.01 g of U-1 as a light yellow oil.

Step 2: Synthesis of ((4R,5S)-2,2-dimethyl-5-(2-methylprop-1-en-1-yl)-1,3-dioxolan-4-yl)methanol (U-2)

In a two neck flask equipped with a thermometer and $N_2$ was added isopropyltriphenylphosphonium iodide (64.9 g, 150 mmol) and 300 mL THF, cooled to −25° C., 1.6 M nBuLi in hexanes (93.8 mL, 150 mmol) was added dropwise to the suspension maintaining the temperature around −25° C. After addition, the dry ice bath was removed and reaction was allowed to warm to rt. Replaced the dry ice bath and cooled to −25° C., (3aR,6aR)-2,2-dimethyltetrahydrofuro[3,4-d][1,3]dioxol-4-ol (U-1) (8.01 g, 50 mmol) in 60 mL THF was added through syringe maintaining the temperature around −25° C. After the addition, the dry ice bath was removed and the reaction was warmed to rt and stirred for 2 hrs. The rxn was quenched with slow addition of 30 mL $H_2O$, the solid was filtered, the filtrate was extracted with EtOAc, concentrated, purified by ISCO 220 g Si column with 20-30% EtOAc/heptanes to afford 8.02 g light yellow oil U-2. $^1H$ NMR (400 MHz, CHLOROFORM-d) δ ppm 5.26 (dt, J=8.93, 1.34 Hz, 1 H) 4.95 (dd, J=8.86, 6.66 Hz, 1 H) 4.21 (td, J=6.60, 5.01 Hz, 1 H) 3.53-3.62 (m, 2H) 1.77-1.80 (m, 3 H) 1.73 (d, J=1.10 Hz, 3 H) 1.51 (s, 3 H) 1.41 (s, 3 H)

Step 3: Synthesis of (4S,5S)-2,2-dimethyl-5-(2-methylprop-1-en-1-yl)-1,3-dioxolane-4-carbaldehyde (U-3)

To a solution of oxalyl chloride (1.02 g, 8.05 mmol) in $CH_2Cl_2$ (20 mL) at −78° C. was added 1.16 mL DMSO, the mixture was stirred for 5 min, a solution of ((4R,5S)-2,2-dimethyl-5-(2-methylprop-1-en-1-yl)-1,3-dioxolan-4-yl) methanol (U-2) (1 g, 5.37 mmol) in $CH_2Cl_2$ (10 mL) was added over 5 min, the mixture was stirred for 30 min, triethylamine (2.72 g, 26.8 mmol) was added dropwise over 5 min. The mixture was stirred for an additional 10 min, dry ice bath was removed and the reaction was warmed to rt. The reaction mixture was quenched by $H_2O$ (30 mL), the layers were separated, extracted the aqueous layer with $CH_2Cl_2$ 3 times. The organic layer was washed with 1N HCl 3 times, saturated $NaHCO_3$ once, and brine (20 mL). The organics were dried, drying reagent filtered, and the organics evaporated to afford crude U-3 (1 g) as a light yellow oil.

Step 4: Synthesis of (R)-((4R,5S)-2,2-dimethyl-5-(2-methylprop-1-en-1-yl)-1,3-dioxolan-4-yl)(phenyl) methanol (U-4b)

To a solution of (4S,5S)-2,2-dimethyl-5-(2-methylprop-1-en-1-yl)-1,3-dioxolane-4-carbaldehyde (U-3) (1 g, 5.43 mmol) in THF (20 mL) at −78° C. was added 1.8 M phenyl lithium in di-n-butyl ether (4.52 mL, 8.14 mmol) under $N_2$. After addition, the dry ice bath was removed and the reaction was warmed to rt and stirred overnight. To the Step 1: Synthesis of (3aR,6aR)-2,2-dimethyltetrahydrofuro[3,4-d][1,3]dioxol-4-ol (U-1)

In a two neck flask equipped with a thermometer and $N_2$ was added (3aR,6aR)-2,2-dimethyldihydrofuro[3,4-d][1,3] dioxol-4(3aH)-one (10 g, 63 mmol) and 250 mL $CH_2Cl_2$, cooled to −78° C., 1.0 M DIBAL in $CH_2Cl_2$ (126 mL, 1.26 mmol) was added dropwise maintaining the temperature reaction mixture was added H₂O (30 mL) and EtOAc, the layers were separated, extracted the aqueous layer with EtOAc 3 times. The organic layer was evaporated, the crude was purified by ISCO 40 g Si column first with 0-40% ether/heptane, then change to 2.5-10% (1:1 Heptane: CH₂Cl₂)/EtOAc to elute the first diastereoisomer (U-4a) 150 mg as a light yellow oil, then the second diastereoisomer (U-4b) 860 mg as a light yellow oil. ¹H NMR (400 MHz, CHLOROFORM-d) δ ppm 7.27-7.44 (m, 5 H) 5.37 (dt, J=9.29, 1.28 Hz, 1 H) 4.78 (dd, J=9.23, 6.42 Hz, 1 H) 4.65 (d, J=6.60 Hz, 1 H) 4.39 (t, J=6.48 Hz, 1 H) 1.68 (d, J=1.10 Hz, 3 H) 1.59 (s, 3 H) 1.43 (s, 3 H) 1.32 (d, J=1.10 Hz, 3 H)

Step 5: Synthesis of (3aR,4R,6S,6aR)-2,2-dimethyl-6-phenyltetrahydrofuro[3,4-d][1,3]dioxol-4-ol (U-5)

To a solution of (R)-((4R,5S)-2,2-dimethyl-5-(2-methylprop-1-en-1-yl)-1,3-dioxolan-4-yl)(phenyl)methanol (U-4b) (750 mg, 2.86 mmol) in 1:1 CH₂Cl₂/MeOH (30 mL) at −78° C. was bubbled O₃ for 5 min. The solution turned a light blue color. Changed gases from O₃ to N₂, bubbled for 1 min, 0.5 mL DMS was added, the dry ice bath was removed and the reaction was warmed to rt for 0.5 hr. The mixture was concentrated, purified by ISCO 24 g Si column with 3% CH₂Cl₂/EtOAc to afford 636 mg of U-5 as a white solid. ¹H NMR (400 MHz, CHLOROFORM-d) δ ppm 7.31-7.44 (m, 5 H) 5.56 (s, 1 H) 5.28 (d, J=3.67 Hz, 1 H) 4.87 (dd, J=5.75, 3.67 Hz, 1 H) 4.74 (d, J=5.75 Hz, 1 H) 1.45 (s, 3 H) 1.29 (s, 3 H)

Step 6: Synthesis of 7-((3aR,4R,6S,6aR)-2,2-dimethyl-6-phenyltetrahydrofuro[3,4-d][1,3]dioxol-4-yl)-4-methyl-7H-pyrrolo[2,3-d]pyrimidine (U-6)

To a solution of (3aR,4R,6S,6aR)-2,2-dimethyl-6-phenyltetrahydrofuro[3,4-d][1,3]dioxol-4-ol (U-5) (250 mg, 1.06 mmol) in toluene (15 mL) was added 154 μL CCl₄. The reaction was cooled in a dry ice/acetone bath (~−50° C.), then tris-(dimethylamino) phosphine (264 mg, 1.38 mmol) in 2 mL toluene was added drop-wise over 10 min. The internal reaction temperature rose to ~35° C. during addition and the clear solution changed to light yellow. The reaction was taken out of the cold bath and the temperature was maintained between −15° C. and 0° C. for 1 h. The reaction was quenched with ice cold brine (3 mL) and the layers were separated. The organic phase was dried over MgSO₄ and filtered then added to a pre-stirred mixture of 4-methyl-7H-pyrrolo[2,3-d]pyrimidine (V-1) (141 mg, 1.06 mmol) in toluene (15 mL), solid KOH (89 mg, 1.59 mmol), tris-(3,6-dioxaheptyl)-amine (144 mg, 0.423 mmol). The reaction mixture was stirred at rt for 40 h then quenched with saturated NH₄Cl solution (25 mL) and extracted with DCM (2×30 mL). The combined organic extracts were dried (MgSO₄), filtered and concentrated. The crude residue was purified by ISCO 40 g Si column with 0-50% EtOAc/Hep to provide 124 mg a white solid U-6. ¹H NMR (400 MHz, CHLOROFORM-d) δ ppm 8.88 (s, 1 H) 7.29-7.45 (m, 6 H) 6.70 (d, J=2.93 Hz, 1 H) 6.23 (s, 1 H) 5.79 (d, J=5.62 Hz, 1 H) 5.44 (d, J=3.55 Hz, 1 H) 5.28-5.34 (m, 1 H) 2.82-2.93 (m, 3 H) 1.57 (s, 3 H) 1.38 (s, 3 H)

Step 7: Synthesis of (2R,3R,4S,5S)-2-(4-methyl-7H-pyrrolo[2,3-d]pyrimidin-7-yl)-5-phenyltetrahydrofuran-3,4-diol (U-7)

7-((3aR,4R,6S,6aR)-2,2-dimethyl-6-phenyltetrahydrofuro[3,4-d][1,3]dioxol-4-yl)-4-methyl-7H-pyrrolo[2,3-d]pyrimidine (U-6) (124 mg, 0.353 mmol) was dissolved in 10 mL TFA, added 2 mL H₂O, stirred at rt for 5 hrs. The reaction was concentrated then purified by SFC with Chiralpak AS-3 4.6×100 mm 3 u column with 10% MeOH at 120 bar and 4 mL/min to provide 85.24 mg of U-7 as a white solid. ¹H NMR (400 MHz, DMSO-d6) δ ppm 8.70 (s, 1H) 7.90 (d, J=3.67 Hz, 1 H) 7.29-7.42 (m, 4 H) 7.22-7.29 (m, 1 H) 6.80 (d, J=3.79 Hz, 1 H) 6.40 (d, J=7.58 Hz, 1 H) 5.60 (d, J=2.32 Hz, 1 H) 5.45 (d, J=6.97 Hz, 1 H) 5.07 (dt, J=7.21, 3.61 Hz, 1 H) 5.04 (d, J=4.65 Hz, 1 H) 4.24-4.30 (m, 1 H) 2.68 (s, 3 H)

Synthesis of Intermediate V-1

Scheme V

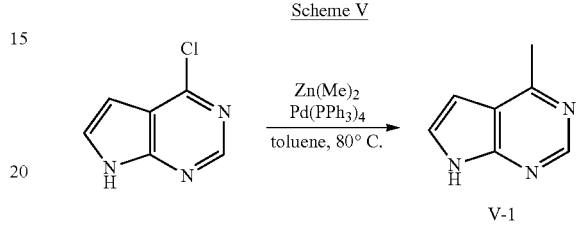

Synthesis of 4-methyl-7H-pyrrolo[2,3-d]pyrimidine (V-1)

A suspension of 4-chloro-7H-pyrrolo[2,3-d]pyrimidine (1.54 g, 10 mmol) and Pd(PPh₃)₄ (116 mg, 0.100 mmol) in THF (10.0 mL, 1M) was vacuum purged with N₂. Then a solution of dimethylzinc (3.82 g, 40.0 mmol, 20.0 mL, 2M in toluene) was added and the mixture was vacuum flushed with N₂ and then heated to 60° C. for 16 h. LCMS-APCI(+) showed ~1:1 mixture of starting material to product. The reaction was heated to 80° C. for another 24 h, in which LCMS showed a ~2:1 mixture of product to starting material. The reaction mixture was cooled in an ice-water bath then quenched with saturated NaHCO₃ (aq) and extracted with EtOAc. The EtOAc was washed with brine, dried with MgSO₄, filter and concentrated to an oil. The crude material was purified by ISCO-Rf on a 24 g column eluting with 0-100% EtOAc-Heptane to give compound V-1 (561 mg, 42%). LCMS [M+1] 134; ¹HNMR (400 MHz, CDCl₃) δ ppm 8.94 (s, 1H), 7.42 (d, J=3.4 Hz, 1H), 6.68 (d, J=3.4 Hz, 1H), 2.87 (s, 3H)

Example 67

(Scheme W) (2R,3R,4S,5S)-2-(4-amino-5-fluoro-7H-pyrrolo[2,3-d]pyrimidin-7-yl)-5-phenyltetrahydrofuran-3,4-diol (W-2)

Scheme W

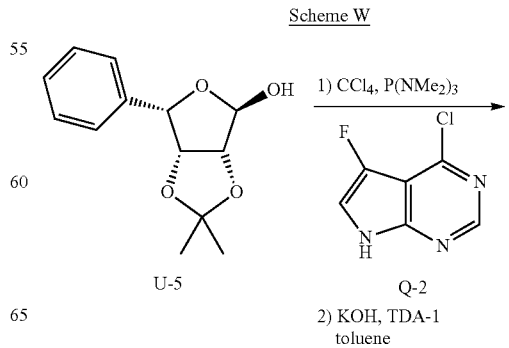

167

-continued

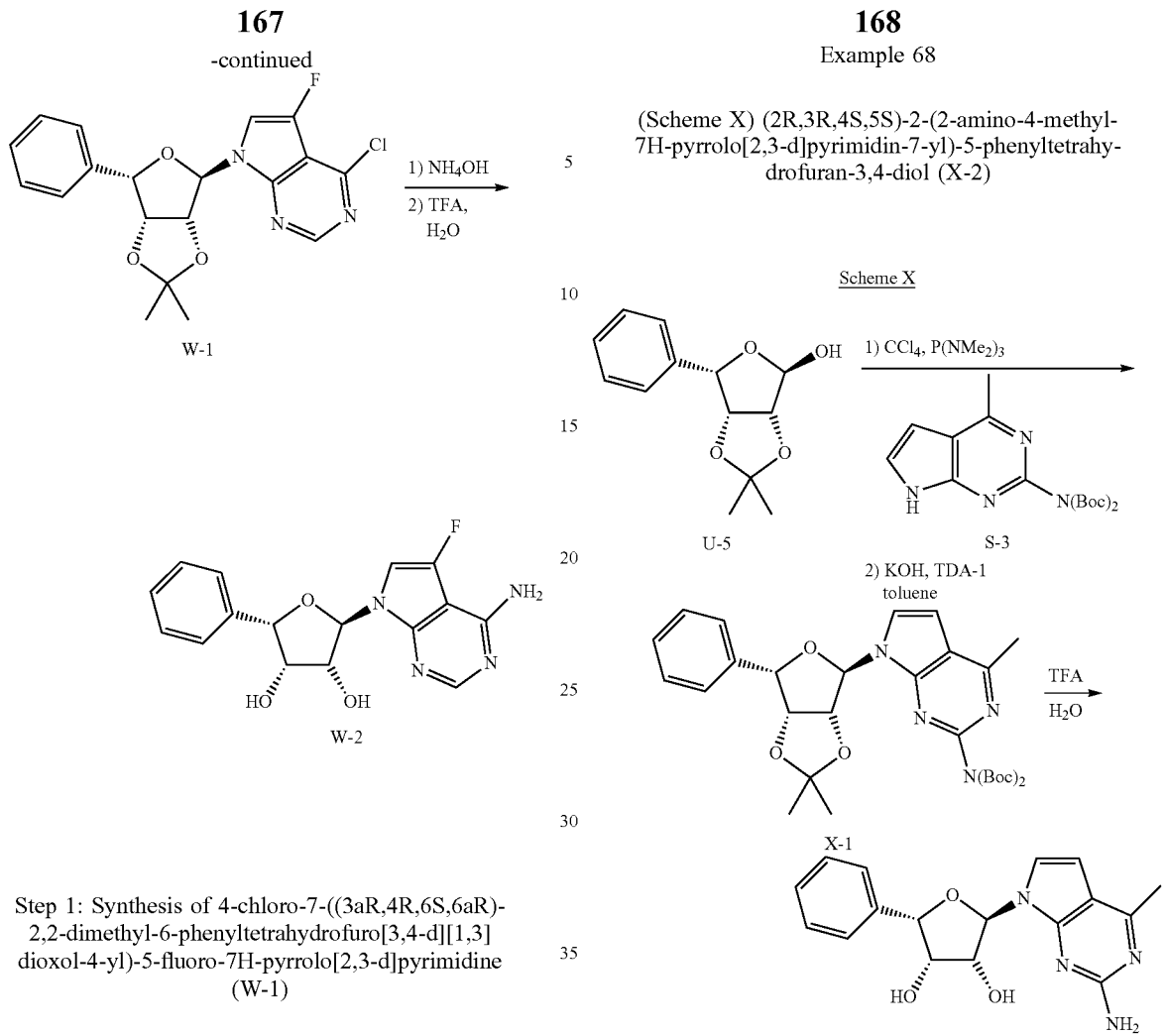

Step 1: Synthesis of 4-chloro-7-((3aR,4R,6S,6aR)-2,2-dimethyl-6-phenyltetrahydrofuro[3,4-d][1,3]dioxol-4-yl)-5-fluoro-7H-pyrrolo[2,3-d]pyrimidine (W-1)

W-1 was prepared analogously to 7-((3aR,4R,6S,6aR)-2,2-dimethyl-6-phenyltetrahydrofuro[3,4-d][1,3]dioxol-4-yl)-4-methyl-7H-pyrrolo[2,3-d]pyrimidine (U-6, Scheme U) where 4-methyl-7H-pyrrolo[2,3-d]pyrimidine (V-1) was substituted by 4-chloro-5-fluoro-7H-pyrrolo[2,3-d]pyrimidine (Q-2).

Step 2: Synthesis of (2R,3R,4S,5S)-2-(4-amino-5-fluoro-7H-pyrrolo[2,3-d]pyrimidin-7-yl)-5-phenyltetrahydrofuran-3,4-diol (W-2)

4-chloro-7-((3aR,4R,6S,6aR)-2,2-dimethyl-6-phenyltetrahydrofuro[3,4-d][1,3]dioxol-4-yl)-5-fluoro-7H-pyrrolo[2,3-d]pyrimidine (W-1) (131 mg, 0.336 mmol) was dissolved in 2 mL dioxane, added 2 mL NH$_4$OH, sealed and heated at 95° C. overnight. The mixture was concentrated and dissolved in 10 mL TFA, added 2 mL H$_2$O, stirred at rt for 1 hr. The reaction was concentrated then purified by SFC with Chiralpak AS-3 4.6×100 mm 3 u column with 10% MeOH at 120 bar and 4 mL/min to provide 68.82 mg of compound W-2 as a white solid. $^1$H NMR (400 MHz, DMSO-d6) δ ppm 8.12 (s, 1 H) 7.52 (d, J=1.47 Hz, 1 H) 7.29-7.39 (m, 4 H) 7.22-7.29 (m, 1 H) 6.97 (br. s., 2 H) 6.32 (d, J=7.34 Hz, 1 H) 5.49 (d, J=2.45 Hz, 1 H) 5.40 (d, J=7.21 Hz, 1 H) 4.96 (d, J=4.65 Hz, 1 H) 4.90 (td, J=7.34, 4.16 Hz, 1 H) 4.17-4.24 (m, 1 H)

168

Example 68

(Scheme X) (2R,3R,4S,5S)-2-(2-amino-4-methyl-7H-pyrrolo[2,3-d]pyrimidin-7-yl)-5-phenyltetrahydrofuran-3,4-diol (X-2)

Scheme X

Step 1: Synthesis of tert-butyl (7-((3aR,4R,6S,6aR)-2,2-dimethyl-6-phenyltetrahydrofuro [3,4-d][1,3]dioxol-4-yl)-4-methyl-7H-pyrrolo[2,3-d]pyrimidin-2-yl) (tert-butoxymethyl) carbamate (X-1)

X-1 was prepared analogously to 7-((3aR,4R,6S,6aR)-2,2-dimethyl-6-phenyltetrahydrofuro[3,4-d][1,3]dioxol-4-yl)-4-methyl-7H-pyrrolo[2,3-d]pyrimidine (U-6, Scheme U) where 4-methyl-7H-pyrrolo[2,3-d]pyrimidine (V-1) was substituted by tert-butyl (4-methyl-7H-pyrrolo[2,3-d]pyrimidin-2-yl) (tert-butoxymethyl) carbamate (S-3).

Step 2: Synthesis of (2R,3R,4S,5S)-2-(2-amino-4-methyl-7H-pyrrolo[2,3-d]pyrimidin-7-yl)-5-phenyltetrahydrofuran-3,4-diol (X-2)

X-2 was prepared in a similar fashion to Example 66 (Step 6, Scheme U)

$^1$H NMR (700 MHz, DMSO-d6) δ ppm 7.38 (d, J=3.74 Hz, 1 H) 7.29-7.36 (m, 3 H) 7.21-7.27 (m, 1 H) 6.50 (d, J=3.74 Hz, 1 H) 6.28 (br. s., 2H) 6.20 (d, J=7.48 Hz, 1 H) 5.49-5.53 (m, 1 H) 5.40 (d, J=6.82 Hz, 1 H) 4.95 (d, J=3.96 Hz, 1 H) 4.89-4.93 (m, 1 H) 4.17-4.23 (m, 1 H) 2.45 (s, 3 H)

Example 69

(Scheme Y) (2R,3R,4S,5R)-2-(4-methyl-7H-pyrrolo[2,3-d]pyrimidin-7-yl)-5-(oxazol-5-yl)tetrahydrofuran-3,4-diol (Y-6)

Scheme Y

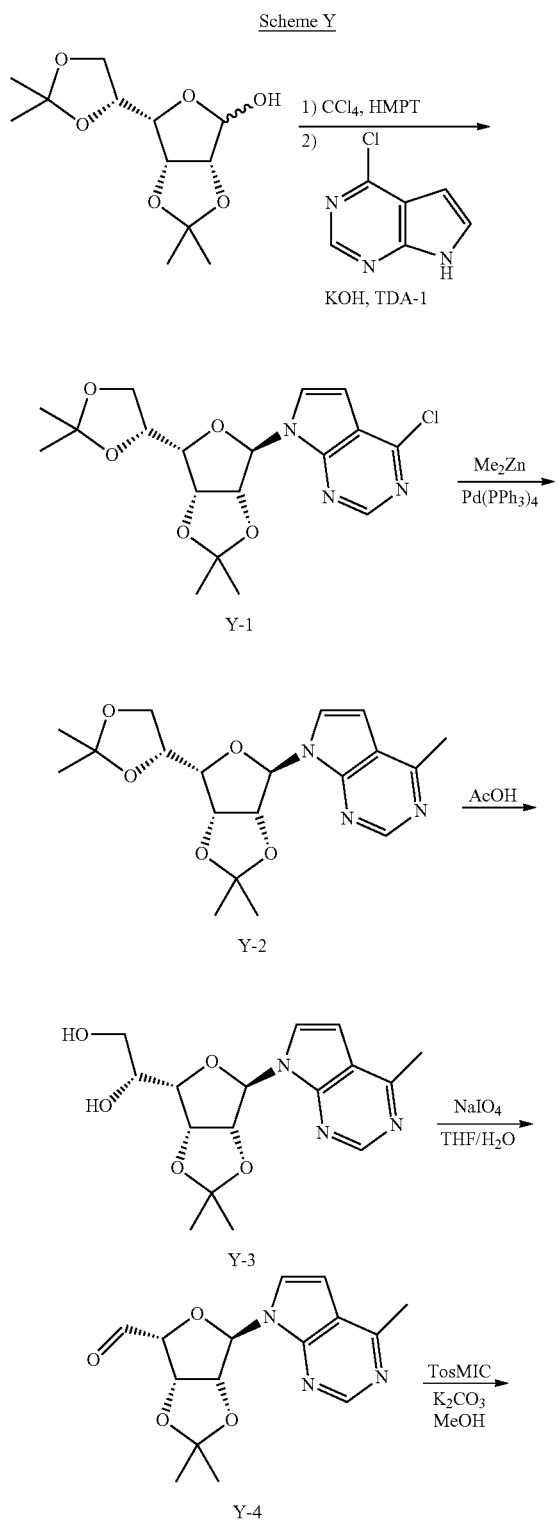

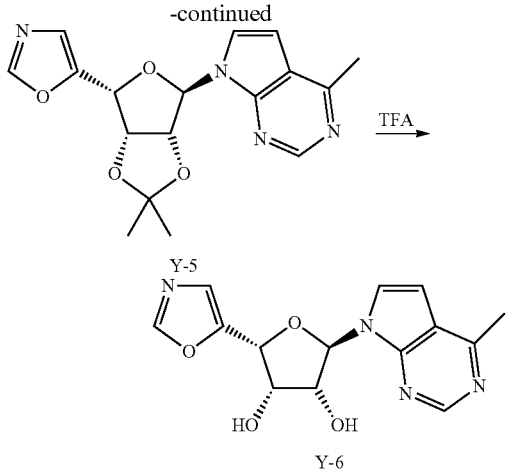

Step 1: Synthesis of 4-chloro-7-((3aR,4R,6S,6aR)-6-((R)-2,2-dimethyl-1,3-dioxolan-4-yl)-2,2-dimethyltetrahydrofuro[3,4-d][1,3]dioxol-4-yl)-7H-pyrrolo[2,3-d]pyrimidine (Y-1)

To a solution of (3aR,6S,6aR)-6-((R)-2,2-dimethyl-1,3-dioxolan-4-yl)-2,2-dimethyltetrahydrofuro[3,4-d][1,3]dioxol-4-ol (2.65 g, 10.2 mmol) in THF (20.4 mL, 0.5 M) was added $CCl_4$ (1.28 ml, 13.2 mmol). The resulting mixture was cooled in a dry-ice/acetone bath then HMPT (2.78 ml, 15.3 mmol) was added. The dry-ice bath was switched for an ice-water bath and the solution was allowed to warm to ~0 C. After 45 minutes the reaction mixture was poured into a separatory funnel containing cold brine then extracted with MTBE (30 ml). The MTBE layer was then dried with $Na_2SO_4$, filtered then placed in a 200 ml RB flask.

A mixture of 4-chloro-7H-pyrrolo[2,3-d]pyrimidine (908 mg, 6.82 mmol) and KOH (857 mg, 15.3 mmol) was suspended in THF (30.0 mL, 0.20 M). To the suspension was added TDA-1 (1.30 ml, 4.07 mmol) after ~10 minutes the mixture became homogenous. The previous made MTBE solution was then added to the reaction mixture via a cannula. The resulting mixture was stirred at r.t. for 16 hours. The reaction mixture was quenched with saturated $NH_4Cl(aq)$ then diluted with water and EtOAc. The EtOAc layer was washed with brine, dried with $Na_2SO_4$, filtered then concentrated to an oil. The crude oil was purified by $SiO_2$ column chromatography (Heptane/EtOAc=100/0 to 1/1) to give Y-1 (1.14 g, 39% yield) as a colorless oil. LCMS-ESI(+): 396 [M+1]$^+$ $^1$H NMR (400 MHz, CHLOROFORM-d) δ ppm 8.62 (s, 1 H) 7.29 (d, J=3.67 Hz, 1 H) 6.62 (d, J=3.67 Hz, 1 H) 6.05 (s, 1 H) 5.57 (d, J=5.87 Hz, 1 H) 5.23 (dd, J=5.75, 3.55 Hz, 1 H) 4.38-4.53 (m, 2 H) 4.22-4.33 (m, 1 H) 3.69-3.85 (m, 1 H) 1.57 (s, 3 H) 1.32-1.45 (m, 9 H)

Step 2: Synthesis of 7-((3aR,4R,6S,6aR)-6-((R)-2,2-dimethyl-1,3-dioxolan-4-yl)-2,2-dimethyltetrahydrofuro[3,4-d][1,3]dioxol-4-yl)-4-methyl-7H-pyrrolo[2,3-d]pyrimidine (Y-2)

A solution of 4-chloro-7-((3aR,4R,6S,6aR)-6-((R)-2,2-dimethyl-1,3-dioxolan-4-yl)-2,2-dimethyltetrahydrofuro[3,4-d][1,3]dioxol-4-yl)-7H-pyrrolo[2,3-d]pyrimidine (Y-1) (611.0 mg, 1.54 mmol) and Pd(PPh$_3$)$_4$ (71.3 mg, 0.0617 mmol) in THF (7.72 ml) was vacuum flushed with $N_2$. Next a solution of Me$_2$Zn 2 M in toluene (4.63 ml, 9.26 mmol) was added and the mixture was vacuum-flushed with N$_2$ and heated to 70° C. for 4 hours. The reaction mixture was cooled in an ice bath and quenched by the drop-wise addition of saturated NaHCO$_3$(aq) (1 ml). Some foaming occurred then subsided upon complete addition. The crude mixture was diluted with EtOAc and water. The aqueous layer contained a white solid that never went into solution. The EtOAc layer was washed with brine, dried with Na$_2$SO$_4$, filtered then concentrated to an oil. The crude oil was purified by SiO$_2$ column chromatography (Heptane/EtOAc=9/1 to 3/7) to give Y-2 (565 mg, 98% yield) as a light amber oil. LCMS-APCI(+): 376 [M+1]$^+$ $^1$H NMR (400 MHz, CHLOROFORM-d) δ ppm 8.78 (s, 1H), 7.30 (d, J=3.7 Hz, 1H), 6.64 (d, J=3.4 Hz, 1H), 6.07 (s, 1H), 5.58 (d, J=5.9 Hz, 1H), 5.23 (dd, J=3.4, 5.9 Hz, 1H), 4.47-4.40 (m, 2H), 4.32-4.20 (m, 1H), 3.85-3.71 (m, 1H), 2.85 (s, 3H), 1.58 (s, 3H), 1.47-1.33 (m, 11H)

Step 3: Synthesis of (R)-1-((3aR,4S,6R,6aR)-2,2-dimethyl-6-(4-methyl-7H-pyrrolo[2,3-d]pyrimidin-7-yl)tetrahydrofuro[3,4-d][1,3]dioxol-4-yl)ethane-1,2-diol (Y-3)

A solution of 7-((3aR,4R,6S,6aR)-6-((R)-2,2-dimethyl-1,3-dioxolan-4-yl)-2,2-dimethyltetrahydrofuro[3,4-d][1,3]dioxol-4-yl)-4-methyl-7H-pyrrolo[2,3-d]pyrimidine (Y-2) (565 mg, 1.50 mmol) in 70% v/v aq ACETIC ACID (3.01 mL, c=0.5 M) was stirred at 50° C. for 4 days.

The reaction mixture was cooled to r.t. then concentrated in-vacuo to an amber oil. The oil was re-dissolved in EtOAc then washed with saturated NaHCO$_3$(aq), dried with MgSO$_4$, filtered and concentrated to a gel like solid. The solid was suspended in MTBE then sonicated and filtered.

The solid was then air dried and further dried under house vacuum to give Y-3 (392 mg, 78% yield) as a white solid. LCMS-ESI(+): 336 [M+1]$^+$ $^1$H NMR (400 MHz, CHLOROFORM-d) δ ppm 8.79 (s, 1 H) 7.33 (d, J=3.67 Hz, 1 H) 6.67 (d, J=3.42 Hz, 1 H) 6.11 (s, 1 H) 5.63 (d, J=5.62 Hz, 1H) 5.25-5.34 (m, 1 H) 4.40-4.48 (m, 1 H) 4.17 (q, J=5.30 Hz, 1H) 3.67-3.86 (m, 2H) 3.22 (s, 1H) 2.85 (s, 3H) 1.42 (s, 3H) 1.32-1.40 (m, 1H) 1.20 (s, 4H).

Step 4: Synthesis of (3aS,4R,6R,6aR)-2,2-dimethyl-6-(4-methyl-7H-pyrrolo[2,3-d]pyrimidin-7-yl)tetrahydrofuro[3,4-d][1,3]dioxole-4-carbaldehyde (Y-4)

To a solution of (R)-1-((3aR,4S,6R,6aR)-2,2-dimethyl-6-(4-methyl-7H-pyrrolo[2,3-d]pyrimidin-7-yl)tetrahydrofuro[3,4-d][1,3]dioxol-4-yl)ethane-1,2-diol (Y-3) (392 mg, 1.1 mmol) in a 2:1 mixture of THF (5 mL) and water (2 mL) at r.t. was added NaIO$_4$. After 2 hours the reaction mixture was diluted with EtOAc and water then the EtOAc layer was washed with brine, dried with MgSO$_4$, filtered then concentrated to an oil to give crude Y-4 (300 mg, 91% yield) as a light amber oil. LCMS-ESI(+)=304 [M+1]$^+$.

$^1$H NMR (400 MHz, CD$_3$OD) δ ppm 8.64 (s, 1H), 7.51 (t, J=3.2 Hz, 1H), 6.78-6.62 (m, 1H), 6.18 (s, 1H), 5.55 (dd, J=3.4, 5.6 Hz, 1H), 5.34-5.16 (m, 1H), 4.78-4.67 (m, 1H), 4.32-4.12 (m, 1H), 3.35 (s, 4H), 2.70 (d, J=2.4 Hz, 4H), 1.56 (d, J=2.4 Hz, 4H), 1.40 (s, 3H).

Step 5: Synthesis of (2R,3R,4S,5R)-2-(4-methyl-7H-pyrrolo[2,3-d]pyrimidin-7-yl)-5-(oxazol-5-yl)tetrahydrofuran-3,4-diol (Y-5)

A mixture of (3aS,4R,6R,6aR)-2,2-dimethyl-6-(4-methyl-7H-pyrrolo[2,3-d]pyrimidin-7-yl)tetrahydrofuro[3,4-d][1,3]dioxole-4-carbaldehyde (Y-4) (100 mg, 0.330 mmol), TOS-MIC (64.4 mg, 0.330 mmol) and K$_2$CO$_3$ (137 mg, 0.989 mmol) in MeOH (1.10 mL) was heated to 80° C. for 2 hours then concentrated to an oil. The crude oil was purified by Prep-HPLC to give 5-((3aR,4R,6R,6aR)-2,2-dimethyl-6-(4-methyl-7H-pyrrolo[2, 3-d]pyrimidin-7-yl)tetrahydrofuro[3,4-d][1,3]dioxol-4-yl)oxazole (Y-5) (41 mg, 36% yield) as a light amber oil. LCMS-ESI(+): 343 [M+1]$^+$.

Step 6: Synthesis of (2R,3R,4S,5R)-2-(4-methyl-7H-pyrrolo[2,3-d]pyrimidin-7-yl)-5-(oxazol-5-yl)tetrahydrofuran-3,4-diol (Y-6)

5-((3aR,4R,6R,6aR)-2,2-dimethyl-6-(4-methyl-7H-pyrrolo[2,aR)-2,2-dimethyl-[2,3-d]pyrimidin-7-yl)tetrahydrofuro[3,4-d][1,3]dioxol-4-yl)oxazole (Y-5) (41 mg, 0.12 mmol) was treated with TFA (250 ul) and water (30 ul) then stirred at r.t. for 24 hours and concentrated to an oil. The crude oil was purified by SFC to give Y-6 (19.6 mg, 20% yield) as a solid. LCMS-ESI(+): 303 [M+1]$^+$.

$^1$H NMR (400 MHz, DMSO-d6) δ ppm 8.67 (s, 1 H) 8.33 (s, 1 H) 7.87 (d, J=3.67 Hz, 1 H) 7.19 (s, 1 H) 6.79 (d, J=3.67 Hz, 1 H) 6.31 (d, J=7.58 Hz, 1 H) 5.66 (d, J=2.69 Hz, 1 H) 5.46-5.58 (m, 2 H) 4.94-5.06 (m, 1 H) 4.33 (q, J=3.91 Hz, 1 H) 2.66 (s, 3 H).

Example 70

(Scheme Z) (2S,3S,4R,5R)-2-((R)-1-hydroxyethyl)-5-(4-methyl-7H-pyrrolo[2,3-d]pyrimidin-7-yl)tetrahydrofuran-3,4-diol (Z-2)

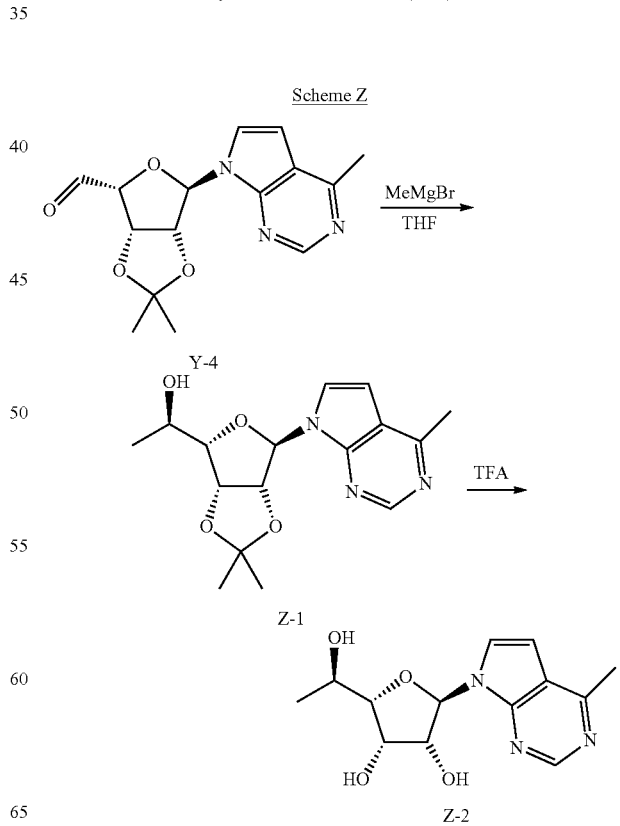

Scheme Z

173

Synthesis of (2S,3S,4R,5R)-2-((R)-1-hydroxyethyl)-5-(4-methyl-7H-pyrrolo[2,3-d]pyrimidin-7-yl)tetrahydrofuran-3,4-diol (Z-2)

To a solution of (3aS,4R,6R,6aR)-2,2-dimethyl-6-(4-methyl-7H-pyrrolo[2,3-d]pyrimidin-7-yl)tetrahydrofuro[3,4-d][1,3]dioxole-4-carbaldehyde (Y-4) (60.7 mg, 0.2 mmol) in THF (0.67 mL, 0.3 M) cooled in a dry-ice acetone bath was added 3.0 M methylmagnesiumbromide (400 ul, 1.20 mmol). After 2 hours more 3.0 M methylmagnesiumbromide (400 ul, 1.20 mmol) was added and the reaction mixture was allowed to warm to r.t. After another 19 hours the reaction mixture was quenched with saturated NH$_4$Cl (aq) then diluted with water and extracted with EtOAc. The EtOAc was washed with brine, dried with MgSO$_4$, filtered then concentrated to an oil. The oil was purified SiO$_2$ column chromatography (Heptane/EtOAc=60/40 to 0/100 then EtOAc/MeOH=100/0 to 70/30) to give Z-1 (23 mg, 36% yield) as a colorless oil.

The oil Z-1 (23 mg, 0.072 mmol) was dissolved in a mixture of TFA (250 ul) and water (30 ul) then stirred at r.t. for 2 hours. The reaction mixture was diluted with toluene (1 ml) then concentrated in vacuo to give a red oil. The oil was purified by SFC chromatography to give Z-2 (5.46 mg, 10% yield); LCMS-APCI(+): 280 [M+1]$^+$. $^1$H NMR (400 MHz, METHANOL-d4) δ ppm 8.63 (s, 1 H) 7.63 (d, J=3.67 Hz, 1 H) 6.76 (d, J=3.67 Hz, 1 H) 6.25 (d, J=7.34 Hz, 1 H) 4.95 (dd, J=7.34, 4.40 Hz, 1 H) 4.42 (t, J=3.30 Hz, 1 H) 4.21 (dd, J=7.70, 2.57 Hz, 1 H) 4.01-4.15 (m, 1 H) 2.72 (s, 3 H) 1.23 (d, J=6.36 Hz, 3 H).

Example 71

(Scheme AA) (2S,3S,4R,5R)-2-(hydroxymethyl)-5-(4-methyl-7H-pyrrolo[2,3-d]pyrimidin-7-yl)tetrahydrofuran-3,4-diol (AA-2)

174

Step 1: Synthesis of ((3aR,4S,6R,6aR)-2,2-dimethyl-6-(4-methyl-7H-pyrrolo[2,3-d]pyrimidin-7-yl)tetrahydrofuro[3,4-d][1,3]dioxol-4-yl)methanol (AA-1)

To a solution of the (3aS,4R,6R,6aR)-2,2-dimethyl-6-(4-methyl-7H-pyrrolo[2,3-d]pyrimidin-7-yl)tetrahydrofuro[3,4-d][1,3]dioxole-4-carbaldehyde (Y-4) (220 mg, 0.725 mmol) in MeOH (2.42 ml) at r.t. was added NaBH$_4$ (31.1 mg, 0.798 mmol). The mixture was stirred at r.t for 3 hours then quenched with water and concentrated to remove MeOH. The residue was re-dissolved in EtOAc then the EtOAc was washed with water, brine, dried with MgSO$_4$, filtered then concentrated to an oil. The crude oil was purified by SiO$_2$ chromatography (50-100% EtOAc-Heptane for 7 minutes then 0-3% MeOH-EtOAc for 7 min) to give AA-1 (192 mg, 87% yield) as a colorless oil. $^1$H NMR (400 MHz, CHLOROFORM-d) δ ppm 8.81 (s, 1H), 7.35 (d, J=3.4 Hz, 1H), 6.70 (d, J=3.4 Hz, 1H), 6.11 (s, 1H), 5.62 (d, J=5.9 Hz, 1H), 5.31 (dd, J=3.9, 5.9 Hz, 1H), 4.56-4.44 (m, 1H), 4.05-3.88 (m, 2H), 2.89 (s, 3H), 1.60 (s, 3H), 1.43 (s, 3H)

Step 2: Synthesis of (2S,3S,4R,5R)-2-(hydroxymethyl)-5-(4-methyl-7H-pyrrolo[2,3-d]pyrimidin-7-yl)tetrahydrofuran-3,4-diol (AA-2)

A mixture of the alcohol AA-1 (24 mg, 0.079 mmol), TFA (2.73 mmol, 209 uL) and H$_2$O (1.36 mmol, 24.6 uL) was stirred at r.t. After 1 hour the reaction mixture was concentrated to an oil. The crude oil was purified by SFC chromatography to give AA-2 (9.33 mg, 30% yield) as a white solid. LCMS-APCI(+): 266 [M+1]$^+$. $^1$H NMR (400 MHz, METHANOL-d4) δ ppm 7.39 (s, 1 H) 6.27-6.29 (m, 1 H) 5.47 (d, J=3.42 Hz, 1 H) 4.95 (d, J=6.60 Hz, 1 H) 3.54 (t, J=5.38 Hz, 1 H) 3.25-3.28 (m, 1 H) 3.14 (t, J=3.79 Hz, 1 H) 2.50-2.65 (m, 2 H) 1.47 (s, 3 H)

Example 72

(Scheme BB) (2R,3R,4S,5S)-2-(4-methyl-7H-pyrrolo[2,3-d]pyrimidin-7-yl)-5-(1H-pyrazol-5-yl)tetrahydrofuran-3,4-diol (BB-4)

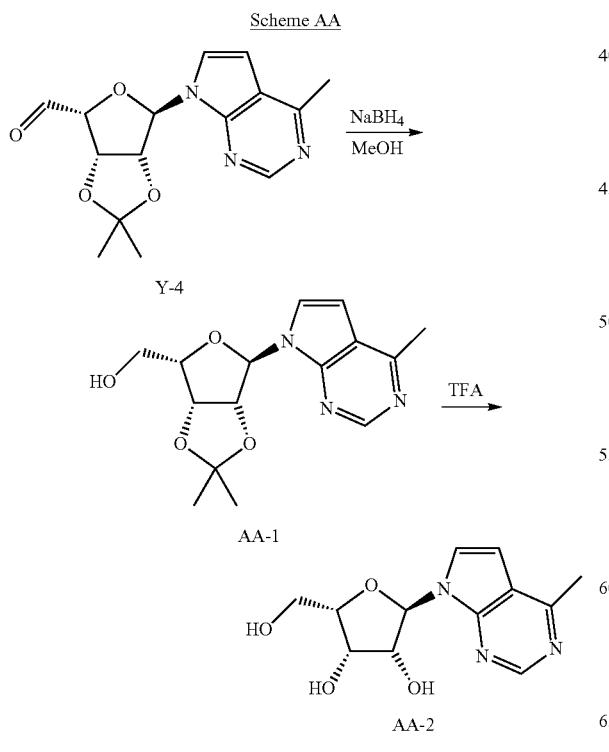

Scheme AA

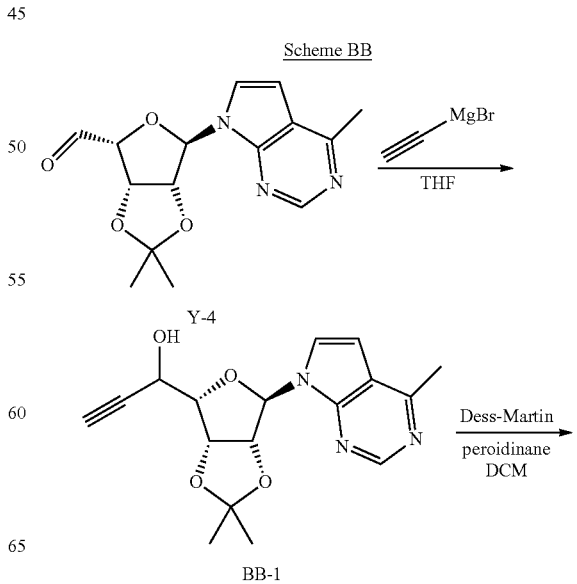

Scheme BB

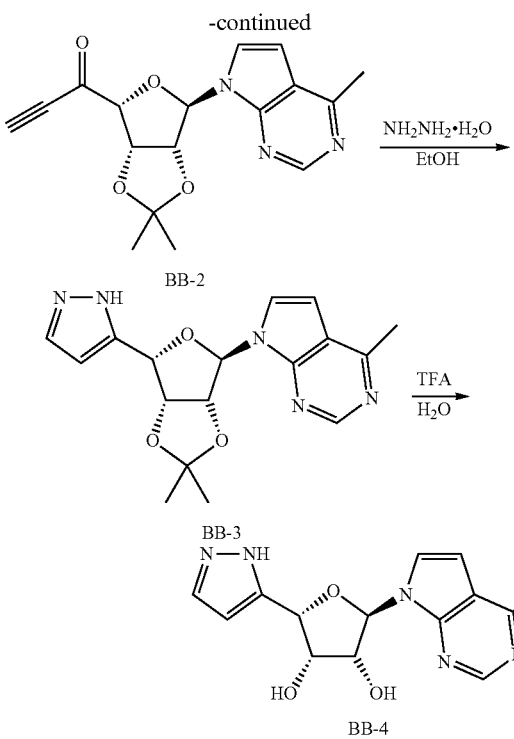

Step 1: Synthesis of 1-((3aR,4S,6R,6aR)-2,2-dimethyl-6-(4-methyl-7H-pyrrolo[2,3-d]pyrimidin-7-yl)tetrahydrofuro[3,4-d][1,3]dioxol-4-yl)prop-2-yn-1-ol (BB-1)

To a solution of (3aS,4R,6R,6aR)-2,2-dimethyl-6-(4-methyl-7H-pyrrolo[2,3-d]pyrimidin-7-yl)tetrahydrofuro[3,4-d][1,3]dioxole-4-carbaldehyde (Y-4) (141 mg, 0.465 mmol) in THF (0.667 mL, 0.3 M) cooled in a dry-ice acetone bath was added ethynylmagnesium bromide (5.58 mL, 2.79 mmol, 0.5 M). The reaction mixture was allowed to slowly warm to r.t. After 45 hours the reaction mixture was cooled again in a dry-ice acetone bath then more ethynylmagnesium bromide (5.58 mL, 2.79 mmol, 0.5 M) was added. The dry-ice acetone bath was replaced with an ice-water bath. After 6 more hours the reaction mixture was quenched with saturated $NH_4Cl(aq)$, diluted with water and extracted with EtOAc. The combined EtOAc was washed with brine, dried with $MgSO_4$, filtered then concentrated to an oil. The crude oil was purified by $SiO_2$ chromatography (Heptane/EtOAc 60/40 to 0/100) for 9 minutes then MeOH/EtOAc 0-3% MeOH for 5 minutes to give BB-1 (70 mg, 46% yield) as a colorless oil. LCMS-ESI(+): 330 [MH]$^+$. $^1$H NMR (400 MHz, CHLOROFORM-d) δ ppm 8.61-8.85 (m, 1 H) 7.20-7.26 (m, 1 H) 6.48-6.69 (m, 1 H) 6.04 (s, 1 H) 5.45-5.75 (m, 2 H) 4.67-4.84 (m, 1 H) 4.57 (dd, J=7.09, 3.67 Hz, 1 H) 2.65-2.82 (m, 3 H) 1.53-1.70 (m, 3 H) 1.33-1.49 (m, 3 H)

Step 2: Synthesis of 1-((3aS,4R,6R,6aR)-2,2-dimethyl-6-(4-methyl-7H-pyrrolo[2,3-d]pyrimidin-7-yl)tetrahydrofuro[3,4-d][1,3]dioxol-4-yl)prop-2-yn-1-one (BB-2)

A mixture of 1-((3aR,4S,6R,6aR)-2,2-dimethyl-6-(4-methyl-7H-pyrrolo[2,3-d]pyrimidin-7-yl)tetrahydrofuro[3,4-d][1,3]dioxol-4-yl)prop-2-yn-1-ol (BB-1) (70 mg, 0.21 mmol) and Dess-Martin Periodinane (108 mg, 0.255 mmol) in DCM (0.708 mL, c=0.3 M) was stirred at r.t. After 40 minutes LCMS indicated that the starting material was consumed. The crude reaction mixture was purified by $SiO_2$ chromatography (Heptane/EtOAc 60/40 to 0/100) to give BB-2 (37 mg, 53% yield) as a red solid. LCMS-ESI(+): 328 [M+1]$^+$. $^1$H NMR (400 MHz, CHLOROFORM-d) δ ppm 8.77 (s, 1H), 7.24 (d, J=3.7 Hz, 1H), 6.59 (d, J=3.7 Hz, 1H), 6.15 (s, 1H), 5.81-5.73 (m, 1H), 5.62 (d, J=5.6 Hz, 1H), 5.31 (s, 1H), 5.19 (d, J=4.4 Hz, 1H), 3.42 (s, 1H), 2.75 (s, 3H), 2.10 (s, 1H), 1.56 (s, 3H), 1.41 (s, 3H)

Step 3: Synthesis of (2R,3R,4S,5S)-2-(4-methyl-7H-pyrrolo[2,3-d]pyrimidin-7-yl)-5-(1H-pyrazol-5-yl)tetrahydrofuran-3,4-diol (BB-2)

To a solution of the 1-((3aS,4R,6R,6aR)-2,2-dimethyl-6-(4-methyl-7H-pyrrolo[2,3-d]pyrimidin-7-yl)tetrahydrofuro[3,4-d][1,3]dioxol-4-yl)prop-2-yn-1-one (BB-2) (37 mg, 0.11 mmol) in EtOH (0.377 ml) at r.t. was added hydrazine monohydrate (6.58 ul, 0.136 mmol). After 7 minutes LCMS indicated that the starting ketone was consumed. The reaction mixture was concentrated to an oil then purified by $SiO_2$ chromatography (Heptane/EtOAc 6/4 to 0/10 for 8 min. then MeOH/EtOAc 0/100 to 3/97) to give 7-((3aR,4R,6S,6aR)-2,2-dimethyl-6-(1H-pyrazol-5-yl)tetrahydrofuro[3,4-d][1,3]dioxol-4-yl)-4-methyl-7H-pyrrolo[2,3-d]pyrimidine (BB-3) (23 mg) as a reddish brown oil. LCMS-ESI(+): 342 [M+1]$^+$.

7-((3aR,4R,6S,6aR)-2,2-dimethyl-6-(1H-pyrazol-5-yl)tetrahydrofuro[3,4-d][1,3]dioxol-4-yl)-4-methyl-7H-pyrrolo[2,3-d]pyrimidine (BB-3) (23 mg) was treated with a mixture of TFA (200 ul) and water (20 ul) then stirred at r.t. After 4 hours the reaction mixture was concentrated to an oil. The crude oil was purified by SFC Chromatography to give BB-4 (7.51 mg, 22% yield) as a solid. LCMS-APCI (+):302 [M+1]$^+$. $^1$H NMR (400 MHz, METHANOL-d4) δ ppm 8.66 (br. s., 1 H) 7.70 (br. s., 1 H) 7.59 (br. s., 1 H) 6.77 (br. s., 1 H) 6.28-6.58 (m, 2 H) 5.76 (br. s., 1 H) 5.18 (br. s., 1 H) 4.42 (br. s., 1 H) 2.73 (br. s., 3 H).

Example 73

(Scheme CC) (2S,3S,4R,5R)-2-((S)-hydroxy(phenyl)methyl)-5-(4-methyl-7H-pyrrolo[2,3-d]pyrimidin-7-yl)tetrahydrofuran-3,4-diol (CC-3)

Example 74

(Scheme CC) (2S,3S,4R,5R)-2-((R)-hydroxy(phenyl)methyl)-5-(4-methyl-7H-pyrrolo[2,3-d]pyrimidin-7-yl)tetrahydrofuran-3,4-diol (CC-4)

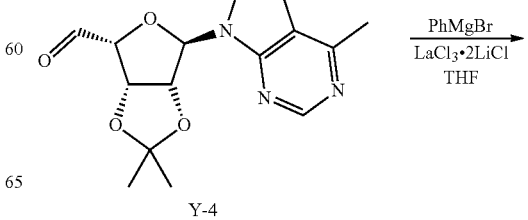

Scheme CC

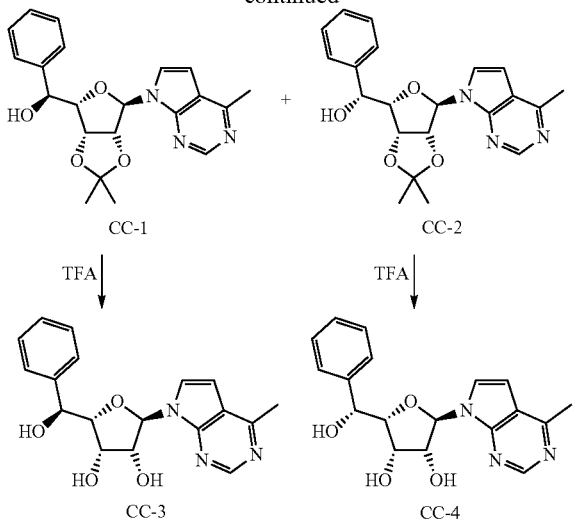

Step 1: Synthesis of (S)-((3aR,4S,6R,6aR)-2,2-dimethyl-6-(4-methyl-7H-pyrrolo[2,3-d]pyrimidin-7-yl)tetrahydrofuro[3,4-d][1,3]dioxol-4-yl)(phenyl)methanol (CC-1) and (R)-((3aR,4S,6R,6aR)-2,2-dimethyl-6-(4-methyl-7H-pyrrolo[2,3-d]pyrimidin-7-yl)tetrahydrofuro[3,4-d][1,3]dioxol-4-yl)(phenyl)methanol (CC-2)

To a solution of 0.6M $LaCl_3 \cdot 2LiCl$ (4.01 ml, 2.41 mmol) in THF cooled in an ice-water bath was added 3M phenyl magnesium bromide (0.73 ml, 2.19 mmol). The mixture was stirred at 0° C. for 1 hour then a solution of (3aS,4R,6R,6aR)-2,2-dimethyl-6-(4-methyl-7H-pyrrolo[2,3-d]pyrimidin-7-yl)tetrahydrofuro[3,4-d][1,3]dioxole-4-carbaldehyde (Y-4) (332 mg, 1.09 mmol) in THF (2.19 ml) was added. After 17 hours the reaction mixture was quenched with saturated $NH_4Cl(aq)$ then diluted with water and EtOAc. The aqueous phase remained an emulsion due to the excess of salts. The EtOAc layer was separated and the aqueous layer was extracted one more time with EtOAc. The pooled EtOAc layers were washed with brine, dried with $MgSO_4$, filtered then concentrated to an oil. The crude oil was purified by $SiO_2$ chromatography (0-100% EtOAc in Heptane) to give a 1:1 mixture of diastereomers (130 mg, 31% yield) as a white foam.

The diastereomers were separated by SFC (Whelk-O1 (S,S) 4.6×100 mm 5 u column, 20% MeOH @120 bar, 4 mL/min) to give CC-1 (56 mg, 13% yield) as a white solid. LCMS-ESI(+): 382 [M+1]$^+$, >99% de, $^1$H NMR (400 MHz, CHLOROFORM-d) δ ppm 7.46-7.39 (m, 2H), 7.37-7.28 (m, 3H), 7.12 (d, J=3.4 Hz, 1H), 6.52 (d, J=3.7 Hz, 1H), 6.05 (s, 1H), 5.65 (d, J=5.9 Hz, 1H), 5.38 (dd, J=3.8, 5.7 Hz, 1H), 5.02 (t, J=6.4 Hz, 1H), 4.59 (dd, J=3.7, 7.1 Hz, 1H), 3.30 (d, J=5.9 Hz, 1H), 2.71 (s, 3H), 1.69 (s, 3H), 1.46 (s, 3H) and CC-2 (41 mg, 10% yield) as a white solid. LCMS-ESI(+): 382 [M+1]$^+$, ~98% de, $^1$H NMR (400 MHz, CHLOROFORM-d) δ ppm 7.40 (d, J=6.8 Hz, 2H), 7.31-7.20 (m, 3H), 7.12 (br. s., 1H), 6.48 (d, J=3.4 Hz, 1H), 6.01 (s, 1H), 5.54 (d, J=5.6 Hz, 1H), 5.07 (d, J=6.8 Hz, 1H), 4.88 (dd, J=3.4, 5.6 Hz, 1H), 4.43 (dd, J=3.3, 7.0 Hz, 1H), 2.75 (d, J=1.2 Hz, 1H), 1.59 (s, 3H), 1.29 (s, 3H)

Step 2: Synthesis of (2S,3S,4R,5R)-2-((S)-hydroxy(phenyl)methyl)-5-(4-methyl-7H-pyrrolo[2,3-d]pyrimidin-7-yl)tetrahydrofuran-3,4-diol (CC-3)

The material CC-1 was treated with TFA in a similar manner to Example 71 (Step 2, Scheme AA). The resulting crude material was purified by $SiO_2$ chromatography (60-100% EtOAc-Heptane for 8 minutes then 0-5% MeOH-EtOAc for 8 minutes) to give CC-3 (17 mg, 34% yield) as a white solid. LCMS-ESI(+): 342 [M+1]$^+$. $^1$H NMR (400 MHz, DMSO-d6) δ ppm 8.62 (s, 1H), 7.73 (d, J=3.7 Hz, 1H), 7.32 (d, J=7.3 Hz, 2H), 7.23 (t, J=7.5 Hz, 2H), 7.19-7.11 (m, 1H), 6.68 (d, J=3.7 Hz, 1H), 6.18 (d, J=7.8 Hz, 1H), 5.43-5.27 (m, 3H), 4.85 (d, J=3.4 Hz, 1H), 4.76 (dd, J=4.4, 8.8 Hz, 1H), 4.44 (dd, J=2.1, 8.9 Hz, 1H), 4.30 (br. s., 1H), 2.60 (s, 3H)

Step 3: Synthesis of (2S,3S,4R,5R)-2-((R)-hydroxy(phenyl)methyl)-5-(4-methyl-7H-pyrrolo[2,3-d]pyrimidin-7-yl)tetrahydrofuran-3,4-diol (CC-4)

The material CC-2 was treated with TFA in a similar manner to Example 71 (Step 2, Scheme AA). The resulting crude material was purified by $SiO_2$ chromatography (60-100% EtOAc-Heptane for 8 minutes then 0-5% MeOH-EtOAc for 8 minutes) to give CC-4 (8 mg, 20% yield) as a white solid. LCMS-ESI(+): 342 [M+1]$^+$. $^1$H NMR (400 MHz, DMSO-d6) δ ppm 8.67 (s, 1H), 7.83 (d, J=3.4 Hz, 1H), 7.47 (d, J=7.3 Hz, 2H), 7.38-7.29 (m, 2H), 7.29-7.20 (m, 1H), 6.77 (d, J=3.7 Hz, 1H), 6.30 (d, J=7.3 Hz, 1H), 5.52 (br. s., 1H), 5.29-5.16 (m, 2H), 4.86 (dd, J=3.5, 7.9 Hz, 1H), 4.79 (br. s., 1H), 4.40 (dd, J=2.2, 8.1 Hz, 1H), 3.65 (br. s., 1H), 2.66 (s, 3H)

Example 75

(Scheme DD) (2S,3S,4R,5R)-2-((S)-(4-fluorophenyl)(hydroxy)methyl)-5-(4-methyl-7H-pyrrolo[2,3-d]pyrimidin-7-yl)tetrahydrofuran-3,4-diol (DD-3)

Example 76

(Scheme DD) (2S,3S,4R,5R)-2-((R)-(4-fluorophenyl)(hydroxy)methyl)-5-(4-methyl-7H-pyrrolo[2,3-d]pyrimidin-7-yl)tetrahydrofuran-3,4-diol (DD-4)

Scheme DD

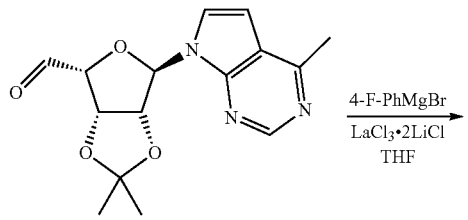

Y-4

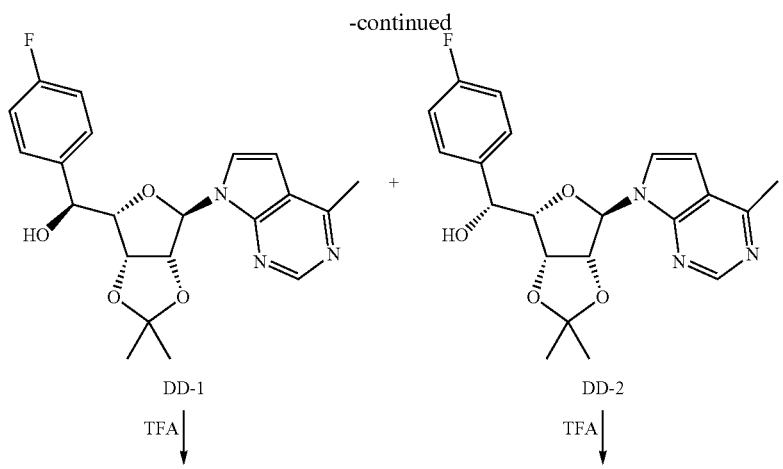

DD-1    DD-2

TFA ↓    TFA ↓

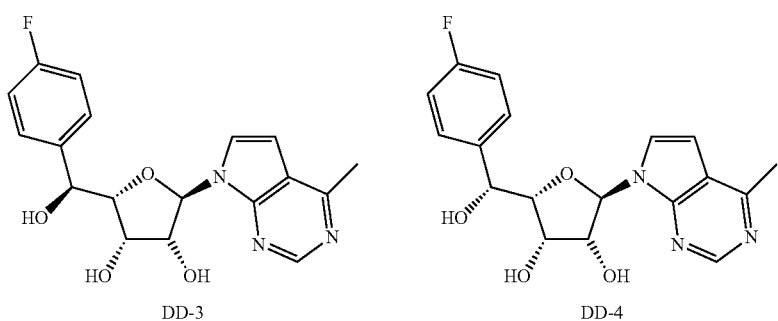

DD-3    DD-4

Step 1: Synthesis of (S)-((3aR,4S,6R,6aR)-2,2-dimethyl-6-(4-methyl-7H-pyrrolo[2,3-d]pyrimidin-7-yl)tetrahydrofuro[3,4-d][1,3]dioxol-4-yl)(4-fluorophenyl)methanol (DD-1) and (R)-((3aR,4S,6R,6aR)-2,2-dimethyl-6-(4-methyl-7H-pyrrolo[2,3-d]pyrimidin-7-yl)tetrahydrofuro[3,4-d][1,3]dioxol-4-yl)(4-fluorophenyl)methanol (DD-2)

The compounds were prepared in a similar method to CC-1 and CC-2 (Scheme CC) using 4-F-phenyl magnesium bromide in place of phenyl magnesium bromide. The diastereomers were separated by SFC (Chiralpak IC-3 4.6×100 mm 3 u column 20% MeOH @120 bar, 4 mL/min) to give DD-1 (63 mg, 18% yield) as a white solid. LCMS-ESI(+): 400 [M+1]$^+$, >99% de, $^1$H NMR (400 MHz, CHLOROFORM-d) δ ppm 8.71 (s, 1H), 7.38 (dd, J=5.5, 8.4 Hz, 2H), 7.11 (d, J=3.4 Hz, 1H), 7.01 (t, J=8.7 Hz, 2H), 6.52 (d, J=3.4 Hz, 1H), 6.04 (s, 1H), 5.64 (d, J=5.9 Hz, 1H), 5.40 (dd, J=3.9, 5.6 Hz, 1H), 5.05-4.82 (m, 1H), 4.53 (dd, J=3.8, 7.5 Hz, 1H), 3.25 (d, J=5.6 Hz, 1H), 2.71 (s, 3H), 1.69 (s, 3H), 1.46 (s, 3H) and DD-2 (55 mg, 15% yield) as a white solid. LCMS-ESI(+): 400 [M+1]$^+$, >99% de, $^1$H NMR (400 MHz, CHLOROFORM-d) δ ppm 8.69 (br. s., 1H), 7.47 (dd, J=5.5, 8.4 Hz, 2H), 7.19 (d, J=3.4 Hz, 1H), 7.03 (t, J=8.7 Hz, 2H), 6.57 (d, J=3.4 Hz, 1H), 6.08 (s, 1H), 5.64 (d, J=5.6 Hz, 1H), 5.13 (d, J=7.1 Hz, 1H), 4.97 (dd, J=3.7, 5.6 Hz, 1H), 4.47 (dd, J=3.4, 7.1 Hz, 1H), 2.87 (s, 1H), 2.73 (s, 3H), 1.67 (s, 4H), 1.38 (s, 3H)

Step 2: Synthesis of (2S,3S,4R,5R)-2-((S)-(4-fluorophenyl)(hydroxy)methyl)-5-(4-methyl-7H-pyrrolo[2,3-d]pyrimidin-7-yl)tetrahydrofuran-3,4-diol (DD-3)

The material DD-1 was treated with TFA in a similar manner to Example 71 (Step 2, Scheme AA). The resulting crude material was purified by SiO$_2$ chromatography (60-100% EtOAc-Heptane for 9 minutes then 0-5% MeOH-EtOAc for 5 minutes) to give DD-3 (37 mg, 66% yield) as a white solid. LCMS-ESI(+): 360 [M+1]$^+$. $^1$H NMR (400 MHz, METHANOL-d4) δ ppm 8.61 (br. s., 1H), 7.53 (br. s., 1H), 7.43 (br. s., 2H), 6.99 (t, J=7.9 Hz, 2H), 6.68 (br. s., 1H), 6.27 (d, J=6.8 Hz, 1H), 4.96 (br. s., 2H), 4.57 (d, J=8.3 Hz, 1H), 4.47 (br. s., 1H), 2.68 (br. s., 3H).

Step 3: Synthesis of (2S,3S,4R,5R)-2-((R)-(4-fluorophenyl)(hydroxy)methyl)-5-(4-methyl-7H-pyrrolo[2,3-d]pyrimidin-7-yl)tetrahydrofuran-3,4-diol (DD-4)

The material DD-2 was treated with TFA in a similar manner to Example 71 (Step 2, Scheme AA). The resulting crude material was purified by SiO$_2$ chromatography (60-100% EtOAc-Heptane for 9 minutes then 0-3% MeOH-EtOAc for 4 minutes) to give DD-4 (26 mg, 50% yield) as a white solid. LCMS-ESI(+): 360 [M+1]$^+$. $^1$H NMR (400 MHz, DMSO-d6) δ ppm 8.67 (s, 1H), 7.83 (d, J=3.7 Hz, 1H), 7.49 (dd, J=6.0, 8.2 Hz, 2H), 7.15 (t, J=8.8 Hz, 2H), 6.77 (d, J=3.7 Hz, 1H), 6.30 (d, J=7.3 Hz, 1H), 5.46 (br. s., 1H), 5.29 (d, J=4.2 Hz, 1H), 5.19 (d, J=2.7 Hz, 1H), 4.92-4.69 (m, 2H), 4.37 (dd, J=2.1, 8.2 Hz, 1H), 3.63 (br. s., 1H), 2.66 (s, 3H), 1.99 (s, 1H)

Example 77

(Scheme FF) (2S,3S,4R,5R)-2-(1-methyl-1H-pyrazol-3-yl)-5-(4-methyl-7H-pyrrolo[2,3-d]pyrimidin-7-yl)tetrahydrofuran-3,4-diol (EE-2)

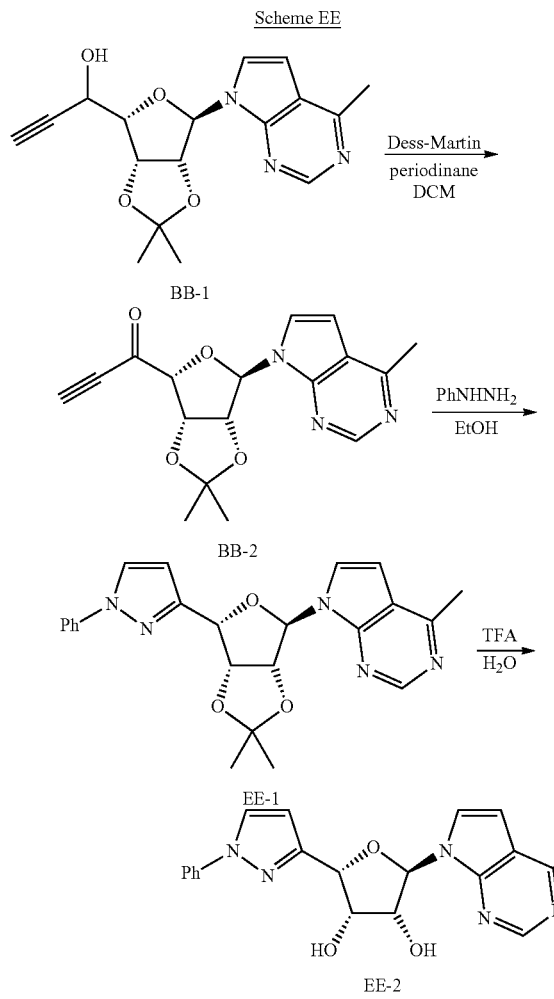

Scheme EE

Step 1: Synthesis of 7-((3aR,4R,6S,6aR)-2,2-dimethyl-6-(1-methyl-1H-pyrazol-3-yl)tetrahydrofuro[3,4-d][1,3]dioxol-4-yl)-4-methyl-7H-pyrrolo[2,3-d]pyrimidine (EE-1)

A solution of 1-((3aR,4S,6R,6aR)-2,2-dimethyl-6-(4-methyl-7H-pyrrolo[2,3-d]pyrimidin-7-yl)tetrahydrofuro[3,4-d][1,3]dioxol-4-yl)prop-2-yn-1-ol (BB-1) (99 mg, 0.30 mmol) and Dess-Martin periodinane (153 mg, 0.361 mmol) in DCM (3.0 ml) was stirred at r.t. for 3 hours then quenched with 10% sodiumthiosulfate(aq). The aqueous layer was extracted with DCM then the combined DCM layer was washed with brine, dried with MgSO₄, filtered then concentrated to an oil. The crude oil was purified by SiO₂ chromatography (40-100% EtOAc in Heptane), to give BB-2.

A mixture of BB-2 and phenyl hydrazine (33 ul, 0.331 mmol) in EtOH (3 ml) was stirred at r.t. for 1 hour then concentrated to an oil. The crude oil was purified by SiO₂ chromatography (0-50% EtOAc in Heptane), to give EE-1 (55 mg, 44% yield) as a yellow foam. LCMS-ESI(+): 418 [M+1]$^+$. $^1$H NMR (400 MHz, CHLOROFORM-d) δ ppm 8.80 (s, 1H), 7.90 (d, J=2.4 Hz, 1H), 7.63 (d, J=7.8 Hz, 2H), 7.42 (t, J=7.9 Hz, 2H), 7.28 (br. s., 1H), 7.26-7.23 (m, 1H), 6.71 (d, J=2.4 Hz, 1H), 6.59 (d, J=3.4 Hz, 1H), 6.16 (s, 1H), 5.87 (d, J=5.6 Hz, 1H), 5.66 (d, J=3.7 Hz, 1H), 5.42 (dd, J=3.8, 5.5 Hz, 1H), 2.75 (s, 3H), 1.68 (s, 3H), 1.45 (s, 3H)

Step 2: Synthesis of (2S,3S,4R,5R)-2-(1-methyl-1H-pyrazol-3-yl)-5-(4-methyl-7H-pyrrolo[2,3-d]pyrimidin-7-yl)tetrahydrofuran-3,4-diol (EE-2)

The material EE-1 was treated with TFA in a similar manner to Example 71 (Step 2, Scheme AA). The resulting crude material was purified by SiO₂ chromatography (60-100% EtOAc-Heptane for 8 minutes then 0-3% MeOH-EtOAc for 6 minutes) to give EE-2 (34 mg, 73% yield) as a white solid. LCMS-ESI(+): 378 [M+1]$^+$. $^1$H NMR (400 MHz, DMSO-d6) δ ppm 8.69 (s, 1H), 8.42 (d, J=2.4 Hz, 1H), 7.91 (d, J=3.7 Hz, 1H), 7.80 (d, J=7.8 Hz, 2H), 7.48 (t, J=7.9 Hz, 2H), 7.34-7.23 (m, 1H), 6.79 (d, J=3.7 Hz, 1H), 6.62 (d, J=2.4 Hz, 1H), 6.37 (d, J=7.3 Hz, 1H), 5.68 (d, J=2.4 Hz, 1H), 5.51 (d, J=6.6 Hz, 1H), 5.30 (d, J=4.4 Hz, 1H), 5.06 (d, J=4.2 Hz, 1H), 4.27 (d, J=2.7 Hz, 1H), 2.67 (s, 3H)

Example 78

(Scheme GG) (2S,3S,4R,5R)-2-(3-(ethoxymethyl)-1H-pyrazol-5-yl)-5-(4-methyl-7H-pyrrolo[2,3-d]pyrimidin-7-yl)tetrahydrofuran-3,4-diol (FF-6)

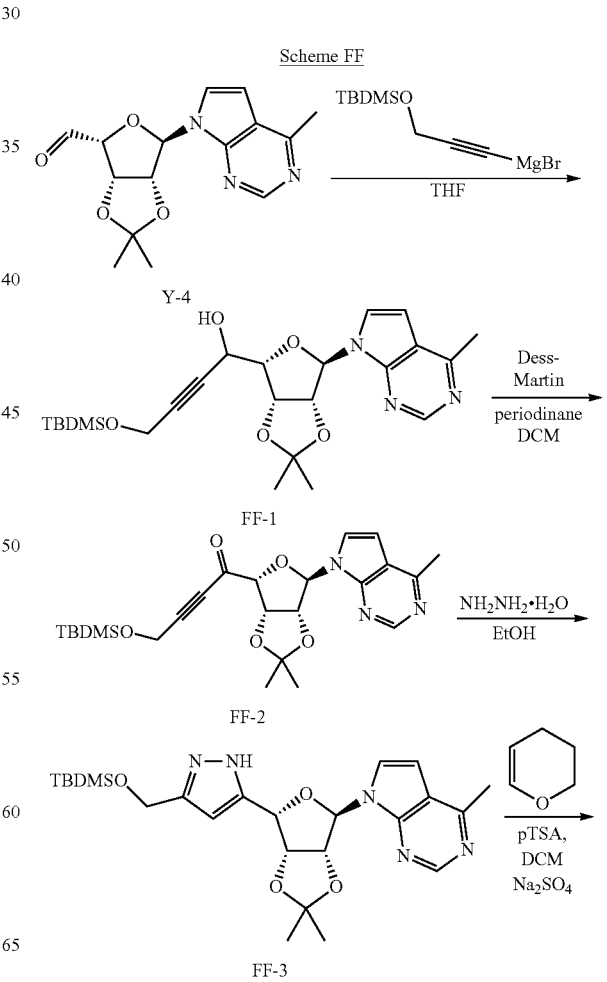

Scheme FF

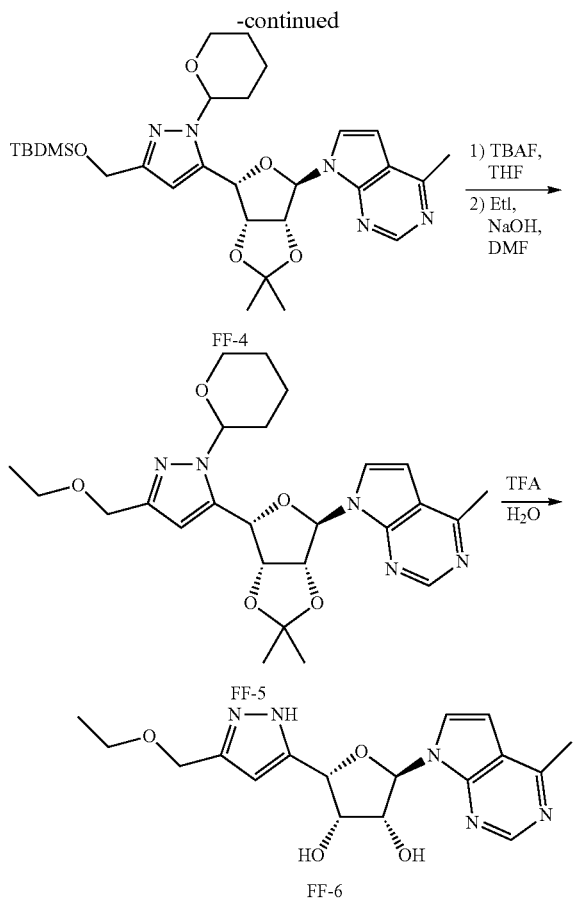

Step 1: Synthesis of 4-((tert-butyldimethylsilyl)oxy)-1-((3aR,4S,6R,6aR)-2,2-dimethyl-6-(4-methyl-7H-pyrrolo[2,3-d]pyrimidin-7-yl)tetrahydrofuro[3,4-d][1,3]dioxol-4-yl)but-2-yn-1-ol (FF-1)

The compound FF-1 was prepared in a similar manner to BB-1 (Scheme BB) using (3-((tert-butyldimethylsilyl)oxy)prop-1-yn-1-yl)magnesium bromide in place of ethynyl magnesium bromide. (289 mg, 62% yield) as an amber glass. LCMS-ESI(+): 474 [M+1]$^+$. $^1$H NMR (400 MHz, CHLOROFORM-d) δ ppm 8.74 (s, 1H), 7.20 (d, J=3.7 Hz, 1H), 6.57 (d, J=3.7 Hz, 1H), 6.11-5.96 (m, 1H), 5.76-5.62 (m, 1H), 5.51 (dd, J=3.8, 5.7 Hz, 1H), 4.87-4.68 (m, 1H), 4.61-4.47 (m, 1H), 4.43-4.30 (m, 2H), 2.74 (s, 3H), 1.68-1.58 (m, 3H), 1.50-1.37 (m, 3H), 0.97-0.76 (m, 9H), 0.19-0.00 (m, 6H)

Step 2: Synthesis of 4-((tert-butyldimethylsilyl)oxy)-1-((3aS,4R,6R,6aR)-2,2-dimethyl-6-(4-methyl-7H-pyrrolo[2,3-d]pyrimidin-7-yl)tetrahydrofuro[3,4-d][1,3]dioxol-4-yl)but-2-yn-1-one (FF-2)

The compound FF-2 was prepared in a similar manner to BB-2 (Scheme BB) using Dess-Martin Periodinane to give material (195 mg, 68% yield) as an amber glass. LCMS-ESI(+): 472 [M+1]$^+$. $^1$H NMR (400 MHz, CHLOROFORM-d) δ ppm 8.74 (s, 1H), 7.21 (d, J=3.7 Hz, 1H), 6.57 (d, J=3.7 Hz, 1H), 6.11 (s, 1H), 5.79-5.71 (m, 1H), 5.63 (d, J=5.6 Hz, 1H), 5.19 (d, J=4.2 Hz, 1H), 4.54 (s, 2H), 2.74 (s, 3H), 1.55 (s, 3H), 1.40 (s, 3H), 0.95 (s, 9H), 0.18 (s, 6H)

Step 3: Synthesis of 7-((3aR,4R,6S,6aR)-6-(3-(((tert-butyldimethylsilyl)oxy)methyl)-1H-pyrazol-5-yl)-2,2-dimethyltetrahydrofuro[3,4-d][1,3]dioxol-4-yl)-4-methyl-7H-pyrrolo[2,3-d]pyrimidine (FF-3)

To a solution of the 4-((tert-butyldimethylsilyl)oxy)-1-((3aS,4R,6R,6aR)-2,2-dimethyl-6-(4-methyl-7H-pyrrolo[2,3-d]pyrimidin-7-yl)tetrahydrofuro[3,4-d][1,3]dioxol-4-yl)but-2-yn-1-one (FF-2) (195 mg, 0.413 mmol) in EtOH (1.38 ml) was added hydrazine monohydrate (22 ul, 0.455 mmol). The reaction mixture was stirred for 4 hours then concentrated to an oil. The crude oil was purified by SiO$_2$ chromatography (0-50% EtOAc in Heptane) to give FF-3 (124 mg, 62% yield) as a light amber oil. LCMS-ESI(+): 486 [M+1]$^+$. $^1$H NMR (400 MHz, CHLOROFORM-d) δ ppm 8.77 (s, 1H), 7.23 (d, J=3.7 Hz, 1H), 6.58 (d, J=3.7 Hz, 1H), 6.31 (s, 1H), 6.08 (s, 1H), 5.83 (d, J=5.6 Hz, 1H), 5.56 (d, J=3.2 Hz, 1H), 5.37 (dd, J=3.5, 5.5 Hz, 1H), 4.88-4.67 (m, 2H), 2.74 (s, 3H), 1.64 (s, 3H), 1.43 (s, 3H), 0.91 (s, 9H), 0.09 (d, J=2.2 Hz, 6H)

Step 4: Synthesis of 7-((3aR,4R,6S,6aR)-6-(3-(((tert-butyldimethylsilyl)oxy)methyl)-1-(tetrahydro-2H-pyran-2-yl)-1H-pyrazol-5-yl)-2,2-dimethyltetrahydrofuro[3,4-d][1,3]dioxol-4-yl)-4-methyl-7H-pyrrolo[2,3-d]pyrimidine (FF-4)

A mixture of the 7-((3aR,4R,6S,6aR)-6-(3-(((tert-butyldimethylsilyl)oxy)methyl)-1H-pyrazol-5-yl)-2,2-dimethyltetrahydrofuro[3,4-d][1,3]dioxol-4-yl)-4-methyl-7H-pyrrolo[2,3-d]pyrimidine (FF-3) (124 mg, 0.255 mmol), dihydropyran (116 ul, 1.28 mmol), Na$_2$SO$_4$ (300 mg, 2.11 mmol) and PTSA (4 mg, 0.0255 mmol) in DCM (0.85 ml) was stirred at r.t. for 31 hours then quenched with saturated NaHCO$_3$(aq). The DCM layer was washed with brine, dried with MgSO$_4$, filtered then concentrated to an oil. The crude oil was purified by SiO$_2$ chromatography (0-70% EtOAc/Heptane to give FF-4 (105 mg, 72% yield) as white foam. LCMS-ESI(+):570 [M+1]$^+$. $^1$H NMR (400 MHz, CHLOROFORM-d) δ ppm 8.76 (d, J=6.6 Hz, 1H), 7.23 (d, J=3.7 Hz, 1H), 6.61-6.51 (m, 1H), 6.42 (d, J=3.9 Hz, 1H), 6.11 (s, 1H), 5.90-5.75 (m, 1H), 5.57-5.36 (m, 2H), 5.33-5.22 (m, 1H), 4.86-4.62 (m, 2H), 4.16-3.92 (m, 1H), 2.82-2.60 (m, 3H), 1.42 (d, J=6.4 Hz, 3H), 0.91 (d, J=6.4 Hz, 9H), 0.15-0.00 (m, 6H).

Step 5: Synthesis of 7-((3aR,4R,6S,6aR)-6-(3-(ethoxymethyl)-1-(tetrahydro-2H-pyran-2-yl)-1H-pyrazol-5-yl)-2,2-dimethyltetrahydrofuro[3,4-d][1,3]dioxol-4-yl)-4-methyl-7H-pyrrolo[2,3-d]pyrimidine (FF-5)

To a solution of 7-((3aR,4R,6S,6aR)-6-(3-(((tert-butyldimethylsilyl)oxy)methyl)-1-(tetrahydro-2H-pyran-2-yl)-1H-pyrazol-5-yl)-2,2-dimethyltetrahydrofuro[3,4-d][1,3]dioxol-4-yl)-4-methyl-7H-pyrrolo[2,3-d]pyrimidine (FF-4) (105 mg, 0.184 mmol) in THF (614 ul) at r.t. was added 1M TBAF in THF (276 ul, 0.276 mmol). After 10 minutes the reaction mixture was concentrated to an oil then re-dissolved in EtOAc. The EtOAc was washed with water, brine, dried with Na$_2$SO$_4$, filtered then concentrated to an oil. The crude oil was dissolved in DMF (614 ul) then cooled in an ice-water bath. Ethyl iodide (57 mg, 0.369 mmol) was added followed by NaH (9 mg, 0.221 mmol). After 4 hours the reaction mixture was quenched with saturated NH$_4$Cl(aq). The mixture was extracted with EtOAc, then washed with brine, dried with Na$_2$SO$_4$, filtered and concentrated to an oil.

The crude oil was purified by SiO₂ chromatography (20-80% EtOAc-Heptane) to give FF-5 (50 mg, 56% yield) as a colorless oil. LCMS-ESI(+): 484 [M+1]⁺. ¹H NMR (400 MHz, CHLOROFORM-d) δ ppm 8.76 (d, J=5.9 Hz, 1H), 7.22 (d, J=3.7 Hz, 1H), 6.57-6.52 (m, 1H), 6.48 (d, J=10.0 Hz, 1H), 6.09 (s, 1H), 5.91-5.77 (m, 1H), 5.56-5.45 (m, 1H), 5.42 (ddd, J=2.4, 4.9, 10.0 Hz, 1H), 5.29 (dd, J=3.7, 5.4 Hz, 1H), 4.72-4.42 (m, 2H), 4.11-3.94 (m, 1H), 3.71-3.56 (m, 1H), 3.48 (qd, J=7.0, 10.6 Hz, 2H), 2.73 (s, 3H), 2.45-2.21 (m, 1H), 1.94-1.78 (m, 1H), 1.64 (d, J=2.4 Hz, 5H), 1.41 (d, J=5.4 Hz, 3H), 1.19 (q, J=7.1 Hz, 3H).

Step 6: Synthesis of (2S,3S,4R,5R)-2-(3-(ethoxymethyl)-1H-pyrazol-5-yl)-5-(4-methyl-7H-pyrrolo[2,3-d]pyrimidin-7-yl)tetrahydrofuran-3,4-diol (FF-6)

The compound FF-5 was treated with TFA in similar manner to Example 71 (Step 2, Scheme AA). The resulting crude material was purified by SFC chromatography to give FF-6 (5 mg, 12% yield) as a white solid. LCMS-ESI(+): 360 [M+1]⁺. ¹H NMR (400 MHz, DMSO-d6) δ ppm 8.67 (s, 1H), 7.87 (d, J=3.2 Hz, 1H), 6.77 (d, J=3.4 Hz, 1H), 6.31 (d, J=7.3 Hz, 1H), 6.27 (s, 1H), 5.56 (br. s., 1H), 5.01 (br. s., 1H), 4.39 (s, 2H), 4.20 (br. s., 1H), 3.44 (q, J=6.8 Hz, 3H), 2.66 (s, 3H), 1.11 (t, J=7.0 Hz, 3H).

Example 79

(Scheme HH) (2S,3S,4R,5R)-2-(1,2-dihydroxyethyl)-5-(4-methyl-7H-pyrrolo[2,3-d]pyrimidin-7-yl)tetrahydrofuran-3,4-diol (GG-1)

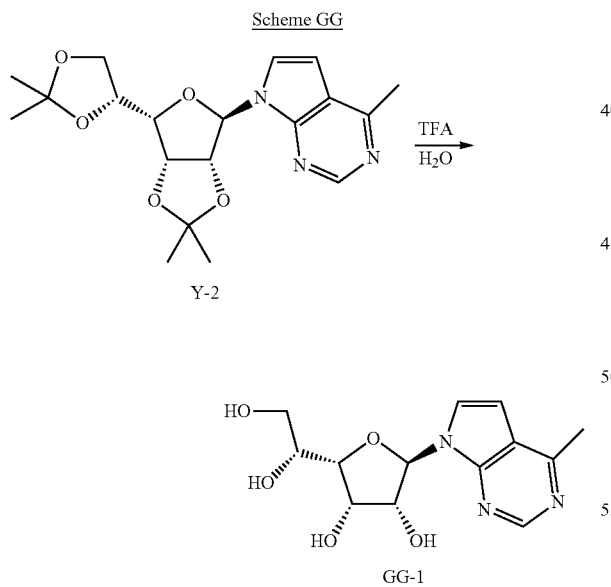

Synthesis of (2S,3S,4R,5R)-2-(1,2-dihydroxyethyl)-5-(4-methyl-7H-pyrrolo[2,3-d]pyrimidin-7-yl)tetrahydrofuran-3,4-diol (GG-1)

A mixture of 7-((3aR,4R,6S,6aR)-6-((R)-2,2-dimethyl-1,3-dioxolan-4-yl)-2,2-dimethyltetrahydrofuro[3,4-d][1,3]dioxol-4-yl)-4-methyl-7H-pyrrolo[2,3-d]pyrimidine (Y-2) (59 mg, 0.16 mmol), TFA (250 ul,) and water (50 ul) was stirred at r.t. for 23 hours then diluted with toluene (1 ml) and concentrated to an oil. The crude oil was purified by SFC (ZymorSpher Diol Monol 150×21.2 mm column with 10-25% MeOH @6%/min, 100 bar, 58 mL/min) to give (2S,3S,4R,5R)-2-(1,2-dihydroxyethyl)-5-(4-methyl-7H-pyrrolo[2,3-d]pyrimidin-7-yl)tetrahydrofuran-3,4-diol (GG-1) (18 mg, 39% yield) as a solid. LCMS-APCI(+): 296 [M+1]⁺. ¹H NMR (400 MHz, METHANOL-d4) δ ppm 8.69 (s, 1 H) 7.71 (d, J=3.91 Hz, 1 H) 6.82 (d, J=3.67 Hz, 1 H) 6.33 (d, J=6.85 Hz, 1 H) 4.90 (dd, J=6.85, 4.40 Hz, 1 H) 4.52 (dd, J=6.36, 3.42 Hz, 1 H) 4.40 (t, J=3.79 Hz, 1 H) 4.03 (d, J=5.38 Hz, 1 H) 3.61-3.77 (m, 2 H) 2.76 (s, 3 H)

Example 80

(Scheme HH) (2S,3R,4S,5R)-2-(4-aminofuro[3,2-d]pyrimidin-7-yl)-5-((R)-(4-fluorophenyl)(hydroxy)methyl)tetrahydrofuran-3,4-diol (HH-10)

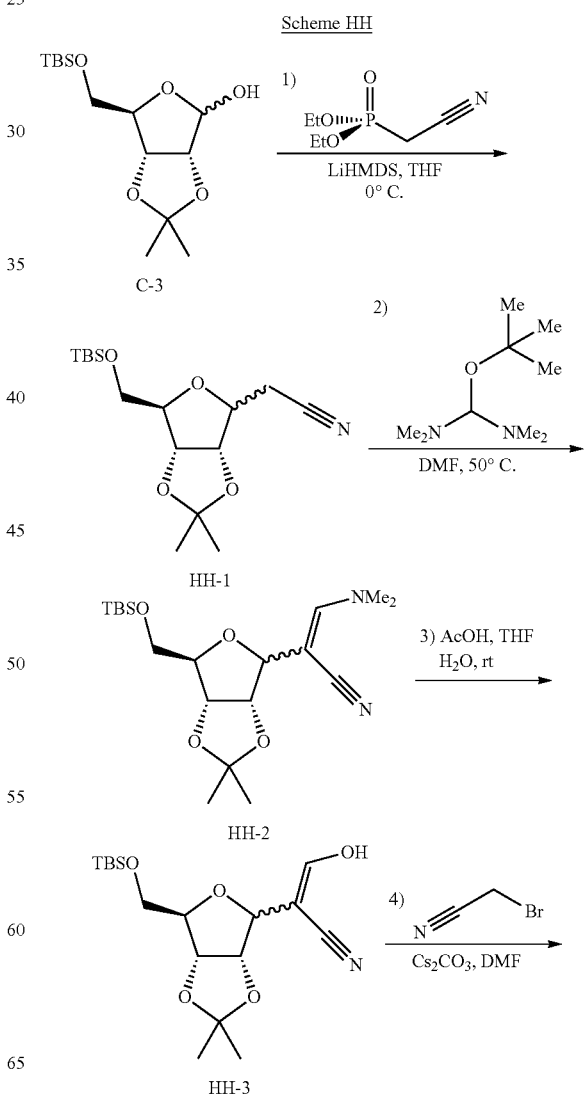

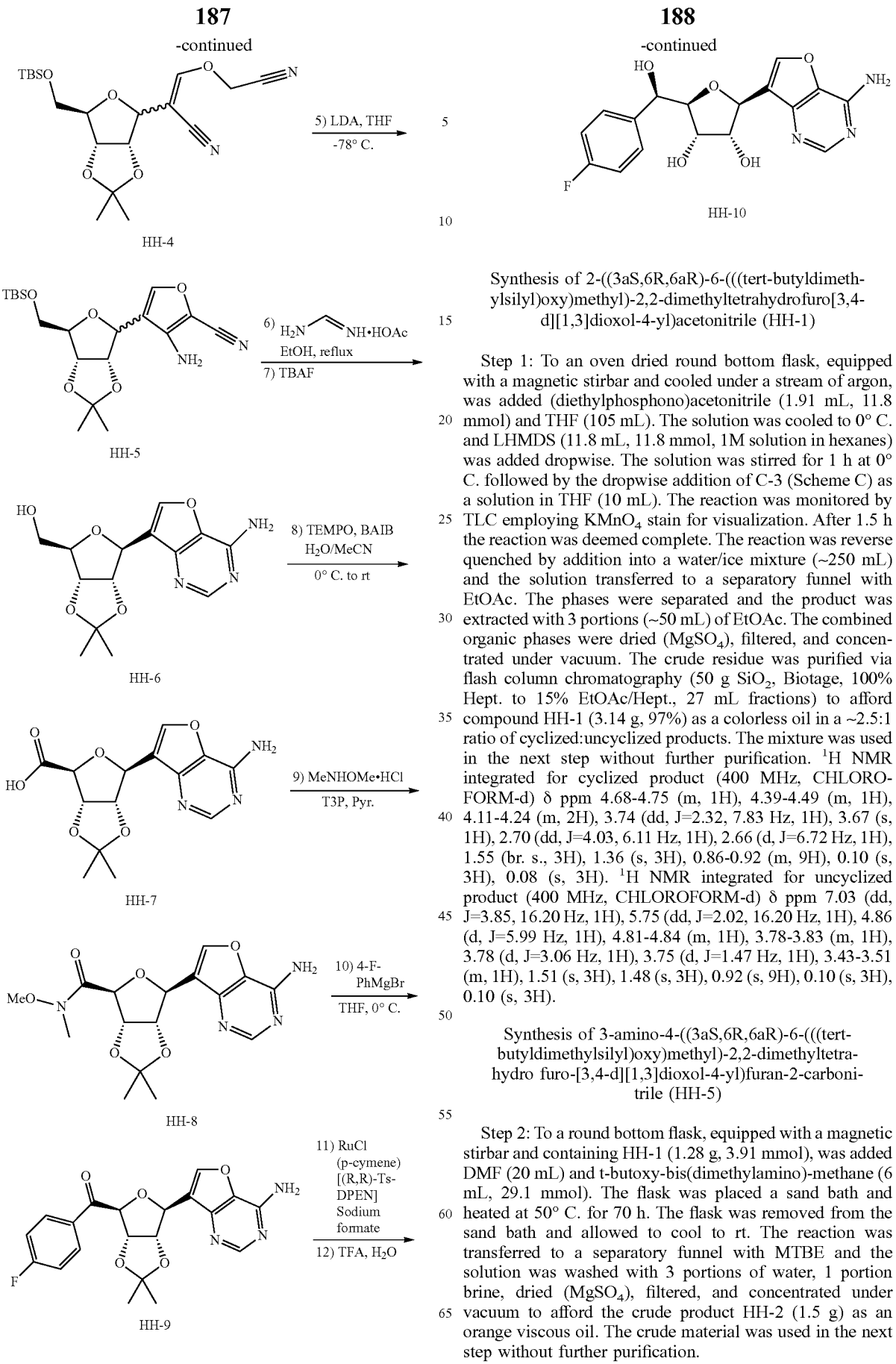

Synthesis of 2-((3aS,6R,6aR)-6-(((tert-butyldimethylsilyl)oxy)methyl)-2,2-dimethyltetrahydrofuro[3,4-d][1,3]dioxol-4-yl)acetonitrile (HH-1)

Step 1: To an oven dried round bottom flask, equipped with a magnetic stirbar and cooled under a stream of argon, was added (diethylphosphono)acetonitrile (1.91 mL, 11.8 mmol) and THF (105 mL). The solution was cooled to 0° C. and LHMDS (11.8 mL, 11.8 mmol, 1M solution in hexanes) was added dropwise. The solution was stirred for 1 h at 0° C. followed by the dropwise addition of C-3 (Scheme C) as a solution in THF (10 mL). The reaction was monitored by TLC employing $KMnO_4$ stain for visualization. After 1.5 h the reaction was deemed complete. The reaction was reverse quenched by addition into a water/ice mixture (~250 mL) and the solution transferred to a separatory funnel with EtOAc. The phases were separated and the product was extracted with 3 portions (~50 mL) of EtOAc. The combined organic phases were dried ($MgSO_4$), filtered, and concentrated under vacuum. The crude residue was purified via flash column chromatography (50 g $SiO_2$, Biotage, 100% Hept. to 15% EtOAc/Hept., 27 mL fractions) to afford compound HH-1 (3.14 g, 97%) as a colorless oil in a ~2.5:1 ratio of cyclized:uncyclized products. The mixture was used in the next step without further purification. $^1H$ NMR integrated for cyclized product (400 MHz, CHLOROFORM-d) δ ppm 4.68-4.75 (m, 1H), 4.39-4.49 (m, 1H), 4.11-4.24 (m, 2H), 3.74 (dd, J=2.32, 7.83 Hz, 1H), 3.67 (s, 1H), 2.70 (dd, J=4.03, 6.11 Hz, 1H), 2.66 (d, J=6.72 Hz, 1H), 1.55 (br. s., 3H), 1.36 (s, 3H), 0.86-0.92 (m, 9H), 0.10 (s, 3H), 0.08 (s, 3H). $^1H$ NMR integrated for uncyclized product (400 MHz, CHLOROFORM-d) δ ppm 7.03 (dd, J=3.85, 16.20 Hz, 1H), 5.75 (dd, J=2.02, 16.20 Hz, 1H), 4.86 (d, J=5.99 Hz, 1H), 4.81-4.84 (m, 1H), 3.78-3.83 (m, 1H), 3.78 (d, J=3.06 Hz, 1H), 3.75 (d, J=1.47 Hz, 1H), 3.43-3.51 (m, 1H), 1.51 (s, 3H), 1.48 (s, 3H), 0.92 (s, 9H), 0.10 (s, 3H), 0.10 (s, 3H).

Synthesis of 3-amino-4-((3aS,6R,6aR)-6-(((tert-butyldimethylsilyl)oxy)methyl)-2,2-dimethyltetrahydro furo-[3,4-d][1,3]dioxol-4-yl)furan-2-carbonitrile (HH-5)

Step 2: To a round bottom flask, equipped with a magnetic stirbar and containing HH-1 (1.28 g, 3.91 mmol), was added DMF (20 mL) and t-butoxy-bis(dimethylamino)-methane (6 mL, 29.1 mmol). The flask was placed a sand bath and heated at 50° C. for 70 h. The flask was removed from the sand bath and allowed to cool to rt. The reaction was transferred to a separatory funnel with MTBE and the solution was washed with 3 portions of water, 1 portion brine, dried ($MgSO_4$), filtered, and concentrated under vacuum to afford the crude product HH-2 (1.5 g) as an orange viscous oil. The crude material was used in the next step without further purification.

Step 3: To a round bottom flask, equipped with a magnetic stirbar and containing crude HH-2 (1.50 g), was added water (30 mL) and acetic acid (0.9 mL). The reaction was stirred at rt for 4 h and an additional aliquot of acetic acid (0.9 mL) was added. The reaction was stirred for an additional 24 h and another aliquot of acetic acid (1.8 mL) was added. After stirring for an additional 22 h the reaction was transferred to a separatory funnel with EtOAc. The solution was washed with one portion water, 2 portions half sat. $NaHCO_3$ aq., 1 portion brine, dried ($MgSO_4$), filtered, and concentrated under vacuum to afford the crude product HH-3 (1.21 g) as a yellow oil. The crude material was used in the next step without further purification.

Step 4: To a round bottom flask, equipped with a magnetic stirbar and containing crude HH-3 (1.21 g), was added DMF (40 mL), cesium carbonate (1.33 g, 4.08 mmol), and bromoacetonitrile (0.28 mL, 4.08 mmol). The reaction was stirred at rt and monitored by TLC employing $KMnO_4$ stain for visualization. After 2 h the reaction was deemed complete. The reaction was quenched with water and transferred to a separatory funnel with EtOAc. The phases were separated and the organic phase washed with 2 portions water and 1 portion brine. The aqueous phase was back extracted with EtOAc and the combined organic phases were dried ($MgSO_4$), filtered, and concentrated under vacuum. The crude residue was purified via flash column chromatography (50 g $SiO_2$, Biotage, 100% Hept. to 40% EtOAc/Hept., 21 mL fractions) to afford the desired product HH-4 (0.71 g) as a pale yellow oil. The desired product was obtained as a mixture of isomers and was used in the next step without further purification.

Step 5: To a round bottom flask, equipped with a magnetic stirbar and containing HH-4 (0.71 g, 1.80 mmol), was added THF (45 mL). The solution was cooled to −78° C. followed by the dropwise addition of LDA (4.5 mL, 9.00 mmol, 2M solution in THF/n-heptanelethylbenzene). The solution was stirred at −78° C. for 3 h. The reaction was quenched at to −78° C. with half saturated $NH_4Cl$ aq. (100 mL) and transferred to a separatory funnel with EtOAc. The phases were separated and the aqueous phase was extracted with 3 portions EtOAc. The combined organic phases were dried ($MgSO_4$), filtered, and concentrated under vacuum. The crude residue was purified via flash column chromatography (10 g $SiO_2$, Biotage, 100% Hept. to 30% EtOAc/Hept., 9 mL fractions) to afford the compound HH-5 (322 mg, 21% over 4 steps) as an orange viscous oil. The product was isolated as a ~3:1 mixture of anomers favoring the beta isomer. LCMS [M+H]395; $^1$H NMR (400 MHz, CHLOROFORM-d) δ ppm 0.09 (s, 3 H) 0.12 (s, 3 H) 0.91 (s, 9 H) 1.37 (s, 3 H) 1.51 (s, 3 H, minor diastereomer) 1.59 (s, 3 H) 3.83 (dd, J=11.37, 2.45 Hz, 2 H) 3.91 (dd, J=11.37, 2.45 Hz, 1 H) 4.15 (q, J=2.57, Hz, 1 H) 4.20-4.23 (m, 1 H, minor diastereomer) 4.62 (t, J=6.24 Hz, 1 H) 4.75 (d, J=5.75 Hz, 1 H) 4.81 (dd, J=6.72, 3.42 Hz, 2 H) 4.83 (d, J=4.03 Hz, 1 H, minor diastereomer) 4.92 (d, J=5.99 Hz, 1 H, minor diastereomer) 5.14 (d, J=4.03 Hz, 1 H, minor diastereomer) 7.22 (s, 1 H) 7.25 (s, 1 H, minor diastereomer).

Synthesis of ((3aR,4R,6S,6aS)-6-(4-aminofuro[3,2-d]pyrimidin-7-yl)-2,2-dimethyltetrahydrofuro[3,4-d][1,3]dioxol-4-yl)methanol (HH-6)

Step 6: To a microwave vial, equipped with a magnetic stirbar and containing HH-5 (322 mg, 0.816 mmol), was added formamidine acetic acid salt (2.55 g, 24.5 mmol) and ethanol (10 mL). The vial was sealed with a teflon cap, placed in a heating block and heated at 90° C. for 3 days. The flask was removed from the heating block and allowed to cool to rt. The reaction was quenched with water and transferred to a separatory funnel with EtOAc. The phases were separated and the aqueous phase was extracted with three portions of EtOAc. The combined organic phases were washed with 1 portion brine. The combined organic phases were dried ($MgSO_4$), filtered, and concentrated under vacuum to afford the desired product (250 mg) as a brown oil containing some desilylated by-product.

Step 7: The crude mixture was dissolved in THF (4.0 mL) followed by the dropwise addition of tetrabutylammonium fluoride (1.22 mL, 1.22 mmol, 1M solution in THF). The reaction was stirred at rt for 21 h. The solution was concentrated under vacuum and the residue purified via flash column chromatography (25 g $SiO_2$, Biotage, 100% Hept. to 100% EtOAc to 10% MeOH/EtOAc, 15 mL fractions) to afford the major anomer (HH-6) (97 mg, 39% over 2 steps) as an orange gum. The minor anomer (40.9 mg, 16% over 2 steps) was also isolated as an orange gum. LCMS [M+H] 308; $^1$H NMR (beta anomer) (400 MHz, CHLOROFORM-d) δ ppm 8.43 (s, 1H), 7.81 (s, 1H), 5.89 (br. s., 2H), 5.05 (dd, J=0.92, 5.81 Hz, 1H), 5.00 (d, J=6.24 Hz, 1H), 4.89 (t, J=5.99 Hz, 1H), 4.45-4.49 (m, 1H), 3.97 (dd, J=1.59, 12.59 Hz, 1H), 3.77 (dd, J=1.53, 12.53 Hz, 1H), 2.10 (s, 1H), 1.64 (s, 3H), 1.37 (s, 3H). $^1$H NMR (alpha anomer) (400 MHz, CHLOROFORM-d) δ ppm 8.40 (br. s., 1H), 8.01 (s, 1H), 5.86 (br. s., 2H), 5.39 (d, J=3.06 Hz, 1H), 5.01 (dd, J=3.79, 5.50 Hz, 1H), 4.87 (d, J=5.87 Hz, 1H), 4.27 (t, J=4.40 Hz, 1H), 3.72-3.87 (m, 2H), 2.09 (s, 1H), 1.49 (s, 3H), 1.35 (s, 3H).

Synthesis of (3aS,4S,6S,6aS)-6-(4-aminofuro[3,2-d]pyrimidin-7-yl)-2,2-dimethyltetrahydrofuro[3,4-d][1,3]dioxole-4-carboxylic acid (HH-7)

Step 8: To a conical bottom flask, equipped with a stirbar and containing HH-6 (97.0 mg, 0.316 mmol), was added acetonitrile (2.8 mL) and water (0.7 mL). The solution was cooled to 0° C. and diacetoxyiodosobenzene (224 mg, 0.694 mmol) was added followed by the addition of TEMPO (9.86 mg, 0.063 mmol). The solution was stirred at 0° C. for 30 minutes and then the ice bath was removed. The solution was allowed to warm to rt gradually. The reaction was stirred at rt for 20 h. The solution was concentrated under vacuum and the crude residue was purified via flash column chromatography (10 g $SiO_2$, Biotage, 100% Hept. to 10% MeOH/EtOAc, 9 mL fractions) to afford the compound HH-7 (75.9 mg, 75%) as a pale yellow solid. LCMS [M+H]322; $^1$H NMR (400 MHz, METHANOL-d4) δ ppm 8.41 (s, 1H), 8.23 (s, 1H), 5.27 (d, J=4.52 Hz, 1H), 5.03 (dd, J=2.45, 5.87 Hz, 1H), 4.59 (d, J=2.32 Hz, 1H), 1.61 (s, 3H), 1.37 (s, 3H).

Synthesis of (3aS,4S,6S,6aS)-6-(4-aminofuro[3,2-d]pyrimidin-7-yl)-N-methoxy-N,2,2-trimethyltetrahydrofuro[3,4-d][1,3]dioxole-4-carboxamide (HH-8)

Step 9: To a 4 dram vial, equipped with a magnetic stirbar and containing HH-7 (75.9 mg, 0.236 mmol), was added dimethylhydroxylamine hydrochloride (26.5 mg, 0.272 mmol), EtOAc (0.33 mL) and pyridine (0.11 mL). The solution was cooled to 0° C. followed by the addition of 1-propanephosphonic anhydride (0.3 mL, 0.500 mmol, 50 wt % solution in EtOAc). The reaction was stirred at 0° C. for 4 h. The reaction was quenched with 0.42 mL 20% Citric Acid aq. and the contents of the vial were extracted with 3 portions EtOAc. The combined organic extracts were washed with 1 portion half saturate NaHCO₃ aq., 1 portion half saturate brine, dried (MgSO₄), filtered, and concentrated under vacuum. The aqueous phases were combined and back-extracted with 3 portions of 3:1 CHCl₃/i-PrOH. The second round of organic extracts were dried (MgSO₄), filtered, combined with first round of extracts, and concentrated under vacuum. The crude residue was purified via flash column chromatography (10 g SiO₂, Biotage, 100% Hept. to 100% EtOAc to 10% MeOH/EtOAc, 9 mL fractions) to afford the desired product contaminated with a minor impurity. The residue was resubmitted to flash column chromatography (10 g SiO₂, Biotage, 100% Hept. to 10% MeOH/EtOAc, 9 mL fractions) to afford the compound HH-8 (29.2 mg, 34%) as a colorless glass. LCMS [M+H] 365; ¹H NMR (400 MHz, CHLOROFORM-d) δ ppm 8.48 (s, 1H), 7.96 (s, 1H), 5.71 (br. s., 2H), 5.46 (s, 1H), 4.98-5.20 (m, 3H), 3.77 (br. s., 3H), 3.22 (s, 3H), 1.65 (s, 3H), 1.40 (s, 3H).

Synthesis of (2S,3R,4S,5R)-2-(4-aminofuro[3,2-d]pyrimidin-7-yl)-5-((R)-(4-fluorophenyl)(hydroxy)methyl)tetrahydrofuran-3,4-diol (HH-10)

Step 10: To an oven dried reaction vial, equipped with a magnetic stirbar and containing HH-8 (29.2 mg, 0.080 mmol), was added THF (0.4 mL). The solution was cooled to 0° C. followed by the dropwise addition of 4-fluorophenylmagnesium bromide (0.16 mL, 0.160 mmol, 1M solution in THF). The solution was stirred at 0° C. for 2 h and an additional aliquot of 4-fluorophenylmagnesium bromide (0.16 mL, 0.160 mmol, 1M solution in THF) was added. The solution was stirred at 0° C. for an additional 1 h. The reaction was quenched at 0° C. with sat. NH₄Cl aq. and further diluted with water. To the solution was added EtOAc and the phases were separated by pipette. The aqueous phase was extracted with 2 portions EtOAc. The organic extracts were combined and filtered over a bed of MgSO₄ and the salts were washed with several small portions of EtOAc. The filtrate was concentrated under vacuum to afford HH-9 (32 mg) as a pale yellow solid contaminated with minor impurities. The crude material was used in the next step without further purification. LCMS [M+H]400; ¹H NMR (400 MHz, METHANOL-d4) δ ppm 8.12 (br. s, 1H), 7.92 (s, 1H), 7.88 (dd, J=5.44, 8.86 Hz, 2H), 7.36 (dd, J=5.56, 8.50 Hz, 2H), 5.52 (dd, J=2.02, 6.05 Hz, 1H), 5.41 (s, 1H), 5.30 (br. s, 1H), 5.23 (d, J=5.99 Hz, 1H), 3.55 (s, 2H), 1.64 (s, 3H), 1.43 (s, 3H).

Step 11: To a conical bottom flask, equipped with a magnetic stirbar and containing crude HH-9 (32 mg, 0.080 mmol), was added sodium formate (218 mg, 3.20 mmol) and RuCl(p-cymene)[(R,R)-Ts-DPEN](5.1 mg, 0.008 mmol). The flask was purged with argon followed by the addition of degassed EtOAc (0.33 mL) and water (1.34 mL). The reaction was stirred at rt for minutes and an additional portion of EtOAc (1.0 mL) was added to improve solubility. The reaction was allowed to continue stirring at rt for 13 h. The reaction was concentrated under vacuum and the aqueous solution of crude product was use in the next step without further purification. LCMS analysis indicates the d.r. is ~2:1.

Step 12: To the conical bottom flask containing the aqueous solution of crude product was added trifluoroacetic acid (2.0 mL). The reaction was stirred at rt for 1 h followed by concentration under vacuum. The residue was taken up in methanol (5 mL) and re-concentrated under vacuum. This process was repeated an additional 3 times. The residue was purified via preparative HPLC (Lux Cellulose-1 4.6×100 mm 3 u column, 25% MeOH @120 bar, 4 mL/min) to separate the diastereomers affording the title compound JJ-10 (major diastereomer, 17.02 mg) as a white solid containing a minor impurity. The material was re-purified via ion exchange chromatography (Varian SCX 20 cc 5 g, 100% MeOH to 100% 7N NH₃/MeOH) to afford the compound HH-10 (7.5 mg, 26% over 3 steps, 99% de) as a white solid. LCMS [M+H]362; [α]$_D^{22}$=−27.3 (c=0.1, MeOH); ¹H NMR (400 MHz, METHANOL-d4) δ ppm 8.28 (s, 1H), 8.02 (s, 1H), 7.50 (dd, J=5.56, 8.38 Hz, 2H), 7.10 (t, J=8.86 Hz, 2H), 5.01 (d, J=1.96 Hz, 1H), 4.92 (d, J=8.80 Hz, 1H), 4.51 (dd, J=5.14, 8.68 Hz, 1H), 4.25 (dd, J=0.98, 2.32 Hz, 1H), 4.15 (d, J=5.14 Hz, 1H).

Example 81

((3aS,4S,6R,6aR)-2,2-dimethyl-6-(4-methyl-7H-pyrrolo[2,3-d]pyrimidin-7-yl)tetrahydrofuro[3,4-d][1,3]dioxol-4-yl)(2-(methylsulfonyl)phenyl)methanone

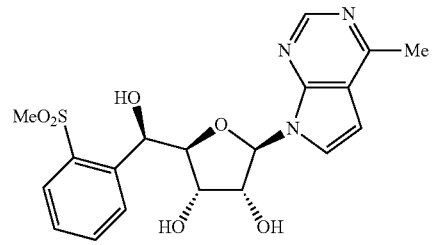 [SMILES: Cc1ncnc2c1ccn2[C@@H]1O[C@H]([C@H](O)c2ccccc2S(C)(=O)=O)[C@@H](O)[C@H]1O]

Synthesis of Examples 81 followed similar procedures to Steps 9-11 of Example 9 (Scheme C) with the appropriate Grignard reagent and an additional oxidation step shown in Scheme II. LCMS [M+1] 442; ¹H NMR (400 MHz, DMSO-d₆) δ ppm 8.67-8.64 (m, 1H), 7.96-7.90 (m, 2H), 7.83-7.80 (m, 1H), 7.80-7.74 (m, 1H), 7.61-7.53 (m, 1H), 6.82-6.77 (m, 1H), 6.25-6.22 (m, 1H), 6.22-6.18 (m, 1H), 5.62-5.58 (m, 1H), 5.35-5.31 (m, 1H), 5.16-5.12 (m, 1H), 4.57-4.50 (m, 1H), 4.35-4.28 (m, 1H), 4.24-4.20 (m, 1H), 3.22 (s, 3H), 2.66 (s, 3H).

Scheme II

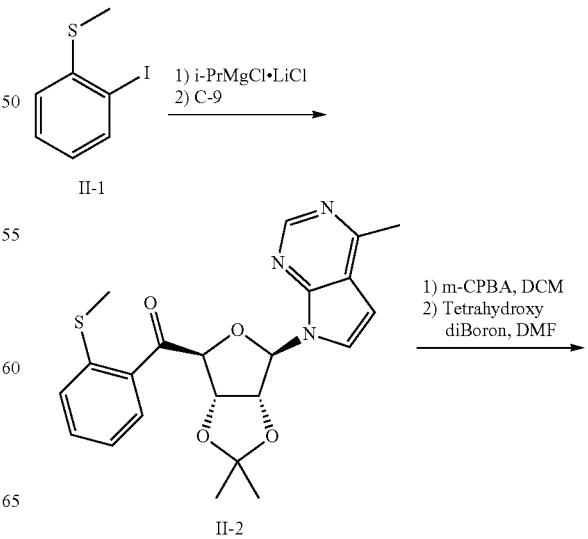

193

-continued

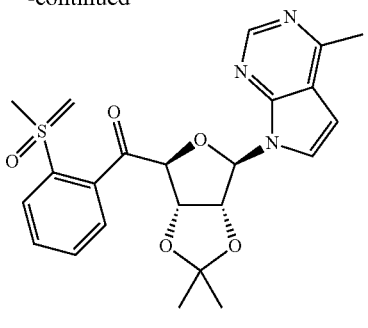

II-3

Step 1: Synthesis of ((3aS,4S,6R,6aR)-2,2-dimethyl-6-(4-methyl-7H-pyrrolo[2,3-d]pyrimidin-7-yl)tetrahydrofuro[3,4-d][1,3]dioxol-4-yl)(2-(methylthio)phenyl)methanone (II-2)

To a solution of 2-iodothioanisole (500 mg, 2 mmol) in dry THF (8 mL) was added iPrMgCl.LiCl (1.54 mL, 2 mmol, 1.3 M) at −60° C. The mixture was stirred at −60° C. for 20 min. The mixture changed to a light yellow color. C-9 (200 mg, 0.552 mmol) in THF (2 mL) was added. The mixture was stirred at −60° C. for 30 min. The mixture was allowed to warmed to rt (15° C.) slowly then at rt (15° C.) for 30 min. TLC (petoleum ether/EtOAc=1:1) showed most of the SM consumed and a good spot was formed. The mixture was quenched with NH$_4$Cl aq (5 mL). The mixture was extracted with EtOAc (5 mL×2). The extract was concentrated in vacuo to afford crude (400 mg). The crude material was purified by silica gel chromatography eluted with EtOAc in petroleum ether from 0-100% to afford 11-2 (130 mg, 55.4%) as a yellow gum. LCMS [M+23]448

Step 2: Synthesis of ((3aS,4S,6R,6aR)-2,2-dimethyl-6-(4-methyl-7H-pyrrolo[2,3-d]pyrimidin-7-yl)tetrahydrofuro[3,4-d][1,3]dioxol-4-yl)(2-(methylsulfonyl)phenyl)methanone (11-3)

To a solution of II-2 (130 mg, 0.306 mmol) in DCM (10 mL) was added m-CPBA (248 mg, 1.22 mmol) at rt (15° C.). The mixture was stirred at rt (15° C.) for 20 hrs. LCMS showed the main peak was 474 (M+16+1)N-oxide was formed. The mixture was concentrated in vacuo to dryness. The residue was dissolved in DMF (10 mL), followed by tetrahydroxydiboron (164 mg, 1.83 mmol). The mixture was stirred at rt (15° C.) for 20 min. LCMS showed desired compound was formed. The mixture was poured into water (20 mL) and extracted with EtOAc (10 mL×2). The extract was washed with brine (10 mL), dried over Na$_2$SO$_4$ and concentrated in vacuo to afford crude (500 mg). The crude was purified by silica gel chromatography eluted with EtOAc in petroleum ether from 0-100% to afford II-3 (130 mg, 93%) as white solid. LCMS [M+1] 458; $^1$H NMR (400 MHz, CDCl$_3$) δ ppm 8.76 (s, 1H), 8.06-8.00 (m, 1H), 7.57 (td, J=2.1, 4.8 Hz, 2H), 7.39-7.35 (m, 1H), 7.34 (d, J=3.8 Hz, 1H), 6.67 (d, J=3.0 Hz, 1H), 6.53 (d, J=3.8 Hz, 1H), 5.47 (dd, J=2.8, 6.3 Hz, 1H), 5.25 (d, J=3.0 Hz, 1H), 5.16 (dd, J=3.0, 6.3 Hz, 1H), 3.27 (s, 3H), 2.68 (br. s., 3H), 1.67 (s, 3H), 1.39 (s, 3H)

194

Example 82

(2R,3S,4R,5R)-2-((R)-hydroxy(1H-indol-7-yl)methyl)-5-(4-methyl-7H-pyrrolo[2,3-d]pyrimidin-7-yl)tetrahydrofuran-3,4-diol (JJ-5)

Scheme JJ

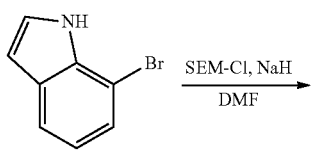

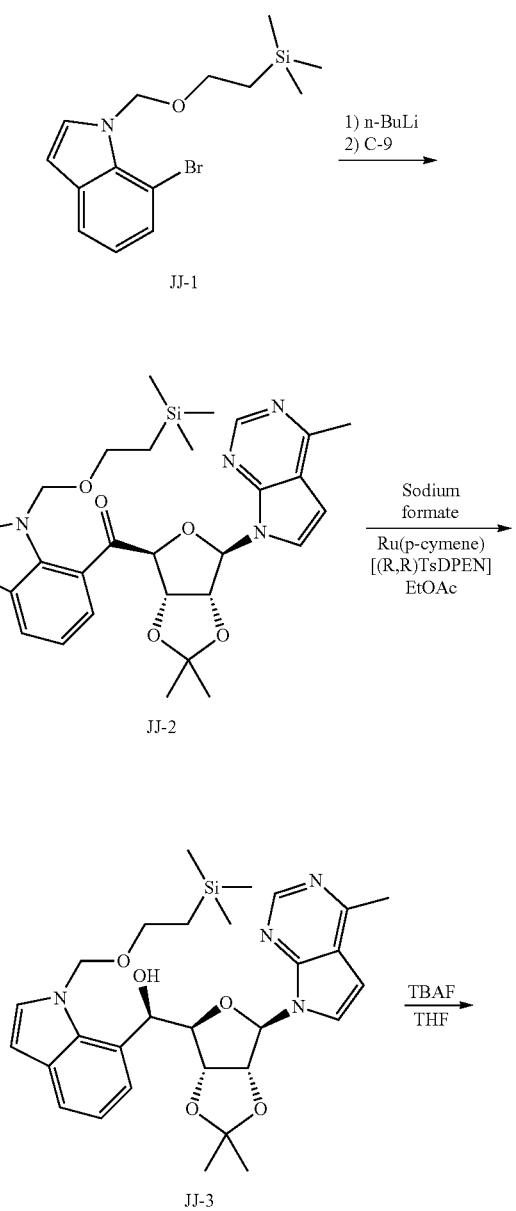

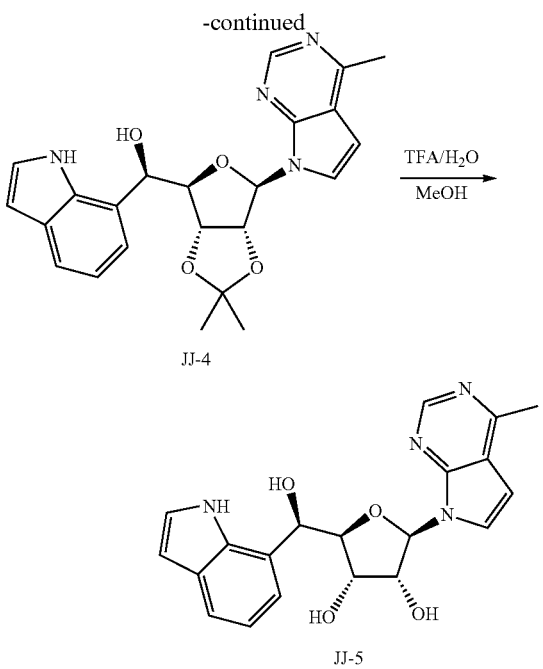

Step 1: Synthesis of 7-bromo-1-((2-(trimethylsilyl) ethoxy)methyl)-1H-indole (JJ-1)

To a solution of 7-bromoindole (1.9 g, 9.692 mmol) in dry DMF (20 mL) was added 60% NaH (581 mg, 14.5 mmol) at 0° C. The mixture was stirred at 0° C. for 30 min. SEM-Cl (1.78 g, 10.7 mmol) was added at 0° C. The mixture was stirred at rt (15° C.) for 20 hrs. TLC (petroleum ether/EtOAc=8:1) showed most of SM was consumed and a good spot was formed. The mixture was poured into water (40 mL) and extracted with EtOAc (30 mL×3). The extract was washed with brine (30 mL), dried over $Na_2SO_4$ and concentrated in vacuo to afford crude (3 g). The crude was purified by silica gel chromatography eluted with EtOAc in petroleum ether from 0-10% to afford JJ-1 (2.3 g, 72.7%) as a colorless oil. HNMR showed about 10% of SM was remaining. $^1$H NMR (400 MHz, $CDCl_3$) δ ppm 7.56 (d, J=8.0 Hz, 1H), 7.40 (d, J=7.5 Hz, 1H), 7.19 (d, J=3.3 Hz, 1H), 7.01-6.95 (m, 1H), 6.53 (d, J=3.3 Hz, 1H), 5.88-5.83 (m, 2H), 3.55-3.46 (m, 2H), 0.94-0.87 (m, 2H), −0.04--0.10 (m, 9H)

Step 2: Synthesis of ((3aS,4S,6R,6aR)-2,2-dimethyl-6-(4-methyl-7H-pyrrolo[2,3-d]pyrimidin-7-yl)tetrahydrofuro[3,4-d][1,3]dioxol-4-yl)(1-((2-(trimethylsilyl)ethoxy)methyl)-1H-indol-7-yl)methanone (JJ-2)

To a colorless solution of JJ-1 (661 mg, 2.03 mmol) in dry THF (6 mL) was added 2.5 M n-BuLi (0.891 mL, 2.23 mmol) at −85--90° C. over 10 min. The resulting slight yellow solution was stirred at −85~--90° C. for 1 hr, in which some solid formed. To the white suspension, a solution of C-9 (200 mg, 0.552 mmol) in dry THF (2 mL) was added at −85° C. The mixture was stirred at −85° C. for 2 hrs then quenched with $NH_4Cl$ aq. LCMS showed most of C-9 was consumed and desired compound was observed. The mixture was extracted with EtOAc (5 mL×2). The extract was concentrated in vacuo to afford crude (400 mg). The crude was purified by silica gel chromatography eluted with EtOAc in petroleum ether from 0-100% to afford JJ-2 (80 mg, 26.4%) as a yellow solid. LCMS [M+23]571

Step 3: Synthesis of (R)-((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)(1-((2-(trimethylsilyl)ethoxy)methyl)-1H-indol-7-yl) methanol (JJ-3)

Compound JJ-2 was subjected to reduction in a similar fashion to Step 10 of Scheme C to give JJ-3. LCMS [M+23]573

Step 4: (R)-((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)(1H-indol-7-yl)methanol (JJ-4)

To a solution of JJ-3 (60 mg, 0.109 mmol) in THF (2 mL) was added TBAF (2 g) and the mixture was stirred at 60° C. for a weekend. LCMS showed most of SM was consumed and the main peak was desired compound. the mixture diluted with EtOAc (30 mL) and washed with water (20 mL×3), dried over $Na_2SO_4$ and concentrated in vacuo to afford crude JJ-4 (24 mg, 52.4%) as a yellow solid, used in the next step directly. LCMS [M+1] 421

Step 5: Synthesis of (2R,3S,4R,5R)-2-((R)-hydroxy (1H-indol-7-yl)methyl)-5-(4-methyl-7H-pyrrolo[2,3-d]pyrimidin-7-yl)tetrahydrofuran-3,4-diol (JJ-5)

Compound JJ-4 was subjected to deprotection conditions in a similar fashion (Step 10, Scheme C) to give JJ-5. LCMS [M+1] 381; $^1$H NMR (400 MHz, MeOD) δ ppm 8.71 (br. s., 1H), 7.53 (d, J=7.3 Hz, 1H), 7.42 (d, J=3.8 Hz, 1H), 7.25-7.16 (m, 2H), 7.11-7.01 (m, 1H), 6.74 (d, J=3.8 Hz, 1H), 6.46 (d, J=3.0 Hz, 1H), 6.19 (d, J=7.3 Hz, 1H), 5.38 (d, J=2.8 Hz, 1H), 4.73 (dd, J=5.3, 7.3 Hz, 1H), 4.54-4.45 (m, 1H), 4.38 (dd, J=1.6, 5.1 Hz, 1H), 2.78 (s, 3H)

Example 83

(2R,3R,4S,5R)-2-(4-amino-5-fluoro-7H-pyrrolo[2,3-d]pyrimidin-7-yl)-5-((R)-(5-fluoropyridin-2-yl)(hydroxy)methyl)tetrahydrofuran-3,4-diol

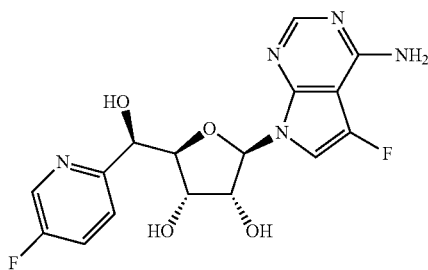 [SMILES: Nc1ncnc2c1c(F)cn2[C@@H]1O[C@H]([C@H](O)c2ccc(F)cn2)[C@@H](O)[C@H]1O]

The title compound (Example 83) was prepared analogously to Example 60 (Scheme R) where 3-fluoro-2-pyridyl magnesium chloride was substituted in place of 3,4-difluorophenylmagnesium bromide. LCMS [M+23]402; $^1$H NMR (400 MHz, DMSO-$d_6$) δ ppm 8.54 (d, J=3.0 Hz, 1H), 8.08 (s, 1H), 7.74 (dt, J=2.9, 8.8 Hz, 1H), 7.61 (dd, J=4.8, 8.8 Hz, 1H), 7.29 (d, J=1.8 Hz, 1H), 7.05 (br. s., 2H), 6.46 (d, J=4.3 Hz, 1H), 6.02 (d, J=8.0 Hz, 1H), 5.24 (d, J=6.8 Hz, 1H), 4.97 (d, J=4.3 Hz, 1H), 4.82 (t, J=3.9 Hz, 1H), 4.48-4.41 (m, 1H), 4.27 (d, J=2.5 Hz, 1H), 4.01 (t, J=3.9 Hz, 1H

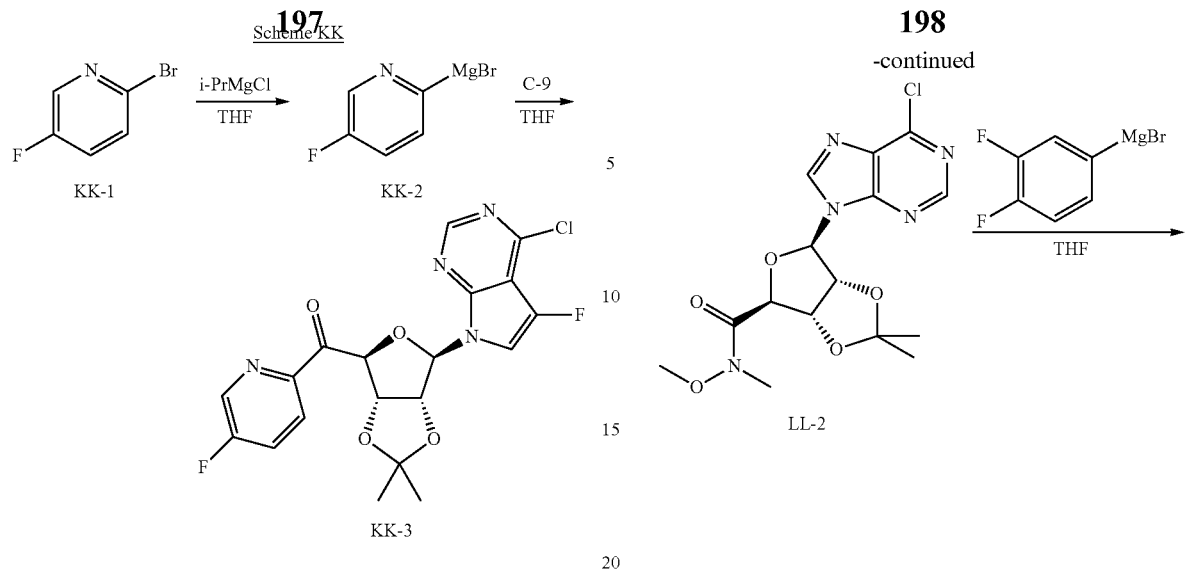

Step 1: Synthesis of (5-fluoropyridin-2-yl)magnesium bromide (KK-2)

To a light yellow solution of 2-bromo-fluoropyridine (1 g, 5.68 mmol) in dry THF (10 mL) was added iPrMgCl.LiCl (1.3 M in THF, 4.37 mL, 5.68 mmol) at 0° C. The mixture was stirred at rt (20° C.) for 2 hrs. The reaction changed from light to dark. An aliquot was quenched with acetone and TLC (petroleum ether/EtOAc=3:1) showed most of SM was consumed and a good spot with high polarity formed. The mixture was used in the next step directly.

Step 2: ((3aS,4S,6R,6aR)-6-(4-chloro-5-fluoro-7H-pyrrolo[2,3-d]pyrimidin-7-yl)-2,2-dimethyltetrahydrofuro[3,4-d][1,3]dioxol-4-yl)(5-fluoropyridin-2-yl)methanone (KK-3)

To a solution of C-9 (100 mg, 0.250 mmol) in dry THF (2 mL) was added 2 (~0.386 M in THF, prepared freshly, 1.29 mL, 0.499 mmol) at 0° C. The mixture was stirred at rt (20° C.) for 2 hrs.
LCMS showed most of SM was consumed and the main peak was desired compound. The mixture was quenched with NH$_4$Cl aq (5 mL) and extracted with EtOAc (3 mL×3). The extract was dried over Na$_2$SO$_4$ and concentrated in vacuo to afford crude (128 mg), used in the next step directly. LCMS [M+1] 437

Example 84

(2R,3R,4S,5R)-2-(6-amino-9H-purin-9-yl)-5-((R)-(3,4-difluorophenyl)(hydroxy)methyl)tetrahydrofuran-3,4-diol (LL-6)

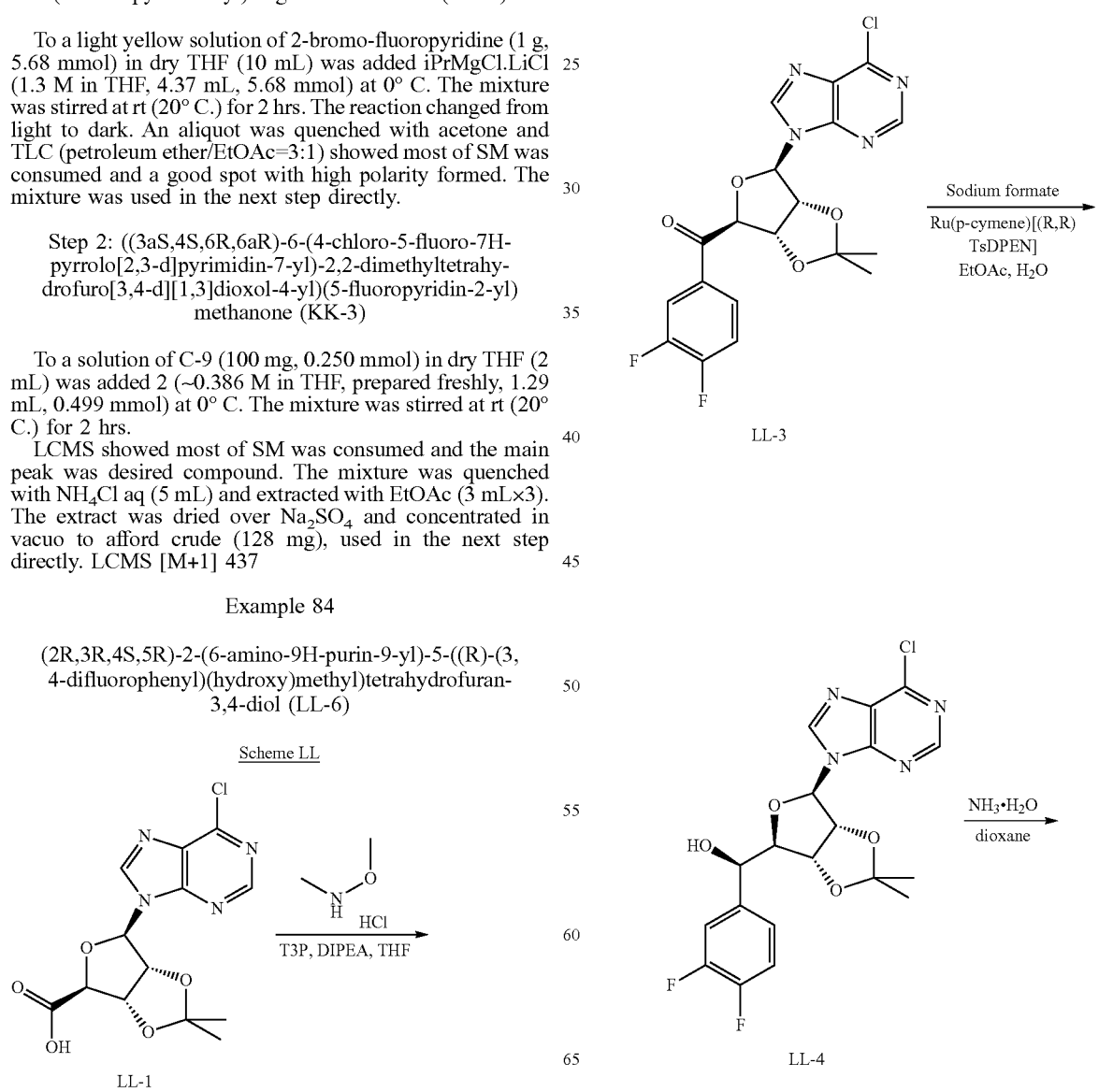

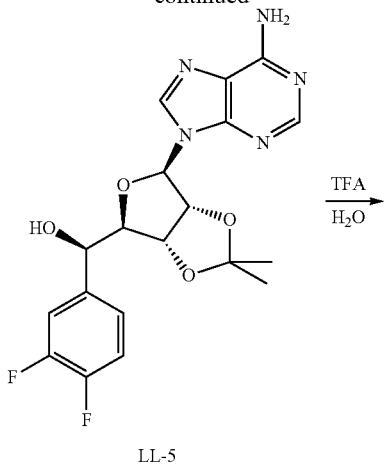

LL-5

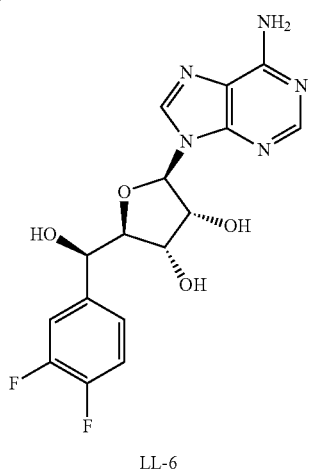

LL-6

Step 1: (3aS,4S,6R,6aR)-6-(6-chloro-9H-purin-9-yl)-N-methoxy-N,2,2-trimethyltetrahydrofuro[3,4-d][1,3]dioxole-4-carboxamide (LL-2)

To a suspension of LL-1 (*Biorganic and Medicinal Chemistry*, 2006, 14, 1618-1629) (1.00 g, 2.93 mmol) and N,O-dimethylhydroxylamine HCl (429 mg, 4.40 mmol) in THF (20 mL) was added DIPEA (1.14 g, 8.80 mmol) and 50% T3P (2.80 g, 2.57 mL, 4.40 mmol) at r.t (12° C.). The resulting colorless solution was stirred at r.t (12° C.) for 20 hrs. TLC (DCM:MeOH=10:1, UV) showed most of SM was consumed and a good spot was formed. The mixture was diluted with EtOAc (100 mL) and washed with $NH_4Cl$ aq (50 mL), $NaHCO_3$ aq (50 mL), brine (50 mL×2), dried over $Na_2SO_4$ and concentrated in vacuo to afford the residue (1.35 g) as yellow oil. The residue was purified by silica gel chromatography eluted with (MeOH:DCM, 0-10%) to give LL-2 (1.10 g, 97.7%) as yellow oil. LCMS [M+23]406; $^1$H NMR (400 MHz, $CDCl_3$) δ ppm 8.75 (s, 1H), 8.59 (s, 1H), 7.26 (s, 1H), 6.46 (m, 1H), 5.43 (d, J=5.8 Hz, 1H), 5.30-5.27 (m, 1H), 5.23 (d, J=5.3 Hz, 1H), 3.74 (s, 3H), 3.17 (s, 3H), 1.67 (s, 3H), 1.43 (s, 3H)

Step 2: ((3aS,4S,6R,6aR)-6-(6-chloro-9H-purin-9-yl)-2,2-dimethyltetrahydrofuro[3,4-d][1,3]dioxol-4-yl)(3,4-difluorophenyl)methanone (LL-3)

To a slight yellow solution of LL-2 (500 mg, 1.30 mmol) in dry THF (19.5 mL) was added 3,4-difluorophenylmagnesium bromide (0.5 M in THF, 4.95 mL, 2.48 mmol) at 5° C. After addition, the mixture was stirred at 5° C. for 10 min. TLC (petroleum ether/EtOAc=1:1, UV) showed most of SM was consumed and a good UV spot was formed. The mixture was quenched with $NH_4Cl$ aq (40 mL) in an ice bath and extracted with EtOAc (50 mL×2). The extract was washed with brine (50 mL), dried over $Na_2SO_4$ and concentrated in vacuo to afford crude LL-3 (800 mg, 141%, purity: 70%) as a yellow gum, used in the next step directly. LCMS [M+1] 437

Step 3: (R)-((3aR,4R,6R,6aR)-6-(6-chloro-9H-purin-9-yl)-2,2-dimethyltetrahydrofuro[3,4-d][1,3]dioxol-4-yl)(3,4-difluorophenyl)methanol (LL-4)

To suspension of crude LL-3 (800 mg, ~1.3 mmol) in $EtOAc/H_2O$ (2 mL/8 mL) (purged with argon or nitrogen for 30 min) was added Ru(p-cymene)[(R,R)TsDPEN](20 mg, 0.031 mmol, 10 mg/mL EtOAc) and sodium formate (1.30 g, 19.1 mmol, ~2.5 mol/L $H_2O$) at r.t (14° C.). The resulting yellow mixture was stirred at rt (14° C.) for 20 h. LCMS showed SM was consumed and desired compound was detected. TLC (petroleum ether/EtOAc=1:1) showed two main spots formed. The mixture was extracted with EtOAc (30 mL×2). The extract was washed with brine (50 mL), dried over $Na_2SO_4$ and concentrated in vacuo to afford crude (630 mg) as brown oil. The crude was purified by silica gel chromatography eluted with EtOAc in petroleum ether from 0-78% to afford LL-4 (280 mg, 50%) as a brown solid. LCMS [M+1] 439; $^1$H NMR (400 MHz, DMSO-$d_6$) δ ppm 8.90 (s, 1H), 8.85 (s, 1H), 7.39-7.24 (m, 2H), 7.07 (br. s., 1H), 6.29 (d, J=2.3 Hz, 1H), 6.08 (d, J=4.8 Hz, 1H), 5.47 (dd, J=2.5, 6.0 Hz, 1H), 5.10 (dd, J=2.4, 6.1 Hz, 1H), 4.75 (t, J=5.0 Hz, 1H), 4.34 (dd, J=2.5, 5.0 Hz, 1H), 1.51 (s, 3H), 1.30 (s, 3H).

Step 4: Synthesis of (R)-((3aR,4R,6R,6aR)-6-(6-amino-9H-purin-9-yl)-2,2-dimethyltetrahydrofuro[3,4-d][1,3]dioxol-4-yl)(3,4-difluorophenyl)methanol (LL-5)

A solution of LL-4 (70 mg, 0.16 mmol) in dioxane/$NH_3.H_2O$ (2 mL/2 mL) was heated under microwave at 120° C. for 20 min. TLC (DCM:MeOH=10:1) and LCMS showed material was consumed and a new spot appeared. The mixture was concentrated in vacuo to afford crude (90 mg) as yellow solid. The crude was purified by prep TLC (DCM:MeOH=15:1) to give LL-5 (38 mg, 57%) as a white solid. LCMS [M+1] 420; $^1$H NMR (400 MHz, DMSO-$d_6$) δ ppm 8.35 (s, 1H), 8.19 (s, 1H), 7.42 (s, 2H), 7.37-7.28 (m, 1H), 7.26-7.16 (m, 1H), 7.02 (br. s., 1H), 6.39 (d, J=4.3 Hz, 1H), 6.13 (d, J=3.3 Hz, 1H), 5.39 (dd, J=3.1, 6.1 Hz, 1H), 5.08 (dd, J=2.0, 6.3 Hz, 1H), 4.75 (t, J=5.0 Hz, 1H), 4.25 (dd, J=2.0, 5.8 Hz, 1H), 1.51 (s, 3H), 1.30 (s, 3H)

Step 5: Synthesis of (2R,3R,4S,5R)-2-(6-amino-9H-purin-9-yl)-5-((R)-(3,4-difluorophenyl)(hydroxy)methyl)tetrahydrofuran-3,4-diol (LL-6)

To a suspension of LL-5 (110 mg, 0.25 mmol) in $H_2O$ (5 mL) was added TFA (5 mL) at (0° C.). The mixture was stirred at rt (12° C.) for 2 hrs. LCMS showed SM was consumed and the desired product was clean. The mixture was poured into 20% $K_2CO_3$ aq (50 mL) and extracted with EtOAc (30 mL×3). The extract was washed with brine (50 mL×2), dried over $Na_2SO_4$ and concentrated in vacuo to afford LL-6 (40 mg, 42%) as a white solid. LCMS [M+1]

380; ¹H NMR (400 MHz, DMSO-d₆) δ ppm 8.33 (s, 1H), 8.16 (s, 1H), 7.52-7.39 (m, 3H), 7.39-7.31 (m, 1H), 7.26 (br. s., 1H), 6.75 (d, J=3.3 Hz, 1H), 5.87 (d, J=7.5 Hz, 1H), 5.42 (d, J=6.8 Hz, 1H), 5.14 (d, J=3.8 Hz, 1H), 4.88 (br. s., 1H), 4.82-4.68 (m, 1H), 4.07 (d, J=4.3 Hz, 2H)

Example 85

(2R,3R,4S,5R)-2-(4-amino-7H-pyrrolo[2,3-d]pyrimidin-7-yl)-5-((R)-(3,4-difluorophenyl)(hydroxy)methyl)tetrahydrofuran-3,4-diol (MM-7)

Scheme MM

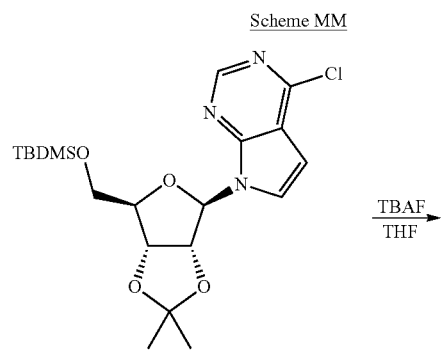

C-5

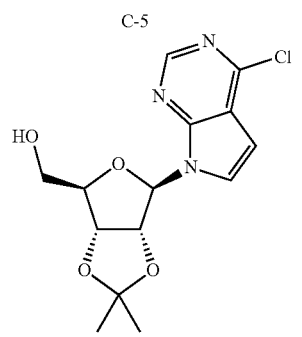

MM-1

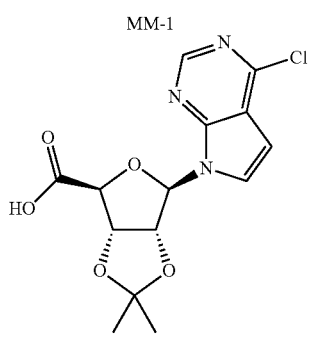

MM-2

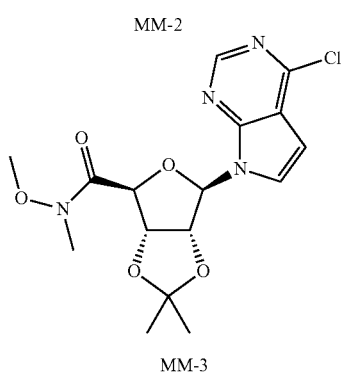

MM-3

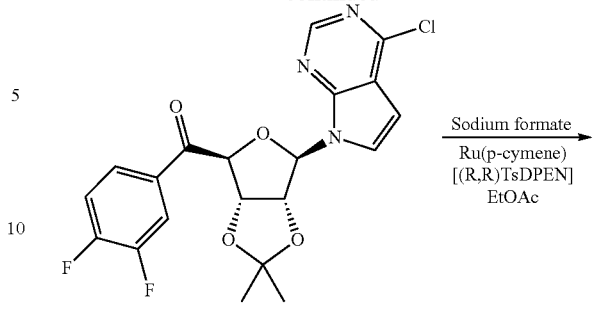

MM-4

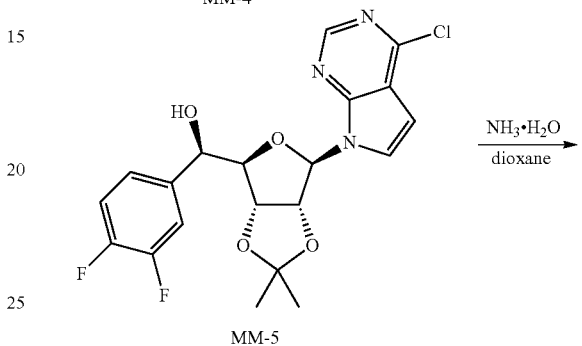

MM-5

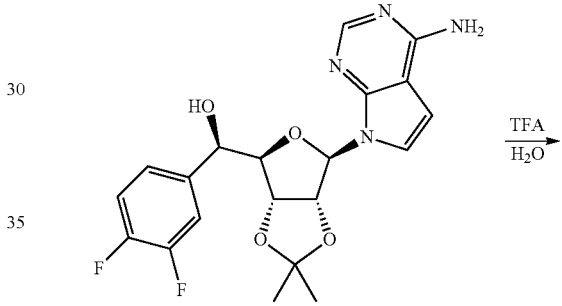

MM-6

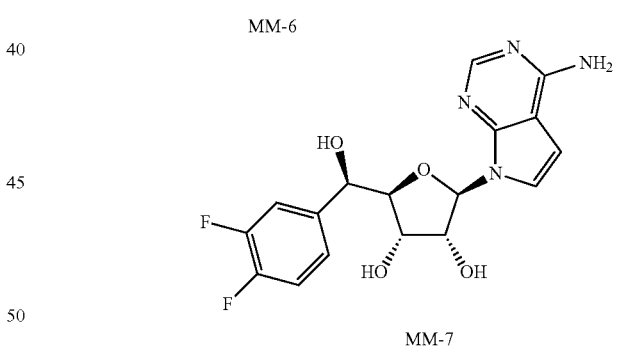

MM-7

Step 1: Synthesis of ((3aR,4R, 6R, 6aR)-6-(4-chloro-7H-pyrrolo[2,3-d]pyrimidin-7-yl)-2,2-dimethyltetrahydrofuro[3,4-d][1,3]dioxol-4-yl)methanol (MM-1)

To a solution of crude C-5 (32.5 g, 66 mmol) in THF (325 mL) was added 1M solution of TBAF in THF (6.65 mL, 6.65 mmol) at rt (15° C.). The yellow solution was stirred at rt (15° C.) for a weekend. TLC (petroleum ether/EtOAc=8:1) showed a lot of SM was remaining. 1M TBAF (6.65 mL, 6.65 mmol) was added. The mixture was stirred at rt (15° C.) for 24 hrs. TLC showed most of SM was consumed and desired spot was clean. The mixture was concentrated in vacuo to 100 mL. The residue was diluted with EtOAc (500 mL) and washed with water (200 mL×2), brine (200 mL), dried over Na$_2$SO$_4$ and concentrated in vacuo to afford crude MM-1 (22.5 g, 100%) as slight yellow oil, used in the next step directly. HNMR showed the purity of product was about 80%. LCMS [M+1] 326; $^1$H NMR (400 MHz, CDCl$_3$) δ ppm 8.64 (s, 1H), 7.33 (d, J=3.5 Hz, 1H), 6.64 (d, J=3.8 Hz, 1H), 5.87 (d, J=5.0 Hz, 1H), 5.35 (d, J=10.8 Hz, 1H), 5.24 (t, J=5.4 Hz, 1H), 5.12 (dd, J=1.5, 6.0 Hz, 1H), 4.50 (d, J=1.8 Hz, 1H), 4.01-3.93 (m, 1H), 3.85-3.77 (m, 1H), 1.65 (s, 3H), 1.39-1.34 (m, 3H)

Step 2: Synthesis of (3aS,4S,6R,6aR)-6-(4-chloro-7H-pyrrolo[2,3-d]pyrimidin-7-yl)-2,2-dimethyltetrahydrofuro[3,4-d][1,3]dioxole-4-carboxylic acid (MM-2)

To a two phase mixture of MM-1 (20 g, 49 mmol) and TEMPO (3.07 g, 19.6 mmol) in CH$_3$CN (200 mL) and phosphate buffer (146 mL, 0.67 M, pH=6.7) was added a solution of NaClO$_2$ (12.3 g, 123 mmol) in water (54 mL) at 35° C. The mixture was stirred at 35° C. for another 16 hrs. The mixture was changed into a dark color. TLC (petroleum ether/EtOAc=1:1) showed most of SM was consumed. The mixture was concentrated in vacuo to remove CH$_3$CN, in which precipitate formed. The mixture was adjusted with 1N HCl to pH=2. The solid was collected by filtration. The solid was dissolved in EtOAc (50 mL), washed with brine (30 mL), dried over Na$_2$SO$_4$ and concentrated in vacuo to dryness to afford MM-2 (12 g, 72%) as a white solid. LCMS [M+1] 340; $^1$H NMR (400 MHz, DMSO-d$_6$) δ ppm 12.82 (br. s., 1H), 8.61 (s, 1H), 7.89 (d, J=3.8 Hz, 1H), 6.72 (d, J=3.5 Hz, 1H), 6.45 (s, 1H), 5.64-5.26 (m, 2H), 4.70 (d, J=1.5 Hz, 1H), 1.53 (s, 3H), 1.36 (s, 3H)

Step 3: Synthesis of(3aS,4S,6R,6aR)-6-(4-chloro-7H-pyrrolo[2,3-d]pyrimidin-7-yl)-N-methoxy-N,2,2-trimethyltetrahydrofuro[3,4-d][1,3]dioxole-4-carboxamide (MM-3)

To a suspension of MM-2 (12 g, 35.32 mmol) and N,O-dimethylhydroxylamine HCl (5.17 g, 53.0 mmol) in THF (200 mL) was added DIPEA (30 mL, 172 mmol) and 50% T3P (33.7 g, 30.9 mL, 53 mmol) at rt (15° C.). After addition of DIPEA, the mixture was changed into red. The resulting red solution was stirred at rt (15° C.) for 20 hrs in which some solid was formed. TLC (Petroleum ether/EtOAc=1:1) showed most of the SM was consumed and a good spot was formed. The mixture was concentrated in vacuo to remove most of THF. The residue was poured into water (200 mL) and extracted with EtOAc (200 mL×2). The extract was washed with NaHCO$_3$ aq (100 mL), brine (200 mL), dried over Na$_2$SO$_4$ and concentrated in vacuo to afford MM-3 (12 g, 88.7%) as a yellow gum. LCMS [M+1] 383

Step 4: Synthesis of ((3aS,4S,6R,6aR)-6-(4-chloro-7H-pyrrolo[2,3-d]pyrimidin-7-yl)-2,2-dimethyltetrahydrofuro[3,4-d][1,3]dioxol-4-yl)(3,4-difluorophenyl)methanone (MM-4)

To a light yellow solution of MM-3 (1.00 g, 2.61 mmol) in dry THF (10 mL) was added 3,4-difluorophenylmagnesium bromide (0.5 M in THF, 6.66 mL, 3.33 mmol) at 5° C. After addition, the mixture was stirred at 5° C. for 1 h. TLC (petroleum ether/EtOAc=1:1) showed most of SM was consumed and a good UV spot and a week UV spot was formed. The mixture was quenched with NH4Cl aq (20 mL) in an ice bath and extracted with EtOAc (10 mL×2). The extract was washed with brine (10 mL), dried over Na$_2$SO$_4$ and concentrated in vacuo to afford crude MM-4 (1.34 g, >100%) as a yellow gum, used in the next step directly. $^1$H NMR (400 MHz, CDCl$_3$) δ ppm 8.46 (s, 1H), 7.69-7.60 (m, 1H), 7.60-7.54 (m, 1H), 7.29 (d, J=3.8 Hz, 1H), 7.14 (ddd, J=7.7, 8.6, 9.6 Hz, 1H), 6.57 (d, J=3.5 Hz, 1H), 6.39 (d, J=0.8 Hz, 1H), 5.71 (dd, J=2.1, 6.1 Hz, 1H), 5.47 (d, J=5.5 Hz, 1H), 5.37 (d, J=2.3 Hz, 1H), 1.69 (s, 3H), 1.45 (s, 3H)

Step 5: Synthesis of (R)-((3aR,4R,6R,6aR)-6-(4-chloro-7H-pyrrolo[2,3-d]pyrimidin-7-yl)-2,2-dimethyltetrahydrofuro[3,4-d][1,3]dioxol-4-yl)(3,4-difluorophenyl)methanol (MM-5)

To a light yellow solution of crude MM-4 (1.34 g, ~2.61 mmol) in EtOAc (8 mL) was added 2.5 M aq sodium formate (41.8 mL, 104 mmol) at rt (20° C.). The mixture was bubbled with N$_2$ for 1 h. Ru(p-cymene)[(R,R)TsDPEN](30 mg, 0.047 mmol) was added. After bubbled with N$_2$ for 5 min, the resulting yellow mixture was stirred at rt (20° C.) for 20 hrs. LCMS showed most of SM was consumed and main peak was desired compound. The mixture was extracted with EtOAc (10 mL×3). The extract was washed with brine (10 mL), dried over Na$_2$SO$_4$ and concentrated in vacuo to afford crude (1.4 g). HNMR showed the ratio of two isomers was about 4:1. The crude was purified by silica gel chromatography eluted with EtOAc/petroleum ether from 0-60% to afford MM-5 (750 mg, 65.6%) as a white solid. LCMS [M+1] 438; $^1$H NMR (400 MHz, CDCl$_3$) b ppm 8.71 (s, 1H), 7.39 (dd, J=7.7, 11.7 Hz, 1H), 7.34 (s, 1H), 7.23-7.18 (m, 2H), 6.71 (d, J=1.3 Hz, 1H), 6.68 (d, J=4.0 Hz, 1H), 5.85 (d, J=5.3 Hz, 1H), 5.24 (t, J=5.7 Hz, 1H), 5.09 (s, 1H), 4.93 (dd, J=1.3, 6.2 Hz, 1H), 4.56 (s, 1H), 1.59 (s, 3H), 1.29 (s, 3H)

Step 6: Synthesis of (R)-((3aR,4R,6R,6aR)-6-(4-amino-7H-pyrrolo[2,3-d]pyrimidin-7-yl)-2,2-dimethyltetrahydrofuro[3,4-d][1,3]dioxol-4-yl)(3,4-difluorophenyl)methanol (MM-6)

A solution of MM-5 (500 mg, 1.14 mmol) in dioxane/NH$_3$.H$_2$O (5 mL/5 mL) was heated at 120° C. with microwave for 20 min. TLC (petroleum ether/EtOAc=3:1) showed SM was remaining. The mixture was heated at 120° C. with microwave for another 40 min. TLC showed most of SM was consumed and a good spot was formed. The reaction mixture was extracted with EtOAc (5 mL×3). The extract was washed with brine (5 mL), dried over Na2SO4 and concentrated in vacuo dryness to afford MM-6 (500 mg, >100%) as a white solid. LCMS showed the purity of product was about 94%. LCMS [M+1] 419

Step 7: Synthesis of (2R,3R,4S,5R)-2-(4-amino-7H-pyrrolo[2,3-d]pyrimidin-7-yl)-5-((R)-(3,4-difluorophenyl)(hydroxy)methyl)tetrahydrofuran-3,4-diol (MM-7)

To compound MM-6 (500 mg, ~1.2 mmol) was added TFA/H$_2$O (7 mL/7 mL, cooled to 0° C.). The resulting suspension was stirred at rt for 1 hr. LCMS showed most of SM was consumed and the main peak was desired compound. The mixture was poured into 20% K$_2$CO$_3$ (30 mL) and extracted with EtOAc (20 mL×3). The extract was washed with brine (20 mL×2), dried over Na$_2$SO$_4$ and concentrated in vacuo to afford crude (450 mg). The crude was recrystallized from EtOAc (20 mL) and pentane (20 mL) to afford the product MM-7 (380 mg, 84%) as a white solid. LCMS [M+23]401; ¹H NMR (400 MHz, DMSO-d₆) δ ppm 8.06 (s, 1H), 7.49-7.36 (m, 2H), 7.34 (d, J=3.8 Hz, 1H), 7.28 (d, J=3.3 Hz, 1H), 7.13 (br. s., 2H), 6.74 (d, J=3.8 Hz, 1H), 6.60 (d, J=3.5 Hz, 1H), 5.92 (d, J=8.0 Hz, 1H), 5.23 (d, J=7.0 Hz, 1H), 5.04 (d, J=4.0 Hz, 1H), 4.82 (t, J=3.9 Hz, 1H), 4.66-4.58 (m, 1H), 4.06-3.99 (m, 2H)

Examples 86-88

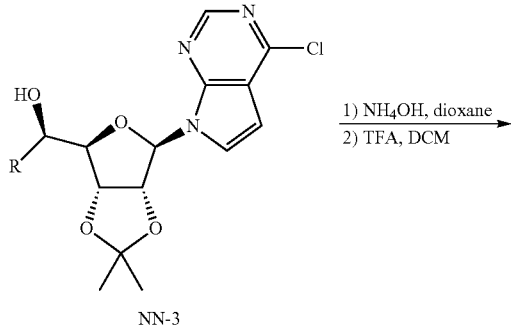

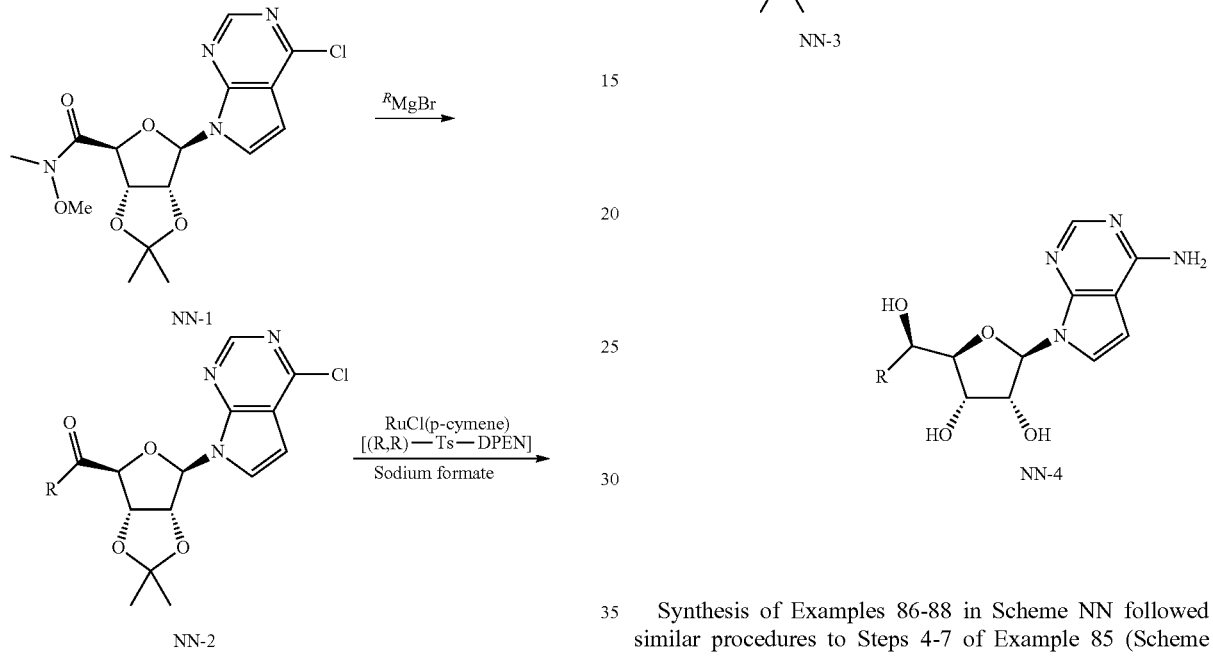

Synthesis of Examples 86-88 in Scheme NN followed similar procedures to Steps 4-7 of Example 85 (Scheme MM) with the appropriate Grignard reagent.

| Example | Structure | MW | IUPAC |
|---------|-----------|-----|-------|
| 86 | 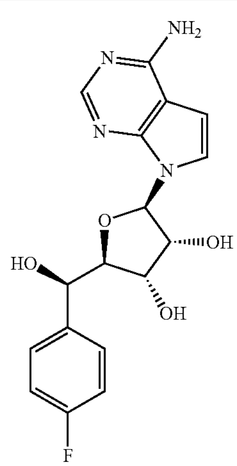 [SMILES: Nc1ncnc2c1ccn2[C@@H]1O[C@H]([C@H](O)c2ccc(F)cc2)[C@@H](O)[C@H]1O] | 383 [M + 23] | (2R,3R,4S,5R)-2-(4-amino-7H-pyrrolo[2,3-d]pyrimidin-7-yl)-5-((R)-(4-fluorophenyl)(hydroxy)methyl)tetrahydrofuran-3,4-diol<br>¹H NMR (400 MHz, DMSO-d₆) δ ppm 8.06 (s, 1H), 7.45 (dd, J = 5.6, 8.4 Hz, 2H), 7.33 (d, J = 3.8 Hz, 1H), 7.20-7.06 (m, 4H), 6.64 (d, J = 3.5 Hz, 1H), 6.60 (d, J = 3.5 Hz, 1H), 5.92 (d, J = 7.8 Hz, 1H), 5.22 (d, J = 7.0 Hz, 1H), 5.00 (d, J = 4.0 Hz, 1H), 4.82 (t, J = 3.8 Hz, 1H), 4.68-4.59 (m, 1H), 4.07-3.98 (m, 2H) |

| Example | Structure | MW | IUPAC |
|---|---|---|---|
| 87 | 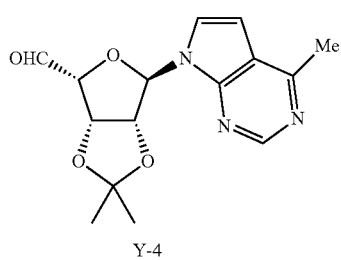 | 377 [M + 1] | (2R,3R,4S,5R)-2-(4-amino-7H-pyrrolo[2,3-d]pyrimidin-7-yl)-5-((R)-(4-chlorophenyl)(hydroxy)methyl)tetrahydrofuran-3,4-diol<br>$^1$H NMR (400 MHz, DMSO-$d_6$) δ ppm 8.06 (s, 1H), 7.45 (d, J = 8.5 Hz, 2H), 7.39 (d, J = 8.5 Hz, 2H), 7.33 (d, J = 3.5 Hz, 1H), 7.13 (br. s., 2H), 6.71 (d, J = 3.3 Hz, 1H), 6.60 (d, J = 3.5 Hz, 1H), 5.91 (d, J = 7.8 Hz, 1H), 5.22 (d, J = 7.3 Hz, 1H), 5.02 (d, J = 4.0 Hz, 1H), 4.82 (t, J = 3.8 Hz, 1H), 4.67-4.60 (m, 1H), 4.02 (d, J = 4.3 Hz, 2H) |
| 88 | 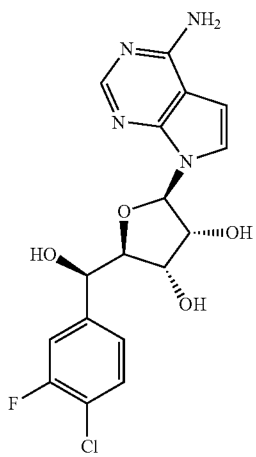 [SMILES: Nc1ncnc2c1ccn2[C@@H]1O[C@H]([C@H](O)c2ccc(Cl)c(F)c2)[C@@H](O)[C@H]1O] | 395 [M + 1] | (2R,3R,4S,5R)-2-(4-amino-7H-pyrrolo[2,3-d]pyrimidin-7-yl)-5-((R)-(4-chloro-3-fluorophenyl)(hydroxy)methyl)tetrahydrofuran-3,4-diol<br>1H NMR (400 MHz, DMSO-$d_6$) δ ppm 8.06 (s, 1H), 7.54 (t, J = 8.0 Hz, 1H), 7.43 (d, J = 10.8 Hz, 1H), 7.35 (d, J = 3.8 Hz, 1H), 7.30 (d, J = 8.3 Hz, 1H), 7.13 (br. s., 2H), 6.81 (d, J = 3.5 Hz, 1H), 6.61 (d, J = 3.5 Hz, 1H), 5.92 (d, J = 7.8 Hz, 1H), 5.24 (d, J = 7.0 Hz, 1H), 5.06 (d, J = 3.8 Hz, 1H), 4.84 (t, J = 3.6 Hz, 1H), 4.68-4.59 (m, 1H), 4.05-4.00 (m, 2H) |

Example 89

(S)-1-((3aR,4S,6R,6aR)-2,2-dimethyl-6-(4-methyl-7H-pyrrolo[2,3-d]pyrimidin-7-yl)tetrahydrofuro[3,4-d][1,3]dioxol-4-yl)ethan-1-ol (OO-2)

Scheme OO

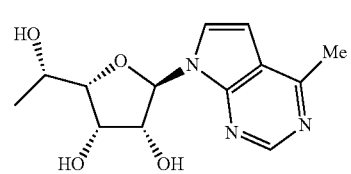

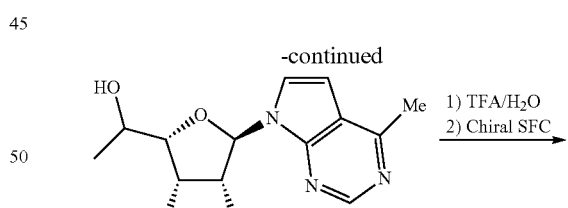

Step 1: Synthesis of 1-((3aR,4S,6R,6aR)-2,2-dimethyl-6-(4-methyl-7H-pyrrolo[2,3-d]pyrimidin-7-yl)tetrahydrofuro[3,4-d][1,3]dioxol-4-yl)ethan-1-ol (Y-7)

CeCl₃ was placed in a 25 mL flask was heated to 150° C. under vacuum for 1 h. The flask was then cooled to rt, and cooled to 0° C. THF (8 mL) and MeMgBr (1.8 mL, 3M) was added and the mixture was stirred at 0° C. for 30 mins. A solution of Y-4 (400 mg, 1.0 mmol) in THF was added dropwise. LCMS showed about 30% of SM was remained. The mixture was quenched by NH₄Cl. The mixture was diluted with H₂O and EtOAc. The organic layer was concentrated to give crude OO-1 (420 mg, 97%) as an oil. LCMS [M+1] 320

Step 2-3: Synthesis of (2S,3S,4R,5R)-2-((S)-1-hydroxyethyl)-5-(4-methyl-7H-pyrrolo[2,3-d]pyrimidin-7-yl)tetrahydrofuran-3,4-diol (OO-2)

A solution of OO-1 (50 mg, 0.16 mmol) in TFA/H₂O (2 mL/2 mL) was stirred at 20° C. for 24 h. TLC DCM:MeOH=10:1 showed the reaction was complete. The solution was concentrated to give 44 mg, 100% as an oil. LCMS [M+1] 280. The desired compound OO-2 was separate by chiral SFC. LCMS [M+1] 280; ¹H NMR (400 MHz, MeOD) δ ppm 8.67 (s, 1H), 7.72 (d, J=3.8 Hz, 1H), 6.86 (d, J=3.8 Hz, 1H), 6.32 (d, J=7.3 Hz, 1H), 4.90 (dd, J=4.4, 7.4 Hz, 1H), 4.39-4.33 (m, 1H), 4.29 (dd, J=3.0, 7.5 Hz, 1H), 4.18-4.03 (m, 1H), 2.76 (s, 3H), 1.25 (d, J=6.5 Hz, 3H).

Example 90  2-((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)propan-2-ol (PP-3)

Scheme PP

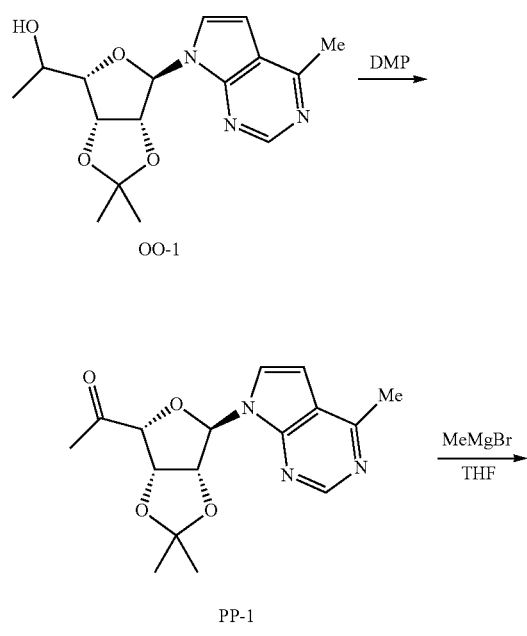

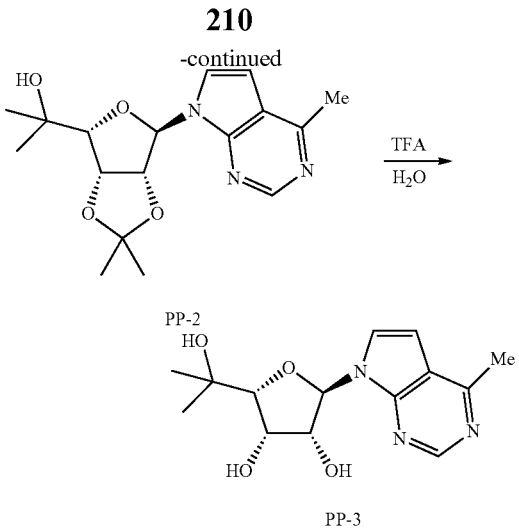

Step 1: 1-((3aS,4R,6R,6aR)-2,2-dimethyl-6-(4-methyl-7H-pyrrolo[2,3-d]pyrimidin-7-yl)tetrahydrofuro[3,4-d][1,3]dioxol-4-yl)ethan-1-one (PP-1)

To a solution of OO-1 (420 mg, 1.32 mmol) in DCM (5 mL) was added DMP (669 mg, 1.2 mmol). The solution was stirred at 25° C. for 1 h in which a lot of solid was formed. The color of reaction became red. TLC DCM/EtOAc=1:1 showed the reaction was complete. The mixture was quenched by 1.0 g Na₂S₂O₃ in 4 mL NaHCO₃. The mixture was stirred at 25° C. for 2 min. The organic layer was concentrated to give crude solid, which was purified by flash column with EtOAc/DCM 0~50% to give PP-1 (270 mg, 64.7%) as a white solid. LCMS [M+1] 318

Step 2: 2-((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)propan-2-ol (PP-2)

To a solution of PP-1 (100 mg, 0.315 mmol) in THF (2 mL) was added MeMgBr (0.42 mL, 1.26 mmol, 3M in Et₂O) and cooled with a dry ice/acetone batch. After the addition, the mixture was stirred at 0° C. for 10 min. A lot of solid was formed, and then became clear. TLC DCM:EtOAc=1:1 showed the reaction was completed. The mixture was quenched by 0.3 mL NH₄Cl. The mixture was extracted with EtOAc. The EtOAc layer was concentrated to give PP-2 (100 mg, 95%) as a colourless oil. LCMS [M+1] 334

Step 3: (2R,3S,4R,5R)-2-(2-hydroxypropan-2-yl)-5-(4-methyl-7H-pyrrolo[2,3-d]pyrimidin-7-yl)tetrahydrofuran-3,4-diol (PP-3)

To a mixture of PP-2 (100 mg, 0.3 mmol) in H₂O (1 mL) was added TFA (1 mL). The solution was stirred at 25° C. for 24 h. TLC (DCM:MeOH=10:1) showed the reaction was complete. The solution was concentrated to give crude oil, which was purified by prep-HPLC to give PP-3. LCMS [M+1] 294; ¹H NMR (400 MHz, D₂O) δ ppm 8.49 (s, 1H), 7.55 (d, J=3.8 Hz, 1H), 6.72 (d, J=3.8 Hz, 1H), 6.24 (d, J=8.0 Hz, 1H), 4.84 (dd, J=4.1, 8.2 Hz, 1H), 4.58-4.49 (m, 1H), 4.27 (d, J=3.0 Hz, 1H), 2.57 (s, 3H), 1.30 (s, 3H), 1.15 (s, 3H)

Example 91

(3,4-difluorophenyl)((2S,3S,4R,5R)-3,4-dihydroxy-5-(4-methyl-7H-pyrrolo[2,3-d]pyrimidin-7-yl)tetrahydrofuran-2-yl)methanone (QQ-1)

Example 92

(2S,3S,4R,5R)-2-((R)-(3,4-difluorophenyl)fluoromethyl)-5-(4-methyl-7H-pyrrolo[2,3-d]pyrimidin-7-yl)tetrahydrofuran-3,4-diol (RR-2)

Example 93

(2S,3S,4R,5R)-2-((S)-(3,4-difluorophenyl)fluoromethyl)-5-(4-methyl-7H-pyrrolo[2,3-d]pyrimidin-7-yl)tetrahydrofuran-3,4-diol (RR-3)

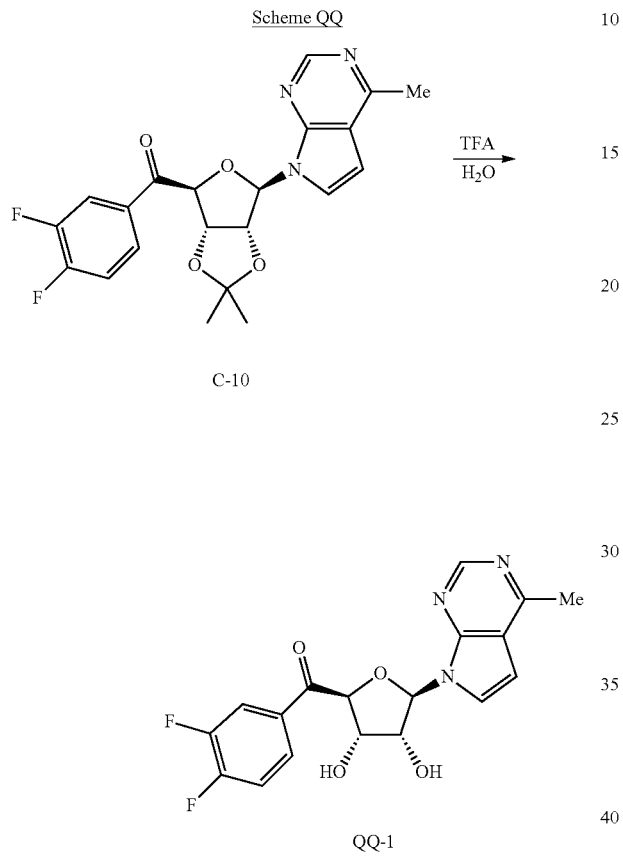

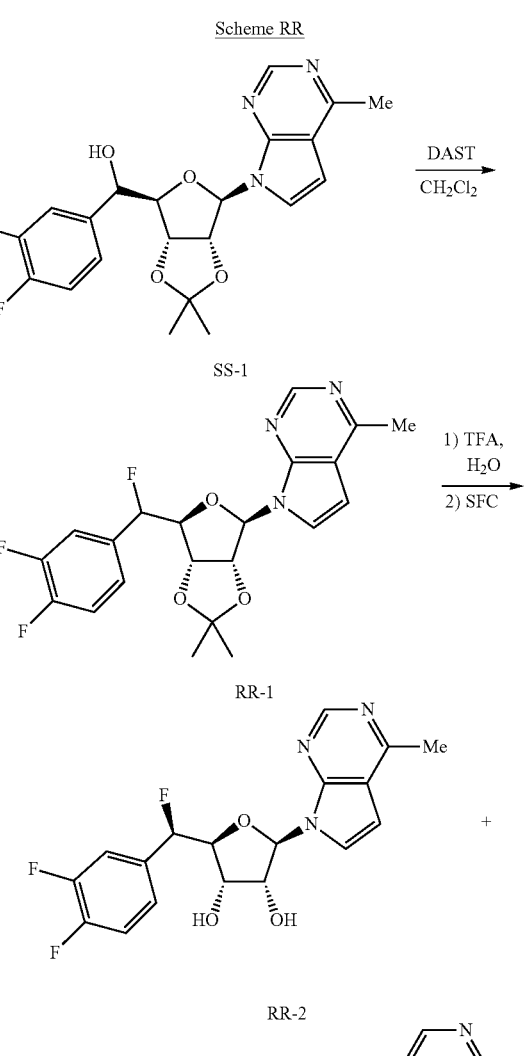

A reaction vial, equipped with a magnetic stirbar, was charged with C-10 (48.6 mg, 117 mmol) and water (0.5 mL) followed by the dropwise addition of trifluoroacetic acid (0.5 mL). The solution was stirred at room temperature for 2 hours. The reaction was transferred to a separatory funnel with EtOAc. The organic phase was washed with 2 portions sat. NaHCO$_3$ aq., dried (MgSO$_4$), filtered, and concentrated under vacuum. The crude residue was purified via supercritical fluid chromatography (ZymorSPHER pyr/diol 150× 4.6 mm column, 5-50% MeOH, 4.5 mL/min) to afford the title compound QQ-1 (15.3 mg, 35%) as a white solid. LCMS [M+H]376; $^1$H NMR (700 MHz, DMSO-d6) δ ppm 8.65 (s, 1H), 8.00-8.06 (m, 1H), 7.91 (d, J=6.49 Hz, 1H), 7.85 (d, J=3.76 Hz, 1H), 7.59-7.65 (m, 1H), 6.81 (d, J=3.59 Hz, 1H), 6.41 (d, J=6.83 Hz, 1H), 5.48 (d, J=2.39 Hz, 1H), 4.37-4.42 (m, 1H), 4.34-4.37 (m, 1H), 2.65 (s, 3H).

Step 1: Synthesis of 7-((3aR,4R,6S,6aS)-6-((3,4-difluorophenyl)fluoromethyl)-2,2-dimethyltetrahydrofuro[3,4-d][1,3]dioxol-4-yl)-4-methyl-7H-pyrrolo[2,3-d]pyrimidine (RR-1)

To a solution of SS-1 (Scheme SS) (500 mg, 1.20 mmol) in 5 mL CH$_2$Cl$_2$ was added DAST (965 mg, 5.99 mmol), stirred at rt for 30 min. The reaction was quenched with water, transferred to a separatory funnel, and diluted with 10 mL water. The phases were separated and the aqueous phase was extracted with 3 portions of 5 mL CH$_2$Cl$_2$. The organic phase was combined and washed with 10 mL brine, dried over Na$_2$SO$_4$ and concentrated in vacuo. The residue was purified by silica gel chromatography with 50% EtOAc/heptane to afford yellow oil RR-1 (190 mg, 37.8%).

Step 3: Synthesis of (2S,3S,4R,5R)-2-((R)-(3,4-difluorophenyl)fluoromethyl)-5-(4-methyl-7H-pyrrolo[2,3-d]pyrimidin-7-yl)tetrahydrofuran-3,4-diol (RR-2) and (2S,3S,4R,5R)-2-((S)-(3,4-difluorophenyl)fluoromethyl)-5-(4-methyl-7H-pyrrolo[2,3-d]pyrimidin-7-yl)tetrahydrofuran-3,4-diol (RR-3)

RR-1 (190 mg, 0.453 mmol) was dissolved in 2 mL TFA, added 2 mL H2O, stirred at rt for 30 min. The reaction was concentrated then purified by SFC with Chiralpak IC-3 4.6×100 mm 3 u column with 20% MeOH/DEA at 120 bar and 4 mL/min to provide 19.96 mg (RR-2) and 59.05 mg (RR-3) as white solids.

RR-2—LCMS [M+1] 380; $^1$H NMR (700 MHz, DMSO-d$_6$) δ ppm 2.67 (s, 3 H) 4.13-4.20 (m, 1 H) 4.20-4.29 (m, 1 H) 4.47 (q, J=5.50 Hz, 1 H) 5.38 (d, J=5.06 Hz, 1 H) 5.54 (d, J=6.38 Hz, 1 H) 5.80-5.90 (m, 1 H) 6.26 (d, J=6.16 Hz, 1 H) 6.84 (d, J=3.74 Hz, 1 H) 7.24-7.32 (m, 1 H) 7.40-7.54 (m, 2 H) 7.71 (d, J=3.74 Hz, 1 H) 8.67 (s, 1 H)

RR-3—LCMS [M+1] 380; $^1$H NMR (700 MHz, DMSO-d$_6$) δ ppm 2.65 (s, 3 H) 4.21-4.30 (m, 2 H) 4.54-4.60 (m, 1 H) 5.48 (d, J=4.40 Hz, 1 H) 5.51 (d, J=6.60 Hz, 1 H) 5.74-5.84 (m, 1 H) 6.21 (d, J=6.82 Hz, 1 H) 6.77 (d, J=3.74 Hz, 1 H) 7.21-7.29 (m, 1 H) 7.36-7.43 (m, 1 H) 7.43-7.49 (m, 1 H) 7.62 (d, J=3.74 Hz, 1 H) 8.64 (s, 1 H)

Example 94

(2R,3S,4R,5R)-2-((R)-amino(3,4-difluorophenyl)methyl)-5-(4-methyl-7H-pyrrolo[2,3-d]pyrimidin-7-yl)tetrahydrofuran-3,4-diol (SS-4)

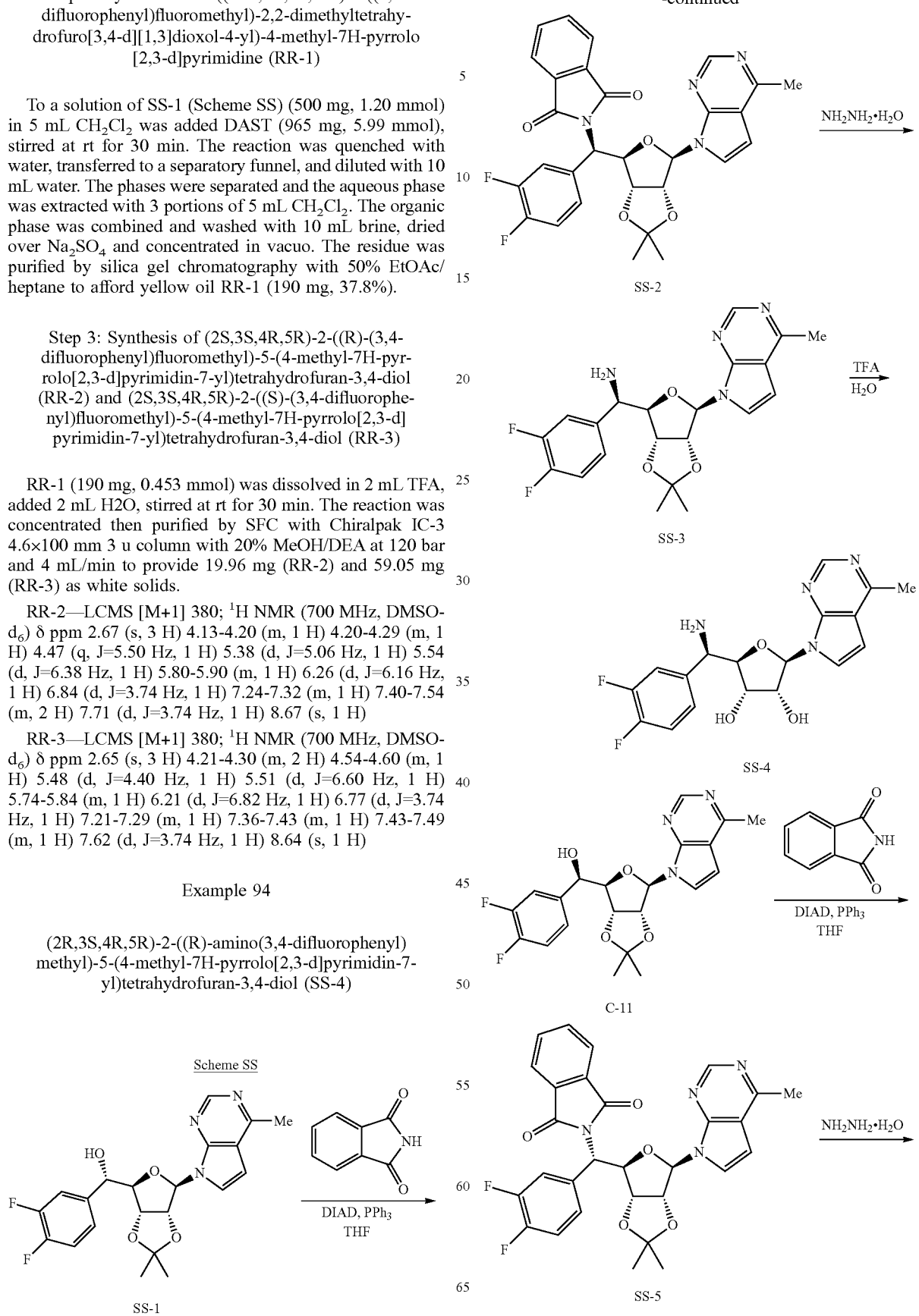

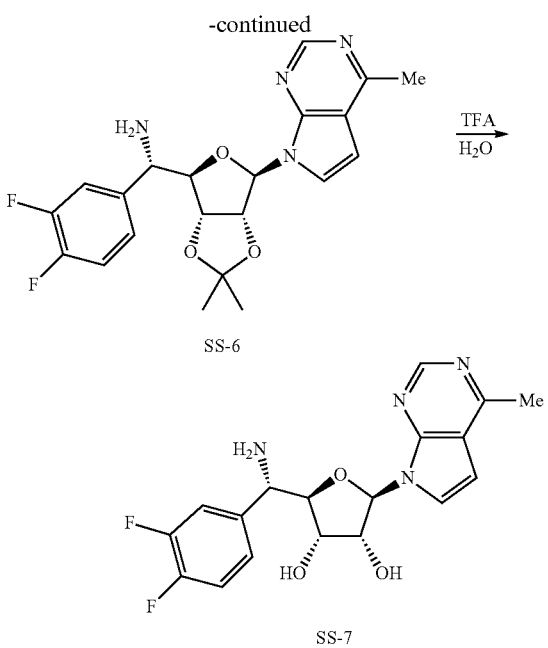

Step 1: Synthesis of 2-((R)-(3,4-difluorophenyl) ((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)methyl)isoindoline-1,3-dione (SS-2)

In a round bottom flask was added SS-1 (Scheme SS) (100 mg, 0.240 mmol), phthalimide (53 mg, 0.359 mmol), triphenylphosphine (94.3 mg, 0.359 mmol), THF (1.20 mL, 0.2 M). The mixture was cooled to 0° C. in an ice bath. DIAD (0.074 mL, 0.359 mmol) was added dropwise and stirred at room temperature for 16 h. The reaction was diluted with EtOAc and water (30 mL each). Extract the aqueous layer with EtOAc (3×20 mL). The combined organics were washed with water and brine, dried over Na$_2$SO$_4$, filtered and concentrated to an oil. The crude material was purified by ISCO 12 g column gold 0-100% EtOAc/Heptanes to give SS-2 (84 mg, 64%). LCMS [M+1] 547; $^1$H NMR (400 MHz, CDCl$_3$) δ ppm 8.91 (s, 1H), 7.87 (dd, J=3.0, 5.4 Hz, 2H), 7.76-7.65 (m, 2H), 7.14 (d, J=3.7 Hz, 2H), 7.03-6.82 (m, 2H), 6.54 (d, J=3.7 Hz, 1H), 6.16 (d, J=1.6 Hz, 1H), 5.80-5.67 (m, 1H), 5.54-5.38 (m, 2H), 5.16 (dd, J=3.9, 6.3 Hz, 1H), 2.74 (s, 3H), 1.61 (s, 3H), 1.29 (s, 3H)

Step 2: Synthesis of (R)-(3,4-difluorophenyl)((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)methanamine (SS-3)

In a round bottom flask was added SS-2 (84 mg, 0.15 mmol) in EtOH (2 mL) and hydrazine hydrate (1.50 mL, 30.7 mmol). The reaction was stirred at r.t. for 16 h. LCMS showed the desired product. The reaction was concentrated and purified by prep HPLC to give a white solid SS-3 (50 mg, 78%). LCMS [M+1] 417; $^1$H NMR (400 MHz, CDCl$_3$) δ ppm 8.74 (s, 1H), 7.38-7.29 (m, 1H), 7.25-7.14 (m, 3H), 6.63 (d, J=3.8 Hz, 1H), 5.96 (d, J=3.8 Hz, 1H), 5.42-5.35 (m, 1H), 5.31 (dd, J=3.8, 6.7 Hz, 1H), 4.55 (d, J=3.8 Hz, 1H), 4.47 (t, J=3.7 Hz, 1H), 2.76 (s, 3H), 1.57 (s, 3H), 1.34 (s, 3H)

Step 3: Synthesis of (2R,3S,4R,5R)-2-((R)-amino(3,4-difluorophenyl)methyl)-5-(4-methyl-7H-pyrrolo[2,3-d]pyrimidin-7-yl)tetrahydrofuran-3,4-diol (SS-4)

In a vial was added SS-3, TFA (1 mL) and water (1 mL) and stirred at r.t. for 16 h. LCMS shows complete deprotection. Concentrate and free-base with a 1 g SCX column flushing with MeOH first, followed by 10% 7N NH$_3$/MeOH to obtain the product. Lyophilize to a white solid to give SS-4 (6 mg, 80%). LCMS 377 [M+1]; $^1$H NMR (400 MHz, MeOD) δ ppm 8.56 (s, 1H), 7.32 (d, J=3.7 Hz, 1H), 7.28-7.17 (m, 1H), 7.16-7.05 (m, 2H), 6.70 (d, J=3.7 Hz, 1H), 6.08 (d, J=5.0 Hz, 1H), 4.60 (t, J=5.3 Hz, 1H), 4.29 (t, J=4.9 Hz, 1H), 4.18 (d, J=2.4 Hz, 2H), 2.71 (s, 3H)

Example 95

(2R,3S,4R,5R)-2-((S)-amino(3,4-difluorophenyl)methyl)-5-(4-methyl-7H-pyrrolo[2,3-d]pyrimidin-7-yl)tetrahydrofuran-3,4-diol (SS-7)

Step 1: Synthesis of 2-((S)-(3,4-difluorophenyl)((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)methyl)isoindoline-1,3-dione (SS-5)

In a round bottom flask was added C-11 (Scheme SS) (100 mg, 0.240 mmol), phthalimide (53 mg, 0.359 mmol), triphenylphosphine (94 mg, 0.359 mmol) in THF (1.20 mL, 0.2 M). The mixture was cooled to 0° C. in an ice bath. DIAD (0.074 mL, 0.359 mmol) was added dropwise and stirred at room temperature for 16 hours. The reaction was diluted with EtOAc and water (30 mL each). Extract the aqueous layer with EtOAc (3×20 mL). The combined organics were washed with water and brine, dried over Na$_2$SO$_4$, filtered and concentrated to an oil which was then purified by ISCO 12 g column gold 0-100% EtOAc/Heptanes to obtained SS-5 (32 mg, 24%). LCMS [M+1] 547; $^1$H NMR (400 MHz, CDCl$_3$) δ ppm 8.85 (s, 1H), 7.69-7.60 (m, 4H), 7.56-7.48 (m, 1H), 7.39-7.32 (m, 1H), 7.23-7.12 (m, 1H), 7.11 (d, J=3.7 Hz, 1H), 6.53 (d, J=3.7 Hz, 1H), 6.15 (d, J=1.3 Hz, 1H), 5.63-5.56 (m, 2H), 5.52-5.44 (m, 1H), 5.10-4.99 (m, 1H), 2.77 (s, 3H), 1.64 (s, 3H), 1.34 (s, 3H)

Step 2: Synthesis of (S)-(3,4-difluorophenyl)((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)methanamine (SS-6)

In a round bottom flask was added SS-5 (32 mg, 0.059 mmol), EtOH (1.17 mL, 0.05 M), and hydrazine hydrate (0.570 mL, 11.7 mmol). The reaction was stirred at r.t. for 16 h. LCMS indicates formation of the desired product. The reaction was concentrated to an oil to give SS-6 (24 mg, 98%). LCMS [M+1] 417

Step 3: Synthesis of (2R,3S,4R,5R)-2-((S)-amino(3,4-difluorophenyl)methyl)-5-(4-methyl-7H-pyrrolo[2,3-d]pyrimidin-7-yl)tetrahydrofuran-3,4-diol (SS-7)

In a round bottom flask containing SS-6 (24 mg, 0.059 mmol) was added TFA (1 mL) and water (1 mL). The reaction was stirred for 16 hours at r.t. LCMS indicated complete deprotection. The reaction was then concentrated and purified by an SCX column, first eluting with MeOH, followed by 10% 7N NH$_3$/MeOH solution to obtain the product. Purify by SFC to obtain a white solid (SS-7) (3 mg, 10%). LCMS [M+1] 377; $^1$H NMR (400 MHz, MeOD) δ ppm 8.56 (s, 1H), 7.47 (d, J=3.5 Hz, 1H), 7.29-7.18 (m, 1H), 7.10 (d, J=4.3 Hz, 2H), 6.67 (d, J=3.5 Hz, 1H), 6.05 (d, J=6.2 Hz, 1H), 4.61 (t, J=5.7 Hz, 1H), 4.13 (d, J=4.8 Hz, 2H), 4.03-3.95 (m, 1H)

Example 96

(2R,3R,4S,5R)-2-(4-(difluoromethyl)-7H-pyrrolo[2,3-d]pyrimidin-7-yl)-5-((R)-(4-fluorophenyl)(hydroxy)methyl)tetrahydrofuran-3,4-diol (TT-7)

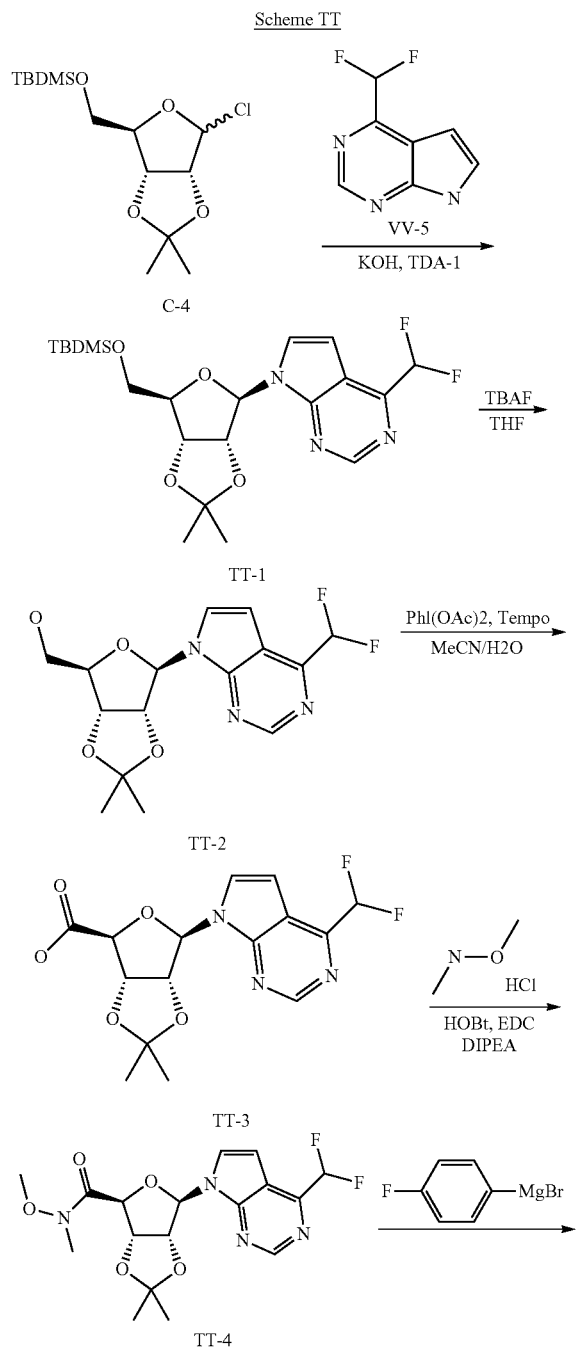

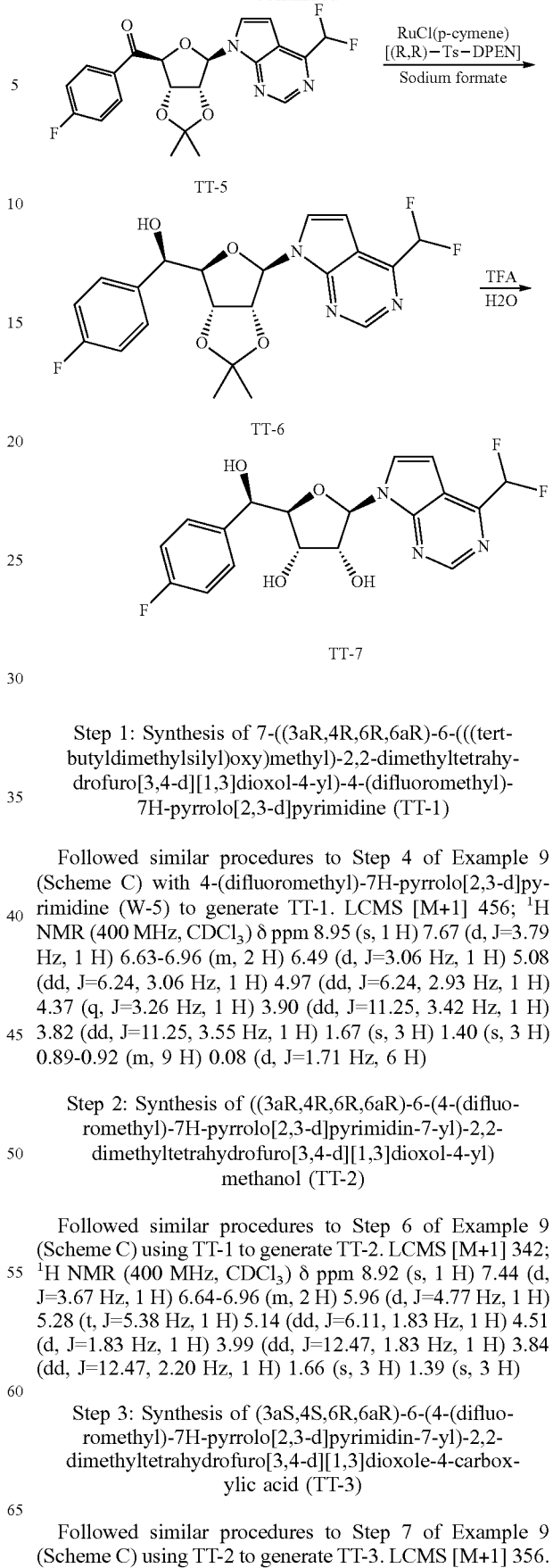

Step 1: Synthesis of 7-((3aR,4R,6R,6aR)-6-(((tert-butyldimethylsilyl)oxy)methyl)-2,2-dimethyltetrahydrofuro[3,4-d][1,3]dioxol-4-yl)-4-(difluoromethyl)-7H-pyrrolo[2,3-d]pyrimidine (TT-1)

Followed similar procedures to Step 4 of Example 9 (Scheme C) with 4-(difluoromethyl)-7H-pyrrolo[2,3-d]pyrimidine (W-5) to generate TT-1. LCMS [M+1] 456; $^1$H NMR (400 MHz, CDCl$_3$) δ ppm 8.95 (s, 1 H) 7.67 (d, J=3.79 Hz, 1 H) 6.63-6.96 (m, 2 H) 6.49 (d, J=3.06 Hz, 1 H) 5.08 (dd, J=6.24, 3.06 Hz, 1 H) 4.97 (dd, J=6.24, 2.93 Hz, 1 H) 4.37 (q, J=3.26 Hz, 1 H) 3.90 (dd, J=11.25, 3.42 Hz, 1 H) 3.82 (dd, J=11.25, 3.55 Hz, 1 H) 1.67 (s, 3 H) 1.40 (s, 3 H) 0.89-0.92 (m, 9 H) 0.08 (d, J=1.71 Hz, 6 H)

Step 2: Synthesis of ((3aR,4R,6R,6aR)-6-(4-(difluoromethyl)-7H-pyrrolo[2,3-d]pyrimidin-7-yl)-2,2-dimethyltetrahydrofuro[3,4-d][1,3]dioxol-4-yl)methanol (TT-2)

Followed similar procedures to Step 6 of Example 9 (Scheme C) using TT-1 to generate TT-2. LCMS [M+1] 342; $^1$H NMR (400 MHz, CDCl$_3$) δ ppm 8.92 (s, 1 H) 7.44 (d, J=3.67 Hz, 1 H) 6.64-6.96 (m, 2 H) 5.96 (d, J=4.77 Hz, 1 H) 5.28 (t, J=5.38 Hz, 1 H) 5.14 (dd, J=6.11, 1.83 Hz, 1 H) 4.51 (d, J=1.83 Hz, 1 H) 3.99 (dd, J=12.47, 1.83 Hz, 1 H) 3.84 (dd, J=12.47, 2.20 Hz, 1 H) 1.66 (s, 3 H) 1.39 (s, 3 H)

Step 3: Synthesis of (3aS,4S,6R,6aR)-6-(4-(difluoromethyl)-7H-pyrrolo[2,3-d]pyrimidin-7-yl)-2,2-dimethyltetrahydrofuro[3,4-d][1,3]dioxole-4-carboxylic acid (TT-3)

Followed similar procedures to Step 7 of Example 9 (Scheme C) using TT-2 to generate TT-3. LCMS [M+1] 356.

Step 4: Synthesis of (3aS,4S,6R,6aR)-6-(4-(difluoromethyl)-7H-pyrrolo[2,3-d]pyrimidin-7-yl)-N-methoxy-N,2,2-trimethyltetrahydrofuro[3,4-d][1,3]dioxole-4-carboxamide (TT-4)

Followed similar procedures to Step 8 of Example 9 (Scheme C) using TT-3 to generate TT-4. LCMS [M+1] 399; ¹H NMR (400 MHz, CDCl₃) δ ppm 8.93 (s, 1 H) 7.81 (br. s., 1 H) 6.64-6.97 (m, 3 H) 5.19-5.31 (m, 3 H) 3.71 (s, 3 H) 3.20 (s, 3 H) 1.69 (s, 3 H) 1.42 (s, 3 H)

Step 5: Synthesis of ((3aS,4S,6R,6aR)-6-(4-(difluoromethyl)-7H-pyrrolo[2,3-d]pyrimidin-7-yl)-2,2-dimethyltetrahydrofuro[3,4-d][1,3]dioxol-4-yl)(4-fluorophenyl)methanone (TT-5)

Followed similar procedures to Step 9 of Example 9 (Scheme C) with (4-fluorophenyl)magnesium bromide and TT-4 to generate TT-5. LCMS [M+1] 434; ¹H NMR (400 MHz, CDCl₃) δ ppm 8.76 (s, 1 H) 7.78-7.86 (m, 2 H) 7.39 (d, J=3.67 Hz, 1 H) 7.01 (t, J=8.68 Hz, 2 H) 6.57-6.88 (m, 2 H) 6.48 (s, 1 H) 5.71 (dd, J=6.11, 2.08 Hz, 1 H) 5.48 (d, J=5.62 Hz, 1 H) 5.43 (d, J=2.20 Hz, 1 H) 1.71 (s, 3 H) 1.46 (s, 3 H)

Step 6: Synthesis of (R)-((3aR,4R,6R,6aR)-6-(4-(difluoromethyl)-7H-pyrrolo[2,3-d]pyrimidin-7-yl)-2,2-dimethyltetrahydrofuro[3,4-d][1,3]dioxol-4-yl)(4-fluorophenyl)methanol (TT-6)

Followed similar procedures to Step 10 of Example 9 (Scheme C) using TT-5 to generate TT-6. LCMS [M+1] 436.

Step 7: Synthesis of (2R,3R,4S,5R)-2-(4-(difluoromethyl)-7H-pyrrolo[2,3-d]pyrimidin-7-yl)-5-((R)-(4-fluorophenyl)(hydroxy)methyl)tetrahydrofuran-3,4-diol (TT-7)

Followed similar procedures to Step 11 of Example 9 (Scheme C) using TT-6 to generate TT-7. LCMS [M+1] 396; ¹H NMR (700 MHz, DMSO-d₆) δ ppm 8.86 (s, 1 H) 8.00 (br. s., 1 H) 7.36 (t, J=6.60 Hz, 2 H) 7.00-7.27 (m, 3 H) 6.80 (br. s., 1H) 6.20 (d, J=7.70 Hz, 1 H) 5.88 (br. s., 1 H) 5.28 (d, J=6.60 Hz, 1 H) 5.09 (br. s., 1 H) 4.70-4.77 (m, 1 H) 4.48-4.55 (m, 1 H) 4.09 (br. s., 1 H) 3.96 (d, J=5.06 Hz, 1 H)

Example 97

(2R,3R,4S,5R)-2-(4-(difluoromethyl)-7H-pyrrolo[2,3-d]pyrimidin-7-yl)-5-((R)-(3,4-difluorophenyl)(hydroxy)methyl)tetrahydrofuran-3,4-diol (UU-3)

Scheme UU

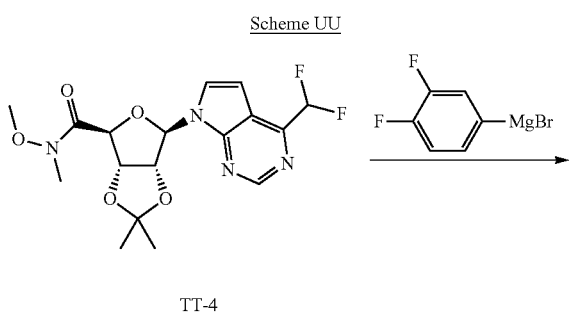

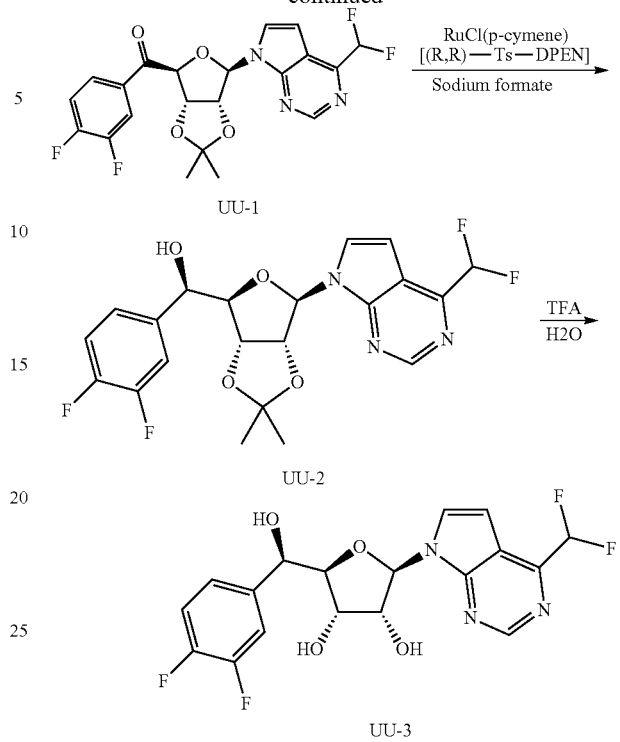

Step 1: Synthesis of ((3aS,4S,6R,6aR)-6-(4-(difluoromethyl)-7H-pyrrolo[2,3-d]pyrimidin-7-yl)-2,2-dimethyltetrahydrofuro[3,4-d][1,3]dioxol-4-yl)(3,4-difluorophenyl)methanone (UU-1)

Followed similar procedures to Step 9 of Example 9 (Scheme C) using TT-4 and (3,4-difluorophenyl)magnesium bromide to generate UU-1. LCMS [M+1] 452; ¹H NMR (400 MHz, CDCl₃) δ ppm 8.76 (s, 1 H) 7.54-7.66 (m, 2 H) 7.36 (d, J=3.67 Hz, 1 H) 7.05-7.14 (m, 1 H) 6.53-6.88 (m, 2 H) 6.46 (s, 1 H) 5.74 (dd, J=6.05, 2.14 Hz, 1 H) 5.50 (d, J=6.11 Hz, 1 H) 5.36 (d, J=2.20 Hz, 1 H) 1.71 (s, 3 H) 1.47 (s, 3 H)

Step 2: Synthesis of (R)-((3aR,4R,6R,6aR)-6-(4-(difluoromethyl)-7H-pyrrolo[2,3-d]pyrimidin-7-yl)-2,2-dimethyltetrahydrofuro[3,4-d][1,3]dioxol-4-yl)(3,4-difluorophenyl)methanol (UU-2)

Followed similar procedures to Step 10 of Example 9 (Scheme C) using UU-1 to generate UU-2. LCMS [M+1] 454.

Step 3: Synthesis of (2R,3R,4S,5R)-2-(4-(difluoromethyl)-7H-pyrrolo[2,3-d]pyrimidin-7-yl)-5-((R)-(3,4-difluorophenyl)(hydroxy)methyl)tetrahydrofuran-3,4-diol (UU-3)

Followed similar procedures to Step 11 of Example 9 (Scheme C) using UU-2 to generate UU-3. LCMS [M+1] 414; ¹H NMR (700 MHz, DMSO-d₆) δ ppm 8.94 (s, 1 H) 8.09 (d, J=3.30 Hz, 1 H) 7.39-7.45 (m, 1 H) 7.33-7.39 (m, 1 H) 7.13-7.33 (m, 2 H) 6.88 (br. s., 1 H) 6.28 (d, J=7.70 Hz, 1 H) 6.08 (d, J=4.62 Hz, 1 H) 5.37 (d, J=6.82 Hz, 1 H) 5.19 (d, J=4.18 Hz, 1 H) 4.82 (t, J=4.51 Hz, 1 H) 4.54-4.64 (m, 1 H) 4.16 (br. s., 1 H) 4.03 (d, J=5.06 Hz, 1 H)

Scheme VV

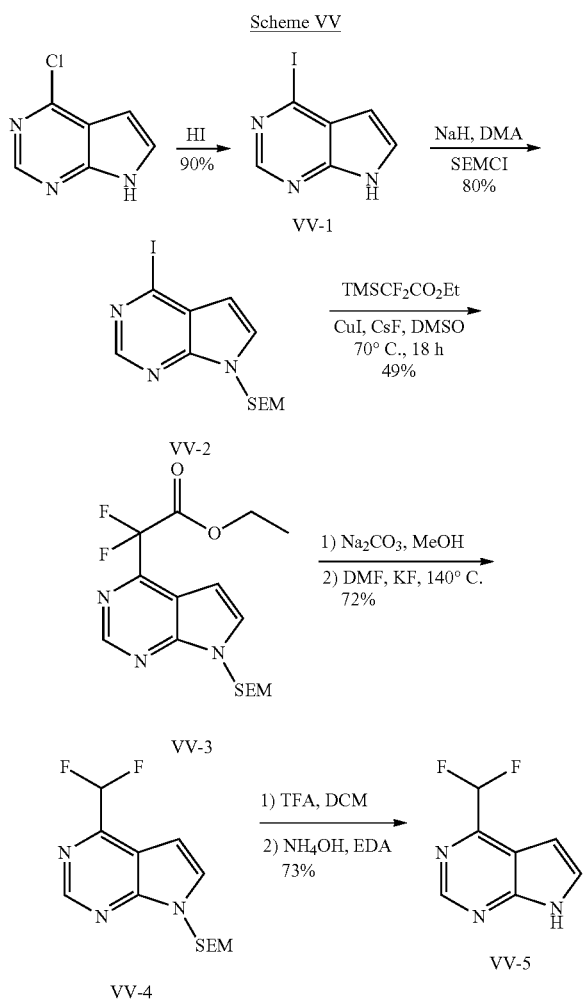

Step 1: 4-iodo-7H-pyrrolo[2,3-d]pyrimidine (W-1)

Hydroiodic acid (10 mL) was cooled in an ice bath then 4-chloro-7H-pyrrolo[2,3D]pyrimidine (565 mg, 3.68 mmol) was added in 5 portions. The yellow slurry was slowly warmed to rt and stirred for 18 h. The mixture was filtered and the solids were rinsed with water then dried on high vacuum to provide 1230 mg (90%) of 4-iodo-7H-pyrrolo[2,3-d]pyrimidine (W-1) as the HI salt. $^1$H NMR (400 MHz, DMSO-d6) δ ppm 12.69 (br. s., 1H), 8.53 (s, 1H), 7.73 (dd, J=2.4, 3.4 Hz, 1H), 6.42 (dd, J=1.8, 3.5 Hz, 1H); LCMS [M+1] 246.

Step 2: 4-iodo-7-((2-(trimethylsilyl)ethoxy)methyl)-7H-pyrrolo[2,3-d]pyrimidine (W-2)

Sodium hydride dispersion (351 mg, 8.77 mmol, 60%) was suspended in DMA (10 mL) then cooled in an ice bath. 4-iodo-7H-pyrrolo[2,3-d]pyrimidine (W-1) (1.79 g, 7.31 mmol) was added drop-wise as a solution in DMA (10 mL) and stirring was continued in the ice bath for 20 min. SEMCL (1350 mg, 7.31 mmol, 1.44 mL) was added dropwise in a solution of DMA (5 mL) and the reaction was slowly warmed to rt and stirred for a total of 2.5 h. The reaction was carefully quenched with water then extracted with EtOAc (2×20). The combined extracts were washed with brine (25 mL) then dried (MgSO4), filtered and concentrated. The crude residue was purified by column chromatography using the ISCO and a 40 g Si column with 0-40% EtOAc/Hep to give 2.2 g (80%) of 4-iodo-7-((2-(trimethylsilyl)ethoxy)methyl)-7H-pyrrolo[2,3-d]pyrimidine (W-2). $^1$H NMR (400 MHz, DMSO-d$_6$) δ ppm 8.52 (s, 1H), 7.83 (d, J=3.7 Hz, 1H), 6.43 (d, J=3.7 Hz, 1H), 5.61 (s, 2H), 3.51 (t, J=7.9 Hz, 2H), 0.82 (t, J=7.9 Hz, 2H), −0.11 (s, 9H); LCMS [M+1] 376.

Step 3: Ethyl 2,2-difluoro-2-(7-((2-(trimethylsilyl)ethoxy)methyl)-7H-pyrrolo[2,3-d]pyrimidin-4-yl)acetate (W-3)

To a vial was added 4-iodo-7-((2-(trimethylsilyl)ethoxy)methyl)-7H-pyrrolo[2,3-d]pyrimidine (W-2) (2000 mg, 5.329 mmol), copper(I)iodide (1220 mg, 6.40 mmol) and potassium fluoride (433 mg, 7.46 mmol). The vial was capped and purged with nitrogen then DMSO (10.7 mL, c=0.5 M) and ethyl difluoro(trimethylsilyl)acetate (2160 mg, 10.7 mmol, 1.74 mL) were added. The reaction was heated to 70° C. for 18 h then diluted with water (10 mL) and EtOAc (30 mL). The mixture was filtered through a bed of Celite then the layers were separated and the organic phase was dried (MgSO$_4$), filtered and concentrated. The crude residue was purified by column chromatography using the ISCO and a 24 g Si column with 0-70% EtOAc/Hep to give 975 mg (49%) of ethyl 2,2-difluoro-2-(7-((2-(trimethylsilyl)ethoxy)methyl)-7H-pyrrolo[2,3-d]pyrimidin-4-yl)acetate (W-3). $^1$H NMR (400 MHz, DMSO-d6) δ ppm 8.96 (s, 1H), 8.01 (d, J=3.7 Hz, 1H), 6.93-6.72 (m, 1H), 5.70 (s, 2H), 4.36 (q, J=7.1 Hz, 2H), 3.54 (t, J=7.9 Hz, 2H), 1.22 (t, J=7.1 Hz, 3H), 0.82 (t, J=8.0 Hz, 2H), −0.11 (s, 9H); LCMS [M+1] 372.

Step 4: 4-(difluoromethyl)-7-((2-(trimethylsilyl)ethoxy)methyl)-7H-pyrrolo[2,3-d]pyrimidine (W-4)

To a solution of ethyl 2,2-difluoro-2-(7-((2-(trimethylsilyl)ethoxy)methyl)-7H-pyrrolo[2,3-d]pyrimidin-4-yl)acetate (W-3) (96.0 mg, 0.26 mmol) in MeOH (1 mL) was added sodium carbonate (100 mg, 1 mmol, 0.5 mL, 2.0 M) at rt. Upon addition of base a precipitate formed. The reaction was stirred at rt for 1 h then concentrated. The residue was taken up in water (15 mL) then the pH was adjusted to 4 with 1 N HCl and extracted with EtOAc (2×15). The combined extracts were dried (MgSO4) filtered and concentrated. The resulting solid was dissolved in DMF (2.0 mL, c=0.086 M) and potassium fluoride (93.8 mg, 1.61 mmol) was added. The reaction was heated to 140° C. for 40 min. The mixture was diluted with water and extracted with EtOAc (2×20 mL). The combined organics were washed with brine then dried (MgSO4), filtered and concentrated to give 56 mg (72%) of 4-(difluoromethyl)-7-((2-(trimethylsilyl)ethoxy)methyl)-7H-pyrrolo[2,3-d]pyrimidine (W-4). $^1$H NMR (400 MHz, DMSO-d6) δ ppm 8.95 (s, 1H), 7.93 (d, J=3.7 Hz, 1H), 7.45-7.04 (m, 1H), 6.91-6.73 (m, 1H), 5.69 (s, 2H), 3.64-3.43 (m, 2H), 0.82 (t, J=7.9 Hz, 2H), −0.10 (s, 9H); LCMS [M+1] 300.

Step 5: 4-(difluoromethyl)-7H-pyrrolo[2,3-d]pyrimidine (W-5)

To a solution of 4-(difluoromethyl)-7-((2-(trimethylsilyl)ethoxy)methyl)-7H-pyrrolo[2,3-d]pyrimidine (W-4) (56 mg, 0.19 mmol) in DCM (1 mL) was added trifluoroacetic acid (740 mg, 6.5 mmol, 0.50 mL). The reaction was stirred at rt for 4 h then concentrated and dried on high vacuum. The yellow solid was dissolved in MeOH (1 mL) then ammonium hydroxide (328 mg, 2.62 mmol, 0.364 mL) and ethylene diamine (5.63 mg, 0.0935 mmol) were added. The reaction was stirred at rt for 2 h then concentrated. The residue was diluted with water and the pH was adjusted to 7 with 1 N HCl then extracted with DCM (3×15 mL). The combined organic extracts were washed with brine, then dried (MgSO4), filtered and concentrated to give 23.0 mg (73%) of 4-(difluoromethyl)-7H-pyrrolo[2,3-d]pyrimidine (W-5). $^1$H NMR (400 MHz, DMSO-d6) δ ppm 12.51 (br. s., 1H), 8.86 (s, 1H), 7.76 (br. s., 1H), 7.18 (t, J=54.2 Hz, 1H), 6.72 (d, J=1.7 Hz, 1H); LCMS [M+1] 170.

Example 98

(2R,3R,4S,5R)-2-(5-fluoro-4-methyl-7H-pyrrolo[2,3-d]pyrimidin-7-yl)-5-((R)-(4-fluorophenyl)(hydroxy)methyl)tetrahydrofuran-3,4-diol (WW-7)

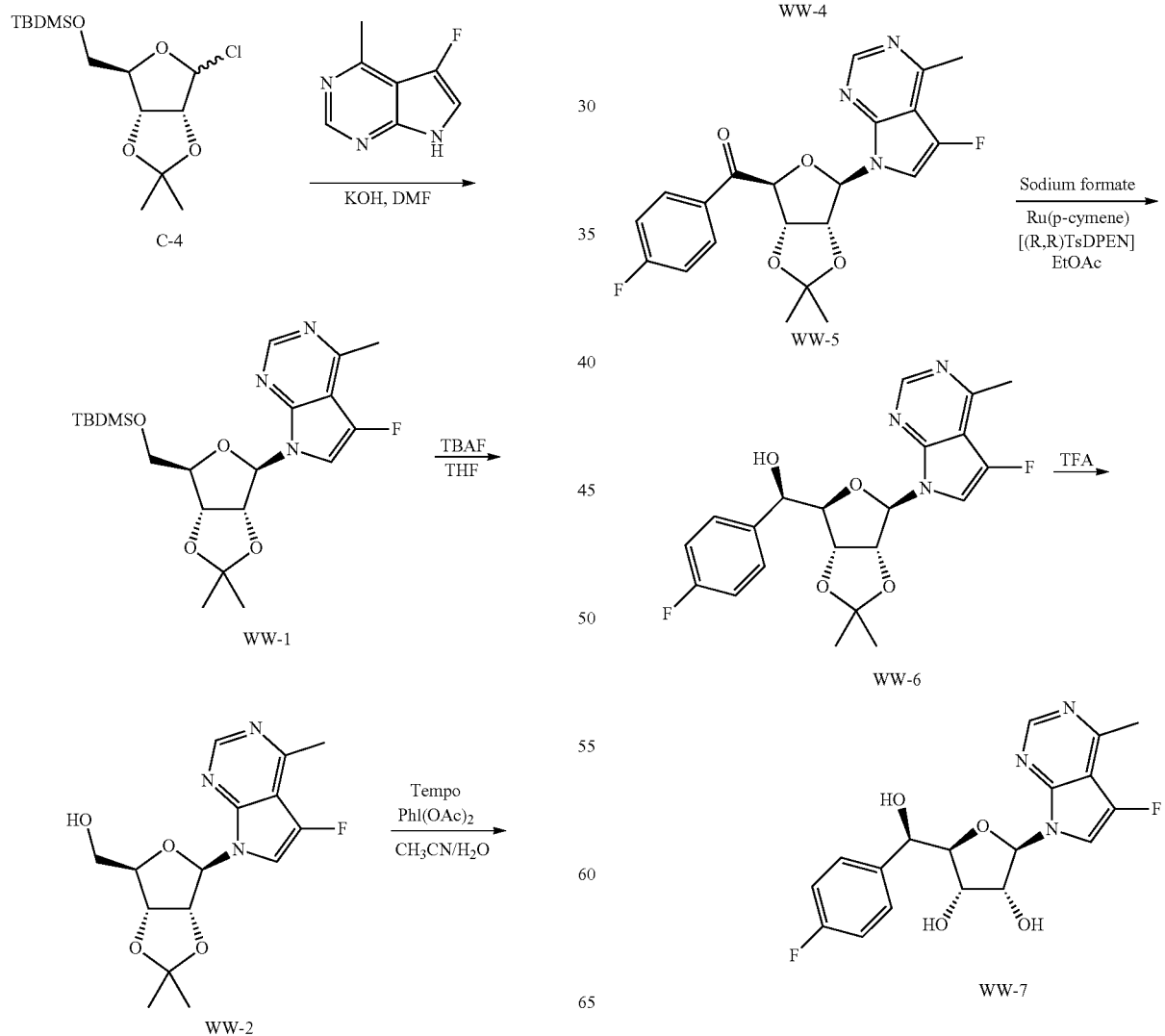

Step 1: Synthesis of 7-((3aR,4R,6R,6aR)-6-(((tert-butyldimethylsilyl)oxy)methyl)-2,2-dimethyltetrahydrofuro[3,4-d][1,3]dioxol-4-yl)-5-fluoro-4-methyl-7H-pyrrolo[2,3-d]pyrimidine (WW-1)

5-fluoro-4-methyl-7H-pyrrolo[2,3-d]pyrimidine (Bioorg. Med. Chem. Lett. 22 (2012) 7742-7747) was used in a similar procedure to Step 4 in Scheme C to generate WW-1. $^1$H NMR (400 MHz, CDCl$_3$) δ ppm 8.76 (s, 1H), 7.26 (br. s., 1H), 6.46 (br. s., 1H), 5.02-4.89 (m, 2H), 4.33 (d, J=2.8 Hz, 1H), 3.91-3.76 (m, 2H), 2.80 (s, 3H), 1.65 (s, 3H), 1.39 (s, 3H), 0.92 (s, 9H), 0.13-0.04 (m, 6H)

Step 2: ((3aR,4R,6R,6aR)-6-(5-fluoro-4-methyl-7H-pyrrolo[2,3-d]pyrimidin-7-yl)-2,2-dimethyltetrahydrofuro[3,4-d][1,3]dioxol-4-yl)methanol (WW-2)

The synthesis followed similar deprotecting procedures as Step 6 in Scheme C using WW-1 to generate WW-2. LCMS [M+1] 324

Step 3: (3aS,4S,6R,6aR)-6-(5-fluoro-4-methyl-7H-pyrrolo[2,3-d]pyrimidin-7-yl)-2,2-dimethyltetrahydrofuro[3,4-d][1,3]dioxole-4-carboxylic acid (WW-3)

The synthesis followed similar oxidation procedures as Step 7 in Scheme C using WW-2 to generate WW-3.

Step 4: (3aS,4S,6R,6aR)-6-(5-fluoro-4-methyl-7H-pyrrolo[2,3-d]pyrimidin-7-yl)-N-methoxy-N,2,2-trimethyltetrahydrofuro[3,4-d][1,3]dioxole-4-carboxamide (WW-4)

The synthesis followed similar amide formation procedures as Step 8 in Scheme C using WW-3 to generate WW-4.

Step 5: ((3aS,4S,6R,6aR)-6-(5-fluoro-4-methyl-7H-pyrrolo[2,3-d]pyrimidin-7-yl)-2,2-dimethyltetrahydrofuro[3,4-d][1,3]dioxol-4-yl)(4-fluorophenyl)methanone (WW-5)

The synthesis followed similar Grignard addition procedures as Step 9 in Scheme C using WW-4 and (4-fluorophenyl)magnesium bromide to generate WW-5.

Step 6: (R)-((3aR,4R,6R,6aR)-6-(5-fluoro-4-methyl-7H-pyrrolo[2,3-d]pyrimidin-7-yl)-2,2-dimethyltetrahydrofuro[3,4-d][1,3]dioxol-4-yl)(4-fluorophenyl)methanol (WW-6)

The synthesis followed similar reduction procedures as Step 10 in Scheme C using WW-5 to generate WW-6. LCMS [M+1] 418

Step 7: (2R,3R,4S,5R)-2-(5-fluoro-4-methyl-7H-pyrrolo[2,3-d]pyrimidin-7-yl)-5-((R)-(4-fluorophenyl)(hydroxy)methyl)tetrahydrofuran-3,4-diol (WW-7)

The synthesis followed similar deprotecting procedures as Step 11 in Scheme C using WW-6 to generate WW-7. LCMS [M+1] 378; $^1$H NMR (400 MHz, DMSO-d$_6$) δ ppm 8.71 (s, 1H), 7.81 (s, 1H), 7.43 (dd, J=5.9, 8.4 Hz, 2H), 7.14 (t, J=8.8 Hz, 2H), 6.24 (d, J=7.8 Hz, 1H), 5.96 (d, J=4.3 Hz, 1H), 5.34 (d, J=6.8 Hz, 1H), 5.16 (d, J=4.0 Hz, 1H), 4.78 (t, J=5.0 Hz, 1H), 4.54-4.44 (m, 1H), 4.13 (t, J=4.4 Hz, 1H), 3.99 (d, J=5.3 Hz, 1H), 2.73 (s, 3H)

Example 99

(2R,3R,4S,5R)-2-(2,4-dimethyl-7H-pyrrolo[2,3-d]pyrimidin-7-yl)-5-((R)-(4-fluorophenyl)(hydroxy)methyl)tetrahydrofuran-3,4-diol (XX-8)

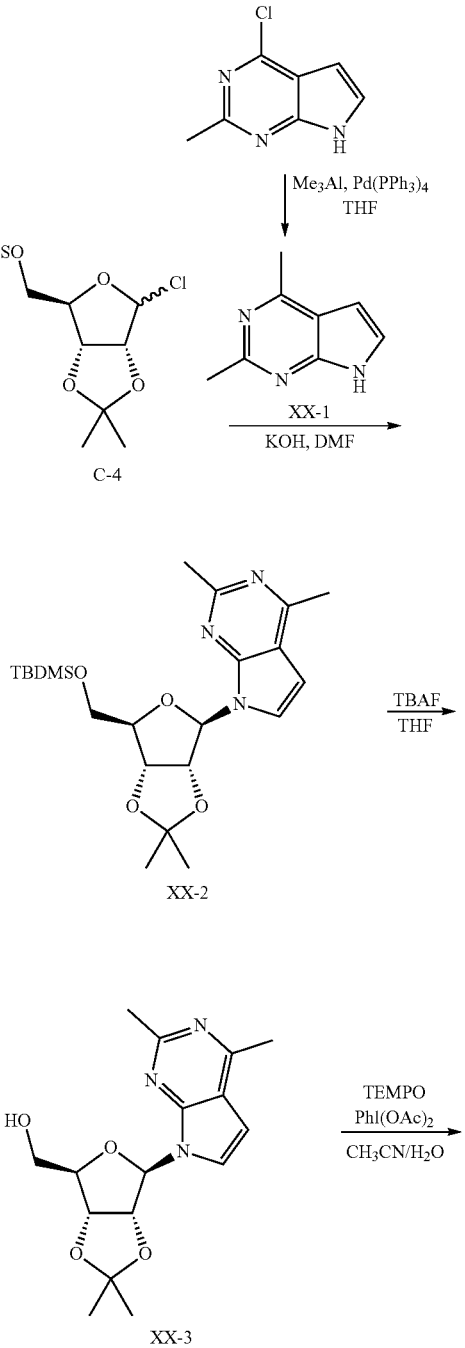

Scheme XX

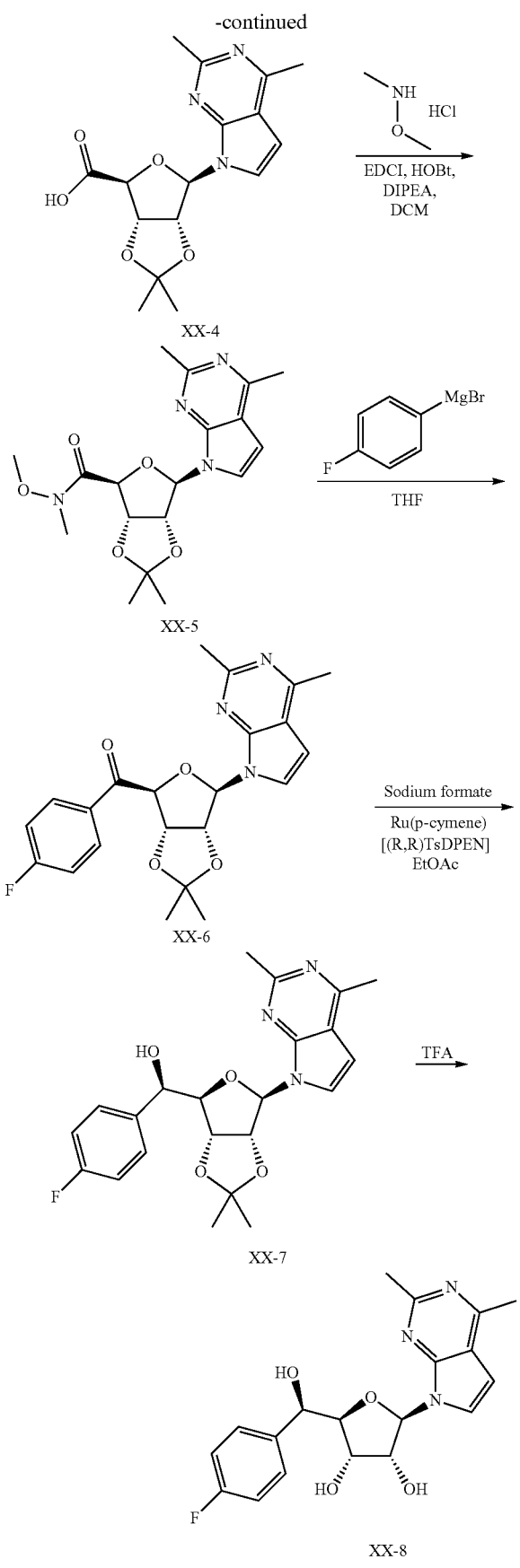

Step 1: Synthesis of 2,4-dimethyl-7H-pyrrolo[2,3-d]pyrimidine (XX-1)

To Pd(PPh$_3$)$_4$(517 mg, 0.448 mmol) was added a solution of 4-chloro-2-methyl-7H-pyrrolo[2,3-d]pyrimidine (*Journal of Medicinal Chemistry*, 2014, 57, 1097-1110) (1.5 g, 8.95 mmol) in dry THF (15 mL). The suspension was degassed with N$_2$ four times. A 2M solution of trimethylaluminum (8.95 mL, 17.9 mmol) was added to the above mixture at ice-water, after the addition, the yellow solution was heated at 80° C. for 16 h. TLC (DCM/MeOH=20:1) showed SM was consumed completely and a main spot was formed. The mixture was quenched with cooled aq Rochelle salt (15 mL) in ice water very carefully, lots of gas was generated, then diluted with water and EtOAc, the solution was filter through celite. The water phase was re-extracted with EtOAc (6 mL×3). The extracts were washed with brine (50 mL), dried over Na$_2$SO$_4$ and concentrated in vacuo to afford crude product, which was purified by flash biotage eluted with DCM/MeOH=1-5% to afford XX-1 (0.9 g, 68.3%) as yellow solid. $^1$H NMR (400 MHz, DMSO-d$_6$) δ ppm 11.74 (br. s., 1H), 7.35 (br. s., 1H), 6.54 (br. s., 1H), 2.59 (s, 3H), 2.57 (s, 3H)

Step 2: Synthesis of 7-((3aR,4R,6R,6aR)-6-(((tert-butyldimethylsilyl)oxy)methyl)-2,2-dimethyltetrahydrofuro[3,4-d][1,3]dioxol-4-yl)-2,4-dimethyl-7H-pyrrolo[2,3-d]pyrimidine (XX-2)

2,4-dimethyl-7H-pyrrolo[2,3-d]pyrimidine (XX-1) was used in a similar procedure to Step 4 in Scheme C to generate XX-2.

Step 3: Synthesis of ((3aR,4R,6R,6aR)-6-(2,4-dimethyl-7H-pyrrolo[2,3-d]pyrimidin-7-yl)-2,2-dimethyltetrahydrofuro[3,4-d][1,3]dioxol-4-yl)methanol (XX-3)

The synthesis followed similar deprotecting procedures as Step 6 in Scheme C using XX-2 to generate XX-3. LCMS [M+1] 320.

Step 4: Synthesis of (3aS,4S,6R,6aR)-6-(2,4-dimethyl-7H-pyrrolo[2,3-d]pyrimidin-7-yl)-2,2-dimethyltetrahydrofuro[3,4-d][1,3]dioxole-4-carboxylic acid (XX-4)

The synthesis followed similar oxidation procedures as Step 7 in Scheme C using XX-3 to generate XX-4. LCMS [M+1] 334.

Step 5: Synthesis of (3aS,4S,6R,6aR)-6-(2,4-dimethyl-7H-pyrrolo[2,3-d]pyrimidin-7-yl)-N-methoxy-N,2,2-trimethyltetrahydrofuro[3,4-d][1,3]dioxole-4-carboxamide (XX-5)

The synthesis followed similar amide formation procedures as Step 8 in Scheme C using XX-4 to generate XX-5.

Step 6: Synthesis of ((3aS,4S,6R,6aR)-6-(2,4-dimethyl-7H-pyrrolo[2,3-d]pyrimidin-7-yl)-2,2-dimethyltetrahydrofuro[3,4-d][1,3]dioxol-4-yl)(4-fluorophenyl)methanone (XX-6)

The synthesis followed similar Grignard addition procedures as Step 9 in Scheme C using XX-5 and (4-fluorophenyl)magnesium bromide to generate XX-6.

Step 7: Synthesis of (R)-((3aR,4R,6R,6aR)-6-(2,4-dimethyl-7H-pyrrolo[2,3-d]pyrimidin-7-yl)-2,2-dimethyltetrahydrofuro[3,4-d][1,3]dioxol-4-yl)(4-fluorophenyl)methanol (XX-7)

The synthesis followed similar reduction procedures as Step 10 in Scheme C using XX-6 to generate XX-7. LCMS [M+1] 414.

Step 8: Synthesis of (2R,3R,4S,5R)-2-(2,4-dimethyl-7H-pyrrolo[2,3-d]pyrimidin-7-yl)-5-((R)-(4-fluorophenyl)(hydroxy)methyl)tetrahydrofuran-3,4-diol (XX-8)

The synthesis followed similar procedures as Step 11 in Scheme C using XX-7 to generate XX-8. LCMS [M+1] 374; $^1$H NMR (400 MHz, DMSO-$d_6$) δ ppm 7.68-7.67 (m, 1H), 7.46-7.42 (m, 2H), 7.17-7.12 (m, 2H), 6.71-6.70 (m, 1H), 6.20-6.19 (m, 1H), 6.11-6.09 (m, 1H), 5.27-5.26 (m, 1H), 5.11-5.10 (m, 1H), 4.83-4.80 (m, 1H), 4.66-4.61 (m, 1H), 4.11-4.10 (m, 1H), 4.01-4.00 (m, 1H), 2.62 (s, 3H), 2.61 (s, 3H)

Example 100

(2R,3S,4R,5R)-2-(4-fluorobenzyl)-5-(4-methyl-7H-pyrrolo[2,3-d]pyrimidin-7-yl)tetrahydrofuran-3,4-diol (YY-7)

Scheme YY

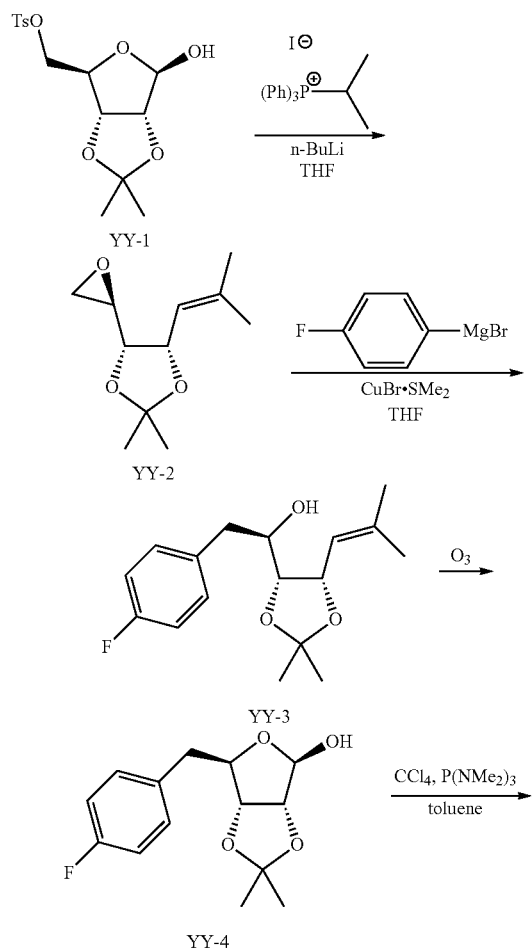

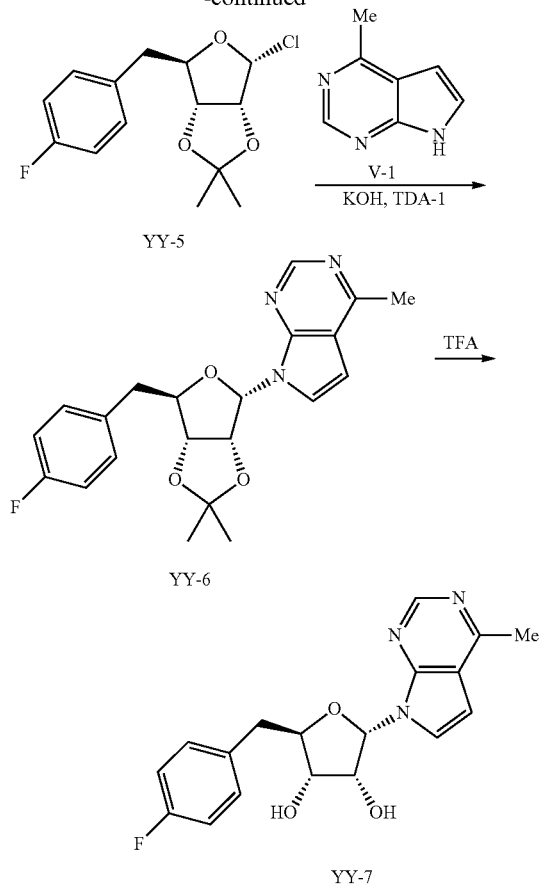

Step 1: Synthesis of (4S,5S)-2,2-dimethyl-4-(2-methylprop-1-en-1-yl)-5-((R)-oxiran-2-yl)-1,3-dioxolane (YY-2)

To an oven dried round bottom flask, equipped with a magnetic stirbar and cooled in a desiccator, was added Triphenylisopropylphosphonium iodide (13.2 g, 30.6 mmol) and THF (23 mL). The solution was cooled to 0° C. followed by the dropwise addition of n-Butyl lithium (12 mL, 30 mmol, 2.5M in Hexane). The reaction was stirred at 0° C. for 15 minutes at which point a dark red solution of ylide was obtained. To the ylide solution was added crude YY-1 (*Tetrahedron Letters*, 1992, 33, 3567) (4.58 g) as a solution in THF (15 mL). The ice bath was removed and the reaction was allowed to warm gradually to room temperature. After 5 hours, TLC analysis indicated no starting material remained. The reaction was quenched by the slow addition of water (~100 mL) triggering precipitation of triphenylphosphine oxide. The solids were filtered through a pad of celite and rinsed with several portions of MTBE. The filtrate was transferred to a separatory funnel and the phases were separated. The aqueous phase was extracted with 3 portions MTBE. The combined organic extracts were dried (MgSO$_4$), filtered, and concentrated under vacuum. The crude residue was purified via flash column chromatography (40 g SiO$_2$, Isco, 100% Hept. to 40% MTBE/Hept., 20 mL fractions) to afford the title compound YY-2 (0.56 g, 21% over 3 steps from d-ribose) as a pale yellow oil. TLC (30% EtOAc/Hept): Rf=0.34 (product visualized with KMnO$_4$ stain); $^1$H NMR (400 MHz, CHLOROFORM-d) δ ppm 5.36-5.48 (m, 1H), 5.01 (dd, J=6.24, 8.80 Hz, 1H), 3.68-3.74 (m, 1H), 3.00 (ddd, J=2.69, 4.07, 7.06 Hz, 1H), 2.83 (dd, J=3.97, 5.07 Hz, 1H), 2.67 (dd, J=2.57, 5.01 Hz, 1H), 1.83 (d, J=0.86 Hz, 3H), 1.77 (d, J=1.22 Hz, 3H), 1.52 (s, 3H), 1.40 (s, 3H).

Step 2: Synthesis of (R)-1-((4R,5S)-2,2-dimethyl-5-(2-methylprop-1-en-1-yl)-1,3-dioxolan-4-yl)-2-(4-fluorophenyl)ethan-1-ol (YY-3)

To an oven dried reaction vial, equipped with a magnetic stirbar and cooled under a stream of argon, was added Copper bromide-dimethyl sulfide complex (697 mg, 3.39 mmol). The vial was purged with a stream of argon for ~5 minutes and THF (8 mL) was added. The solution was cooled to 0° C. and 4-Fluorophenylmagnesium bromide (7.0 mL, 7.0 mmol, 1.0M in THF) was added. The solution was stirred at 0° C. for 30 minutes followed by the addition of YY-2 (0.56 g, 2.8 mmol) as a solution in THF (6 mL). The reaction was stirred at 0° C. for an additional 30 minutes at which point TLC analysis showed no remaining starting material. The reaction was quenched by the dropwise addition of sat. $NH_4Cl$ aq. and transferred to a separatory funnel with water. The aqueous solution was extracted with 4 portions of EtOAc. The combined organic extracts were dried ($MgSO_4$), filtered, and concentrated under vacuum. The crude residue was purified via flash column chromatography (24 g $SiO_2$, Isco, 100% Hept. to 40% MTBE/Hept., 9 mL fractions) to afford the title compound YY-3 (0.57 g, 69%) as a colorless oil. TLC (20% EtOAc/Hept.): Rf=0.34; $^1$H NMR (400 MHz, CHLOROFORM-d) δ ppm 7.24 (dd, J=5.62, 8.31 Hz, 2H), 6.95-7.06 (m, 3H), 5.40 (d, J=9.29 Hz, 1H), 4.96 (dd, J=6.30, 9.23 Hz, 1H), 3.94 (dd, J=6.30, 8.62 Hz, 1H), 3.83 (dt, J=2.81, 8.56 Hz, 1H), 3.07 (dd, J=2.57, 14.06 Hz, 1H), 2.68 (dd, J=8.56, 13.94 Hz, 1H), 1.78 (s, 3H), 1.74 (s, 3H), 1.52 (s, 3H), 1.40 (s, 3H).

Step 3: Synthesis of (3aR,4R,6R,6aR)-6-(4-fluorobenzyl)-2,2-dimethyltetrahydrofuro[3,4-d][1,3]dioxol-4-ol (YY-4)

To a round bottom flask, equipped with a magnetic stirbar and containing YY-3 (0.57 g, 1.9 mmol), was added DCM (10 mL) and MeOH (10 mL). The solution was cooled to −78° C. and sparged with a stream of ozone. After continuous sparging for 1 hour, TLC analysis showed no remaining starting material. The reaction was sparged with nitrogen for ~15 minutes followed by the addition of dimethylsulfide (1.4 mL, 19 mmol). The ice bath was removed and the solution was allowed to warm gradually to room temperature overnight. The solution was concentrated under vacuum and the crude residue was purified via flash column chromatography (12 g $SiO_2$, Isco, 100% Hept. to 40% EtOAc/Hept., 9 mL fractions) to afford the title compound YY-4 (0.42 g, 81%) as a white solid. $^1$H NMR (400 MHz, CHLOROFORM-d) δ ppm 7.16-7.24 (m, 2H), 6.96-7.05 (m, 2H), 5.48 (d, J=2.57 Hz, 1H), 4.71 (d, J=5.87 Hz, 1H), 4.67 (d, J=5.75 Hz, 1H), 4.45 (t, J=7.89 Hz, 1H), 3.01 (dd, J=8.44, 14.43 Hz, 1H), 2.91 (dd, J=7.58, 13.82 Hz, 1H), 2.65 (d, J=2.81 Hz, 1H), 1.47 (s, 3H), 1.32 (s, 3H).

Step 4: Synthesis of (3aR,4R,6R,6aR)-4-chloro-6-(4-fluorobenzyl)-2,2-dimethyltetrahydrofuro[3,4-d][1,3]dioxole (YY-5)

To an oven dried reaction vial, equipped with a magnetic stirbar and cooled under a stream of argon, was added YY-4 (226 mg, 0.841 mmol), toluene (1.9 mL) and carbon tetrachloride (0.11 mL, 1.09 mmol). The solution was cooled to −50° C. and hexamethyltriaminophosphine (0.23 mL, 1.26 mmol) was added dropwise. Upon completing the addition the vial was transferred to an ice bath and the reaction was stirred at 0° C. for 1 hour. The reaction was quenched with ice cold brine (0.5 mL) and the organic phase was separated via pipette. The organic phase was dried ($MgSO_4$) and the crude solution of chloride YY-5 was used immediately in the next step without further purification.

Step 5: Synthesis of 7-((3aR,4R,6R,6aR)-6-(4-fluorobenzyl)-2,2-dimethyltetrahydrofuro[3,4-d][1,3]dioxol-4-yl)-4-methyl-7H-pyrrolo[2,3-d]pyrimidine (YY-6)

To an oven dried reaction vial, equipped with a magnetic stirbar and cooled under a stream of argon, was added pyrrolopyrimidine V-1 (75.0 mg, 0.56 mmol), potassium hydroxide (70.7 mg, 1.26 mmol), toluene (2.3 mL), acetonitrile (0.38 mL) and TDA-1 (0.11 mL, 0.34 mmol). The solution was stirred for 30 minutes at room temperature at which point the crude solution of chloride YY-5 was added to the vial. The reaction was stirred at room temperature for 24 hours. The reaction was quenched with sat. $NH_4Cl$ aq. and transferred to a separatory funnel with EtOAc. The product was extracted with 3 portions EtOAc and the combined organic phases were dried ($MgSO_4$), filtered, and concentrated under vacuum. The crude residue was purified via flash column chromatography (12 g $SiO_2$, Isco, 100% Hept. to 100% EtOAc, 9 mL fractions) to afford the title compound YY-6 (120 mg, 55% over 2 steps) as a yellow gum. LCMS [M+H]384; $^1$H NMR (400 MHz, CHLOROFORM-d) δ ppm 8.87 (s, 1H), 7.04-7.18 (m, 2H), 6.88-7.03 (m, 2H), 6.72 (br. s, 1H), 6.25 (d, J=2.57 Hz, 1H), 5.15-5.29 (m, 1H), 4.86 (dd, J=6.30, 4.46 Hz, 1H), 4.34-4.47 (m, 1H), 2.83-3.12 (m, 5H), 1.62 (s, 3H), 1.37 (s, 3H).

Step 6: Synthesis of (2R,3S,4R,5R)-2-(4-fluorobenzyl)-5-(4-methyl-7H-pyrrolo[2,3-d]pyrimidin-7-yl)tetrahydrofuran-3,4-diol (YY-7)

To a reaction vial, equipped with a magnetic stirbar and containing YY-6 (120 mg, 0.313 mmol) was added water (2.0 mL) and trifluoroacetic acid (1.0 mL). The reaction was stirred at room temperature for 30 minutes. The reaction was transferred to a separatory funnel with EtOAc. The organic phase was washed with 3 portions of sat. $NaHCO_3$ aq., dried ($MgSO_4$), filtered, and concentrated under vacuum. The crude residue was purified via supercritical fluid chromatography (ZymorSpher HADP column, 4.6×150 mm column with 10% to 50% MeOH, 3.0 mL/min.) to afford the title compound YY-7 (35.2 mg, 33%) as a white solid. LCMS [M+H]344; $^1$H NMR (400 MHz, METHANOL-d4) δ ppm 8.61 (s, 1H), 7.36 (d, J=3.79 Hz, 1H), 7.23 (dd, J=5.50, 8.44 Hz, 2H), 6.95 (t, J=8.80 Hz, 2H), 6.73 (d, J=3.67 Hz, 1H), 6.21 (d, J=4.65 Hz, 1H), 5.49 (s, 1H), 4.47 (t, J=4.89 Hz, 1H), 4.12-4.26 (m, 2H), 3.09 (dd, J=4.65, 14.18 Hz, 1H), 2.99 (dd, J=6.36, 13.94 Hz, 1H), 2.72 (s, 3H); $^{19}$F PCD NMR (376 MHz, METHANOL-d4) δ ppm−119.11 (s, 1F).

Example 101

(2R,3R,4S,5R)-2-(4-amino-5-fluoro-7H-pyrrolo[2,3-d]pyrimidin-7-yl)-5-(4-fluorobenzyl)tetrahydrofuran-3,4-diol (ZZ-3)

Scheme ZZ

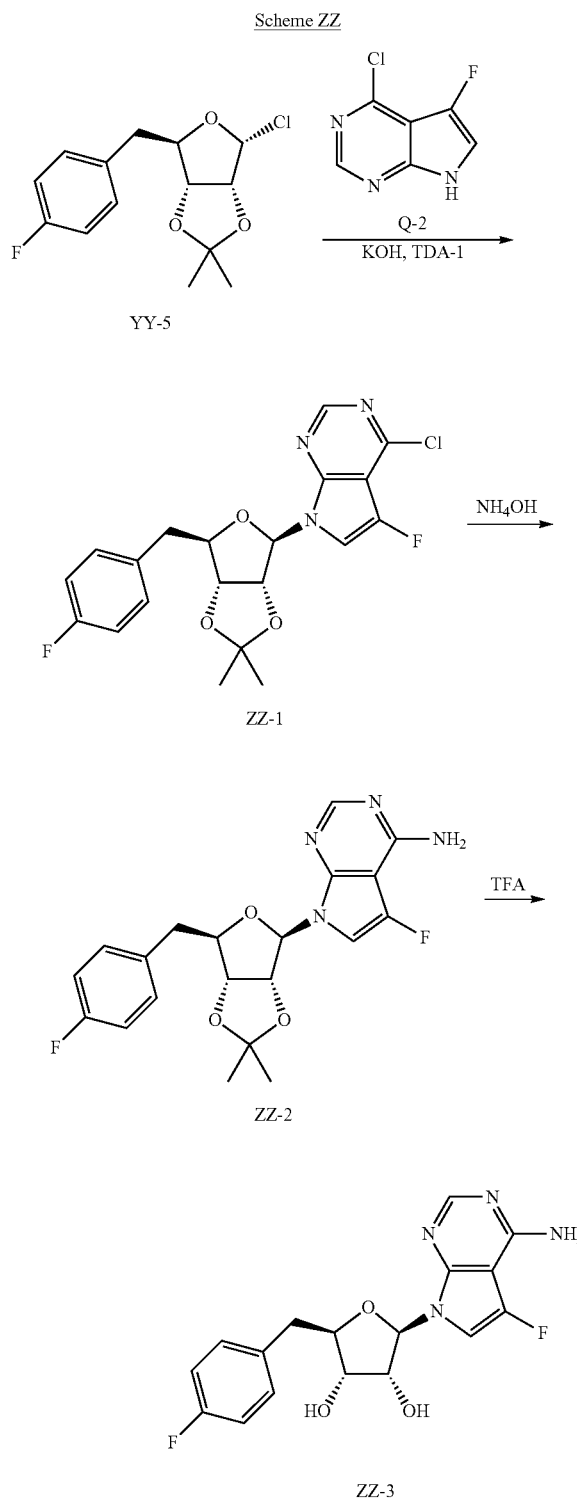

Step 1: Synthesis of 4-chloro-5-fluoro-7-((3aR,4R,6R,6aR)-6-(4-fluorobenzyl)-2,2-dimethyltetrahydrofuro[3,4-d][1,3]dioxol-4-yl)-7H-pyrrolo[2,3-d]pyrimidine (ZZ-1)

To an oven dried reaction vial, equipped with a magnetic stirbar and cooled under a stream of argon, was added pyrolopyrimidine Q-2 (64 mg, 0.37 mmol), potassium hydroxide (46.9 mg, 0.835 mmol), toluene (1.59 mL), acetonitrile (0.26 mL) and TDA-1 (71 μL, 0.223 mmol). The solution was allowed to stir for 30 minutes at room temperature at which point a crude solution of chloride YY-5 was added. The reaction was stirred at room temperature for 15 hours. The reaction was quenched with half sat. NH$_4$Cl aq. and transferred to a separatory funnel with EtOAc. The product was extracted with 3 portions of EtOAc and the combined organic extracts were dried (MgSO$_4$), filtered, and concentrated under vacuum. The crude residue was purified via flash column chromatography (12 g SiO$_2$, Isco, 100% Hept. to 100% EtOAc, 9 mL fractions) to afford the title compound ZZ-1 (60.5 mg, 38% over 2 steps) as a colorless gum. LCMS [M+H]422; $^1$H NMR (400 MHz, CHLOROFORM-d) δ ppm 8.66 (s, 1H), 7.12 (dd, J=5.44, 8.50 Hz, 2H), 6.97-7.01 (m, 2H), 6.95 (d, J=2.81 Hz, 1H), 6.21 (d, J=2.57 Hz, 1H), 5.13 (dd, J=2.81, 6.60 Hz, 1H), 4.80 (dd, J=4.34, 6.54 Hz, 1H), 4.35-4.42 (m, 1H), 2.98 (dq, J=6.30, 14.28 Hz, 2H), 1.61 (s, 3H), 1.36 (s, 3H).

Step 2: Synthesis of 5-fluoro-7-((3aR,4R,6R,6aR)-6-(4-fluorobenzyl)-2,2-dimethyltetrahydrofuro[3,4-d][1,3]dioxol-4-yl)-7H-pyrrolo[2,3-d]pyrimidin-4-amine (ZZ-2)

A microwave vial, equipped with a magnetic stirbar and containing ZZ-1 (60.5 mg, 0.143 mmol), was charged with dioxane (0.36 mL) and ammonium hydroxide (0.36 mL). The vial was sealed with a teflon cap and placed in a heating block. The reaction was heated to 120° C. for 22 hours. The reaction was lyophilized and the crude product ZZ-2 (65.7 mg) was used in the next step without further purification. LCMS [M+H]403

Step 3: Synthesis of (2R,3R,4S,5R)-2-(4-amino-5-fluoro-7H-pyrrolo[2,3-d]pyrimidin-7-yl)-5-(4-fluorobenzyl)tetrahydrofuran-3,4-diol (ZZ-3)

To a reaction vial, equipped with a magnetic stirbar and containing crude ZZ-2 (65.7 mg), was added water (0.7 mL) followed by the dropwise addition of trifluoroacetic acid (0.7 mL). The reaction was stirred at room temperature for 3 hours. The reaction was transferred to a separatory funnel with EtOAc and the phases were separated. The organic phase was washed with 3 portions sat. NaHCO$_3$ aq. and the combined aqueous washes were back extracted with 1 portion of EtOAc. The combined organic extracts were dried (MgSO$_4$), filtered, and concentrated under vacuum. The crude residue was purified via supercritical fluid chromatography (ZymorSpher HADP 150×21.2 mm column, 20-30% MeOH, 60 mL/min) to afford the title compound ZZ-3 (19.6 mg) as a white solid. LCMS [M+H]363; $^1$H NMR (700 MHz, DMSO-d6) b ppm 8.05 (s, 1H), 7.23 (dd, J=5.72, 8.46 Hz, 2H), 7.20 (d, J=1.37 Hz, 1H), 7.07 (t, J=8.88 Hz, 2H), 6.97 (br. s., 2H), 6.06 (d, J=5.12 Hz, 1H), 4.31 (t, J=5.47 Hz, 1H), 3.97-4.02 (m, 1H), 3.93 (t, J=4.53 Hz, 1H), 2.97 (dd, J=5.04, 14.09 Hz, 1H), 2.87 (dd, J=8.20, 14.18 Hz, 1H).

Example 102

(2R,3R,4S,5R)-2-(4-aminothieno[3,4-d]pyrimidin-7-yl)-5-((R)-(4-fluorophenyl)(hydroxy)methyl)tetrahydrofuran-3,4-diol (AAA-7)

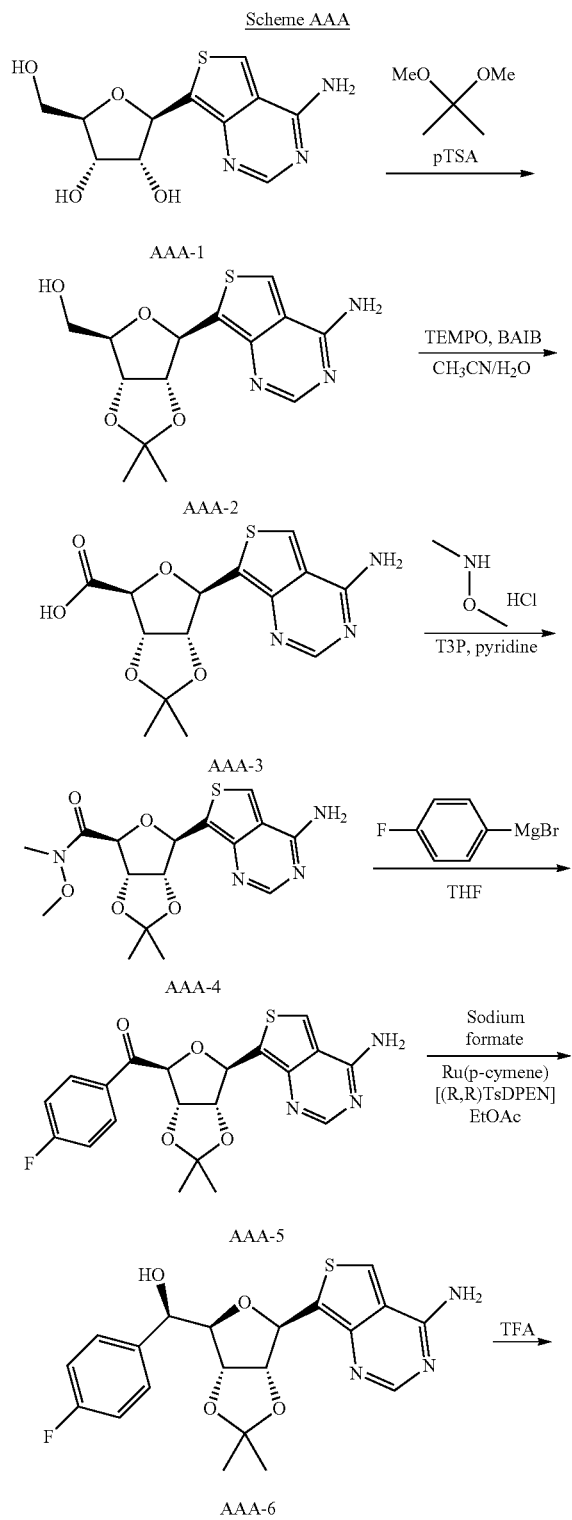

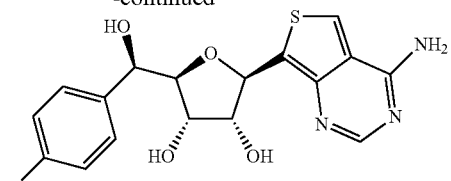

Step 1: Synthesis of ((3aR,4R,6R,6aR)-6-(4-aminothieno[3,4-d]pyrimidin-7-yl)-2,2-dimethyltetrahydrofuro[3,4-d][1,3]dioxol-4-yl)methanol (AAA-2)

To a suspension of AAA-1 (*Journal of American Chemistry Society*, 2011, 133, 14912) (243 mg, 0.858 mmol) in acetone (8.58 mL, 1M) was added dimethyoxypropane (0.737 mL, 6.00 mmol) and PTSA (163 mg, 0.858 mmol) and stirred at room temperature for 16 hours. The reaction was concentrated and purified on an 12 g-ISCO column eluting with 100% EtOAc and 10% MeOH/EtOAc to give a clear gum AAA-2 (80 mg, 29%, beta anomer). LCMS [M+1] 324; $^1$H NMR (400 MHz, MeOD) δ ppm 8.33 (s, 1 H), 8.07 (s, 1 H), 5.49 (d, J=5.26 Hz, 1 H), 4.89-4.95 (m, 1 H), 4.86 (dd, J=6.30, 3.00 Hz, 1 H), 4.23 (d, J=3.18 Hz, 1 H), 3.69-3.82 (m, 2 H), 1.61 (s, 3 H), 1.35 (s, 3 H)

Step 2: Synthesis of (3aS,4S,6R,6aR)-6-(4-aminothieno[3,4-d]pyrimidin-7-yl)-2,2-dimethyltetrahydrofuro[3,4-d][1,3]dioxole-4-carboxylic acid (AAA-3)

In a round bottom flask was added AAA-2 (86 mg, 0.27 mmol), acetonitrile (2.8 mL), and water (0.7 mL). The solution was cooled to 0° C. (ice bath) and diacetoxyiodobenzene (BAIB, 188 mg, 0.585 mmol) followed by TEMPO (8.31 mg, 0.05 mmol) was added and stirred at 0° C. (clear yellow solution). After 2.5 hours LCMS shows full conversion to the acid. The reaction was concentrated and used as crude (AAA-3) for the next reaction (formation of Weinreb amide); LCMS [M+1] 338.

Step 3: Synthesis of (3aS,4S,6R,6aR)-6-(4-aminothieno[3,4-d]pyrimidin-7-yl)-N-methoxy-N,2,2-tri methyltetrahydrofuro[3,4-d][1,3]dioxole-4-carboxamide (AAA-4)

In a round bottom flask was added AAA-3 (80 mg, 0.24 mmol), N,O-dimethylhydroxylamine HCl (115 mg, 1.18 mmol), THF (2 mL), and pyridine (0.095 mL, 1.18 mmol). The reaction was cooled to 0° C. and added T3P (50% in EtOAc, 0.3 mL, 0.5 mmol) dropwise. At the 4th drop (viscous), a gum appeared. Another 5 eq of pyridine was added (0.095 mL, 1.18 mmol). Remove ice bath and stir at room temperature overnight. LCMS shows product mass at a very polar region. Concentrate and use as crude AAA-4 (96 mg) into the next reaction. LCMS [M+1] 381.

Step 4: Synthesis of ((3aS,4S,6R,6aR)-6-(4-aminothieno[3,4-d]pyrimidin-7-yl)-2,2-dimethyltetrahydrofuro[3,4-d][1,3]dioxol-4-yl)(4-fluorophenyl)methanone (AAA-5)

In a dry vial containing the AAA-4 (96 mg, 0.25 mmol) and THF (2 mL), cooled to 0° C. with an ice bath, was added the 4-fluorophenylmagnesium bromide (0.75 mL, 0.756 mmol, 1M in THF) dropwise at 0° C. The reaction was stirred for 16 hours at room temperature. The reaction was diluted with EtOAc and quenched with sat. NH₄Cl. The aqueous layer was extracted with EtOAc (3×10 mL). The combined organics were dried over Na2SO4, filtered and concentrated to an oil. The crude material was purified on an ISCO 12 g column 0-100% EtOAc/heptanes, then 10% MeOH/EtOAc to give AAA-5 as an oil (6 mg, 6%). LCMS [M+1] 416

Step 5-6: Synthesis of (R)-((3aR,4R,6R,6aR)-6-(4-aminothieno[3,4-d]pyrimidin-7-yl)-2,2-dimethyltetrahydrofuro[3,4-d][1,3]dioxol-4-yl)(4-fluorophenyl)methanol (AAA-6) and (2R,3R,4S,5R)-2-(4-aminothieno[3,4-d]pyrimidin-7-yl)-5-((R)-(4-fluorophenyl)(hydroxy)methyl)tetrahydrofuran-3,4-diol (AAA-7)

To a conical bottom microwave vial, equipped with a magnetic stirbar and containing AAA-5 (6 mg, 0.01 mmol) was added sodium formate (40 mg, 0.578 mmol) and the Ru(p-cymene)[(R,R)TsDPEN](0.1 mg, 0.001 mmol). Purge with argon. Water (0.240 mL, purged with argon for 30 min) and EtOAc (0.06 mL, purged with argon for 30 min) were added and stirred at room temp for 24 h. LCMS shows product AAA-6. Concentrate the reaction to dryness to give a brown oil. Add 2 mL of TFA and 1 mL of water and stir at room temp for 1 hour. LCMS shows product AAA-7. Concentrated and free base with an SCX column (eluting with MeOH, then 10% NH₃/MeOH). The crude product was then purified by SFC to give AAA-7. LCMS [M+1] 378.

Example 103

(2R,3R,4S,5S)-2-(4-amino-7H-pyrrolo[2,3-d]pyrimidin-7-yl)-5-((R)-1-(3,4-difluorophenyl)-1-hydroxyethyl)tetrahydrofuran-3,4-diol (BBB-4)

Scheme BBB

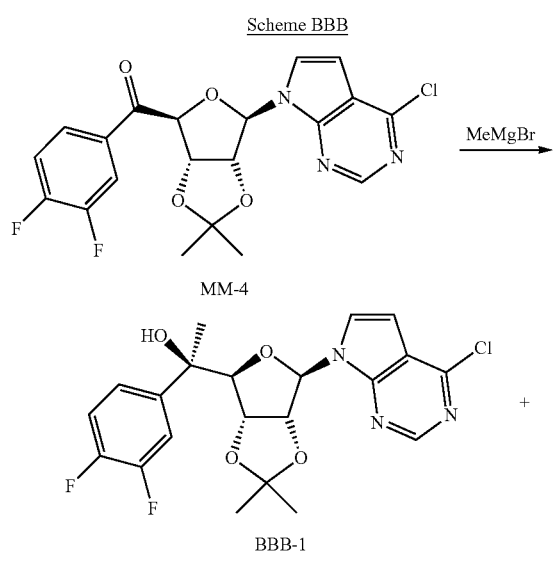

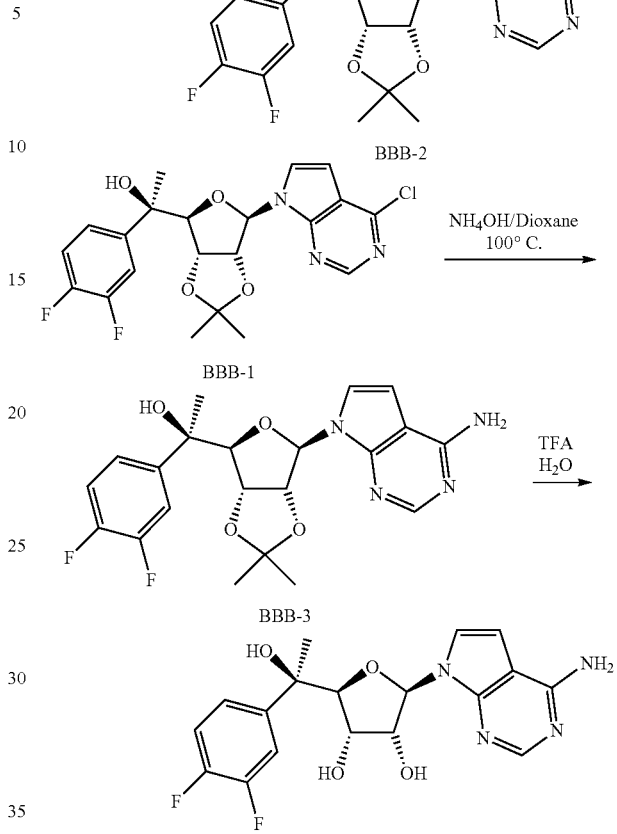

Step 1: Synthesis of (R)-1-((3aR,4S,6R,6aR)-6-(4-chloro-7H-pyrrolo[2,3-d]pyrimidin-7-yl)-2,2-dimethyltetrahydrofuro[3,4-d][1,3]dioxol-4-yl)-1-(3,4-difluorophenyl)ethan-1-ol (BBB-1) and (S)-1-((3aR,4S,6R,6aR)-6-(4-chloro-7H-pyrrolo[2,3-d]pyrimidin-7-yl)-2,2-dimethyltetrahydrofuro[3,4-d][1,3]dioxol-4-yl)-1-(3,4-difluorophenyl)ethan-1-ol (BBB-2)

To a solution of ((3aS,4S,6R,6aR)-6-(4-chloro-7H-pyrrolo[2,3-d]pyrimidin-7-yl)-2,2-dimethyltetrahydrofuro[3,4-d][1,3]dioxol-4-yl)(3,4-difluorophenyl)methanone (MM-4) (200 mg, 0.456 mmol) in dry THF (4.5 mL, c=0.10 M) at rt was added methylmagnesium bromide (0.765 mL, 2.29 mmol, 3.0 M), the resulting solution was stirred at rt for 0.5 h. The mixture was added NH₄Cl aq (40 mL) slowly, the mixture was extracted with EtOAc (25 mL×3). The extract was combined and washed with brine (25 mL), dried over Na₂SO₄ and concentrated in vacuo, purified by column chromatography with 30% EtOAc/heptane, to give 170 mg (82% yield) (R)-1-((3aR,4S,6R,6aR)-6-(4-chloro-7H-pyrrolo[2,3-d]pyrimidin-7-yl)-2,2-dimethyltetrahydrofuro[3,4-d][1,3]dioxol-4-yl)-1-(3,4-difluorophenyl)ethan-1-ol (BBB-1) as white solid. LCMS [M+1] 452; ¹H NMR (400 MHz, CDCl₃) δ ppm 1.22 (s, 3 H) 1.51 (s, 3 H) 1.58 (s, 4 H) 4.67 (d, J=6.11 Hz, 1 H) 5.12-5.17 (m, 1 H) 5.86 (d, J=5.26 Hz, 1 H) 6.68 (d, J=3.67 Hz, 1 H) 7.18-7.22 (m, 1 H) 7.22-7.26

(m, 1 H) 7.32-7.36 (m, 1 H) 7.44-7.52 (m, 1 H) 8.72 (s, 1 H). Eluting with 40% EtOAc/heptane gave 26 mg (13% yield) (S)-1-((3aR,4S,6R,6aR)-6-(4-chloro-7H-pyrrolo[2,3-d]pyrimidin-7-yl)-2,2-dimethyltetrahydrofuro[3,4-d][1,3]dioxol-4-yl)-1-(3,4-difluorophenyl)ethan-1-ol (BBB-2) as oil.

LCMS [M+1] 452; $^1$H NMR (400 MHz, CDCl$_3$) δ ppm 1.41 (s, 3 H) 1.59 (s, 3 H) 1.67 (s, 3 H) 4.64 (d, J=2.57 Hz, 1 H) 5.14 (dd, J=6.66, 4.46 Hz, 1 H) 5.30 (dd, J=6.72, 2.57 Hz, 1 H) 5.78 (d, J=4.40 Hz, 1 H) 6.58 (d, J=3.67 Hz, 1 H) 6.99-7.08 (m, 1 H) 7.09-7.15 (m, 1 H) 7.20-7.26 (m, 2 H) 8.71 (s, 1 H).

Step 2: Synthesis of (R)-1-((3aR,4S,6R,6aR)-6-(4-amino-7H-pyrrolo[2,3-d]pyrimidin-7-yl)-2,2-dimethyltetrahydrofuro[3,4-d][1,3]dioxol-4-yl)-1-(3,4-difluorophenyl)ethan-1-ol (BBB-3)

(R)-1-((3aR,4S,6R,6aR)-6-(4-chloro-7H-pyrrolo[2,3-d]pyrimidin-7-yl)-2,2-dimethyltetrahydrofuro[3,4-d][1,3]dioxol-4-yl)-1-(3,4-difluorophenyl)ethan-1-ol (170 mg, 0.376 mmol) was dissolved in 5 mL dioxane, 5 mL ammonium hydroxide was added, the reaction vessel was sealed and heated at 100° C. overnight. The reaction mixture was concentrated, the residue was added H$_2$O, extracted with EtOAc, purified by column chromatography with 70-80% EtOAc/heptane to give 159 mg (100% yield) title compound as colorless oil (BBB-3) which solidified upon vacuum.

LCMS [M+1] 433; $^1$H NMR (400 MHz, CDCl$_3$) δ ppm 1.21 (s, 3 H) 1.51 (s, 3 H) 1.57 (s, 3 H) 4.49-4.56 (m, 1H) 4.63-4.70 (m, 1 H) 5.16 (t, J=5.62 Hz, 1 H) 5.81 (d, J=5.26 Hz, 1 H) 5.90 (br. s., 2 H) 6.51 (d, J=3.55 Hz, 1 H) 7.09 (d, J=3.55 Hz, 1 H) 7.19 (dd, J=9.90, 8.19 Hz, 1 H) 7.23-7.27 (m, 1 H) 7.48 (ddd, J=11.98, 7.76, 2.14 Hz, 1 H) 8.33 (s, 1 H)

Step 3: Synthesis of (2R,3R,4S,5S)-2-(4-amino-7H-pyrrolo[2,3-d]pyrimidin-7-yl)-5-((R)-1-(3,4-difluorophenyl)-1-hydroxyethyl)tetrahydrofuran-3,4-diol (BBB-4)

Followed similar procedures to Steps 11 of Example 9 (Scheme C). LCMS [M+1] 393; 1H NMR (700 MHz, DMSO-d6) δ ppm 1.41 (s, 2 H) 3.68 (d, J=4.84 Hz, 1 H) 4.13 (s, 1 H) 4.58 (br. s., 1 H) 4.86 (br. s., 1 H) 5.17 (br. s., 1 H) 5.86 (d, J=7.92 Hz, 1 H) 6.67 (d, J=3.52 Hz, 1 H) 7.34-7.42 (m, 3 H) 7.47 (br. s., 2 H) 7.54-7.60 (m, 1 H) 8.13 (br. s., 1 H)

Example 104

(2R,3R,4S,5S)-2-(4-amino-7H-pyrrolo[2,3-d]pyrimidin-7-yl)-5-((S)-1-(3,4-difluorophenyl)-1-hydroxyethyl)tetrahydrofuran-3,4-diol (CCC-2)

Scheme CCC

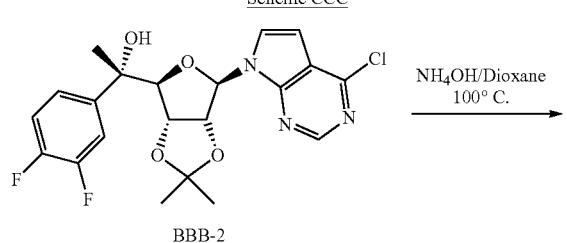

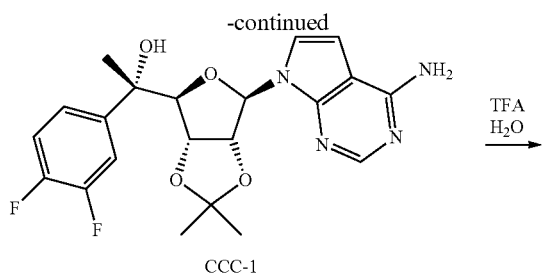

Step 1: Synthesis of (S)-1-((3aR,4S,6R,6aR)-6-(4-amino-7H-pyrrolo[2,3-d]pyrimidin-7-yl)-2,2-dimethyltetrahydrofuro[3,4-d][1,3]dioxol-4-yl)-1-(3,4-difluorophenyl)ethan-1-ol (CCC-2)

(S)-1-((3aR,4S,6R,6aR)-6-(4-chloro-7H-pyrrolo[2,3-d]pyrimidin-7-yl)-2,2-dimethyltetrahydrofuro[3,4-d][1,3]dioxol-4-yl)-1-(3,4-difluorophenyl)ethan-1-ol (BBB-2) (26 mg, 0.058 mmol) was dissolved in 1 mL dioxane, 1 mL ammonium hydroxide was added, the reaction vessel was sealed and heated at 100° C. overnight. The reaction mixture was concentrated, the residue was added H2O, extracted with EtOAc. The organic layers were combined, washed with brine, dried over Na$_2$SO$_4$, concentrated to give 25 mg (100% yield) of CCC-1 as an oil.

LCMS [M+1] 433; $^1$H NMR (400 MHz, CDCl$_3$) δ ppm 1.40 (s, 3 H) 1.58 (s, 3 H) 1.65 (s, 3 H) 4.62 (d, J=2.32 Hz, 1 H) 5.14 (dd, J=6.60, 4.52 Hz, 1 H) 5.28 (dd, J=6.60, 2.32 Hz, 1 H) 5.61 (br. s., 2 H) 5.69 (d, J=4.40 Hz, 1 H) 6.31 (d, J=3.55 Hz, 1 H) 6.91 (d, J=3.55 Hz, 1 H) 6.97-7.07 (m, 1 H) 7.10-7.16 (m, 1 H) 7.26 (ddd, J=11.92, 7.64, 2.20 Hz, 1 H) 8.33 (s, 1 H)

Step 2: Synthesis of (2R,3R,4S,5S)-2-(4-amino-7H-pyrrolo[2,3-d]pyrimidin-7-yl)-5-((S)-1-(3,4-difluorophenyl)-1-hydroxyethyl)tetrahydrofuran-3,4-diol (CCC-2)

Followed similar procedures to Steps 11 of Example 9 (Scheme C). LCMS [M+1] 393; 1H NMR (700 MHz, DMSO-d6) δ ppm 1.48 (s, 3 H) 4.17 (s, 1 H) 4.21-4.28 (m, 2 H) 5.93 (d, J=6.16 Hz, 1 H) 6.89 (d, J=3.52 Hz, 1 H) 7.20-7.33 (m, 2 H) 7.39-7.47 (m, 1 H) 7.56 (d, J=3.30 Hz, 1 H) 8.33 (br. s., 1 H)

Example 105

(2R,3R,4S,5S)-2-(4-amino-7H-pyrrolo[2,3-d]pyrimidin-7-yl)-5-((R)-1-(4-chloro-3-fluorophenyl)-1-hydroxyethyl)tetrahydrofuran-3,4-diol (DDD-5)

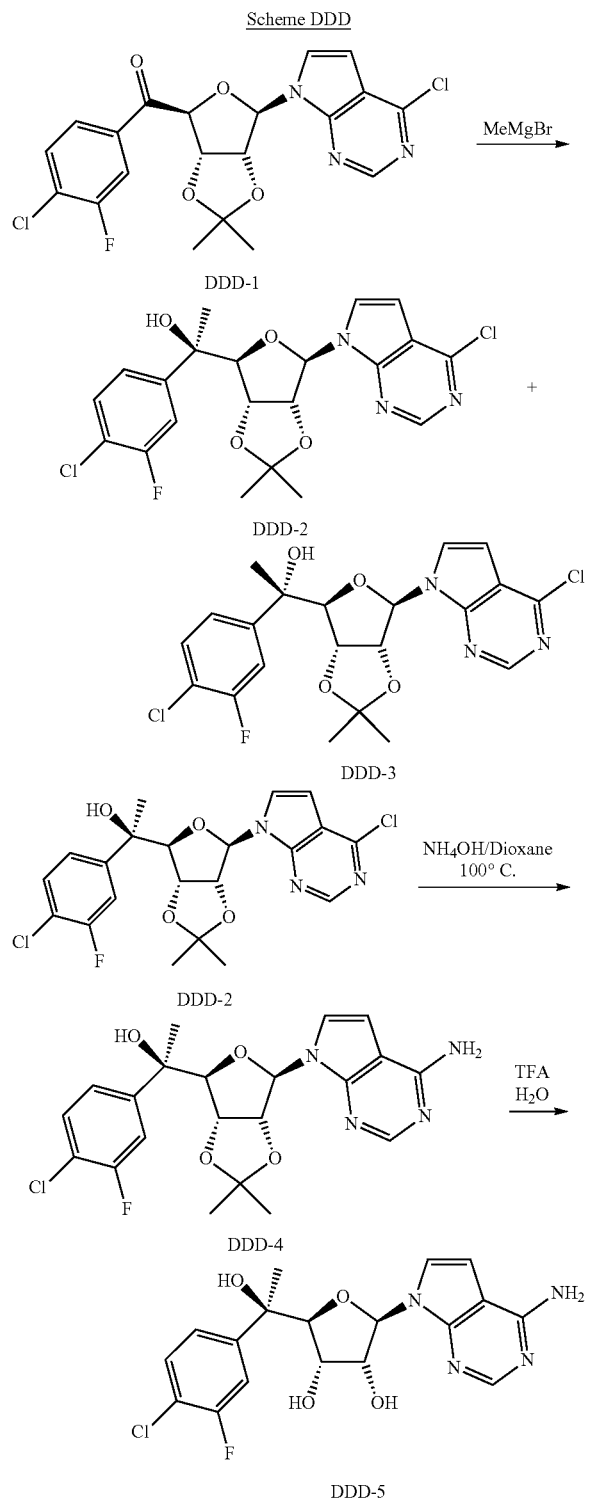

Scheme DDD

Step 1: Synthesis of (R)-1-(4-chloro-3-fluorophenyl)-1-((3aR,4S,6R,6aR)-6-(4-chloro-7H-pyrrolo[2,3-d]pyrimidin-7-yl)-2,2-dimethyltetrahydrofuro[3,4-d][1,3]dioxol-4-yl)ethan-1-ol (DDD-2) and (S)-1-(4-chloro-3-fluorophenyl)-1-((3aR,4S,6R,6aR)-6-(4-chloro-7H-pyrrolo[2,3-d]pyrimidin-7-yl)-2,2-dimethyltetrahydrofuro[3,4-d][1,3]dioxol-4-yl)ethan-1-ol (DDD-3)

To a solution of (4-chloro-3-fluorophenyl)((3aS,4S,6R,6aR)-6-(4-chloro-7H-pyrrolo[2,3-d]pyrimidin-7-yl)-2,2-dimethyltetrahydrofuro[3,4-d][1,3]dioxol-4-yl)methanone (DDD-1, Scheme DDD prepared in a similar fashion to MM-4 using 4-chloro-3-fluorophenylmagnesiu bromide) (230 mg, 0.509 mmol) in dry THF (5.0 mL, c=0.10 M) at rt was added methylmagnesium bromide (0.848 mL, 2.54 mmol, 3.0 M), the resulting solution was stirred at rt for 0.5 h. The mixture was added $NH_4Cl$ aq (40 mL) slowly, the mixture was extracted with EtOAc (25 mL×3). The extract was combined and washed with brine (25 mL), dried over $Na_2SO_4$ and concentrated in vacuo, purified by column chromatography with 25% EtOAc/heptane to give 175 mg (73.5% yield) (R)-1-(4-chloro-3-fluorophenyl)-1-((3aR,4S,6R,6aR)-6-(4-chloro-7H-pyrrolo[2,3-d]pyrimidin-7-yl)-2,2-dimethyltetrahydrofuro[3,4-d][1,3]dioxol-4-yl)ethan-1-ol (DDD-2) as a white solid.

LCMS [M+1] 468; $^1$H NMR (400 MHz, $CDCl_3$) δ ppm 1.22 (s, 3 H) 1.51 (s, 3 H) 1.58 (s, 3 H) 4.56 (d, J=1.22 Hz, 1 H) 4.66 (dd, J=6.11, 1.10 Hz, 1 H) 5.15 (t, J=5.75 Hz, 1 H) 5.86 (d, J=5.26 Hz, 1 H) 6.68 (d, J=3.67 Hz, 1 H) 7.25-7.29 (m, 1 H) 7.34 (d, J=3.67 Hz, 1 H) 7.40-7.48 (m, 2 H) 8.72 (s, 1H).

Elution with 30% EtOAc/heptane gave 26 mg (11% yield) of (S)-1-(4-chloro-3-fluorophenyl)-1-((3aR,4S,6R,6aR)-6-(4-chloro-7H-pyrrolo[2,3-d]pyrimidin-7-yl)-2,2-dimethyltetrahydrofuro[3,4-d][1,3]dioxol-4-yl)ethan-1-ol (DDD-3) as an oil.

LCMS [M+1] 468; $^1$H NMR (400 MHz, $CDCl_3$) δ ppm 1.41 (s, 3 H) 1.59 (s, 3 H) 1.67 (s, 3 H) 4.65 (d, J=2.57 Hz, 1 H) 5.14 (dd, J=6.66, 4.46 Hz, 1 H) 5.30 (dd, J=6.72, 2.57 Hz, 1 H) 5.77 (d, J=4.40 Hz, 1 H) 6.58 (d, J=3.67 Hz, 1 H) 7.11-7.16 (m, 1 H) 7.19-7.24 (m, 2 H) 7.25-7.29 (m, 1 H) 8.71 (s, 1 H)

Step 2: Synthesis of (R)-1-((3aR,4S,6R,6aR)-6-(4-amino-7H-pyrrolo[2,3-d]pyrimidin-7-yl)-2,2-dimethyltetrahydrofuro[3,4-d][1,3]dioxol-4-yl)-1-(4-chloro-3-fluorophenyl)ethan-1-ol (DDD-4)

(R)-1-(4-chloro-3-fluorophenyl)-1-((3aR,4S,6R,6aR)-6-(4-chloro-7H-pyrrolo[2,3-d]pyrimidin-7-yl)-2,2-dimethyltetrahydrofuro[3,4-d][1,3]dioxol-4-yl)ethan-1-ol (175 mg, 0.374 mmol) was dissolved in 5 mL dioxane, 5 mL ammonium hydroxide was added, the reaction vessel was sealed and heated at 100° C. overnight. The reaction mixture was concentrated, the residue was added $H_2O$, extracted with EtOAc. The organic layers were combined, washed with brine, dried over $Na_2SO_4$, concentrated to give 168 mg (100% yield) of DDD-4 as an oil.

LCMS [M+1] 449; $^1$H NMR (400 MHz, $CDCl_3$) δ ppm 1.21 (s, 3 H) 1.52 (s, 3 H) 1.57 (s, 3 H) 4.52 (d, J=1.22 Hz, 1 H) 4.62-4.68 (m, 1 H) 5.09 (t, J=5.62 Hz, 1 H) 5.88 (d, J=5.14 Hz, 1 H) 6.82 (d, J=3.55 Hz, 1 H) 7.17 (br. s., 2 H) 7.20-7.26 (m, 2 H) 7.39-7.46 (m, 2 H) 8.28 (s, 1 H)

Step 3: Synthesis of (2R,3R,4S,5S)-2-(4-amino-7H-pyrrolo[2,3-d]pyrimidin-7-yl)-5-((R)-1-(4-chloro-3-fluorophenyl)-1-hydroxyethyl)tetrahydrofuran-3,4-diol (DDD-5)

Followed similar procedures to Steps 11 of Example 9 (Scheme C). LCMS [M+1] 409; 1H NMR (700 MHz, DMSO-d6) δ ppm 1.41 (s, 3 H) 3.67 (d, J=5.06 Hz, 1 H) 4.13 (s, 1 H) 4.58 (br. s., 1 H) 4.88 (br. s., 1 H) 5.18 (br. s., 1 H) 5.86 (d, J=8.14 Hz, 1 H) 6.66 (d, J=3.52 Hz, 1 H) 7.38 (d, J=3.30 Hz, 1 H) 7.40-7.42 (m, 1 H) 7.44 (br. s., 1 H) 7.53-7.58 (m, 2 H) 8.13 (br. s., 1 H)

Example 106

(2R,3R,4S,5S)-2-(4-amino-7H-pyrrolo[2,3-d]pyrimidin-7-yl)-5-((S)-1-(4-chloro-3-fluorophenyl)-1-hydroxyethyl)tetrahydrofuran-3,4-diol (EEE-2)

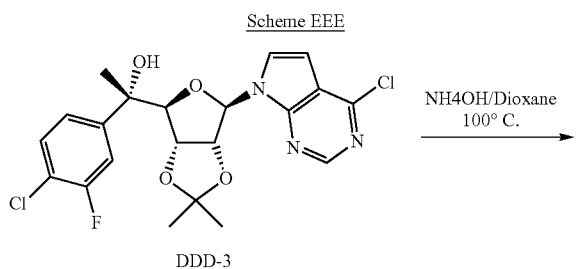

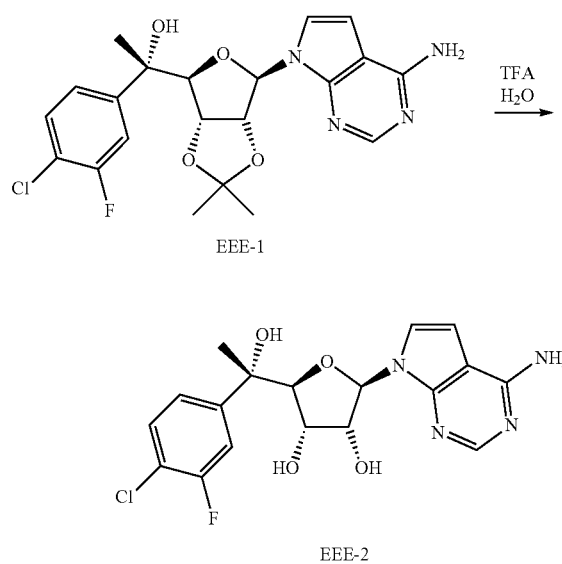

Step 1: Synthesis of (S)-1-((3aR,4S,6R,6aR)-6-(4-amino-7H-pyrrolo[2,3-d]pyrimidin-7-yl)-2,2-dimethyltetrahydrofuro[3,4-d][1,3]dioxol-4-yl)-1-(4-chloro-3-fluorophenyl)ethan-1-ol (EEE-1)

(S)-1-(4-chloro-3-fluorophenyl)-1-((3aR,4S,6R,6aR)-6-(4-chloro-7H-pyrrolo[2,3-d]pyrimidin-7-yl)-2,2-dimethyltetrahydrofuro[3,4-d][1,3]dioxol-4-yl)ethan-1-ol (26 mg, 0.056 mmol) was dissolved in 1 mL dioxane, 1 mL ammonium hydroxide was added, the reaction vessel was sealed and heated at 100° C. overnight. The reaction mixture was concentrated, the residue was added H₂O, extracted with EtOAc, the organic layers were combined, washed with brine, dried over Na₂SO₄, concentrated to give 25 mg (100% yield) of EEE-1 as an oil.

LCMS [M+1] 449; ¹H NMR (400 MHz, CDCl₃) δ ppm 1.40 (s, 3 H) 1.57 (s, 3 H) 1.65 (s, 3 H) 4.62 (d, J=2.32 Hz, 1 H) 5.14 (dd, J=6.48, 4.52 Hz, 1 H) 5.28 (dd, J=6.60, 2.32 Hz, 1 H) 5.69 (d, J=4.40 Hz, 1 H) 5.77 (br. s., 2 H) 6.34 (d, J=3.42 Hz, 1 H) 6.92 (d, J=3.67 Hz, 1 H) 7.14 (dd, J=8.38, 1.77 Hz, 1 H) 7.21-7.24 (m, 1 H) 7.26 (s, 1 H) 8.31 (br. s., 1 H)

Step 2: Synthesis of (2R,3R,4S,5S)-2-(4-amino-7H-pyrrolo[2,3-d]pyrimidin-7-yl)-5-((S)-1-(4-chloro-3-fluorophenyl)-1-hydroxyethyl)tetrahydrofuran-3,4-diol (EEE-2)

Followed similar procedures to Steps 11 of Example 9 (Scheme C). LCMS [M+1] 409; 1H NMR (700 MHz, DMSO-d6) δ ppm 1.48 (s, 3 H) 4.20 (d, J=1.54 Hz, 1 H) 4.26 (dd, J=5.39, 1.43 Hz, 1 H) 4.28-4.35 (m, 1 H) 5.34 (br. s., 2 H) 5.89 (d, J=7.04 Hz, 1 H) 6.83 (d, J=3.52 Hz, 1 H) 7.29 (dd, =8.58, 1.76 Hz, 1 H) 7.37-7.48 (m, 2 H) 7.51 (d, J=3.30 Hz, 1 H) 8.29 (s, 1 H)

Example 107

(2R,3S,4R,5R)-2-((R)-(3,4-difluorophenyl)(hydroxy)methyl)-5-(4-(fluoromethyl)-7H-pyrrolo[2,3-d]pyrimidin-7-yl)tetrahydrofuran-3,4-diol (FFF-6)

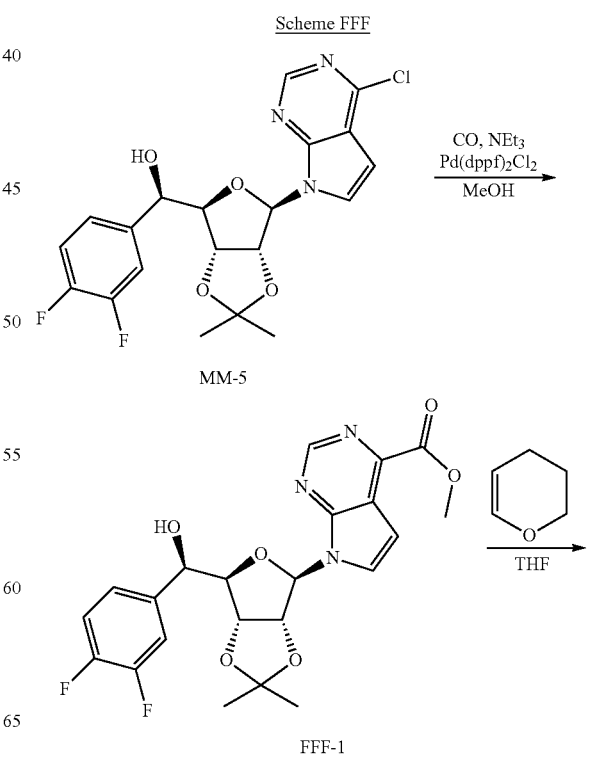

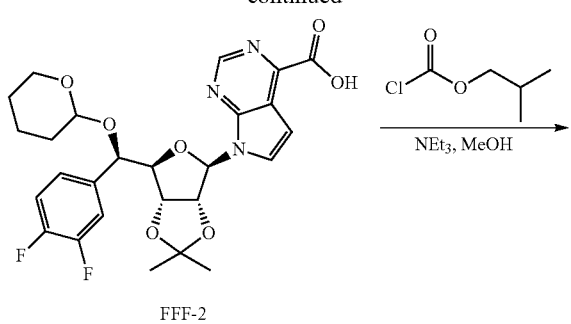

FFF-2

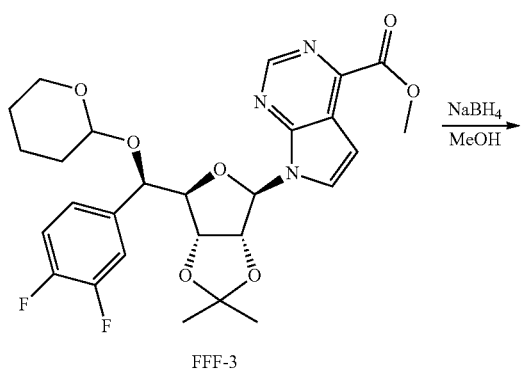

FFF-3

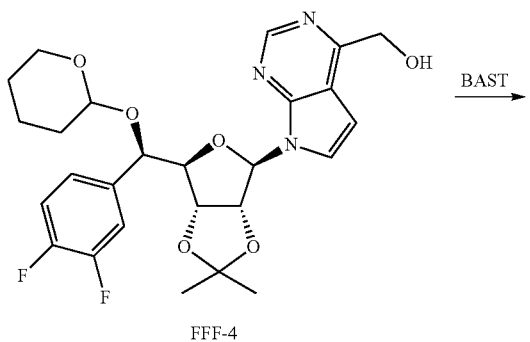

FFF-4

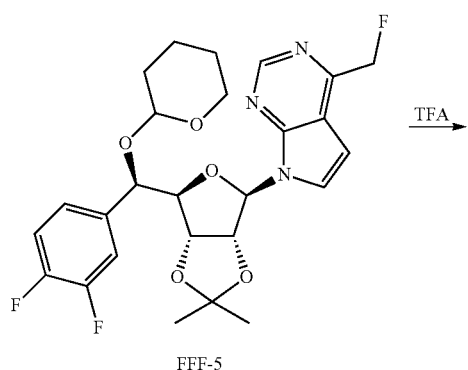

FFF-5

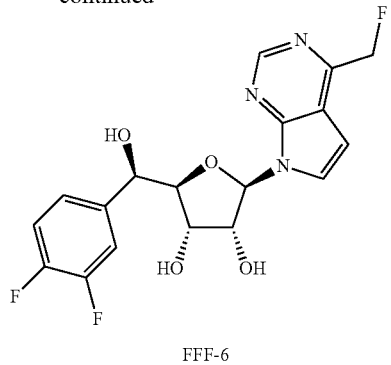

FFF-6

Step 1—Synthesis of methyl 7-((3aR,4R,6R,6aR)-6-((R)-(3,4-difluorophenyl)(hydroxy)methyl)-2,2-dimethyltetrahydrofuro[3,4-d][1,3]dioxol-4-yl)-7H-pyrrolo[2,3-d]pyrimidine-4-carboxylate (FFF-1)

A mixture MM-5 (Scheme FFF) (500 mg, 1.14 mmol), Pd(dppf)Cl$_2$ (167 mg, 0.228 mmol) and Et$_3$N (462 mg, 4.57 mmol) in MeOH (50 mL) was degassed with CO four times. The mixture was stirred at 100° C. under CO (2 MPa) in an autoclave for 20 hrs. TLC (petroleum ether/EtOAc=1:1) showed the reaction was complete and the product was clean. The mixture was concentrated in vacuo and the residue was purified by silica gel chromatography eluted with EtOAc in petroleum ether from 0 to 100% to afford FFF-1 (500 mg, 94.9%) as a white solid. LCMS [M+1] 462; $^1$H NMR (400 MHz, CDCl$_3$) δ ppm 9.07 (s, 1H), 7.48 (d, J=3.8 Hz, 1H), 7.39 (dd, J=7.8, 11.5 Hz, 1H), 7.24-7.18 (m, 2H), 7.16 (d, J=3.5 Hz, 1H), 6.63 (d, J=1.3 Hz, 1H), 5.90 (d, J=5.0 Hz, 1H), 5.27 (t, J=5.6 Hz, 1H), 5.10 (s, 1H), 4.94 (dd, J=1.4, 6.1 Hz, 1H), 4.57 (s, 1H), 4.12 (s, 3H), 1.59 (s, 3H), 1.29 (s, 3H)

Step 2—Synthesis of 7-((3aR,4R,6R,6aR)-6-((1R)-(3,4-difluorophenyl)((tetrahydro-2H-pyran-2-yl)oxy)methyl)-2,2-dimethyltetrahydrofuro[3,4-d][1,3]dioxol-4-yl)-7H-pyrrolo[2,3-d]pyrimidine-4-carboxylic acid (FFF-2)

To a solution of FFF-1 (300 mg, 0.60 mmol) and PPTS (32.7 mg, 0.13 mmol) in THF (3 mL) was added 3,4-dihydro-2H-pyran (109 mg, 1.3 mmol) at rt (25° C.). The mixture was stirred at rt (25° C.) for 1 hr. The mixture was stirred at rt under N$_2$ for 12 hrs. TLC (petroleum ether/EtOAc=1:1) showed the ratio of SM: product was about 5:1. CuSO$_4$ (1 eq) and 3,4-dihydro-2H-pyran (1.09 g, 13 mmol) was added. The mixture was stirred at rt for 24 hrs. TLC (petroleum ether/EtOAc=1:1) showed most of SM was consumed. The mixture was purified by silica gel chromatography eluted with EtOAc in petroleum ether from 0-100 to afford FFF-2 (120 mg, 34.7%) as a solid. LCMS [M+1] 532

Step 3—Synthesis of methyl 7-((3aR,4R,6R,6aR)-6-((1R)-(3,4-difluorophenyl)((tetrahydro-2H-pyran-2-yl)oxy)methyl)-2,2-dimethyltetrahydrofuro[3,4-d][1,3]dioxol-4-yl)-7H-pyrrolo[2,3-d]pyrimidine-4-carboxylate (FFF-3)

To a solution of FFF-2 (110 mg, 0.207 mmol) and Et$_3$N (83.8 mg, 0.828 mmol) in dry THF (2 mL) was added isobutyl chloroformate (56.5 mg, 0.414 mmol) at 0° C. The mixture was stirred at rt (25° C.) for 1 hr. To the mixture was added MeOH (2 mL). The mixture was stirred at rt (25° C.) for 1 hr. TLC (petroleum ether/EtOAc=1:1) showed a new spot formed. The mixture was poured into brine (10 mL) and extracted with EtOAc (10 mL×2). The extract was dried over Na₂SO₄ and concentrated in vacuo to afford FFF-3 (100 mg, 88%) as a gum and was used in the next step directly. LCMS [M+23]568

Step 4—Synthesis of (7-((3aR,4R,6R,6aR)-6-((1R)-(3,4-difluorophenyl)((tetrahydro-2H-pyran-2-yl)oxy)methyl)-2,2-dimethyltetrahydrofuro[3,4-d][1,3]dioxol-4-yl)-7H-pyrrolo[2,3-d]pyrimidin-4-yl)methanol (FFF-4)

To a solution of FFF-3 (150 mg, 3.96 mmol) in MeOH (15 mL) was added NaBH₄ (150 mg, 3.96 mmol) at rt (25° C.). The mixture was stirred at rt for 1 h. TLC (petroleum ether/EtOAc=1:1) showed most of SM was consumed and a new spot formed. The mixture was concentrated in vacuo to dryness. The residue was purified by prep-TLC (petroleum ether/EtOAc=1:1) to afford FFF-4 (90 mg, 63.2%) as white solid. LCMS [M+1] 518

Step 5—Synthesis of 7-((3aR,4R,6R,6aR)-6-((1R)-(3,4-difluorophenyl)((tetrahydro-2H-pyran-2-yl)oxy)methyl)-2,2-dimethyltetrahydrofuro[3,4-d][1,3]dioxol-4-yl)-4-(fluoromethyl)-7H-pyrrolo[2,3-d]pyrimidine (FFF-5)

To a solution FFF-4 (50 mg, 0.0966 mmol) in dry DCM (5 mL) was added bis(2-methoxyethyl)aminosulfur trifluoride (150 mg, 0.678 mmol) at −70° C. The resulting yellow solution was warmed to rt and stirred at rt (25° C.) for 2 h. TLC (petroleum ether/EtOAc=1:1) showed most of SM was consumed and the main peak had the desired mass. The mixture was purified by silica gel chromatography eluted EtOAc in petroleum ether from 0 to 50% to give FFF-5 (25 mg, 50%) as a white solid. LMCS [M+1] 520

Step 6—Synthesis of (2R,3S,4R,5R)-2-((R)-(3,4-difluorophenyl)(hydroxy)methyl)-5-(4-(fluoromethyl)-7H-pyrrolo[2,3-d]pyrimidin-7-yl)tetrahydrofuran-3,4-diol (FFF-6)

To compound FFF-5 (25 mg, 0.0481 mmol) was added TFA/H₂O (1 mL/1 mL) at rt (25° C.). The mixture was stirred at rt for 2 hr. LCMS showed most of SM was consumed and the main peak was desired compound. The mixture was poured into 20% K₂CO₃ aq (10 mL) and extracted with EtOAc (10 mL×2). The extract was washed with brine (10 mL×2), dried over MgSO₄ and concentrated in vacuo to afford crude (18 mg). The crude was purified by prep-TLC (DCM/MeOH=10:11) to give FFF-6 (13 mg, 68.3%) as a white solid. LCMS [M+1] 396; ¹H NMR (400 MHz, DMSO-d6) δ ppm 8.80 (s, 1H), 7.94 (d, J=3.8 Hz, 1H), 7.46-7.32 (m, 2H), 7.28-7.21 (m, 1H), 6.85-6.80 (m, 1H), 6.23 (d, J=7.8 Hz, 1H), 6.11 (d, J=4.5 Hz, 1H), 5.86 (s, 1H), 5.74 (s, 1H), 5.33 (d, J=6.8 Hz, 1H), 5.17 (d, J=4.3 Hz, 1H), 4.81 (t, J=4.9 Hz, 1H), 4.65-4.54 (m, 1H), 4.14 (t, J=4.5 Hz, 1H), 4.01 (d, J=5.5 Hz, 1H)

Example 108

(2R,3S,4R,5R)-2-((R)-(3,4-difluorophenyl)(hydroxy)methyl)-5-(4-(hydroxymethyl)-7H-pyrrolo[2,3-d]pyrimidin-7-yl)tetrahydrofuran-3,4-diol (GGG-2)

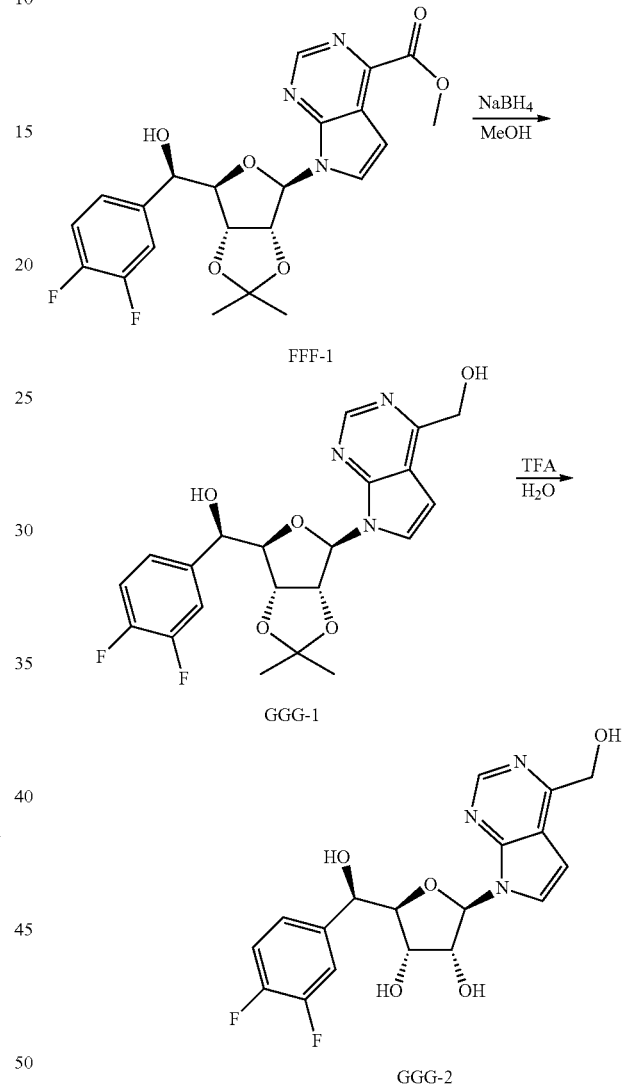

Step 1—Synthesis of (R)-(3,4-difluorophenyl)((3aR,4R,6R,6aR)-6-(4-(hydroxymethyl)-7H-pyrrolo[2,3-d]pyrimidin-7-yl)-2,2-dimethyltetrahydrofuro[3,4-d][1,3]dioxol-4-yl)methanol (GGG-1)

To a solution of FFF-1 (Scheme GGG) (200 mg) in MeOH (30 mL) was added NaBH₄ (492 mg, 13 mmol) at rt (25° C.). The mixture was stirred at rt for 30 min. TLC (petroleum ether/EtOAc=1:1) showed most of SM was consumed. The mixture was concentrated in vacuo to remove most of MeOH. The residue was diluted with water (30 mL) and extracted with EtOAc (20 mL×3). The extract was washed with brine (20 mL), dried over Na₂SO₄ and concentrated in vacuo to afford crude material, which was purified by prep TLC (petroleum ether/EtOAc=2:3) to afford GGG-1 (80 mg, 42.6%) as a light yellow solid. LCMS [M+1] 434; ¹HNMR (400 MHz, CDCl₃) δ ppm 8.88 (s, 1H), 7.48-7.35 (m, 1H), 7.31 (br. s., 1H), 7.24-7.14 (m, 2H), 7.12 (br. s., 1H), 6.61 (br. s., 1H), 5.85 (d, J=4.8 Hz, 1H), 5.27 (br. s., 1H), 5.16-5.02 (m, 3H), 4.94 (d, J=6.0 Hz, 1H), 4.56 (br. s., 1H), 3.90 (br. s., 1H), 1.58 (br. s., 3H), 1.29 (s, 3H)

Step 2—Synthesis of (2R,3S,4R,5R)-2-((R)-(3,4-difluorophenyl)(hydroxy)methyl)-5-(4-(hydroxymethyl)-7H-pyrrolo[2,3-d]pyrimidin-7-yl)tetrahydrofuran-3,4-diol (GGG-2)

To a solution of TFA/H₂O (2 mL/2 mL) was added GGG-1 (60 mg, 0.138 mmol) at 0° C. The mixture was stirred at rt (30° C.) for 1 h. TLC (petroleum ether/EtOAc=1:1) showed most of SM was consumed. The mixture was poured into 20% K₂CO₃ (20 mL) and extracted with EtOAc (20 mL×2). The extract was washed with brine (20 mL×2), dried over Na₂SO₄ and concentrated in vacuo to afford GGG-2 (45 mg, 83%) as a white solid. LCMS [M+1] 394; ¹H NMR (400 MHz, DMSO-d6) δ ppm 8.70 (s, 1H), 7.81 (d, J=3.8 Hz, 1H), 7.48-7.31 (m, 2H), 7.25 (br. s., 1H), 6.91 (d, J=3.8 Hz, 1H), 6.20 (d, J=7.8 Hz, 1H), 6.15 (d, J=4.5 Hz, 1H), 5.61 (t, J=6.0 Hz, 1H), 5.29 (d, J=6.8 Hz, 1H), 5.14 (d, J=4.0 Hz, 1H), 4.88-4.75 (m, 3H), 4.64-4.52 (m, 1H), 4.13 (t, J=4.5 Hz, 1H), 4.00 (d, J=5.5 Hz, 1H)

Example 109

(2R,3S,4R,5R)-2-((R)-(3,4-difluorophenyl)(methylamino)methyl)-5-(4-methyl-7H-pyrrolo[2,3-d]pyrimidin-7-yl)tetrahydrofuran-3,4-diol (HHH-3)

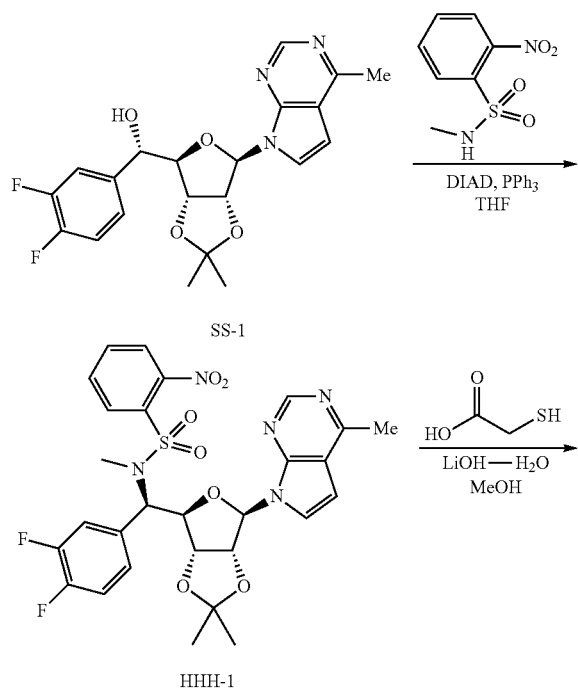

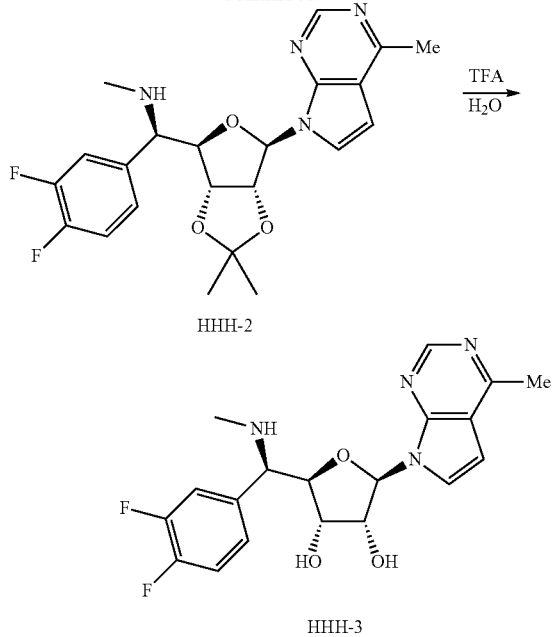

Step 1: Synthesis of N—((R)-(3,4-difluorophenyl)((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)methyl)-N-methyl-2-nitrobenzenesulfonamide (HHH-1)

In a round bottom flask was added SS-1 (Scheme HHH) (100.0 mg, 0.240 mmol), N-methyl-2-nitrobenzenesulfonamide (62.2 mg, 0.287 mmol), triphenylphosphine (94.3 mg, 0.359 mmol), and THF (17.3 mg, 0.240 mmol, 1.20 mL, 0.2 M). The mixture was cooled to 00° C. in an ice bath. DIAD (77.3 mg, 0.359 mmol, 0.0740 mL) was added drop-wise and stirred at room temperature for 16 h. LCMS shows complete conversion to the product. The reaction was diluted with EtOAc and water (30 mL each). Extract the aqueous layer with EtOAc (3×20 mL). Purify by prep HPLC to obtain HHH-1 as a solid (57 mg, 39%). LCMS [M+1] 616; ¹H NMR (400 MHz, CDCl₃) δ ppm 8.84 (s, 1H), 7.97-7.90 (m, 1H), 7.73-7.66 (m, 1H), 7.66-7.59 (m, 2H), 7.15 (d, J=3.8 Hz, 1H), 6.97-6.86 (m, 3H), 6.58 (d, J=3.7 Hz, 1H), 6.21 (d, J=2.4 Hz, 1H), 5.40 (d, J=8.7 Hz, 1H), 5.29 (dd, J=2.5, 6.7 Hz, 1H), 5.18 (dd, J=4.2, 6.5 Hz, 1H), 4.64 (dd, J=4.2, 8.7 Hz, 1H), 2.95 (s, 3H), 2.74 (s, 3H), 1.62 (s, 3H), 1.30 (s, 3H)

Step 2: Synthesis of (R)-1-(3,4-difluorophenyl)-1-((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)-N-methylmethanamine (HHH-2)

A suspension HHH-1 (57.0 mg, 0.093 mmol) in MeOH was treated mercaptoacetic acid with (0.020 mL, 0.277 mmol) and lithium hydroxide hydrate (23.3 mg, 0.556 mmol). The rxn was stirred at 55° C. for 24 h. The reaction was passed directly into an SCX column first flushing with MeOH, followed by 10% 7N NH₃/MeOH to obtain the product (HHH-2) as a clear oil. LCMS [M+1] 431

Step 3: (2R,3S,4R,5R)-2-((R)-(3,4-difluorophenyl)(methylamino)methyl)-5-(4-methyl-7H-pyrrolo[2,3-d]pyrimidin-7-yl)tetrahydrofuran-3,4-diol (HHH-3)

The crude clear oil HHH-2 was dissolved in TFA and water (1 mL each) and stirred at r.t. for 16 h. The reaction was passed directly into an SCX column first flushing with MeOH, followed by 10% 7N $NH_3$/MeOH to obtain the product as a clear oil. Purify by SFC to obtain HHH-3 as a white solid (17.4 mg, 48%) LCMS [M+1] 391; $^1$H NMR (400 MHz, DMSO-$d_6$) δ ppm 8.62 (s, 1H), 7.55 (br. s., 1H), 7.38-7.26 (m, 2H), 7.18 (br. s., 1H), 6.73 (d, J=3.7 Hz, 1H), 6.05 (d, J=6.4 Hz, 1H), 5.33 (d, J=6.1 Hz, 1H), 5.20-5.09 (m, 1H), 4.48 (q, J=6.2 Hz, 1H), 4.19-4.12 (m, 1H), 4.05-3.96 (m, 1H), 3.87-3.73 (m, 1H), 2.65 (s, 3H), 2.17 (s, 3H)

Synthesis of Examples 110-112 followed similar procedures to Steps 9-11 of Example 9 (Scheme C) using the appropriate arylhalide to make the Grignard reagent. Procedures to make the arylhalide used for Example 112 are below.

| Example | | [M+1] | Name / $^1$H NMR |
|---|---|---|---|
| Example 110 | 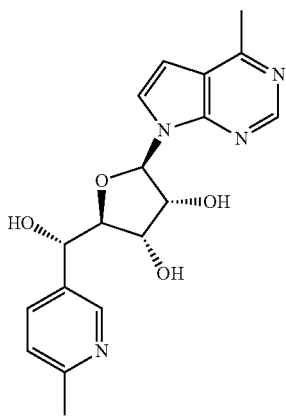 [SMILES: Cc1ccc([C@H](O)[C@H]2O[C@@H](n3ccc4c(C)ncnc43)[C@H](O)[C@@H]2O)cn1] | 357 | (2R,3S,4R,5R)-2-((R)-hydroxy(6-methylpyridin-3-yl)methyl)-5-(4-methyl-7H-pyrrolo[2,3-d]pyrimidin-7-yl)tetrahydrofuran-3,4-diol<br>$^1$H NMR (400 MHz, MeOD) δ ppm 8.62 (s, 1H), 8.46 (d, J = 1.8 Hz, 1H), 7.79 (dd, J = 2.1, 8.2 Hz, 1H), 7.62 (d, J = 3.8 Hz, 1H), 7.26 (d, J = 8.0 Hz, 1H), 6.75 (d, J = 3.8 Hz, 1H), 6.14 (d, J = 6.8 Hz, 1H), 5.02 (d, J = 3.8 Hz, 1H), 4.81 (dd, J = 5.3, 6.8 Hz, 1H), 4.31 (dd, J = 2.3, 5.3 Hz, 1H), 4.25 (dd, J = 2.3, 3.8 Hz, 1H), 2.74 (s, 3H), 2.50 (s, 3H) |
| Example 111 | 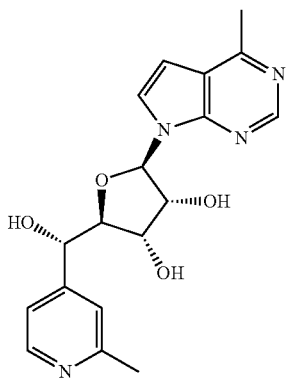 [SMILES: Cc1cc([C@H](O)[C@H]2O[C@@H](n3ccc4c(C)ncnc43)[C@H](O)[C@@H]2O)ccn1] | 357 | (2R,3S,4R,5R)-2-((R)-hydroxy(2-methylpyridin-4-yl)methyl)-5-(4-methyl-7H-pyrrolo[2,3-d]pyrimidin-7-yl)tetrahydrofuran-3,4-diol<br>$^1$H NMR (400 MHz, MeOD) δ ppm 8.64 (s, 1H), 8.36 (d, J = 5.3 Hz, 1H), 7.66 (d, J = 3.8 Hz, 1H), 7.41 (s, 1H), 7.35 (d, J = 5.0 Hz, 1H), 6.77 (d, J = 3.8 Hz, 1H), 6.15 (d, J = 7.5 Hz, 1H), 4.99 (d, J = 3.0 Hz, 1H), 4.79 (dd, J = 5.3, 7.3 Hz, 1H), 4.28 (t, J = 3.1 Hz, 1H), 4.20 (tt, J = 1.0, 5.5 Hz, 1H), 2.75 (s, 3H), 2.52 (s, 3H) |
| Example 112 | 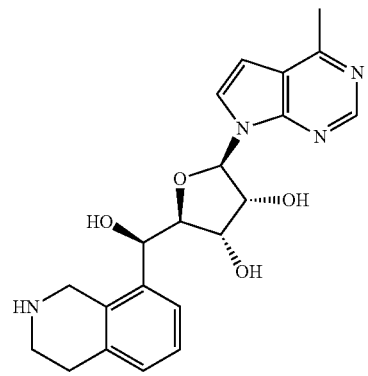 [SMILES: Cc1ncnc2c1ccn2[C@@H]1O[C@H]([C@H](O)c2cccc3c2CNCC3)[C@@H](O)[C@H]1O] | 397 | (2R,3S,4R,5R)-2-((R)-hydroxy(1,2,3,4-tetrahydroisoquinolin-8-yl)methyl)-5-(4-methyl-7H-pyrrolo[2,3-d]pyrimidin-7-yl)tetrahydrofuran-3,4-diol<br>$^1$H NMR (400 MHz, DMSO-$d_6$) δ ppm 8.66 (s, 1H), 8.31 (s, 1H), 7.79 (d, J = 4.0 Hz, 1H), 7.38 (d, J = 7.5 Hz, 1H), 7.21-7.14 (m, 1H), 7.02 (d, J = 7.5 Hz, 1H), 6.78 (d, J = 4.0 Hz, 1H), 6.16 (d, J = 8.0 Hz, 1H), 6.05-5.94 (m, 1H), 4.82 (d, J = 4.5 Hz, 1H), 4.70-4.64 (m, 1H), 4.24 (d, J = 5.3 Hz, 1H), 4.11-3.89 (m, 3H), 3.05-2.95 (m, 2H), 2.82-2.76 (m, 2H), 2.67 (s, 3H) |

Synthesis of tert-butyl 8-iodo-3,4-dihydroisoquinoline-2(1H)-carboxylate (used in Example 112)

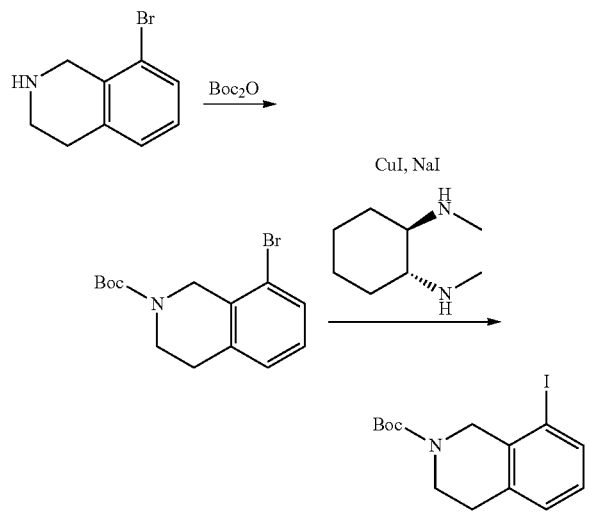

Step 1: Synthesis of tert-butyl 8-bromo-3,4-dihydroisoquinoline-2(1H)-carboxylate To the solution of 8-bromo-1,2,3,4-tetrahydroisoquinoline HCl (1 g, 4.72 mmol) in DCM (20 mL) was added Boc$_2$O (1030 mg, 4.72 mmol) and NEt$_3$ (960 mg, 9.43 mmol). The mixture was stirred at 20° C. for 1.5 h. The mixture was concentrated in vacuo to afford crude product (2000 mg). The crude was purified by silica gel chromatography eluted with EtOAc in petroleum ether from 0 to 30% to afford the desired product (1.36 mg, 94%). $^1$H NMR (400 MHz, CDCl$_3$) δ ppm 7.42 (d, J=7.5 Hz, 1H), 7.14-6.97 (m, 2H), 4.61-4.48 (m, 2H), 3.64 (t, J=5.4 Hz, 2H), 2.90-2.75 (m, 2H), 1.50 (s, 9H)

Step 2: Synthesis of tert-butyl 8-iodo-3,4-dihydroisoquinoline-2(1H)-carboxylate A mixture of tert-butyl 8-bromo-3,4-dihydroisoquinoline-2(1H)-carboxylate (500 mg, 1.60 mmol), NaI (720 mg, 4.80 mmol), CuI (45.8 mg, 0.240 mmol) and trans-N,N-dimethylcyclohexanediamine (68 mg, 0.48 mmol) in dioxane (10 mL) was purged with N$_2$ for 10 min. The resulting yellow suspension was stirred at 110° C. in a sealed tube for 20 hrs. LCMS showed 50% conversion, therefore additional NaI (720 mg, 4.80 mmol), CuI (45.8 mg, 0.24 mmol) and trans-N,N-dimethylcyclohexanediamine (68 mg, 0.40 mmol) was added followed by N$_2$ purging for 10 min. The resulting yellow suspension was stirred at 110° C. in a sealed tube for 20 hrs. The mixture was poured into water (20 mL) and extracted with EtOAc (10 mL×3). The extract was concentrated in vacuo to afford crude material which was purified by silica gel chromatography eluted with EtOAc in petroleum ether from 0 to 20% to afford the product (450 mg, 78%) as a light yellow oil. LCMS [M-tBu]304; $^1$H NMR (400 MHz, CDCl$_3$) δ ppm 7.70 (d, J=8.0 Hz, 1H), 7.12 (d, J=7.0 Hz, 1H), 6.94-6.82 (m, 1H), 4.44 (m, 2H), 3.62 (t, J=5.5 Hz, 2H), 2.81 (br. s., 2H), 1.50 (s, 9H)

Example 113

6-((R)-((2R,3S,4R,5R)-3,4-dihydroxy-5-(4-methyl-7H-pyrrolo[2,3-d]pyrimidin-7-yl)tetrahydrofuran-2-yl)(hydroxy)methyl)pyridin-2(1H)-one (III -4)

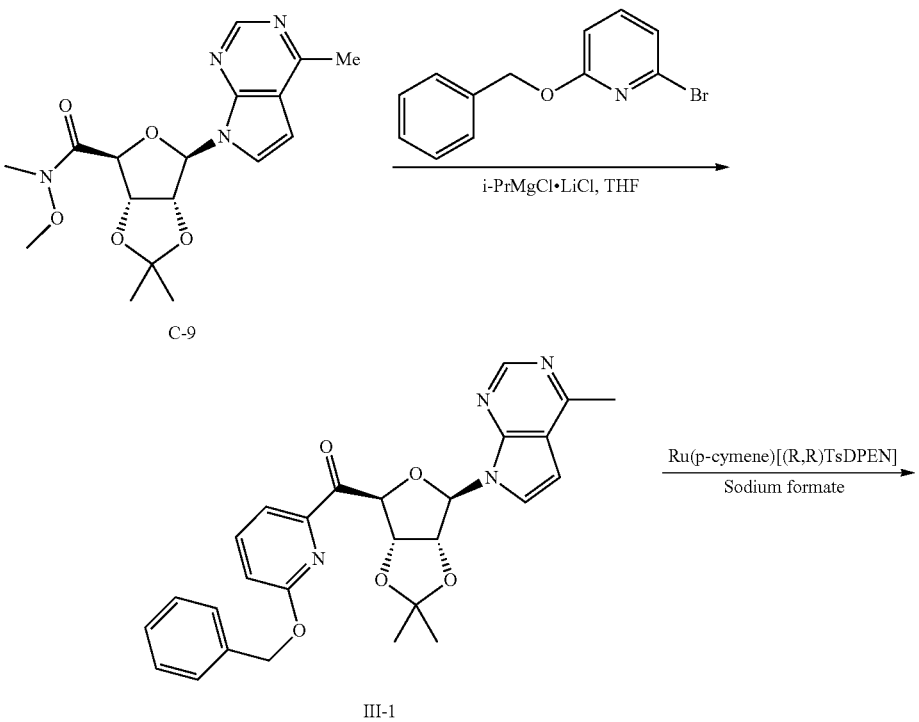

-continued

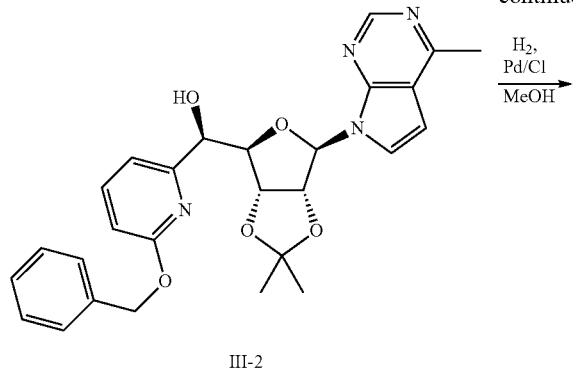

III-2

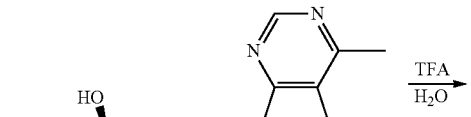

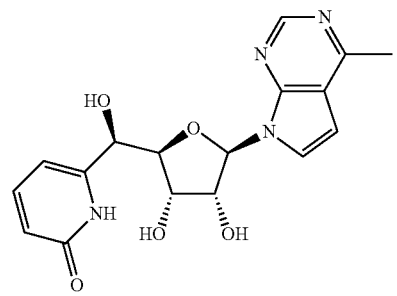

III-3

III-4

Step 1: Synthesis of (6-(benzyloxy)pyridin-2-yl) ((3aS,4S,6R,6aR)-2,2-dimethyl-6-(4-methyl-7H-pyrrolo[2,3-d]pyrimidin-7-yl)tetrahydrofuro[3,4-d][1,3]dioxol-4-yl)methanone (III-1)

To a solution of 2-(benzyloxy)-6-bromopyridine (437 mg, 1.66 mmol) in dry THF (10 mL) was added 2.5 M n-BuLi (0.662 mL, 1.66 mmol) at −65° C. The yellow slurry was stirred at −65° C. for 1 hr. A solution of C-9 (150 mg, 0.414 mmol) in THF (1 mL) was added. The mixture was stirred at rt for 1 h. TLC (petroleum ether/EtOAc=1:1) showed most of the starting material was consumed and a good new spot was formed. The mixture was poured into water (20 mL) and extracted with EtOAc (10 mL×3). The extract was washed with brine (10 mL), dried over Na$_2$SO$_4$ and concentrated in vacuo to afford crude material and used in the next step directly. LCMS [M+1] 487.

Step 2: Synthesis of (R)-(6-(benzyloxy)pyridin-2-yl)((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)methanol (III-2)

A light yellow mixture of crude III-1 (411 mg, 0.41 mmol) in EtOAc (2.5 mL) and 2.5 M aq sodium formate (11.6 mL, 29 mmol) was purged with N$_2$ for 5 min. To the mixture was added Ru(p-cymene)[(R,R)TsDPEN](30 mg, 0.047 mmol) at rt (20° C.). The resulting yellow mixture was stirred under N$_2$ at rt (20° C.) for 20 hrs. The mixture was extracted with EtOAc (10 mL×3). The extract was washed with brine (10 mL), dried over Na$_2$SO$_4$ and concentrated in vacuo. The residue was purified by silica gel chromatography eluted with EtOAc in petroleum ether from 0 to 100% to afford (80 mg, 40% in two steps) as a brown gum. LCMS [M+1] 489; $^1$H NMR (400 MHz, CDCl$_3$) δ ppm 8.82 (s, 1H), 7.65 (t, J=7.8 Hz, 1H), 7.47 (d, J=7.0 Hz, 2H), 7.38 (t, J=7.3 Hz, 2H), 7.34-7.29 (m, 2H), 7.19 (d, J=7.3 Hz, 1H), 7.05 (d, J=2.3 Hz, 1H), 6.74 (d, J=8.3 Hz, 1H), 6.60 (d, J=3.8 Hz, 1H), 5.93 (d, J=5.0 Hz, 1H), 5.39 (d, J=2.8 Hz, 2H), 5.34-5.32 (m, 1H), 5.09-5.03 (m, 2H), 4.94 (s, 1H), 2.77 (s, 3H), 1.61 (s, 3H), 1.29 (s, 3H)

Step 3: Synthesis of 6-((R)-((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)(hydroxy)methyl)pyridin-2(1H)-one (III-3)

A mixture of III-2 (80 mg, 0.16 mmol) and Pd/C (35 mg, 0.0164 mmol) in MeOH (4 mL) was degassed with H$_2$ four times. The mixture was stirred at rt (15° C.) under H$_2$ balloon for 16 hrs. LCMS showed most of the starting material was consumed and the main peak was the desired compound. The mixture was filtered and concentrated in vacuo. The residue was purified by prep-TLC to afford the product (60 mg, 92%) as a brown gum. LCMS [M+1] 399; $^1$H NMR (400 MHz, CDCl$_3$) δ ppm 10.53 (br. s, 1H), 8.74 (s, 1H), 8.36 (br. s., 1H), 7.43 (t, J=9.3 Hz, 1H), 7.24 (d, J=3.8 Hz, 1H), 6.60 (d, J=3.8 Hz, 1H), 6.51 (d, J=9.0 Hz, 1H), 6.20 (d, J=7.0 Hz, 1H), 5.85 (d, J=5.0 Hz, 1H), 5.21 (t, J=5.5 Hz, 1H), 5.03 (s, 1H), 4.85 (d, J=6.3 Hz, 1H), 4.65 (s, 1H), 2.78 (s, 3H), 1.61 (s, 3H), 1.31 (s, 3H)

Step 4: Synthesis of 6-((R)-((2R,3S,4R,5R)-3,4-dihydroxy-5-(4-methyl-7H-pyrrolo[2,3-d]pyrimidin-7-yl)tetrahydrofuran-2-yl)(hydroxy)methyl)pyridin-2(1H)-one (III-4)

To III-3 (60 mg, 0.151 mmol) was added TFA/H$_2$O (1 mL/1 mL, cooled to 0° C. previously). The mixture was stirred at rt (25° C.) for 2 hrs. LCMS showed most of the starting material was consumed and a peak (0.15 min) was observed. The mixture was poured into 20% K$_2$CO$_3$ (10 mL). The aqueous was saturated with NaCl and extracted with EtOcA/THF (5 mL/5 mL×6). The extract was dried over Na$_2$SO$_4$ overnight. The mixture was filtered and concentrated in vacuo to afford crude material which was purified by prep-HPLC to give the product (25 mg, 43%). LCMS [M+1] 359; 1H NMR (400 MHz, DMSO-d$_6$) δ ppm 11.43 (br. s, 1H), 8.70 (s, 1H), 7.83 (d, J=3.8 Hz, 1H), 7.47-7.36 (m, 1H), 6.84 (d, J=3.5 Hz, 1H), 6.32 (br. s, 2H), 6.19 (d, J=7.8 Hz, 2H), 5.31 (br. s, 2H), 4.60 (s, 1H), 4.53-4.45 (m, 1H), 4.16-4.05 (m, 2H), 2.68 (s, 3H)
Example 114
(2R,3S,4R,5R)-2-((R)-(4-fluoro-3-(hydroxymethyl)phenyl)(hydroxy)methyl)-5-(4-methyl-7H-pyrrolo[2,3-d]pyrimidin-7-yl)tetrahydrofuran-3,4-diol (JJJ-5)
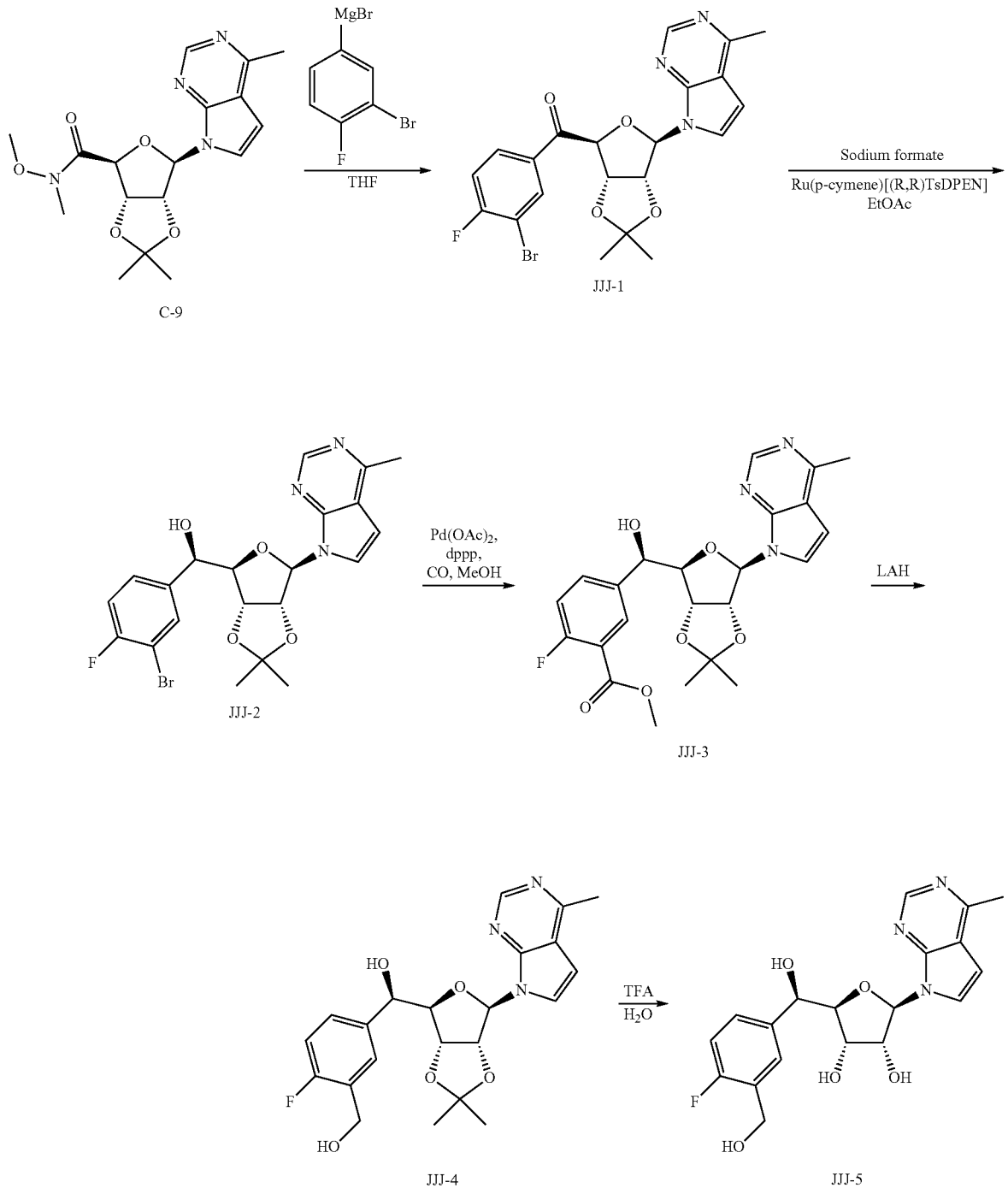

Step 1: Synthesis of (3-bromo-4-fluorophenyl) ((3aS,4S,6R,6aR)-2,2-dimethyl-6-(4-methyl-7H-pyrrolo[2,3-d]pyrimidin-7-yl)tetrahydrofuro[3,4-d][1,3]dioxol-4-yl)methanone (JJJ-1)

To a colorless solution of (3-bromo-4-fluorophenyl) magnesium bromide (1 g, 3.3 mmol) in dry THF (10 mL) was added 1.3 M i-PrMgCl.LiCl (3.4 mL, 4.4 mmol) at −60° C. The mixture was stirred at −20°-40° C. for 1 h, in which the reaction turned yellow. C-9 (400 mg, 1.1 mmol) in THF (6 mL) was added and the mixture became red and stirred at 0° C. for 1 hr. TLC (DCM/MeOH=20:1, UV) showed the reaction was complete. The mixture was quenched with NH$_4$Cl aq (50 mL) and extracted with EtOAc (40 mL×3). The combined organic layers were concentrated in vacuo to afford crude product (445 mg, 85%) as a yellow oil, which was used to the next step directly. LCMS [M+1] 476

Step 2: Synthesis of (R)-(3-bromo-4-fluorophenyl) ((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)methanol (JJJ-2)

The solution of crude JJJ-1 (445 mg, 0.93 mmol) and sodium formate (2540 mg, 37.4 mmol) in EtOAc/H$_2$O (3.2 mL/12 mL) was purged with N$_2$ for 30 mins, then added Ru(p-cymene) [(R,R)TsDPEN](30 mg, 0.047 mmol). The resulting yellow mixture was stirred at rt (25° C.) for 24 h. TLC (DCM/MeOH=20:1, UV) showed the starting material was consumed completely and the new spot formed (desired compound). The reaction was extracted with EtOAc (40 mL×3). The extract was concentrated in vacuo to afford crude product, which was purified by silica gel chromatography (petroleum ether/EtOAc=10-60%) to give JJJ-2 (300 mg, 67%) as a brown solid. LCMS [M+1] 478; $^1$H NMR (400 MHz, CDCl$_3$) δ ppm 8.80 (s, 1H), 7.77 (td, J=0.9, 7.7 Hz, 1H), 7.50 (s, 1H), 7.45-7.38 (m, 1H), 7.25 (d, J=3.5 Hz, 1H), 7.17 (t, J=8.4 Hz, 1H), 6.60 (d, J=3.8 Hz, 1H), 5.83 (d, J=5.0 Hz, 1H), 5.32-5.24 (m, 1H), 5.11 (s, 1H), 4.93 (dd, J=1.3, 6.3 Hz, 1H), 4.59-4.56 (m, 1H), 2.78 (s, 3H), 1.59 (s, 3H), 1.29 (br. s., 3H)

Step 3: Synthesis of methyl 5-((R)-((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)(hydroxy)methyl)-2-fluorobenzoate (JJJ-3)

In a seal tube was charged a solution of JJJ-2 (150 mg, 0.31 mmol) in MeOH (10 mL) and DMF (5 mL). Pd(OAc)$_2$ (49 mg, 0.22 mmol), DPPP (91 mg, 0.22 mmol) followed by Et$_3$N (95 mg, 0.94 mmol) were added. The reaction was degassed and purged with CO three times. The reaction mixture was heated at 120° C. under 3 MPa of CO for 16 h. TLC (DCM/MeOH=20:1, UV) showed that about 50% starting material was remained and the main new spot was the desired product. The reaction was stopped and the solvent removed. The residue was purified by flash column to give JJJ-3 (26 mg, 27%) and starting material (50 mg). LCMS [M+1] 458; 1H NMR (400 MHz, CDCl$_3$) δ ppm 8.81 (s, 1H), 8.12-8.08 (m, 1H), 7.71 (d, J=4.5 Hz, 1H), 7.53-7.50 (m, 1H), 7.26-7.18 (m, 2H), 6.60 (d, J=3.8 Hz, 1H), 5.83 (d, J=5.3 Hz, 1H), 5.29 (t, J=5.6 Hz, 1H), 5.16 (s, 1H), 4.95-4.90 (m, 1H), 4.60 (s, 1H), 3.96 (s, 3H), 2.78 (s, 3H), 1.58 (s, 3H), 1.28 (s, 3H)

Step 4: Synthesis of (R)-((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)(4-fluoro-3-(hydroxymethyl)phenyl)methanol (JJJ-4)

To a solution of JJJ-3 (26 mg, 0.06 mmol) in dry THF (1 mL) was added LAH (7 mg, 0.17 mmol) under N$_2$ in one portion at 0° C. The resulting yellow suspension was stirred at 10° C. for 2 h. TLC (DCM/MeOH=20:1, UV) showed the reaction was almost complete then quenched with EtOAc, stirred for 30 min. The mixture was filtered through celite and concentrated. The residue was purified by prep-TLC to give the product, JJJ-4 (15 mg, 61%) as a white solid. LCMS [M+1] 430

Step 5: Synthesis of (2R,3S,4R,5R)-2-((R)-(4-fluoro-3-(hydroxymethyl)phenyl)(hydroxy)methyl)-5-(4-methyl-7H-pyrrolo[2,3-d]pyrimidin-7-yl)tetrahydrofuran-3,4-diol (JJJ-5)

To a solution of JJJ-4 (15 mg, 0.04 mmol) in water (0.2 mL) was added TFA (0.1 mL), then the reaction was stirred at 5° C. for 3 h. LCMS showed the reaction was complete and the solvent was removed in vacuo. The residue was dissolved in MeOH (1 mL) and K$_2$CO$_3$ (6 mg) was added and stirred at r.t. (8° C.) for 30 min. The solvent was removed and the residue was diluted with EtOAc, and washed with water (5 mL×2). The organic layer was dried over sodium sulfate, concentrated in vacuo, wand purified by prep-TLC to give JJJ-5 (3 mg, 20%) as a white solid. LCMS [M+1] 390; $^1$H NMR (400 MHz, MeOD) δ ppm 8.65 (s, 1H), 7.64 (d, J=3.5 Hz, 1H), 7.59 (d, J=5.8 Hz, 1H), 7.44-7.38 (m, J=4.5 Hz, 1H), 7.09-7.03 (m, 1H), 6.77 (d, J=3.8 Hz, 1H), 6.15 (d, J=7.5 Hz, 1H), 5.00 (d, J=2.8 Hz, 1H), 4.79 (dd, J=5.0, 7.3 Hz, 1H), 4.67 (s, 2H), 4.30-4.27 (m, 2H), 2.75 (s, 3H)

Example 115

(2R,3S,4R,5R)-2-((R)-(4-chloro-3-fluorophenyl)(hydroxy)methyl)-5-(7H-pyrrolo[2,3-d]pyrimidin-7-yl)tetrahydrofuran-3,4-diol (KKK-4)

Scheme KKK

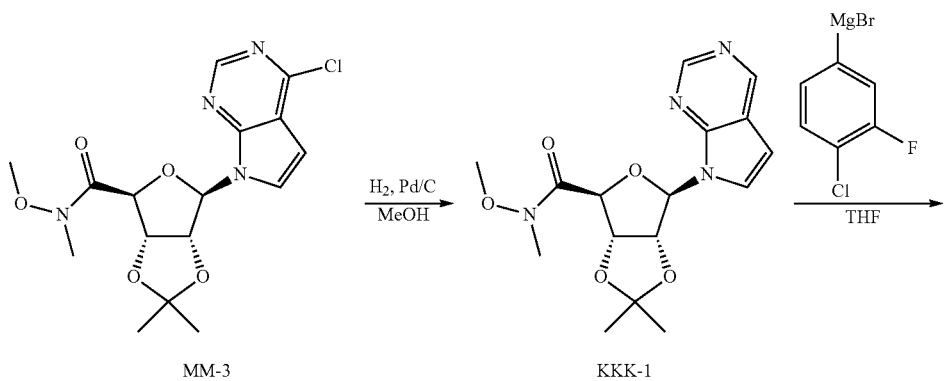

MM-3          KKK-1

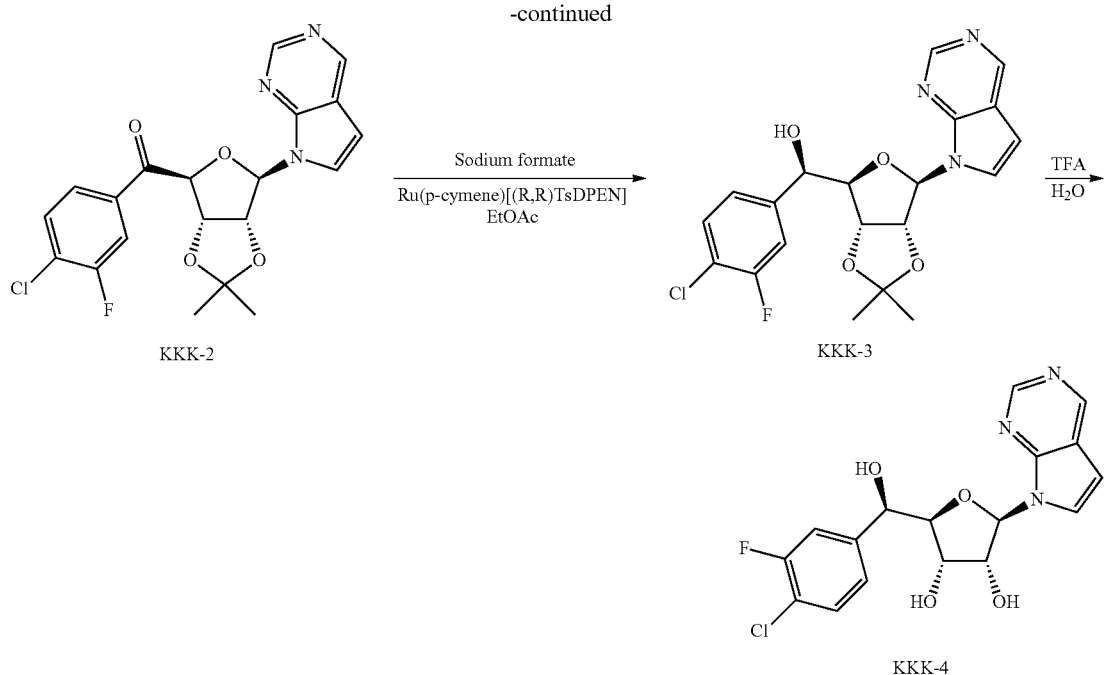

Step 1: Synthesis of (3aS,4S,6R,6aR)-N-methoxy-N,2,2-trimethyl-6-(7H-pyrrolo[2,3-d]pyrimidin-7-yl) tetrahydrofuro[3,4-d][1,3]dioxole-4-carboxamide (KKK-1)

A mixture of MM-3 (1 g, 2.6 mmol) and Pd/C (200 mg) in MeOH (30 mL) was degassed with $H_2$ four times. The mixture was stirred at rt (25° C.) under $H_2$ balloon for 2 hr. TLC (petroleum ether/EtOAc=1:1) most of the starting material was consumed and a good spot was formed. The mixture was filtered and concentrated in vacuo. The residue was purified by silica gel chromatography eluted with EtOAc in petroleum ether from 0 to 100% then 10% MeOH in DCM to afford the product KKK-1 (530 mg, 58%) as a yellow gum. LCMS [M+1] 349; $^1$H NMR (400 MHz, CDCl$_3$) δ ppm 8.99 (br. s., 1H), 8.91 (br. s., 1H), 7.65 (br. s., 1H), 6.72 (d, J=2.0 Hz, 1H), 6.61 (d, J=3.8 Hz, 1H), 5.35-5.26 (m, 1H), 5.25-5.16 (m, 2H), 3.69 (s, 3H), 3.18 (s, 3H), 1.68 (s, 3H), 1.41 (s, 3H)

Step 2: Synthesis of (4-chloro-3-fluorophenyl) ((3aS,4S,6R,6aR)-2,2-dimethyl-6-(7H-pyrrolo[2,3-d]pyrimidin-7-yl)tetrahydrofuro[3,4-d][1,3]dioxol-4-yl)methanone (KKK-2)

To a solution of KKK-1 (265 mg, 0.76 mmol) in dry THF (5 mL) was added (4-chloro-3-fluorophenyl) magnesium bromide (2.0 mL, 1.0 mmol) at 0° C. The mixture was stirred at 0° C. for 1 hr. TLC (petroleum ether/EtOAc=1:1) showed most of the starting material was consumed and a good spot was formed. The mixture was quenched with NH$_4$Cl aq (5 mL) and diluted with EtOAc (5 mL×3). The organic layer was washed with brine (10 mL), dried over Na$_2$SO$_4$ and concentrated in vacuo to afford crude material KKK-2 (380 mg, >99%) as a yellow oil which was used in the next step directly. LCMS [M+1]418; $^1$H NMR (400 MHz, CDCl$_3$) δ ppm 8.86 (s, 1H), 8.68 (s, 1H), 7.57-7.47 (m, 2H), 7.38-7.30 (m, 1H), 7.24 (d, J=3.8 Hz, 1H), 6.52 (d, J=3.8 Hz, 1H), 6.39 (s, 1H), 5.80-5.72 (m, 1H), 5.51 (d, J=6.0 Hz, 1H), 5.35 (d, J=1.8 Hz, 1H), 1.70 (s, 3H), 1.46 (s, 3H)

Step 3: Synthesis of (R)-(4-chloro-3-fluorophenyl) ((3aR,4R,6R,6aR)-2,2-dimethyl-6-(7H-pyrrolo[2,3-d]pyrimidin-7-yl)tetrahydrofuro[3,4-d][1,3]dioxol-4-yl)methanol (KKK-3)

A light yellow mixture of crude KKK-2 (75 mg, 0.16 mmol) in EtOAc (0.5 mL) and 2.5 M aq sodium formate (4 mL, 10 mmol) was purged with N$_2$ for 1 hr. To the mixture was added Ru(p-cymene)[(R,R)TsDPEN](10 mg, 0.02 mmol) at rt (25° C.). The resulting yellow mixture was stirred under N$_2$ at rt (25° C.) for 20 hrs. TLC (petroleum ether/EtOAc=1:1) showed most of the starting material was consumed. The mixture was extracted with EtOAc (1 mL×2). The extract purified by prep-TLC (petroleum ether/EtOAc=1:1) to afford the product KKK-3 (25 mg, 38%) as a white solid. LCMS [M+1]420; $^1$H NMR (400 MHz, CDCl$_3$) δ ppm 9.07 (s, 1H), 8.92 (s, 1H), 7.47-7.36 (m, 2H), 7.31 (d, J=3.8 Hz, 1H), 7.25-7.20 (m, 2H), 6.62 (d, J=3.8 Hz, 1H), 5.85 (d, J=5.3 Hz, 1H), 5.29 (t, J=5.6 Hz, 1H), 5.12 (s, 1H), 4.92 (d, J=6.0 Hz, 1H), 4.58 (s, 1H), 1.59 (s, 3H), 1.29 (s, 3H)

Step 4: Synthesis of (2R,3S,4R,5R)-2-((R)-(4-chloro-3-fluorophenyl)(hydroxy)methyl)-5-(7H-pyrrolo[2,3-d]pyrimidin-7-yl)tetrahydrofuran-3,4-diol (KKK-4)

KKK-3 (25 mg, 0.06 mmol) was cooled to 0° C. and TFA/H$_2$O was added (1 mL each). The mixture was stirred at rt (25° C.) for 2 hrs. LCMS showed most of the starting material was consumed. The mixture was poured into 20% K$_2$CO$_3$ (10 mL) and extracted with EtOAc (10 mL×2). The extract was washed with brine (10 mL×2), dried over MgSO$_4$ and concentrated in vacuo. The product was lyophilized to afford a white solid (20 mg, 88%). LCMS [M+1] 380; $^1$H NMR (400 MHz, DMSO-d$_6$) δ ppm 9.05 (s, 1H), 8.81 (s, 1H), 7.89 (d, J=3.8 Hz, 1H), 7.52 (t, J=7.9 Hz, 1H), 7.40 (d, J=12.0 Hz, 1H), 7.27 (d, J=8.5 Hz, 1H), 6.75 (d, J=3.5 Hz, 1H), 6.21 (d, J=7.5 Hz, 1H), 6.17 (d, J=4.8 Hz, 1H), 5.33 (d, J=7.0 Hz, 1H), 5.17 (d, J=4.3 Hz, 1H), 4.83 (t, J=4.9 Hz, 1H), 4.64-4.56 (m, 1H), 4.16-4.10 (m, 1H), 4.02 (d, J=5.0 Hz, 1H)

Example 116

(2R,3S,4R,5R)-2-((R)-amino(4-chloro-3-fluorophenyl)methyl)-5-(7H-pyrrolo[2,3-d]pyrimidin-7-yl)tetrahydrofuran-3,4-diol (LLL-4)

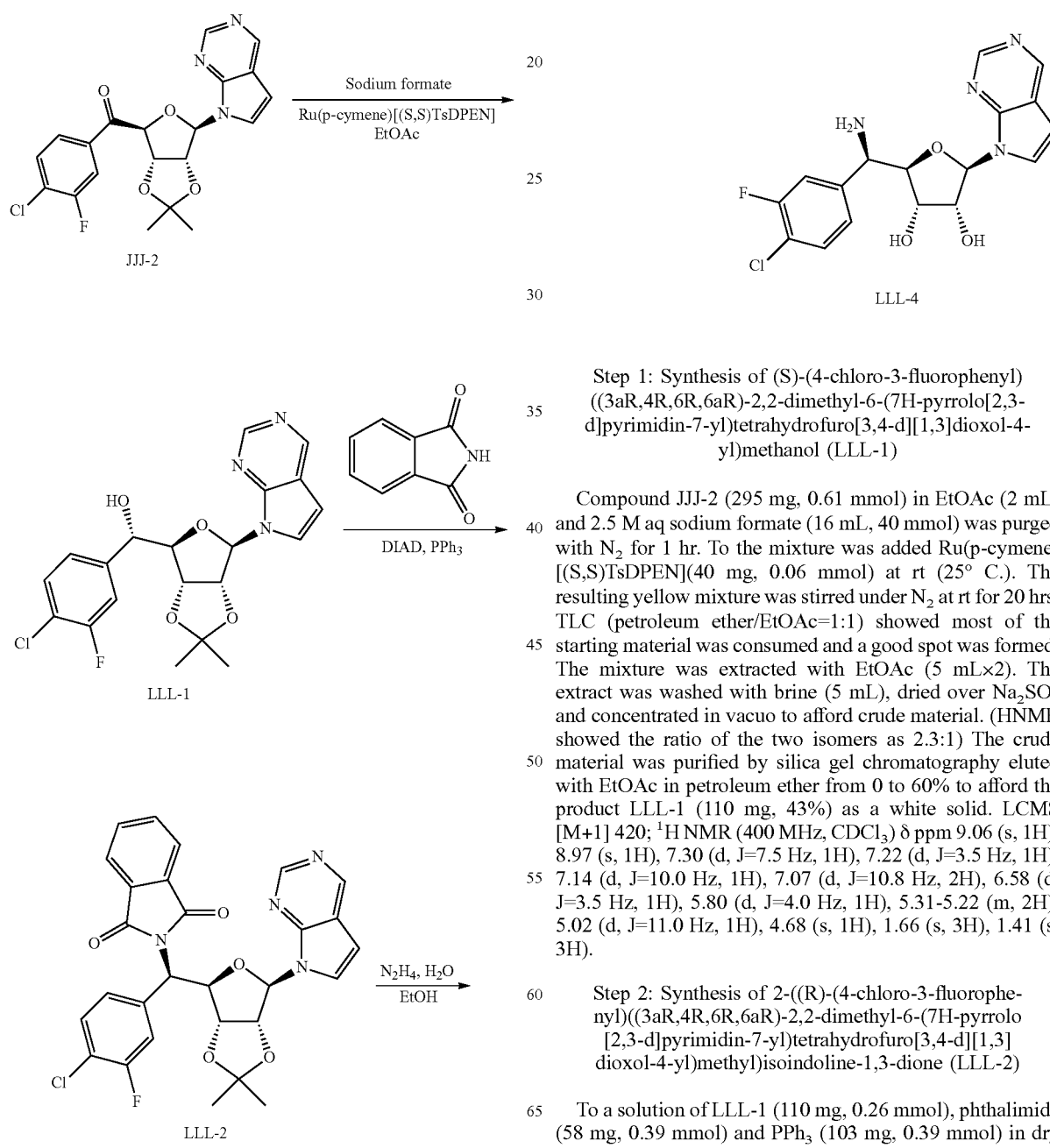

Step 1: Synthesis of (S)-(4-chloro-3-fluorophenyl)((3aR,4R,6R,6aR)-2,2-dimethyl-6-(7H-pyrrolo[2,3-d]pyrimidin-7-yl)tetrahydrofuro[3,4-d][1,3]dioxol-4-yl)methanol (LLL-1)

Compound JJJ-2 (295 mg, 0.61 mmol) in EtOAc (2 mL) and 2.5 M aq sodium formate (16 mL, 40 mmol) was purged with N₂ for 1 hr. To the mixture was added Ru(p-cymene)[(S,S)TsDPEN](40 mg, 0.06 mmol) at rt (25° C.). The resulting yellow mixture was stirred under N₂ at rt for 20 hrs. TLC (petroleum ether/EtOAc=1:1) showed most of the starting material was consumed and a good spot was formed. The mixture was extracted with EtOAc (5 mL×2). The extract was washed with brine (5 mL), dried over Na₂SO₄ and concentrated in vacuo to afford crude material. (HNMR showed the ratio of the two isomers as 2.3:1) The crude material was purified by silica gel chromatography eluted with EtOAc in petroleum ether from 0 to 60% to afford the product LLL-1 (110 mg, 43%) as a white solid. LCMS [M+1] 420; ¹H NMR (400 MHz, CDCl₃) δ ppm 9.06 (s, 1H), 8.97 (s, 1H), 7.30 (d, J=7.5 Hz, 1H), 7.22 (d, J=3.5 Hz, 1H), 7.14 (d, J=10.0 Hz, 1H), 7.07 (d, J=10.8 Hz, 2H), 6.58 (d, J=3.5 Hz, 1H), 5.80 (d, J=4.0 Hz, 1H), 5.31-5.22 (m, 2H), 5.02 (d, J=11.0 Hz, 1H), 4.68 (s, 1H), 1.66 (s, 3H), 1.41 (s, 3H).

Step 2: Synthesis of 2-((R)-(4-chloro-3-fluorophenyl)((3aR,4R,6R,6aR)-2,2-dimethyl-6-(7H-pyrrolo[2,3-d]pyrimidin-7-yl)tetrahydrofuro[3,4-d][1,3]dioxol-4-yl)methyl)isoindoline-1,3-dione (LLL-2)

To a solution of LLL-1 (110 mg, 0.26 mmol), phthalimide (58 mg, 0.39 mmol) and PPh₃ (103 mg, 0.39 mmol) in dry THF (2 mL) was added DIAD (80 mg, 0.393 mmol) at 0° C.

The mixture was stirred at rt (25° C.) under N$_2$ for 20 hrs. TLC (petroleum ether/EtOAc=1:1) showed most of the starting material was consumed. The mixture was purified by prep-TLC (petroleum ether/EtOAc=1:1) to afford the product LLL-2 (95 mg, 66%) as a light yellow solid. LCMS [M+1] 549; $^1$H NMR (400 MHz, CDCl$_3$) δ ppm 9.05 (s, 1H), 9.01 (s, 1H), 7.92-7.83 (m, 2H), 7.76 (dd, J=3.0, 5.5 Hz, 2H), 7.22-7.14 (m, 3H), 6.98 (d, J=8.5 Hz, 1H), 6.57 (d, J=3.8 Hz, 1H), 6.19 (s, 1H), 5.76 (d, J=10.8 Hz, 1H), 5.57-5.39 (m, 2H), 5.18 (dd, J=3.9, 6.1 Hz, 1H), 1.62 (s, 3H), 1.31 (s, 3H)

Step 3: Synthesis of (R)-(4-chloro-3-fluorophenyl) ((3aR,4R,6R,6aR)-2,2-dimethyl-6-(7H-pyrrolo[2,3-d]pyrimidin-7-yl)tetrahydrofuro[3,4-d][1,3]dioxol-4-yl)methanamine (LLL-3)

To a light yellow suspension of LLL-2 (90 mg, 0.16 mmol) in EtOH (2 mL) was added 85% N$_2$H$_4$.H$_2$O (0.5 mL). The resulting yellow solution was stirred at rt (25° C.) for 16 hrs. TLC (petroleum ether/EtOAc=1:1) showed most of the starting material was consumed. The mixture was purified by pre-TLC (petroleum ether/EtOAc=1:1) to afford the product LLL-3 (50 mg, 72.8%) as a white solid. LCMS [M+1] 419; $^1$H NMR (400 MHz, CDCl$_3$) δ ppm 9.01 (s, 1H), 8.90 (s, 1H), 7.33 (t, J=7.9 Hz, 1H), 7.25 (d, J=3.8 Hz, 1H), 7.15 (dd, J=1.9, 10.2 Hz, 1H), 7.03 (d, J=8.0 Hz, 1H), 6.61 (d, J=3.8 Hz, 1H), 6.10 (d, J=3.8 Hz, 1H), 5.42 (dd, J=3.6, 6.7 Hz, 1H), 5.15 (dd, J=3.5, 6.8 Hz, 1H), 4.35-4.13 (m, 2H), 1.58 (s, 3H), 1.34 (s, 3H)

Step 4: Synthesis of (2R,3S,4R,5R)-2-((R)-amino (4-chloro-3-fluorophenyl)methyl)-5-(7H-pyrrolo[2,3-d]pyrimidin-7-yl)tetrahydrofuran-3,4-diol (LLL-4)

To LLL-3 (50 mg, 0.12 mmol) was added TFA/H$_2$O (1 mL each, cooled to 0° C. previously). The mixture was stirred at rt (25° C.) for 2 hrs. LCMS showed most of the starting material was consumed and the main peak was desired compound. The mixture was poured into 20% K$_2$CO$_3$(10 mL), diluted with brine (10 mL) and extracted with EtOAc (10 mL×3). The extract was washed with brine (10 mL×2), dried over MgSO$_4$, filtered, and concentrated in vacuo. The product, LLL-4, was lyophilized to a white solid (30 mg, 66%). LCMS [M+1] 379; $^1$H NMR (400 MHz, DMSO-d$_6$) δ ppm 9.03 (s, 1H), 8.79 (s, 1H), 7.84 (d, J=3.8 Hz, 1H), 7.51-7.39 (m, 2H), 7.24 (d, J=8.0 Hz, 1H), 6.71 (d, J=3.8 Hz, 1H), 6.12 (d, J=7.3 Hz, 1H), 5.34 (d, J=6.5 Hz, 1H), 5.15 (br. s., 1H), 4.66-4.54 (m, 1H), 4.24 (br. s., 1H), 4.09 (d, J=6.8 Hz, 1H), 3.95 (dd, J=2.1, 6.9 Hz, 1H).

Example 117

(2R,3S,4R,5R)-2-((R)-(3,4-difluorophenyl)(hydroxy) methyl)-5-(7H-pyrrolo[2,3-d]pyrimidin-7-yl)tetrahydrofuran-3,4-diol Example 117 was prepared under similar procedures as Example 115 (Scheme KKK) except using 3,4-difluorophenylmagnesiumbromide in Step 2.

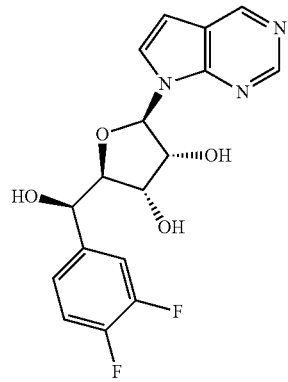 [SMILES: O[C@@H]1[C@H](O)[C@@H]([C@H](O)c2ccc(F)c(F)c2)O[C@H]1n1ccc2cncnc21]

LCMS [M+1] 364; $^1$H NMR (400 MHz, DMSO-d$_6$) δ ppm 9.04 (s, 1H), 8.80 (s, 1H), 7.88 (d, J=3.8 Hz, 1H), 7.45-7.28 (m, 2H), 7.24 (br. s., 1H), 6.74 (d, J=3.8 Hz, 1H), 6.20 (d, J=7.5 Hz, 1H), 6.12 (d, J=4.3 Hz, 1H), 5.32 (d, J=7.0 Hz, 1H), 5.15 (d, J=4.0 Hz, 1H), 4.80 (t, J=4.9 Hz, 1H), 4.59 (d, J=5.0 Hz, 1H), 4.13 (t, J=4.9 Hz, 1H), 4.00 (d, J=4.5 Hz, 1H)

Example 118

(2R,3S,4R,5R)-2-((R)-amino(3,4-difluorophenyl) methyl)-5-(7H-pyrrolo[2,3-d]pyrimidin-7-yl)tetrahydrofuran-3,4-diol Example 118 was prepared under similar procedures as Example 116 (Scheme LLL) except using 3,4-difluorophenylmagnesiumbromide in Step 2 of Example 117 (Scheme KKK).

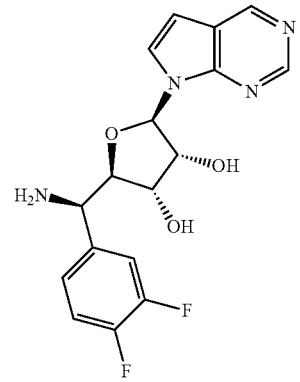 [SMILES: N[C@H](c1ccc(F)c(F)c1)[C@H]1O[C@@H](n2ccc3cncnc32)[C@H](O)[C@@H]1O]

LCMS [M+1] 363; $^1$H NMR (400 MHz, DMSO-d$_6$) δ ppm 9.02 (s, 1H), 8.78 (s, 1H), 7.81 (d, J=3.8 Hz, 1H), 7.47-7.38 (m, 1H), 7.28 (dd, J=8.3, 10.8 Hz, 1H), 7.21 (br. s., 1H), 6.70 (d, J=3.5 Hz, 1H), 6.11 (d, J=7.3 Hz, 1H), 5.33 (d, J=6.5 Hz, 1H), 5.13 (br. s., 1H), 4.56 (d, J=5.5 Hz, 1H), 4.22 (d, J=3.3 Hz, 1H), 4.08 (d, J=6.5 Hz, 1H), 3.94 (dd, J=2.1, 6.7 Hz, 1H)

Example 119

(2R,3R,4S,5R)-2-(4-amino-5-iodo-7H-pyrrolo[2,3-d]pyrimidin-7-yl)-5-((R)-(3,4-difluorophenyl)(hydroxy)methyl)tetrahydrofuran-3,4-diol (MMM-6)

Scheme MMM

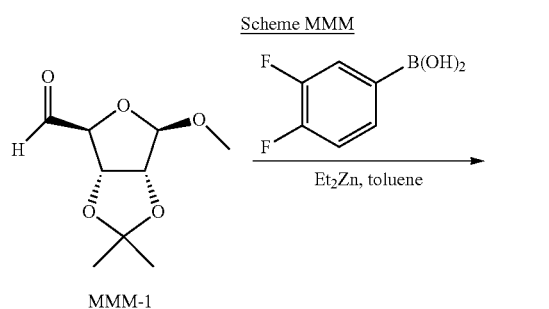

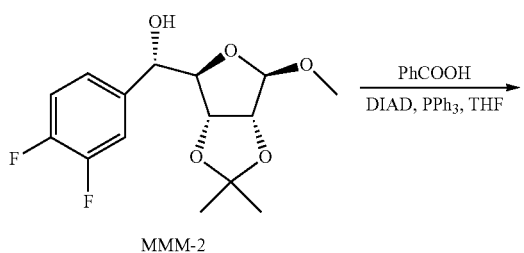

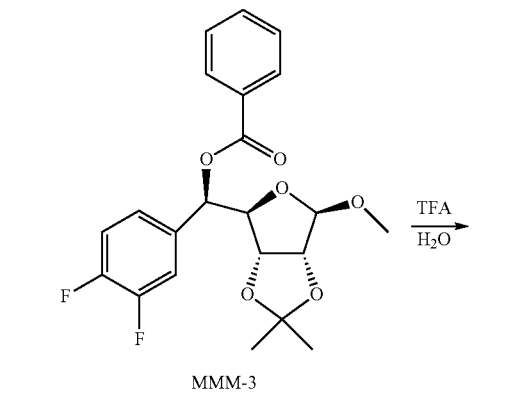

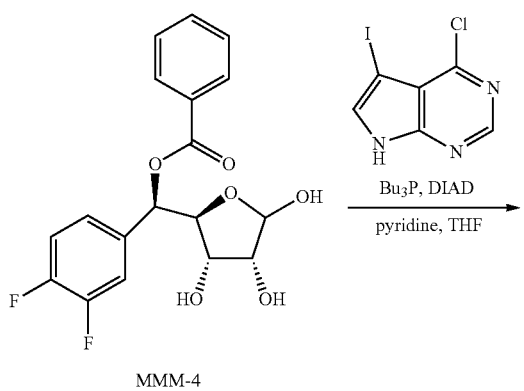

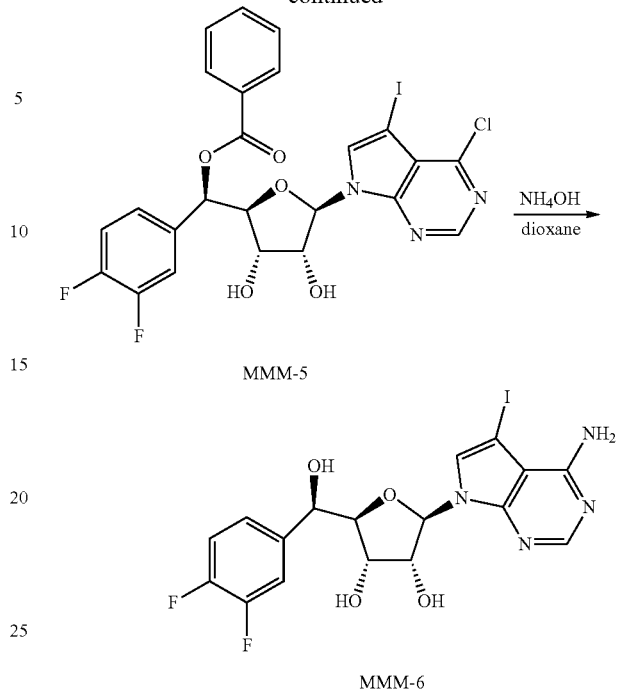

Step 1: Synthesis of (S)-(3,4-difluorophenyl)((3aR,4R,6R,6aR)-6-methoxy-2,2-dimethyltetrahydrofuro[3,4-d][1,3]dioxol-4-yl)methanol (MMM-2)

(3aR,4S,6R,6aR)-6-methoxy-2,2-dimethyltetrahydrofuro[3,4-d][1,3]dioxole-4-carbaldehyde MMM-1 was prepared using a two-step literature procedure from *Tetrahedron*, 2013, 10581-10592 and *Organic Letters, Vol.* 4, No. 17, 2002, 3001. To a white suspension of (3,4-difluorophenyl)boronic acid (3.2 g, 20.26 mmol) in dry toluene (79 mL) was added a solution of $Et_2Zn$ (70.9 mL, 1M in toluene, 70.9 mmol) slowly at 20° C. under $N_2$. The mixture was heated at 60° C. for 1 hour and most of white solid was dissolved. Then a solution MMM-1 (4.1 g, 20.3 mmol) in toluene (5 mL) was added slowly at 60° C. The mixture was stirred at 60° C. for another 1.5 hours. TLC (petroleum ether:EtOAc=1:1, PMA stain) showed the starting material was consumed and a new spot was detected. The mixture was quenched by water (40 mL) at 10° C. slowly and a yellow solid was formed. The mixture was diluted with EtOAc (50 mL). The filtrate was separated and the aqueous was extracted with EtOAc (50 mL). The combined organic layers were washed with brine (100 mL), dried over $Na_2SO_4$, filtered and concentrated to yield crude product as a yellow oil which was purified by ISCO (silica gel, petroleum ether:EtOAc=4:1) to yield 4 g of MMM-2 (63% yield) as a yellow oil. $^1$H NMR (400 MHz, $CDCl_3$) δ ppm 7.26-7.01 (m, 3H), 4.98 (s, 1H), 4.89 (d, J=6.0 Hz, 1H), 4.70-4.65 (m, 2H), 4.63 (d, J=4.0 Hz, 1H), 4.03 (d, J=9.0 Hz, 1H), 3.39 (s, 3H), 1.48 (s, 3H), 1.33 (s, 3H)

Step 2: Synthesis of (R)-(3,4-difluorophenyl)((3aR,4R,6R,6aR)-6-methoxy-2,2-dimethyltetrahydrofuro[3,4-d][1,3]dioxol-4-yl)methyl benzoate (MMM-3)

To a mixture of MMM-2 (4 g, 12.65 mmol), PhCOOH (2.32 g, 19 mmol), $PPh_3$ (4.98 g, 19 mmol) in toluene (90 mL) was added DIAD (3840 mg, 19 mmol) at 0° C. under N₂. The yellow solution was stirred at 20° C. for 3 hours. TLC (petroleum ether: EtOAc=4:1) showed the starting material was consumed and a lower polar spot was detected. The mixture was diluted with EtOAc (50 mL) and washed with sat.Na₂CO₃ (50 mL×2), brine (50 mL), dried over Na₂SO₄ and filtered. The filtrate was concentrated to yield crude product as a colorless oil, which was purified by ISCO (silica gel, EtOAc/petroleum ether=12%) to give 4.3 g of MMM-3 (81% yield) as a colorless gum. ¹H NMR (400 MHz, CDCl₃) δ ppm 8.06 (dd, J=1.3, 8.3 Hz, 2H), 7.61-7.59 (m, 1H), 7.47 (d, J=8.0 Hz, 2H), 7.37-7.28 (m, 1H), 7.25-7.08 (m, 2H), 5.93 (d, J=9.3 Hz, 1H), 4.94 (s, 1H), 4.89-4.83 (m, 1H), 4.74-4.68 (m, 1H), 4.67-4.61 (m, 1H), 3.21 (s, 3H), 1.50 (s, 3H), 1.33 (s, 3H); HRMS m/z C₂₂H₂₂F₂O₆ [M+23] 443.

Step 3: Synthesis of (1R)-(3,4-difluorophenyl)((2S,3S,4R)-3,4,5-trihydroxytetrahydrofuran-2-yl)methyl benzoate (MMM-4)

The solution of MMM-3 (1060 mg, 2.521 mmol) in 10 mL trifluoroacetic acid and 5 mL distilled water was stirred at r.t. overnight. The reaction mixture was neutralized by std. NaHCO₃, extracted with EtOAc 3 times, the organic layers were combined, washed with brine, dried over Na₂SO₄, concentrated, purified by column chromatography with 100% EtOAc to give 0.9 g (97% yield) MMM-4 as white solid. ¹H NMR (400 MHz, CDCl₃) δ ppm 2.61 (d, J=6.36 Hz, 1 H) 2.90 (d, J=7.34 Hz, 1 H) 3.46 (d, J=6.85 Hz, 1 H) 3.98-4.07 (m, 1 H) 4.15-4.23 (m, 1 H) 4.49-4.55 (m, 1 H) 5.35 (dd, J=6.72, 4.28 Hz, 1 H) 6.07 (d, J=5.01 Hz, 1 H) 7.14-7.24 (m, 2 H) 7.28-7.36 (m, 1 H) 7.49 (t, J=7.70 Hz, 2 H) 7.62 (t, J=7.46 Hz, 1 H) 8.05-8.10 (m, 2 H)

Step 4: Synthesis of (R)-((2S,3S,4R,5R)-5-(4-chloro-5-iodo-7H-pyrrolo[2,3-d]pyrimidin-7-yl)-3,4-dihydroxytetrahydrofuran-2-yl)(3,4-difluorophenyl) methyl benzoate (MMM-5)

To a solution of 4-chloro-5-iodo-7H-pyrrolo[2,3-d]pyrimidine (76.2 mg, 0.27 mmol) in 10 ml THF was added pyridine (21.6 mg, 0.27 mmol, 0.02 mL) at r.t., diisopropyl azodiformate (116.0 mg, 0.57 mmol) was added followed by tri-N-butylphosphine (114 mg, 0.546 mmol) at r.t., MMM-4 (100 mg, 0.27 mmol) was added all at once. The reaction was stirred at r.t. for 30 min. The reaction mixture was concentrated, added EtOAc and H₂O, extracted with EtOAc 3 times, the organic layers were combined, washed with brine, dried over Na₂SO₄, concentrated, purified by reverse phase preparative HPLC to give 60 mg (35% yield) MMM-5 as white solid. LCMS [M+1] 627.9; ¹H NMR (400 MHz, CDCl₃) δ ppm 4.56 (dd, J=5.32, 2.75 Hz, 1 H) 4.62-4.73 (m, 2 H) 6.06 (d, J=5.26 Hz, 1 H) 6.38 (d, J=4.28 Hz, 1 H) 7.15-7.24 (m, 2 H) 7.24-7.32 (m, 3 H) 7.38 (t, J=7.76 Hz, 2 H) 7.55 (t, J=7.46 Hz, 1H) 7.90-7.97 (m, 2 H) 8.48 (s, 1 H)

Step 5: Synthesis of (2R,3R,4S,5R)-2-(4-amino-5-iodo-7H-pyrrolo[2,3-d]pyrimidin-7-yl)-5-((R)-(3,4-difluorophenyl)(hydroxy)methyl)tetrahydrofuran-3,4-diol (MMM-6)

MMM-5 (23 mg, 0.037 mmol) was dissolved in 1 mL dioxane, 1 mL ammonium hydroxide solution was added. The reaction vessel was sealed and heated at 100° C. overnight. After cooled to r.t., the reaction mixture was concentrated, redissolved in MeOH, purified by reverse phase preparative HPLC to give 15.8 mg (86% yield) MMM-6 as white solid. LCMS [M+1] 505.0; ¹H NMR (400 MHz, MeOD) δ ppm 4.17 (dd, J=5.26, 1.83 Hz, 1 H) 4.20-4.27 (m, 1 H) 4.69 (dd, J=7.09, 5.38 Hz, 1 H) 4.96 (d, J=2.81 Hz, 1 H) 5.96 (d, J=7.09 Hz, 1 H) 7.20-7.27 (m, 2 H) 7.34-7.41 (m, 1 H) 7.42 (s, 1 H) 8.10 (s, 1 H)

Example 120

(2R,3R,4S,5R)-2-(2-amino-4-methyl-7H-pyrrolo[2,3-d]pyrimidin-7-yl)-5-((R)-(3,4-difluorophenyl)(hydroxy)methyl)tetrahydrofuran-3,4-diol (NNN-6)

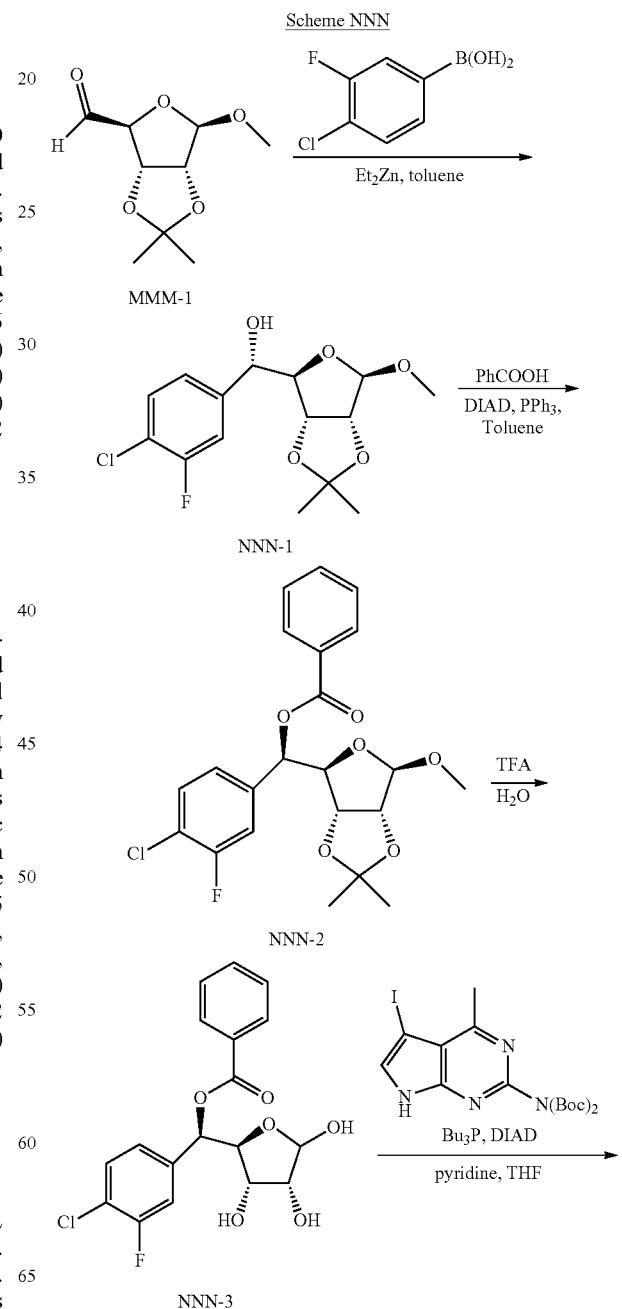

Scheme NNN

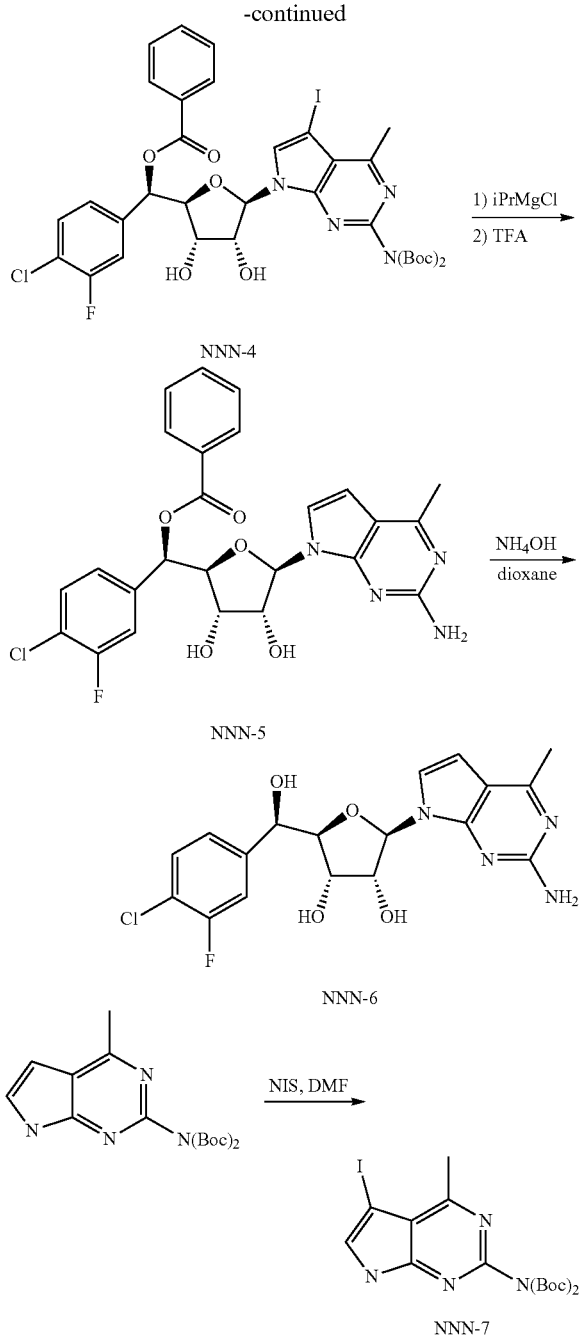

NNN-4

NNN-5

NNN-6

NNN-7

Step 1: Synthesis of (S)-(4-chloro-3-fluorophenyl) ((3aR,4R,6R,6aR)-6-methoxy-2,2-dimethyltetrahydrofuro[3,4-d][1,3]dioxol-4-yl)methanol (NNN-1)

To a white suspension of (4-chloro-3-fluorophenyl)boronic acid (3550 mg, 20.36 mmol) in dry toluene (92 mL) was added a solution of $Et_2Zn$ (71.3 mL, 1M in toluene, 71.3 mmol) slowly at 20° C. under $N_2$. The mixture was heated at 60° C. for 1 hour. White solid was dissolved and the mixture turned to clear. Then a solution of MMM-1 (4.11 g, 20.33 mmol) in toluene (10 mL) was added slowly at 60° C. The mixture was stirred at 60° C. for another 1.5 hours. The mixture turned to yellow. TLC (petroleum ether:EtOAc=2:1, PMA stain, Rf~0.6) showed the starting material was consumed and a new spot was detected. The mixture was quenched by water (40 mL) at 10° C. slowly and yellow solid was formed. The mixture was diluted with EtOAc (80 mL) and filtered. The filtrate was separated and washed with brine (30 mL), dried over $Na_2SO_4$, filtered and concentrated to yield crude product as a yellow oil. The crude product was purified by ISCO (silica gel, petroleum ether: EtOAc=4:1) to yield 3.75 g of NNN-1 (55% yield) as a colorless gum. $^1$H NMR (400 MHz, $CDCl_3$) δ ppm 7.40 (t, J=7.9 Hz, 1H), 7.20 (dd, J=1.8, 10.0 Hz, 1H), 7.13-7.05 (m, 1H), 4.97 (s, 1H), 4.91 (d, J=6.3 Hz, 1H), 4.75-4.62 (m, 3H), 4.09 (d, J=9.3 Hz, 1H), 3.38 (s, 3H), 1.49 (s, 3H), 1.34 (s, 3H)

Step 2: Synthesis of (R)-(4-chloro-3-fluorophenyl) ((3aR,4R,6R,6aR)-6-methoxy-2,2-dimethyltetrahydrofuro[3,4-d][1,3]dioxol-4-yl)methyl benzoate (NNN-2)

To a mixture of NNN-1 (2.91 g, 8.745 mmol), PhCOOH (1.6 g, 13.1 mmol), $PPh_3$ (3440 mg, 13.1 mmol) in toluene (60 mL) was added DIAD (2.65 g, 13.1 mmol) at 0° C. under $N_2$. The yellow solution was stirred at 20° C. for 3 hours. TLC (petroleum ether:EtOAc=10:1) showed starting material was consumed and a lower polar spot was detected. The mixture was diluted with EtOAc (60 mL) and washed with sat.$Na_2CO_3$ (30 mL×2), brine (60 mL), dried over $Na_2SO_4$ and filtered. The filtrate was concentrated to yield crude product as a yellow oil. The crude product was purified by ISCO (silica gel, EtOAc: petroleum ether=0~10%) to yield 3.1 g of NNN-2 (81% yield) as a colorless gum. $^1$H NMR (400 MHz, $CDCl_3$) δ ppm 8.06 (dd, J=1.3, 8.5 Hz, 2H), 7.63-7.56 (m, 1H), 7.47 (d, J=7.8 Hz, 2H), 7.43-7.37 (m, 1H), 7.31-7.27 (m, 1H), 7.24-7.19 (m, 1H), 5.96-5.90 (m, 1H), 4.94 (s, 1H), 4.88-4.85 (m, 1H), 4.70 (d, J=6.0 Hz, 1H), 4.67-4.61 (m, 1H), 3.22 (s, 3H), 1.50 (s, 3H), 1.33 (s, 3H) HRMS m/z for $C_{22}H_{22}FClO_6$ [M+23]+459.0567

Step 3: Synthesis of bis-tert-butyl (5-iodo-4-methyl-7H-pyrrolo[2,3-d]pyrimidin-2-yl)carbamate (NNN-7)

To a solution of bis-tert-butyl (4-methyl-7H-pyrrolo[2,3-d]pyrimidin-2-yl)carbamate (350 mg, 1.00 mmol) in 5 mL DMF was added N-iodosuccinimide (271 mg, 1.21 mmol), stirred at r.t. overnight. The reaction mixture was added EtOAc and $H_2O$, washed with $H_2O$ 3 times, concentrated and purified by column chromatography with 50% EtOAc/heptane to give 288 mg (60% yield)NNN-7 as light yellow solid. LCMS [M+1] 475.0; $^1$H NMR (400 MHz, DMSO-$d_6$) δ ppm 1.39 (s, 17 H) 2.86 (s, 3 H) 7.79 (d, J=2.32 Hz, 1 H) 12.54 (br. s., 1 H)

Step 4: Synthesis of (1R)-(4-chloro-3-fluorophenyl) ((2S,3S,4R)-3,4,5-trihydroxytetrahydrofuran-2-yl) methyl benzoate (NNN-3)

Followed similar procedures to Step 3 of Example 119. $^1$H NMR (400 MHz, $CDCl_3$) δ ppm 2.61 (br. s., 1 H) 3.98-4.11 (m, 1 H) 4.19 (br. s., 1 H) 4.48-4.56 (m, 1 H) 5.28-5.39 (m, 1 H) 6.03-6.15 (m, 1 H) 7.17-7.25 (m, 1 H) 7.27-7.33 (m, 1 H) 7.37-7.45 (m, 1 H) 7.45-7.53 (m, 2 H) 7.55-7.68 (m, 1 H) 8.01-8.16 (m, 2 H)

Step 5: Synthesis of (R)-((2S,3S,4R,5R)-5-(2-((bis-tert-butoxycarbonyl)amino)-5-iodo-4-methyl-7H-pyrrolo[2,3-d]pyrimidin-7-yl)-3,4-dihydroxytetrahydrofuran-2-yl)(4-chloro-3-fluorophenyl)methyl benzoate (NNN-4)

Followed similar procedures to Step 4 of Example 119. LCMS [M+1] 839.0.

Step 6: Synthesis of (R)-((2S,3S,4R,5R)-5-(2-amino-4-methyl-7H-pyrrolo[2,3-d]pyrimidin-7-yl)-3,4-dihydroxytetrahydrofuran-2-yl)(4-chloro-3-fluorophenyl)methyl benzoate (NNN-5)

NNN-4 (150 mg, 0.179 mmol) was dissolved in 2.0 mL THF, isopropyl magnesium chloride (64.9 mg, 0.447 mmol, 0.344 mL, 1.3 M) was added at r.t., stirred at r.t. for 1 h. The rxn was quenched by $H_2O$, added std. $NH_4Cl$ and EtOAc, extracted with EtOAc 3 times, the organic layers were combined, washed with brine, dried over $Na_2SO_4$ and concentrated.

The solution of above crude material in 1 mL DCM and 1 mL trifluoroacetic acid was stirred at r.t. for overnight. The reaction mixture was concentrated, added EtOAc, washed with water, the organic layers were combined and concentrated, purified by reverse phase preparative HPLC to give 44 mg (48% two steps) NNN-5 as yellow oil. LCMS [M+1] 513.0.

Step 6: Synthesis of (2R,3R,4S,5R)-2-(2-amino-4-methyl-7H-pyrrolo[2,3-d]pyrimidin-7-yl)-5-((R)-(4-chloro-3-fluorophenyl)(hydroxy)methyl)tetrahydrofuran-3,4-diol (NNN-6)

Followed similar procedures to Step 5 of Example 119. LCMS [M+1] 408.9; $^1$H NMR (700 MHz, DMSO-$d_6$) δ ppm 2.42 (s, 3 H) 3.92 (d, J=4.84 Hz, 1H) 4.07 (br. s., 1 H) 4.43-4.52 (m, 1 H) 4.77 (br. s., 1 H) 5.00 (d, J=3.74 Hz, 1 H) 5.17 (d, J=6.82 Hz, 1 H) 5.97 (d, J=7.48 Hz, 1 H) 6.09 (br. s., 2 H) 6.12 (d, J=4.40 Hz, 1 H) 6.44 (br. s., 1 H) 7.20-7.29 (m, 1 H) 7.38 (d, J=10.34 Hz, 1 H) 7.50 (t, J=7.81 Hz, 1 H)

Example 121

(2R,3R,4S,5R)-2-(2-chloro-5-fluoro-7H-pyrrolo[2,3-d]pyrimidin-7-yl)-5-((R)-(3,4-difluorophenyl)(hydroxy)methyl)tetrahydrofuran-3,4-diol (000-2)

Example 122

(2R,3R,4S,5R)-2-(2-amino-5-fluoro-7H-pyrrolo[2,3-d]pyrimidin-7-yl)-5-((R)-(3,4-difluorophenyl)(hydroxy)methyl)tetrahydrofuran-3,4-diol (000-3)

Scheme OOO

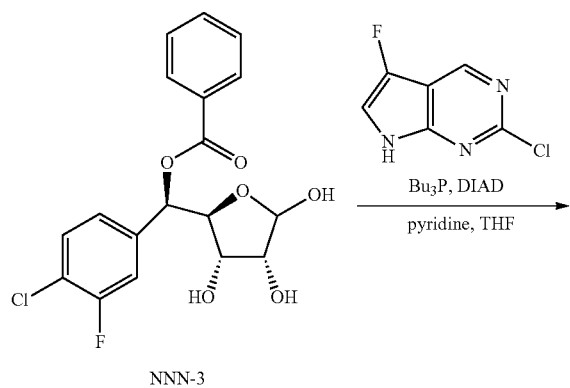

NNN-3

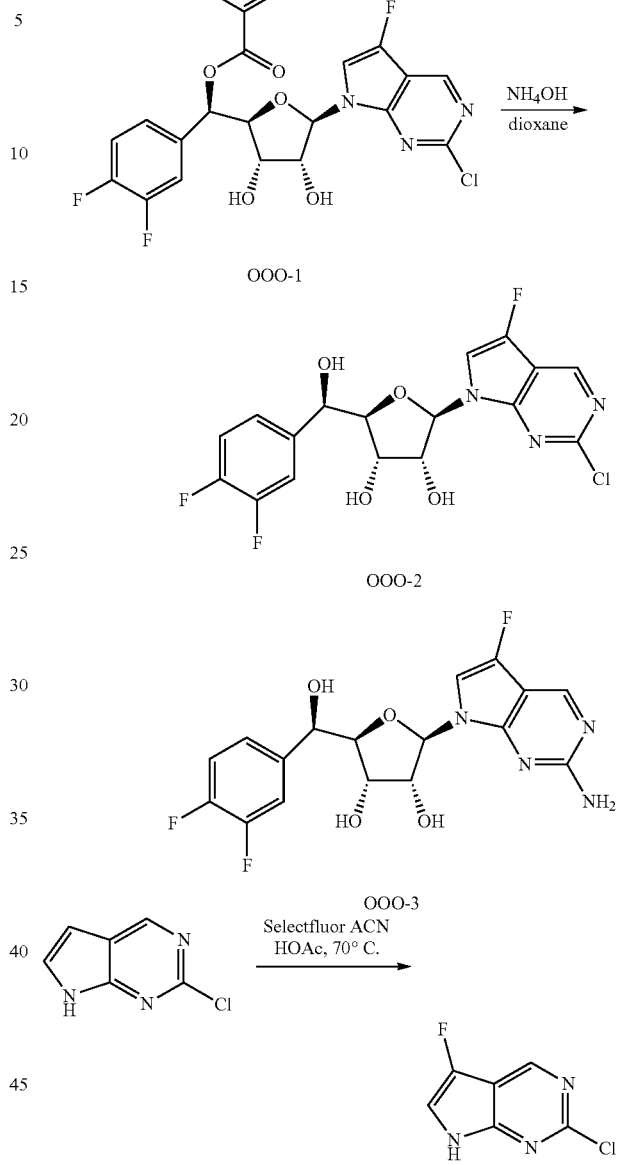

Step 1: Synthesis of 2-chloro-5-fluoro-7H-pyrrolo[2,3-d]pyrimidine (000-4)

To a suspension of 2-chloro-7H-pyrrolo[2,3-d]pyrimidine (2.4 g, 15.63 mmol) in MeCN (80 mL) was added selectfluor (8.3 g, 23.4 mmol). Acetic acid (8 mL) was added and the reaction was heated at 70° C. for 17 h. The volatiles were removed and the residue dissolved in water, neutralized with $NaHCO_3$ and extracted with EtOAc 3 times. The organics were combined, concentrated and the residue was purified by column chromatography with 40% EtOAc/heptane to give 460 mg (17% yield) 000-4 as white solid. LCMS [M+1]172.0; $^1$H NMR (400 MHz, MeOD) δ ppm 7.30 (d, J=2.57 Hz, 1 H) 8.89 (s, 1 H)

Step 2: Synthesis of (R)-(4-chloro-3-fluorophenyl) ((2S,3S,4R,5R)-5-(2-chloro-5-fluoro-7H-pyrrolo[2,3-d]pyrimidin-7-yl)-3,4-dihydroxytetrahydrofuran-2-yl)methyl benzoate (OOO-1)

Followed similar procedures to Step 4 of Example 119. LCMS [M+1] 536.0; $^1$H NMR (400 MHz, DMSO-$d_6$) δ ppm 4.25-4.34 (m, 1 H) 4.37 (dd, J=6.24, 3.55 Hz, 1 H) 4.52 (q, J=6.15 Hz, 1 H) 5.53 (d, J=5.50 Hz, 1 H) 5.58 (d, J=6.24 Hz, 1 H) 6.13 (d, J=6.11 Hz, 1 H) 6.19 (d, J=6.36 Hz, 1 H) 7.36 (d, J=8.56 Hz, 1 H) 7.49-7.56 (m, 2 H) 7.59 (t, J=7.70 Hz, 2 H) 7.67 (d, J=1.71 Hz, 1 H) 7.70-7.76 (m, 1 H) 8.07 (s, 1 H) 8.09 (s, 1 H) 9.06 (s, 1 H)

Step 3: Synthesis of (2R,3S,4R,5R)-2-((R)-(4-chloro-3-fluorophenyl)(hydroxy)methyl)-5-(2-chloro-5-fluoro-7H-pyrrolo[2,3-d]pyrimidin-7-yl)tetrahydrofuran-3,4-diol (OOO-2) and (2R,3R,4S,5R)-2-(2-amino-5-fluoro-7H-pyrrolo[2,3-d]pyrimidin-7-yl)-5-((R)-(4-chloro-3-fluorophenyl)(hydroxy)methyl) tetrahydrofuran-3,4-diol (OOO-3)

Followed similar procedures to Step 5 of Example 119.
OOO-2 LCMS [M+1] 432.0. $^1$H NMR (700 MHz, DMSO-d6) δ ppm 3.93 (br. s., 1 H) 4.05 (br. s., 1 H) 4.39 (br. s., 1 H) 4.72 (br. s., 1 H) 5.10-5.20 (m, 1 H) 5.33 (d, J=6.38 Hz, 1 H) 5.94-6.03 (m, 1 H) 6.04-6.13 (m, 1 H) 7.19 (d, J=7.70 Hz, 1 H) 7.32 (d, J=10.12 Hz, 1 H) 7.44 (t, J=7.15 Hz, 1 H) 7.87 (br. s., 1 H) 9.02 (br. s., 1 H)

OOO-3 LCMS [M+1] 413.0; $^1$H NMR (400 MHz, MeOD) δ ppm 4.14-4.23 (m, 2 H) 4.60 (dd, J=6.97, 5.26 Hz, 1 H) 4.93 (d, J=3.42 Hz, 1 H) 5.96-6.03 (m, 1 H) 7.02 (d, J=2.08 Hz, 1 H) 7.24 (dd, J=8.19, 1.83 Hz, 1 H) 7.35 (dd, J=10.51, 1.59 Hz, 1 H) 7.43 (t, J=7.89 Hz, 1 H) 8.51 (br. s., 1 H)

Example 123

(2R,3R,4S,5R)-2-(2-amino-5-fluoro-4-methyl-7H-pyrrolo[2,3-d]pyrimidin-7-yl)-5-((R)-(4-chloro-3-fluorophenyl)(hydroxy)methyl)tetrahydrofuran-3,4-diol acetate (PPP-2)

Scheme PPP

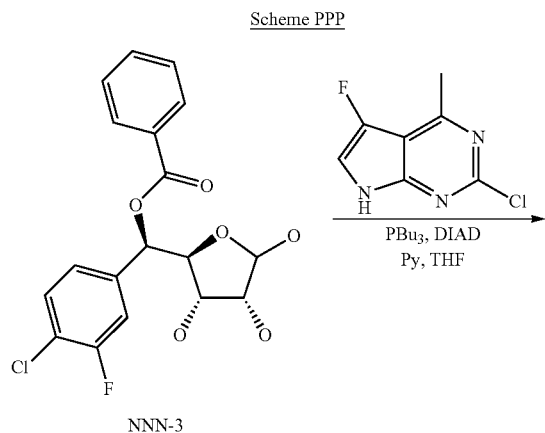

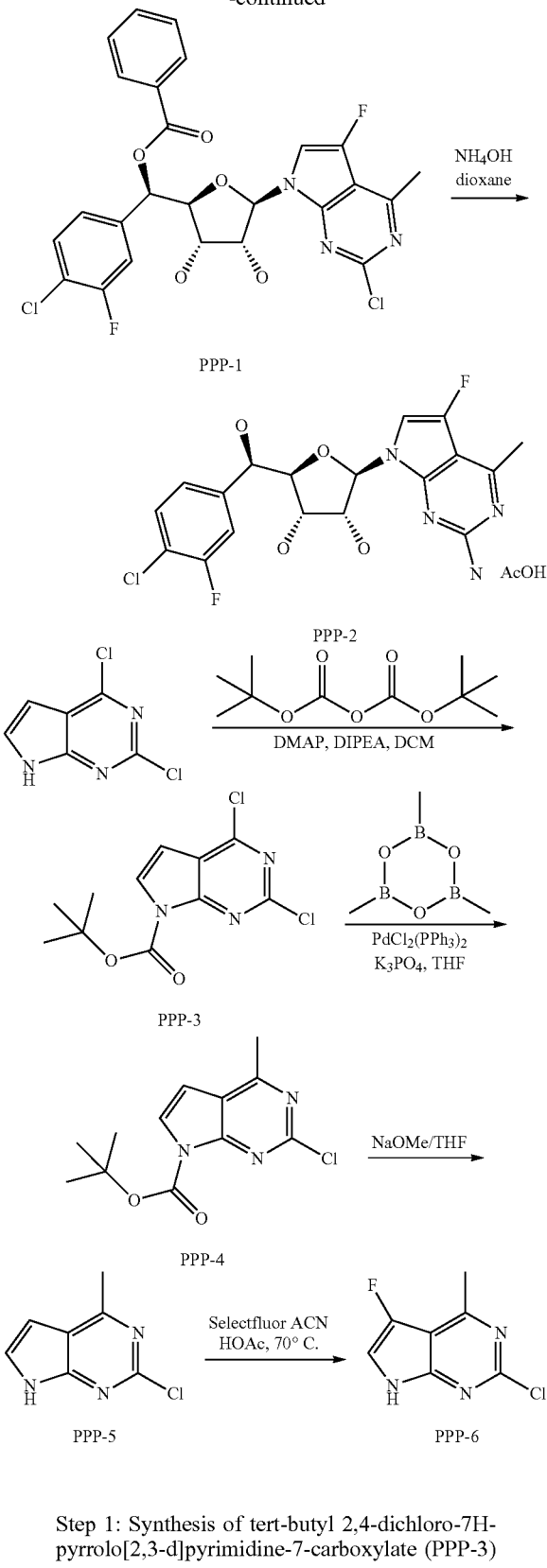

Step 1: Synthesis of tert-butyl 2,4-dichloro-7H-pyrrolo[2,3-d]pyrimidine-7-carboxylate (PPP-3)

4-Dimethylamino pyridine (650 mg, 5.32 mmol), Boc anhydride (8710 mg, 39.9 mmol) and diisopropyl ethylamine (4120 mg, 31.9 mmol) were subsequently added to a stirred suspension of 2,4-dichloro-7H-pyrrolo[2,3-d]pyrimidine (5000 mg, 26.59 mmol) in dichloromethane (50 ml) and the mixture was stirred for 2 h at r.t. The solvent was removed under reduced pressure to give crude product which was purified by column chromatography with dichloromethane to give 5.4 g (70.5% yield) PPP-3 as yellow solid. LCMS [M+1-2Cl-Boc] 120.1; $^1$H NMR (400 MHz, CDCl$_3$) δ ppm 1.70 (s, 9 H) 6.66 (d, J=4.03 Hz, 1 H) 7.71 (d, J=4.16 Hz, 1 H)

Step 2: Synthesis of tert-butyl 2-chloro-4-methyl-7H-pyrrolo[2,3-d]pyrimidine-7-carboxylate (PPP-4)

PPP-3 (4600 mg, 15.96 mmol), trimethylboroxin (5010 mg, 39.9 mmol), potassium phosphate-tribasic (6780 mg, 31.9 mmol) and PdCl$_2$(PPh$_3$)$_2$(1120 mg, 1.60 mmol) was added tetrahydrofuran (50 ml), the mixture was degassed, sealed and heat at 100° C. to reflux for 1.5 h. The reaction was cooled to r.t., the solvent was evaporated, the residue was added dichloromethane and H$_2$O, the layers were separated, the aqueous layer with dichloromethane 3 times, the organic layers were combined and concentrated to give crude product which was purified by column chromatography with 10% EtOAc/DCM to afford 2.5 g (58.5% yield) PPP-4 as off white solid. LCMS [M+1-C$_1$-Boc]134.1; $^1$H NMR (400 MHz, CDCl$_3$) δ ppm 1.69 (s, 9 H) 2.72 (s, 3 H) 6.58 (d, J=4.03 Hz, 1 H) 7.62 (d, J=4.03 Hz, 1 H)

Step 3: Synthesis of 2-chloro-4-methyl-7H-pyrrolo[2,3-d]pyrimidine (PPP-5)

To a cooled (ice bath) solution of PPP-4 (1940 mg, 7.246 mmol) in tetrahydrofuran (60 mL, c=0.12 M) was added sodium methoxide 25 wt % in methanol (2350 mg, 10.9 mmol, 2.49 mL) drop-wise. The reaction was stirred in the ice bath for 10 min before water was added. The mixture was extracted with EtOAc (3×25 mL). The combined organics were washed with brine then dried over MgSO$_4$, filtered and concentrated. The solid was triturated with DCM, filtered and rinsed with DCM to give 1.13 g (93% yield) PPP-5 as yellow solid. LCMS [M+1-Cl] 134.1; $^1$H NMR (400 MHz, CDCl$_3$) δ ppm 2.77 (s, 3 H) 6.61 (dd, J=3.67, 1.96 Hz, 1 H) 7.32 (dd, J=3.55, 2.32 Hz, 1 H) 10.36 (br. s., 1 H)

Step 4: Synthesis of 2-chloro-5-fluoro-4-methyl-7H-pyrrolo[2,3-d]pyrimidine (PPP-6)

Followed similar procedures to Step 1 of Example 121 and Example 122. LCMS [M+1] 186.0; $^1$H NMR (400 MHz, DMSO-d$_6$) δ ppm 2.70 (s, 3 H) 7.53 (t, J=2.32 Hz, 1 H) 12.14 (br. s., 1 H)

Step 5: Synthesis of (R)-(4-chloro-3-fluorophenyl)((2S,3S,4R,5R)-5-(2-chloro-5-fluoro-4-methyl-7H-pyrrolo[2,3-d]pyrimidin-7-yl)-3,4-dihydroxytetrahydrofuran-2-yl)methyl benzoate (PPP-1)

Followed similar procedures to Step 4 of Example 119. LCMS [M+1] 550.0; $^1$H NMR (400 MHz, DMSO-d$_6$) d ppm 2.68 (s, 3 H) 4.23-4.31 (m, 1 H) 4.35 (dd, J=6.17, 3.48 Hz, 1 H) 4.50 (q, J=5.79 Hz, 1 H) 5.51 (d, J=5.38 Hz, 1 H) 5.56 (d, J=6.11 Hz, 1 H) 6.09 (d, J=6.11 Hz, 1 H) 6.17 (d, J=6.11 Hz, 1 H) 7.34 (dd, J=8.25, 1.65 Hz, 1 H) 7.47-7.54 (m, 2 H) 7.54-7.61 (m, 3 H) 7.68-7.76 (m, 1 H) 8.03-8.10 (m, 2 H)

Step 6: Synthesis of (2R,3R,4S,5R)-2-(2-amino-5-fluoro-4-methyl-7H-pyrrolo[2,3-d]pyrimidin-7-yl)-5-((R)-(4-chloro-3-fluorophenyl)(hydroxy)methyl)tetrahydrofuran-3,4-diol acetate (PPP-2)

Followed similar procedures to Step 5 of Example 119. LCMS [M+1] 427.0; $^1$H NMR (400 MHz, MeOD) b ppm 1.99 (s, 3 H) 2.56 (s, 3 H) 4.15-4.21 (m, 2 H) 4.62 (dd, J=6.97, 5.01 Hz, 1 H) 4.93 (d, J=3.18 Hz, 1 H) 5.94 (d, J=6.97 Hz, 1 H) 6.94 (d, J=2.08 Hz, 1 H) 7.23 (dd, J=8.25, 1.77 Hz, 1 H) 7.34 (dd, J=10.51, 1.59 Hz, 1 H) 7.41 (t, J=7.89 Hz, 1 H)

Biological Examples
Biochemical Assay Methods

Compounds were solubilized in DMSO and serially diluted, using 3-fold dilutions, into 100% DMSO at a concentration 50-fold greater than the desired assay concentration. Following dilution, 1 ul was added to an empty 96-well microtiter plate. PRMT5/MEP50 protein complex was combined with H4(1-21) peptide (SGRGKGGKGLG-KGGAKRHRKV) in PRMT5 assay buffer (50 mM Tris pH 8.5, 50 mM NaCl, 5 mM MgCl$_2$, 1 mM EDTA, 1 mM TCEP) and 44 ul was added to the microtiter plate containing compound. S-Adenosyl-L-methionine (SAM) was prepared by combining $^3$H labelled SAM with unlabelled SAM in PRMT5 assay buffer such that the final SAM concentration was 10 uM and the specific activity was 0.2 uCi/ul. The reaction was initiated by adding 5 ul of SAM stock to the microtiter plate. The final reaction conditions were 10 nM PRMT5/MEP50 complex, 200 nM peptide and 1 uM SAM. Following a 25 minute incubation at room temperature, the reaction was stopped with the addition of 100 uL of 20% TCA. The 3H-peptide product was captured using a 96-well filter plate (MSIPN4B, Millipore) and washed 5 times with PBS buffer. Scintillation fluid (100 ul) was added to the dried filter plate and counted in a liquid scintillation counter. IC$_{50}$ values were determined by fitting the data to the standard 4-parameter dose response equation using Pfizer proprietary software.

Results for the biochemical assay of examples are summarized in Table 1, shown as IC$_{50}$ values in μM.

TABLE 1

| PRMT5 Enzyme Inhibition | |
|---|---|
| Example | PRMT5 IC50 (uM) |
| 1 | 0.082 |
| 2 | 3.906 |
| 3 | 0.333 |
| 4 | 44.06 |
| 5 | 0.159 |
| 6 | 21.10 |
| 7 | 1.834 |
| 8 | 17.90 |
| 9 | 0.003 |
| 10 | 0.007 |
| 11 | 0.003 |
| 12 | 0.012 |
| 13 | 0.004 |
| 14 | 0.017 |
| 15 | 0.039 |
| 16 | 0.023 |
| 17 | 2.267 |
| 18 | 0.004 |
| 19 | 0.065 |
| 20 | 0.054 |
| 21 | 0.033 |
| 22 | 0.108 |

TABLE 1-continued

PRMT5 Enzyme Inhibition

| Example | PRMT5 IC50 (uM) |
|---|---|
| 23 | 0.793 |
| 24 | 30.79 |
| 25 | 0.010 |
| 26 | 0.018 |
| 27 | 5.166 |
| 28 | 11.22 |
| 29 | 200 |
| 30 | 0.752 |
| 31 | 61.70 |
| 32 | 0.005 |
| 33 | 2.638 |
| 34 | 0.006 |
| 35 | 1.738 |
| 36 | 0.006 |
| 37 | 2.641 |
| 38 | 0.005 |
| 39 | 1.552 |
| 40 | 0.114 |
| 41 | 3.849 |
| 42 | 0.663 |
| 43 | 73.99 |
| 44 | 0.052 |
| 45 | 1.743 |
| 46 | 0.367 |
| 47 | 15.37 |
| 48 | 0.517 |
| 49 | 37.47 |
| 50 | 0.050 |
| 51 | 14.73 |
| 52 | 1.261 |
| 53 | 9.229 |
| 54 | 0.024 |
| 55 | 4.757 |
| 56 | 0.011 |
| 57 | 6.311 |
| 58 | 1.983 |
| 59 | 0.491 |
| 60 | 0.002 |
| 61 | 0.003 |
| 62 | 0.052 |
| 63 | 0.038 |
| 64 | 0.005 |
| 65 | 0.488 |
| 66 | 1.988 |
| 67 | 1.560 |
| 68 | 5.497 |
| 69 | 1.054 |
| 70 | 0.050 |
| 71 | 0.052 |
| 72 | 2.031 |
| 73 | 23.32 |
| 74 | 3.144 |
| 75 | 21.74 |
| 76 | 1.809 |
| 77 | 24.36 |
| 78 | 51.14 |
| 79 | 5.231 |
| 80 | 0.032 |
| 81 | 91.72 |
| 82 | 0.150 |
| 83 | 0.013 |
| 84 | 0.003 |
| 85 | 0.001 |
| 86 | 0.002 |
| 87 | 0.001 |
| 88 | 0.001 |
| 89 | 1.734 |
| 90 | 3.241 |
| 91 | 0.355 |
| 92 | 0.014 |
| 93 | 0.299 |
| 94 | 0.009 |
| 95 | 0.150 |
| 96 | 0.051 |
| 97 | 0.030 |
| 98 | 0.018 |
| 99 | 0.021 |
| 100 | 0.090 |
| 101 | 0.030 |
| 102 | 0.304 |
| 103 | 0.002 |
| 104 | 0.147 |
| 105 | 0.002 |
| 106 | 0.079 |
| 107 | 0.007 |
| 108 | 0.050 |
| 109 | 4.836 |
| 110 | 0.024 |
| 111 | 0.012 |
| 112 | 0.001 |
| 113 | 0.087 |
| 114 | |
| 115 | 0.002 |
| 116 | 0.005 |
| 117 | 0.005 |
| 118 | 0.035 |
| 119 | 0.007 |
| 120 | |
| 121 | |
| 122 | |
| 123 | |

A549 Proliferation Assay

A549 lung adenocarcinoma cells (American Type Culture Collection) were maintained in DMEM growth media (Life Technologies) supplemented with 10% v/v heat inactivated fetal bovine serum (Sigma) and cultured at 37° C., 5% $CO_2$. Exponentially growing A549 cells were plated in 96-well black tissue culture treated plates (Corning) at a density of 2500 cells/ml in a volume of 100 µl culture media and allowed to adhere overnight at 37° C., 5% $CO_2$. The following day, compound plates were prepared by making nine-point 3.3-fold dilutions in DMSO with a top concentration of 10 mM. Compounds were further diluted in culture media and 11 µl was added to the cells (final top assay concentration was 10 µM and DMSO was 0.2%). Cells were incubated with compound at 37° C., 5% $CO_2$ for 7 days with media and compound replacement on day 4. Cell viability was assayed on Day 7 by adding 100 µl Cell Titer Glo (Promega) reagent to the plate to measure the amount of ATP present in the cells. Luminescence was read using the Envision 2104 Multilabel Reader (Perkin Elmer). The 50% inhibitory concentration ($IC_{50}$) was determined using a 4-parameter fit model normalized to the DMSO control in dose response.

Results for the A549 proliferation assay of examples are summarized in Table 2, shown as IC50 values in µM.

TABLE 2

A549 Cell Proliferation IC50

| Example | A549 Cell IC50 (uM) |
|---|---|
| 9 | 0.016 |
| 10 | 0.043 |
| 11 | 0.015 |
| 12 | 0.100 |
| 13 | 0.112 |
| 26 | 0.211 |
| 27 | 8.700 |

TABLE 2-continued

A549 Cell Proliferation IC50

| Example | A549 Cell IC50 (uM) |
| --- | --- |
| 32 | 0.025 |
| 33 | 4.400 |
| 34 | 0.026 |
| 36 | 0.044 |
| 37 | 3.000 |
| 38 | 0.042 |
| 39 | 10.50 |
| 40 | 2.700 |
| 44 | 3.400 |
| 50 | 3.200 |
| 60 | 0.010 |
| 61 | 0.014 |
| 62 | 2.300 |
| 63 | 3.400 |
| 64 | 0.018 |
| 83 | 0.323 |
| 84 | 0.048 |
| 85 | 0.006 |
| 86 | 0.009 |
| 87 | 0.005 |
| 88 | 0.003 |
| 92 | 0.257 |
| 94 | 1.785 |
| 98 | 0.250 |
| 99 | 0.364 |
| 110 | 1.730 |
| 111 | 0.148 |
| 112 | 0.350 |
| 115 | 0.046 |
| 116 | 1.640 |
| 117 | 0.092 |
| 119 | 0.322 |

Molecular Biology

Gene encoding full length PRMT5 open reading frame (ORF) was fused directly at Ala2 to MDYKDDDDKGRAT sequence encoding Flag tag (SEQ ID: 1) and full length untagged MEP50 (SEQ ID: 2) were codon optimized for mammalian expression and synthetized by GenScript, Piscataway, N.J. Synthetized genes were cloned into insect cell expression vector pFASTBac Dual (Life Technologies) using standard restriction enzyme based cloning procedures. In the final construct PRMT5 ORF was under control of polyhedrin promoter (polH) while MEP50 ORF was under control of p10 promoter. Additionally, MEP50 (SEQ ID: 2) was subcloned into pFASTBac1 vector using standard restriction enzyme based cloning procedures.

Protein Expression

Viruses were generated using standard Bac-to-Bac viral generation protocols (Life Technologies) and amplified to high-titer passage two (P2) stocks. Protein over expression was conducted in exponentially growing Sf21 cells infected at 2×106 with P2 viral stock at MOI=1 of PRMT5-Mep50 dual construct virus and Mep50 construct virus at 1:1 ratio. The co-expression protocol was used to supplement additional Mep50 for FlagPRMT5-Mep50 heterodimer formation. Cells were harvested at 72 h post infection by centrifugation and frozen pellet was stored at −80° C.

Protein Purification

FlagPRMT5-Mep50 complex was purified from cell lysate using Flag affinity chromatography. Cell were lyzed in 50 mM Tris 7.5, 200 mM NaCl, 10% glycerol, 0.25 mM TCEP supplemented with EDTA-free protease inhibitor cocktail (Roche). 1.5 ml of lysis buffer was added per 1 g of frozen pellet. The clarified lysate was obtained by centrifugation of cell lysate at 10,000 g for 1 h at 4 C. 5 ml of Anti-FLAG M2 Agarose (Sigma) for 3 h to isolate was added to the clarified lysate to isolate FlagPRMT5-Mep50. Following batch binding for 3 h at 4 C, Flag resin bound to FlagPRMT5-Mep50 washed with 20 column volumes (CV) of 50 mM Tris 7.5, 200 mM NaCl, 10% glycerol, 0.25 mM TCEP followed by elution of FlagPRMT5-Mep50 complex using 3 CV of 50 mM Tris 7.5, 200 mM NaCl, 10% glycerol, 0.25 mM TCEP supplemented with 200 ug/ml of FLAG Peptide (DYKDDDDK). FlagPRMT5-Mep50 was further purified using S300 26/600 column (GE Healthcare) pre-equilibrated with 2 CV of 25 mM Tris pH7.5, 150 mM NaCl, 5% glycerol, 0.5 mM TCEP buffer. Peak fractions containing FlagPRMT5-Mep50 complex were concentrated to 1.6 mg/ml, flash frozen in small aliquots using liquid nitrogen and stored at −80° C.

Sequences

```
                                                  SEQ ID: 1
MDYKDDDDKGRATAAMAVGGAGGSRVSSGRDLNCVPEIADTLGAVAKQGF

DFLCMPVFHPRFKREFIQEPAKNRPGPQTRSDLLLSGRDWNTLIVGKLSP

WIRPDSKVEKIRRNSEAAMLQELNFGAYLGLPAFLLPLNQEDNTNLARVL

TNHIHTGHHSSMFWMRVPLVAPEDLRDDIIENAPTTHTEEYSGEEKTWMW

WHNFRTLCDYSKRIAVALEIGADLPSNHVIDRWLGEPIKAAILPTSIFLT

NKKGFPVLSKMHQRLIFRLLKLEVQFIITGTNHHSEKEFCSYLQYLEYLS

QNRPPPNAYELFAKGYEDYLQSPLQPLMDNLESQTYEVFEKDPIKYSQYQ

QAIYKCLLDRVPEEEKDTNVQVLMVLGAGRGPLVNASLRAAKQADRRIKL

YAVEKNPNAVVTLENWQFEEWGSQVTVVSSDMREWVAPEKADIIVSELLG

SFADNELSPECLDGAQHFLKDDGVSIPGEYTSFLAPISSSKLYNEVRACR

EKDRDPEAQFEMPYVVRLHNFHQLSAPQPCFTFSHPNRDPMIDNNRYCTL

EFPVEVNTVLHGFAGYFETVLYQDITLSIRPETHSPGMFSWFPILFPIKQ

PITVREGQTICVRFWRCSNSKKVWYEWAVTAPVCSAIHNPTGRSYTIGL*

SEQ ID: 2
MRKETPPPLVPPAAREWNLPPNAPACMERQLEAARYRSDGALLLGASSLS

GRCWAGSLWLFKDPCAAPNEGFCSAGVQTEAGVADLTWVGERGILVASDS

GAVELWELDENETLIVSKFCKYEHDDIVSTVSVLSSGTQAVSGSKDICIK

VWDLAQQVVLSSYRAHAAQVTCVAASPHKDSVFLSCSEDNRILLWDTRCP

KPASQIGCSAPGYLPTSLAWHPQQSEVFVFGDENGTVSLVDTKSTSCVLS

SAVHSQCVTGLVFSPHSVPFLASLSEDCSLAVLDSSLSELFRSQAHRDFV

RDATWSPLNHSLLTTVGWDHQVVHHVVPTEPLPAPGPASVTE*
```

We claim:

1. A compound selected from:

(2R,3S,4R,5R)-2-((R)-(3,4-difluorophenyl)(hydroxy)methyl)-5-(4-methyl-7H-pyrrolo[2,3-d]pyrimidin-7-yl)tetrahydrofuran-3,4-diol, (2R,3S,4R,5R)-2-((R)-(4-fluoro-3-methylphenyl)(hydroxy)methyl)-5-(4-methyl-7H-pyrrolo[2,3-d]pyrimidin-7-yl)tetrahydrofuran-3,4-diol, (2R,3S,4R,5R)-2-((R)-(3-chloro-4-fluorophenyl)(hydroxy)methyl)-5-(4-methyl-7H-pyrrolo[2,3-d]pyrimidin-7-yl)tetrahydrofuran-3,4-diol, (2R,3S,4R,5R)-2-((R)-(4-fluoro-3-methoxyphenyl)(hydroxy)methyl)-5-(4-methyl-7H-pyrrolo[2,3-d]pyrimidin-7-yl)tetrahydrofuran-3,4-diol, 5-((R)-((2R,3S,4R,5R)-3,4-dihydroxy-5-(4-methyl-7H-pyrrolo[2,3-d]pyrimidin-7-yl)tetrahydrofuran-2-yl)(hydroxy)methyl)-2-fluorobenzonitrile, (2R,3S,4R,5R)-2-((R)-(2-(dimethylamino)pyridin-4-yl)(hydroxy)methyl)-5-(4-methyl-7H-pyrrolo[2,3-d]pyrimidin-7-yl)tetrahydrofuran-3,4-diol, (2R,3S,4R,5R)-2-((R)-hydroxy(1-methyl-1H-indazol-6-yl)methyl)-5-(4-methyl-7H-pyrrolo[2,3-d]pyrimidin-7-yl)tetrahydrofuran-3,4-diol, (2R,3S,4R,5R)-2-((R)-hydroxy(3-(trifluoromethyl)phenyl)methyl)-5-(4-methyl-7H-pyrrolo[2,3-d]pyrimidin-7-yl)tetrahydrofuran-3,4-diol, (3S,4R,5R)-2-((3-fluoro-5-(trifluoromethyl)phenyl)(hydroxy)methyl)-5-(4-methyl-7H-pyrrolo[2,3-d]pyrimidin-7-yl)tetrahydrofuran-3,4-diol, (2R,3S,4R,5R)-2-((R)-(4-fluoro-3-(trifluoromethyl)phenyl)(hydroxy)methyl)-5-(4-methyl-7H-pyrrolo[2,3-d]pyrimidin-7-yl)tetrahydrofuran-3,4-diol, (2R,3S,4R,5R)-2-((R)-hydroxy(3-(methylsulfonyl)phenyl)methyl)-5-(4-methyl-7H-pyrrolo[2,3-d]pyrimidin-7-yl)tetrahydrofuran-3,4-diol, (2R,3S,4R,5R)-2-((R)-hydroxy(4-(methylsulfonyl)phenyl)methyl)-5-(4-methyl-7H-pyrrolo[2,3-d]pyrimidin-7-yl)tetrahydrofuran-3,4-diol, (2R,3S,4R,5R)-2-((R)-(3-(difluoromethyl)benzofuran-5-yl)(hydroxy)methyl)-5-(4-methyl-7H-pyrrolo[2,3-d]pyrimidin-7-yl)tetrahydrofuran-3,4-diol, (2R,3S,4R,5R)-2-((R)-(1-(difluoromethyl)-1H-benzo[d]imidazol-6-yl)(hydroxy)methyl)-5-(4-methyl-7H-pyrrolo[2,3-d]pyrimidin-7-yl)tetrahydrofuran-3,4-diol, (2R,3S,4R,5R)-2-((R)-(1-(difluoromethyl)-1H-benzo[d]imidazol-5-yl)(hydroxy)methyl)-5-(4-methyl-7H-pyrrolo[2,3-d]pyrimidin-7-yl)tetrahydrofuran-3,4-diol, (2S,3S,4R,5R)-2-((R)-1-hydroxy-2-(phenylsulfonyl)ethyl)-5-(4-methyl-7H-pyrrolo[2,3-d]pyrimidin-7-yl)tetrahydrofuran-3,4-diol, (2R,3S,4R,5R)-2-((R)-hydroxy(1-methyl-1H-indol-6-yl)methyl)-5-(4-methyl-7H-pyrrolo[2,3-d]pyrimidin-7-yl)tetrahydrofuran-3,4-diol, (2R,3S,4R,5R)-2-((R)-hydroxy(phenyl)methyl)-5-(4-methyl-7H-pyrrolo[2,3-d]pyrimidin-7-yl)tetrahydrofuran-3,4-diol, (2R,3S,4R,5R)-2-((S)-hydroxy(phenyl)methyl)-5-(4-methyl-7H-pyrrolo[2,3-d]pyrimidin-7-yl)tetrahydrofuran-3,4-diol, (2R,3S,4R,5R)-2-((R)-1-hydroxy-2-phenylethyl)-5-(4-methyl-7H-pyrrolo[2,3-d]pyrimidin-7-yl)tetrahydrofuran-3,4-diol, (2R,3S,4R,5R)-2((S)-1-hydroxy-2-phenylethyl)-5-(4-methyl-7H-pyrrolo[2,3-d]pyrimidin-7-yl)tetrahydrofuran-3,4-diol, (2R,3S,4R,5R)-2-((R)-1-hydroxy-3-phenylpropyl)-5-(4-methyl-7H-pyrrolo[2,3-d]pyrimidin-7-yl)tetrahydrofuran-3,4-diol, (2R,3S,4R,5R)-2-((S)-1-hydroxy-3-phenylpropyl)-5-(4-methyl-7H-pyrrolo[2,3-d]pyrimidin-7-yl)tetrahydrofuran-3,4-diol, (2R,3S,4R,5R)-2-((R)-(3-chlorophenyl)(hydroxy)methyl)-5-(4-methyl-7H-pyrrolo[2,3-d]pyrimidin-7-yl)tetrahydrofuran-3,4-diol, (2R,3S,4R,5R)-2-((S)-(3-chlorophenyl)(hydroxy)methyl)-5-(4-methyl-7H-pyrrolo[2,3-d]pyrimidin-7-yl)tetrahydrofuran-3,4-diol, (2R,3S,4R,5R)-2-((R)-(3-fluorophenyl)(hydroxy)methyl)-5-(4-methyl-7H-pyrrolo[2,3-d]pyrimidin-7-yl)tetrahydrofuran-3,4-diol, (2R,3S,4R,5R)-2-((S)-(3-fluorophenyl)(hydroxy)methyl)-5-(4-methyl-7H-pyrrolo[2,3-d]pyrimidin-7-yl)tetrahydrofuran-3,4-diol, (2R,3S,4R,5R)-2-((R)-(3,5-difluorophenyl)(hydroxy)methyl)-5-(4-methyl-7H-pyrrolo[2,3-d]pyrimidin-7-yl)tetrahydrofuran-3,4-diol, (2R,3S,4R,5R)-2-((S)-(3,5-difluorophenyl)(hydroxy)methyl)-5-(4-methyl-7H-pyrrolo[2,3-d]pyrimidin-7-yl)tetrahydrofuran-3,4-diol, (2R,3S,4R,5R)-2-((R)-(4-fluorophenyl)(hydroxy)methyl)-5-(4-methyl-7H-pyrrolo[2,3-d]pyrimidin-7-yl)tetrahydrofuran-3,4-diol, (2R,3S,4R,5R)-2-((S)-(4-fluorophenyl)(hydroxy)methyl)-5-(4-methyl-7H-pyrrolo[2,3-d]pyrimidin-7-yl)tetrahydrofuran-3,4-diol, (2R,3S,4R,5R)-2-((R)-1-hydroxypropyl)-5-(4-methyl-7H-pyrrolo[2,3-d]pyrimidin-7-yl)tetrahydrofuran-3,4-diol, (2R,3S,4R,5R)-2-((S)-1-hydroxypropyl)-5-(4-methyl-7H-pyrrolo[2,3-d]pyrimidin-7-yl)tetrahydrofuran-3,4-diol, (2R,3S,4R,5R)-2-((R)-cyclopentyl(hydroxy)methyl)-5-(4-methyl-7H-pyrrolo[2,3-d]pyrimidin-7-yl)tetrahydrofuran-3,4-diol, (2R,3S,4R,5R)-2-((S)-cyclopentyl(hydroxy)methyl)-5-(4-methyl-7H-pyrrolo[2,3-d]pyrimidin-7-yl)tetrahydrofuran-3,4-diol, (2R,3S,4R,5R)-2-((R)-1-hydroxyethyl)-5-(4-methyl-7H-pyrrolo[2,3-d]pyrimidin-7-yl)tetrahydrofuran-3,4-diol, (2R,3S,4R,5R)-2-((S)-1-hydroxyethyl)-5-(4-methyl-7H-pyrrolo[2,3-d]pyrimidin-7-yl)tetrahydrofuran-3,4-diol, (2R,3S,4R,5R)-2-((R)-cyclopropyl(hydroxy)methyl)-5-(4-methyl-7H-pyrrolo[2,3-d]pyrimidin-7-yl)tetrahydrofuran-3,4-diol, (2R,3S,4R,5R)-2-((S)-cyclopropyl(hydroxy)methyl)-5-(4-methyl-7H-pyrrolo[2,3-d]pyrimidin-7-yl)tetrahydrofuran-3,4-diol, (2R,3S,4R,5R)-2-((R)-1-hydroxy-2-methylpropyl)-5-(4-methyl-7H-pyrrolo[2,3-d]pyrimidin-7-yl)tetrahydrofuran-3,4-diol, (2R,3S,4R,5R)-2-((S)-1-hydroxy-2-methylpropyl)-5-(4-methyl-7H-pyrrolo[2,3-d]pyrimidin-7-yl)tetrahydrofuran-3,4-diol, (2R,3S,4R,5R)-2-((R)-hydroxy(1-methyl-1H-pyrazol-4-yl)methyl)-5-(4-methyl-7H-pyrrolo[2,3-d]pyrimidin-7-yl)tetrahydrofuran-3,4-diol, (2R,3S,4R,5R)-2-((S)-hydroxy(1-methyl-1H-pyrazol-4-yl)methyl)-5-(4-methyl-7H-pyrrolo[2,3-d]pyrimidin-7-yl)tetrahydrofuran-3,4-diol, (2R,3S,4R,5R)-2-((R)-cyclobutyl(hydroxy)methyl)-5-(4-methyl-7H-pyrrolo[2,3-d]pyrimidin-7-yl)tetrahydrofuran-3,4-diol, (2R,3S,4R,5R)-2-((S)-cyclobutyl(hydroxy)methyl)-5-(4-methyl-7H-pyrrolo[2,3-d]pyrimidin-7-yl)tetrahydrofuran-3,4-diol, (2S,3S,4R,5R)-2-((S)-furan-2-yl(hydroxy)methyl)-5-(4-methyl-7H-pyrrolo[2,3-d]pyrimidin-7-yl)tetrahydrofuran-3,4-diol, (2S,3S,4R,5R)-2-((R)-furan-2-yl(hydroxy)methyl)-5-(4-methyl-7H-pyrrolo[2,3-d]pyrimidin-7-yl)tetrahydrofuran-3,4-diol, (2R,3R,4S,5S)-2-(4-methyl-7H-pyrrolo[2,3-d]pyrimidin-7-yl)-5-((S)-2,2,2-trifluoro-1-hydroxyethyl)tetrahydrofuran-3,4-diol, (2R,3R,4S,5S)-2-(4-methyl-7H-pyrrolo[2,3-d]pyrimidin-7-yl)-5-((R)-2,2,2-trifluoro-1-hydroxyethyl)tetrahydrofuran-3,4-diol, (2R,3S,4R,5R)-2-((1H-pyrazol-1-yl)methyl)-5-(4-methyl-7H-pyrrolo[2,3-d]pyrimidin-7-yl)tetrahydrofuran-3,4-diol, (3S,4R,5R)-2-(difluoro(4-fluorophenyl)methyl)-5-(4-methyl-7H-pyrrolo[2,3-d]pyrimidin-7-yl)tetrahydrofuran-3,4-diol, (2R,3R,4S,5R)-2-(4-amino-5-fluoro-7H-pyrrolo[2,3-d]pyrimidin-7-yl)-5-((R)-(3,4-difluorophenyl)(hydroxy)methyl)tetrahydrofuran-3,4-diol, (2R,3R,4S,5R)-2-(4-amino-5-fluoro-7H-pyrrolo[2,3-d]pyrimidin-7-yl)-5-((R)-(4-fluorophenyl)(hydroxy)methyl)tetrahydrofuran-3,4-diol, (2R,3R,4S,5R)-2-(2-amino-4-methyl-7H-pyrrolo[2,3-d]pyrimidin-7-yl)-5-((R)-1-hydroxypropyl)tetrahydrofuran-3,4-diol, (2R,3R,4S,5R)-2-(2-amino-4-methyl-7H-pyrrolo[2,3-d]pyrimidin-7-yl)-5-((R)-1-hydroxybutyl)tetrahydrofuran-3,4-diol, (2R,3R,4S,5R)-2-(2-amino-4-methyl-7H-pyrrolo[2,3-d]pyrimidin-7-yl)-5-((R)-(4-fluorophenyl)(hydroxy)methyl)tetrahydrofuran-3,4-diol, (2R,3R,4S,5R)-2-(2-amino-4-methyl-7H-pyrrolo[2,3-d]pyrimidin-7-yl)-5-((S)-(4-fluorophenyl)(hydroxy)methyl)tetrahydrofuran-3,4-diol, (2R,3R,4S,5S)-2-(4-methyl-7H-pyrrolo[2,3-d]pyrimidin-7-yl)-5-phenyltetrahydrofuran-3,4-diol, (2R,3R,4S,5S)-2-(4-amino-5-fluoro-7H-pyrrolo[2,3-d]pyrimidin-7-yl)-5-phenyltetrahydrofuran-3,4-diol, (2R,3R,4S,5S)-2-(2-amino-4-methyl-7H-pyrrolo[2,3-d]pyrimidin-7-yl)-5-phenyltetrahydrofuran-3,4-diol, (2R,3R,4S,5R)-2-(4-methyl-7H-pyrrolo[2,3-d]pyrimidin-7-yl)-5-(oxazol-5-yl)tetrahydrofuran-3,4-diol, (2S,3S,4R,5R)-2-((R)-1-hydroxyethyl)-5-(4-methyl-7H-pyrrolo[2,3-d]pyrimidin-7-yl)tetrahydrofuran-3,4-diol, (2S,3S,4R,5R)-2-(hydroxymethyl)-5-(4-methyl-7H-pyrrolo[2,3-d]pyrimidin-7-yl)tetrahydrofuran-3,4-diol, (2R,3R,4S,5S)-2-(4-methyl-7H-pyrrolo[2,3-d]pyrimidin-7-yl)-5-(1H-pyrazol-5-yl)tetrahydrofuran-3,4-diol, (2S,3S,4R,5R)-2-((S)-hydroxy(phenyl)methyl)-5-(4-methyl-7H-pyrrolo[2,3-d]pyrimidin-7-yl)tetrahydrofuran-3,4-diol, (2S,3S,4R,5R)-2-((R)-hydroxy(phenyl)methyl)-5-(4-methyl-7H-pyrrolo[2,3-d]pyrimidin-7-yl)tetrahydrofuran-3,4-diol, (2S,3S,4R,5R)-2-((S)-(4-fluorophenyl)(hydroxy)methyl)-5-(4-methyl-7H-pyrrolo[2,3-d]pyrimidin-7-yl)tetrahydrofuran-3,4-diol, (2S,3S,4R,5R)-2-((R)-(4-fluorophenyl)(hydroxy)methyl)-5-(4-methyl-7H-pyrrolo[2,3-d]pyrimidin-7-yl)tetrahydrofuran-3,4-diol, (2S,3S,4R,5R)-2-(1-methyl-1H-pyrazol-3-yl)-5-(4-methyl-7H-pyrrolo[2,3-d]pyrimidin-7-yl)tetrahydrofuran-3,4-diol, (2S,3S,4R,5R)-2-(3-(ethoxymethyl)-1H-pyrazol-5-yl)-5-(4-methyl-7H-pyrrolo[2,3-d]pyrimidin-7-yl)tetrahydrofuran-3,4-diol, (2S,3S,4R,5R)-2-(1,2-dihydroxyethyl)-5-(4-methyl-7H-pyrrolo[2,3-d]pyrimidin-7-yl)tetrahydrofuran-3,4-diol, ((3aS,4S,6R,6aR)-2,2-dimethyl-6-(4-methyl-7H-pyrrolo[2,3-d]pyrimidin-7-yl)tetrahydrofuro[3,4-d][1,3]dioxol-4-yl)(2-(methylsulfonyl)phenyl)methanone, (2R,3S,4R,5R)-2-((R)-hydroxy(1H-indol-7-yl)methyl)-5-(4-methyl-7H-pyrrolo[2,3-d]pyrimidin-7-yl)tetrahydrofuran-3,4-diol, (2R,3R,4S,5R)-2-(4-amino-5-fluoro-7H-pyrrolo[2,3-d]pyrimidin-7-yl)-5-((R)-(5-fluoropyridin-2-yl)(hydroxy)methyl)tetrahydrofuran-3,4-diol, (2R,3R,4S,5R)-2-(4-amino-7H-pyrrolo[2,3-d]pyrimidin-7-yl)-5-((R)-(3,4-difluorophenyl)(hydroxy)methyl)tetrahydrofuran-3,4-diol, (2R,3R,4S,5R)-2-(4-amino-7H-pyrrolo[2,3-d]pyrimidin-7-yl)-5-((R)-(4-fluorophenyl)(hydroxy)methyl)tetrahydrofuran-3,4-diol, (2R,3R,4S,5R)-2-(4-amino-7H-pyrrolo[2,3-d]pyrimidin-7-yl)-5-((R)-(4-chlorophenyl)(hydroxy)methyl)tetrahydrofuran-3,4-diol, (2R,3R,4S,5R)-2-(4-amino-7H-pyrrolo[2,3-d]pyrimidin-7-yl)-5-((R)-(4-chloro-3-fluorophenyl)(hydroxy)methyl)tetrahydrofuran-3,4-diol, (S)-1-((3aR,4S,6R,6aR)-2,2-dimethyl-6-(4-methyl-7H-pyrrolo[2,3-d]pyrimidin-7-yl)tetrahydrofuro[3,4-d][1,3]dioxol-4-yl)ethan-1-ol, 2-((3aR,4R,6R,6aR)-2,2-dimethyl-6-(4-methyl-7H-pyrrolo[2,3-d]pyrimidin-7-yl)tetrahydrofuro[3,4-d][1,3]dioxol-4-yl)propan-2-ol, (3,4-difluorophenyl)((2S,3S,4R,5R)-3,4-dihydroxy-5-(4-methyl-7H-pyrrolo[2,3-d]pyrimidin-7-yl)tetrahydrofuran-2-yl)methanone, (2S,3S,4R,5R)-2-((R)-(3,4-difluorophenyl)fluoromethyl)-5-(4-methyl-7H-pyrrolo[2,3-d]pyrimidin-7-yl)tetrahydrofuran-3,4-diol, (2S,3S,4R,5R)-2-((S)-(3,4-difluorophenyl)fluoromethyl)-5-(4-methyl-7H-pyrrolo[2,3-d]pyrimidin-7-yl)tetrahydrofuran-3,4-diol, (2R,3S,4R,5R)-2-((R)-amino(3,4-difluorophenyl)methyl)-5-(4-methyl-7H-pyrrolo[2,3-d]pyrimidin-7-yl)tetrahydrofuran-3,4-diol, (2R,3S,4R,5R)-2-((S)-amino(3,4-difluorophenyl)methyl)-5-(4-methyl-7H-pyrrolo[2,3-d]pyrimidin-7-yl)tetrahydrofuran-3,4-diol, (2R,3R,4S,5R)-2-(4-(difluoromethyl)-7H-pyrrolo[2,3-d]pyrimidin-7-yl)-5-((R)-(4-fluorophenyl)(hydroxy)methyl)tetrahydrofuran-3,4-diol, (2R,3R,4S,5R)-2-(4-(difluoromethyl)-7H-pyrrolo[2,3-d]pyrimidin-7-yl)-5-((R)-(3,4-difluorophenyl)(hydroxy)methyl)tetrahydrofuran-3,4-diol, (2R,3R,4S,5R)-2-(5-fluoro-4-methyl-7H-pyrrolo[2,3-d]pyrimidin-7-yl)-5-((R)-(4-fluorophenyl)(hydroxy)methyl)tetrahydrofuran-3,4-diol, (2R,3R,4S,5R)-2-(2,4-dimethyl-7H-pyrrolo[2,3-d]pyrimidin-7-yl)-5-((R)-(4-fluorophenyl)(hydroxy)methyl)tetrahydrofuran-3,4-diol, (2R,3R,4S,5R)-2-(4-fluorobenzyl)-5-(4-methyl-7H-pyrrolo[2,3-d]pyrimidin-7-yl)tetrahydrofuran-3,4-diol, (2R,3R,4S,5R)-2-(4-amino-5-fluoro-7H-pyrrolo[2,3-d]pyrimidin-7-yl)-5-(4-fluorobenzyl)tetrahydrofuran-3,4-diol, (2R,3R,4S,5S)-2-(4-amino-7H-pyrrolo[2,3-d]pyrimidin-7-yl)-5-((R)-1-(3,4-difluorophenyl)-1-hydroxyethyl)tetrahydrofuran-3,4-diol, (2R,3R,4S,5S)-2-(4-amino-7H-pyrrolo[2,3-d]pyrimidin-7-yl)-5-((S)-1-(3,4-difluorophenyl)-1-hydroxyethyl)tetrahydrofuran-3,4-diol, (2R,3R,4S,5S)-2-(4-amino-7H-pyrrolo[2,3-d]pyrimidin-7-yl)-5-((R)-1-(4-chloro-3-fluorophenyl)-1-hydroxyethyl)tetrahydrofuran-3,4-diol, (2R,3R,4S,5S)-2-(4-amino-7H-pyrrolo[2,3-d]pyrimidin-7-yl)-5-((S)-1-(4-chloro-3-fluorophenyl)-1-hydroxyethyl)tetrahydrofuran-3,4-diol, (2R,3S,4R,5R)-2-((R)-(3,4-difluorophenyl)(hydroxy)methyl)-5-(4-(fluoromethyl)-7H-pyrrolo[2,3-d]pyrimidin-7-yl)tetrahydrofuran-3,4-diol, (2R,3S,4R,5R)-2-((R)-(3,4-difluorophenyl)(hydroxy)methyl)-5-(4-(hydroxymethyl)-7H-pyrrolo[2,3-d]pyrimidin-7-yl)tetrahydrofuran-3,4-diol, (2R,3S,4R,5R)-2-((R)-(3,4-difluorophenyl)(methylamino)methyl)-5-(4-methyl-7H-pyrrolo[2,3-d]pyrimidin-7-yl)tetrahydrofuran-3,4-diol, (2R,3S,4R,5R)-2-((R)-hydroxy(6-methylpyridin-3-yl)methyl)-5-(4-methyl-7H-pyrrolo[2,3-d]pyrimidin-7-yl)tetrahydrofuran-3,4-diol, (2R,3S,4R,5R)-2-((R)-hydroxy(2-methylpyridin-4-yl)methyl)-5-(4-methyl-7H-pyrrolo[2,3-d]pyrimidin-7-yl)tetrahydrofuran-3,4-diol, (2R,3S,4R,5R)-2-((R)-hydroxy(1,2,3,4-tetrahydroisoquinolin-8-yl)methyl)-5-(4-methyl-7H-pyrrolo[2,3-d]pyrimidin-7-yl)tetrahydrofuran-3,4-diol, 6-((R)-((2R,3S,4R,5R)-3,4-dihydroxy-5-(4-methyl-7H-pyrrolo[2,3-d]pyrimidin-7-yl)tetrahydrofuran-2-yl)(hydroxy)methyl)pyridin-2(1H)-one, (2R,3S,4R,5R)-2-((R)-(4-fluoro-3-(hydroxymethyl)phenyl)(hydroxy)methyl)-5-(4-methyl-7H-pyrrolo[2,3-d]pyrimidin-7-yl)tetrahydrofuran-3,4-diol, (2R,3S,4R,5R)-2-((R)-(4-chloro-3-fluorophenyl)(hydroxy)methyl)-5-(7H-pyrrolo[2,3-d]pyrimidin-7-yl)tetrahydrofuran-3,4-diol, (2R,3S,4R,5R)-2-((R)-amino(4-chloro-3-fluorophenyl)methyl)-5-(7H-pyrrolo[2,3-d]pyrimidin-7-yl)tetrahydrofuran-3,4-diol, (2R,3S,4R,5R)-2-((R)-(3,4-difluorophenyl)(hydroxy)methyl)-5-(7H-pyrrolo[2,3-d]pyrimidin-7-yl)tetrahydrofuran-3,4-diol, (2R,3S,4R,5R)-2-((R)-amino(3,4-difluorophenyl)methyl)-5-(7H-pyrrolo[2,3-d]pyrimidin-7-yl)tetrahydrofuran-3,4-diol, (2R,3R,4S,5R)-2-(4-amino-5-iodo-7H-pyrrolo[2,3-d]pyrimidin-7-yl)-5-((R)-(3,4-difluorophenyl)(hydroxy)methyl)tetrahydrofuran-3,4-diol, (2R,3R,4S,5R)-2-(2-amino-4-methyl-7H-pyrrolo[2,3-d]
pyrimidin-7-yl)-5-((R)-(3,4-difluorophenyl)(hydroxy)
methyl)tetrahydrofuran-3,4-diol,
(2R,3R,4S,5R)-2-(2-chloro-5-fluoro-7H-pyrrolo[2,3-d]
pyrimidin-7-yl)-5-((R)-(3,4-difluorophenyl)(hydroxy)
methyl)tetrahydrofuran-3,4-diol,
(2R,3R,4S,5R)-2-(2-amino-5-fluoro-7H-pyrrolo[2,3-d]
pyrimidin-7-yl)-5-((R)-(3,4-difluorophenyl)(hydroxy)
methyl)tetrahydrofuran-3,4-diol, and
(2R,3R,4S,5R)-2-(2-amino-5-fluoro-4-methyl-7H-pyrrolo[2,3-d]pyrimidin-7-yl)-5-((R)-(4-chloro-3-fluorophenyl)(hydroxy)methyl)tetrahydrofuran-3,4-diol
acetate,
or a pharmaceutically acceptable salt thereof.

2. A compound selected from:
(2R,3S,4R,5R)-2-((R)-(3,4-difluorophenyl)(hydroxy)
methyl)-5-(4-methyl-7H-pyrrolo[2,3-d]pyrimidin-7-
yl)tetrahydrofuran-3,4-diol,
(2R,3S,4R,5R)-2-((R)-(4-fluoro-3-methylphenyl)(hydroxy)methyl)-5-(4-methyl-7H-pyrrolo[2,3-d]pyrimidin-7-yl)tetrahydrofuran-3,4-diol,
(2R,3S,4R,5R)-2-((R)-(3-chloro-4-fluorophenyl)(hydroxy)methyl)-5-(4-methyl-7H-pyrrolo[2,3-d]pyrimidin-7-yl)tetrahydrofuran-3,4-diol,
(2R,3S,4R,5R)-2-((R)-(4-fluoro-3-methoxyphenyl)(hydroxy)methyl)-5-(4-methyl-7H-pyrrolo[2,3-d]pyrimidin-7-yl)tetrahydrofuran-3,4-diol,
5-((R)-((2R,3S,4R,5R)-3,4-dihydroxy-5-(4-methyl-7H-pyrrolo[2,3-d]pyrimidin-7-yl)tetrahydrofuran-2-yl)
(hydroxy)methyl)-2-fluorobenzonitrile,
(2R,3S,4R,5R)-2-((R)-hydroxy(phenyl)methyl)-5-(4-
methyl-7H-pyrrolo[2,3-d]pyrimidin-7-yl)tetrahydrofuran-3,4-diol,
(2R,3S,4R,5R)-2-((S)-hydroxy(phenyl)methyl)-5-(4-
methyl-7H-pyrrolo[2,3-d]pyrimidin-7-yl)tetrahydrofuran-3,4-diol,
(2R,3S,4R,5R)-2-((R)-(3-chlorophenyl)(hydroxy)
methyl)-5-(4-methyl-7H-pyrrolo[2,3-d]pyrimidin-7-
yl)tetrahydrofuran-3,4-diol,
(2R,3S,4R,5R)-2-((S)-(3-chlorophenyl)(hydroxy)
methyl)-5-(4-methyl-7H-pyrrolo[2,3-d]pyrimidin-7-
yl)tetrahydrofuran-3,4-diol,
(2R,3S,4R,5R)-2-((R)-(3,5-difluorophenyl)(hydroxy)
methyl)-5-(4-methyl-7H-pyrrolo[2,3-d]pyrimidin-7-
yl)tetrahydrofuran-3,4-diol,
(2R,3S,4R,5R)-2-((S)-(3,5-difluorophenyl)(hydroxy)
methyl)-5-(4-methyl-7H-pyrrolo[2,3-d]pyrimidin-7-
yl)tetrahydrofuran-3,4-diol,
(2R,3S,4R,5R)-2-((R)-(4-fluorophenyl)(hydroxy)
methyl)-5-(4-methyl-7H-pyrrolo[2,3-d]pyrimidin-7-
yl)tetrahydrofuran-3,4-diol,
(2R,3S,4R,5R)-2-((S)-(4-fluorophenyl)(hydroxy)
methyl)-5-(4-methyl-7H-pyrrolo[2,3-d]pyrimidin-7-
yl)tetrahydrofuran-3,4-diol,
(2R,3S,4R,5R)-2-((R)-1-hydroxypropyl)-5-(4-methyl-
7H-pyrrolo[2,3-d]pyrimidin-7-yl)tetrahydrofuran-3,4-
diol,
(2R,3S,4R,5R)-2-((R)-1-hydroxyethyl)-5-(4-methyl-7H-
pyrrolo[2,3-d]pyrimidin-7-yl)tetrahydrofuran-3,4-diol,
(2R,3S,4R,5R)-2-((R)-hydroxy(1-methyl-1H-pyrazol-4-
yl)methyl)-5-(4-methyl-7H-pyrrolo[2,3-d]pyrimidin-
7-yl)tetrahydrofuran-3,4-diol,
(2R,3R,4S,5R)-2-(4-amino-5-fluoro-7H-pyrrolo[2,3-d]
pyrimidin-7-yl)-5-((R)-(3,4-difluorophenyl)(hydroxy)
methyl)tetrahydrofuran-3,4-diol,
(2R,3R,4S,5R)-2-(4-amino-5-fluoro-7H-pyrrolo[2,3-d]
pyrimidin-7-yl)-5-((R)-(4-fluorophenyl)(hydroxy)
methyl)tetrahydrofuran-3,4-diol,
(2R,3R,4S,5R)-2-(2-amino-4-methyl-7H-pyrrolo[2,3-d]
pyrimidin-7-yl)-5-((R)-1-hydroxypropyl)tetrahydrofuran-3,4-diol,
(2R,3R,4S,5R)-2-(2-amino-4-methyl-7H-pyrrolo[2,3-d]
pyrimidin-7-yl)-5-((R)-1-hydroxybutyl)tetrahydrofuran-3,4-diol,
(2R,3R,4S,5R)-2-(2-amino-4-methyl-7H-pyrrolo[2,3-d]
pyrimidin-7-yl)-5-((R)-(4-fluorophenyl)(hydroxy)
methyl)tetrahydrofuran-3,4-diol,
(2R,3R,4S,5R)-2-(4-amino-7H-pyrrolo[2,3-d]pyrimidin-
7-yl)-5-((R)-(3,4-difluorophenyl)(hydroxy)methyl)tetrahydrofuran-3,4-diol,
(2R,3R,4S,5R)-2-(4-amino-7H-pyrrolo[2,3-d]pyrimidin-
7-yl)-5-((R)-(4-fluorophenyl)(hydroxy)methyl)tetrahydrofuran-3,4-diol,
(2R,3R,4S,5R)-2-(4-amino-7H-pyrrolo[2,3-d]pyrimidin-
7-yl)-5-((R)-(4-chlorophenyl)(hydroxy)methyl)tetrahydrofuran-3,4-diol,
(2R,3R,4S,5R)-2-(4-amino-7H-pyrrolo[2,3-d]pyrimidin-
7-yl)-5-((R)-(4-chloro-3-fluorophenyl)(hydroxy)
methyl)tetrahydrofuran-3,4-diol,
(2S,3S,4R,5R)-2-((R)-(3,4-difluorophenyl)fluoromethyl)-5-(4-methyl-7H-pyrrolo[2,3-d]pyrimidin-7-yl)
tetrahydrofuran-3,4-diol,
(2R,3S,4R,5R)-2-((R)-amino(3,4-difluorophenyl)
methyl)-5-(4-methyl-7H-pyrrolo[2,3-d]pyrimidin-7-
yl)tetrahydrofuran-3,4-diol,
(2R,3R,4S,5R)-2-(4-(difluoromethyl)-7H-pyrrolo[2,3-d]
pyrimidin-7-yl)-5-((R)-(4-fluorophenyl)(hydroxy)
methyl)tetrahydrofuran-3,4-diol,
(2R,3R,4S,5R)-2-(5-fluoro-4-methyl-7H-pyrrolo[2,3-d]
pyrimidin-7-yl)-5-((R)-(4-fluorophenyl)(hydroxy)
methyl)tetrahydrofuran-3,4-diol,
(2R,3R,4S,5R)-2-(2,4-dimethyl-7H-pyrrolo[2,3-d]pyrimidin-7-yl)-5-((R)-(4-fluorophenyl)(hydroxy)
methyl)tetrahydrofuran-3,4-diol,
(2R,3S,4R,5R)-2-((R)-hydroxy(6-methylpyridin-3-yl)
methyl)-5-(4-methyl-7H-pyrrolo[2,3-d]pyrimidin-7-
yl)tetrahydrofuran-3,4-diol,
(2R,3S,4R,5R)-2-((R)-hydroxy(2-methylpyridin-4-yl)
methyl)-5-(4-methyl-7H-pyrrolo[2,3-d]pyrimidin-7-
yl)tetrahydrofuran-3,4-diol,
(2R,3S,4R,5R)-2-((R)-hydroxy(1,2,3,4-tetrahydroisoquinolin-8-yl)methyl)-5-(4-methyl-7H-pyrrolo[2,3-d]pyrimidin-7-yl)tetrahydrofuran-3,4-diol,
(2R,3S,4R,5R)-2-((R)-(4-chloro-3-fluorophenyl)(hydroxy)methyl)-5-(7H-pyrrolo[2,3-d]pyrimidin-7-yl)
tetrahydrofuran-3,4-diol,
(2R,3S,4R,5R)-2-((R)-amino(4-chloro-3-fluorophenyl)
methyl)-5-(7H-pyrrolo[2,3-d]pyrimidin-7-yl)tetrahydrofuran-3,4-diol,
(2R,3S,4R,5R)-2-((R)-(3,4-difluorophenyl)(hydroxy)
methyl)-5-(7H-pyrrolo[2,3-d]pyrimidin-7-yl)tetrahydrofuran-3,4-diol,
(2R,3R,4S,5R)-2-(4-amino-5-iodo-7H-pyrrolo[2,3-d]pyrimidin-7-yl)-5-((R)-(3,4-difluorophenyl)(hydroxy)
methyl)tetrahydrofuran-3,4-diol,
or a pharmaceutically acceptable salt thereof.

3. The compound: (2R,3R,4S,5R)-2-(4-amino-7H-pyrrolo[2,3-d]pyrimidin-7-yl)-5-((R)-(4-chloro-3-fluorophenyl)(hydroxy)methyl)tetrahydrofuran-3,4-diol, or a pharmaceutically acceptable salt thereof.

* * * * *

SEQUENCE LISTING

<160> NUMBER OF SEQ ID NOS: 2

<210> SEQ ID NO 1

```
<211> LENGTH: 649
<212> TYPE: PRT
<213> ORGANISM: Homo sapiens

<400> SEQUENCE: 1

Met Asp Tyr Lys Asp Asp Asp Lys Gly Arg Ala Thr Ala Ala Met
1               5                   10                  15

Ala Val Gly Gly Ala Gly Ser Arg Val Ser Ser Gly Arg Asp Leu
            20                  25                  30

Asn Cys Val Pro Glu Ile Ala Asp Thr Leu Gly Ala Ala Lys Gln
            35                  40                  45

Gly Phe Asp Phe Leu Cys Met Pro Val Phe His Pro Arg Phe Lys Arg
50                      55                  60

Glu Phe Ile Gln Glu Pro Ala Lys Asn Arg Pro Gly Pro Gln Thr Arg
65                  70                  75                  80

Ser Asp Leu Leu Ser Gly Arg Asp Trp Asn Thr Leu Ile Val Gly
                85                  90                  95

Lys Leu Ser Pro Trp Ile Arg Pro Asp Ser Lys Val Glu Lys Ile Arg
                100                 105                 110

Arg Asn Ser Glu Ala Ala Met Leu Gln Glu Leu Asn Phe Gly Ala Tyr
                115                 120                 125

Leu Gly Leu Pro Ala Phe Leu Leu Pro Leu Asn Gln Glu Asp Asn Thr
130                 135                 140

Asn Leu Ala Arg Val Leu Thr Asn His Ile His Thr Gly His His Ser
145                 150                 155                 160

Ser Met Phe Trp Met Arg Val Pro Leu Val Ala Pro Glu Asp Leu Arg
                165                 170                 175

Asp Asp Ile Ile Glu Asn Ala Pro Thr Thr His Thr Glu Glu Tyr Ser
                180                 185                 190

Gly Glu Glu Lys Thr Trp Met Trp Trp His Asn Phe Arg Thr Leu Cys
            195                 200                 205

Asp Tyr Ser Lys Arg Ile Ala Val Ala Leu Glu Ile Gly Ala Asp Leu
            210                 215                 220

Pro Ser Asn His Val Ile Asp Arg Trp Leu Gly Glu Pro Ile Lys Ala
225                 230                 235                 240

Ala Ile Leu Pro Thr Ser Ile Phe Leu Thr Asn Lys Lys Gly Phe Pro
                245                 250                 255

Val Leu Ser Lys Met His Gln Arg Leu Ile Phe Arg Leu Leu Lys Leu
                260                 265                 270

Glu Val Gln Phe Ile Ile Thr Gly Thr Asn His His Ser Glu Lys Glu
            275                 280                 285

Phe Cys Ser Tyr Leu Gln Tyr Leu Glu Tyr Leu Ser Gln Asn Arg Pro
            290                 295                 300

Pro Pro Asn Ala Tyr Glu Leu Phe Ala Lys Gly Tyr Glu Asp Tyr Leu
305                 310                 315                 320

Gln Ser Pro Leu Gln Pro Leu Met Asp Asn Leu Glu Ser Gln Thr Tyr
                325                 330                 335

Glu Val Phe Glu Lys Asp Pro Ile Lys Tyr Ser Gln Tyr Gln Gln Ala
            340                 345                 350

Ile Tyr Lys Cys Leu Leu Asp Arg Val Pro Glu Glu Lys Asp Thr
            355                 360                 365

Asn Val Gln Val Leu Met Val Leu Gly Ala Gly Arg Gly Pro Leu Val
            370                 375                 380

Asn Ala Ser Leu Arg Ala Ala Lys Gln Ala Asp Arg Arg Ile Lys Leu
```

```
            385                 390                 395                 400

Tyr Ala Val Glu Lys Asn Pro Asn Ala Val Thr Leu Glu Asn Trp
                    405                 410                 415

Gln Phe Glu Glu Trp Gly Ser Gln Val Thr Val Ser Ser Asp Met
                420                 425                 430

Arg Glu Trp Val Ala Pro Glu Lys Ala Asp Ile Ile Val Ser Glu Leu
                435                 440                 445

Leu Gly Ser Phe Ala Asp Asn Glu Leu Ser Pro Glu Cys Leu Asp Gly
            450                 455                 460

Ala Gln His Phe Leu Lys Asp Asp Gly Val Ser Ile Pro Gly Glu Tyr
    465                 470                 475                 480

Thr Ser Phe Leu Ala Pro Ile Ser Ser Ser Lys Leu Tyr Asn Glu Val
                        485                 490                 495

Arg Ala Cys Arg Glu Lys Asp Arg Asp Pro Glu Ala Gln Phe Glu Met
                    500                 505                 510

Pro Tyr Val Val Arg Leu His Asn Phe His Gln Leu Ser Ala Pro Gln
                515                 520                 525

Pro Cys Phe Thr Phe Ser His Pro Asn Arg Asp Pro Met Ile Asp Asn
            530                 535                 540

Asn Arg Tyr Cys Thr Leu Glu Phe Pro Val Glu Val Asn Thr Val Leu
    545                 550                 555                 560

His Gly Phe Ala Gly Tyr Phe Glu Thr Val Leu Tyr Gln Asp Ile Thr
                        565                 570                 575

Leu Ser Ile Arg Pro Glu Thr His Ser Pro Gly Met Phe Ser Trp Phe
                    580                 585                 590

Pro Ile Leu Phe Pro Ile Lys Gln Pro Ile Thr Val Arg Glu Gly Gln
                595                 600                 605

Thr Ile Cys Val Arg Phe Trp Arg Cys Ser Asn Ser Lys Lys Val Trp
            610                 615                 620

Tyr Glu Trp Ala Val Thr Ala Pro Val Cys Ser Ala Ile His Asn Pro
    625                 630                 635                 640

Thr Gly Arg Ser Tyr Thr Ile Gly Leu
                        645

<210> SEQ ID NO 2
<211> LENGTH: 342
<212> TYPE: PRT
<213> ORGANISM: Homo sapiens

<400> SEQUENCE: 2

Met Arg Lys Glu Thr Pro Pro Pro Leu Val Pro Pro Ala Ala Arg Glu
    1               5                   10                  15

Trp Asn Leu Pro Pro Asn Ala Pro Ala Cys Met Glu Arg Gln Leu Glu
                    20                  25                  30

Ala Ala Arg Tyr Arg Ser Asp Gly Ala Leu Leu Leu Gly Ala Ser Ser
                35                  40                  45

Leu Ser Gly Arg Cys Trp Ala Gly Ser Leu Trp Leu Phe Lys Asp Pro
            50                  55                  60

Cys Ala Ala Pro Asn Glu Gly Phe Cys Ser Ala Gly Val Gln Thr Glu
    65                  70                  75                  80

Ala Gly Val Ala Asp Leu Thr Trp Val Gly Glu Arg Gly Ile Leu Val
                        85                  90                  95

Ala Ser Asp Ser Gly Ala Val Glu Leu Trp Glu Leu Asp Glu Asn Glu
                    100                 105                 110
```

```
Thr Leu Ile Val Ser Lys Phe Cys Lys Tyr Glu His Asp Asp Ile Val
            115                 120                 125
Ser Thr Val Ser Val Leu Ser Ser Gly Thr Gln Ala Val Ser Gly Ser
        130                 135                 140
Lys Asp Ile Cys Ile Lys Val Trp Asp Leu Ala Gln Gln Val Val Leu
145                 150                 155                 160
Ser Ser Tyr Arg Ala His Ala Ala Gln Val Thr Cys Val Ala Ala Ser
                165                 170                 175
Pro His Lys Asp Ser Val Phe Leu Ser Cys Ser Glu Asp Asn Arg Ile
            180                 185                 190
Leu Leu Trp Asp Thr Arg Cys Pro Lys Pro Ala Ser Gln Ile Gly Cys
        195                 200                 205
Ser Ala Pro Gly Tyr Leu Pro Thr Ser Leu Ala Trp His Pro Gln Gln
        210                 215                 220
Ser Glu Val Phe Val Phe Gly Asp Glu Asn Gly Thr Val Ser Leu Val
225                 230                 235                 240
Asp Thr Lys Ser Thr Ser Cys Val Leu Ser Ser Ala Val His Ser Gln
                245                 250                 255
Cys Val Thr Gly Leu Val Phe Ser Pro His Ser Val Pro Phe Leu Ala
            260                 265                 270
Ser Leu Ser Glu Asp Cys Ser Leu Ala Val Leu Asp Ser Ser Leu Ser
        275                 280                 285
Glu Leu Phe Arg Ser Gln Ala His Arg Asp Phe Val Arg Asp Ala Thr
        290                 295                 300
Trp Ser Pro Leu Asn His Ser Leu Leu Thr Thr Val Gly Trp Asp His
305                 310                 315                 320
Gln Val Val His His Val Val Pro Thr Glu Pro Leu Pro Ala Pro Gly
                325                 330                 335
Pro Ala Ser Val Thr Glu
            340
```